US009926577B2

(12) United States Patent
Feldman et al.

(10) Patent No.: US 9,926,577 B2
(45) Date of Patent: *Mar. 27, 2018

(54) YEAST ORGANISM PRODUCING ISOBUTANOL AT A HIGH YIELD

(71) Applicant: GEVO, INC., Englewood, CO (US)

(72) Inventors: Reid M. Renny Feldman, San Marino, CA (US); Uvini Gunawardena, Irvine, CA (US); Jun Urano, Aurora, CO (US); Peter Meinhold, Denver, CO (US); Aristos Aristidou, Highlands Ranch, CO (US); Catherine Asleson Dundon, Englewood, CO (US); Christopher Smith, Englewood, CO (US)

(73) Assignee: Gevo, Inc., Englewood, CO (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/482,308

(22) Filed: Sep. 10, 2014

(65) Prior Publication Data

US 2015/0218596 A1    Aug. 6, 2015

Related U.S. Application Data

(60) Continuation of application No. 13/907,394, filed on May 31, 2013, now abandoned, which is a continuation of application No. 12/820,505, filed on Jun. 22, 2010, now Pat. No. 8,455,239, which is a continuation-in-part of application No. 12/696,645, filed on Jan. 29, 2010, now abandoned, which is a division of application No. 12/343,375, filed on Dec. 23, 2008, now Pat. No. 8,017,375.

(60) Provisional application No. 61/219,173, filed on Jun. 22, 2009, provisional application No. 61/016,483, filed on Dec. 23, 2007.

(51) Int. Cl.
| | |
|---|---|
| C12N 1/19 | (2006.01) |
| C12N 15/81 | (2006.01) |
| C12P 7/16 | (2006.01) |
| C12N 9/04 | (2006.01) |
| C12N 9/02 | (2006.01) |
| C12N 9/10 | (2006.01) |
| C12N 9/88 | (2006.01) |
| C12N 9/90 | (2006.01) |
| C12N 9/60 | (2006.01) |

(52) U.S. Cl.
CPC .............. *C12P 7/16* (2013.01); *C12N 9/0006* (2013.01); *C12N 9/0008* (2013.01); *C12N 9/1022* (2013.01); *C12N 9/88* (2013.01); *C12N 9/90* (2013.01); *C12N 15/81* (2013.01); *C12Y 101/05003* (2013.01); *C12Y 202/01006* (2013.01); *C12Y 401/01001* (2013.01); *C12Y 402/01009* (2013.01); *C12Y 101/01001* (2013.01); *C12Y 101/01008* (2013.01); *C12Y 101/01086* (2013.01); *C12Y 401/01074* (2013.01); *Y02E 50/10* (2013.01)

(58) Field of Classification Search
CPC .... C12N 15/81; C12N 9/0006; C12N 9/0008; C12N 9/1022; C12N 9/88; C12N 9/90; C12P 7/16; C12Y 101/01001; C12Y 101/01008; C12Y 101/01086; C12Y 101/05003; C12Y 202/01006; C12Y 401/01001; C12Y 401/01074; C12Y 402/01009; Y02E 50/10; Y02P 20/52

See application file for complete search history.

(56) References Cited

U.S. PATENT DOCUMENTS

| | | |
|---|---|---|
| 6,660,507 B2 | 12/2003 | Cheng et al. |
| 7,109,010 B2 | 9/2006 | Rajgarhia et al. |
| 7,851,188 B2 | 12/2010 | Donaldson et al. |
| 7,993,889 B1 | 8/2011 | Donaldson et al. |
| 8,017,375 B2 | 9/2011 | Feldman et al. |
| 2003/0032152 A1 | 2/2003 | Porro et al. |
| 2004/0029256 A1 | 2/2004 | Rajgarhia et al. |
| 2004/0146996 A1 | 7/2004 | Yocum et al. |
| 2005/0059136 A1 | 3/2005 | van Maris et al. |

(Continued)

FOREIGN PATENT DOCUMENTS

| | | |
|---|---|---|
| WO | WO 99/14335 A1 | 3/1999 |
| WO | WO 03/102152 A2 | 12/2003 |

(Continued)

OTHER PUBLICATIONS

Valadi et al., Applied Microbiology and Biotechnology 50:434-439, 1998.*
U.S. Appl. No. 61/058,970, filed Jun. 5, 2008, Anthony et al.
"Answer to Amended Complaint Answer to Amended Complaint, with Jury Demand, Counterclaim against Butamax(TM) Advanced Biofuels LLC, E.I. DuPont De Nemours and Co. by Gevo Inc.," *ButamaxTM Advanced Biofuels LLC v. Gevo, Inc. v. E.I. DuPont de Nemours & Co.*, 1:11-cv-00054-SLR, United States District Court for the District of Delaware (filed Sep. 13, 2011).
"Answering Brief in Opposition re Sealed Motion for Leave to File Amended Answer to Counterclaims, Defenses, and Counter-Counterclaims filed by Gevo Inc.," *ButamaxTM Advanced Biofuels LLC v. Gevo, Inc. v. E.I. DuPont de Nemours & Co.*, 1:11-cv-00054-SLR, United States District Court for the District of Delaware (filed Apr. 16, 2012).

(Continued)

*Primary Examiner* — Delia M Ramirez
(74) *Attorney, Agent, or Firm* — Cooley LLP

(57) ABSTRACT

The present invention provides recombinant microorganisms comprising an isobutanol producing metabolic pathway and methods of using said recombinant microorganisms to produce isobutanol. In various aspects of the invention, the recombinant microorganisms may comprise a modification resulting in the reduction of pyruvate decarboxylase and/or glycerol-3-phosphate dehydrogenase activity. In various embodiments described herein, the recombinant microorganisms may be microorganisms of the *Saccharomyces clade*, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

14 Claims, 41 Drawing Sheets

(56) References Cited

U.S. PATENT DOCUMENTS

| | | |
|---|---|---|
| 2006/0234364 A1 | 10/2006 | Rajgarhia et al. |
| 2007/0092957 A1 | 4/2007 | Donaldson et al. |
| 2009/0226691 A1 | 9/2009 | Feldman et al. |
| 2009/0305363 A1 | 12/2009 | Anthony et al. |
| 2010/0120105 A1 | 5/2010 | Anthony et al. |
| 2011/0020889 A1 | 1/2011 | Feldman et al. |
| 2011/0111472 A1 | 5/2011 | Donaldson et al. |
| 2011/0112334 A1 | 5/2011 | Donaldson et al. |
| 2011/0183392 A1 | 7/2011 | Feldman et al. |
| 2011/0301388 A1 | 12/2011 | Donaldson et al. |
| 2011/0313206 A1 | 12/2011 | Donaldson et al. |
| 2011/0318799 A1 | 12/2011 | Feldman et al. |
| 2012/0028323 A1 | 2/2012 | Feldman et al. |
| 2012/0034666 A1 | 2/2012 | Hawkins et al. |
| 2013/0252298 A1 | 9/2013 | Feldman et al. |

FOREIGN PATENT DOCUMENTS

| | | |
|---|---|---|
| WO | WO 2004/099425 A2 | 11/2004 |
| WO | WO 2006/102342 A2 | 9/2006 |
| WO | WO 2007/032792 A2 | 3/2007 |
| WO | WO 2007/061590 A1 | 5/2007 |
| WO | WO 2008/042338 A2 | 4/2008 |
| WO | WO 2008/052991 A2 | 5/2008 |
| WO | WO 2008/063650 A2 | 5/2008 |
| WO | WO 2008/080124 A2 | 7/2008 |
| WO | WO 2008/098277 A2 | 8/2008 |
| WO | WO 2008/121701 A1 | 10/2008 |
| WO | WO 2008/130372 A2 | 10/2008 |
| WO | WO 2009/086423 A2 | 7/2009 |
| WO | WO 2009/103533 A1 | 8/2009 |
| WO | WO 2010/151525 A1 | 12/2010 |

OTHER PUBLICATIONS

"Decision on Petition Under 37 C.F.R. §§ 1.927 & 1.181," 13 pages, U.S. Reexamination Control No. 95/002,158 (Jul. 26, 2013).

"First Supplemental Objections and Responses to Gevo, Inc.'s Second Set of Interrogatories to Butamax Advanced Biofuels LLC (Nos. 8-16)" for *ButamaxTM Advanced Biofuels LLC v. Gevo, Inc. v. E.I. DuPont de Nemours & Co.*, 1:11-cv-00054-SLR, United States District Court for the District of Delaware (dated May 18, 2012).

"Memorandum Opinion," *Gevo, Inc. v. ButamaxTM Advanced Biofuels LLC and E. I. Dupont de Nemours and Company*, 46 pages, Case I: 13-cv-00576-SLR (Jul. 26, 2013).

"Objections and Responses to Gevo, Inc.'s Second Set of Interrogatories to Butamax Advanced Biofuels LLC (Nos. 8-16)" for *ButamaxTM Advanced Biofuels LLC v. Gevo, Inc. v. E.I. DuPont de Nemours & Co.*, 1:11-cv-00054-SLR, United States District Court for the District of Delaware (dated Mar. 26, 2012).

"Office Action in Inter Partes Reexamination of U.S. Pat. No. 8,017,375," 37 pages, U.S. Reexamination Control No. 95/002,158 (dated Nov. 14, 2012).

"Order," *Gevo, Inc. v. ButamaxTM Advanced Biofuels LLC and E. I. Dupont de Nemours and Company*, 2 pages, Case 1: 13-cv-00576-SLR (Jul. 26, 2013).

"Order Granting Inter Partes Reexamination of U.S. Pat. No. 8,017,375," 14 pages, U.S. Reexamination Control No. 95/002,158 (dated Nov. 14, 2012).

"Patent Owner's Response to Office Action," 50 pages, U.S. Reexamination Control No. 95/002,158 (dated Feb. 14, 2013).

"Request for Inter Partes Reexamination of U.S. Pat. No. 8,017,375 Under 35 U.S.C. § 311 and 37 C.F.R. § 1.913," 3049 pages, U.S. Reexamination Control No. 95/002,158 (filed Sep. 7, 2012).

"Sealed Answer to Answer to Amended Complaint, Counterclaim, Counterclaim against Gevo Inc. by E.I. DuPont De Nemours and Co., Butamax(Tm) Advanced Biofuels LLC," *ButamaxTM Advanced Biofuels LLC v. Gevo, Inc. v. E.I. DuPont de Nemours & Co.*, 1:11-cv-00054-SLR, United States District Court for the District of Delaware (filed Nov. 18, 2011).

"Sealed Opening Brief in Support re Sealed Motion for Leave to File Amended Answer to Counterclaims, Defenses, and Counter-Counterclaims filed by Butamax(Tm) Advanced Biofuels LLC, E.I. DuPont De Nemours and Co.," *ButamaxTM Advanced Biofuels LLC v. Gevo, Inc. v. E.I. DuPont de Nemours & Co.*, 1:11-cv-00054-SLR, United States District Court for the District of Delaware (filed Mar. 30, 2012).

"Sealed Reply Brief re Sealed Motion for Leave to File Amended Answer to Counterclaims, Defenses, and Counter-Counterclaims Reply Brief in Support of Plainitff's and Counterclaim Defendants' Motion for Leave to Amend the Pleadings filed by Butamax(Tm) Advanced Biofuels LLC, E.I. DuPont De Nemours and Co.," *ButamaxTM Advanced Biofuels LLC v. Gevo, Inc. v. E.I. DuPont de Nemours & Co.*, 1:11-cv-00054-SLR, United States District Court for the District of Delaware (filed Apr. 26, 2012).

"Third Party Requester Comments Under 37 C.F.R. § 1.947," 44 pages, U.S. Reexamination Control No. 95/002,158 (Jul. 11, 2013).

Butamax's and DuPont's Notification of Concurrent Proceedings Under 37 C.F.R. § 1.985, of the of the '375 and '376 Patents, dated Sep. 3, 2013, *Gevo, Inc. v. Butamax™ Advanced Biofuels LLC and E.I. Du Pont de Nemours and Company*, USDC—District of Delaware, No. 1:13-cv-00576-SLR, C.A. No. 13-576 (SLR) (Public Version), 54 pages.

"Notice of Intent to Issue a Reexamination Certificate", U.S. Reexamination Control No. 95/002,158 (Jul. 25, 2014), 6 pages.

"Reexamination Petition Granted", 13 pages, U.S. Reexamination Control No. 95/002,158 (Jul. 26, 2013).

Abbott et al., "Metabolic engineering of *Saccharomyces cerevisiae* for production of carboxylic acids: currnet status and challenges," FEMS Yeast Res. 9:1123-1136 (2009).

Adachi, E, et al. (1998) Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value. Journal of Fermentation and Bioengineering 86(3):284-9.

Askwith et al., "The FET3 Gene of *S. cerevisiae* encodes a multicopper oxidase required for ferrous iron uptake," Cell 76:403-410 (1994).

Atsumi and Liao, "Metabolic engineering for advanced biofuels production from *Escherichia coli*," Curr. Op. Biotechnol. 19:414-419, Elsevier Ltd., England (2008).

Atsumi, S, et al. (2008) "Non-fermentative pathways for synthesis of branched-chain higher alcohols as biofuels," Nature 451(7174):86-90.

Baburina, et al., "Reactivity at the substrate activation site of yeast pyruvate decarboxylase: inhibition by distortion of domain interactions," Biochemistry 37: 1245-55 (1998).

Bengtsson et al., "Xylose reductase from Pichia stipitis with altered coenzyme preference improves ethanolic xylose fermentation by recombinant *Saccharomyces cerevisiae*," Biotechnol. Biofuels 2:1-10 (2009).

Björkqvist et al., "Physiological Response to Anaerobicity of Glycerol-3-Phosphate Dehydrogenase Mutants of *Saccharomyces cerevisiae*," Appl. Environ. Microbiol. 63(1):128-132 (1997).

Bode, "Valine inhibition of β-isopropylmalate dehydrogenase takes part in the regulation of leucine biosynthesis in Candida maltosa," Antonie van Leeuwenhoek 60:125-130 (1991).

Boulton et al., Brewing Yeast & Fermentation, Chapters 3-4, first ed., Blackwell Science Ltd, Oxford, United Kingdom, pp. 69-259, 2001.

Branden et al., "Prediction, Engineering, and Design of Protein Structures," Introduction to Protein Structure, Garland Publishing Inc., New York, p. 247 (1991).

Butamax and Dupont's Opening Brief in Support of Their Motion for Summary Judgment of Invalidity of the '375 and '376 Patents, 54 pages, Nov. 30, 2012, *Butamax198 Advanced Biofuels LLC v. Gevo, Inc.*, USDC—District of Delaware, No. 1:11-cv-00054-SLR (Public Version).

Butamax and Dupont's Opening Brief in Support of Their Motion for Summary Judgment of Invalidity of the '375 and '376 Patents, 47 pages, Dec. 12, 2012, *Butamax™ Advanced Biofuels LLC v. Gevo, Inc.*, USDC—District of Delaware, No. 1:11-cv-00054-SLR, Document 604 (Public Version).

Gevo, Inc.'s Opposition to Butamax's Motion re Invalidity of the '375 and '376 Patents and Cross Motion for Summary Judgement of Written Description and Enablement of the '376 Patent, 45 pages,

(56) References Cited

OTHER PUBLICATIONS

Dec. 21, 2012, *Butamax™ Advanced Biofuels LLC v. Gevo, Inc.*, USDC—District of Delaware, No. 1: 11-cv-00054-SLR, Document 633 (Public Version).

Butamax and Dupont's Opening Brief in Support of Their Motion for Summary Judgment of Non-Infringement of the '375 and '376 Patents, 47 pages, Dec. 26, 2012, *Butamax™ Advanced Biofuels LLC v. Gevo, Inc.*, USDC—District of Delaware, No. 1: 11-cv-00054-SLR, Document 635 (Public Version).

Gevo, Inc.'s Opposition to Butamax's Motion for Summary Judgment of Non-Infringement of the '375 and '376 Patents, 47 pages, Jan. 8, 2013, *Butamax™ Advanced Biofuels LLC v. Gevo, Inc.*, USDC—District of Delaware, No. 1: 11-cv-00054-SLR, Document 663 (Public Version).

Declaration of Jeremy A Tigan in Support of Defendant Gevo, Inc.'s Opposition to Butamax's Motion for Summary Judgment of Non-Infringement of the '375 and '376 Patents, 4 pages, Jan. 8, 2013, *Butamax™ Advanced Biofuels LLC v. Gevo, Inc.*, USDC—District of Delaware, No. 1:11-cv-00054-SLR, Document 664 (Public Version).

Butamax and Dupont's Responsive and Reply Brief in Support of its Motion for Summary Judgement of Invalidity of the '375 and '376 Patents, 48 pages, Jan. 9, 2013, *Butamax™ Advanced Biofuels LLC v. Gevo, Inc.*, USDC—District of Delaware, No. 1: 11-cv-00054-SLR, Document 671 (Public Version).

Butamax and Dupont's Reply Brief in Support of Their Motion for Summary Judgement of Non-Infringement of the '375 and '376 Patents, 27 pages, Jan. 10, 2013, *Butamax™ Advanced Biofuels LLC v. Gevo, Inc.*, USDC—District of Delaware, No. 1:11-cv-00054-SLR, Document 675 (Public Version).

Memorandum Opinion issued in *Gevo, Inc. v. Butamax™ Advanced Biofuels LLC*, USDC—District of Delaware, No. 1: 13-cv-00576-SLR; dated Jul. 26, 2013, 46 pages.

Butamax and Dupont's Responsive and Reply Brief in Support of its Motion for Summary Judgment of Invalidity of the '375 and '376 Patents, 48 pages, Dec. 28, 2012, *Butama™ Advanced Biofuels LLC v. Gevo, Inc.*, USDC—District of Delaware, No. 1:11-cv-00054-SLR (Public Version).

Butamax's and DuPont's Responsive Brief in Support of Butamax's and DuPont's Claim Construction of the '375 and '376 Patents, Oct. 16, 2012, *Butamax™ Advanced Biofuels LLC v. Gevo, Inc.*, USDC—District of Delaware, No. 1:11-cv-00054-SLR, Docket No. 546 (Public Version).

Butamax's and DuPont's Sur-Reply Brief in Support of Butamax's and DuPont's Claim Constructions of the '375 and '376 Patents, Nov. 6, 2012, *Butamax™ Advanced Biofuels LLC v. Gevo, Inc.*, USDC—District of Delaware, No. 1:11-cv-00054-SLR, Docket No. 574 (Public Version).

Butler, et al., "Identification of an upstream activation site in the pyruvate decarboxylase structural gene (PDC1) of *Saccharomyces cerevisiae*," Current Genetics 14: 405-12 (1988).

Ph.D. Thesis, McGill University (Montreal, Canada), Formation and Analysis of Fusel Alcohols in Beer, Submitted to the Faculty of Graduate Studies and Research, Department of Agricultural Chemistry, 1978.

Connor et al., "Engineering of an *Escherichia coli* Strain for the Production of 3-Methyl-1-Butanol," Appl. Environ. Microbiol. 74(18):5769-5775 (2008).

De La Plaza, et al., "Biochemical and molecular characterization of α-ketoisovalerate decarboxylase, an enzyme involved in the formation of aldehydes from amino acids by Lactococcus lactis," FEMS Microbiology Letters 238: 367-374 (Aug. 2004).

Eberhardt, et al., "Autoregulation of yeast pyruvate decarboxylase gene expression requires the enzyme but not its catalytic activity," Eur. J. Biochem. 262: 191-201 (1999).

Expert Rebuttal Report of Christopher Voigt, Ph.D., Oct. 12, 2012, *Butamax™ Advanced Biofuels LLC v. Gevo, Inc.*, USDC—District of Delaware, No. 1:11-cv-00054-SLR (Public Version).

Expert Report of Corinne Michels, Ph.D. in Support of Butamax's Defense of Invalidity of U.S. Pat. No. 8,017,375 Under 35 USC §§ 102 and 103, Aug. 31, 2012, *Butamax™ Advanced Biofuels LLC v. Gevo, Inc.*, USDC—District of Delaware, No. 1:11-cv-00054-SLR (Public Version).

Expert Report of Dr. Hans van Dijken, Ph.D., in Support of Butamax's Defense of Invalidity of U.S. Pat. No. 8,017,375 Under 35 USC § 103, Aug. 31, 2012, *Butamax™ Advanced Biofuels LLC v. Gevo, Inc.*, USDC—District of Delaware, No. 1:11-cv-00054-SLR.

Expert Report of Eleftherios Terry Papoutsakis, Ph.D., Oct. 12, 2012, *Butamax™ Advanced Biofuels LLC v. Gevo, Inc.*, USDC—District of Delaware, No. 1:11-cv-00054-SLR (Public Version).

Expert Report of Professor Susan Henry, Aug. 31, 2012, *Butamax™ Advanced Biofuels LLC v. Gevo, Inc.*, USDC—District of Delaware, No. 1:11-cv-00054-SLR (Public Version).

Fernandez De Palencia, et al., "Diversity of amino acid converting enzymes in wild lactic acid bacteria," Enzyme and Microbiol Technology 38: 88-93 (Jan. 2006).

Flint et al., "The inactivation of dihydroxy-acid dehydratase in *Esherichia coli* treated with hyperbaric oxygen occurs because of the destruction of its Fe—S Cluster, but the enzyme remains in the cell in a form that can be reactivated," J. Biol. Chem. 268(34):25547-25552 (1993).

Gevo, Inc.'s Opposition to Butamax's Motion re Invalidity of the '375 and '376 Patents and Cross Motion for Summary Judgement of Written Description and Enablement of the '376 Patent, 45 pages, Dec. 14, 2012, *Butamax™ Advanced Biofuels LLC v. Gevo, Inc.*, USDC—District of Delaware, No. 1:11-cv-00054-SLR (Public Version).

Gevo's Opening Brief in Support of Gevo's Claim Constructions, Aug. 31, 2012, *Butamax™ Advanced Biofuels LLC v. Gevo, Inc.*, USDC—District of Delaware, No. 1:11-cv-00054-SLR, Docket No. 499.

Gevo's Reply Claim Construction Brief in Support of the Proper Construction of Disputed Terms of Gevo's '375 and '376 Patents, Oct. 17, 2012, *Butamax™ Advanced Biofuels LLC v. Gevo, Inc.*, USDC—District of Delaware, No. 1:11-cv-00054-SLR, Docket No. 551.

Guo et al., "Interruption of glycerol pathway in industrial alcoholic yeasts to improve the ethanol production," Appl. Microbiol. Biotechnol. 82(2):287-292 (2008).

Hansen, et al., "Brewer's yeast: genetic structure and targets for improvement," Topics in Current Genetics, vol. 2., J.H. de Winde (Ed.): Functional Genetics of Industrial Yeasts (2003).

Hausmann et al., "The eukaryotic P loop NTPase Nbp35: An essential component of the cytosolic and nuclear iron-sulfur protein assembly machinery," Proc. Natl. Acad. Sci., 102(9):3266-71 (2005).

Hohmann et al., "Autoregulation may control the expression of yeast pyruvate decarboxylase structural genes PDCJ and PDC5," Eur. J. Biochem. 188:615-621, 1990.

Hohmann et al., "PDC6, a weakly expressed pyruvate decarboxylase gene from yeast, is activated when fused spontaneously under the control of the PDC1 promoter," Curr. Genet. 20:373-378, 1991.

International Search Report and Written Opinion dated Aug. 30, 2010 in the International (PCT) Application No. PCT/US10/39447, 9 pages.

International Preliminary Report on Patentability dated Jan. 4, 2012, in International (PCT) Application No. PCT/US10/39447, 6 pages.

International Search Report and Written Opinion dated Jul. 23, 2009 in International (PCT) Application No. PCT/US08/88235, 10 pages.

International Preliminary Report on Patentability dated Jun. 29, 2010, in International (PCT) Application No. PCT/US08/88235, 6 pages.

Ishida et al., "The Effect of Pyruvate Decarboxylase Gene Knockout in *Saccharomyces cerevisiae* on L-Lactic Acid Production," Biosci. Biotechnol. Biochem. 70(5):1148-1153 (2006).

Joseph, et al., "Function of a conserved loop of the β-domain, not involved in thiamin diphosphate binding, in catalysis and substrate activation in yeast pyruvate decarboxylase," Biochemistry 45: 13517-27 (2006).

(56) References Cited

OTHER PUBLICATIONS

Kassow, A. (1992). Metabolic effects of deleting the region encoding the transit peptide in *Saccharomyces cerevisiae* ILV5. PhD thesis, University of Copenhagen.
Kellermann, et al., "Analysis of the primary structure and promoter function of a pyruvate decarboxylase gene (PDC1) from *Saccharomyces cerevisiae*," Nucl. Acids Res. 14(22): 8963-77 (1986).
Kellermann, et al., "The glucose- and ethanol-dependent regulation of PDC1 from *Saccharomyces cerevisiae* are controlled by two distinct promoter regions," Current Genetics 14: 337-44 (1988).
Kozak, "Initiation of translation in prokaryotes and eukaryotes," Gene 234:187-208 (1999).
Kutter, et al., "Covalently bound substrate at the regulatory site triggers allosteric enzyme activation," Nature Precedings: hdl:10101/npre.2008.1639.1 (Posted Feb. 27, 2008, Available Online Feb. 28, 2008); Available from Nature Precedings <http://hdl.handle.net/10101/npre.2008.1639.1>.
Langkjaer et al., "Yeast genome duplication was followed by asynchronous differentiation of duplicated genes," Nature 421:848-852 (2003).
Lee et al., "Metabolic engineering of microorganisms for biofuels production: from bugs to synthetic biology to fuels," Curr. Opin. Biotechnol. 19(6):556-563 (2008).
Li, et al., "Effects of substitution of tryptophan 412 in the substrate activation pathway of yeast pyruvate decarboxylase," Biochemistry 38: 10004-10012 (1999).
Li, et al., "Role of glutamate 91 in information transfer during substrate activation of yeast pyruvate decarboxylase," Biochemistry 38: 9992-10003 (1999).
Merico et al., "Fermentative lifestyle in yeasts belonging to the *Saccharomyces* complex," FEBS Journal 274:976-989 (2007).
Michnick, S, et al. (1997) "Modulation of Glycerol and Ethanol Yields During Alcoholic Fermentation in *Saccharomyces cerevisiae* Strains Overexpressed or Disrupted for GPD1 Encoding Glycerol 3-Phosphate Dehydrogenase," Yeast 13(9):783-793.
Møller et al., "Pyruvate decarboxylases from the petite-negative yeast *Saccharomyces kluyveri*," Mol. Gen. Genomics 270:558-568, 2004.
Nevoigt, E and Stahl, U. (1996) "Reduced pyruvate decarboxylase and increased glycerol-3-phosphate dehydrogenase [NAD+] levels enhance glycerol production in *Saccharomyces cerevisiae*," Yeast 12(13):1331-7.
Nissen et al., "Anaerobic and aerobic batch cultivations of *Saccharomyces cerevisiae* mutants impaired in glycerol synthesis," Yeast 16:463-474 (2000).
Oshita et al., "Clarification of the relationship between fusel alcohol formation and amino acid assimilation by brewing yeast using 13C-labeled amino acid," Proceedings of the European Brewery Convention Congress, pp. 387-394, 1995.
Overkamp, KM, et al. (2002) "Metabolic Engineering of Glycerol Production in *Saccharomyces cerevisiae*," Applied and Environmental Microbiology 68(6):2814-21.
Papini et al., "Systems Biology of Industrial Microorganisms," Adv. Biochem. Engin./Biotechnol. 120:51-99 (2010).
Porro, D, et al. (1995) "Development of Metabolically Engineered *Saccharomyces cerevisiae* Cells for the Production of Lactic Acid," Biotechnol Prog 11:294-8.
Porro, D, et al. (1999) "Replacement of a Metabolic Pathway for Large-Scale Production of Lactic Acid from Engineered Yeasts," Applied and Environmental Microbiology 65(9), 4211-5.
Pronk, J.T., et al. (1996) "Pyruvate Metabolism in *Saccharomyces cerevisiae*," Yeast 12:1607-1633.
Rane et al., "Reversal of the Nucleotide Specificity of Ketol Acid Reductoisomerase by Site-Directed Mutagenesis Identifies the NADPH Binding Site," Arch. Biochem. Biophys. 338(1) :83-89 (1997).
Salani, F and Bianchi, M. (2006) "Production of glucoamylase in pyruvate decarboxylase deletion mutants of the yeast Kluyveromyces lactis," Applied Microbiology and Biotechnology 69(5):564-72.

Seffernick et al., "Melamine Deaminase and Atrazine Chlorohydrolase: 98 Percent Identical but Functionally Different," J. Bacteriol. 183(8):2405-2410 (2001).
Seguin et al., "Overexpression of the yeast frataxin homolog (Yth1): Contrasting effects on iron-sulfur cluster assembly, heme synthesis and resistance to oxidative stress," Mitochondrion 9: 130-8 (2009).
Sergienko, et al., "Catalytic acid-base groups in yeast pyruvate decarboxylase. 2. Insights into the specific roles of D28 and E477 from the rates and stereospecificity of formation of carboligase side products," Biochemistry 40: 7369-7381 (2001).
Sergienko, et al., "Catalytic acid-base groups in yeast pyruvate decarboxylase. 3. A steady-state kinetic model consistent with the behavior of both wild-type and variant enzymes at all relevant pH values," Biochemistry 40: 7382-7403 (2001).
Sergienko, et al., "Yeast pyruvate decarboxylase tetramers can dissociate into dimers along two interfaces. Hybrids of low-activity D28A (or D28N) and E477Q variants, with substitution of adjacent active center acidic groups from different subunits, display restored activity," Biochemistry 41: 6164-6169 (2002).
Skory, "Lactic acid production by *Saccharomyces cerevisiae* expressing a Rhizopus oryzae lactate dehydrogenase gene," J. Ind. Microbial. Biotechnol. 30:22-27 (2003).
Smit, "Formation of amino acid derived cheese flavour compounds," Thesis Wageningen University, The Netherlands, 2004.
Smit, et al., "Identification, cloning, and characterization of a Lactococcus lactis branched-chain α-keto acid decarboxylase involved in flavor formation," Applied and Environmental Microbiology 71(1): 303-311 (Jan. 2005).
Stemmler et al., "Frataxin and Mitochondrial FeS Cluster Biogenesis," J. Biol. Chem., 285:26737-43 (2010).
Supplemental Expert Report of Corinne A. Michels, Ph.D., Oct. 24, 2012, *Butamax™ Advanced Biofuels LLC v. Gevo, Inc.*, USDC—District of Delaware, No. 1:11-cv-00054-SLR (Public Version).
Supplementary European Search Report, EP Appl. No. 10792562.0, 7 pages (dated Jan. 16, 2013).
U.S Appl. No. 61/058,970, Anthony et al., filed Jun. 5, 2008.
Van Maris, Aja, et al. (2004) "Directed Evolution of Pyruvate Decarboxylase-Negative *Saccharomyces cerevisiae*, Yielding a C2-Independent, Glucose-Tolerant, and Pyruvate-Hyperproducing Yeast," Applied and Environmental Microbiology 70(1):159-66.
Van Vleet et al., "Yeast metabolic engineering for hemicellulosic ethanol production," Curr. Opin. Biotechnol. 20(3) :300-306 (2009).
Vuralhan et al., "Physiological characterization of the ARO10-Dependent, Broad-Substrate-Specificity 2-Oxo Acid Decarboxylase Activity of *Saccharomyces cerevisiae*," Appl. Environ. Micro. 71(6):3276-3284, 2005.
Wang, Q, et al. (2005) "Metabolic engineering of Torulopsis glabrata for improved pyruvate production," Enzyme and Microbial Technology 36(5-6):832-9.
Witkowski et al., "Conversion of a β-Ketoacyl Synthase to a Malonyl Decarboxylase by Replacement of the Active-Site Cysteine with Glutamine," Biochem. 38:11643-11650 (1999).
Yonehara, T and Mirata, R. (1994) "Fermentative Production of Pyruvic Acid by Yeast," Baiosaiensu to Indasutori 52(7):567-70. (English Abstract).
Yoshimoto et al., "Genetic and physiological analysis of branched-chain alcohols and isoamyl acetate production in *Saccharomyces cerevisiae*," Appl. Microbiol. Biotechnol. 59: 501-508, 2002.
Yoshimoto et al., "Pyruvate Decarbosylase Encoded by the PDC1 Gene Contributes, at Least Partially, to the Decarboxylation of α-Ketoisocaproate for Isoamyl Alcohol Formation in *Saccharomyces cerevisiae*," J. Biosci. Bioeng. 92:83-85 (2001).
Zelle et al., "Malic Acid Production by *Saccharomyces cerevisiae*: Engineering of Pyruvate Carboxylation, Oxaloacetate Reduction, and Malate Export," Appl. Environ. Microbiol. 74(9):2766-2777 (2008).
Zhou et al., "Global analysis of gene transcription regulation in prokaryotes," Cell. Mol. Life Sci. 63(19-20):2260-2290 (2006).

\* cited by examiner

SEQUENCE LISTING

<160> NUMBER OF SEQ ID NOS: 78

<210> SEQ ID NO 1
<211> LENGTH: 4831
<212> TYPE: DNA
<213> ORGANISM: Artificial Sequence
<220> FEATURE:
<223> OTHER INFORMATION: Synthetic polynucleotide

<400> SEQUENCE: 1

```
gcttagttta catttctttc ccaagtttaa ttcaatttct tcaacaaaga tttagagagt       60
atacttgcgc cgtcatcata ctggctgcct ttccgtttca tcaataaata tatgtattct      120
ctaattaatt ttatgctcat aatatatcgg ttgcacgaga tggtcattcc gatggtttca      180
gactctagtt aaaagaagaa gctagatgct gataatattg atttcggatg ttactgattg      240
aatattttga gctattataa taatatcaac aaagaaaatt ttaacgtggg ttgattctta      300
ggtttaaaaa gacccatcgt atatctcacc aaatatcggt accgtattcg aaggataagg      360
actaacgact taatctctaa cttgtggtaa ctaaatttag tcctttatct acaatttctc      420
tatagagcat tcaacaaaga ttgtggtttt tatctatcaa gtattattcc attactatta      480
atgtacttat aaaattctgt atatgaagag tatcaagaaa actgtgactt ctccacatca      540
gtatagtaaa gccaacaaag gggatacctt tgcagttgta gcaactattg gcgtaaacgt      600
ttcaaatggg gtaaagaaa gaaataaaga gtatatcgtt catatatatc atttagaaat       660
caaatcacta aaattcgatt agttcttagc gttggtagca gcagtcaatt cgagctcata      720
gcttcaaaat gtttctactc cttttttact cttccagatt ttctcggact ccgcgcatcg      780
ccgtaccact tcaaaacacc caagcacagc atactaaatt tcccctcttt cttcctctag      840
ggtgtcgtta attcccgta ctaaaggttt ggaaaagaaa aaagagaccg cctcgtttct       900
ttttcttcgt cgaaaaaggc aataaaaatt tttatcacgt ttctttttct tgaaaattt       960 ttttttgatt tttttctctt tcgatgacct cccattgata tttaagttaa taaacggtct     1020
tcaatttctc aagtttcagt ttcattttc ttgttctatt acaacttttt ttacttcttg     1080
ctcattagaa agaaagcata gcaatctaat ctaagttttc tagtatgatt gaacaagatg     1140
gattgcacgc aggttctccg gccgcttggg tggagaggct attcggctat gactgggcac     1200
aacagacaat cggctgctct gatgccgccg tgttccggct gtcagcgcag gggcgcccgg     1260 ttcttttgt caagaccgac ctgtccggtg ccctgaatga actgcaggac gaggcagcgc      1320
ggctatcgtg gctggccacg acgggcgttc cttgcgcagc tgtgctcgac gttgtcactg     1380
aagcgggaag ggactggctg ctattgggcg aagtgccggg gcaggatctc ctgtcatctc     1440
accttgctcc tgccgagaaa gtatccatca tggctgatgc aatgcggcgg ctgcatacgc     1500
ttgatccggc tacctgccca ttcgaccacc aagcgaaaca tcgcatcgag cgagcacgta     1560
ctcggatgga agccggtctt gtcgatcagg atgatctgga cgaagagcat caggggctcg     1620
cgccagccga actgttcgcc aggctcaagg cgcgcatgcc cgacggcgag gatctcgtcg     1680
```

```
tgacccatgg cgatgcctgc ttgccgaata tcatggtgga aaatggccgc ttttctggat    1740
tcatcgactg tggccggctg ggtgtggcgg accgctatca ggacatagcg ttggctaccc    1800
gtgatattgc tgaagagctt ggcggcgaat gggctgaccg cttcctcgtg ctttacggta    1860
tcgccgctcc cgattcgcag cgcatcgcct tctatcgcct tcttgacgag ttcttctgaa    1920
ccggtagagt tctccgagaa caagcagagg ttcgagtgta ctcggatcag aagttacaag    1980
ttgatcgttt atatataaac tatacagaga tgttagagtg taatggcatt gcgtaagctt    2040
ggcgtaatca tggtcatagc tgtttcctgt gtgaaattgt tatccgctca caattccaca    2100
caacatacga gccggaagca taaagtgtaa agcctgggt gcctaatgag tgagctaact     2160
cacattaatt gcgttgcgct cactgcccgc tttccagtcg gaaacctgt cgtgccagct     2220 gcattaatga atcggccaac gcgcggggag aggcggtttg cgtattggc gctcttccgc     2280 ttcctcgctc actgactcgc tgcgctcggt cgttcggctg cggcgagcgg tatcagctca    2340
ctcaaaggcg gtaatacggt tatccacaga atcaggggat aacgcaggaa agaacatgtg    2400
agcaaaaggc cagcaaaagg ccaggaaccg taaaaaggcc gcgttgctgg cgttttccha    2460
taggctccgc ccccctgacg agcatcacaa aaatcgacgc tcaagtcaga ggtggcgaaa    2520
cccgacagga ctataaagat accaggcgtt ccccctgga agctcctcg tgcgctctcc      2580 tgttccgacc ctgccgctta ccggatacct gtccgccttt ctcccttcgg aagcgtggc     2640 gctttctcat agctcacgct gtaggtatct cagttcggtg taggtcgttc gctccaagct    2700
gggctgtgtg cacgaacccc ccgttcagcc cgaccgctgc gccttatccg gtaactatcg    2760
tcttgagtcc aacccggtaa gacacgactt atcgccactg gcagcagcca ctggtaacag    2820
gattagcaga gcgaggtatg taggcggtgc tacagagttc ttgaagtggt ggcctaacta    2880
cggctacact agaaggacag tatttggtat ctgcgctctg ctgaagccag ttaccttcgg    2940
aaaaagagtt ggtagctctt gatccggcaa acaaaccacc gctggtagcg gtggttttt    3000 tgtttgcaag cagcagatta cgcgcagaaa aaaaggatct caagaagatc ctttgatctt    3060
ttctacgggg tctgacgctc agtggaacga aaactcacgt taagggattt tggtcatgag    3120
attatcaaaa aggatcttca cctagatcct tttaaattaa aaatgaagtt ttaaatcaat    3180
ctaaagtata tatgagtaaa cttggtctga cagttaccaa tgcttaatca gtgaggcacc    3240
tatctcagcg atctgtctat ttcgttcatc catagttgcc tgactccccg tcgtgtagat    3300
aactacgata cgggagggct taccatctgg ccccagtgct gcaatgatac cgcgagaccc    3360
acgctcaccg gctccagatt tatcagcaat aaaccagcca gccggaaggg ccgagcgcag    3420
aagtggtcct gcaactttat ccgcctccat ccagtctatt aattgttgcc gggaagctag    3480
agtaagtagt tcgccagtta atagtttgcg caacgttgtt gccattgcta caggcatcgt    3540
ggtgtcacgc tcgtcgtttg gtatggcttc attcagctcc ggttcccaac gatcaaggcg    3600
agttacatga tcccccatgt tgtgcaaaaa agcggttagc tccttcggtc ctccgatcgt    3660
tgtcagaagt aagttggccg cagtgttatc actcatggtt atggcagcac tgcataattc    3720
tcttactgtc atgccatccg taagatgctt ttctgtgact ggtgagtact caaccaagtc    3780
attctgagaa tagtgtatgc ggcgaccgag ttgctcttgc ccggcgtcaa tacgggataa    3840
taccgcgcca catagcagaa ctttaaaagt gctcatcatt ggaaaacgtt cttcggggcg    3900
aaaactctca aggatcttac cgctgttgag atccagttcg atgtaaccca ctcgtgcacc    3960
caactgatct tcagcatctt ttactttcac cagcgtttct gggtgagcaa aaacaggaag    4020
gcaaaatgcc gcaaaaaagg gaataagggc gacacggaaa tgttgaatac tcatactctt    4080
```

```
ccttttcaa tattattgaa gcatttatca gggttattgt ctcatgagcg gatacatatt      4140
tgaatgtatt tagaaaaata aacaaatagg ggttccgcgc acatttcccc gaaaagtgcc      4200
acctgacgtc acctggtaga ccaaagatgg tttgaacttc gacttgcttt aatctttcga      4260
acaagtaacg acctaatgta atttcagaca ttgtaattta agttggtttt gagttgtagt      4320
tttatcctta atattaatag ttaatactat aatatgtttg gctttagtgg atggttttg      4380 aggtaatcaa aagtatataa ttaagattat gattaagaca tgatgggaaa ctctagccat      4440
tacagataat catgcccatg tatttatact ttatctgagt taactaaaaa aaatagaaag      4500
gtcatattca ccacccagcc agccctgcct ctcacctcac tctcccccct taatggataa      4560
ttgacacaag tggtactact attccaacct taagatattc atgggccaat actacgtata      4620
caccttaaaa ggttgaatct tttcacaaat attgcataat ctatcccatg gttctacata      4680
gcaaatacag aatatgcaaa atacaggaca cgcacaaggg ccagcaatgg ttagctaatt      4740
tgaataattt ccaataccat gaaattatcc caccttttac cttggttgac tctcatttcc      4800
gattttctat accacagaaa ccgcacgtgt c                                    4831

<210> SEQ ID NO 2
<211> LENGTH: 7441
<212> TYPE: DNA
<213> ORGANISM: Artificial Sequence
<220> FEATURE:
<223> OTHER INFORMATION: Synthetic polynucleotide

<400> SEQUENCE: 2
ccagttaact gtgggaatac tcaggtatcg taagatgcaa gagttcgaat ctcttagcaa        60
ccattatttt tttcctcaac ataacgagaa cacacagggg cgctatcgca cagaatcaaa       120
ttcgatgact ggaaattttt tgttaatttc agaggtcgcc tgacgcatat acctttttca       180
actgaaaaat tgggagaaaa aggaaaggtg agagcgccgg aaccggcttt tcatatagaa       240
tagagaagcg ttcatgacta aatgcttgca tcacaatact tgaagttgac aatattattt       300
aaggacctat tgttttttcc aataggtggt tagcaatcgt cttactttct aacttttctt       360 acctttaca tttcagcaat atatatatat atatttcaag gatataccat tctaatgtct       420 gccctaaga agatcgtcgt tttgccaggt gaccacgttg gtcaagaaat cacagccgaa       480
gccattaagg ttcttaaagc tatttctgat gttcgttcca atgtcaagtt cgatttcgaa       540
aatcatttaa ttggtggtgc tgctatcgat gctacaggtg ttccacttcc agatgaggcg       600
ctggaagcct ccaagaaggc tgatgccgtt tgttaggtg ctgtgggtgg tcctaaatgg       660
ggtaccggta gtgttagacc tgaacaaggt ttactaaaaa tccgtaaaga acttcaattg       720
tacgccaact taagaccatg taactttgca tccgactctc ttttagactt atctccaatc       780
aagccacaat ttgctaaagg tactgacttc gttgttgtca gagaattagt gggaggtatt       840
tactttggta agagaaagga agacgatggt gatggtgtcg cttgggatag tgaacaatac       900
accgttccag aagtgcaaag aatcacaaga atggccgctt tcatggccct acaacatgag       960
ccaccattgc ctatttggtc cttggataaa gctaatgttt tggcctcttc aagattatgg      1020
agaaaaactg tggaggaaac catcaagaac gaattcccta cattgaaggt tcaacatcaa      1080
ttgattgatt ctgccgccat gatcctagtt aagaacccaa cccacctaaa tggtattata      1140
atcaccagca acatgtttgg tgatatcatc tccgatgaag cctccgttat cccaggttcc      1200 ttgggttttgt tgccatctgc gtccttggcc tctttgccag acaagaacac cgcatttggt      1260
```

```
ttgtacgaac catgccacgg ttctgctcca gatttgccaa agaataaggt caaccctatc    1320
gccactatct tgtctgctgc aatgatgttg aaattgtcat tgaacttgcc tgaagaaggt    1380
aaggccattg aagatgcagt taaaaaggtt ttggatgcag gtatcagaac tggtgattta    1440
ggtggttcca acagtaccac cgaagtcggt gatgctgtcg ccgaagaagt taagaaaatc    1500
cttgcttaaa aagattctct ttttttatga tatttgtaca taaactttat aaatgaaatt    1560
cataatagaa acgacacgaa attacaaaat ggaatatgtt cataggggtag acgaaactat    1620 atacgcaatc tacatacatt tatcaagaag gagaaaaagg aggatgtaaa ggaatacagg    1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860
aaaacactca atgacctgac catttgatgg agttgccggc gatcacagcg gacggtggtg    1920
gcatgatggg gcttgcgatg ctatgttgt ttgttttgtg atgatgtata ttattattga    1980
aaaacgatat cagacatttg tctgataatg cttcattatc agacaaatgt ctgatatcgt    2040
ttggagaaaa agaaaaggaa aacaaactaa atatctacta taccactg tattttatac     2100 taatgacttt ctacgcctag tgtcaccctc tcgtgtaccc attgaccctg tatcggcgcg    2160
ttgcctcgcg ttcctgtacc atatattttt gtttatttag gtattaaaat ttactttcct    2220
catacaaata ttaaattcac caaacttctc aaaaactaat tattcgtagt tacaaactct    2280
attttacaat cacgtttatt caaccattct acatccaata accaaaatgc ccatgtacct    2340
ctcagcgaag tccaacggta ctgtccaata ttctcattaa atagtctttc atctatatat    2400
cagaaggtaa ttataattag agatttcgaa tcattaccgt gccgattcgc acgctgcaac    2460
ggcatgcatc actaatgaaa agcatacgac gcctgcgtct gacatgcact cattctgaag    2520
aagattctgg gcgcgtttcg ttctcgtttt cctctgtata ttgtactctg gtggacaatt    2580
tgaacataac gtctttcacc tcgccattct caataatggg ttccaattct atccaggtag    2640
cggttaattg acggtgctta agccgtatgc tcactctaac gctaccgttg tccaaacaac    2700 ggacccctt tgtgacgggtg taagacccat catgaagtaa aacatctcta acggtatgga    2760
aaagagtggt acggtcaagt ttcctggcac gagtcaattt tccctcttcg tgtagatcgg    2820
taccggccgc aaattaaagc cttcgagcgt cccaaaacct tctcaagcaa ggttttcagt    2880
ataatgttac atgcgtacac gcgtctgtac agaaaaaaaa gaaaaatttg aaatataaat    2940
aacgttctta atactaacat aactataaaa aaataaatag ggacctagac ttcaggttgt    3000
ctaactcctt cctttcggt tagagcggat gtggggggag ggcgtgaatg taagcgtgac     3060
ataactaatt acatgactcg agcggccgcg gatcctcaat aaaactcttc aggcaataat    3120
ttttctgcta atttaatgtt atcagaatag tccaaaggaa cgtcaattac tactggtcca    3180
gtagtatctg ggattgattt aagaatttca gcaagttctt ctttgctgtg tgcacggtaa    3240
ccttttgctc ccattgcttc agcatatttt acgtaatcaa catagccaaa atcaacggct    3300
gctgaacgac catatttcat ttcttcttgg aatttaacca tatcataatg gccgtcattc    3360
cagataattt gaacgattgg aagattcaaa cgtacagctg tttccaactc ttgccctgtg    3420
aaaaggaagc ctccatcacc agagtgtgaa taaactttt tacctgggcg caacaatgcg     3480
gctgtaattg cccaaggaag tgcaactcca agtgtttgca ttccgtttga gaagaggaga    3540
tgacgtggtt cgtatgattt gaatgacgt gccatccaaa tgtagagtga acctacgtca     3600
acggttactg tttcatcatc tttaacgatt tcttggaaag tgctgaccaa atcaagaggg    3660
```

-continued

| | | | | |
|---|---|---|---|---|
| tgcattctac | cttcttcagt | attttcagta | tcaaattcgt | gttgctcagc | aacttcatga | 3720 |
| aggccatcga | gataatcttt | tgttcctttt | ggaattttgt | atccacgaac | agctggtaaa | 3780 |
| agattatcca | atgttgctgc | gatatcacca | attaattcac | gttctggttg | gtagtaagta | 3840 |
| tcaatttcag | caatggcatt | atcaataacg | ataattcgac | tatcaatttc | tgcattccag | 3900 |
| ttacgagctt | catattcaat | tgggtcataa | ccaacagcaa | taacaaggtc | agaacgtttc | 3960 |
| agaagcatat | ctcctggttg | attgcggaaa | agaccgatac | gtccataaaa | agtatgttct | 4020 |
| aaatcatgtg | aaataacccc | tgcaccttgg | aatgtttcaa | cgacaggaat | attaacatga | 4080 |
| gttaatagat | tacgcaatga | tgaagcgact | ttagcatctg | aagcaccagc | tccaaccaaa | 4140 |
| attactggca | atacagcatt | tttaattgct | tgtgctaaat | aattaatgtc | atcaatagag | 4200 |
| gcattcccca | ttttagggtc | tgaaagtggt | tgaatggcct | tgattgatac | ttcggcatcc | 4260 |
| gttacatctt | ggggattga | taagaaagtt | gcacctggat | gtcctgattt | tgcaatacga | 4320 |
| taagcgttgg | caattgattc | agaaagtgta | tcagggtcaa | gaacttctgc | tgaatatttt | 4380 |
| gttgctgatt | gcatcattcc | agcattatcc | attgattggt | gcgcacgttt | aagacggtca | 4440 |
| cttcgtttaa | cttgtccacc | gatagccaaa | atagcatcac | cttctgaagt | cgcggtcaaa | 4500 |
| agcggagtcg | caaggtttga | tacaccaggc | ccactcgtaa | caactactac | accaggttcg | 4560 |
| ccagtcaaac | gaccaacagc | ttgagccatg | aaagcagctc | cttgctcatg | acgagtcacg | 4620 |
| accatttgag | ggccttcttc | attttctaat | aaatcaaaaa | cccggtcaat | ttttgctcct | 4680 |
| ggaatcccaa | atacatactt | cactttatgg | ttaatcaaac | tatcgacaac | caagttcgcc | 4740 |
| ccaaattgtt | tctcagacat | gtcgacaccg | atatacctgt | atgtgtcacc | accaatgtat | 4800 |
| ctataagtat | ccatgctagt | tctagaaaac | ttagattaga | ttgctatgct | ttcttctaa | 4860 |
| tgagcaagaa | gtaaaaaaag | ttgtaataga | acaagaaaaa | tgaaactgaa | acttgagaaa | 4920 |
| ttgaagaccg | tttattaact | taaatatcaa | tgggaggtca | tcgaaagaga | aaaaaatcaa | 4980 |
| aaaaaaatt | ttcaagaaaa | agaaacgtga | taaaaatttt | tattgccttt | ttcgacgaag | 5040 |
| aaaaagaaac | gaggcggtct | cttttttctt | ttccaaacct | ttagtacggg | taattaacga | 5100 |
| caccctagag | gaagaaagag | gggaaattta | gtatgctgtg | cttgggtgtt | ttgaagtggt | 5160 |
| acggcgatgc | gcggagtccg | agaaaatctg | gaagagtaaa | aaaggagtag | aaacattttg | 5220 |
| aagctatgag | ctccagcttt | tgttcccttt | agtgagggtt | aattgcgcgc | ttggcgtaat | 5280 |
| catggtcata | gctgtttcct | gtgtgaaatt | gttatccgct | cacaattcca | cacaacatag | 5340 |
| gagccggaag | cataaagtgt | aaagcctggg | gtgcctaatg | agtgaggtaa | ctcacattaa | 5400 |
| ttgcgttgcg | ctcactgccc | gctttccagt | cgggaaacct | gtcgtgccag | ctgcattaat | 5460 |
| gaatcggcca | acgcgcgggg | agaggcggtt | tgcgtattgg | gcgctcttcc | gcttcctcgc | 5520 |
| tcactgactc | gctgcgctcg | gtcgttcggc | tgcggcgagc | ggtatcagct | cactcaaagg | 5580 |
| cggtaatacg | gttatccaca | gaatcagggg | ataacgcagg | aaagaacatg | tgagcaaaag | 5640 |
| gccagcaaaa | ggccaggaac | cgtaaaaagg | ccgcgttgct | ggcgtttttc | cataggctcc | 5700 |
| gcccccctga | cgagcatcac | aaaaatcgac | gctcaagtca | gaggtggcga | aacccgacag | 5760 |
| gactataaag | ataccaggcg | tttccccctg | gaagctccct | cgtgcgctct | cctgttccga | 5820 |
| ccctgccgct | taccggatac | ctgtccgcct | ttctccctc | gggaagcgtg | gcgctttctc | 5880 |
| atagctcacg | ctgtaggtat | ctcagttcgg | tgtaggtcgt | tcgctccaag | ctgggctgtg | 5940 |
| tgcacgaacc | ccccgttcag | cccgaccgct | gcgccttatc | cggtaactat | cgtcttgagt | 6000 |

| | |
|---|---|
| ccaacccggt aagacacgac ttatcgccac tggcagcagc cactggtaac aggattagca | 6060 |
| gagcgaggta tgtaggcggt gctacagagt tcttgaagtg gtggcctaac tacggctaca | 6120 |
| ctagaaggac agtatttggt atctgcgctc tgctgaagcc agttaccttc ggaaaaagag | 6180 |
| ttggtagctc ttgatccggc aaacaaacca ccgctggtag cggtggtttt tttgtttgca | 6240 |
| agcagcagat tacgcgcaga aaaaaggat ctcaagaaga tcctttgatc ttttctacgg | 6300 |
| ggtctgacgc tcagtggaac gaaaactcac gttaagggat tttggtcatg agattatcaa | 6360 |
| aaaggatctt cacctagatc cttttaaatt aaaaatgaag ttttaaatca atctaaagta | 6420 |
| tatatgagta aacttggtct gacagttacc aatgcttaat cagtgaggca cctatctcag | 6480 |
| cgatctgtct atttcgttca tccatagttg cctgactccc cgtcgtgtag ataactacga | 6540 |
| tacgggaggg cttaccatct ggccccagtg ctgcaatgat accgcgagac ccacgctcac | 6600 |
| cggctccaga tttatcagca ataaaccagc cagccggaag ggccgagcgc agaagtggtc | 6660 |
| ctgcaacttt atccgcctcc atccagtcta ttaattgttg ccgggaagct agagtaagta | 6720 |
| gttcgccagt taatagtttg cgcaacgttg ttgccattgc tacaggcatc gtggtgtcac | 6780 |
| gctcgtcgtt tggtatggct tcattcagct ccggttccca acgatcaagg cgagttacat | 6840 |
| gatccccat gttgtgcaaa aaagcggtta gctccttcgg tcctccgatc gttgtcagaa | 6900 |
| gtaagttggc cgcagtgtta tcactcatgg ttatggcagc actgcataat tctcttactg | 6960 |
| tcatgccatc cgtaagatgc ttttctgtga ctggtgagta ctcaaccaag tcattctgag | 7020 |
| aatagtgtat gcggcgaccg agttgctctt gcccggcgtc aatacgggat aataccgcgc | 7080 |
| cacatagcag aactttaaaa gtgctcatca ttggaaaacg ttcttcgggg cgaaaactct | 7140 |
| caaggatctt accgctgttg agatccagtt cgatgtaacc cactcgtgca cccaactgat | 7200 |
| cttcagcatc ttttactttc accagcgttt ctgggtgagc aaaaacagga aggcaaaatg | 7260 |
| ccgcaaaaaa gggaataagg gcgacacgga aatgttgaat actcatactc ttcctttttc | 7320 |
| aatattattg aagcatttat cagggttatt gtctcatgag cggatacata tttgaatgta | 7380 |
| tttagaaaaa taaacaaata ggggttccgc gcacatttcc ccgaaaagtg ccacctgacg | 7440 |
| t | 7441 |

<210> SEQ ID NO 3
<211> LENGTH: 8949
<212> TYPE: DNA
<213> ORGANISM: Artificial Sequence
<220> FEATURE:
<223> OTHER INFORMATION: Synthetic polynucleotide

<400> SEQUENCE: 3

| | |
|---|---|
| caggcaagtg cacaaacaat acttaaataa atactactca gtaataacct atttcttagc | 60 |
| attttgacg aaatttgcta ttttgttaga gtctttaca ccatttgtct ccacacctcc | 120 |
| gcttacatca acaccaataa cgccatttaa tctaagcgca tcaccaacat ttctggcgt | 180 |
| cagtccacca gctaacataa aatgtaagct ttcggggctc tcttgccttc caacccagtc | 240 |
| agaaatcgag ttccaatcca aaagttcacc tgtcccacct gcttctgaat caacaagggg | 300 |
| aataaacgaa tgaggtttct gtgaagctgc actgagtagt atgttgcagt cttttggaaa | 360 |
| tacgagtctt ttaataactg gcaaaccgag gaactcttgg tattcttgcc acgactcatc | 420 |
| tccatgcagt tggacgatat caatgccgta atcattgacc agagccaaaa catcctcctt | 480 |
| aggttgatta cgaaacacgc caaccaagta tttcggagtg cctgaactat ttttatatgc | 540 |
| ttttacaaga cttgaaattt tccttgcaat aaccgggtca attgttctct ttctattggg | 600 |

-continued

```
cacacatata ataccagca agtcagcatc ggaatctaga gcacattctg cggcctctgt    660
gctctgcaag ccgcaaactt tcaccaatgg accagaacta cctgtgaaat taataacaga   720
catactccaa gctgcctttg tgtgcttaat cacgtatact cacgtgctca atagtcacca   780
atgccctccc tcttggccct ctccttttct tttttcgacc gaattaattc ttaatcggca   840
aaaaaagaaa agctccggat caagattgta cgtaaggtga caagctattt ttcaataaag   900
aatatcttcc actactgcca tctggcgtca taactgcaaa gtacacatat attacgatgc   960
tgtctattaa atgcttccta tattatatat atagtaatgt cgttgacgtc gccggcgatc   1020
acagcggacg gtggtggcat gatgggggctt gcgatgctat gtttgtttgt tttgtgatga  1080
tgtatattat tattgaaaaa cgatatcaga catttgtctg ataatgcttc attatcagac   1140
aaatgtctga tatcgtttgg agaaaaagaa aaggaaaaca aactaaatat ctactatata   1200
ccactgtatt ttatactaat gactttctac gcctagtgtc accctctcgt gtacccattg   1260
accctgtatc ggcgcgttgc ctcgcgttcc tgtaccatat attttttgttt atttaggtat  1320 taaaatttac tttcctcata caaatattaa attcaccaaa cttctcaaaa actaattatt   1380
cgtagttaca aactctattt tacaatcacg tttattcaac cattctacat ccaataacca   1440
aaatgcccat gtacctctca gcgaagtcca acggtactgt ccaatattct cattaaatag   1500
tctttcatct atatatcaga aggtaattat aattagagat ttcgaatcat taccgtgccg   1560
attcgcacgc tgcaacggca tgcatcacta atgaaaagca tacgacgcct gcgtctgaca   1620
tgcactcatt ctgaagaaga ttctgggcgc gtttcgttct cgtttttcctc tgtatattgt  1680 actctggtgg acaatttgaa cataacgtct ttcacctcgc cattctcaat aatgggttcc   1740
aattctatcc aggtagcggt taattgacgg tgcttaagcc gtatgctcac tctaacgcta   1800
ccgttgtcca acaacggac ccctttgtga cgggtgtaag acccatcatg aagtaaaaca    1860
tctctaacgg tatggaaaag agtggtacgg tcaagtttcc tggcacgagt caattttccc   1920
tcttcgtgta gatcggtacc ggccgcaaat taaagccttc gagcgtccca aaaccttctc   1980
aagcaaggtt ttcagtataa tgttacatgc gtacacgcgt ctgtacagaa aaaaaagaaa   2040
aatttgaaat ataaataacg ttcttaatac taacataact ataaaaaaat aaataggggac  2100 ctagacttca ggttgtctaa ctccttcctt ttcggttaga gcggatgtgg ggggagggcg   2160
tgaatgtaag cgtgacataa ctaattacat gactcgagcg gccgcggatc cttaacccgc   2220
aacagcaata cgtttcatat ctgtcatata gccgcgcagt ttcttaccta cctgctcaat   2280
cgcatggctg cgaatcgctt cgttcacatc acgcagttgc ccgttatcta ccgcgccttc   2340
cggaatagct ttacccaggt cgcccggttg cagctctgcc ataaacggtt tcagcaacgg   2400
cacacaagcg taagagaaca gatagttacc gtactcagcg gtatcagaga taaccacgtt   2460
catttcgtac agacgcttac gggcgatggt gttggcaatc agcggcagct cgtgcagtga   2520
ttcataatat gcagactctt caatgatgcc ggaatcgacc atggtttcga acgccagttc   2580
aacgcccgct ttcaccatcg caatcatcag tacgccttta tcgaagtact cctgctcgcc   2640
gattttgcct tcatactgcg cgcggtttc aaacgcggtt ttgccggtct cttcacgcca    2700
ggtcagcagt ttcttatcat cgttggccca gtccgccatc ataccggaag agaattcgcc   2760
ggagatgatg tcgtccatat gtttctggaa caggggtgcc atgatctctt tcagctgttc   2820
agaaagcgca taagcacgca gtttcgccgg gttagagaga cggtccatca tcagggtgat   2880
gccgccctgt ttcagtgctt cggtgatggt ttcccaaccg aactgaatca gttttttctgc  2940
```

```
gtatgctgga tcggtacctt cttccaccag cttgtcgaag cacagcagag agccagcctg    3000
caacataccg cacaggatgg tttgctcgcc catcaggtca gatttcactt ccgcaacgaa    3060
ggacgattcc agcacacccg cacggtgacc accggttgca gccgcccagg ctttggcaat    3120
cgccatgcct tcgcctttcg gatcgttttc cgggtgaacg gcaatcagcg tcggtacgcc    3180
gaacccacgt ttgtactctt cacgcacttc ggtgcctggg catttcggcg caaccatcac    3240
tacggtgata tctttacgga tctgctcgcc cacttcgacg atgttgaaac cgtgcgagta    3300
gcccagcgcc gcgccgtctt tcatcagtgg ctgtacggtg cgcactacat cagagtgctg    3360
cttgtccggc gtcaggttaa tcaccagatc cgcctgtggg atcagttctt cgtaagtacc    3420
cactttaaaa ccattttcgg tcgctttacg ccaggacgcg cgcttctcgg caatcgcttc    3480
tttacgcaga gcgtaggaga tatcgagacc agaatcacgc atgttcaggc cctggttcag    3540
accctgtgcg ccacagccga cgatgactac tttttttaccc tgaaggtagc tcgcgccatc    3600
ggcgaattca tcgcggccca taaagcgaca tttgcccagc tgtgccagct gctggcgcag    3660
attcagtgta ttgaagtagt tagccatgtc gacaccatct tcttctgaga tgagtttttg    3720
ttccatgcta gttctagaat ccgtcgaaac taagttctgg tgttttaaaa ctaaaaaaaa    3780
gactaactat aaaagtagaa tttaagaagt ttaagaaata gatttacaga attacaatca    3840
atacctaccg tctttatata cttattagtc aagtagggga ataatttcag ggaactggtt    3900
tcaacctttt ttttcagctt tttccaaatc agagagagca gaaggtaata gaaggtgtaa    3960
gaaaatgaga tagatacatg cgtgggtcaa ttgccttgtg tcatcattta ctccaggcag    4020
gttgcatcac tccattgagg ttgtgcccgt tttttgcctg tttgtgcccc tgttctctgt    4080
agttgcgcta agagaatgga cctatgaact gatggttggt gaagaaaaca atattttggt    4140
gctgggattc ttttttttttc tggatgccag cttaaaaagc gggctccatt atatttagtg    4200
gatgccagga ataaactgtt cacccagaca cctacgatgt tatatattct gtgtaacccg    4260
cccctatttt tgggcatgta cggggttacag cagaattaaa aggctaattt tttgactaaa    4320
taaagttagg aaaatcacta ctattaatta tttacgtatt ctttgaaatg gcgagtattg    4380
ataatgataa actgagctag atctgggccg cggatcctta accccccagt ttcgatttat    4440
cgcgcaccgc gcctttgtcg gcgctggttg ccaggctggc ataagcacgc agggcaaagg    4500
agacctgacg ttcacgattt ttcggcgtcc aggctttgtc acctcgagcg tcctgcgctt    4560
cacgacgcgc cgccagttcg gcatcgctta cctgtaactg aatgccacgg ttcgggatgt    4620
cgatagcgat caggtcacca tcttcaatca ggccaatgct gccgccgctt gccgcttccg    4680
gtgagacgtg gccgatggaa agaccagagg tgccaccaga gaaacgaccg tcggtgatca    4740
gcgcacaggc tttgccgaga cccattgatt tcaggaagct ggttgggtag agcatttcct    4800
gcatccccgg accgcctttc gggccttcat agcgaattac taccacatct ccggcgacaa    4860
ctttaccgcc gagaatcgct tctaccgcat cgtcctggct ttcgtacact ttcgccgggc    4920
cggtgaattt gaggatgctg tcatcgacgc ctgccgtttt cacgatgcag ccgttttccg    4980
caaagttacc gtagagcacc gccaggccgc cgtctttgct gtaggcgtgt ccagcgagc    5040 ggatacagcc attggcgcga tcgtcgtcca gcgtatccca acggcaatct gcgagaatg    5100 cctgtgtggt acgaatgcct gcaggacctg cgcggaacat atttttttacc gcgtcatcct    5160 gggtcagcat aacgtcgtat tgttccagcg tttgcggcaa cgtcaggcca agtacgtttt    5220
tcacatcacg gttcagtaac cccgcgcgat ccagttcgcc gagaataccg ataacaccac    5280
cagcacggtg aacatcttcc atatggtatt tctgggtgct cggcgcaact ttacacagct    5340
```

```
gtggaacctt gcgggaaagc ttatcgatat cactcatggt gaagtcgatt tccgcttcct   5400
gcgccgccgc cagcaggtga agtacggtgt tagtcgatcc acccatcgcg atatccagcg   5460
tcatggcgtt ttcaaacgcc gccttactgg cgatattacg cggcagtgca ctttcgtcgt   5520
tttgctcgta ataacgtttg gtcaattcaa caatgcgttt accagcatta aggaacagct   5580
gcttacggtc ggcgtgggtt gccagcagcg agccgttgcc cggctgcgac aggcccagcg   5640
cttcggtcag gcagttcatt gagttagcgg taaacatccc ggagcaggaa ccgcaggtcg   5700
gacacgcgga acgttcaacc tgatcgctct gggagtcaga tactttcggg tctgcgccct   5760
ggatcatcgc atcaaccaga tcgagcttga tgatctgatc ggaaagtttg gttttcccgg   5820
cctccatcgg gccgccggaa acaaagatca ccggaatatt caggcgcagg aagccatca    5880 gcatccccgg ggtgattttg tcgcagttag agatgcagac catggcgtcg gcgcagtggg   5940
cgttgaccat atactcaacg gaatcagcga tcagttcgcg agatggcagt gaataaagca   6000
tccccccgtg gcccatggca atcccatcat ccaccgcaat ggtgttgaac tctttggcaa   6060
cgccgccagc cgcttcaatt tgttcggcga ccagtttacc gagatcgcgc agatggacgt   6120
gacccggtac aaattgggtg aacgagttca caaccgcgat aatcggctta ccgaaatcgg   6180
cgtcggtcat tccggtggcg cgccacagcg cacgagcacc cgccatatta cgaccatgag   6240
tggtggtggc ggaacggtac ttaggcatgt cgacaccgat atacctgtat gtgtcaccac   6300
caatgtatct ataagtatcc atgctagttc tagaaaactt agattagatt gctatgcttt   6360
ctttctaatg agcaagaagt aaaaaaagtt gtaatagaac aagaaaaatg aaactgaaac   6420
ttgagaaatt gaagaccgtt tattaactta aatatcaatg ggaggtcatc gaaagagaaa   6480
aaaatcaaaa aaaaattttt caagaaaaag aaacgtgata aaaattttta ttgccttttt   6540
cgacgaagaa aaagaaacga ggcggtctct tttttctttt ccaaacccttt agtacgggta   6600 attaacgaca ccctagagga agaaagaggg gaaatttagt atgctgtgct tgggtgtttt   6660
gaagtggtac ggcgatgcgc ggagtccgag aaaatctgga agagtaaaaa aggagtagaa   6720
acattttgaa gctatgagct ccagcttttt ttcccttttag tgagggttaa ttgcgcgctt   6780
ggcgtaatca tggtcatagc tgtttcctgt gtgaaattgt tatccgctca caattccaca   6840
caacatagga gccggaagca taaagtgtaa agcctgggt gcctaatgag tgaggtaact   6900
cacattaatt gcgttgcgct cactgcccgc tttccagtcg ggaaacctgt cgtgccagct   6960
gcattaatga atcggccaac gcgcgggag aggcggtttg cgtattgggc gctcttccgc   7020
ttcctcgctc actgactcgc tgcgctcggt cgttcggctg cggcgagcgg tatcagctca   7080
ctcaaaggcg gtaatacggt tatccacaga atcagggat aacgcaggaa agaacatgtg   7140
agcaaaaggc cagcaaaagg ccaggaaccg taaaaaggcc gcgttgctgg cgtttttcca   7200
taggctccgc cccctgacg agcatcacaa aaatcgacgc tcaagtcaga ggtggcgaaa   7260
cccgacagga ctataaagat accaggcgtt tccccctgga agctccctcg tgcgctctcc   7320
tgttccgacc ctgccgctta ccggatacct gtccgccttt ctcccttcgg gaagcgtggc   7380
gctttctcat agctcacgct gtaggtatct cagttcggtg taggtcgttc gctccaagct   7440
gggctgtgtg cacgaacccc ccgttcagcc cgaccgctgc gccttatccg gtaactatcg   7500
tcttgagtcc aacccggtaa gacacgactt atcgccactg gcagcagcca ctggtaacag   7560
gattagcaga gcgaggtatg taggcggtgc tacagagttc ttgaagtggt ggcctaacta   7620
cggctacact agaaggacag tatttggtat ctgcgctctg ctgaagccag ttaccttcgg   7680
```

| | |
|---|---:|
| aaaaagagtt ggtagctctt gatccggcaa acaaaccacc gctggtagcg gtggttttttt | 7740 |
| tgtttgcaag cagcagatta cgcgcagaaa aaaaggatct caagaagatc ctttgatctt | 7800 |
| ttctacgggg tctgacgctc agtggaacga aaactcacgt taagggattt tggtcatgag | 7860 |
| attatcaaaa aggatcttca cctagatcct tttaaattaa aaatgaagtt ttaaatcaat | 7920 |
| ctaaagtata tatgagtaaa cttggtctga cagttaccaa tgcttaatca gtgaggcacc | 7980 |
| tatctcagcg atctgtctat ttcgttcatc catagttgcc tgactccccg tcgtgtagat | 8040 |
| aactacgata cgggagggct taccatctgg ccccagtgct gcaatgatac cgcgagaccc | 8100 |
| acgctcaccg gctccagatt tatcagcaat aaaccagcca gccggaaggg ccgagcgcag | 8160 |
| aagtggtcct gcaactttat ccgcctccat ccagtctatt aattgttgcc gggaagctag | 8220 |
| agtaagtagt tcgccagtta atagtttgcg caacgttgtt gccattgcta caggcatcgt | 8280 |
| ggtgtcacgc tcgtcgtttg gtatggcttc attcagctcc ggttcccaac gatcaaggcg | 8340 |
| agttacatga tcccccatgt tgtgcaaaaa agcggttagc tccttcggtc ctccgatcgt | 8400 |
| tgtcagaagt aagttggccg cagtgttatc actcatggtt atggcagcac tgcataattc | 8460 |
| tcttactgtc atgccatccg taagatgctt ttctgtgact ggtgagtact caaccaagtc | 8520 |
| attctgagaa tagtgtatgc ggcgaccgag ttgctcttgc ccggcgtcaa tacgggataa | 8580 |
| taccgcgcca catagcagaa ctttaaaagt gctcatcatt ggaaaacgtt cttcggggcg | 8640 |
| aaaactctca aggatcttac cgctgttgag atccagttcg atgtaaccca ctcgtgcacc | 8700 |
| caactgatct tcagcatctt ttactttcac cagcgtttct gggtgagcaa aaacaggaag | 8760 |
| gcaaaatgcc gcaaaaaagg gaataagggc gacacggaaa tgttgaatac tcatactctt | 8820 |
| cctttttcaa tattattgaa gcatttatca gggttattgt ctcatgagcg gatacatatt | 8880 |
| tgaatgtatt tagaaaaata aacaataggg gttccgcgc acatttcccc gaaaagtgcc | 8940 |
| acctgacgt | 8949 |

<210> SEQ ID NO 4
<211> LENGTH: 8800
<212> TYPE: DNA
<213> ORGANISM: Artificial Sequence
<220> FEATURE:
<223> OTHER INFORMATION: Synthetic polynucleotide

<400> SEQUENCE: 4

| | |
|---|---:|
| ctgattggaa agaccattct gctttacttt tagagcatct tggtcttctg agctcattat | 60 |
| acctcaatca aaactgaaat taggtgcctg tcacggctct ttttttactg tacctgtgac | 120 |
| ttcctttctt atttccaagg atgctcatca caatacgctt ctagatctat tatgcattat | 180 |
| aattaatagt tgtagctaca aaaggtaaaa gaaagtccgg ggcaggcaac aatagaaatc | 240 |
| ggcaaaaaaa actacagaaa tactaagagc ttcttcccca ttcagtcatc gcatttcgaa | 300 |
| acaagagggg aatggctctg gctagggaac taaccaccat cgcctgactc tatgcactaa | 360 |
| ccacgtgact acatatatgt gatcgttttt aacatttttc aaaggctgtg tgtctggctg | 420 |
| tttccattaa ttttcactga ttaagcagtc atattgaatc tgagctcatc accaacaaga | 480 |
| aatactaccg taaagtgta aaagttcgtt taaatcattt gtaaactgga acagcaagag | 540 |
| gaagtatcat cagctagccc cataaactaa tcaaggagg atgtctacta agagttactc | 600 |
| ggaaagagca gctgctcata gaagtccagt tgctgccaag cttttaaact tgatggaaga | 660 |
| gaagaagtca aacttatgtg cttctcttga tgttcgtaaa acagcagagt tgttaagatt | 720 |
| agttgaggtt ttgggtccat atatctgtct attgaagaca catgtagata tcttggagga | 780 |

```
tttcagcttt gagaatacca ttgtgccgtt gaagcaatta gcagagaaac acaagttttt      840
gatatttgaa gacaggaagt ttgccgacat tgggaacact gttaaattac aatacacgtc      900
tggtgtatac cgtatcgccg aatggtctga tatcaccaat gcacacggtg tgactggtgc      960
gggcattgtt gctggtttga agcaaggtgc cgaggaagtt acgaaagaac ctagagggtt     1020
gttaatgctt gccgagttat cgtccaaggg gtctctagcg cacggtgaat acactcgtgg     1080
gaccgtggaa attgccaaga gtgataagga ctttgttatt ggatttattg ctcaaaacga     1140
tatgggtgga agagaagagg gctacgattg gttgatcatg acgccaggtg ttggtcttga     1200
tgacaaaggt gatgctttgg gacaacaata cagaactgtg gatgaagttg ttgccggtgg     1260
atcagacatc attattgttg gtagaggtct tttcgcaaag ggaagagatc ctgtagtgga     1320
aggtgagaga tacagaaagg cgggatggga cgcttacttg aagagagtag gcagatccgc     1380
ttaagagttc tccgagaaca agcagaggtt cgagtgtact cggatcagaa gttacaagtt     1440
gatcgtttat atataaacta tacagagatg ttagagtgta atggcattgc gtgccggcga     1500
tcacagcgga cggtggtggc atgatggggc ttgcgatgct atgtttgttt gttttgtgat     1560
gatgtatatt attattgaaa aacgatatca gacatttgtc tgataatgct tcattatcag     1620
acaaatgtct gatatcgttt ggagaaaaag aaaaggaaaa caaactaaat atctactata     1680
taccactgta ttttatacta atgactttct acgcctagtg tcaccctctc gtgtacccat     1740
tgaccctgta tcggcgcgtt gcctcgcgtt cctgtaccat atattttgt ttatttaggt      1800 attaaaattt actttcctca tacaaatatt aaattcacca aacttctcaa aaactaatta     1860
ttcgtagtta caaactctat tttacaatca cgtttattca accattctac atccaataac     1920
caaaatgccc atgtacctct cagcgaagtc caacggtact gtccaatatt ctcattaaat     1980
agtctttcat ctatatatca gaaggtaatt ataattagag atttcgaatc attaccgtgc     2040
cgattcgcac gctgcaacgg catgcatcac taatgaaaag catacgacgc ctgcgtctga     2100
catgcactca ttctgaagaa gattctgggc gcgtttcgtt ctcgttttcc tctgtatatt     2160
gtactctggt ggacaatttg aacataacgt ctttcacctc gccattctca ataatgggtt     2220
ccaattctat ccaggtagcg gttaattgac ggtgcttaag ccgtatgctc actctaacgc     2280
taccgttgtc caaacaacgg acccctttgt gacgggtgta agacccatca tgaagtaaaa     2340
catctctaac ggtatggaaa agagtggtac ggtcaagttt cctggcacga gtcaattttc     2400
cctcttcgtg tagatcggta ccggccgcaa attaaagcct tcgagcgtcc caaaaccttc     2460
tcaagcaagg ttttcagtat aatgttacat gcgtacacgc gtctgtacag aaaaaaaaga     2520
aaaatttgaa atataaataa cgttcttaat actaacataa ctataaaaaa ataaataggg     2580
acctagactt caggttgtct aactccttcc ttttcggtta gagcggatgt ggggggaggg     2640
cgtgaatgta agcgtgacat aactaattac atgactcgag cggccgccta tttatggaat     2700
ttcttatcat aatcgaccaa agtaaatctg tatttgacgt ctccgctttc catccttgta     2760
aaggcatggc tgacgccttc ttcgctgatc ggaagttttt ccacccatat tttgacattc     2820
ttttcggaaa ctaatttcaa tagttgttcg atttccttcc tagatccgat agcactgctt     2880
gagattgata ctcccattag gcccaacggt tttaaaacaa gcttttcatt aacttcagga     2940
gcagcaattg aaacgatgga gcctccaatc ttcataatct taacgatact gtcaaaatta     3000
actttcgaca aagatgatga gcaaacgaca agaaggtcca aagcgttaga gtattgttct     3060
gtccagcctt tatcctccaa catagcaata tagtgatcag caccgagttt catagaatcc     3120
```

```
tcccgcttgg agtggcctcg cgaaaacgca taaacctcgg ctcccatagc tttagccaac    3180
agaatcccca tatgcccaat accaccgatg ccaacaatac ctaccctctt acctggacca    3240
cagccatttc ttagtagtgg agagaaaact gtaataccac cacacaataa tggagcggct    3300
agcggacttg gaatattttc tggtatttga atagcaaagt gttcatgaag cctcacgtgg    3360
gaggcaaagc ctccttgtga atgtagccg tccttgtaag gagtccacat agtcaaaacg     3420
tggtcattgg tacagtattg ctcgttgtca cttttgcaac gttcacactc aaaacacgcc    3480
aaggcttggg caccaacacc aacacggtca ccgatttta ccccagtgtg gcacttggat     3540
ccaaccttca ccacgcggcc aattatttca tgtccaagga tttgattttc tgggactgga    3600
ccccaattac caacggctat atgaaaatca gatccgcaga taccacaggc ttcaatttca    3660
acatcaacgt catgatcgcc aaagggtttt gggtcaaaac tcactaattt aggatgcttc    3720
caatcctttg cgttggaaat accgatgccc tgaaattttt ctgggtaaag catgtcgaca    3780
ccatcttctt ctgagatgag ttttgttcc atgctagttc tagaatccgt cgaaactaag     3840
ttctggtgtt ttaaaactaa aaaaaagact aactataaaa gtagaattta agaagtttaa    3900
gaaatagatt tacagaatta caatcaatac ctaccgtctt tatatactta ttagtcaagt    3960
aggggaataa tttcagggaa ctggtttcaa cctttttttt cagcttttc caaatcagag     4020 agagcagaag gtaatagaag gtgtaagaaa atgagataga tacatgcgtg ggtcaattgc    4080
cttgtgtcat catttactcc aggcaggttg catcactcca ttgaggttgt gcccgttttt    4140
tgcctgtttg tgcccctgtt ctctgtagtt gcgctaagag aatggaccta tgaactgatg    4200
gttggtgaag aaaacaatat tttggtgctg ggattctttt tttttctgga tgccagctta    4260
aaaagcgggc tccattatat ttagtggatg ccaggaataa actgttcacc cagacaccta    4320
cgatgttata tattctgtgt aacccgcccc ctattttggg catgtacggg ttacagcaga    4380
attaaaaggc taattttttg actaaataaa gttaggaaaa tcactactat taattattta    4440
cgtattcttt gaaatggcga gtattgataa tgataaactg aggatcctta ggatttattc    4500
tgttcagcaa acagcttgcc cattttcttc agtaccttcg gtgcgccttc tttcgccagg    4560
atcagttcga tccagtacat acggttcgga tcggcctggg cctctttcat cacgctcaca    4620
aattcgtttt cggtacgcac aattttagac acaacacggt cctcagttgc gccgaaggac    4680
tccggcagtt tagagtagtt ccacataggg atatcgttgt aagactggtt cggaccgtgg    4740
atctcacgct caacggtgta gccgtcattg ttaataatga agcaaatcgg gttgatcttt    4800
tcacgaattg ccagacccag ttcctgtacg gtcagctgca gggaaccgtc accgatgaac    4860
agcagatgac gagattcttt atcagcgatc tgagagccca gcgctgccgg gaaagtatag    4920
ccaatgctac cccacagcgg ctgaccgata aaatggcttt tggatttcag aaagatagaa    4980
gacgcgccga aaagctcgt accttgttcc gccacgatgg tttcattgct ctgggtcagg     5040
ttctccacgg cctgccacag gcgatcctgg acagcagtg cgttagatgg tacgaaatct     5100
tcttgctttt tgtcaatgta tttgcctta tactcgattt cggacaggtc cagcagagag     5160
ctgatcaggc tttcgaagtc gaagttctgg atacgctcgt tgaagatttt accctcgtcg    5220
atgttcaggc taatcatttt gttttcgttc agatggtgag tgaatgcacc ggtagaagag    5280
tcggtcagtt taacgcccag catcaggatg aagtccgcag attcaacaaa ttctttcagg    5340
ttcggttcgc tcagagtacc gttgtagatg cccaggaaag acggcagagc ctcgtcaaca    5400
gaggacttgc cgaagttcag ggtggtaatc ggcagtttgg ttttgctgat gaattgggtc    5460
acggtcttct ccagaccaaa agaaatgatt tcgtggccgg tgatcacgat tggtttcttt    5520
```

```
gcgtttttca gagactcctg gattttgttc aggatttcct ggtcgctagt gttagaagtg    5580
gagttttctt tcttcagcgg caggctcggt ttttccgctt tagctgccgc aacatccaca    5640
ggcaggttga tgtaaactgg tttgcgttct ttcagcagcg cagacagaac gcggtcgatt    5700
tccacagtag cgttctctgc agtcagcagc gtacgtgccg cagtcacagg ttcatgcatt    5760
ttcatgaagt gtttgaaatc gccgtcagcc agagtgtggt ggacgaattt accttcgttc    5820
tgaactttgc tcgttgggct gcctacgatc tccaccaccg gcaggttttc ggcgtaggag    5880
cccgccagac cgttgacggc gctcagttcg ccaacaccga aagtggtcag aaatgccgcg    5940
gctttcttgg tacgtgcata accatctgcc atgtagcttg cgttcagttc gttagcgtta    6000
cccacccatt tcatgtcttt atgagagatg atctgatcca ggaactgcag attgtaatca    6060
cccggaacgc cgaagatttc ttcgataccc agttcatgca gacggtccag cagataatca    6120
ccaacagtat acatgtcgac acccgcatag tcaggaacat cgtatgggta catgctagtt    6180
ctagaaaact tagattagat tgctatgctt tctttctaat gagcaagaag taaaaaaagt    6240
tgtaatagaa caagaaaaat gaaactgaaa cttgagaaat tgaagaccgt ttattaactt    6300
aaatatcaat gggaggtcat cgaaagagaa aaaatcaaa aaaaaattt tcaagaaaaa    6360
gaaacgtgat aaaaattttt attgcctttt tcgacgaaga aaagaaacg aggcggtctc    6420
ttttttcttt tccaaacctt tagtacgggg aattaacgac accctagagg aagaaagagg    6480
ggaaatttag tatgctgtgc ttgggtgttt tgaagtggta cggcgatgcg cggagtccga    6540
gaaaatctgg aagagtaaaa aaggagtaga acattttga agctatgagc tccagctttt    6600
gttcccttta gtgagggtta attgcgcgct tggcgtaatc atggtcatag ctgtttcctg    6660
tgtgaaattg ttatccgctc acaattccac acaacatagg agccgaagc ataaagtgta    6720
aagcctgggg tgcctaatga gtgaggtaac tcacattaat tgcgttgcgc tcactgcccg    6780
ctttccagtc gggaaacctg tcgtgccagc tgcattaatg aatcggccaa cgcgcgggga    6840
gaggcggttt gcgtattggg cgctcttccg cttcctcgct cactgactcg ctgcgctcgg    6900
tcgttcggct gcggcgagcg gtatcagctc actcaaaggc ggtaatacgg ttatccacag    6960
aatcagggga taacgcagga agaacatgt gagcaaaagg ccagcaaaag gccaggaacc    7020
gtaaaaaggc cgcgttgctg gcgttttttcc ataggctccg ccccctgac gagcatcaca    7080
aaaatcgacg ctcaagtcag aggtggcgaa acccgacagg actataaaga taccaggcgt    7140
ttccccctgg aagctccctc gtgcgctctc ctgttccgac cctgccgctt accggatacc    7200
tgtccgcctt tctcccttcg ggaagcgtgg cgctttctca tagctcacgc tgtaggtatc    7260
tcagttcggt gtaggtcgtt cgctccaagc tgggctgtgt gcacgaaccc cccgttcagc    7320
ccgaccgctg cgccttatcc ggtaactatc gtcttgagtc caacccggta agacacgact    7380
tatcgccact ggcagcagcc actggtaaca ggattagcag agcgaggtat gtaggcggtg    7440
ctacagagtt cttgaagtgg tggcctaact acggctacac tagaaggaca gtatttggta    7500
tctgcgctct gctgaagcca gttaccttcg gaaaaagagt ggtagctct tgatccggca    7560
aacaaaccac cgctggtagc ggtggttttt tgtttgcaa gcagcagatt acgcgcagaa    7620
aaaaaggatc tcaagaagat cctttgatct ttttctacggg gtctgacgct cagtggaacg    7680
aaaactcacg ttaagggatt ttggtcatga gattatcaaa aaggatcttc acctagatcc    7740
ttttaaatta aaatgaagt tttaaatcaa tctaaagtat atatgagtaa acttggtctg    7800
acagttacca atgcttaatc agtgaggcac ctatctcagc gatctgtcta tttcgttcat    7860
```

| | |
|---|---|
| ccatagttgc ctgactcccc gtcgtgtaga taactacgat acgggagggc ttaccatctg | 7920 |
| gccccagtgc tgcaatgata ccgcgagacc cacgctcacc ggctccagat ttatcagcaa | 7980 |
| taaaccagcc agccggaagg gccgagcgca gaagtggtcc tgcaacttta tccgcctcca | 8040 |
| tccagtctat taattgttgc cgggaagcta gagtaagtag ttcgccagtt aatagtttgc | 8100 |
| gcaacgttgt tgccattgct acaggcatcg tggtgtcacg ctcgtcgttt ggtatggctt | 8160 |
| cattcagctc cggttcccaa cgatcaaggc gagttacatg atcccccatg ttgtgcaaaa | 8220 |
| aagcggttag ctccttcggt cctccgatcg ttgtcagaag taagttggcc gcagtgttat | 8280 |
| cactcatggt tatggcagca ctgcataatt ctcttactgt catgccatcc gtaagatgct | 8340 |
| tttctgtgac tggtgagtac tcaaccaagt cattctgaga atagtgtatg cggcgaccga | 8400 |
| gttgctcttg cccggcgtca atacgggata ataccgcgcc acatagcaga actttaaaag | 8460 |
| tgctcatcat tggaaaacgt tcttcggggc gaaaactctc aaggatctta ccgctgttga | 8520 |
| gatccagttc gatgtaaccc actcgtgcac ccaactgatc ttcagcatct tttactttca | 8580 |
| ccagcgtttc tgggtgagca aaaacaggaa ggcaaaatgc cgcaaaaaag gaataagggc | 8640 |
| gacacggaaa tgttgaata ctcatactct tcctttttca atattattga agcatttatc | 8700 |
| agggttattg tctcatgagc ggatacatat ttgaatgtat ttagaaaaat aaacaaatag | 8760 |
| gggttccgcg cacatttccc cgaaaagtgc cacctgacgt | 8800 |

<210> SEQ ID NO 5
<211> LENGTH: 1677
<212> TYPE: DNA
<213> ORGANISM: Artificial Sequence
<220> FEATURE:
<223> OTHER INFORMATION: Synthetic polynucleotide

<400> SEQUENCE: 5

| | |
|---|---|
| gtcgacatgt ctgagaaaca atttggggcg aacttggttg tcgatagttt gattaaccat | 60 |
| aaagtgaagt atgtatttgg gattccagga gcaaaaattg accgggtttt tgatttatta | 120 |
| gaaaatgaag aaggccctca aatggtcgtg actcgtcatg agcaaggagc tgctttcatg | 180 |
| gctcaagctg ttggtcgttt gactggcgaa cctggtgtag tagttgttac gagtgggcct | 240 |
| ggtgtatcaa accttgcgac tccgcttttg accgcgactt cagaaggtga tgctattttg | 300 |
| gctatcggtg gacaagttaa acgaagtgac cgtcttaaac gtgcgcacca atcaatggat | 360 |
| aatgctggaa tgatgcaatc agcaacaaaa tattcagcag aagttcttga ccctgataca | 420 |
| ctttctgaat caattgccaa cgcttatcgt attgcaaaat caggacatcc aggtgcaact | 480 |
| ttcttatcaa tcccccaaga tgtaacggat gccgaagtat caatcaaggc cattcaacca | 540 |
| ctttcagacc ctaaaatggg gaatgcctct attgatgaca ttaattattt agcacaagca | 600 |
| attaaaaatg ctgtattgcc agtaattttg gttggagctg gtgcttcaga tgctaaagtc | 660 |
| gcttcatcat tgcgtaatct attaactcat gttaatattc ctgtcgttga acattccaa | 720 |
| ggtgcagggg ttatttcaca tgatttagaa catactttt atggacgtat cggtctttc | 780 |
| cgcaatcaac caggagatat gcttctgaaa cgttctgacc ttgttattgc tgttggttat | 840 |
| gacccaattg aatatgaagc tcgtaactgg aatgcagaaa ttgatagtcg aattatcgtt | 900 |
| attgataatg ccattgctga aattgatact tactaccaac agaacgtga attaattggt | 960 |
| gatatcgcag caacattgga taatctttta ccagctgttc gtggatacaa aattccaaaa | 1020 |
| ggaacaaaag attatctcga tggccttcat gaagttgctg agcaacacga atttgatact | 1080 |
| gaaaatactg aagaaggtag aatgcaccct cttgatttgg tcagcacttt ccaagaaatc | 1140 |

| | |
|---|---|
| gttaaagatg atgaaacagt aaccgttgac gtaggttcac tctacatttg gatggcacgt | 1200 |
| catttcaaat catacgaacc acgtcatctc ctcttctcaa acggaatgca aacacttgga | 1260 |
| gttgcacttc cttgggcaat tacagccgca ttgttgcgcc caggtaaaaa agtttattca | 1320 |
| cactctggtg atggaggctt ccttttcaca gggcaagagt tggaaacagc tgtacgtttg | 1380 |
| aatcttccaa tcgttcaaat tatctggaat gacggccatt atgatatggt taaattccaa | 1440 |
| gaagaaatga aatatggtcg ttcagcagcc gttgattttg ctatgttga ttacgtaaaa | 1500 |
| tatgctgaag caatgggagc aaaaggttac cgtgcacaca gcaaagaaga acttgctgaa | 1560 |
| attcttaaat caatcccaga tactactgga ccagtagtaa ttgacgttcc tttggactat | 1620 |
| tctgataaca ttaaattagc agaaaaatta ttgcctgaag agttttattg aggatcc | 1677 |

<210> SEQ ID NO 6
<211> LENGTH: 1488
<212> TYPE: DNA
<213> ORGANISM: Artificial Sequence
<220> FEATURE:
<223> OTHER INFORMATION: Synthetic polynucleotide

<400> SEQUENCE: 6

| | |
|---|---|
| gtcgacatgg ctaactactt caatacactg aatctgcgcc agcagctggc acagctgggc | 60 |
| aaatgtcgct ttatgggccg cgatgaattc gccgatggcg cgagctacct tcagggtaaa | 120 |
| aaagtagtca tcgtcggctg tggcgcacag ggtctgaacc agggcctgaa catgcgtgat | 180 |
| tctggtctcg atatctccta cgctctgcgt aaagaagcga ttgccgagaa gcgcgcgtcc | 240 |
| tggcgtaaag cgaccgaaaa tggttttaaa gtgggtactt acgaagaact gatcccacag | 300 |
| gcggatctgg tgattaacct gacgccggac aagcagcact ctgatgtagt gcgcaccgta | 360 |
| cagccactga tgaaagacgg cgcggcgctg ggctactcgc acggtttcaa catcgtcgaa | 420 |
| gtgggcgagc agatccgtaa agatatcacc gtagtgatgg ttgcgccgaa atgcccaggc | 480 |
| accgaagtgc gtgaagagta caaacgtggg ttcggcgtac cgacgctgat tgccgttcac | 540 |
| ccggaaaacg atccgaaagg cgaaggcatg gcgattgcca aagcctgggc ggctgcaacc | 600 |
| ggtggtcacc gtgcgggtgt gctggaatcg tccttcgttg cggaagtgaa atctgacctg | 660 |
| atgggcgagc aaaccatcct gtgcggtatg ttgcaggctg gctctctgct gtgcttcgac | 720 |
| aagctggtgg aagaaggtac cgatccagca tacgcagaaa aactgattca gttcggttgg | 780 |
| gaaaccatca ccgaagcact gaaacagggc ggcatcaccc tgatgatgga ccgtctctct | 840 |
| aacccggcga aactgcgtgc ttatgcgctt tctgaacagc tgaaagagat catggcaccc | 900 |
| ctgttccaga acatatgga cgacatcatc tccggcgaat tctcttccgg tatgatggcg | 960 |
| gactgggcca acgatgataa gaaactgctg acctggcgtg aagagaccgg caaaccgcg | 1020 |
| tttgaaaccg cgccgcagta tgaaggcaaa atcggcgagc aggagtactt cgataaaggc | 1080 |
| gtactgatga ttgcgatggt gaaagcgggc gttgaactgg cgttcgaaac catggtcgat | 1140 |
| tccggcatca ttgaagagtc tgcatattat gaatcactgc acgagctgcc gctgattgcc | 1200 |
| aacaccatcg cccgtaagcg tctgtacgaa atgaacgtgg ttatctctga taccgctgag | 1260 |
| tacggtaact atctgttctc ttacgcttgt gtgccgttgc tgaaaccgtt tatggcagag | 1320 |
| ctgcaaccgg gcgacctggg taaagctatt ccggaaggcg cggtagataa cgggcaactg | 1380 |
| cgtgatgtga acgaagcgat tgcagccat gcgattgagc aggtaggtaa gaaactgcgc | 1440 |
| ggctatatga cagatatgaa acgtattgct gttgcgggtt aaggatcc | 1488 |

<210> SEQ ID NO 7
<211> LENGTH: 1863
<212> TYPE: DNA
<213> ORGANISM: Artificial Sequence
<220> FEATURE:
<223> OTHER INFORMATION: Synthetic polynucleotide

<400> SEQUENCE: 7

```
gtcgacatgc ctaagtaccg ttccgccacc accactcatg gtcgtaatat ggcgggtgct     60
cgtgcgctgt ggcgcgccac cggaatgacc gacgccgatt tcggtaagcc gattatcgcg    120
gttgtgaact cgttcaccca atttgtaccg ggtcacgtcc atctgcgcga tctcggtaaa    180
ctggtcgccg aacaaattga agcggctggc ggcgttgcca aagagttcaa caccattgcg    240
gtggatgatg ggattgccat gggccacggg ggatgctttt attcactgcc atctcgcgaa    300
ctgatcgctg attccgttga gtatatggtc aacgcccact gcgccgacgc catggtctgc    360
atctctaact gcgacaaaat caccccgggg atgctgatgg cttccctgcg cctgaatatt    420
ccggtgatct ttgtttccgg cggcccgatg gaggccggga aaaccaaact ttccgatcag    480
atcatcaagc tcgatctggt tgatgcgatg atccagggcg cagacccgaa agtatctgac    540
tcccagagcg atcaggttga acgttccgcg tgtccgacct gcggttcctg ctccgggatg    600
tttaccgcta actcaatgaa ctgcctgacc gaagcgctgg gcctgtcgca gccgggcaac    660
ggctcgctgc tggcaaccca cgccgaccgt aagcagctgt tccttaatgc tggtaaacgc    720
attgttgaat tgaccaaacg ttattacgag caaaacgacg aaagtgcact gccgcgtaat    780
atcgccagta aggcggcgtt tgaaaacgcc atgacgctgg atatcgcgat gggtggatcg    840
actaacaccg tacttcacct gctggcggcg gcgcaggaag cggaaatcga cttcaccatg    900
agtgatatcg ataagctttc ccgcaaggtt ccacagctgt gtaaagttgc gccgagcacc    960
cagaaatacc atatggaaga tgttcaccgt gctggtggtg ttatcggtat tctcggcgaa   1020
ctggatcgcg cggggttact gaaccgtgat gtgaaaaacg tacttggcct gacgttgccg   1080
caaacgctgg aacaatacga cgttatgctg acccaggatg acgcggtaaa aaatatgttc   1140
cgcgcaggtc ctgcaggcat tcgtaccaca caggcattct cgcaagattg ccgttgggat   1200
acgctggacg acgatcgcgc caatggctgt atccgctcgc tggaacacgc ctacagcaaa   1260
gacggcggcc tggcggtgct ctacggtaac tttgcggaaa acggctgcat cgtgaaaacg   1320
gcaggcgtcg atgacagcat cctcaaattc accggcccgg cgaaagtgta cgaaagccag   1380
gacgatgcgg tagaagcgat tctcggcggt aaagttgtcg ccggagatgt ggtagtaatt   1440
cgctatgaag gcccgaaagg cggtccgggg atgcaggaaa tgctctaccc aaccagcttc   1500
ctgaaatcaa tggtctcgg caaagcctgt gcgctgatca ccgacggtcg tttctctggt   1560
ggcacctctg gtctttccat cggccacgtc tcaccggaag cggcaagcgg cggcagcatt   1620
ggcctgattg aagatggtga cctgatcgct atcgacatcc gaaccgtgg cattcagtta   1680
caggtaagcg atgccgaact ggcggcgcgt cgtgaagcgc aggacgctcg aggtgacaaa   1740
gcctggacgc cgaaaaatcg tgaacgtcag gtctcctttg ccctgcgtgc ttatgccagc   1800
ctggcaacca gcgccgacaa aggcgcggtg cgcgataaat cgaaactggg gggttaagga   1860
tcc                                                                 1863
```

<210> SEQ ID NO 8
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 8

```
gtcgacatgt atactgttgg tgattatctg ctggaccgtc tgcatgaact gggtatcgaa    60
gaaatcttcg gcgttccggg tgattacaat ctgcagttcc tggatcagat catctctcat   120
aaagacatga atgggtggg taacgctaac gaactgaacg caagctacat ggcagatggt   180
tatgcacgta ccaagaaagc cgcggcattt ctgaccactt tcggtgttgg cgaactgagc   240
gccgtcaacg gtctggcggg ctcctacgcc gaaaacctgc cggtggtgga gatcgtaggc   300
agcccaacga gcaaagttca gaacgaaggt aaattcgtcc accacactct ggctgacggc   360
gatttcaaac acttcatgaa aatgcatgaa cctgtgactg cggcacgtac gctgctgact   420
gcagagaacg ctactgtgga aatcgaccgc gttctgtctg cgctgctgaa agaacgcaaa   480
ccagtttaca tcaacctgcc tgtggatgtt gcggcagcta aagcggaaaa accgagcctg   540
ccgctgaaga aagaaaactc cacttctaac actagcgacc aggaaatcct gaacaaaatc   600
caggagtctc tgaaaaacgc aaagaaacca atcgtgatca ccggccacga aatcatttct   660
tttggtctgg agaagaccgt gacccaattc atcagcaaaa ccaaactgcc gattaccacc   720
ctgaacttcg gcaagtcctc tgttgacgag gctctgccgt ctttcctggg catctacaac   780
ggtactctga gcgaaccgaa cctgaaagaa tttgttgaat ctgcggactt catcctgatg   840
ctgggcgtta aactgaccga ctcttctacc ggtgcattca ctcaccatct gaacgaaaac   900
aaaatgatta gcctgaacat cgacgagggt aaaatcttca acgagcgtat ccagaacttc   960
gacttcgaaa gcctgatcag ctctctgctg gacctgtccg aaatcgagta taaaggcaaa  1020
tacattgaca aaaagcaaga agatttcgta ccatctaacg cactgctgtc ccaggatcgc  1080
ctgtggcagg ccgtggagaa cctgacccag agcaatgaaa ccatcgtggc ggaacaaggt  1140
acgagctttt tcggcgcgtc ttctatcttt ctgaaatcca aagccatttt tatcggtcag  1200
ccgctgtggg gtagcattgg ctatactttc ccggcagcgc tgggctctca gatcgctgat  1260
aaagaatctc gtcatctgct gttcatcggt gacggttccc tgcagctgac cgtacaggaa  1320
ctgggtctgg caattcgtga aagatcaac ccgatttgct tcattattaa caatgacggc  1380
tacaccgttg agcgtgagat ccacggtccg aaccagtctt acaacgatat ccctatgtgg  1440
aactactcta actgccgga gtccttcggc gcaactgagg accgtgttgt gtctaaaatt  1500
gtgcgtaccg aaaacgaatt tgtgagcgtg atgaagagg cccaggccga tccgaaccgt  1560
atgtactgga tcgaactgat cctggcgaaa gaaggcgcac cgaaggtact gaagaaaatg  1620
ggcaagctgt ttgctgaaca gaataaatcc taaggatcc                          1659
```

<210> SEQ ID NO 9
<211> LENGTH: 1059
<212> TYPE: DNA
<213> ORGANISM: Artificial Sequence
<220> FEATURE:
<223> OTHER INFORMATION: Synthetic polynucleotide

<400> SEQUENCE: 9

```
gtcgacatgt ctattccaga aactcaaaaa gccattatct tctacgaatc caacggcaag    60
ttggagcata aggatatccc agttccaaag ccaaagccca acgaattgtt aatcaacgtc   120
aagtactctg gtgtctgcca caccgatttg cacgcttggc atggtgactg gccattgcca   180
actaagttac cattagttgg tggtcacgaa ggtgccggtg tcgttgtcgg catgggtgaa   240
```

```
aacgttaagg gctggaagat cggtgactac gccggtatca aatggttgaa cggttcttgt      300
atggcctgtg aatactgtga attgggtaac gaatccaact gtcctcacgc tgacttgtct      360
ggttacaccc acgacggttc tttccaagaa tacgctaccg ctgacgctgt tcaagccgct      420
cacattcctc aaggtactga cttggctgaa gtcgcgccaa tcttgtgtgc tggtatcacc      480
gtatacaagg ctttgaagtc tgccaacttg agagcaggcc actgggcggc catttctggt      540
gctgctggtg gtctaggttc tttggctgtt caatatgcta aggcgatggg ttacagagtc      600
ttaggtattg atggtggtcc aggaaaggaa gaattgttta cctcgctcgg tggtgaagta      660
ttcatcgact tcaccaaaga gaaggacatt gttagcgcag tcgttaaggc taccaacggc      720
ggtgcccacg gtatcatcaa tgtttccgtt tccgaagccg ctatcgaagc ttctaccaga      780
tactgtaggg cgaacggtac tgttgtcttg gttggtttgc cagccggtgc aaagtgctcc      840
tctgatgtct tcaaccacgt tgtcaagtct atctccattg tcggctctta cgtggggaac      900
agagctgata ccagagaagc cttagatttc tttgccagag gtctagtcaa gtctccaata      960
aaggtagttg gcttatccag tttaccagaa atttacgaaa agatggagaa gggccaaatt     1020
gctggtagat acgttgttga cacttctaaa taaggatcc                            1059

<210> SEQ ID NO 10
<211> LENGTH: 9761
<212> TYPE: DNA
<213> ORGANISM: Artificial Sequence
<220> FEATURE:
<223> OTHER INFORMATION: Synthetic polynucleotide

<400> SEQUENCE: 10
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accataccac agcttttcaa ttcaattcat catttttttt ttattctttt ttttgatttc      240
ggtttctttg aaattttttt gattcggtaa tctccgaaca gaaggaagaa cgaaggaagg      300
agcacagact tagattggta tatatacgca tatgtagtgt tgaagaaaca tgaaattgcc      360
cagtattctt aacccaactg cacagaacaa aaacctgcag gaaacgaaga taaatcatgt      420
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat tgttttacta aaaacacatg      600
tggatatctt gactgatttt tccatggagg gcacagttaa gccgctaaag gcattatccg      660
ccaagtacaa tttttttactc ttcgaagaca gaaaatttgc tgacattggt aatacagtca      720
aattgcagta ctctgcgggt gtatacagaa tagcagaatg ggcagacatt acgaatgcac      780
acggtgtggt gggcccaggt attgttagcg gtttgaagca ggcggcagaa gaagtaacaa      840
aggaacctag aggccttttg atgttagcag aattgtcatg caagggctcc ctatctactg      900
gagaatatac taagggtact gttgacattg cgaagagcga caagattttt gttatcggct      960
ttattgctca agagacatg gtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttggaag aggactattt gcaagggaa     1140 gggatgctaa ggtagagggt gaacgttaca gaaaagcagg ctgggaagca tatttgagaa     1200
gatgcggcca gcaaaactaa aaaactgtat tataagtaaa tgcatgtata ctaaactcac     1260
```

```
aaattagagc ttcaatttaa ttatatcagt tattaccta tgcggtgtga ataccgcac    1320 agatgcgtaa ggagaaaata ccgcatcagg aaattgtaaa cgttaatatt ttgttaaaat    1380
tcgcgttaaa ttttgttaa atcagctcat tttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt ttggggtcg aggtgccgta    1620 aagcactaaa tcggaacct aaagggagcc ccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccgcaaatt aaagccttcg agcgtcccaa    2040
aaccttctca gcaaggtttt tcagtataat gttacatgcg tacacgcgtc tgtacagaaa    2100
aaaaagaaaa atttgaaata taaataacgt tcttaatact aacataacta taaaaaaata    2160
aatagggacc tagacttcag gttgtctaac tccttccttt tcggttagag cggatgtggg    2220
gggagggcgt gaatgtaagc gtgacataac taattacatg actcgagcgg ccgcggatcc    2280
ttatttagaa gtgtcaacaa cgtatctacc agcaatttgg cccttctcca tcttttcgta    2340
aatttctggt aaactggata agccaactac ctttattgga gacttgacta gacctctggc    2400
aaagaaatct aaggcttctc tggtatcagc tctgttcccc acgtaagagc cgacaatgga    2460
gatagacttg acaacgtggt tgaagacatc agaggagcac tttgcaccgg ctggcaaacc    2520
aaccaagaca acagtaccgt tcgccctaca gtatctggta gaagcttcga tagcggcttc    2580
ggaaacggaa acattgatga taccgtgggc accgccgttg gtagccttaa cgactgcgct    2640
aacaatgtcc ttctctttgg tgaagtcgat gaatacttca ccaccgagcg aggtaaacaa    2700
ttcttccttt cctggaccac catcaatacc taagactctg taacccatcg ccttagcata    2760
ttgaacagcc aaagaaccta gaccaccagc agcaccagaa atggccgccc agtggcctgc    2820
tctcaagttg gcagacttca aagccttgta tacggtgata ccagcacaca agattggcgc    2880
gacttcagcc aagtcagtac cttgaggaat gtgagcggct tgaacagcgt cagcggtagc    2940
gtattcttgg aaagaaccgt cgtgggtgta accagacaag tcagcgtgag gacagttgga    3000
ttcgttaccc aattcacagt attcacaggc catacaagaa ccgttcaacc atttgatacc    3060
ggcgtagtca ccgatcttcc agcccttaac gttttcaccc atgccgacaa cgacaccggc    3120
accttcgtga ccaccaacta atggtaactt agttggcaat ggccagtcac catgccaagc    3180
gtgcaaatcg gtgtggcaga caccagagta cttgacgttg attaacaatt cgttgggctt    3240
tggctttgga actgggatat ccttatgctc caacttgccg ttggattcgt agaagataat    3300 ggcttttga gtttctggaa tagacatgtc gacaccatct tcttctgaga tgagtttttg    3360
ttccatgcta gttctagaat ccgtcgaaac taagttctgg tgttttaaaa ctaaaaaaaa    3420
gactaactat aaaagtagaa tttaagaagt ttaagaaata gatttacaga attacaatca    3480
atacctaccg tctttatata cttattagtc aagtagggga ataatttcag ggaactggtt    3540 tcaaccttt ttttcagctt tttccaaatc agagagagca gaaggtaata gaaggtgtaa    3600
```

```
gaaaatgaga tagatacatg cgtgggtcaa ttgccttgtg tcatcattta ctccaggcag    3660
gttgcatcac tccattgagg ttgtgcccgt tttttgcctg tttgtgcccc tgttctctgt    3720
agttgcgcta agagaatgga cctatgaact gatggttggt gaagaaaaca atattttggt    3780
gctgggattc ttttttttc tggatgccag cttaaaaagc gggctccatt atatttagtg    3840
gatgccagga ataaactgtt cacccagaca cctacgatgt tatatattct gtgtaacccg    3900
ccccctattt tgggcatgta cgggttacag cagaattaaa aggctaattt tttgactaaa    3960
taaagttagg aaaatcacta ctattaatta tttacgtatt ctttgaaatg gcgagtattg    4020
ataatgataa actgaggatc cttaggattt attctgttca gcaaacagct tgcccatttt    4080
cttcagtacc ttcggtgcgc cttctttcgc caggatcagt tcgatccagt acatacggtt    4140
cggatcggcc tgggcctctt tcatcacgct cacaaattcg ttttcggtac gcacaatttt    4200
agacacaaca cggtcctcag ttgcgccgaa ggactccggc agtttagagt agttccacat    4260
agggatatcg ttgtaagact ggttcggacc gtggatctca cgctcaacgg tgtagccgtc    4320
attgttaata atgaagcaaa tcgggttgat cttttcacga attgccagac ccagttcctg    4380
tacggtcagc tgcagggaac cgtcaccgat gaacagcaga tgacgagatt ctttatcagc    4440
gatctgagag cccagcgctg ccgggaaagt atagccaatg ctaccccaca gcggctgacc    4500
gataaaatgg cttttggatt tcagaaagat agaagacgcg ccgaaaaagc tcgtaccttg    4560
ttccgccacg atggtttcat tgctctgggt caggttctcc acggcctgcc acaggcgatc    4620
ctgggacagc agtgcgttag atggtacgaa atcttcttgc tttttgtcaa tgtatttgcc    4680
tttatactcg atttcggaca ggtccagcag agagctgatc aggcttttcga agtcgaagtt    4740 ctggatacgc tcgttgaaga ttttaccctc gtcgatgttc aggctaatca ttttgttttc    4800
gttcagatgt tgagtgaatg caccggtaga agagtcggtc agtttaacgc ccagcatcag    4860
gatgaagtcc gcagattcaa caaattcttt caggttcggt tcgctcagag taccgttgta    4920 gatgccagg aaagacggca gagcctcgtc aacagaggac ttgccgaagt tcagggtggt    4980
aatcggcagt ttggttttgc tgatgaattg ggtcacggtc ttctccagac caaaagaaat    5040
gatttcgtgg ccggtgatca cgattggttt cttggcgttt tcagagact cctggatttt    5100 gttcaggatt tcctggtcgc tagtgttaga agtggagttt tcttcttca gcggcaggct    5160 cggttttttcc gctttagctg ccgcaacatc cacaggcagg ttgatgtaaa ctggtttgcg    5220 ttcttttcagc agcgcagaca gaacgcggtc gatttccaca gtagcgttct ctgcagtcag    5280
cagcgtacgt gccgcagtca caggttcatg cattttcatg aagtgtttga aatcgccgtc    5340
agccagagtg tggtggacga atttaccttc gttctgaact ttgctcgttg ggctgcctac    5400
gatctccacc accggcaggt tttcggcgta ggagcccgcc agaccgttga cggcgctcag    5460
ttcgccaaca ccgaaagtgg tcagaaatgc cgcggctttc ttggtacgtg cataaccatc    5520
tgccatgtag cttgcgttca gttcgttagc gttacccacc catttcatgt ctttatgaga    5580
gatgatctga tccaggaact gcagattgta atcacccgga acgccgaaga tttcttcgat    5640
acccagttca tgcagacggt ccagcagata atcaccaaca gtatacatgt cgacacccgc    5700
atagtcagga acatcgtatg ggtacatgct agttctagaa aacttagatt agattgctat    5760 gctttcttc taatgagcaa gaagtaaaaa aagttgtaat agaacaagaa aaatgaaact    5820
gaaacttgag aaattgaaga ccgtttatta acttaaatat caatgggagg tcatcgaaag    5880 agaaaaaat caaaaaaaa atttcaaga aaagaaacg tgataaaaat ttttattgcc    5940 ttttttcgacg aagaaaaaga aacgaggcgg tctctttttt cttttccaaa cctttagtac    6000
```

```
gggtaattaa cgacacccta gaggaagaaa gagggggaaat ttagtatgct gtgcttgggt   6060
gttttgaagt ggtacggcga tgcgcggagt ccgagaaaat ctggaagagt aaaaaaggag   6120
tagaaacatt ttgaagctat gagctccagc ttttgttccc tttagtgagg gttaattgcg   6180
cgcttggcgt aatcatggtc atagctgttt cctgtgtgaa attgttatcc gctcacaatt   6240
ccacacaaca taggagccgg aagcataaag tgtaaagcct ggggtgccta atgagtgagg   6300
taactcacat taattgcgtt gcgctcactg cccgctttcc agtcgggaaa cctgtcgtgc   6360
cagctgcatt aatgaatcgg ccaacgcgcg gggagaggcg gtttgcgtat tgggcgctct   6420
tccgcttcct cgctcactga ctcgctgcgc tcggtcgttc ggctgcggcg agcggtatca   6480
gctcactcaa aggcggtaat acggttatcc acagaatcag gggataacgc aggaaagaac   6540
atgtgagcaa aaggccagca aaaggccagg aaccgtaaaa aggccgcgtt gctggcgttt   6600
ttccataggc tccgcccccc tgacgagcat cacaaaaatc gacgctcaag tcagaggtgg   6660
cgaaacccga caggactata agataccagg cgtttccccc tggaagctc cctcgtgcgc   6720 tctcctgttc cgaccctgcc gcttaccgga tacctgtccg cctttctccc ttcgggaagc   6780
gtggcgcttt ctcatagctc acgctgtagg tatctcagtt cggtgtaggt cgttcgctcc   6840
aagctgggct gtgtgcacga accccccgtt cagcccgacc gctgcgcctt atccggtaac   6900
tatcgtcttg agtccaaccc ggtaagacac gacttatcgc cactggcagc agccactggt   6960
aacaggatta gcagagcgag gtatgtaggc ggtgctacag agttcttgaa gtggtggcct   7020
aactacggct acactagaag gacagtattt ggtatctgcg ctctgctgaa gccagttacc   7080
ttcggaaaaa gagttggtag ctcttgatcc ggcaaacaaa ccaccgctgg tagcggtggt   7140
ttttttgttt gcaagcagca gattacgcgc agaaaaaaag gatctcaaga agatcctttg   7200
atcttttcta cggggtctga cgctcagtgg aacgaaaact cacgttaagg gattttggtc   7260
atgagattat caaaaaggat cttcacctag atccttttaa attaaaaatg aagttttaaa   7320
tcaatctaaa gtatatatga gtaaacttgg tctgacagtt accaatgctt aatcagtgag   7380
gcacctatct cagcgatctg tctatttcgt tcatccatag ttgcctgact ccccgtcgtg   7440
tagataacta cgatacggga gggcttacca tctggcccca gtgctgcaat gataccgcga   7500
gacccacgct caccggctcc agatttatca gcaataaacc agccagccgg aagggccgag   7560
cgcagaagtg gtcctgcaac tttatccgcc tccatccagt ctattaattg ttgccgggaa   7620
gctagagtaa gtagttcgcc agttaatagt ttgcgcaacg ttgttgccat tgctacaggc   7680
atcgtggtgt cacgctcgtc gtttggtatg gcttcattca gctccggttc caacgatca   7740 aggcgagtta catgatcccc catgttgtgc aaaaaagcgg ttagctcctt cggtcctccg   7800
atcgttgtca gaagtaagtt ggccgcagtg ttatcactca tggttatggc agcactgcat   7860
aattctctta ctgtcatgcc atccgtaaga tgcttttctg tgactggtga gtactcaacc   7920
aagtcattct gagaatagtg tatgcggcga ccgagttgct cttgcccggc gtcaatacgg   7980
gataataccg cgccacatag cagaacttta aaagtgctca tcattggaaa acgttcttcg   8040
gggcgaaaac tctcaaggat cttaccgctg ttgagatcca gttcgatgta acccactcgt   8100
gcacccaact gatcttcagc atcttttact ttcaccagcg tttctgggtg agcaaaaaca   8160
ggaaggcaaa atgccgcaaa aaagggaata agggcgacac ggaaatgttg aatactcata   8220
ctcttccttt ttcaatatta ttgaagcatt tatcagggtt attgtctcat gagcggatac   8280
atatttgaat gtatttagaa aaataaacaa ataggggttc cgcgcacatt tccccgaaaa   8340
```

```
gtgccacctg aacgaagcat ctgtgcttca ttttgtagaa caaaaatgca acgcgagagc    8400
gctaattttt caaacaaaga atctgagctg cattttttaca gaacagaaat gcaacgcgaa   8460
agcgctattt taccaacgaa gaatctgtgc ttcattttttg taaaacaaaa atgcaacgcg   8520
agagcgctaa ttttttcaaac aaagaatctg agctgcattt ttacagaaca gaaatgcaac   8580
gcgagagcgc tattttacca acaaagaatc tatacttctt ttttgttcta caaaaatgca   8640
tcccgagagc gctatttttc taacaaagca tcttagatta cttttttttct cctttgtgcg   8700
ctctataatg cagtctcttg ataacttttt gcactgtagg tccgttaagg ttagaagaag   8760
gctactttgg tgtctatttt ctcttccata aaaaaagcct gactccactt cccgcgttta   8820
ctgattacta gcgaagctgc gggtgcattt tttcaagata aaggcatccc cgattatatt   8880
ctataccgat gtggattgcg catactttgt gaacagaaag tgatagcgtt gatgattctt   8940
cattggtcag aaaattatga acggtttctt ctattttgtc tctatatact acgtatagga   9000
aatgtttaca ttttcgtatt gttttcgatt cactctatga atagttctta ctacaatttt   9060
tttgtctaaa gagtaatact agagataaac ataaaaaatg tagaggtcga gtttagatgc   9120
aagttcaagg agcgaaaggt ggatgggtag gttatatagg gatatagcac agagatatat   9180
agcaaagaga tacttttgag caatgttttgt ggaagcggta ttcgcaatat tttagtagct   9240
cgttacagtc cggtgcgttt ttggttttttt gaaagtgcgt cttcagagcg cttttggttt   9300
tcaaaagcgc tctgaagttc ctatactttc tagagaatag gaacttcgga ataggaactt   9360
caaagcgttt ccgaaaacga gcgcttccga aaatgcaacg cgagctgcgc acatacagct   9420
cactgttcac gtcgcaccta tatctgcgtg ttgcctgtat atatatatac atgagaagaa   9480
cggcatagtg cgtgtttatg cttaaatgcg tacttatatg cgtctattta tgtaggatga   9540
aaggtagtct agtacctcct gtgatattat cccattccat gcggggtatc gtatgcttcc   9600
ttcagcacta ccctttagct gttctatatg ctgccactcc tcaattggat tagtctcatc   9660
cttcaatgct atcatttcct ttgatattgg atcatactaa gaaaccatta ttatcatgac   9720
attaacctat aaaaataggc gtatcacgag gcccttcgt c                        9761
```

<210> SEQ ID NO 11
<211> LENGTH: 7990
<212> TYPE: DNA
<213> ORGANISM: Artificial Sequence
<220> FEATURE:
<223> OTHER INFORMATION: Synthetic polynucleotide

<400> SEQUENCE: 11

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga agtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
```

-continued

```
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa agactcgta tttccaaaag       840 actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttgttaa atcagctcat tttttaacca ataggccgaa      1320
atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt ttgggggtcg     1500
aggtgccgta aagcactaaa tcggaaccct aaagggagcc ccgatttag agcttgacgg      1560 ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctggcgaaag ggggatgtgc tgcaaggcga     1800
ttaagttggg taacgccagg gttttcccag tcacgacgtt gtaaaacgac ggccagtgag     1860
cgcgcgtaat acgactcact ataggggcgaa ttgggtaccg gccgcaaatt aaagccttcg     1920
agcgtcccaa aaccttctca agcaaggttt tcagtataat gttacatgcg tacacgcgtc     1980
tgtacagaaa aaaagaaaa atttgaaata taaataacgt tcttaatact aacataacta     2040
taaaaaaata aatagggacc tagacttcag gttgtctaac tccttccttt tcggttagag     2100
cggatgtggg gggagggcgt gaatgtaagc gtgacataac taattacatg actcgagcgg     2160
ccgcggatcc ttaacccgca acagcaatac gtttcatatc tgtcatatag ccgcgcagtt     2220
tcttacctac ctgctcaatc gcatggctgc gaatcgcttc gttcacatca cgcagttgcc     2280
cgttatctac cgcgccttcc ggaatagctt tacccaggtc gcccggttgc agctctgcca     2340
taaacggttt cagcaacggc acacaagcgt aagagaacag atagttaccg tactcagcgg     2400
tatcagagat aaccacgttc atttcgtaca gacgcttacg ggcgatggtg ttggcaatca     2460
gcggcagctc gtgcagtgat tcataatatg cagactcttc aatgatgccg gaatcgacca     2520
tggtttcgaa cgccagttca acgcccgctt tcaccatcgc aatcatcagt acgcctttat     2580
cgaagtactc ctgctcgccg attttgcctt catactgcgg cgcggtttca aacgcgtttt     2640
tgccggtctc ttcacgccag gtcagcagtt tcttatcatc gttggcccag tccgccatca     2700
taccggaaga gaattcgccg gagatgatgt cgtccatatg tttctggaac aggggtgcca     2760
tgatctcttt cagctgttca gaaagcgcat aagcacgcag tttcgccggg ttagagagac     2820
ggtccatcat cagggtgatg ccgccctgtt tcagtgcttc ggtgatggtt tcccaaccga     2880
actgaatcag ttttttctgcg tatgctggat cggtaccttc ttccaccagc ttgtcgaagc     2940
acagcagaga gccagcctgc aacataccgc acaggatggt ttgctcgccc atcaggtcag     3000
```

```
atttcacttc cgcaacgaag gacgattcca gcacacccgc acggtgacca ccggttgcag   3060
ccgcccaggc tttggcaatc gccatgcctt cgcctttcgg atcgttttcc gggtgaacgg   3120
caatcagcgt cggtacgccg aacccacgtt tgtactcttc acgcacttcg gtgcctgggc   3180
atttcggcgc aaccatcact acggtgatat ctttacggat ctgctcgccc acttcgacga   3240
tgttgaaacc gtgcgagtag cccagcgccg cgccgtcttt catcagtggc tgtacggtgc   3300
gcactacatc agagtgctgc ttgtccggcg tcaggttaat caccagatcc gcctgtggga   3360
tcagttcttc gtaagtaccc actttaaaac cattttcggt cgctttacgc caggacgcgc   3420
gcttctcggc aatcgcttct ttacgcagag cgtaggagat atcgagacca gaatcacgca   3480
tgttcaggcc ctggttcaga ccctgtgcgc acagccgac gatgactact tttttaccct    3540
gaaggtagct cgcgccatcg gcgaattcat cgcggcccat aaagcgacat tgcccagct    3600 gtgccagctg ctggcgcaga ttcagtgtat tgaagtagtt agccatgtcg acaccatctt   3660
cttctgagat gagttttgt tccatgctag ttctagaatc cgtcgaaact aagttctggt     3720
gttttaaaac taaaaaaaag actaactata aagtagaat ttaagaagtt taagaaatag     3780
atttacagaa ttacaatcaa tacctaccgt ctttatatac ttattagtca agtaggggaa   3840
taatttcagg gaactggttt caaccttttt tttcagcttt ttccaaatca gagagagcag   3900
aaggtaatag aaggtgtaag aaaatgagat agatacatgc gtgggtcaat tgccttgtgt   3960
catcatttac tccaggcagg ttgcatcact ccattgaggt tgtgcccgtt ttttgcctgt   4020
ttgtgcccct gttctctgta gttgcgctaa gagaatggac ctatgaactg atggttggtg   4080
aagaaaacaa tattttggtg ctgggattct tttttttct ggatgccagc ttaaaaagcg    4140
ggctccatta tatttagtgg atgccaggaa taaactgttc acccagacac ctacgatgtt   4200
atatattctg tgtaacccgc ccctatttt gggcatgtac gggttacagc agaattaaaa    4260
ggctaatttt ttgactaaat aaagttagga aaatcactac tattaattat ttacgtattc   4320
tttgaaatgg cgagtattga taatgataaa ctgagctaga tctgggcccg agctccagct   4380
tttgttccct ttagtgaggg ttaattgcgc gcttggcgta atcatggtca tagctgtttc   4440
ctgtgtgaaa ttgttatccg ctcacaattc cacacaacat aggagccgga agcataaagt   4500
gtaaagcctg gggtgcctaa tgagtgaggt aactcacatt aattgcgttg cgctcactgc   4560
ccgctttcca gtcgggaaac ctgtcgtgcc agctgcatta atgaatcggc caacgcgcgg   4620
ggagaggcgg tttgcgtatt gggcgctctt ccgcttcctc gctcactgac tcgctgcgct   4680
cggtcgttcg gctgcggcga gcggtatcag ctcactcaaa ggcggtaata cggttatcca   4740
cagaatcagg ggataacgca ggaaagaaca tgtgagcaaa aggccagcaa aaggccagga   4800
accgtaaaaa ggccgcgttg ctggcgtttt tccataggct ccgcccccct gacgagcatc   4860
acaaaaatcg acgctcaagt cagaggtggc gaaacccgac aggactataa agataccagg   4920
cgtttccccc tggaagctcc ctcgtgcgct ctcctgttcc gaccctgccg cttaccggat   4980
acctgtccgc ctttctccct tcgggaagcg tggcgctttc tcatagctca cgctgtaggt   5040
atctcagttc ggtgtaggtc gttcgctcca agctgggctg tgtgcacgaa ccccccgttc   5100
agcccgaccg ctgcgcctta tccggtaact atcgtcttga gtccaacccg gtaagacacg   5160
acttatcgcc actggcagca gccactggta acaggattag cagagcgagg tatgtaggcg   5220
gtgctacaga gttcttgaag tggtggccta actacggcta cactagaagg acagtatttg   5280
gtatctgcgc tctgctgaag ccagttacct tcggaaaaag agttggtagc tcttgatccg   5340
gcaaacaaac caccgctggt agcggtggtt tttttgtttg caagcagcag attacgcgca   5400
```

```
gaaaaaaagg atctcaagaa gatcctttga tcttttctac ggggtctgac gctcagtgga    5460
acgaaaactc acgttaaggg attttggtca tgagattatc aaaaaggatc ttcacctaga    5520
tccttttaaa ttaaaaatga agttttaaat caatctaaag tatatatgag taaacttggt    5580
ctgacagtta ccaatgctta atcagtgagg cacctatctc agcgatctgt ctatttcgtt    5640
catccatagt tgcctgactc cccgtcgtgt agataactac gatacgggag ggcttaccat    5700
ctggccccag tgctgcaatg ataccgcgag acccacgctc accggctcca gatttatcag    5760
caataaacca gccagccgga agggccgagc gcagaagtgg tcctgcaact ttatccgcct    5820
ccatccagtc tattaattgt tgccgggaag ctagagtaag tagttcgcca gttaatagtt    5880
tgcgcaacgt tgttgccatt gctacaggca tcgtggtgtc acgctcgtcg tttggtatgg    5940
cttcattcag ctccggttcc caacgatcaa ggcgagttac atgatccccc atgttgtgca    6000
aaaaagcggt tagctccttc ggtcctccga tcgttgtcag aagtaagttg gccgcagtgt    6060
tatcactcat ggttatggca gcactgcata attctcttac tgtcatgcca tccgtaagat    6120
gcttttctgt gactggtgag tactcaacca agtcattctg agaatagtgt atgcggcgac    6180
cgagttgctc ttgcccggcg tcaatacggg ataataccgc gccacatagc agaactttaa    6240
aagtgctcat cattggaaaa cgttcttcgg ggcgaaaact ctcaaggatc ttaccgctgt    6300
tgagatccag ttcgatgtaa cccactcgtg cacccaactg atcttcagca tcttttactt    6360
tcaccagcgt ttctgggtga gcaaaaacag gaaggcaaaa tgccgcaaaa aagggaataa    6420
gggcgacacg gaaatgttga atactcatac tcttcctttt tcaatattat tgaagcattt    6480
atcagggtta ttgtctcatg agcggataca tatttgaatg tatttagaaa aataaacaaa    6540
taggggttcc gcgcacattt ccccgaaaag tgccacctga acgaagcatc tgtgcttcat    6600
tttgtagaac aaaaatgcaa cgcgagagcg ctaatttttc aaacaaagaa tctgagctgc    6660
atttttacag aacagaaatg caacgcgaaa gcgctatttt accaacgaag aatctgtgct    6720
tcattttgt aaaacaaaaa tgcaacgcga gagcgctaat ttttcaaaca agaatctga    6780
gctgcatttt tacagaacag aaatgcaacg cgagagcgct attttaccaa caaagaatct    6840
atacttcttt tttgttctac aaaaatgcat cccgagagcg ctattttttct aacaaagcat    6900
cttagattac ttttttttctc ctttgtgcgc tctataatgc agtctcttga taacttttttg    6960
cactgtaggt ccgttaaggt tagaagaagg ctactttggt gtctattttc tcttccataa    7020
aaaaagcctg actccacttc ccgcgtttac tgattactag cgaagctgcg ggtgcatttt    7080
ttcaagataa aggcatcccc gattatattc tataccgatg tggattgcgc atactttgtg    7140
aacagaaagt gatagcgttg atgattcttc attggtcaga aaattatgaa cggtttcttc    7200
tattttgtct ctatatacta cgtataggaa atgtttacat tttcgtattg ttttcgattc    7260
actctatgaa tagttcttac tacaattttt ttgtctaaag agtaatacta gagataaaca    7320
taaaaaatgt agaggtcgag tttagatgca agttcaagga gcgaaggtg gatgggtagg    7380
ttatataggg atatagcaca gagatatata gcaaagagat acttttgagc aatgtttgtg    7440
gaagcggtat tcgcaatatt ttagtagctc gttacagtcc ggtgcgtttt tggttttttg    7500
aaagtgcgtc ttcagagcgc ttttggtttt caaaagcgct ctgaagttcc tatactttct    7560
agagaatagg aacttcggaa taggaacttc aaagcgtttc cgaaaacgag cgcttccgaa    7620
aatgcaacgc gagctgcgca catacagctc actgttcacg tcgcacctat atctgcgtgt    7680
tgcctgtata tatatataca tgagaagaac ggcatagtgc gtgtttatgc ttaaatgcgt    7740
```

| acttatatgc gtctatttat gtaggatgaa aggtagtcta gtacctcctg tgatattatc | 7800 |
| ccattccatg cggggtatcg tatgcttcct tcagcactac cctttagctg ttctatatgc | 7860 |
| tgccactcct caattggatt agtctcatcc ttcaatgcta tcatttcctt tgatattgga | 7920 |
| tcatattaag aaaccattat tatcatgaca ttaacctata aaaataggcg tatcacgagg | 7980 |
| ccctttcgtc | 7990 |

<210> SEQ ID NO 12
<211> LENGTH: 8167
<212> TYPE: DNA
<213> ORGANISM: Artificial Sequence
<220> FEATURE:
<223> OTHER INFORMATION: Synthetic polynucleotide

<400> SEQUENCE: 12

| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat atttttttat gcctcggtaa tgattttcat | 360 |
| ttttttttt cccctagcgg atgactcttt tttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taaagggtgg tccctagcg atagagcact | 600 |
| cgatcttccc agaaaagag gcagaagcag tagcagaaca ggccacacaa tcgcaagtga | 660 |
| ttaacgtcca cacaggtata gggtttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag cttttaaaga ggccctaggg gccgtgcgtg | 840 |
| gagtaaaaag gtttggatca ggatttgcgc ctttggatga ggcactttcc agagcggtgg | 900 |
| tagatctttc gaacaggccg tacgcagttg tcgaacttgg tttgcaaagg gagaaagtag | 960 |
| gagatctctc ttgcgagatg atcccgcatt ttcttgaaag ctttgcagag gctagcagaa | 1020 |
| ttaccctcca cgttgattgt ctgcgaggca agaatgatca tcaccgtagt gagagtgcgt | 1080 |
| tcaaggctct tgcggttgcc ataagagaag ccacctcgcc caatggtacc aacgatgttc | 1140 |
| cctccaccaa aggtgttctt atgtagtgac accgattatt taaagctgca gcatacgata | 1200 |
| tatatacatg tgtatatatg tatacctatg aatgtcagta agtatgtata cgaacagtat | 1260 |
| gatactgaag atgacaaggt aatgcatcat tctatacgtg tcattctgaa cgaggcgcgc | 1320 |
| tttcctttt tcttttgct ttttcttttt ttttctcttg aactcgacgg atctatgcgg | 1380 |
| tgtgaaatac cgcacagatg cgtaaggaga aaataccgca tcaggaaatt gtaaacgtta | 1440 |
| atattttgtt aaaattcgcg ttaaattttt gttaaatcag ctcatttttt aaccaatagg | 1500 |
| ccgaaatcgg caaaatccct tataaatcaa agaatagac cgagataggg ttgagtgttg | 1560 |
| ttccagtttg gaacaagagt ccactattaa agaacgtgga ctccaacgtc aaagggcgaa | 1620 |
| aaaccgtcta tcagggcgat ggcccactac gtgaaccatc acctaatca gttttttgg | 1680 |
| ggtcgaggtg ccgtaaagca ctaaatcgga accctaaagg gagcccccga tttagagctt | 1740 |
| gacggggaaa gccggcgaac gtggcgagaa aggaagggaa gaaagcgaaa ggagcgggcg | 1800 |

```
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaagggga tgtgctgcaa    1980 ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggag ggcgtgaatg taagcgtgac ataactaatt acatgactcg    2340
agcggccgcg gatcctcaat aaaactcttc aggcaataat ttttctgcta atttaatgtt   2400
atcagaatag tccaaaggaa cgtcaattac tactggtcca gtagtatctg ggattgattt   2460
aagaatttca gcaagttctt ctttgctgtg tgcacggtaa ccttttgctc ccattgcttc   2520
agcatatttt acgtaatcaa catagccaaa atcaacggct gctgaacgac catatttcat   2580
ttcttcttgg aatttaacca tatcataatg gccgtcattc cagataattt gaacgattgg   2640
aagattcaaa cgtacagctg tttccaactc ttgccctgtg aaaaggaagc ctccatcacc   2700
agagtgtgaa taaacttttt tacctgggcg caacaatgcg gctgtaattg cccaaggaag   2760
tgcaactcca agtgtttgca ttccgtttga gaagaggaga tgacgtggtt cgtatgattt   2820
gaaatgacgt gccatccaaa tgtagagtga acctacgtca acggttactg tttcatcatc   2880
tttaacgatt tcttggaaag tgctgaccaa atcaagaggg tgcattctac cttcttcagt   2940
attttcagta tcaaattcgt gttgctcagc aacttcatga aggccatcga gataatcttt   3000 tgttccttt ggaattttgt atccacgaac agctggtaaa agattatcca atgttgctgc     3060
gatatcacca attaattcac gttctggttg gtagtaagta tcaatttcag caatggcatt    3120
atcaataacg ataattcgac tatcaatttc tgcattccag ttacgagctt catattcaat    3180
tgggtcataa ccaacagcaa taacaaggtc agaacgtttc agaagcatat ctcctggttg    3240
attgcggaaa agaccgatac gtccataaaa agtatgttct aaatcatgtg aaataacccc    3300
tgcaccttgg aatgtttcaa cgacaggaat attaacatga gttaatagat tacgcaatga    3360
tgaagcgact ttagcatctg aagcaccagc tccaaccaaa attactggca atacagcatt    3420
tttaattgct tgtgctaaat aattaatgtc atcaatagag gcattcccca ttttagggtc    3480
tgaaagtggt tgaatggcct tgattgatac ttcggcatcc gttacatctt ggggattga    3540 taagaaagtt gcacctggat gtcctgattt tgcaatacga taagcgttgg caattgattc    3600
agaaagtgta tcagggtcaa gaacttctgc tgaatatttt gttgctgatt gcatcattcc    3660
agcattatcc attgattggt gcgcacgttt aagacggtca cttcgtttaa cttgtccacc    3720
gatagccaaa atagccatcac cttctgaagt cgcggtcaaa agcggagtcg caaggtttga   3780
tacaccaggc ccactcgtaa caactactac accaggttcg ccagtcaaac gaccaacagc    3840
ttgagccatg aaagcagctc cttgctcatg acgagtcacg accatttgag ggccttcttc    3900
attttctaat aaatcaaaaa cccggtcaat ttttgctcct ggaatcccaa atacatactt    3960
cactttatgg ttaatcaaac tatcgacaac caagttcgcc ccaaattgtt tctcagacat    4020
gtcgacaccg atatacctgt atgtgtcacc accaatgtat ctataagtat ccatgctagc    4080
cctaggttta tgtgatgatt gattgattga ttgtacagtt tgttttctt aatatctatt     4140
```

```
tcgatgactt ctatatgata ttgcactaac aagaagatat tataatgcaa ttgatacaag    4200
acaaggagtt atttgcttct cttttatatg attctgacaa tccatattgc gttggtagtc    4260 tttttttgctg aacggttca gcggaaaaga cgcatcgctc ttttttgcttc tagaagaaat   4320 gccagcaaaa gaatctcttg acagtgactg acagcaaaaa tgtcttttc taactagtaa    4380 caaggctaag atatcagcct gaaataaagg gtggtgaagt aataattaaa tcatccgtat    4440
aaacctatac acatatatga ggaaaaataa tacaaaagtg ttttaaatac agatacatac    4500
atgaacatat gcacgtatag cgcccaaatg tcggtaatgg gatcggcgag ctccagcttt    4560
tgttcccttt agtgagggtt aattgcgcgc ttggcgtaat catggtcata gctgtttcct    4620
gtgtgaaatt gttatccgct cacaattcca cacaacatag gagccggaag cataaagtgt    4680
aaagcctggg gtgcctaatg agtgaggtaa ctcacattaa ttgcgttgcg ctcactgccc    4740
gctttccagt cgggaaacct gtcgtgccag ctgcattaat gaatcggcca acgcgcgggg    4800
agaggcggtt tgcgtattgg gcgctcttcc gcttcctcgc tcactgactc gctgcgctcg    4860
gtcgttcggc tgcggcgagc ggtatcagct cactcaaagg cggtaatacg gttatccaca    4920
gaatcagggg ataacgcagg aaagaacatg tgagcaaaag gccagcaaaa ggccaggaac    4980
cgtaaaaagg ccgcgttgct ggcgtttttc cataggctcc gcccccctga cgagcatcac    5040
aaaaatcgac gctcaagtca gaggtggcga aacccgacag gactataaag ataccaggcg    5100
tttccccctg gaagctccct cgtgcgctct cctgttccga ccctgccgct taccggatac    5160
ctgtccgcct ttctcccttc gggaagcgtg gcgctttctc atagctcacg ctgtaggtat    5220
ctcagttcgg tgtaggtcgt tcgctccaag ctgggctgtg tgcacgaacc ccccgttcag    5280
cccgaccgct gcgccttatc cggtaactat cgtcttgagt ccaacccggt aagacacgac    5340
ttatcgccac tggcagcagc cactggtaac aggattagca gagcgaggta tgtaggcggt    5400
gctacagagt tcttgaagtg gtggcctaac tacggctaca ctagaaggac agtatttggt    5460
atctgcgctc tgctgaagcc agttaccttc ggaaaaagag ttggtagctc ttgatccggc    5520
aaacaaacca ccgctggtag cggtggtttt tttgtttgca agcagcagat tacgcgcaga    5580
aaaaaaggat ctcaagaaga tcctttgatc ttttctacgg ggtctgacgc tcagtggaac    5640
gaaaactcac gttaagggat tttggtcatg agattatcaa aaaggatctt cacctagatc    5700
cttttaaatt aaaaatgaag ttttaaatca atctaaagta tatatgagta aacttggtct    5760
gacagttacc aatgcttaat cagtgaggca cctatctcag cgatctgtct atttcgttca    5820
tccatagttg cctgactccc cgtcgtgtag ataactacga tacgggaggg cttaccatct    5880
ggccccagtg ctgcaatgat accgcgagac ccacgctcac cggctccaga tttatcagca    5940 ataaccagc cagccggaag ggccgagcgc agaagtggtc ctgcaacttt atccgcctcc    6000
atccagtcta ttaattgttg ccgggaagct agagtaagta gttcgccagt taatagtttg    6060
cgcaacgttg ttgccattgc tacaggcatc gtggtgtcac gctcgtcgtt tggtatggct    6120
tcattcagct ccggttccca acgatcaagg cgagttacat gatcccccat gttgtgcaaa    6180
aaagcggtta gctccttcgg tcctccgatc gttgtcagaa gtaagttggc cgcagtgtta    6240
tcactcatgg ttatggcagc actgcataat tctcttactg tcatgccatc cgtaagatgc    6300
ttttctgtga ctggtgagta ctcaaccaag tcattctgag aatagtgtat gcggcgaccg    6360
agttgctctt gcccggcgtc aatacgggat aataccgcgc cacatagcag aactttaaaa    6420
gtgctcatca ttggaaaacg ttcttcgggg cgaaaactct caaggatctt accgctgttg    6480
agatccagtt cgatgtaacc cactcgtgca cccaactgat cttcagcatc ttttactttc    6540
```

```
accagcgttt ctgggtgagc aaaaacagga aggcaaaatg ccgcaaaaaa gggaataagg    6600
gcgacacgga aatgttgaat actcatactc ttccttttc aatattattg aagcatttat    6660
cagggttatt gtctcatgag cggatacata tttgaatgta tttagaaaaa taaacaaata    6720
ggggttccgc gcacatttcc ccgaaaagtg ccacctgaac gaagcatctg tgcttcattt    6780
tgtagaacaa aaatgcaacg cgagagcgct aattttcaa acaaagaatc tgagctgcat    6840
ttttacagaa cagaaatgca acgcgaaagc gctattttac caacgaagaa tctgtgcttc    6900
atttttgtaa aacaaaatg caacgcgaga gcgctaattt tcaaacaaa gaatctgagc    6960 tgcattttta cagaacagaa atgcaacgcg agagcgctat tttaccaaca agaatctat    7020 acttctttt tgttctacaa aaatgcatcc cgagagcgct attttctaa caaagcatct    7080 tagattactt tttttctcct tgtgcgctc tataatgcag tctcttgata acttttgca    7140 ctgtaggtcc gttaaggtta agaaggct actttggtgt ctattttctc ttccataaaa    7200
aaagcctgac tccacttccc gcgtttactg attactagcg aagctgcggg tgcattttt    7260 caagataaag gcatccccga ttatattcta taccgatgtg gattgcgcat actttgtgaa    7320
cagaaagtga tagcgttgat gattcttcat tggtcagaaa attatgaacg gtttcttcta    7380
ttttgtctct atatactacg tataggaaat gtttacattt tcgtattgtt ttcgattcac    7440
tctatgaata gttcttacta caattttttt gtctaaagag taatactaga gataaacata    7500
aaaaatgtag aggtcgagtt tagatgcaag ttcaaggagc gaaaggtgga tgggtaggtt    7560
atatagggat atagcacaga gatatatagc aaagagatac ttttgagcaa tgtttgtgga    7620
agcggtattc gcaatatttt agtagctcgt tacagtccgg tgcgttttg gttttttgaa    7680 agtgcgtctt cagagcgctt ttggttttca aaagcgctct gaagttccta tactttctag    7740
agaataggaa cttcggaata ggaacttcaa agcgtttccg aaaacgagcg cttccgaaaa    7800
tgcaacgcga gctgcgcaca tacagctcac tgttcacgtc gcacctatat ctgcgtgttg    7860
cctgtatata tatatacatg agaagaacgg catagtgcgt gtttatgctt aaatgcgtac    7920
ttatatgcgt ctatttatgt aggatgaaag gtagtctagt acctcctgtg atattatccc    7980
attccatgcg gggtatcgta tgcttccttc agcactaccc tttagctgtt ctatatgctg    8040
ccactcctca attggattag tctcatcctt caatgctatc atttcctttg atattggatc    8100
atctaagaaa ccattattat catgacatta acctataaaa ataggcgtat cacgaggccc    8160
tttcgtc    8167
```

<210> SEQ ID NO 13
<211> LENGTH: 9598
<212> TYPE: DNA
<213> ORGANISM: Artificial Sequence
<220> FEATURE:
<223> OTHER INFORMATION: Synthetic polynucleotide

<400> SEQUENCE: 13

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtattttttt tttttagag aaaatcctcc aatatcaaat    360
```

```
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaacctttt aactgcatct     780 tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc tccataatct tgaagaggcc aaaagattag ctttatccaa ggaccaaata    1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttcttttacgg attttagta aaccttgttc aggtctaaca    1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat gctttaaga    1680 accttaatgg cttcggctgt gatttcttga ccaacgtggt cacctggcaa aacgacgatc   1740
ttcttagggg cagacatagg ggcagacatt agaatggtat atccttgaaa tatatata     1800 tattgctgaa atgtaaaagg taagaaaagt tagaaagtaa gacgattgct aaccaccctat   1860 tggaaaaaac aataggtcct taaataatat tgtcaacttc aagtattgtg atgcaagcat   1920
ttagtcatga acgcttctct attctatatg aaaagccggt tccggcctct cacctttcct   1980
ttttctccca atttttcagt tgaaaaggt atatgcgtca ggcgacctct gaaattaaca    2040
aaaaatttcc agtcatcgaa tttgattctg tgcgatagcg ccctgtgtg ttctcgttat    2100 gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca ttttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaattttgt    2520 taaatcagct catttttta ccaataggcc gaaatcggca aatcccctta taaatcaaaa     2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag tttttgggg tcgaggtgcc gtaaagcact aaatcggaac    2760
```

```
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc     3060
cagtcacgac gttgtaaaac gacggccagt gagcgcgcgt aatacgactc actatagggc    3120
gaattgggta ccggccgcaa attaaagcct tcgagcgtcc caaaaccttc tcaagcaagg    3180
ttttcagtat aatgttacat gcgtacacgc gtctgtacag aaaaaaaaga aaaatttgaa    3240
atataaataa cgttcttaat actaacataa ctataaaaaa ataaataggg acctagactt    3300
caggttgtct aactccttcc ttttcggtta gagcggatgt gggggggaggg cgtgaatgta   3360
agcgtgacat aactaattac atgactcgag cggccgcgga tccttaaccc cccagtttcg    3420
atttatcgcg caccgcgcct ttgtcggcgc tggttgccag gctggcataa gcacgcaggg    3480
caaaggagac ctgacgttca cgattttcg gcgtccaggc tttgtcacct cgagcgtcct     3540
gcgcttcacg acgcgccgcc agttcggcat cgcttacctg taactgaatg ccacggttcg    3600
ggatgtcgat agcgatcagg tcaccatctt caatcaggcc aatgctgccg ccgcttgccg    3660
cttccggtga gacgtggccg atggaaagac cagaggtgcc accagagaaa cgaccgtcgg    3720
tgatcagcgc acaggctttg ccgagaccca ttgatttcag gaagctggtt gggtagagca    3780
tttcctgcat cccccggaccg cctttcgggc cttcatagcg aattactacc acatctccgg   3840
cgacaacttt accgccgaga atcgcttcta ccgcatcgtc ctggctttcg tacactttcg    3900
ccgggccggt gaatttgagg atgctgtcat cgacgcctgc cgttttcacg atgcagccgt    3960
tttccgcaaa gttaccgtag agcaccgcca ggccgccgtc tttgctgtag gcgtgttcca    4020
gcgagcggat acagccattg gcgcgatcgt cgtccagcgt atcccaacgg caatcttgcg    4080
agaatgcctg tgtggtacga atgcctgcag gacctgcgcg gaacatattt tttaccgcgt    4140
catcctgggt cagcataacg tcgtattgtt ccagcgtttg cggcaacgtc aggccaagta    4200
cgtttttcac atcacggttc agtaaccccg cgcgatccag ttcgccgaga ataccgataa    4260
caccaccagc acggtgaaca tcttccatat ggtatttctg ggtgctcggc gcaactttac    4320
acagctgtgg aaccttgcgg gaaagcttat cgatatcact catggtgaag tcgatttccg    4380
cttcctgcgc cgccgccagc aggtgaagta cggtgttagt cgatccaccc atcgcgatat    4440
ccagcgtcat ggcgttttca aacgccgcct tactggcgat attgcgcggc agtgcacttt    4500
cgtcgttttg ctcgtaataa cgtttggtca attcaacaat gcgtttacca gcattaagga    4560
acagctgctt acggtcggcg tgggttgcca gcagcgagcc gttgcccggc tgcgacaggc    4620
ccagcgcttc ggtcaggcag ttcattgagt tagcggtaaa catcccggag caggaaccgc    4680
aggtcggaca cgcggaacgt tcaacctgat cgctctggga gtcagatact ttcgggtctg    4740
cgccctggat catcgcatca accagatcga gcttgatgat ctgatcggaa agtttggttt    4800
tcccggcctc catcgggccg ccggaaacaa agatcaccgg aatattcagg cgcagggaag    4860
ccatcagcat ccccggggtg attttgtcgc agttagagat gcagaccatg gcgtcggcgc    4920
agtgggcgtt gaccatatac tcaacggaat cagcgatcag ttcgcgagat ggcagtgaat    4980
aaagcatccc ccgtggccc atggcaatcc catcatccac cgcaatggtg ttgaactctt     5040
tggcaacgcc gccagccgct tcaatttgtt cggcgaccag tttaccgaga tcgcgcagat    5100
```

```
ggacgtgacc cggtacaaat tgggtgaacg agttcacaac cgcgataatc ggcttaccga    5160
aatcggcgtc ggtcattccg gtggcgcgcc acagcgcacg agcacccgcc atattacgac    5220
catgagtggt ggtggcggaa cggtacttag gcatgtcgac accatcttct tctgagatga    5280 gttttttgttc catgctagtt ctagaatccg tcgaaactaa gttctggtgt tttaaaacta    5340
aaaaaaagac taactataaa agtagaattt aagaagttta agaaatagat ttacagaatt    5400
acaatcaata cctaccgtct ttatatactt attagtcaag tagggaata atttcaggga     5460 actggtttca acctttttt tcagctttt ccaaatcaga gagagcagaa ggtaatagaa      5520
ggtgtaagaa aatgagatag atacatgcgt gggtcaattg ccttgtgtca tcatttactc    5580
caggcaggtt gcatcactcc attgaggttg tgcccgtttt ttgcctgttt gtgccctgt     5640 tctctgtagt tgcgctaaga gaatggacct atgaactgat ggttggtgaa gaaaacaata   5700
ttttggtgct gggattcttt ttttttctgg atgccagctt aaaaagcggg ctccattata    5760
tttagtggat gccaggaata aactgttcac ccagacacct acgatgttat atattctgtg    5820 taaccccgccc cctatttgg gcatgtacgg gttacagcag aattaaaagg ctaatttttt    5880
gactaaataa agttaggaaa atcactacta ttaattattt acgtattctt tgaaatggcg    5940
agtattgata atgataaact gagctagatc tgggcccgag ctccagcttt tgttccctt     6000 agtgagggtt aattgcgcgc ttggcgtaat catggtcata gctgtttcct gtgtgaaatt    6060
gttatccgct cacaattcca cacaacatag gagccggaag cataaagtgt aaagcctggg    6120
gtgcctaatg agtgaggtaa ctcacattaa ttgcgttgcg ctcactgccc gctttccagt    6180
cgggaaacct gtcgtgccag ctgcattaat gaatcggcca acgcgcgggg agaggcggtt    6240
tgcgtattgg gcgctcttcc gcttcctcgc tcactgactc gctgcgctcg gtcgttcggc    6300
tgcggcgagc ggtatcagct cactcaaagg cggtaatacg gttatccaca gaatcagggg    6360
ataacgcagg aaagaacatg tgagcaaaag gccagcaaaa ggccaggaac cgtaaaaagg    6420
ccgcgttgct ggcgtttttc cataggctcc gcccccctga cgagcatcac aaaaatcgac    6480
gctcaagtca gaggtggcga aacccgacag gactataaag ataccaggcg tttccccctg    6540
gaagctccct cgtgcgctct cctgttccga ccctgccgct taccggatac ctgtccgcct    6600
ttctcccttc gggaagcgtg cgctttctc atagctcacg ctgtaggtat ctcagttcgg    6660
tgtaggtcgt tcgctccaag ctgggctgtg tgcacgaacc ccccgttcag cccgaccgct    6720
gcgccttatc cggtaactat cgtcttgagt ccaacccggt aagacacgac ttatcgccac    6780
tggcagcagc cactggtaac aggattagca gagcgaggta tgtaggcggt gctacagagt    6840
tcttgaagtg gtgcctaac tacggctaca ctagaaggac agtatttggt atctgcgctc     6900
tgctgaagcc agttaccttc ggaaaaagag ttggtagctc ttgatccggc aaacaaacca    6960
ccgctggtag cggtggtttt tttgtttgca agcagcagat tacgcgcaga aaaaaggat     7020 ctcaagaaga tccttttgatc ttttctacgg ggtctgacgc tcagtggaac gaaaactcac   7080
gttaagggat tttggtcatg agattatcaa aaaggatctt cacctagatc cttttaaatt    7140
aaaaatgaag ttttaaatca atctaaagta tatatgagta aacttggtct gacagttacc    7200
aatgcttaat cagtgaggca cctatctcag cgatctgtct atttcgttca tccatagttg    7260
cctgactccc cgtcgtgtag ataactacga tacgggaggg cttaccatct ggccccagtg    7320
ctgcaatgat accgcgagac ccacgctcac cggctccaga tttatcagca ataaaccagc    7380
cagccggaag ggccgagcgc agaagtggtc ctgcaacttt atccgcctcc atccagtcta    7440
ttaattgttg ccgggaagct agagtaagta gttcgccagt taatagtttg cgcaacgttg    7500
```

```
ttgccattgc tacaggcatc gtggtgtcac gctcgtcgtt tggtatggct tcattcagct    7560
ccggttccca acgatcaagg cgagttacat gatccccat gttgtgcaaa aaagcggtta     7620
gctccttcgg tcctccgatc gttgtcagaa gtaagttggc cgcagtgtta tcactcatgg    7680
ttatggcagc actgcataat tctcttactg tcatgccatc cgtaagatgc ttttctgtga    7740
ctggtgagta ctcaaccaag tcattctgag aatagtgtat gcggcgaccg agttgctctt    7800
gcccggcgtc aatacgggat aataccgcgc acatagcag aactttaaaa gtgctcatca     7860
ttggaaaacg ttcttcgggg cgaaaactct caaggatctt accgctgttg agatccagtt    7920
cgatgtaacc cactcgtgca cccaactgat cttcagcatc ttttactttc accagcgttt    7980
ctgggtgagc aaaaacagga aggcaaaatg ccgcaaaaaa gggaataagg cgacacgga     8040 aatgttgaat actcatactc ttccttttc aatattattg aagcatttat cagggttatt     8100
gtctcatgag cggatacata tttgaatgta tttagaaaaa taaacaaata ggggttccgc    8160
gcacatttcc ccgaaaagtg ccacctgaac gaagcatctg tgcttcattt tgtagaacaa    8220
aaatgcaacg cgagagcgct aattttcaa acaagaatc tgagctgcat ttttacagaa     8280
cagaaatgca acgcgaaagc gctattttac caacgaagaa tctgtgcttc attttgtaa     8340 aacaaaaatg caacgcgaga gcgctaattt ttcaaacaaa gaatctgagc tgcatttta    8400 cagaacagaa atgcaacgcg agagcgctat tttaccaaca aagaatctat acttctttt     8460 tgttctacaa aaatgcatcc cgagagcgct attttctaa caaagcatct tagattactt     8520 ttttctcct ttgtgcgctc tataatgcag tctcttgata acttttttgca ctgtaggtcc    8580 gttaaggtta gaagaaggct actttggtgt ctattttctc ttccataaaa aaagcctgac   8640
tccacttccc gcgtttactg attactagcg aagctgcggg tgcatttttt caagataaag    8700 gcatcccga ttatattcta taccgatgtg gattgcgcat actttgtgaa cagaaagtga    8760
tagcgttgat gattcttcat tggtcagaaa attatgaacg gtttcttcta ttttgtctct    8820
atatactacg tataggaaat gtttacattt tcgtattgtt ttcgattcac tctatgaata    8880
gttcttacta caatttttt gtctaaagag taatactaga gataaacata aaaaatgtag    8940
aggtcgagtt tagatgcaag ttcaaggagc gaaaggtgga tgggtaggtt atatagggat    9000
atagcacaga gatatatagc aaagagatac ttttgagcaa tgtttgtgga agcggtattc    9060
gcaatatttt agtagctcgt tacagtccgg tgcgttttg gttttttgaa agtgcgtctt     9120
cagagcgctt ttggttttca aaagcgctct gaagttccta tactttctag agaataggaa   9180
cttcggaata ggaacttcaa agcgtttccg aaaacgagcg cttccgaaaa tgcaacgcga    9240
gctgcgcaca tacagctcac tgttcacgtc gcacctatat ctgcgtgttg cctgtatata    9300
tatatacatg agaagaacgg catagtgcgt gtttatgctt aaatgcgtac ttatatgcgt    9360
ctatttatgt aggatgaaag gtagtctagt acctcctgtg atattatccc attccatgcg    9420
gggtatcgta tgcttccttc agcactaccc tttagctgtt ctatatgctg ccactcctca    9480
attggattag tctcatcctt caatgctatc atttcctttg atattggatc atactaagaa    9540
accattatta tcatgacatt aacctataaa aataggcgta tcacgaggcc ctttcgtc     9598
```

<210> SEQ ID NO 14
<211> LENGTH: 8698
<212> TYPE: DNA
<213> ORGANISM: Artificial Sequence
<220> FEATURE:
<223> OTHER INFORMATION: Synthetic polynucleotide

<400> SEQUENCE: 14

```
ctgattggaa agaccattct gctttacttt tagagcatct tggtcttctg agctcattat      60
acctcaatca aaactgaaat taggtgcctg tcacggctct tttttactg tacctgtgac     120
ttcctttctt atttccaagg atgctcatca caatacgctt ctagatctat tatgcattat     180
aattaatagt tgtagctaca aaaggtaaaa gaaagtccgg ggcaggcaac aatagaaatc     240
ggcaaaaaaa actacagaaa tactaagagc ttcttcccca ttcagtcatc gcatttcgaa     300
acaagagggg aatggctctg ctagggaac taaccaccat cgcctgactc tatgcactaa      360
ccacgtgact acatatatgt gatcgttttt aacattttc aaaggctgtg tgtctggctg      420
tttccattaa ttttcactga ttaagcagtc atattgaatc tgagctcatc accaacaaga     480
aatactaccg taaagtgta aaagttcgtt taaatcattt gtaaactgga acagcaagag      540
gaagtatcat cagctagccc cataaactaa tcaaggagg atgtctacta agagttactc      600
ggaaagagca gctgctcata gaagtccagt tgctgccaag cttttaaact tgatggaaga     660
gaagaagtca aacttatgtg cttctcttga tgttcgtaaa acagcagagt tgttaagatt     720
agttgaggtt ttgggtccat atatctgtct attgaagaca catgtagata tcttggagga    780
tttcagcttt gagaatacca ttgtgccgtt gaagcaatta gcagagaaac acaagttttt    840
gatatttgaa gacaggaagt ttgccgacat tgggaacact gttaaattac aatacacgtc    900
tggtgtatac cgtatcgccg aatggtctga tatcaccaat gcacacgtg tgactggtgc      960
gggcattgtt gctggtttga agcaaggtgc cgaggaagtt acgaaagaac ctagagggtt   1020
gttaatgctt gccgagttat cgtccaaggg gtctctagcg cacggtgaat acactcgtgg   1080
gaccgtggaa attgccaaga gtgataagga ctttgttatt ggatttattg ctcaaaacga   1140
tatgggtgga agagaagagg gctacgattg gttgatcatg acgccaggtg ttggtcttga   1200
tgacaaaggt gatgctttgg gacaacaata cagaactgtg gatgaagttg ttgccggtgg   1260
atcagacatc attattgttg gtagaggtct tttcgcaaag ggaagagatc ctgtagtgga   1320
aggtgagaga tacagaaagg cgggatggga cgcttacttg aagagagtag gcagatccgc   1380
ttaagagttc tccgagaaca agcagaggtt cgagtgtact cggatcagaa gttacaagtt   1440
gatcgtttat atataaacta tacagagatg ttagagtgta atggcattgc gtgccggcga   1500
tcacagcgga cggtggtggc atgatgggc ttgcgatgct atgtttgttt gttttgtgat    1560
gatgtatatt attattgaaa acgatatca gacatttgtc tgataatgct tcattatcag    1620
acaaatgtct gatatcgttt ggagaaaaag aaaaggaaaa caaactaaat atctactata   1680
taccactgta ttttatacta atgactttct acgcctagtg tcaccctctc gtgtacccat   1740
tgaccctgta tcggcgcgtt gcctcgcgtt cctgtaccat atattttgt ttatttaggt    1800
attaaatttt actttcctca tacaaatatt aaattcacca aacttctcaa aaactaatta   1860
ttcgtagtta caaactctat tttacaatca cgtttattca accattctac atccaataac   1920
caaaatgccc atgtacctct cagcgaagtc caacggtact gtccaatatt ctcattaaat   1980
agtctttcat ctatatatca gaaggtaatt ataattagag atttcgaatc attaccgtgc   2040
cgattcgcac gctgcaacgg catgcatcac taatgaaaag catacgacgc ctgcgtctga   2100
catgcactca ttctgaagaa gattctgggc gcgtttcgtt ctcgttttcc tctgtatatt   2160
gtactctggt ggacaatttg aacataacgt cttttcacctc gccattctca ataatgggtt   2220
ccaattctat ccaggtagcg gttaattgac ggtgcttaag ccgtatgctc actctaacgc   2280
taccgttgtc caaacaacgg accccttgt gacgggtgta agacccatca tgaagtaaaa   2340
```

```
catctctaac ggtatggaaa agagtggtac ggtcaagttt cctggcacga gtcaattttc    2400
cctcttcgtg tagatcggta ccggccgcaa attaaagcct tcgagcgtcc caaaaccttc    2460
tcaagcaagg ttttcagtat aatgttacat gcgtacacgc gtctgtacag aaaaaaaaga    2520
aaaatttgaa atataaataa cgttcttaat actaacataa ctataaaaaa ataaataggg    2580
acctagactt caggttgtct aactccttcc ttttcggtta gagcggatgt gggggaggg     2640 cgtgaatgta agcgtgacat aactaattac atgagcggcc gcctatttat ggaatttctt    2700
atcataatcg accaaagtaa atctgtattt gacgtctccg ctttccatcc ttgtaaaggc    2760
atggctgacg ccttcttcgc tgatcggaag ttttcccacc catattttga cattcttttc    2820
ggaaactaat ttcaatagtt gttcgatttc cttcctagat ccgatagcac tgcttgagat    2880
tgatactccc attaggccca acggttttaa aacaagcttt tcattaactt caggagcagc    2940
aattgaaacg atggagcctc caatcttcat aatcttaacg atactgtcaa aattaacttt    3000
cgacaaagat gatgagcaaa cgacaagaag gtccaaagcg ttagagtatt gttctgtcca    3060
gcctttatcc tccaacatag caatatagtg atcagcaccg agtttcatag aatcctcccg    3120
cttggagtgg cctcgcgaaa acgcataaac ctcggctccc atagctttag ccaacagaat    3180
ccccatatgc ccaataccac cgatgccaac aatacctacc ctcttacctg gaccacagcc    3240
atttcttagt agtggagaga aaactgtaat accaccacac aataatggag cggctagcgg    3300
acttggaata ttttctggta tttgaatagc aaagtgttca tgaagcctca cgtgggaggc    3360
aaagcctcct tgtgaaatgt agccgtcctt gtaaggagtc cacatagtca aaacgtggtc    3420
attggtacag tattgctcgt tgtcactttt gcaacgttca cactcaaaac acgccaaggc    3480
ttgggcacca acaccaacac ggtcaccgat ttttaccccca gtgtggcact tggatccaac    3540
cttcaccacg cggccaatta tttcatgtcc aaggatttga ttttctggga ctggacccca    3600
attaccaacg gctatatgaa atcagatcc gcagatacca caggcttcaa tttcaacatc    3660
aacgtcatga tcgccaaagg gttttgggtc aaaactcact aatttaggat gcttccaatc    3720
ctttgcgttg gaaataccga tgccctgaaa tttttctggg taaagcatgt cgagtcgaaa    3780
ctaagttctg gtgttttaaa actaaaaaaa agactaacta taaagtaga atttaagaag     3840 tttaagaaat agatttacag aattacaatc aatacctacc gtctttatat acttattagt    3900
caagtagggg aataatttca gggaactggt ttcaaccttt tttttcagct ttttccaaat    3960
cagagagagc agaaggtaat agaaggtgta agaaaatgag atagatacat gcgtgggtca    4020
attgccttgt gtcatcattt actccaggca ggttgcatca ctccattgag gttgtgcccg    4080 tttttttgcct gtttgtgccc ctgttctctg tagttgcgct aagagaatgg acctatgaac    4140
tgatggttgg tgaagaaaac aatattttgg tgctgggatt ctttttttt ctggatgcca    4200 gcttaaaaag cgggctccat tatatttagt ggatgccagg aataaactgt tcacccagac    4260
acctacgatg ttatatattc tgtgtaaccc gcccctatt ttgggcatgt acggttaca     4320 gcagaattaa aaggctaatt ttttgactaa ataaagttag gaaaatcact actattaatt    4380
atttacgtat tcttttgaaat ggcgagtatt gataatgata aactggatcc ttaggattta    4440
ttctgttcag caaacagctt gcccatttc ttcagtacct tcggtgcgcc ttctttcgcc     4500
aggatcagtt cgatccagta catacggttc ggatcggcct gggcctcttt catcacgctc    4560
acaaattcgt tttcggtacg cacaatttta gacacaacac ggtcctcagt tgcgccgaag    4620
gactccggca gtttagagta gttccacata gggatatcgt tgtaagactg gttcggaccg    4680
```

```
tggatctcac gctcaacggt gtagccgtca ttgttaataa tgaagcaaat cgggttgatc      4740 tttttcacgaa ttgccagacc cagttcctgt acggtcagct gcagggaacc gtcaccgatg     4800
aacagcagat gacgagattc tttatcagcg atctgagagc ccagcgctgc cgggaaagta     4860
tagccaatgc tacccacag cggctgaccg ataaaatggc ttttggattt cagaaagata      4920
gaagacgcgc cgaaaaagct cgtaccttgt tccgccacga tggtttcatt gctctgggtc     4980
aggttctcca cggcctgcca caggcgatcc tgggacagca gtgcgttaga tggtacgaaa     5040
tcttcttgct ttttgtcaat gtatttgcct ttatactcga tttcggacag gtccagcaga     5100
gagctgatca ggcttttcgaa gtcgaagttc tggatacgct cgttgaagat tttaccctcg    5160
tcgatgttca ggctaatcat tttgttttcg ttcagatggt gagtgaatgc accggtagaa    5220
gagtcggtca gtttaacgcc cagcatcagg atgaagtccg cagattcaac aaattctttc     5280
aggttcggtt cgctcagagt accgttgtag atgcccagga agacggcag agcctcgtca      5340 acagaggact tgccgaagtt cagggtggta atcggcagtt tggttttgct gatgaattgg     5400
gtcacggtct tctccagacc aaaagaaatg atttcgtggc cggtgatcac gattggtttc    5460
tttgcgtttt tcagagactc ctggattttg ttcaggattt cctggtcgct agtgttagaa    5520
gtggagtttt ctttcttcag cggcaggctc ggttttccg ctttagctgc cgcaacatcc      5580
acaggcaggt tgatgtaaac tggtttgcgt tctttcagca gcgcagacag aacgcggtcg    5640 attttccacag tagcgttctc tgcagtcagc agcgtacgtg ccgcagtcac aggttcatgc    5700 atttcatga agtgtttgaa atcgccgtca gccagagtgt ggtggacgaa tttaccttcg     5760
ttctgaactt tgctcgttgg gctgcctacg atctccacca ccggcaggtt ttcggcgtag    5820
gagcccgcca accgttgac ggcgctcagt tcgccaacac cgaaagtggt cagaaatgcc      5880
gcggctttct tggtacgtgc ataaccatct gccatgtagc ttgcgttcag ttcgttagcg    5940
ttacccaccc atttcatgtc tttatgagag atgatctgat ccaggaactg cagattgtaa    6000
tcacccggaa cgccgaagat ttcttcgata cccagttcat gcagacggtc cagcagataa    6060
tcaccaacag tatacatgtc gacaaactta gattagattg ctatgctttc tttctaatga    6120
gcaagaagta aaaaaagttg taatagaaca agaaaaatga aactgaaact tgagaaattg    6180
aagaccgttt attaacttaa atatcaatgg gaggtcatcg aaagagaaaa aaatcaaaaa    6240
aaaaattttc aagaaaaaga aacgtgataa aaattttat tgcctttttc gacgaagaaa    6300
aagaaacgag gcggtctctt ttttctttc caaaccttta gtacgggtaa ttaacgacac     6360
cctagaggaa gaaagagggg aaatttagta tgctgtgctt gggtgttttg aagtggtacg    6420
gcgatgcgcg gagtccgaga aaatctggaa gagtaaaaaa ggagtagaaa catttttgaag   6480 ctatgagctc cagcttttgt tcccttttagt gagggttaat tgcgcgcttg gcgtaatcat    6540
ggtcatagct gtttcctgtg tgaaattgtt atccgctcac aattccacac aacataggag    6600
ccggaagcat aaagtgtaaa gcctggggtg cctaatgagt gaggtaactc acattaattg    6660
cgttgcgctc actgcccgct ttccagtcgg gaaacctgtc gtgccagctg cattaatgaa    6720
tcggccaacg cgcggggaga ggcggtttgc gtattgggcg ctcttccgct tcctcgctca    6780
ctgactcgct gcgctcggtc gttcggctgc ggcgagcggt atcagctcac tcaaaggcgg    6840
taatacggtt atccacagaa tcaggggata acgcaggaaa gaacatgtga gcaaaaggcc    6900
agcaaaaggc caggaaccgt aaaaaggccg cgttgctggc gtttttccat aggctccgcc    6960
cccctgacga gcatcacaaa aatcgacgct caagtcagag gtggcgaaac ccgacaggac    7020
tataaagata ccaggcgttt ccccctggaa gctccctcgt gcgctctcct gttccgaccc    7080
```

```
tgccgcttac cggatacctg tccgcctttc tcccttcggg aagcgtggcg ctttctcata    7140
gctcacgctg taggtatctc agttcggtgt aggtcgttcg ctccaagctg ggctgtgtgc    7200
acgaaccccc cgttcagccc gaccgctgcg ccttatccgg taactatcgt cttgagtcca    7260
acccggtaag acacgactta tcgccactgg cagcagccac tggtaacagg attagcagag    7320
cgaggtatgt aggcggtgct acagagttct tgaagtggtg gcctaactac ggctacacta    7380
gaaggacagt atttggtatc tgcgctctgc tgaagccagt taccttcgga aaaagagttg    7440
gtagctcttg atccggcaaa caaaccaccg ctggtagcgg tggttttttt gtttgcaagc    7500
agcagattac gcgcagaaaa aaggatctc aagaagatcc tttgatcttt tctacggggt    7560
ctgacgctca gtggaacgaa aactcacgtt aagggatttt ggtcatgaga ttatcaaaaa    7620
ggatcttcac ctagatcctt ttaaattaaa aatgaagttt taaatcaatc taaagtatat    7680
atgagtaaac ttggtctgac agttaccaat gcttaatcag tgaggcacct atctcagcga    7740
tctgtctatt tcgttcatcc atagttgcct gactccccgt cgtgtagata actacgatac    7800
gggagggctt accatctggc cccagtgctg caatgatacc gcgagaccca cgctcaccgg    7860
ctccagattt atcagcaata aaccagccag ccggaagggc cgagcgcaga agtggtcctg    7920
caactttatc cgcctccatc cagtctatta attgttgccg ggaagctaga gtaagtagtt    7980
cgccagttaa tagtttgcgc aacgttgttg ccattgctac aggcatcgtg gtgtcacgct    8040
cgtcgtttgg tatggcttca ttcagctccg gttcccaacg atcaaggcga gttacatgat    8100
cccccatgtt gtgcaaaaaa gcggttagct ccttcggtcc tccgatcgtt gtcagaagta    8160
agttggccgc agtgttatca ctcatggtta tggcagcact gcataattct cttactgtca    8220
tgccatccgt aagatgcttt tctgtgactg gtgagtactc aaccaagtca ttctgagaat    8280
agtgtatgcg gcgaccgagt tgctcttgcc cggcgtcaat acgggataat accgcgccac    8340
atagcagaac tttaaaagtg ctcatcattg gaaaacgttc ttcggggcga aaactctcaa    8400
ggatcttacc gctgttgaga tccagttcga tgtaacccac tcgtgcaccc aactgatctt    8460
cagcatcttt tactttcacc agcgtttctg ggtgagcaaa aacaggaagg caaaatgccg    8520
caaaaaaggg aataagggcg acacggaaat gttgaatact catactcttc cttttcaat     8580 attattgaag catttatcag ggttattgtc tcatgagcgg atacatattt gaatgtattt    8640
agaaaaataa acaaataggg gttccgcgca catttccccg aaaagtgcca cctgacgt     8698
```

<210> SEQ ID NO 15
<211> LENGTH: 6012
<212> TYPE: DNA
<213> ORGANISM: Artificial Sequence
<220> FEATURE:
<223> OTHER INFORMATION: Synthetic polynucleotide

<400> SEQUENCE: 15

```
caggcaagtg cacaaacaat acttaaataa atactactca gtaataaccct atttcttagc      60 attttttgacg aaatttgcta ttttgttaga gtcttttaca ccatttgtct ccacacctcc     120
gcttacatca acaccaataa cgccatttaa tctaagcgca tcaccaacat tttctggcgt     180
cagtccacca gctaacataa aatgtaagct ttcggggctc tcttgccttc caacccagtc     240
agaaatcgag ttccaatcca aaagttcacc tgtcccacct gcttctgaat caaacaaggg     300
aataaacgaa tgaggtttct gtgaagctgc actgagtagt atgttgcagt cttttggaaa     360
tacgagtctt ttaataactg gcaaaccgag gaactcttgg tattcttgcc acgactcatc     420
```

```
tccatgcagt tggacgatat caatgccgta atcattgacc agagccaaaa catcctcctt      480
aggttgatta cgaaacacgc caaccaagta tttcggagtg cctgaactat ttttatatgc      540
ttttacaaga cttgaaattt tccttgcaat aaccgggtca attgttctct ttctattggg      600
cacacatata atacccagca agtcagcatc ggaatctaga gcacattctg cggcctctgt      660
gctctgcaag ccgcaaactt tcaccaatgg accagaacta cctgtgaaat taataacaga      720
catactccaa gctgcctttg tgtgcttaat cacgtatact cacgtgctca atagtcacca      780
atgccctccc tcttggccct ctccttttct tttttcgacc gaattaattc ttaatcggca      840 aaaaagaaa agctccggat caagattgta cgtaaggtga caagctattt ttcaataaag       900
aatatcttcc actactgcca tctggcgtca taactgcaaa gtacacatat attacgatgc      960
tgtctattaa atgcttccta tattatatat atagtaatgt cgttgacgtc gccggcgaac     1020
gtggcgagaa aggaagggaa gaaagcgaaa ggagcgggcg ctagggcgct ggcaagtgta     1080
gcggtcacgc tgcgcgtaac caccacaccc gccgcgctta atgcgccgct acagggcgcg     1140
tcgcgccatt cgccattcag gctgcgcaac tgttgggaag ggcgatcggt gcgggcctct     1200
tcgctattac gccagctggc gaaaggggga tgtgctgcaa ggcgattaag ttgggtaacg     1260
ccagggtttt cccagtcacg acgttgtaaa acgacggcca gtgagcgcgc gtaatacgac     1320
tcactatagg gcgaattggg taccggccgc aaattaaagc cttcgagcgt cccaaaacct     1380
tctcaagcaa ggttttcagt ataatgttac atgcgtacac gcgtctgtac agaaaaaaaa     1440
gaaaaatttg aaatataaat aacgttctta atactaacat aactataaaa aataaaatag     1500
ggacctagac ttcaggttgt ctaactcctt ccttttcggt tagagcggat gtgggggag      1560 ggcgtgaatg taagcgtgac ataactaatt acatgactcg agcggccgcg gatccctaga     1620
gagctttcgt tttcatgagt tccccgaatt ctttcggaag cttgtcactt gctaaattaa     1680
cgttatcact gtagtcaacc gggacatcaa tgatgacagg cccctcagcg ttcatgcctt     1740
gacgcagaac atctgccagc tggtctggtg attctacgcg taagccagtt gctccgaagc     1800
tttccgcgta tttcacgata tcgatatttc cgaaatcgac cgcagatgta cgattatatt     1860
ttttcaattg ctggaatgca accatgtcat atgtgctgtc gttccataca atgtgtacaa     1920
ttggtgcttt taaacgaact gctgtctcta attccatagc tgagaataag aaaccgccat     1980
caccggagac tgatactact ttttctcccg gtttcaccaa tgaagcgccg attgcccaag     2040
gaagcgcaac gccgagtgtt tgcataccgt tactaatcat taatgttaac ggctcgtagc     2100
tgcggaaata acgtgacatc caaatcgcgt gtgaaccgat atcgcaagtc actgtaaacat    2160 gatcatcgac tgcgtttcgc aattctttaa cgatttcaag aggatgcact ctgtctgatt     2220
tccaatctgc aggcacctgc tcaccctcat gcatatattg ttttaaatca gaaaggatct     2280
tctgctcacg ttccgcaaag tctactttca cagcatcgtg ttcgatatga ttgatcgtag     2340
atggaatatc accgatcagt tcaagatccg gctggtaagc atgatcaatg tcagccagaa     2400
tctcgtctaa atggatgatc gtccggtctc cattgacatt ccagaatttc ggatcatatt     2460
caattgggtc atagccgatt gtcagaacaa catcagcctg ctcaagcagc agatcgccag     2520
gctggttgcg gaataaaccg atccggccaa aatactgatc ctctaaatct ctcgtaagag     2580
taccggcagc ttgatatgtt tcaacgaatg gaagctgcac ttttttcaat agcttgcgaa     2640
ccgctttaat cgcttccggt cttccgccct tcatgccgac taaaacgaca ggaagttttg     2700
ctgtttgaat ttttgcaatg ccatactgat ttgcgtcatc tgctgcggga ccaagttttg     2760
gcgctgcgac agcacgtacg tttttttgtat ttgtgacttc attcacaaca tcttgcggaa    2820
```

-continued

```
aactcacaaa agcggcccca gcctgccctg ctgacgctat cctaaacgca tttgtaacag    2880
cttccggtat attttttaca tcttgaactt ctacactgta ttttgtaatc ggctggaata    2940
gcgccgcatt atccaaagat tgatgtgtcc gttttaaacg atctgcacgg atcacgttcc    3000
cagcaagcgc aacgacaggg tcaccttcag tgtttgctgt cagcagtcct gttgccaagt    3060
tcgaagcacc tggtcctgat gtgactaaca cgactcccgg ttttccagtt aaacggccga    3120
ctgcttgcgc cataaatgct gcattttgtt catgccgggc aacgataatt tcaggccctt    3180
tatcttgtaa agcgtcaaat accgcatcaa ttttttgcacc tggaatgcca aatacatgtg    3240
tgacaccttg ctccgctaag caatcaacaa caagctccgc ccctctgctt ttcacaaggg    3300 attttttgttc ttttgttgct tttgtcaaca tgtcgacttt atgtgatgat tgattgattg    3360
attgtacagt ttgttttttct taatatctat ttcgatgact tctatatgat attgcactaa    3420
caagaagata ttataatgca attgatacaa gacaaggagt tatttgcttc tcttttatat    3480
gattctgaca atccatattg cgttggtagt cttttttgct ggaacggttc agcggaaaag    3540
acgcatcgct ctttttgctt ctagaagaaa tgccagcaaa agaatctctt gacagtgact    3600
gacagcaaaa atgtctttttt ctaactagta acaaggctaa gatatcagcc tgaaataaag    3660
ggtggtgaag taataattaa atcatccgta taaacctata cacatatatg aggaaaaata    3720
atacaaaagt gttttaaata cagatacata catgaacata tgcacgtata gcgcccaaat    3780
gtcggtaatg ggatcggcga gctccagctt ttgttcccctt tagtgagggt taattgcgcg    3840
cttggcgtaa tcatggtcat agctgttttcc tgtgtgaaat tgttatccgc tcacaattcc    3900
acacaacata ggagccggaa gcataaagtg taaagcctgg ggtgcctaat gagtgaggta    3960
actcacatta attgcgttgc gctcactgcc cgctttccag tcgggaaacc tgtcgtgcca    4020
gctgcattaa tgaatcggcc aacgcgcggg gagaggcggt ttgcgtattg ggcgctcttc    4080
cgcttcctcg ctcactgact cgctgcgctc ggtcgttcgg ctgcggcgag cggtatcagc    4140
tcactcaaag gcggtaatac ggttatccac agaatcaggg gataacgcag gaaagaacat    4200
gtgagcaaaa ggccagcaaa aggccaggaa ccgtaaaaag gccgcgttgc tggcgttttt    4260
ccataggctc cgccccccctg acgagcatca caaaaatcga cgctcaagtc agaggtggcg    4320
aaacccgaca ggactataaa gataccaggc gtttccccct ggaagctccc tcgtgcgctc    4380
tcctgttccg accctgccgc ttaccggata cctgtccgcc tttctccctt cgggaagcgt    4440
ggcgctttct catagctcac gctgtaggta tctcagttcg gtgtaggtcg ttcgctccaa    4500
gctgggctgt gtgcacgaac ccccccgttca gcccgaccgc tgcgccttat ccggtaacta    4560
tcgtcttgag tccaacccgg taagacacga cttatcgcca ctggcagcag ccactggtaa    4620
caggattagc agagcgaggt atgtaggcgg tgctacagag ttcttgaagt ggtggcctaa    4680
ctacggctac actagaagga cagtatttgg tatctgcgct ctgctgaagc cagttacctt    4740
cggaaaaaga gttggtagct cttgatccgg caaacaaacc accgctggta gcggtggttt    4800
ttttgtttgc aagcagcaga ttacgcgcag aaaaaaagga tctcaagaag atcctttgat    4860
cttttctacg gggtctgacg ctcagtggaa cgaaaactca cgttaaggga ttttggtcat    4920
gagattatca aaaaggatct tcacctagat ccttttaaat taaaaatgaa gttttaaatc    4980
aatctaaagt atatatgagt aaacttggtc tgacagttac caatgcttaa tcagtgaggc    5040
acctatctca gcgatctgtc tatttcgttc atccatagtt gcctgactcc ccgtcgtgta    5100
gataactacg atacgggagg gcttaccatc tggccccagt gctgcaatga taccgcgaga    5160
```

| | |
|---|---|
| cccacgctca ccggctccag atttatcagc aataaaccag ccagccggaa gggccgagcg | 5220 |
| cagaagtggt cctgcaactt tatccgcctc catccagtct attaattgtt gccgggaagc | 5280 |
| tagagtaagt agttcgccag ttaatagttt gcgcaacgtt gttgccattg ctacaggcat | 5340 |
| cgtggtgtca cgctcgtcgt ttggtatggc ttcattcagc tccggttccc aacgatcaag | 5400 |
| gcgagttaca tgatccccca tgttgtgcaa aaaagcggtt agctccttcg gtcctccgat | 5460 |
| cgttgtcaga gtaagttgg ccgcagtgtt atcactcatg gttatggcag cactgcataa | 5520 |
| ttctcttact gtcatgccat ccgtaagatg cttttctgtg actggtgagt actcaaccaa | 5580 |
| gtcattctga gaatagtgta tgcggcgacc gagttgctct gcccggcgt caatacggga | 5640 |
| taataccgcg ccacatagca gaactttaaa agtgctcatc attggaaaac gttcttcggg | 5700 |
| gcgaaaactc tcaaggatct taccgctgtt gagatccagt tcgatgtaac ccactcgtgc | 5760 |
| acccaactga tcttcagcat cttttacttt caccagcgtt tctgggtgag caaaaacagg | 5820 |
| aaggcaaaat gccgcaaaaa agggaataag ggcgacacgg aaatgttgaa tactcatact | 5880 |
| cttcctttt caatattatt gaagcattta tcagggttat tgtctcatga gcggatacat | 5940 |
| atttgaatgt atttagaaaa ataaacaaat aggggttccg cgcacatttc cccgaaaagt | 6000 |
| gccacctgac gt | 6012 |

<210> SEQ ID NO 16
<211> LENGTH: 8969
<212> TYPE: DNA
<213> ORGANISM: Artificial Sequence
<220> FEATURE:
<223> OTHER INFORMATION: Synthetic polynucleotide

<400> SEQUENCE: 16

| | |
|---|---|
| ccagttaact gtgggaatac tcaggtatcg taagatgcaa gagttcgaat ctcttagcaa | 60 |
| ccattatttt tttcctcaac ataacgagaa cacacagggg cgctatcgca cagaatcaaa | 120 |
| ttcgatgact ggaaattttt tgttaatttc agaggtcgcc tgacgcatat accttttca | 180 |
| actgaaaaat tgggagaaaa aggaaaggtg agagcgccgg aaccggcttt tcatatagaa | 240 |
| tagagaagcg ttcatgacta aatgcttgca tcacaatact tgaagttgac aatattattt | 300 |
| aaggacctat tgttttttcc aataggtggt tagcaatcgt cttactttct aacttttctt | 360 |
| acctttaca tttcagcaat atatatat atatttcaag gatataccat tctaatgtct | 420 |
| gccccctaaga agatcgtcgt tttgccaggt gaccacgttg gtcaagaaat cacagccgaa | 480 |
| gccattaagg ttcttaaagc tatttctgat gttcgttcca atgtcaagtt cgatttcgaa | 540 |
| aatcatttaa ttggtggtgc tgctatcgat gctacaggtg ttccacttcc agatgaggcg | 600 |
| ctggaagcct ccaagaaggc tgatgccgtt ttgttaggtg ctgtgggtgg tcctaaatgg | 660 |
| ggtaccggta gtgttagacc tgaacaaggt ttactaaaaa tccgtaaaga acttcaattg | 720 |
| tacgccaact taagaccatg taacttttgca tccgactctc ttttagactt atctccaatc | 780 |
| aagccacaat ttgctaaagg tactgacttc gttgttgtca gagaattagt gggaggtatt | 840 |
| tactttggta agagaaagga agacgatggt gatggtgtcg cttgggatag tgaacaatac | 900 |
| accgttccag aagtgcaaag aatcacaaga atggccgctt tcatgccct acaacatgag | 960 |
| ccaccattgc ctatttggtc cttggataaa gctaatgttt tggcctcttc aagattatgg | 1020 |
| agaaaaactg tggaggaaac catcaagaac gaattcccta cattgaaggt tcaacatcaa | 1080 |
| ttgattgatt ctgccgccat gatcctagtt aagaacccaa cccacctaaa tggtattata | 1140 |
| atcaccagca acatgtttgg tgatatcatc tccgatgaag cctccgttat cccaggttcc | 1200 |

```
ttgggtttgt tgccatctgc gtccttggcc tctttgccag acaagaacac cgcatttggt    1260
ttgtacgaac catgccacgg ttctgctcca gatttgccaa agaataaggt caaccctatc    1320
gccactatct tgtctgctgc aatgatgttg aaattgtcat tgaacttgcc tgaagaaggt    1380
aaggccattg aagatgcagt taaaaaggtt ttggatgcag gtatcagaac tggtgattta    1440
ggtggttcca acagtaccac cgaagtcggt gatgctgtcg ccgaagaagt taagaaaatc    1500
cttgcttaaa aagattctct tttttttatga tatttgtaca taaactttat aaatgaaatt    1560
cataatagaa acgacacgaa attacaaaat ggaatatgtt cataggtag acgaaactat     1620 atacgcaatc tacatacatt tatcaagaag gagaaaaagg aggatgtaaa ggaatacagg    1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860
aaaacactca atgacctgac catttgatgg agttgccggc gaacgtggcg agaaaggaag    1920
ggaagaaagc gaaaggagcg ggcgctaggg cgctggcaag tgtagcggtc acgctgcgcg    1980
taaccaccac acccgccgcg cttaatgcgc cgctacaggg cgcgtcgcgc cattcgccat    2040
tcaggctgcg caactgttgg gaagggcgat cggtgcgggc ctcttcgcta ttacgccagc    2100
tggcgaaagg gggatgtgct gcaaggcgat taagttgggt aacgccaggg ttttcccagt    2160
cacgacgttg taaaacgacg gccagtgagc gcgcgtaata cgactcacta tagggcgaat    2220
tgggtaccgg ccgcaaatta aagccttcga gcgtcccaaa accttctcaa gcaaggtttt    2280
cagtataatg ttacatgcgt acacgcgtct gtacagaaaa aaagaaaaa tttgaaatat     2340 aaataacgtt cttaatacta acataactat aaaaaaataa atagggacct agacttcagg    2400
ttgtctaact ccttcctttt cggttagagc ggatgtgggg ggagggcgtg aatgtaagcg    2460
tgacataact aattacatga gcggccgcag atctttaacc cgcaacagca atacgtttca    2520
tatctgtcat atagccgcgc agtttcttac ctacctgctc aatcgcatgg ctgcgaatcg    2580
cttcgttcac atcacgcagt tgcccgttat ctaccgcgcc ttccggaata gctttaccca    2640
ggtcgcccgg ttgcagctct gccataaacg gtttcagcaa cggcacacaa gcgtaagaga    2700
acagatagtt accgtactca gcggtatcag agataaccac gttcatttcg tacagacgct    2760
tacgggcgat ggtgttggca atcagcggca gctcgtgcag tgattcataa tatgcagact    2820
cttcaatgat gccggaatcg accatggttt cgaacgccag ttcaacgccc gctttcacca    2880
tcgcaatcat cagtacgcct ttatcgaagt actcctgctc gccgattttg ccttcatact    2940
gcggcgcggt ttcaaacgcg gttttgccgg tctcttcacg ccaggtcagc agtttcttat    3000
catcgttggc ccagtccgcc atcataccgg aagagaattc gccggagatg atgtcgtcca    3060
tatgtttctg gaacaggggt gccatgatct ctttcagctg ttcagaaagc gcataagcac    3120
gcagtttcgc cgggttagag agacggtcca tcatcgggt gatgccgccc tgtttcagtg     3180
cttcggtgat ggtttcccaa ccgaactgaa tcagtttttc tgcgtatgct ggatcggtac    3240
cttcttccac cagcttgtcg aagcacagca gagagccagc ctgcaacata ccgcacagga    3300
tggtttgctc gcccatcagg tcagatttca cttccgcaac gaaggacgat tccagcacac    3360
ccgcacggtg accaccggtt gcagccgccc aggctttggc aatcgccatg ccttcgcctt    3420
tcggatcgtt ttccgggtga acggcaatca gcgtcggtac gccgaaccca cgtttgtact    3480
cttcacgcac ttcggtgcct gggcatttcg gcgcaaccat cactacggtg atatctttac    3540
```

```
ggatctgctc gcccacttcg acgatgttga aaccgtgcga gtagcccagc gccgcgccgt    3600
ctttcatcag tggctgtacg gtgcgcacta catcagagtg ctgcttgtcc ggcgtcaggt    3660
taatcaccag atccgcctgt gggatcagtt cttcgtaagt acccacttta aaaccatttt    3720
cggtcgcttt acgccaggac gcgcgcttct cggcaatcgc ttctttacgc agagcgtagg    3780
agatatcgag accagaatca cgcatgttca ggccctggtt cagaccctgt gcgccacagc    3840
cgacgatgac tacttttta ccctgaaggt agctcgcgcc atcggcgaat tcatcgcggc    3900
ccatctcgag tcgaaactaa gttctggtgt tttaaaacta aaaaaagac taactataaa     3960 agtagaattt aagaagttta agaaatagat ttacagaatt acaatcaata cctaccgtct    4020
ttatatactt attagtcaag taggggaata atttcaggga actggtttca acctttttt     4080 tcagcttttt ccaaatcaga gagagcagaa ggtaatagaa ggtgtaagaa aatgagatag    4140
atacatgcgt gggtcaattg ccttgtgtca tcatttactc caggcaggtt gcatcactcc    4200
attgaggttg tgcccgtttt ttgcctgttt gtgcccctgt tctctgtagt tgcgctaaga    4260
gaatggacct atgaactgat ggttggtgaa gaaaacaata ttttggtgct gggattcttt    4320 tttttctgg atgccagctt aaaaagcggg ctccattata tttagtggat gccaggaata     4380
aactgttcac ccagacacct acgatgttat atattctgtg taacccgccc cctattttgg    4440
gcatgtacgg gttacagcag aattaaaagg ctaatttttt gactaaataa agttaggaaa    4500
atcactacta ttaattattt acgtattctt tgaaatggcg agtattgata atgataaact    4560
ggatcctcat ccacccaact tcgatttgtc tcttactgcc cccttatcgg ctgaagtagc    4620
caatgaagca taagccctaa gggcgaaact tacttgacgt tctctatttt taggagtcca    4680
agccttatct cctctggcat cttgtgcttc tcttcttgca gccaattcag cgtctgagac    4740
ttgtaattgg atacctctat ttgggatatc tatggcgatc aaatctccat cttcaatcaa    4800
tccaatcgaa ccaccagaag ctgcctctgg tgatacgtga ccgatactta aacccgaagt    4860
gccaccagag aatctaccgt cagtgataag ggcacaagct tttcctagtc ccatggactt    4920
caaaaatgaa gttgggtaaa gcatttcctg catacctggt cctccctttg gtccctcata    4980
tcttatcact accacgtctc ctgctaccac ctttccgcca agtatagcct caacagcatc    5040
gtcttgactt tcgtaaactt tagcgggtcc agtaaatttc aaaatactat catctacacc    5100
agcagttttc acaatgcaac cattttcagc gaagtttcca tataatactg ctaaaccacc    5160
atccttacta taagcatgct caagcgatct tatacatcca tttgctctat catcgtccaa    5220
agtgtcccac ctacagtctt gcgagaatgc ttgggtggtt ctgatccctg ctggacctgc    5280
cctgaacatg ttttcacgg catcatcttg agttaacatg acatcgtatt gctctaatgt     5340
ctgtggaagt gttaaaccca atacattctt cacatccctg tttaaaagac cggctctgtc    5400
caactcccct aaaataccaa taacccctcc tgcacgatga acgtcttcca tgtgatactt    5460
ttgagttgat ggtgcaacct tacataactg tggaacctta cgtgaaagct tgtcgatatc    5520
agacatggtg aaatctatct cagcttcttg ggctgcagct agaagatgta agaccgtgtt    5580
tgtactacca cccattgcaa tatccaatgt catggcattt tcgaatgcag cctttgaagc    5640
tatattcctc ggtaatgctg attcatcatt ttgttcgtaa tacctttcg ttagttccac     5700 aattcttttt ccggcattta agaacaattg ctttctgtct gcatgggtcg ctaataatga    5760
accatttcct ggttgagata aacctagagc ttcagtcaag caattcatag agttagccgt    5820
gaacattcca ctgcaagaac cacaagttgg acatgcactt ctttcaactt ggtctgactg    5880
cgagtctgaa acttttggat ctgcaccttg aatcattgca tccacaagat caagtttgat    5940
```

```
gatctgatca cttaacttag ttttaccagc ctccattggg ccgccagata cgaagattac   6000
tgggatgttc aatctcaagg acgccatcaa cataccaggc gttatcttat cacaattaga   6060
gatacaaacc attgcatcgg cacaatgagc attaaccata tattcgactg agtctgcaat   6120
taattctctc gatggtaaag agtataacat accgccatgc cccatagcta taccgtcgtc   6180
cacagcaata gtattaaact cttttgcgac accacctgca gcttcaattt gttcggcaac   6240
aagcttacct agatcacgca aatggacatg acccggaacg aattgtgtaa aagagttgac   6300
gacggcaatg attggctttc cgaaatctgc atcagtcatg ccagtcatgt cgacaaactt   6360
agattagatt gctatgcttt ctttctaatg agcaagaagt aaaaaaagtt gtaatagaac   6420
aagaaaaatg aaactgaaac ttgagaaatt gaagaccgtt tattaactta aatatcaatg   6480
ggaggtcatc gaaagagaaa aaatcaaaa aaaaattttt caagaaaaag aaacgtgata   6540
aaaattttta ttgccttttt cgacgaagaa aaagaaacga ggcggtctct ttttctttt   6600
ccaaaccttt agtacgggta attaacgaca ccctagagga agaaagaggg gaaatttagt   6660
atgctgtgct tgggtgtttt gaagtggtac ggcgatgcgc ggagtccgag aaaatctgga   6720
agagtaaaaa aggagtagaa acattttgaa gctatgagct ccagcttttg ttccctttag   6780
tgagggttaa ttgcgcgctt ggcgtaatca tggtcatagc tgtttcctgt gtgaaattgt   6840
tatccgctca caattccaca caacatagga gccggaagca taagtgtaa agcctggggt   6900
gcctaatgag tgaggtaact cacattaatt gcgttgcgct cactgcccgc tttccagtcg   6960
ggaaacctgt cgtgccagct gcattaatga atcggccaac gcgcggggag aggcggtttg   7020
cgtattgggc gctcttccgc ttcctcgctc actgactcgc tgcgctcggt cgttcggctg   7080
cggcgagcgg tatcagctca ctcaaaggcg gtaatacggt tatccacaga atcaggggat   7140
aacgcaggaa agaacatgtg agcaaaaggc cagcaaaagg ccaggaaccg taaaaaggcc   7200
gcgttgctgg cgttttttcca taggctccgc cccctgacg agcatcacaa aaatcgacgc   7260
tcaagtcaga ggtggcgaaa cccgacagga ctataaagat accaggcgtt tccccctgga   7320
agctccctcg tgcgctctcc tgttccgacc ctgccgctta ccggatacct gtccgccttt   7380
ctcccttcgg gaagcgtggc gctttctcat agctcacgct gtaggtatct cagttcggtg   7440
taggtcgttc gctccaagct gggctgtgtg cacgaacccc ccgttcagcc cgaccgctgc   7500
gccttatccg gtaactatcg tcttgagtcc aacccggtaa gacacgactt atcgccactg   7560
gcagcagcca ctggtaacag gattagcaga gcgaggtatg taggcggtgc tacagagttc   7620
ttgaagtggt ggcctaacta cggctacact agaaggacag tatttggtat ctgcgctctg   7680
ctgaagccag ttaccttcgg aaaaagagtt ggtagctctt gatccggcaa acaaaccacc   7740
gctggtagcg gtggtttttt tgtttgcaag cagcagatta cgcgcagaaa aaaggatct   7800
caagaagatc ctttgatctt ttctacgggg tctgacgctc agtggaacga aaactcacgt   7860
taagggattt tggtcatgag attatcaaaa aggatcttca cctagatcct ttttaaattaa   7920
aaatgaagtt ttaaatcaat ctaaagtata tatgagtaaa cttggtctga cagttaccaa   7980
tgcttaatca gtgaggcacc tatctcagcg atctgtctat ttcgttcatc catagttgcc   8040
tgactccccg tcgtgtagat aactacgata cgggagggct taccatctgg ccccagtgct   8100
gcaatgatac cgcgagaccc acgctcaccg gctccagatt tatcagcaat aaaccagcca   8160
gccgaagggg ccgagcgcag aagtggtcct gcaactttat ccgcctccat ccagtctatt   8220
aattgttgcc gggaagctag agtaagtagt tcgccagtta atagtttgcg caacgttgtt   8280
```

-continued

| | |
|---|---|
| gccattgcta caggcatcgt ggtgtcacgc tcgtcgtttg gtatggcttc attcagctcc | 8340 |
| ggttcccaac gatcaaggcg agttacatga tcccccatgt tgtgcaaaaa agcggttagc | 8400 |
| tccttcggtc ctccgatcgt tgtcagaagt aagttggccg cagtgttatc actcatggtt | 8460 |
| atggcagcac tgcataattc tcttactgtc atgccatccg taagatgctt ttctgtgact | 8520 |
| ggtgagtact caaccaagtc attctgagaa tagtgtatgc ggcgaccgag ttgctcttgc | 8580 |
| ccggcgtcaa tacgggataa taccgcgcca catagcagaa ctttaaaagt gctcatcatt | 8640 |
| ggaaaacgtt cttcggggcg aaaactctca aggatcttac cgctgttgag atccagttcg | 8700 |
| atgtaaccca ctcgtgcacc caactgatct tcagcatctt ttactttcac cagcgtttct | 8760 |
| gggtgagcaa aaacaggaag gcaaaatgcc gcaaaaaagg gaataagggc gacacggaaa | 8820 |
| tgttgaatac tcatactctt cctttttcaa tattattgaa gcatttatca gggttattgt | 8880 |
| ctcatgagcg gatacatatt tgaatgtatt tagaaaaata acaaataggg gttccgcgc | 8940 |
| acatttcccc gaaaagtgcc acctgacgt | 8969 |

<210> SEQ ID NO 17
<211> LENGTH: 5853
<212> TYPE: DNA
<213> ORGANISM: Artificial Sequence
<220> FEATURE:
<223> OTHER INFORMATION: Synthetic polynucleotide

<400> SEQUENCE: 17

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgcgtg | 120 |
| ttggcgggtg tcgggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| tttttttttt cccctagcgg atgactcttt ttttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaaagag gcagaagcag tagcagaaca ggccacacaa tcgcaagtga | 660 |
| ttaacgtcca cacaggtata gggtttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag cttttaaaga ggccctaggg gccgtgcgtg | 840 |
| gagtaaaaag gtttggatca ggatttgcgc ctttggatga ggcactttcc agagcggtgg | 900 |
| tagatctttc gaacaggccg tacgcagttg tcgaacttgg tttgcaaagg gagaaagtag | 960 |
| gagatctctc ttgcgagatg atcccgcatt ttcttgaaag ctttgcagag gctagcagaa | 1020 |
| ttaccctcca cgttgattgt ctgcgaggca agaatgatca tcaccgtagt gagagtgcgt | 1080 |
| tcaaggctct tgcggttgcc ataagagaag ccacctcgcc caatggtacc aacgatgttc | 1140 |
| cctccaccaa aggtgttctt atgtagtgac accgattatt taaagctgca gcatacgata | 1200 |
| tatatacatg tgtatatatg tatacctatg aatgtcagta agtatgtata cgaacagtat | 1260 |
| gatactgaag atgacaaggt aatgcatcat tctatacgtg tcattctgaa cgaggcgcgc | 1320 |
| tttccttttt tcttttttgct tttcttttt ttttctcttg aactcgacgg atctatgcgg | 1380 |

```
tgtgaaatac cgcacagatg cgtaaggaga aaataccgca tcaggaaatt gtaaacgtta    1440
atattttgtt aaaattcgcg ttaaattttt gttaaatcag ctcattttttt aaccaatagg   1500 ccgaaatcgg caaaatccct tataaatcaa agaatagac cgagataggg ttgagtgttg     1560
ttccagtttg gaacaagagt ccactattaa agaacgtgga ctccaacgtc aaagggcgaa    1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaaggggga tgtgctgcaa    1980
ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaaa gaaaaatttg aaatataaat aacgttctta atactaacat    2220
aactataaaa aaataaatag ggacctagac ttcaggttgt ctaactcctt ccttttcggt    2280
tagagcggat gtgggggggag ggcgtgaatg taagcgtgac ataactaatt acatgactcg    2340
aggtcgacgg tatcgataag cttgatatcg aattcctgca gcccggggga tccactagtt    2400
ctagaatccg tcgaaactaa gttctggtgt tttaaaacta aaaaaaagac taactataaa    2460
agtagaattt aagaagttta agaaatagat ttacagaatt acaatcaata cctaccgtct    2520
ttatatactt attagtcaag tagggaata atttcaggga actggtttca acctttttt     2580 tcagcttttt ccaaatcaga gagagcagaa ggtaatagaa ggtgtaagaa aatgagatag    2640
atacatgcgt gggtcaattg ccttgtgtca tcatttactc caggcaggtt gcatcactcc    2700
attgaggttg tgcccgtttt ttgcctgttt gtgcccctgt tctctgtagt tgcgctaaga    2760
gaatggacct atgaactgat ggttggtgaa gaaaacaata ttttggtgct gggattcttt    2820
ttttttctgg atgccagctt aaaaagcggg ctccattata tttagtggat gccaggaata    2880
aactgttcac ccagacacct acgatgttat atattctgtg taacccgccc cctattttgg    2940
gcatgtacgg gttacagcag aattaaaagg ctaattttttt gactaaataa agttaggaaa    3000
atcactacta ttaattattt acgtattctt tgaaatggcg agtattgata atgataaact    3060
gagctccagc ttttgttccc tttagtgagg gttaattgcg cgcttggcgt aatcatggtc    3120
atagctgttt cctgtgtgaa attgttatcc gctcacaatt ccacacaaca taggagccgg    3180
aagcataaag tgtaaagcct ggggtgccta atgagtgagg taactcacat taattgcgtt    3240
gcgctcactg cccgctttcc agtcgggaaa cctgtcgtgc cagctgcatt aatgaatcgg    3300
ccaacgcgcg gggagaggcg gtttgcgtat gggcgctct ccgcttcct cgctcactga     3360 ctcgctgcgc tcggtcgttc ggctgcggcg agcggtatca gctcactcaa aggcggtaat    3420
acggttatcc acagaatcag gggataacgc aggaaagaac atgtgagcaa aaggccagca    3480
aaaggccagg aaccgtaaaa aggccgcgtt gctggcgttt ttccataggc tccgccccc     3540 tgacgagcat cacaaaaatc gacgctcaag tcagaggtgg cgaaacccga caggactata    3600
aagataccag gcgtttcccc ctggaagctc cctcgtgcgc tctcctgttc cgaccctgcc    3660
gcttaccgga tacctgtccg cctttctccc ttcgggaagc gtggcgcttt ctcatagctc    3720
```

| | |
|---|---|
| acgctgtagg tatctcagtt cggtgtaggt cgttcgctcc aagctgggct gtgtgcacga | 3780 |
| accccccgtt cagcccgacc gctgcgcctt atccggtaac tatcgtcttg agtccaaccc | 3840 |
| ggtaagacac gacttatcgc cactggcagc agccactggt aacaggatta gcagagcgag | 3900 |
| gtatgtaggc ggtgctacag agttcttgaa gtggtggcct aactacggct acactagaag | 3960 |
| gacagtattt ggtatctgcg ctctgctgaa gccagttacc ttcggaaaaa gagttggtag | 4020 |
| ctcttgatcc ggcaaacaaa ccaccgctgg tagcggtggt ttttttgttt gcaagcagca | 4080 |
| gattacgcgc agaaaaaaag gatctcaaga agatcctttg atcttttcta cggggtctga | 4140 |
| cgctcagtgg aacgaaaact cacgttaagg gattttggtc atgagattat caaaaaggat | 4200 |
| cttcacctag atccttttaa attaaaaatg aagttttaaa tcaatctaaa gtatatatga | 4260 |
| gtaaacttgg tctgacagtt accaatgctt aatcagtgag gcacctatct cagcgatctg | 4320 |
| tctatttcgt tcatccatag ttgcctgact ccccgtcgtg tagataacta cgatacggga | 4380 |
| gggcttacca tctggcccca gtgctgcaat gataccgcga gacccacgct caccggctcc | 4440 |
| agatttatca gcaataaacc agccagccgg aagggccgag cgcagaagtg gtcctgcaac | 4500 |
| tttatccgcc tccatccagt ctattaattg ttgccgggaa gctagagtaa gtagttcgcc | 4560 |
| agttaatagt ttgcgcaacg ttgttgccat tgctacaggc atcgtggtgt cacgctcgtc | 4620 |
| gtttggtatg gcttcattca gctccggttc ccaacgatca aggcgagtta catgatcccc | 4680 |
| catgttgtgc aaaaaagcgg ttagctcctt cggtcctccg atcgttgtca gaagtaagtt | 4740 |
| ggccgcagtg ttatcactca tggttatggc agcactgcat aattctctta ctgtcatgcc | 4800 |
| atccgtaaga tgcttttctg tgactggtga gtactcaacc aagtcattct gagaatagtg | 4860 |
| tatgcggcga ccgagttgct cttgcccggc gtcaatacgg gataataccg cgccacatag | 4920 |
| cagaacttta aaagtgctca tcattggaaa acgttcttcg gggcgaaaac tctcaaggat | 4980 |
| cttaccgctg ttgagatcca gttcgatgta acccactcgt gcacccaact gatcttcagc | 5040 |
| atcttttact ttcaccagcg tttctgggtg agcaaaaaca ggaaggcaaa atgccgcaaa | 5100 |
| aaagggaata agggcgacac ggaaatgttg aatactcata ctcttccttt ttcaatatta | 5160 |
| ttgaagcatt tatcagggtt attgtctcat gagcggatac atatttgaat gtatttagaa | 5220 |
| aaataaacaa ataggggttc cgcgcacatt tccccgaaaa gtgccacctg gtccttttc | 5280 |
| atcacgtgct ataaaaataa ttataattta aattttttaa tataaatata taaattaaaa | 5340 |
| atagaaagta aaaaagaaa ttaaagaaaa aatagttttt gttttccgaa gatgtaaaag | 5400 |
| actctagggg gatcgccaac aaatactacc ttttatcttg ctcttcctgc tctcaggtat | 5460 |
| taatgccgaa ttgtttcatc ttgtctgtgt agaagaccac acacgaaaat cctgtgattt | 5520 |
| tacattttac ttatcgttaa tcgaatgtat atctatttaa tctgcttttc ttgtctaata | 5580 |
| aatatatatg taaagtacgc ttttgttga aatttttaa acctttgttt attttttttt | 5640 |
| cttcattccg taactcttct accttcttta tttactttct aaaatccaaa tacaaaacat | 5700 |
| aaaaataaat aaacacagag taaattccca aattattcca tcattaaaag atacgaggcg | 5760 |
| cgtgtaagtt acaggcaagc gatccgtcct aagaaaccat tattatcatg acattaacct | 5820 |
| ataaaaatag gcgtatcacg aggccctttc gtc | 5853 |

<210> SEQ ID NO 18
<211> LENGTH: 5778
<212> TYPE: DNA
<213> ORGANISM: Artificial Sequence
<220> FEATURE:
<223> OTHER INFORMATION: Synthetic polynucleotide

<400> SEQUENCE: 18

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataccac agcttttcaa ttcaattcat cattttttt ttattcttt ttttgatttc       240
ggtttctttg aaattttttt gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taaatcatgt     420
cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa gccgctaaag gcattatccg     660
ccaagtacaa tttttactc ttcgaagaca gaaaatttgc tgacattggt aatacagtca     720
aattgcagta ctctgcgggt gtatacgaaa tagcagaatg ggcagacatt acgaatgcac     780
acggtgtggt gggcccaggt attgttagcg gtttgaagca ggcggcagaa gaagtaacaa     840
aggaacctag aggcctttg atgttagcag aattgtcatg caagggctcc ctatctactg      900
gagaatatac taagggtact gttgacattg cgaagagcga caaagatttt gttatcggct     960
ttattgctca aagagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattacccta tgcggtgtga aataccgcac    1320
agatgcgtaa ggagaaaata ccgcatcagg aaattgtaaa cgttaatatt ttgttaaaat    1380
tcgcgttaaa tttttgttaa atcagctcat tttttaacca ataggccgaa atcggcaaaa    1440
tcccttataa atcaaaagaa tagaccgaga taggggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaaggggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccgcaaatt aaagccttcg agcgtcccaa    2040
aaccttctca gcaaggtttt tcagtataat gttacatgcg tacacgcgtc tgtacagaaa    2100
aaaagaaaa atttgaaata taaataacgt tcttaatact aacataacta taaaaaaata    2160
aatagggacc tagacttcag gttgtctaac tccttccttt tcggttagag cggatgtggg    2220
gggagggcgt gaatgtaagc gtgacataac taattacatg actcgaggtc gacggtatcg    2280
```

```
ataagcttga tatcgaattc ctgcagcccg ggggatccac tagttctaga atccgtcgaa      2340
actaagttct ggtgttttaa aactaaaaaa aagactaact ataaaagtag aatttaagaa      2400
gtttaagaaa tagatttaca gaattacaat caatacctac cgtctttata tacttattag      2460
tcaagtaggg gaataatttc agggaactgg tttcaaccct tttttttcagc tttttccaaa     2520 tcagagagag cagaaggtaa tagaaggtgt aagaaaatga gatagataca tgcgtgggtc      2580
aattgccttg tgtcatcatt tactccaggc aggttgcatc actccattga ggttgtgccc      2640
gttttttgcc tgtttgtgcc cctgttctct gtagttgcgc taagagaatg gacctatgaa      2700
ctgatggttg gtgaagaaaa caatattttg gtgctgggat tcttttttt tctggatgcc       2760 agcttaaaaa gcgggctcca ttatatttag tggatgccag gaataaactg ttcacccaga      2820
cacctacgat gttatatatt ctgtgtaacc cgcccctat tttgggcatg tacgggttac        2880
agcagaatta aaaggctaat ttttttgacta aataaagtta ggaaaatcac tactattaat    2940
tatttacgta ttctttgaaa tggcgagtat tgataatgat aaactgagct ccagcttttg     3000
ttccctttag tgagggttaa ttgcgcgctt ggcgtaatca tggtcatagc tgtttcctgt    3060
gtgaaattgt tatccgctca caattccaca caacatagga gccggaagca taaagtgtaa    3120
agcctggggt gcctaatgag tgaggtaact cacattaatt gcgttgcgct cactgcccgc    3180
tttccagtcg ggaaacctgt cgtgccagct gcattaatga atcggccaac gcgcggggag    3240
aggcggtttg cgtattgggc gctcttccgc ttcctcgctc actgactcgc tgcgctcggt    3300
cgttcggctg cggcgagcgg tatcagctca ctcaaaggcg gtaatacggt tatccacaga    3360
atcaggggat aacgcaggaa agaacatgtg agcaaaaggc cagcaaaagg ccaggaaccg    3420
taaaaaggcc gcgttgctgg cgttttccca taggctccgc cccctgacg agcatcacaa     3480 aaatcgacgc tcaagtcaga ggtggcgaaa cccgacagga ctataaagat accaggcgtt    3540
tccccctgga agctccctcg tgcgctctcc tgttccgacc ctgccgctta ccggatacct    3600
gtccgccttt ctcccttcgg gaagcgtggc gctttctcat agctcacgct gtaggtatct    3660
cagttcggtg taggtcgttc gctccaagct gggctgtgtg cacgaacccc ccgttcagcc    3720
cgaccgctgc gccttatccg gtaactatcg tcttgagtcc aacccggtaa gacacgactt    3780
atcgccactg gcagcagcca ctggtaacag gattagcaga gcgaggtatg taggcggtgc    3840
tacagagttc ttgaagtggt ggcctaacta cggctacact agaaggacag tatttggtat    3900
ctgcgctctg ctgaagccag ttaccttcgg aaaaagagtt ggtagctctt gatccggcaa    3960
acaaaccacc gctggtagcg gtggtttttt tgtttgcaag cagcagatta cgcgcagaaa    4020
aaaaggatct caagaagatc ctttgatctt ttctacgggg tctgacgctc agtggaacga    4080
aaactcacgt taagggattt tggtcatgag attatcaaaa aggatcttca cctagatcct    4140
tttaaattaa aaatgaagtt ttaaatcaat ctaaagtata tatgagtaaa cttggtctga    4200
cagttaccaa tgcttaatca gtgaggcacc tatctcagcg atctgtctat ttcgttcatc    4260
catagttgcc tgactccccg tcgtgtagat aactacgata cgggagggct taccatctgg    4320
ccccagtgct gcaatgatac cgcgagaccc acgctcaccg gctccagatt tatcagcaat    4380
aaaccagcca gccggaaggg ccgagcgcag aagtggtcct gcaactttat ccgcctccat    4440
ccagtctatt aattgttgcc gggaagctag agtaagtagt tcgccagtta atagtttgcg    4500
caacgttgtt gccattgcta caggcatcgt ggtgtcacgc tcgtcgtttg gtatggcttc    4560
attcagctcc ggttcccaac gatcaaggcg agttacatga tcccccatgt tgtgcaaaaa    4620
agcggttagc tccttcggtc ctccgatcgt tgtcagaagt aagttggccg cagtgttatc    4680
```

```
actcatggtt atggcagcac tgcataattc tcttactgtc atgccatccg taagatgctt    4740
ttctgtgact ggtgagtact caaccaagtc attctgagaa tagtgtatgc ggcgaccgag    4800
ttgctcttgc ccggcgtcaa tacgggataa taccgcgcca catagcagaa ctttaaaagt    4860
gctcatcatt ggaaaacgtt cttcggggcg aaaactctca aggatcttac cgctgttgag    4920
atccagttcg atgtaaccca ctcgtgcacc caactgatct tcagcatctt ttactttcac    4980
cagcgtttct gggtgagcaa aaacaggaag gcaaaatgcc gcaaaaaagg gaataagggc    5040
gacacggaaa tgttgaatac tcatactctt cctttttcaa tattattgaa gcatttatca    5100
gggttattgt ctcatgagcg gatacatatt tgaatgtatt tagaaaaata aacaaatagg    5160
ggttccgcgc acatttcccc gaaaagtgcc acctgggtcc ttttcatcac gtgctataaa    5220
aataattata atttaaattt tttaatataa atatataaat taaaaataga aagtaaaaaa    5280
agaaattaaa gaaaaaatag ttttttgtttt ccgaagatgt aaaagactct aggggggatcg   5340 ccaacaaata ctaccttta tcttgctctt cctgctctca ggtattaatg ccgaattgtt    5400
tcatcttgtc tgtgtagaag accacacacg aaaatcctgt gattttacat tttacttatc    5460
gttaatcgaa tgtatatcta tttaatctgc ttttcttgtc taataaatat atatgtaaag    5520 tacgctttt gttgaaatt tttaaacctt tgtttatttt tttttcttca ttccgtaact     5580
cttctacctt ctttatttac tttctaaaat ccaaatacaa aacataaaaa taaataaaca    5640
cagagtaaat tcccaaatta ttccatcatt aaaagatacg aggcgcgtgt aagttacagg    5700
caagcgatcc gtcctaagaa accattatta tcatgacatt aacctataaa aataggcgta    5760
tcacgaggcc ctttcgtc                                                  5778
```

<210> SEQ ID NO 19
<211> LENGTH: 6362
<212> TYPE: DNA
<213> ORGANISM: Artificial Sequence
<220> FEATURE:
<223> OTHER INFORMATION: Synthetic polynucleotide

<400> SEQUENCE: 19

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataccac agcttttcaa ttcaattcat catttttttt ttattctttt ttttgatttc     240
ggtttctttg aaatttttt gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taatcatgt      420 cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaacacatg      600 tggatatctt gactgatttt tccatggagg gcacagttaa gccgctaaag gcattatccg     660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
```

```
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga ataccgcac    1320
agatgcgtaa ggagaaaata ccgcatcagg aaattgtaaa cgttaatatt ttgttaaaat   1380
tcgcgttaaa ttttttgttaa atcagctcat tttttaacca ataggccgaa atcggcaaaa   1440
tcccttataa atcaaaagaa tagaccgaga taggggttgag tgttgttcca gtttggaaca   1500
agagtccact attaaagaac gtggactcca acgtcaaagg gcgaaaaacc gtctatcagg   1560
gcgatgccc actacgtgaa ccatcaccct aatcaagttt tttggggtcg aggtgccgta    1620
aagcactaaa tcggaacct aaagggagcc cccgatttag agcttgacgg ggaaagccgg    1680
cgaacgtggc gagaaaggaa gggaagaaag cgaaggagc gggcgctagg gcgctggcaa    1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taataacgt tcttaatact aacataacta taaaaaaata    2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacacccg catagtcagg aacatcgtat gggtacatgc tagttctaga   2340
aaacttagat tagattgcta tgcttttcttt ctaatgagca agaagtaaaa aaagttgtaa   2400
tagaacaaga aaatgaaac tgaaacttga gaaattgaag accgtttatt aacttaaata    2460
tcaatgggag gtcatcgaaa gagaaaaaaa tcaaaaaaaa aattttcaag aaaaagaaac   2520
gtgataaaaa ttttttattgc cttttttcgac gaagaaaaag aaacgaggcg gtctctttttt 2580
tcttttccaa acctttagta cgggtaatta acgacaccct agaggaagaa agaggggaaa   2640
tttagtatgc tgtgcttggg tgttttgaag tggtacggcg atgcgcggag tccgagaaaa   2700
tctggaagag taaaaaagga gtagaaacat tttgaagcta tgagctccag cttttgttcc   2760
ctttagtgag ggttaattgc gcgcttggcg taatcatggt catagctgtt tcctgtgtga   2820
aattgttatc cgctcacaat tccacacaac ataggagccg gaagcataaa gtgtaaagcc   2880
tggggtgcct aatgagtgag gtaactcaca ttaattgcgt tgcgctcact gcccgctttc   2940
cagtcgggaa acctgtcgtg ccagctgcat taatgaatcg gccaacgcgc ggggagaggc   3000
ggtttgcgta ttgggcgctc ttccgcttcc tcgctcactg actcgctgcg ctcggtcgtt   3060
cggctgcggc gagcggtatc agctcactca aaggcggtaa tacggttatc cacagaatca   3120
ggggataacg caggaaagaa catgtgagca aaaggccagc aaaaggccag gaaccgtaaa   3180
aaggccgcgt tgctggcgtt tttccatagg ctccgccccc ctgacgagca tcacaaaaat   3240
cgacgctcaa gtcagaggtg gcgaaacccg acaggactat aaagatacca ggcgtttccc   3300
```

```
cctggaagct ccctcgtgcg ctctcctgtt ccgaccctgc cgcttaccgg atacctgtcc    3360
gcctttctcc cttcgggaag cgtggcgctt tctcatagct cacgctgtag gtatctcagt    3420
tcggtgtagg tcgttcgctc caagctgggc tgtgtgcacg aaccccccgt tcagcccgac    3480
cgctgcgcct tatccggtaa ctatcgtctt gagtccaacc cggtaagaca cgacttatcg    3540
ccactggcag cagccactgg taacaggatt agcagagcga ggtatgtagg cggtgctaca    3600
gagttcttga agtggtggcc taactacggc tacactagaa ggacagtatt tggtatctgc    3660
gctctgctga agccagttac cttcggaaaa agagttggta gctcttgatc cggcaaacaa    3720
accaccgctg gtagcggtgg ttttttttgtt tgcaagcagc agattacgcg cagaaaaaaa    3780
ggatctcaag aagatccttt gatcttttct acggggtctg acgctcagtg gaacgaaaac    3840
tcacgttaag ggattttggt catgagatta tcaaaaagga tcttcaccta gatcctttta    3900
aattaaaaat gaagttttaa atcaatctaa agtatatatg agtaaacttg gtctgacagt    3960
taccaatgct taatcagtga ggcacctatc tcagcgatct gtctatttcg ttcatccata    4020
gttgcctgac tccccgtcgt gtagataact acgatacggg agggcttacc atctggcccc    4080
agtgctgcaa tgataccgcg agacccacgc tcaccggctc cagatttatc agcaataaac    4140
cagccagccg gaagggccga gcgcagaagt ggtcctgcaa ctttatccgc ctccatccag    4200
tctattaatt gttgccggga agctagagta agtagttcgc cagttaatag tttgcgcaac    4260
gttgttgcca ttgctacagg catcgtggtg tcacgctcgt cgtttggtat ggcttcattc    4320
agctccggtt cccaacgatc aaggcgagtt acatgatccc ccatgttgtg caaaaaagcg    4380
gttagctcct tcggtcctcc gatcgttgtc agaagtaagt tggccgcagt gttatcactc    4440
atggttatgg cagcactgca taattctctt actgtcatgc catccgtaag atgcttttct    4500
gtgactggtg agtactcaac caagtcattc tgagaatagt gtatgcggcg accgagttgc    4560
tcttgcccgg cgtcaatacg ggataatacc gcgccacata gcagaacttt aaaagtgctc    4620
atcattggaa aacgttcttc ggggcgaaaa ctctcaagga tcttaccgct gttgagatcc    4680
agttcgatgt aacccactcg tgcacccaac tgatcttcag catctttttac tttcaccagc    4740 gtttctgggt gagcaaaaac aggaaggcaa aatgccgcaa aaaagggaat aagggcgaca    4800
cggaaatgtt gaatactcat actcttcctt tttcaatatt attgaagcat ttatcagggt    4860
tattgtctca tgagcggata catatttgaa tgtatttaga aaaataaaca ataggggtt    4920 ccgcgcacat ttccccgaaa agtgccacct gaacgaagca tctgtgcttc attttgtaga    4980
acaaaaatgc aacgcgagag cgctaatttt tcaaacaaag aatctgagct gcatttttac    5040
agaacagaaa tgcaacgcga aagcgctatt ttaccaacga agaatctgtg cttcattttt    5100
gtaaaacaaa aatgcaacgc gagagcgcta attttcaaa caagaatct gagctgcatt    5160 tttacagaac agaaatgcaa cgcgagagcg ctattttacc aacaaagaat ctatacttct    5220
tttttgttct acaaaaatgc atcccgagag cgctattttt ctaacaaagc atcttagatt    5280 acttttttc tcctttgtgc gctctataat gcagtctctt gataactttt tgcactgtag    5340
gtccgttaag gttagaagaa ggctactttg gtgtctattt tctcttccat aaaaaaagcc    5400
tgactccact tcccgcgttt actgattact agcgaagctg cgggtgcatt ttttcaagat    5460
aaaggcatcc ccgattatat tctataccga tgtggattgc gcatactttg tgaacagaaa    5520
gtgatagcgt tgatgattct tcattggtca gaaaattatg aacggtttct tctatttgt    5580 ctctatatac tacgtatagg aaatgtttac attttcgtat tgttttcgat tcactctatg    5640
```

```
aatagttctt actacaatttt ttttgtctaa agagtaatac tagagataaa cataaaaaat    5700
gtagaggtcg agtttagatg caagttcaag gagcgaaagg tggatgggta ggttatatag    5760
ggatatagca cagagatata tagcaaagag atacttttga gcaatgtttg tggaagcggt    5820
attcgcaata ttttagtagc tcgttacagt ccggtgcgtt tttggttttt tgaaagtgcg    5880
tcttcagagc gcttttggtt ttcaaaagcg ctctgaagtt cctatacttt ctagagaata    5940
ggaacttcgg aataggaact tcaaagcgtt tccgaaaacg agcgcttccg aaaatgcaac    6000
gcgagctgcg cacatacagc tcactgttca cgtcgcacct atatctgcgt gttgcctgta    6060
tatatatata catgagaaga acggcatagt gcgtgtttat gcttaaatgc gtacttatat    6120
gcgtctattt atgtaggatg aaaggtagtc tagtacctcc tgtgatatta tcccattcca    6180
tgcggggtat cgtatgcttc cttcagcact acccttagc tgttctatat gctgccactc     6240
ctcaattgga ttagtctcat ccttcaatgc tatcatttcc tttgatattg gatcatacta    6300
agaaaccatt attatcatga cattaaccta taaaaatagg cgtatcacga ggccctttcg    6360
tc                                                                   6362
```

<210> SEQ ID NO 20
<211> LENGTH: 6690
<212> TYPE: DNA
<213> ORGANISM: Artificial Sequence
<220> FEATURE:
<223> OTHER INFORMATION: Synthetic polynucleotide

<400> SEQUENCE: 20

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accataaatt cccgttttaa gagcttggtg agcgctagga gtcactgcca ggtatcgttt     240
gaacacggca ttagtcaggg aagtcataac acagtccttt cccgcaattt tcttttttcta    300 ttactcttgg cctcctctag tacactctat attttttttat gcctcggtaa tgattttcat    360 ttttttttt cccctagcgg atgactcttt tttttcttta gcgattggca ttatcacata      420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga     660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag cttttaaaga ggccctaggg gccgtgcgtg     840
gagtaaaaag gtttggatca ggatttgcgc ctttggatga ggcactttcc agagcggtgg     900
tagatctttc gaacaggccg tacgcagttg tcgaacttgg tttgcaaagg agaaagtag     960 gagatctctc ttgcgagatg atcccgcatt ttcttgaaag ctttgcagag gctagcagaa    1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
```

```
tttcctttt  tcttttgct   ttttcttttt   tttctcttg  aactcgacgg  atctatgcgg    1380
tgtgaaatac  cgcacagatg  cgtaaggaga  aataccgca  tcaggaaatt  gtaaacgtta    1440
atattttgtt  aaaattcgcg  ttaaatttt   gttaaatcag  ctcattttt   aaccaatagg   1500 ccgaaatcgg  caaaatccct  tataaatcaa  agaatagac   cgagataggg  ttgagtgttg   1560
ttccagtttg  gaacaagagt  ccactattaa  agaacgtgga  ctccaacgtc  aaagggcgaa   1620
aaaccgtcta  tcagggcgat  ggcccactac  gtgaaccatc  accctaatca  agttttttgg   1680
ggtcgaggtg  ccgtaaagca  ctaaatcgga  acccctaaagg  gagcccccga  tttagagctt   1740
gacggggaaa  gccggcgaac  gtggcgagaa  aggaagggaa  gaaagcgaaa  ggagcgggcg   1800
ctagggcgct  ggcaagtgta  gcggtcacgc  tgcgcgtaac  caccacaccc  gccgcgctta   1860
atgcgccgct  acagggcgcg  tcgcgccatt  cgccattcag  gctgcgcaac  tgttgggaag   1920
ggcgatcggt  gcgggcctct  tcgctattac  gccagctggc  gaaaggggga  tgtgctgcaa   1980
ggcgattaag  ttgggtaacg  ccagggtttt  cccagtcacg  acgttgtaaa  acgacggcca   2040
gtgagcgcgc  gtaatacgac  tcactatagg  gcgaattggg  taccggccgc  aaattaaagc   2100
cttcgagcgt  cccaaaacct  tctcaagcaa  ggttttcagt  ataatgttac  atgcgtacac   2160
gcgtctgtac  agaaaaaaaa  gaaaaatttg  aaatataaat  aacgttctta  atactaacat   2220
aactataaaa  aaataaatag  gaacctagac  ttcaggttgt  ctaactcctt  ccttttcggt   2280
tagagcggat  gtgggggggag  ggcgtgaatg  taagcgtgac  ataactaatt  acatgactcg   2340
agcggccgcg  gatcccggga  attcgtcgac  accatcttct  tctgagatga  gttttttgttc  2400 catgctagtt  ctagaatccg  tcgaaactaa  gttctggtgt  tttaaaacta  aaaaaaagac   2460
taactataaa  agtagaattt  aagaagttta  agaaatagat  ttacagaatt  acaatcaata   2520
cctaccgtct  ttatatactt  attagtcaag  taggggaata  atttcaggga  actggtttca   2580 acctttttt   tcagcttttt  ccaaatcaga  gagagcagaa  ggtaatgaaa  ggtgtaagaa   2640
aatgagatag  atacatgcgt  gggtcaattg  ccttgtgtca  tcatttactc  caggcaggtt   2700
gcatcactcc  attgaggttg  tgcccgtttt  ttgcctgttt  gtgccccctgt  tctctgtagt   2760 tgcgctaaga  gaatggacct  atgaactgat  ggttggtgaa  gaaaacaata  ttttggtgct   2820
gggattcttt  tttttttctgg  atgccagctt  aaaaagcggg  ctccattata  tttagtggat   2880
gccaggaata  aactgttcac  ccagacacct  acgatgttat  atattctgtg  taacccgccc   2940
cctattttgg  gcatgtacgg  gttacagcag  aattaaaagg  ctaattttt   gactaaataa   3000 agttaggaaa  atcactacta  ttaattattt  acgtattctt  tgaaatggcg  agtattgata   3060
atgataaact  gagctccagc  ttttgttccc  tttagtgagg  gttaattgcg  cgcttggcgt   3120
aatcatggtc  atagctgttt  cctgtgtgaa  attgttatcc  gctcacaatt  ccacacaaca   3180
taggagccgg  aagcataaag  tgtaaagcct  ggggtgccta  atgagtgagg  taactcacat   3240
taattgcgtt  gcgctcactg  cccgctttcc  agtcgggaaa  cctgtcgtgc  cagctgcatt   3300
aatgaatcgg  ccaacgcgcg  gggagaggcg  gtttgcgtat  tgggcgctct  tccgcttcct   3360
cgctcactga  ctcgctgcgc  tcggtcgttc  ggctgcggcg  agcggtatca  gctcactcaa   3420
aggcggtaat  acgttatcc   acagaatcag  gggataacgc  aggaaagaac  atgtgagcaa   3480
aaggccagca  aaaggccagg  aaccgtaaaa  aggccgcgtt  gctggcgttt  ttccataggc   3540
tccgcccccc  tgacgagcat  cacaaaaatc  gacgctcaag  tcagaggtgg  cgaaacccga   3600
caggactata  aagataccag  gcgtttcccc  ctggaagctc  cctcgtgcgc  tctcctgttc   3660
```

```
cgaccctgcc gcttaccgga tacctgtccg cctttctccc ttcgggaagc gtggcgcttt    3720
ctcatagctc acgctgtagg tatctcagtt cggtgtaggt cgttcgctcc aagctgggct    3780
gtgtgcacga accccccgtt cagcccgacc gctgcgcctt atccggtaac tatcgtcttg    3840
agtccaaccc ggtaagacac gacttatcgc cactggcagc agccactggt aacaggatta    3900
gcagagcgag gtatgtaggc ggtgctacag agttcttgaa gtggtggcct aactacggct    3960
acactagaag gacagtattt ggtatctgcg ctctgctgaa gccagttacc ttcggaaaaa    4020
gagttggtag ctcttgatcc ggcaaacaaa ccaccgctgg tagcggtggt ttttttgttt    4080
gcaagcagca gattacgcgc agaaaaaaag gatctcaaga agatcctttg atcttttcta    4140
cggggtctga cgctcagtgg aacgaaaact cacgttaagg gattttggtc atgagattat    4200
caaaaaggat cttcacctag atccttttaa attaaaaatg aagttttaaa tcaatctaaa    4260
gtatatatga gtaaacttgg tctgacagtt accaatgctt aatcagtgag gcacctatct    4320
cagcgatctg tctatttcgt tcatccatag ttgcctgact ccccgtcgtg tagataacta    4380
cgatacggga gggcttacca tctggcccca gtgctgcaat gataccgcga gacccacgct    4440
caccggctcc agatttatca gcaataaacc agccagccgg aagggccgag cgcagaagtg    4500
gtcctgcaac tttatccgcc tccatccagt ctattaattg ttgccgggaa gctagagtaa    4560
gtagttcgcc agttaatagt ttgcgcaacg ttgttgccat tgctacaggc atcgtggtgt    4620
cacgctcgtc gtttggtatg gcttcattca gctccggttc ccaacgatca aggcgagtta    4680
catgatcccc catgttgtgc aaaaaagcgg ttagctcctt cggtcctccg atcgttgtca    4740
gaagtaagtt ggccgcagtg ttatcactca tggttatggc agcactgcat aattctctta    4800
ctgtcatgcc atccgtaaga tgcttttctg tgactggtga gtactcaacc aagtcattct    4860
gagaatagtg tatgcggcga ccgagttgct cttgcccggc gtcaatacgg gataataccg    4920
cgccacatag cagaacttta aaagtgctca tcattggaaa acgttcttcg ggcgaaaac    4980 tctcaaggat cttaccgctg ttgagatcca gttcgatgta acccactcgt gcacccaact    5040
gatcttcagc atcttttact ttcaccagcg tttctgggtg agcaaaaaca ggaaggcaaa    5100
atgccgcaaa aaagggaata agggcgacac ggaaatgttg aatactcata ctcttccttt    5160
ttcaatatta ttgaagcatt tatcagggtt attgtctcat gagcggatac atatttgaat    5220
gtatttagaa aaataaacaa ataggggttc cgcgcacatt tccccgaaaa gtgccacctg    5280
aacgaagcat ctgtgcttca ttttgtagaa caaaaatgca acgcgagagc gctaattttt    5340
caaacaaaga atctgagctg cattttaca gaacagaaat gcaacgcgaa agcgctattt    5400
taccaacgaa gaatctgtgc ttcattttg taaacaaaa atgcaacgcg agagcgctaa    5460
tttttcaaac aaagaatctg agctgcattt ttacagaaca gaaatgcaac gcgagagcgc    5520
tattttacca acaaagaatc tatacttctt ttttgttcta caaaaatgca tcccgagagc    5580 gctattttc taacaaagca tcttagatta ctttttttct cctttgtgcg ctctataatg    5640
cagtctcttg ataactttt gcactgtagg tccgttaagg ttagaagaag ctactttgg    5700 tgtctatttt ctcttccata aaaaagcct gactccactt cccgcgttta ctgattacta    5760
gcgaagctgc gggtgcattt tttcaagata aaggcatccc cgattatatt ctataccgat    5820
gtggattgcg catactttgt gaacagaaag tgatagcgtt gatgattctt cattggtcag    5880
aaaattatga acggtttctt ctattttgtc tctatatact acgtatagga atgtttaca    5940 ttttcgtatt gttttcgatt cactctatga atagttctta ctacaatttt tttgtctaaa    6000
gagtaatact agagataaac ataaaaaatg tagaggtcga gtttagatgc aagttcaagg    6060
```

-continued

```
agcgaaaggt ggatgggtag gttatatagg gatatagcac agagatatat agcaaagaga     6120
tacttttgag caatgtttgt ggaagcggta ttcgcaatat tttagtagct cgttacagtc     6180
cggtgcgttt ttggttttt gaaagtgcgt cttcagagcg cttttggttt tcaaaagcgc      6240
tctgaagttc ctatactttc tagagaatag gaacttcgga ataggaactt caaagcgttt     6300
ccgaaaacga gcgcttccga aaatgcaacg cgagctgcgc acatacagct cactgttcac     6360
gtcgcaccta tatctgcgtg ttgcctgtat atatatatac atgagaagaa cggcatagtg     6420
cgtgtttatg cttaaatgcg tacttatatg cgtctattta tgtaggatga aaggtagtct     6480
agtacctcct gtgatattat cccattccat gcggggtatc gtatgcttcc ttcagcacta     6540
ccctttagct gttctatatg ctgccactcc tcaattggat tagtctcatc cttcaatgct     6600
atcatttcct ttgatattgg atcatctaag aaaccattat tatcatgaca ttaacctata     6660
aaaataggcg tatcacgagg ccctttcgtc                                      6690
```

<210> SEQ ID NO 21
<211> LENGTH: 6506
<212> TYPE: DNA
<213> ORGANISM: Artificial Sequence
<220> FEATURE:
<223> OTHER INFORMATION: Synthetic polynucleotide

<400> SEQUENCE: 21

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg       120 ttggcgggtg tcgggctgg cttaactatg cggcatcaga gcagattgta ctgagagtgc      180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga ggagggcat tggtgactat       420 tgagcacgtg agtatacgtg attaagcaca caaaggcagc ttggagtatg tctgttatta     480
atttcacagg tagttctggt ccattggtga agtttgcgg cttgcagagc acagaggccg      540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
attcagaagc aggtgggaca ggtgaacttt tggattggaa ctcgatttct gactgggttg     960
gaaggcaaga gagccccgaa agcttacatt ttatgttagc tggtggactg acgccagaaa    1020
atgttggtga tgcgcttaga ttaaatggcg ttattggtgt tgatgtaagc ggaggtgtgg    1080
agacaaatgg tgtaaaagac tctaacaaaa tagcaaattt cgtcaaaat gctaagaaat      1140 aggttattac tgagtagtat ttatttaagt attgttgtg cacttgccta tgcggtgtga      1200
aataccgcac agatgcgtaa ggagaaaata ccgcatcagg aaattgtaaa cgttaatatt     1260
ttgttaaaat tcgcgttaaa ttttgttaa atcagctcat ttttaacca ataggccgaa       1320 atcggcaaaa tccctatata atcaaaagaa tagaccgaga tagggttgag tgttgttcca    1380
```

```
gtttggaaca agagtccact attaaagaac gtggactcca acgtcaaagg gcgaaaaacc    1440
gtctatcagg gcgatggccc actacgtgaa ccatcaccct aatcaagttt tttggggtcg    1500
aggtgccgta aagcactaaa tcggaaccct aaagggagcc ccgatttag agcttgacgg     1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg gttttcccag tcacgacgtt gtaaaacgac ggccagtgag    1860
cgcgcgtaat acgactcact ataggggcgaa ttgggtaccg gccgcaaatt aaagccttcg   1920
agcgtcccaa aaccttctca agcaaggttt tcagtataat gttacatgcg tacacgcgtc    1980
tgtacagaaa aaaagaaaaa atttgaaata taaataacgt tcttaatact aacataacta    2040
taaaaaaata aatagggacc tagacttcag gttgtctaac tccttccttt tcggttagag    2100
cggatgtggg gggagggcgt gaatgtaagc gtgacataac taattacatg actcgagcgg    2160
ccgcggatcc cgggaattcg tcgacaccat cttcttctga gatgagtttt tgttccatgc    2220
tagttctaga atccgtcgaa actaagttct ggtgttttaa aactaaaaaa aagactaact    2280
ataaaagtag aatttaagaa gtttaagaaa tagatttaca gaattacaat caatacctac    2340
cgtctttata tacttattag tcaagtaggg gaataatttc agggaactgg tttcaacctt    2400
ttttttcagc tttttccaaa tcagagagag cagaaggtaa tagaaggtgt aagaaaatga    2460
gatagataca tgcgtgggtc aattgccttg tgtcatcatt tactccaggc aggttgcatc    2520
actccattga ggttgtgccc gttttttgcc tgtttgtgcc cctgttctct gtagttgcgc    2580
taagagaatg gacctatgaa ctgatggttg gtgaagaaaa caatattttg gtgctgggat    2640
tctttttttt tctggatgcc agcttaaaaa gcgggctcca ttatatttag tggatgccag    2700
gaataaactg ttcacccaga cacctacgat gttatatatt ctgtgtaacc cgccccctat    2760
tttgggcatg tacgggttac agcagaatta aaaggctaat ttttttgacta aataaagtta   2820
ggaaaatcac tactattaat tatttacgta ttctttgaaa tggcgagtat tgataatgat    2880
aaactgagct ccagcttttg ttcccttttag tgagggttaa ttgcgcgctt ggcgtaatca   2940
tggtcatagc tgtttcctgt gtgaaattgt tatccgctca caattccaca caacatagga    3000
gccggaagca taaagtgtaa agcctggggt gcctaatgag tgaggtaact cacattaatt    3060
gcgttgcgct cactgcccgc tttccagtcg ggaaacctgt cgtgccagct gcattaatga    3120
atcggccaac gcgcgggag aggcggtttg cgtattgggc gctcttccgc ttcctcgctc     3180
actgactcgc tgcgctcggt cgttcggctg cggcgagcgg tatcagctca ctcaaaggcg    3240
gtaatacggt tatccacaga atcagggat aacgcaggaa agaacatgtg agcaaaaggc     3300
cagcaaaagg ccaggaaccg taaaaaggcc gcgttgctgg cgtttttcca taggctccgc    3360
cccccctgacg agcatcacaa aaatcgacgc tcaagtcaga ggtggcgaaa cccgacagga   3420
ctataaagat accaggcgtt tcccctggaa agctccctcg tgcgctctcc tgttccgacc    3480
ctgccgctta ccggatacct gtccgccttt ctcccttcgg gaagcgtggc gctttctcat    3540
agctcacgct gtaggtatct cagttcggtg taggtcgttc gctccaagct gggctgtgtg    3600
cacgaacccc ccgttcagcc cgaccgctgc gccttatccg gtaactatcg tcttgagtcc    3660
aacccggtaa gacacgactt atcgccactg gcagcagcca ctggtaacag gattagcaga    3720
gcgaggtatg taggcggtgc tacagagttc ttgaagtggt ggcctaacta cggctacact    3780
```

```
agaaggacag tatttggtat ctgcgctctg ctgaagccag ttaccttcgg aaaaagagtt    3840
ggtagctctt gatccggcaa acaaaccacc gctggtagcg gtggtttttt tgtttgcaag    3900
cagcagatta cgcgcagaaa aaaggatct  caagaagatc ctttgatctt ttctacgggg    3960
tctgacgctc agtggaacga aaactcacgt taagggattt tggtcatgag attatcaaaa    4020
aggatcttca cctagatcct tttaaattaa aatgaagtt  ttaaatcaat ctaaagtata    4080
tatgagtaaa cttggtctga cagttaccaa tgcttaatca gtgaggcacc tatctcagcg    4140
atctgtctat ttcgttcatc catagttgcc tgactccccg tcgtgtagat aactacgata    4200
cgggagggct taccatctgg ccccagtgct gcaatgatac cgcgagaccc acgctcaccg    4260
gctccagatt tatcagcaat aaaccagcca gccggaaggg ccgagcgcag aagtggtcct    4320
gcaactttat ccgcctccat ccagtctatt aattgttgcc gggaagctag agtaagtagt    4380
tcgccagtta atagtttgcg caacgttgtt gccattgcta caggcatcgt ggtgtcacgc    4440
tcgtcgtttg gtatggcttc attcagctcc ggttcccaac gatcaaggcg agttacatga    4500
tcccccatgt tgtgcaaaaa agcggttagc tccttcggtc ctccgatcgt tgtcagaagt    4560
aagttggccg cagtgttatc actcatggtt atggcagcac tgcataattc tcttactgtc    4620
atgccatccg taagatgctt ttctgtgact ggtgagtact caaccaagtc attctgagaa    4680
tagtgtatgc ggcgaccgag ttgctcttgc ccggcgtcaa tacgggataa taccgcgcca    4740
catagcagaa ctttaaaagt gctcatcatt ggaaaacgtt cttcggggcg aaaactctca    4800
aggatcttac cgctgttgag atccagttcg atgtaaccca ctcgtgcacc caactgatct    4860
tcagcatctt ttactttcac cagcgtttct gggtgagcaa aaacaggaag gcaaaatgcc    4920
gcaaaaaagg gaataagggc gacacggaaa tgttgaatac tcatactctt cctttttcaa    4980
tattattgaa gcatttatca gggttattgt ctcatgagcg gatacatatt tgaatgtatt    5040
tagaaaaata aacaaatagg ggttccgcgc acatttcccc gaaaagtgcc acctgaacga    5100
agcatctgtg cttcattttg tagaacaaaa atgcaacgcg agagcgctaa ttttttcaaac    5160 aaagaatctg agctgcattt ttacagaaca gaaatgcaac gcgaaagcgc tattttacca    5220
acgaagaatc tgtgcttcat ttttgtaaaa caaaaatgca acgcgagagc gctaattttt    5280
caaacaaaga atctgagctg catttttaca gaacagaaat gcaacgcgag agcgctattt    5340
taccaacaaa gaatctatac ttcttttttg ttctacaaaa atgcatcccg agagcgctat    5400
ttttctaaca aagcatctta gattactttt tttctccttt gtgcgctcta taatgcagtc    5460
tcttgataac ttttttgcact gtaggtccgt taaggttaga agaaggctac tttggtgtct    5520
attttctctt ccataaaaaa agcctgactc cacttcccgc gtttactgat tactagcgaa    5580
gctgcgggtg cattttttca agataaaggc atccccgatt atattctata ccgatgtgga    5640
ttgcgcatac tttgtgaaca gaaagtgata gcgttgatga ttcttcattg gtcagaaaat    5700
tatgaacggt ttcttctatt ttgtctctat atactacgta taggaaatgt ttacattttc    5760
gtattgtttt cgattcactc tatgaatagt tcttactaca atttttttgt ctaaagagta    5820
atactagaga taaacataaa aaatgtagag gtcgagttta gatgcaagtt caaggagcga    5880
aaggtggatg ggtaggttat atagggatat agcacagaga tatatagcaa agagatactt    5940
ttgagcaatg tttgtggaag cggtattcgc aatattttag tagctcgtta cagtccggtg    6000 cgttttggt  tttttgaaag tgcgtcttca gagcgctttt ggttttcaaa agcgctctga    6060
agttcctata ctttctagag aataggaact tcggaatagg aacttcaaag cgtttccgaa    6120
```

| aacgagcgct tccgaaaatg caacgcgagc tgcgcacata cagctcactg ttcacgtcgc | 6180 |
| acctatatct gcgtgttgcc tgtatatata tatacatgag aagaacggca tagtgcgtgt | 6240 |
| ttatgcttaa atgcgtactt atatgcgtct atttatgtag gatgaaaggt agtctagtac | 6300 |
| ctcctgtgat attatcccat tccatgcggg gtatcgtatg cttccttcag cactacccct | 6360 |
| tagctgttct atatgctgcc actcctcaat tggattagtc tcatccttca atgctatcat | 6420 |
| ttcctttgat attggatcat attaagaaac cattattatc atgacattaa cctataaaaa | 6480 |
| taggcgtatc acgaggccct ttcgtc | 6506 |

<210> SEQ ID NO 22
<211> LENGTH: 6616
<212> TYPE: DNA
<213> ORGANISM: Artificial Sequence
<220> FEATURE:
<223> OTHER INFORMATION: Synthetic polynucleotide

<400> SEQUENCE: 22

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accataccac agcttttcaa ttcaattcat catttttttt ttattctttt ttttgatttc | 240 |
| ggtttctttg aaatttttt gattcggtaa tctccgaaca aaggaagaa cgaaggaagg | 300 |
| agcacagact tagattggta tatatacgca tatgtagtgt tgaagaaaca tgaaattgcc | 360 |
| cagtattctt aacccaactg cacagaacaa aaacctgcag gaaacgaaga taaatcatgt | 420 |
| cgaaagctac atataaggaa cgtgctgcta ctcatcctag tcctgttgct gccaagctat | 480 |
| ttaatatcat gcacgaaaag caaacaaact tgtgtgcttc attggatgtt cgtaccacca | 540 |
| aggaattact ggagttagtt gaagcattag gtcccaaaat ttgtttacta aaaacacatg | 600 |
| tggatatctt gactgatttt tccatggagg gcacagttaa gccgctaaag gcattatccg | 660 |
| ccaagtacaa ttttttactc ttcgaagaca gaaaatttgc tgacattggt aatacagtca | 720 |
| aattgcagta ctctgcgggt gtatacagaa tagcagaatg ggcagacatt acgaatgcac | 780 |
| acggtgtggt gggcccaggt attgttagcg gtttgaagca ggcggcagaa gaagtaacaa | 840 |
| aggaacctag aggccttttg atgttagcag aattgtcatg caagggctcc ctatctactg | 900 |
| gagaatatac taagggtact gttgacattg cgaagagcga caaagatttt gttatcggct | 960 |
| ttattgctca agagacatg ggtggaagag atgaaggtta cgattggttg attatgacac | 1020 |
| ccggtgtggg tttagatgac aagggagacg cattgggtca acagtataga accgtggatg | 1080 |
| atgtggtctc tacaggatct gacattatta ttgttggaag aggactattt gcaaagggaa | 1140 |
| gggatgctaa ggtagagggt gaacgttaca gaaaagcagg ctgggaagca tatttgagaa | 1200 |
| gatgcggcca gcaaaactaa aaaactgtat tataagtaaa tgcatgtata ctaaactcac | 1260 |
| aaattagagc ttcaatttaa ttatatcagt tattacccta tgcggtgtga ataccgcac | 1320 |
| agatgcgtaa ggagaaaata ccgcatcagg aaattgtaaa cgttaatatt tgttaaaat | 1380 |
| tcgcgttaaa ttttgttaa atcagctcat tttttaacca ataggccgaa atcggcaaaa | 1440 |
| tcccttataa atcaaaagaa tagaccgaga tagggttgag tgttgttcca gtttggaaca | 1500 |
| agagtccact attaaagaac gtggactcca acgtcaaagg gcgaaaaacc gtctatcagg | 1560 |
| gcgatggccc actacgtgaa ccatcaccct aatcaagttt tttggggtcg aggtgccgta | 1620 |
| aagcactaaa tcggaaccct aaagggagcc cccgatttag agcttgacgg ggaaagccgg | 1680 |

-continued

```
cgaacgtggc gagaaaggaa gggaagaaag cgaaaggagc gggcgctagg gcgctggcaa      1740
gtgtagcggt cacgctgcgc gtaaccacca cacccgccgc gcttaatgcg ccgctacagg      1800
gcgcgtcgcg ccattcgcca ttcaggctgc gcaactgttg ggaagggcga tcggtgcggg      1860
cctcttcgct attacgccag ctggcgaaag ggggatgtgc tgcaaggcga ttaagttggg      1920
taacgccagg ttttcccag tcacgacgtt gtaaaacgac ggccagtgag cgcgcgtaat       1980
acgactcact atagggcgaa ttgggtaccg gccgcaaatt aaagccttcg agcgtcccaa      2040
aaccttctca agcaaggttt tcagtataat gttacatgcg tacacgcgtc tgtacagaaa      2100
aaaaagaaaa atttgaaata taataacgt tcttaatact aacataacta taaaaaaata       2160
aatagggacc tagacttcag gttgtctaac tccttccttt tcggttagag cggatgtggg      2220
gggagggcgt gaatgtaagc gtgacataac taattacatg actcgagcgg ccgcggatcc      2280
cgggaattcg tcgacaccat cttcttctga gatgagtttt tgttccatgc tagttctaga      2340
atccgtcgaa actaagttct ggtgttttaa aactaaaaaa aagactaact ataaaagtag      2400
aatttaagaa gtttaagaaa tagatttaca gaattacaat caatacctac cgtctttata      2460
tacttattag tcaagtaggg gaataatttc agggaactgg tttcaaccctt ttttttcagc     2520
tttttccaaa tcagagagag cagaaggtaa tagaaggtgt aagaaaatga gatagataca     2580
tgcgtgggtc aattgccttg tgtcatcatt tactccaggc aggttgcatc actccattga     2640
ggttgtgccc gtttttttgcc tgtttgtgcc cctgttctct gtagttgcgc taagagaatg    2700
gacctatgaa ctgatggttg gtgaagaaaa caatattttg gtgctgggat tcttttttt      2760
tctggatgcc agcttaaaaa gcgggctcca ttatatttag tggatgccag gaataaactg     2820
ttcacccaga cacctacgat gttatatatt ctgtgtaacc cgcccccat tttgggcatg      2880
tacgggttac agcagaatta aaaggctaat ttttgactaa aataaagtta ggaaaatcac     2940
tactattaat tatttacgta ttctttgaaa tggcgagtat tgataatgat aaactgagct    3000
ccagcttttg ttccctttag tgagggttaa ttgcgcgctt ggcgtaatca tggtcatagc    3060
tgtttcctgt gtgaaattgt tatccgctca caattccaca caacatagga gccggaagca    3120
taaagtgtaa agcctgggt gcctaatgag tgaggtaact cacattaatt gcgttgcgct     3180
cactgcccgc tttccagtcg ggaaacctgt cgtgccagct gcattaatga atcggccaac    3240
gcgcggggag aggcggtttg cgtattgggc gctcttccgc ttcctcgctc actgactcgc    3300
tgcgctcggt cgttcggctg cggcgagcgg tatcagctca ctcaaaggcg gtaatacggt    3360
tatccacaga atcaggggat aacgcaggaa agaacatgtg agcaaaaggc cagcaaaagg    3420
ccaggaaccg taaaaaggcc gcgttgctgg cgttttttcca taggctccgc cccctgacg    3480
agcatcacaa aaatcgacgc tcaagtcaga ggtggcgaaa cccgacagga ctataaagat    3540
accaggcgtt cccccctgga agctccctcg tgcgctctcc tgttccgacc ctgccgctta    3600
ccggatacct gtccgccttt ctcccttcgg aagcgtggc gctttctcat agctcacgct     3660
gtaggtatct cagttcggtg taggtcgttc gctccaagct gggctgtgtg cacgaacccc    3720
ccgttcagcc cgaccgctgc gccttatccg gtaactatcg tcttgagtcc aacccggtaa    3780
gacacgactt atcgccactg gcagcagcca ctggtaacag gattagcaga gcgaggtatg    3840
taggcggtgc tacagagttc ttgaagtggt ggcctaacta cggctacact agaaggacag    3900
tatttggtat ctgcgctctg ctgaagccag ttaccttcgg aaaaagagtt ggtagctctt    3960
gatccggcaa acaaaccacc gctggtagcg gtggtttttt tgtttgcaag cagcagatta    4020
```

```
cgcgcagaaa aaaaggatct caagaagatc ctttgatctt ttctacgggg tctgacgctc    4080
agtggaacga aaactcacgt taagggattt tggtcatgag attatcaaaa aggatcttca    4140
cctagatcct tttaaattaa aaatgaagtt ttaaatcaat ctaaagtata tatgagtaaa    4200
cttggtctga cagttaccaa tgcttaatca gtgaggcacc tatctcagcg atctgtctat    4260
ttcgttcatc catagttgcc tgactccccg tcgtgtagat aactacgata cgggagggct    4320
taccatctgg ccccagtgct gcaatgatac cgcgagaccc acgctcaccg gctccagatt    4380
tatcagcaat aaaccagcca gccggaaggg ccgagcgcag aagtggtcct gcaactttat    4440
ccgcctccat ccagtctatt aattgttgcc gggaagctag agtaagtagt tcgccagtta    4500
atagtttgcg caacgttgtt gccattgcta caggcatcgt ggtgtcacgc tcgtcgtttg    4560
gtatggcttc attcagctcc ggttcccaac gatcaaggcg agttacatga tcccccatgt    4620
tgtgcaaaaa agcggttagc tccttcggtc tccgatcgt tgtcagaagt aagttggccg    4680
cagtgttatc actcatggtt atggcagcac tgcataattc tcttactgtc atgccatccg    4740
taagatgctt ttctgtgact ggtgagtact caaccaagtc attctgagaa tagtgtatgc    4800
ggcgaccgag ttgctcttgc ccggcgtcaa tacgggataa taccgcgcca catagcagaa    4860
cttttaaaagt gctcatcatt ggaaaacgtt cttcggggcg aaaactctca aggatcttac    4920
cgctgttgag atccagttcg atgtaaccca ctcgtgcacc caactgatct tcagcatctt    4980
ttactttcac cagcgtttct gggtgagcaa aaacaggaag gcaaaatgcc gcaaaaaagg    5040
gaataagggc gacacggaaa tgttgaatac tcatactctt cctttttcaa tattattgaa    5100
gcatttatca gggttattgt ctcatgagcg gatacatatt tgaatgtatt tagaaaaata    5160
aacaaatagg ggttccgcgc acatttcccc gaaaagtgcc acctgaacga agcatctgtg    5220
cttcattttg tagaacaaaa atgcaacgcg agagcgctaa ttttttcaaac aaagaatctg    5280
agctgcattt ttacagaaca gaaatgcaac gcgaaagcgc tattttacca acgaagaatc    5340
tgtgcttcat ttttgtaaaa caaaaatgca acgcgagagc gctaattttt caaacaaaga    5400
atctgagctg cattttttaca gaacagaaat gcaacgcgag agcgctattt taccaacaaa    5460
gaatctatac ttcttttttg ttctacaaaa atgcatcccg agagcgctat ttttctaaca    5520
aagcatctta gattactttt tttctccttt gtgcgctcta taatgcagtc tcttgataac    5580
tttttgcact gtaggtccgt taaggttaga agaaggctac tttggtgtct attttctctt    5640
ccataaaaaa agcctgactc cacttcccgc gtttactgat tactagcgaa gctgcgggtg    5700
cattttttca agataaaggc atccccgatt atattctata ccgatgtgga ttgcgcatac    5760
tttgtgaaca gaaagtgata gcgttgatga ttcttcattg gtcagaaaat tatgaacggt    5820
ttcttctatt ttgtctctat atactacgta taggaaatgt ttacattttc gtattgtttt    5880
cgattcactc tatgaatagt tcttactaca attttttgt ctaaagagta atactagaga    5940
taaacataaa aaatgtagag gtcgagttta gatgcaagtt caaggagcga aaggtggatg    6000
ggtaggttat atagggatat agcacagaga tatatagcaa agagatactt ttgagcaatg    6060
tttgtggaag cggtattcgc aatatttag tagctcgtta cagtccggtg cgttttttggt    6120
ttttgaaag tgcgtcttca gagcgctttt ggttttcaaa agcgctctga agttcctata    6180
ctttctagag aataggaact tcggaatagg aacttcaaag cgtttccgaa aacgagcgct    6240
tccgaaaatg caacgcgagc tgcgcacata cagctcactg ttcacgtcgc acctatatct    6300
gcgtgttgcc tgtatatata tatacatgag aagaacggca tagtgcgtgt ttatgcttaa    6360
atgcgtactt atatgcgtct atttatgtag gatgaaaggt agtctagtac ctcctgtgat    6420
```

| | |
|---|---|
| attatcccat tccatgcggg gtatcgtatg cttccttcag cactacccct tagctgttct | 6480 |
| atatgctgcc actcctcaat tggattagtc tcatccttca atgctatcat ttcctttgat | 6540 |
| attggatcat actaagaaac cattattatc atgacattaa cctataaaaa taggcgtatc | 6600 |
| acgaggccct ttcgtc | 6616 |

<210> SEQ ID NO 23
<211> LENGTH: 7974
<212> TYPE: DNA
<213> ORGANISM: Artificial Sequence
<220> FEATURE:
<223> OTHER INFORMATION: Synthetic polynucleotide

<400> SEQUENCE: 23

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accataaacg acattactat atatataata taggaagcat ttaatagaca gcatcgtaat | 240 |
| atatgtgtac tttgcagtta tgacgccaga tggcagtagt ggaagatatt ctttattgaa | 300 |
| aaatagcttg tcaccttacg tacaatcttg atccggagct tttctttttt tgccgattaa | 360 |
| gaattaattc ggtcgaaaaa agaaaaggag agggccaaga ggggggcat tggtgactat | 420 |
| tgagcacgtg agtatacgtg attaagcaca caaaggcagc ttggagtatg tctgttatta | 480 |
| atttcacagg tagttctggt ccattggtga agtttgcgg cttgcagagc acagaggccg | 540 |
| cagaatgtgc tctagattcc gatgctgact tgctgggtat tatatgtgtg cccaatagaa | 600 |
| agagaacaat tgacccggtt attgcaagga aaatttcaag tcttgtaaaa gcatataaaa | 660 |
| atagttcagg cactccgaaa tacttggttg gcgtgtttcg taatcaacct aaggaggatg | 720 |
| ttttggctct ggtcaatgat tacggcattg atatcgtcca actgcatgga gatgagtcgt | 780 |
| ggcaagaata ccaagagttc ctcggttttgc cagttattaa aagactcgta tttccaaaag | 840 |
| actgcaacat actactcagt gcagcttcac agaaacctca ttcgtttatt cccttgtttg | 900 |
| attcagaagc aggtgggaca ggtgaacttt tggattggaa ctcgatttct gactgggttg | 960 |
| gaaggcaaga gagccccgaa agcttacatt ttatgttagc tggtggactg acgccagaaa | 1020 |
| atgttggtga tgcgcttaga ttaaatggcg ttattggtgt tgatgtaagc ggaggtgtgg | 1080 |
| agacaaatgg tgtaaaagac tctaacaaaa tagcaaattt cgtcaaaaat gctaagaaat | 1140 |
| aggttattac tgagtagtat ttatttaagt attgtttgtg cacttgccta tgcggtgtga | 1200 |
| aataccgcac agatgcgtaa ggagaaaata ccgcatcagg aaattgtaaa cgttaatatt | 1260 |
| ttgttaaaat tcgcgttaaa ttttttgttaa atcagctcat tttttaacca ataggccgaa | 1320 |
| atcggcaaaa tcccttataa atcaaaagaa tagaccgaga tagggttgag tgttgttcca | 1380 |
| gtttggaaca agagtccact attaaagaac gtggactcca acgtcaaagg gcgaaaaacc | 1440 |
| gtctatcagg gcgatggccc actacgtgaa ccatcaccct aatcaagttt tttggggtcg | 1500 |
| aggtgccgta aagcactaaa tcggaaccct aaagggagcc ccgatttag agcttgacgg | 1560 |
| ggaaagccgg cgaacgtggc gagaaaggaa gggaagaaag cgaaaggagc gggcgctagg | 1620 |
| gcgctggcaa gtgtagcggt cacgctgcgc gtaaccacca cacccgccgc gcttaatgcg | 1680 |
| ccgctacagg gcgcgtcgcg ccattcgcca ttcaggctgc gcaactgttg ggaagggcga | 1740 |
| tcggtgcggg cctcttcgct attacgccag ctggcgaaag gggatgtgc tgcaaggcga | 1800 |

-continued

```
ttaagttggg taacgccagg gttttcccag tcacgacgtt gtaaaacgac ggccagtgag    1860
cgcgcgtaat acgactcact atagggcgaa ttgggtaccg gccgcaaatt aaagccttcg    1920
agcgtcccaa aaccttctca agcaaggttt tcagtataat gttacatgcg tacacgcgtc    1980
tgtacagaaa aaaagaaaaa atttgaaata taaataacgt tcttaatact aacataacta    2040
taaaaaaata aatagggacc tagacttcag gttgtctaac tccttcctttt tcggttagag    2100
cggatgtggg gggagggcgt gaatgtaagc gtgacataac taattacatg actcgagcgg    2160
ccgcggatcc ctagagagct tcgttttca tgagttcccc gaattctttc ggaagcttgt    2220
cacttgctaa attaacgtta tcactgtagt caaccgggac atcaatgatg acaggcccct    2280
cagcgttcat gccttgacgc agaacatctg ccagctggtc tggtgattct acgcgtaagc    2340
cagttgctcc gaagctttcc gcgtatttca cgatatcgat atttccgaaa tcgaccgcag    2400
atgtacgatt atatttttc aattgctgga atgcaaccat gtcatatgtg ctgtcgttcc    2460
atacaatgtg tacaattggt gcttttaaac gaactgctgt ctctaattcc atagctgaga    2520
ataagaaacc gccatcaccg gagactgata ctacttttc tcccggtttc accaatgaag    2580
cgccgattgc ccaaggaagc gcaacgccga gtgtttgcat accgttacta atcattaatg    2640
ttaacggctc gtagctgcgg aaataacgtg acatccaaat cgcgtgtgaa ccgatatcgc    2700
aagtcactgt aacatgatca tcgactgcgt ttcgcaattc tttaacgatt tcaagaggat    2760
gcactctgtc tgatttccaa tctgcaggca cctgctcacc ctcatgcata tattgtttta    2820
aatcagaaag gatcttctgc tcacgttccg caaagtctac tttcacagca tcgtgttcga    2880
tatgattgat cgtagatgga atatcaccga tcagttcaag atccggctgg taagcatgat    2940
caatgtcagc cagaatctcg tctaaatgga tgatcgtccg gtctccattg acattccaga    3000
atttcggatc atattcaatt gggtcatagc cgattgtcag aacaacatca gcctgctcaa    3060
gcagcagatc gccaggctgg ttgcggaata aaccgatccg gccaaaatac tgatcctcta    3120
aatctctcgt aagagtaccg gcagcttgat atgtttcaac gaatggaagc tgcacttttt    3180
tcaatagctt gcgaaccgct ttaatcgctt ccggtcttcc gcccttcatg ccgactaaaa    3240
cgacaggaag ttttgctgtt tgaattttg caatggccat actgattgcg tcatctgctg    3300
cgggaccaag ttttggcgct gcgacagcac gtacgttttt tgtatttgtg acttcattca    3360
caacatcttg cggaaaactc acaaaagcgg ccccagcctg ccctgctgac gctatcctaa    3420
acgcatttgt aacagcttcc ggtatatttt ttacatcttg aacttctaca ctgtatttg    3480
taatcggctg gaatagcgcc gcattatcca aagattgatg tgtccgtttt aaacgatctg    3540
cacggatcac gttcccagca agcgcaacga cagggtcacc ttcagtgttt gctgtcagca    3600
gtcctgttgc caagttcgaa gcacctggtc ctgatgtgac taacacgact cccggttttc    3660
cagttaaacg gccgactgct tgcgccataa atgctgcatt ttgttcatgc cgggcaacga    3720
taatttcagg ccctttatct tgtaaagcgt caaataccgc atcaattttt gcacctggaa    3780
tgccaaatac atgtgtgaca ccttgctccg ctaagcaatc aacaacaagc tccgcccctc    3840
tgcttttcac aagggatttt tgttcttttg ttgcttttgt caacatgtcg actttatgtg    3900
atgattgatt gattgattgt acagtttgtt tttcttaata tctatttcga tgacttctat    3960
atgatattgc actaacaaga agatattata atgcaattga tacaagacaa ggagttattt    4020
gcttctcttt tatatgattc tgacaatcca tattgcgttg gtagtctttt ttgctggaac    4080
ggttcagcgg aaaagacgca tcgctctttt tgcttctaga agaaatgcca gcaaaagaat    4140
ctcttgacag tgactgacag caaaaatgtc ttttctcaac tagtaacaag gctaagatat    4200
```

```
cagcctgaaa taaagggtgg tgaagtaata attaaatcat ccgtataaac ctatacacat   4260
atatgaggaa aaataataca aaagtgtttt aaatacagat acatacatga acatatgcac   4320
gtatagcgcc caaatgtcgg taatgggatc ggcgagctcc agcttttgtt ccctttagtg   4380
agggttaatt gcgcgcttgg cgtaatcatg gtcatagctg tttcctgtgt gaaattgtta   4440
tccgctcaca attccacaca ataggagc cggaagcata agtgtaaag cctggggtgc   4500 ctaatgagtg aggtaactca cattaattgc gttgcgctca ctgcccgctt ccagtcggg   4560 aaacctgtcg tgccagctgc attaatgaat cggccaacgc gcggggagag gcggtttgcg   4620
tattgggcgc tcttccgctt cctcgctcac tgactcgctg cgctcggtcg ttcggctgcg   4680
gcgagcggta tcagctcact caaaggcggt aatacggtta ccacagaat caggggataa   4740 cgcaggaaag aacatgtgag caaaaggcca gcaaaaggcc aggaaccgta aaaaggccgc   4800
gttgctggcg tttttccata ggctccgccc ccctgacgag catcacaaaa atcgacgctc   4860
aagtcagagg tggcgaaacc cgacaggact ataaagatac caggcgtttc ccctggaag   4920 ctccctcgtg cgctctcctg ttccgaccct gccgcttacc ggatacctgt ccgcctttct   4980
cccttcggga agcgtggcgc tttctcatag ctcacgctgt aggtatctca gttcggtgta   5040
ggtcgttcgc tccaagctgg gctgtgtgca cgaaccccc gttcagcccg accgctgcgc   5100
cttatccggt aactatcgtc ttgagtccaa cccggtaaga cacgacttat cgccactggc   5160
agcagccact ggtaacagga ttagcagagc gaggtatgta ggcggtgcta cagagttctt   5220
gaagtggtgg cctaactacg gctacactag aaggacagta tttggtatct gcgctctgct   5280
gaagccagtt accttcggaa aaagagttgg tagctcttga tccggcaaac aaaccaccgc   5340
tggtagcggt ggtttttttg tttgcaagca gcagattacg cgcagaaaaa aaggatctca   5400
agaagatcct ttgatctttt ctacggggtc tgacgctcag tggaacgaaa actcacgtta   5460
agggattttg gtcatgagat tatcaaaaag gatcttcacc tagatccttt taaattaaaa   5520
atgaagtttt aaatcaatct aaagtatata tgagtaaact tggtctgaca gttaccaatg   5580
cttaatcagt gaggcaccta tctcagcgat ctgtctattt cgttcatcca tagttgcctg   5640
actccccgtc gtgtagataa ctacgatacg ggagggctta ccatctggcc ccagtgctgc   5700
aatgataccg cgagacccac gctcaccggc tccagattta tcagcaataa accagccagc   5760
cggaagggcc gagcgcagaa gtggtcctgc aactttatcc gcctccatcc agtctattaa   5820
ttgttgccgg gaagctagag taagtagttc gccagttaat agtttgcgca acgttgttgc   5880
cattgctaca ggcatcgtgg tgtcacgctc gtcgtttggt atggcttcat tcagctccgg   5940
ttcccaacga tcaaggcgag ttacatgatc ccccatgttg tgcaaaaaag cggttagctc   6000
cttcggtcct ccgatcgttg tcagaagtaa gttggccgca gtgttatcac tcatggttat   6060
ggcagcactg cataattctc ttactgtcat gccatccgta agatgctttt ctgtgactgg   6120
tgagtactca accaagtcat tctgagaata gtgtatgcgg cgaccgagtt gctcttgccc   6180
ggcgtcaata cgggataata ccgcgccaca tagcagaact ttaaaagtgc tcatcattgg   6240
aaaacgttct cggggcgaa aactctcaag gatcttaccg ctgttgagat ccagttcgat   6300
gtaacccact cgtgcaccca actgatcttc agcatctttt actttcacca gcgtttctgg   6360
gtgagcaaaa acaggaaggc aaaatgccgc aaaaaaggga ataagggcga cacggaaatg   6420
ttgaatactc atactcttcc ttttcaata ttattgaagc atttatcagg gttattgtct   6480
catgagcgga tacatatttg aatgtattta gaaaaataaa caaatagggg ttccgcgcac   6540
```

```
atttccccga aaagtgccac ctgaacgaag catctgtgct tcattttgta gaacaaaaat    6600
gcaacgcgag agcgctaatt tttcaaacaa agaatctgag ctgcattttt acagaacaga    6660
aatgcaacgc gaaagcgcta ttttaccaac gaagaatctg tgcttcattt ttgtaaaaca    6720
aaaatgcaac gcgagagcgc taattttttca aacaaagaat ctgagctgca tttttacaga    6780
acagaaatgc aacgcgagag cgctatttta ccaacaaaga atctatactt ctttttttgtt    6840 ctacaaaaat gcatcccgag agcgctattt ttctaacaaa gcatcttaga ttactttttt    6900
tctcctttgt gcgctctata atgcagtctc ttgataactt tttgcactgt aggtccgtta    6960
aggttagaag aaggctactt tggtgtctat tttctcttcc ataaaaaaag cctgactcca    7020
cttcccgcgt ttactgatta ctagcgaagc tgcgggtgca ttttttcaag ataaaggcat    7080
ccccgattat attctatacc gatgtggatt gcgcatactt tgtgaacaga aagtgatagc    7140
gttgatgatt cttcattggt cagaaaatta tgaacggttt cttctatttt gtctctatat    7200
actacgtata ggaaatgttt acattttcgt attgttttcg attcactcta tgaatagttc    7260
ttactacaat tttttttgtct aaagagtaat actagagata aacataaaaaa atgtagaggt    7320 cgagtttaga tgcaagttca aggagcgaaa ggtggatggg taggttatat agggatatag    7380
cacagagata tatagcaaag agatactttt gagcaatgtt tgtggaagcg gtattcgcaa    7440
tattttagta gctcgttaca gtccggtgcg tttttggttt tttgaaagtg cgtcttcaga    7500
gcgcttttgg ttttcaaaag cgctctgaag ttcctatact ttctagagaa taggaacttc    7560
ggaataggaa cttcaaagcg tttccgaaaa cgagcgcttc cgaaaatgca acgcgagctg    7620
cgcacataca gctcactgtt cacgtcgcac ctatatctgc gtgttgcctg tatatatata    7680
tacatgagaa gaacggcata gtgcgtgttt atgcttaaat gcgtacttat atgcgtctat    7740
ttatgtagga tgaaaggtag tctagtacct cctgtgtatat tatcccattc catgcggggt    7800
atcgtatgct tccttcagca ctaccctta gctgttctat atgctgccac tcctcaattg    7860
gattagtctc atccttcaat gctatcattt cctttgatat tggatcatat taagaaacca    7920
ttattatcat gacattaacc tataaaaata ggcgtatcac gaggccctttt cgtc           7974
```

<210> SEQ ID NO 24
<211> LENGTH: 9692
<212> TYPE: DNA
<213> ORGANISM: Artificial Sequence
<220> FEATURE:
<223> OTHER INFORMATION: Synthetic polynucleotide

<400> SEQUENCE: 24

```
ttggatcata ctaagaaacc attattatca tgacattaac ctataaaaat aggcgtatca      60
cgaggccctt tcgtctcgcg cgtttcggtg atgacggtga aaacctctga cacatgcagc     120
tcccggagac ggtcacagct tgtctgtaag cggatgccgg gagcagacaa gcccgtcagg     180
gcgcgtcagc gggtgttggc gggtgtcggg gctggcttaa ctatgcggca tcagagcaga     240
ttgtactgag agtgcaccat accacagctt tcaattcaa ttcatcatt ttttttttatt     300 cttttttttg atttcggttt ctttgaaatt ttttgattc ggtaatctcc gaacagaagg     360
aagaacgaag gaaggagcac agacttagat tggtatatat acgcatatgt agtgttgaag     420
aaacatgaaa ttgcccagta ttcttaaccc aactgcacag aacaaaaacc tgcaggaaac     480
gaagataaat catgtcgaaa gctacatata aggaacgtgc tgctactcat cctagtcctg     540
ttgctgccaa gctatttaat atcatgcacg aaaagcaaac aaacttgtgt gcttcattgg     600
atgttcgtac caccaaggaa ttactggagt tagttgaagc attaggtccc aaaatttgtt     660
```

```
tactaaaaac acatgtggat atcttgactg attttccat ggagggcaca gttaagccgc    720
taaaggcatt atccgccaag tacaattttt tactcttcga agacagaaaa tttgctgaca    780
ttggtaatac agtcaaattg cagtactctg cgggtgtata cagaatagca gaatgggcag    840
acattacgaa tgcacacggt gtggtgggcc caggtattgt tagcggtttg aagcaggcgg    900
cagaagaagt aacaaaggaa cctagaggcc ttttgatgtt agcagaattg tcatgcaagg    960
gctccctatc tactggagaa tatactaagg gtactgttga cattgcgaag agcgacaaag   1020
attttgttat cggctttatt gctcaaagag acatgggtgg aagagatgaa ggttacgatt   1080
ggttgattat gacacccggt gtgggtttag atgacaaggg agacgcattg ggtcaacagt   1140
atagaaccgt ggatgatgtg gtctctacag gatctgacat tattattgtt ggaagaggac   1200
tatttgcaaa gggaagggat gctaaggtag agggtgaacg ttacagaaaa gcaggctggg   1260
aagcatattt gagaagatgc ggccagcaaa actaaaaaac tgtattataa gtaaatgcat   1320
gtatactaaa ctcacaaatt agagcttcaa tttaattata tcagttatta ccctatgcgg   1380
tgtgaaatac cgcacagatg cgtaaggaga aaataccgca tcaggaaatt gtaaacgtta   1440
atattttgtt aaaattcgcg ttaaattttt gttaaatcag ctcatttttt aaccaatagg   1500
ccgaaatcgg caaaatccct tataaatcaa agaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaaggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaagggggga tgtgctgcaa   1980 ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggag ggcgtgaatg taagcgtgac ataactaatt acatgagcgg   2340
ccgcctattt atggaatttc ttatcataat cgaccaaagt aaatctgtat ttgacgtctc   2400
cgctttccat ccttgtaaag gcatggctga cgccttcttc gctgatcgga agtttttcca   2460
cccatatttt gacattcttt tcggaaacta atttcaatag ttgttcgatt ccttcctag   2520 atccgatagc actgcttgag attgatactc ccattaggcc caacggtttt aaaacaagct   2580
tttcattaac ttcaggagca gcaattgaaa cgatggagcc tccaatcttc ataatcttaa   2640
cgatactgtc aaaattaact ttcgacaaag atgatgagca aacgacaaga aggtccaaag   2700
cgttagagta ttgttctgtc cagcctttat cctccaacat agcaatatag tgatcagcac   2760
cgagtttcat agaatcctcc cgcttggagt ggcctcgcga aaacgcataa acctcggctc   2820
ccatagcttt agccaacaga atccccatat gcccaatacc accgatgcca acaatacata   2880
ccctcttacc tggaccacag ccatttctta gtagtggaga gaaaactgta ataccaccac   2940
acaataatgg agcggctagc ggacttggaa tattttctgg tatttgaata gcaaagtgtt   3000
```

```
catgaagcct cacgtgggag gcaaagcctc cttgtgaaat gtagccgtcc ttgtaaggag    3060
tccacatagt caaaacgtgg tcattggtac agtattgctc gttgtcactt ttgcaacgtt    3120
cacactcaaa acacgccaag gcttgggcac caacaccaac acggtcaccg attttttaccc  3180 cagtgtggca cttggatcca accttcacca cgcggccaat tatttcatgt ccaaggattt    3240
gattttctgg gactggaccc caattaccaa cggctatatg aaaatcagat ccgcagatac    3300
cacaggcttc aatttcaaca tcaacgtcat gatcgccaaa gggttttggg tcaaaactca    3360
ctaatttagg atgcttccaa tcctttgcgt tggaaatacc gatgccctga aattttctg     3420 ggtaaagcat gtcgagtcga aactaagttc tggtgtttta aaactaaaaa aaagactaac    3480
tataaaagta gaatttaaga agtttaagaa atagatttac agaattacaa tcaatacccta  3540 ccgtctttat atacttatta gtcaagtagg ggaataattt cagggaactg gtttcaacct    3600 ttttttttcag cttttttccaa atcagagaga gcagaaggta atagaaggtg taagaaaatg  3660
agatagatac atgcgtgggt caattgcctt gtgtcatcat ttactccagg caggttgcat   3720
cactccattg aggttgtgcc cgtttttttgc ctgtttgtgc ccctgttctc tgtagttgcg   3780
ctaagagaat ggacctatga actgatggtt ggtgaagaaa acaatatttt ggtgctggga    3840
ttcttttttt ttctggatgc cagcttaaaa agcgggctcc attatattta gtggatgcca   3900
ggaataaact gttcacccag acacctacga tgttatatat tctgtgtaac ccgcccccta    3960
ttttgggcat gtacgggtta cagcagaatt aaaaggctaa ttttttgact aaataaagtt    4020
aggaaaatca ctactattaa ttatttacgt attctttgaa atggcgagta ttgataatga    4080
taaactggat ccttaggatt tattctgttc agcaaacagc ttgcccattt tcttcagtac    4140
cttcggtgcg ccttctttcg ccaggatcag ttcgatccag tacatacggt tcggatcggc    4200
ctgggcctct ttcatcacgc tcacaaattc gttttcggta cgcacaattt tagacacaac    4260
acggtcctca gttgcgccga aggactccgg cagtttagag tagttccaca tagggatatc   4320
gttgtaagac tggttcggac cgtggatctc acgctcaacg gtgtagccgt cattgttaat   4380
aatgaagcaa atcgggttga tcttttcacg aattgccaga cccagttcct gtacggtcag    4440
ctgcagggaa ccgtcaccga tgaacagcag atgacgagat tctttatcag cgatctgaga    4500
gcccagcgct gccgggaaag tatagccaat gctaccccac agcggctgac cgataaaatg    4560
gcttttggat ttcagaaaga tagaagacgc gccgaaaaag ctcgtacctt gttccgccac    4620
gatggtttca ttgctctggg tcaggttctc cacggcctgc cacaggcgat cctgggacag    4680
cagtgcgtta gatggtacga aatcttcttg cttttttgtca atgtatttgc ctttatactc   4740
gatttcggac aggtccagca gagagctgat caggctttcg aagtcgaagt tctggatacg    4800
ctcgttgaag attttacccct cgtcgatgtt caggctaatc attttgtttt cgttcagatg   4860
gtgagtgaat gcaccggtag aagagtcggt cagtttaacg cccagcatca ggatgaagtc    4920
cgcagattca acaaattctt tcaggttcgg ttcgctcaga gtaccgttgt agatgcccag    4980
gaaagacggc agagcctcgt caacagagga cttgccgaag ttcagggtgg taatcggcag    5040
tttggttttg ctgatgaatt gggtcacggt cttctccaga ccaaaagaaa tgatttcgtg    5100
gccggtgatc acgattggtt tctttgcgtt tttcagagac tcctggattt tgttcaggat    5160
ttcctggtcg ctagtgttag aagtggagtt ttcttcttc agcggcaggc tcggttttc     5220 cgctttagct gccgcaacat ccacaggcag gttgatgtaa actggtttgc gttcttcag    5280 cagcgcagac agaacgcggt cgatttccac agtagcgttc tctgcagtca gcagcgtacg    5340
tgccgcagtc acaggttcat gcattttcat gaagtgtttg aaatcgccgt cagccagagt    5400
```

```
gtggtggacg aatttacctt cgttctgaac tttgctcgtt gggctgccta cgatctccac    5460
caccggcagg ttttcggcgt aggagcccgc cagaccgttg acggcgctca gttcgccaac    5520
accgaaagtg gtcagaaatg ccgcggcttt cttggtacgt gcataaccat ctgccatgta    5580
gcttgcgttc agttcgttag cgttacccac ccatttcatg tctttatgag agatgatctg    5640
atccaggaac tgcagattgt aatcacccgg aacgccgaag atttcttcga tacccagttc    5700
atgcagacgt tccagcagat aatcaccaac agtatacatg tcgacaaact tagattagat    5760
tgctatgctt tctttctaat gagcaagaag taaaaaaagt tgtaatagaa caagaaaaat    5820
gaaactgaaa cttgagaaat tgaagaccgt ttattaactt aaatatcaat gggaggtcat    5880
cgaaagagaa aaaatcaaa aaaaaattt tcaagaaaaa gaaacgtgat aaaaattttt    5940
attgcctttt tcgacgaaga aaaagaaacg aggcggtctc ttttttcttt tccaaacctt    6000
tagtacgggt aattaacgac accctagagg aagaagagg ggaaatttag tatgctgtgc    6060
ttgggtgttt tgaagtggta cggcgatgcg cggagtccga gaaatctgg aagagtaaaa    6120 aaggagtaga aacattttga agctatgagc tccagctttt gttcccttta gtgagggtta    6180
attgcgcgct tggcgtaatc atggtcatag ctgtttcctg tgtgaaattg ttatccgctc    6240
acaattccac acaacatagg agccggaagc ataaagtgta aagcctgggg tgcctaatga    6300
gtgaggtaac tcacattaat tgcgttgcgc tcactgcccg ctttccagtc gggaaacctg    6360
tcgtgccagc tgcattaatg aatcggccaa cgcgcgggga gaggcggttt gcgtattggg    6420
cgctcttccg cttcctcgct cactgactcg ctgcgctcgg tcgttcggct gcggcgagcg    6480
gtatcagctc actcaaaggc ggtaatacgg ttatccacag aatcagggga taacgcagga    6540
aagaacatgt gagcaaaagg ccagcaaaag gccaggaacc gtaaaaaggc cgcgttgctg    6600 gcgttttcc ataggctccg ccccctgac gagcatcaca aaaatcgacg ctcaagtcag    6660
aggtggcgaa acccgacagg actataaaga taccaggcgt ttccccctgg aagctccctc    6720
gtgcgctctc ctgttccgac cctgccgctt accggatacc tgtccgcctt tctcccttcg    6780
ggaagcgtgg cgctttctca tagctcacgc tgtaggtatc tcagttcggt gtaggtcgtt    6840
cgctccaagc tgggctgtgt gcacgaaccc cccgttcagc ccgaccgctg cgccttatcc    6900
ggtaactatc gtcttgagtc aacccggta agacacgact tatcgccact ggcagcagcc    6960
actggtaaca ggattagcag agcgaggtat gtaggcggtg ctacagagtt cttgaagtgg    7020
tggcctaact acggctacac tagaaggaca gtatttggta tctgcgctct gctgaagcca    7080
gttaccttcg gaaaaagagt tggtagctct tgatccggca acaaaccac cgctggtagc    7140 ggtggttttt ttgtttgcaa gcagcagatt acgcgcagaa aaaaggatc tcaagaagat    7200 cctttgatct tttctacggg gtctgacgct cagtggaacg aaaactcacg ttaagggatt    7260
ttggtcatga gattatcaaa aaggatcttc acctagatcc ttttaaatta aaaatgaagt    7320
tttaaatcaa tctaaagtat atatgagtaa acttggtctg acagttacca atgcttaatc    7380
agtgaggcac ctatctcagc gatctgtcta tttcgttcat ccatagttgc ctgactcccc    7440
gtcgtgtaga taactacgat acgggagggc ttaccatctg gccccagtgc tgcaatgata    7500
ccgcgagacc cacgctcacc ggctccagat ttatcagcaa taaaccagcc agccggaagg    7560
gccgagcgca gaagtggtcc tgcaacttta tccgcctcca tccagtctat taattgttgc    7620
cgggaagcta gagtaagtag ttcgccagtt aatagtttgc gcaacgttgt tgccattgct    7680
acaggcatcg tggtgtcacg ctcgtcgttt ggtatggctt cattcagctc cggttcccaa    7740
```

| | | |
|---|---|---|
| cgatcaaggc gagttacatg atcccccatg ttgtgcaaaa aagcggttag ctccttcggt | 7800 |
| cctccgatcg ttgtcagaag taagttggcc gcagtgttat cactcatggt tatggcagca | 7860 |
| ctgcataatt ctcttactgt catgccatcc gtaagatgct tttctgtgac tggtgagtac | 7920 |
| tcaaccaagt cattctgaga atagtgtatg cggcgaccga gttgctcttg cccggcgtca | 7980 |
| atacgggata ataccgcgcc acatagcaga actttaaaag tgctcatcat tggaaaacgt | 8040 |
| tcttcggggc gaaaactctc aaggatctta ccgctgttga gatccagttc gatgtaaccc | 8100 |
| actcgtgcac ccaactgatc ttcagcatct tttactttca ccagcgtttc tgggtgagca | 8160 |
| aaaacaggaa ggcaaaatgc cgcaaaaaag gaataagggc gacacggaaa atgttgaata | 8220 |
| ctcatactct tcctttttca atattattga agcatttatc agggttattg tctcatgagc | 8280 |
| ggatacatat ttgaatgtat ttagaaaaat aaacaaatag gggttccgcg cacatttccc | 8340 |
| cgaaaagtgc cacctgaacg aagcatctgt gcttcatttt gtagaacaaa aatgcaacgc | 8400 |
| gagagcgcta attttcaaa caaagaatct gagctgcatt tttacagaac agaaatgcaa | 8460 |
| cgcgaaagcg ctattttacc aacgaagaat ctgtgcttca tttttgtaaa acaaaaatgc | 8520 |
| aacgcgagag cgctaatttt tcaaacaaag aatctgagct gcatttttac agaacagaaa | 8580 |
| tgcaacgcga gagcgctatt ttaccaacaa agaatctata cttctttttt gttctacaaa | 8640 |
| aatgcatccc gagagcgcta ttttctaac aaagcatctt agattacttt ttttctcctt | 8700 |
| tgtgcgctct ataatgcagt ctcttgataa cttttgcac tgtaggtccg ttaaggttag | 8760 |
| aagaaggcta ctttggtgtc tattttctct tccataaaaa aagcctgact ccacttcccg | 8820 |
| cgttactga ttactagcga agctgcgggt gcattttttc aagataaagg catcccgat | 8880 |
| tatattctat accgatgtgg attgcgcata ctttgtgaac agaaagtgat agcgttgatg | 8940 |
| attcttcatt ggtcagaaaa ttatgaacgg tttcttctat tttgtctcta tatactacgt | 9000 |
| ataggaaatg tttacatttt cgtattgttt tcgattcact ctatgaatag ttcttactac | 9060 |
| aatttttttg tctaaagagt aatactagag ataaacataa aaaatgtaga ggtcgagttt | 9120 |
| agatgcaagt tcaaggagcg aaaggtggat gggtaggtta tatagggata tagcacagag | 9180 |
| atatatagca aagagatact tttgagcaat gtttgtggaa gcggtattcg caatatttta | 9240 |
| gtagctcgtt acagtccggt gcgtttttgg tttttgaaa gtgcgtcttc agagcgcttt | 9300 |
| tggttttcaa aagcgctctg aagttcctat actttctaga aataggaac ttcggaatag | 9360 |
| gaacttcaaa gcgtttccga aaacgagcgc ttccgaaaat gcaacgcgag ctgcgcacat | 9420 |
| acagctcact gttcacgtcg cacctatatc tgcgtgttgc ctgtatatat atatacatga | 9480 |
| gaagaacggc atagtgcgtg tttatgctta aatgcgtact tatatgcgtc tatttatgta | 9540 |
| ggatgaaagg tagtctagta cctcctgtga tattatccca ttccatgcgg ggtatcgtat | 9600 |
| gcttccttca gcactaccct ttagctgttc tatatgctgc cactcctcaa ttggattagt | 9660 |
| ctcatccttc aatgctatca tttcctttga ta | 9692 |

<210> SEQ ID NO 25
<211> LENGTH: 5439
<212> TYPE: DNA
<213> ORGANISM: Artificial Sequence
<220> FEATURE:
<223> OTHER INFORMATION: Synthetic polynucleotide

<400> SEQUENCE: 25

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |

```
ttggcgggtg tcggggctgg cttaactatg cggcatcaga gcagattgta ctgagagtgc      180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttt tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagg tagttctggt ccattggtga agtttgcgg cttgcagagc acagaggccg       540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttttgttaa atcagctcat ttttaaccca ataggccgaa     1320
atcggcaaaa tcccttataa atcaaaagaa tagaccgaga tagggttgag tgttgttcca     1380
gtttggaaca agagtccact attaagaac gtggactcca acgtcaaagg gcgaaaaacc      1440
gtctatcagg gcgatggccc actacgtgaa ccatcaccct aatcaagttt ttgggtcg       1500 aggtgccgta aagcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctggcgaaag ggggatgtgc tgcaaggcga     1800
ttaagttggg taacgccagg gttttcccag tcacgacgtt gtaaaacgac ggccagtgag     1860
cgcgcgtaat acgactcact atagggcgaa ttgggtaccg gccgcaaatt aaagccttcg     1920
agcgtcccaa aaccttctca agcaaggttt tcagtatat gttacatgcg tacacgcgtc      1980
tgtacagaaa aaaagaaaa atttgaaata taataacgt tcttaatact aacataacta       2040 taaaaaata aatagggacc tagacttcag gttgtctaac tccttccttt tcggttagag      2100
cggatgtggg gggagggcgt gaatgtaagc gtgacataac taattacatg actcgagcgg     2160
ccgcggatcc cgggaattcg tcgactttat gtgatgattg attgattgat tgtacagttt     2220
gttttcttaa atatctattt cgatgacttc tatatgatat tgcactaaca agaagatatt     2280
ataatgcaat tgatacaaga caaggagtta tttgcttctc ttttatatga ttctgacaat     2340
ccatattgcg ttggtagtct ttttttgctgg aacggttcag cggaaaagac gcatcgctct    2400
ttttgcttct agaagaaatg ccagcaaaag aatctcttga cagtgactga cagcaaaaat    2460
```

```
gtcttttcct aactagtaac aaggctaaga tatcagcctg aaataaaggg tggtgaagta    2520
ataattaaat catccgtata aacctataca catatatgag gaaaaataat acaaaagtgt    2580
tttaaataca gatacataca tgaacatatg cacgtatagc gcccaaatgt cggtaatggg    2640
atcggcgagc tccagctttt gttcccttta gtgagggtta attgcgcgct tggcgtaatc    2700
atggtcatag ctgtttcctg tgtgaaattg ttatccgctc acaattccac acaacatagg    2760
agccggaagc ataaagtgta aagcctgggg tgcctaatga gtgaggtaac tcacattaat    2820
tgcgttgcgc tcactgcccg ctttccagtc gggaaacctg tcgtgccagc tgcattaatg    2880
aatcggccaa cgcgcgggga gaggcggttt gcgtattggg cgctcttccg cttcctcgct    2940
cactgactcg ctgcgctcgg tcgttcggct gcggcgagcg gtatcagctc actcaaaggc    3000
ggtaatacgg ttatccacag aatcagggga taacgcagga agaacatgt gagcaaaagg    3060 ccagcaaaag gccaggaacc gtaaaaaggc cgcgttgctg gcgttttttcc ataggctccg    3120 ccccctgac gagcatcaca aaaatcgacg ctcaagtcag aggtggcgaa acccgacagg    3180
actataaaga taccaggcgt ttccccctgg aagctccctc gtgcgctctc ctgttccgac    3240
cctgccgctt accggatacc tgtccgcctt tctcccttcg ggaagcgtgg cgctttctca    3300
tagctcacgc tgtaggtatc tcagttcggt gtaggtcgtt cgctccaagc tgggctgtgt    3360
gcacgaaccc cccgttcagc ccgaccgctg cgccttatcc ggtaactatc gtcttgagtc    3420
caacccggta agacacgact tatcgccact ggcagcagcc actggtaaca ggattagcag    3480
agcgaggtat gtaggcggtg ctacagagtt cttgaagtgg tggcctaact acggctacac    3540
tagaaggaca gtatttggta tctgcgctct gctgaagcca gttaccttcg aaaaagagt    3600 tggtagctct tgatccggca aacaaaccac cgctggtagc ggtggttttt tgtttgcaa    3660 gcagcagatt acgcgcagaa aaaaaggatc tcaagaagat cctttgatct tttctacggg    3720
gtctgacgct cagtggaacg aaaactcacg ttaagggatt ttggtcatga gattatcaaa    3780
aaggatcttc acctagatcc ttttaaatta aaaatgaagt tttaaatcaa tctaaagtat    3840
atatgagtaa acttggtctg acagttacca atgcttaatc agtgaggcac ctatctcagc    3900
gatctgtcta tttcgttcat ccatagttgc ctgactcccc gtcgtgtaga taactacgat    3960
acgggagggc ttaccatctg gccccagtgc tgcaatgata ccgcgagacc cacgctcacc    4020
ggctccagat ttatcagcaa taaaccagcc agccggaagg gccgagcgca gaagtggtcc    4080 tgcaactta tccgcctcca tccagtctat taattgttgc cgggaagcta gagtaagtag    4140
ttcgccagtt aatagtttgc gcaacgttgt tgccattgct acaggcatcg tggtgtcacg    4200
ctcgtcgttt ggtatggctt cattcagctc cggttcccaa cgatcaaggc gagttacatg    4260
atcccccatg ttgtgcaaaa aagcggttag ctccttcggt cctccgatcg ttgtcagaag    4320
taagttggcc gcagtgttat cactcatggt tatggcagca ctgcataatt ctcttactgt    4380
catgccatcc gtaagatgct tttctgtgac tggtgagtac tcaaccaagt cattctgaga    4440
atagtgtatg cggcgaccga gttgctcttg cccggcgtca atacgggata ataccgcgcc    4500
acatagcaga actttaaaag tgctcatcat tggaaaacgt tcttcggggc gaaaactctc    4560
aaggatctta ccgctgttga gatccagttc gatgtaaccc actcgtgcac caactgatc    4620 ttcagcatct tttactttca ccagcgtttc tgggtgagca aaaacaggaa ggcaaaatgc    4680
cgcaaaaaag ggaataaggg cgacacggaa atgttgaata ctcatactct tcctttttca    4740
atattattga agcatttatc agggttattg tctcatgagc ggatacatat ttgaatgtat    4800
ttagaaaaat aaacaaatag gggttccgcg cacatttccc cgaaaagtgc cacctgggtc    4860
```

```
cttttcatca cgtgctataa aaataattat aatttaaatt ttttaatata aatatataaa    4920
ttaaaaatag aaagtaaaaa aagaaattaa agaaaaaata gttttttgttt tccgaagatg    4980 taaaagactc tagggggatc gccaacaaat actaccttt atcttgctct tcctgctctc    5040
aggtattaat gccgaattgt ttcatcttgt ctgtgtagaa gaccacacac gaaaatcctg    5100
tgattttaca ttttacttat cgttaatcga atgtatatct atttaatctg cttttcttgt    5160
ctaataaata tatatgtaaa gtacgctttt tgttgaaatt ttttaaacct ttgtttattt    5220
ttttttcttc attccgtaac tcttctacct tctttattta ctttctaaaa tccaaataca    5280
aaacataaaa ataaataaac acagagtaaa ttcccaaatt attccatcat taaaagatac    5340
gaggcgcgtg taagttacag gcaagcgatc cgtcctaaga aaccattatt atcatgacat    5400
taacctataa aaataggcgt atcacgaggc cctttcgtc                           5439
```

<210> SEQ ID NO 26
<211> LENGTH: 7146
<212> TYPE: DNA
<213> ORGANISM: Artificial Sequence
<220> FEATURE:
<223> OTHER INFORMATION: Synthetic polynucleotide

<400> SEQUENCE: 26

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
attcagaagc aggtgggaca ggtgaacttt tggattggaa ctcgatttct gactgggttg     960
gaaggcaaga gagccccgaa agcttacatt ttatgttagc tggtggactg acgccagaaa    1020
atgttggtga tgcgcttaga ttaaatggcg ttattggtgt tgatgtaagc ggaggtgtgg    1080
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa ttttgttaa atcagctcat ttttaacca ataggccgaa    1320 atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
```

```
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg gttttcccag tcacgacgtt gtaaaacgac ggccagtgag    1860
cgcgcgtaat acgactcact ataggggcgaa ttgggtaccg gccgcaaatt aaagccttcg    1920
```

```
tgcttttcac aagggatttt tgttcttttg ttgcttttgt caacatgtcg actttatgtg    3900
atgattgatt gattgattgt acagtttgtt tttcttaata tctatttcga tgacttctat    3960
atgatattgc actaacaaga agatattata atgcaattga tacaagacaa ggagttattt    4020
gcttctcttt tatatgattc tgacaatcca tattgcgttg gtagtctttt ttgctggaac    4080
ggttcagcgg aaaagacgca tcgctctttt tgcttctaga agaaatgcca gcaaaagaat    4140
ctcttgacag tgactgacag caaaaatgtc tttttctaac tagtaacaag gctaagatat    4200
cagcctgaaa taagggtgg tgaagtaata attaaatcat ccgtataaac ctatacacat    4260
atatgaggaa aaataataca aaagtgtttt aaatacagat acatcatga acatatgcac    4320
gtatagcgcc caaatgtcgg taatgggatc ggcgagctcc agcttttgtt ccctttagtg    4380
agggttaatt gcgcgcttgg cgtaatcatg gtcatagctg tttcctgtgt gaaattgtta    4440
tccgctcaca attccacaca ataggagc cggaagcata aagtgtaaag cctggggtgc     4500
ctaatgagtg aggtaactca cattaattgc gttgcgctca ctgcccgctt tccagtcggg    4560
aaacctgtcg tgccagctgc attaatgaat cggccaacgc gcggggagag cggtttgcg    4620
tattgggcgc tcttccgctt cctcgctcac tgactcgctg cgctcggtcg ttcggctgcg    4680
gcgagcggta tcagctcact caaaggcggt aatacggtta ccacagaat cagggggataa    4740
cgcaggaaag aacatgtgag caaaaggcca gcaaaaggcc aggaaccgta aaaaggccgc    4800
gttgctggcg ttttttccata ggctccgccc ccctgacgag catcacaaaa atcgacgctc    4860
aagtcagagg tggcgaaacc cgacaggact ataaagatac caggcgtttc ccctggaag    4920
ctccctcgtg cgctctcctg ttccgaccct gccgcttacc ggatacctgt ccgcctttct    4980
cccttcggga agcgtggcgc tttctcatag ctcacgctgt aggtatctca gttcggtgta    5040
ggtcgttcgc tccaagctgg gctgtgtgca cgaaccccc gttcagcccg accgctgcgc    5100
cttatccggt aactatcgtc ttgagtccaa cccggtaaga cacgacttat cgccactggc    5160
agcagccact ggtaacagga ttagcagagc gaggtatgta ggcggtgcta cagagttctt    5220
gaagtggtgg cctaactacg gctacactag aaggacagta tttggtatct gcgctctgct    5280
gaagccagtt accttcggaa aaagagttgg tagctcttga tccggcaaac aaaccaccgc    5340
tggtagcggt ggtttttttg tttgcaagca gcagattacg cgcagaaaaa aaggatctca    5400
agaagatcct ttgatctttt ctacggggtc tgacgctcag tggaacgaaa actcacgtta    5460
agggattttg gtcatgagat tatcaaaaag gatcttcacc tagatccttt taaattaaaa    5520
atgaagtttt aaatcaatct aaagtatata tgagtaaact tggtctgaca gttaccaatg    5580
cttaatcagt gaggcaccta tctcagcgat ctgtctattt cgttcatcca tagttgcctg    5640
actccccgtc gtgtagataa ctacgatacg ggagggctta ccatctggcc ccagtgctgc    5700
aatgataccg cgagacccac gctcaccggc tccagattta tcagcaataa accagccagc    5760
cggaagggcc gagcgcagaa gtggtcctgc aactttatcc gcctccatcc agtctattaa    5820
ttgttgccgg gaagctagag taagtagttc gccagttaat agtttgcgca acgttgttgc    5880
cattgctaca ggcatcgtgg tgtcacgctc gtcgtttggt atggcttcat tcagctccgg    5940
ttcccaacga tcaaggcgag ttacatgatc ccccatgttg tgcaaaaaag cggttagctc    6000
cttcggtcct ccgatcgttg tcagaagtaa gttggccgca gtgttatcac tcatggttat    6060
ggcagcactg cataattctc ttactgtcat gccatccgta agatgctttt ctgtgactgg    6120
tgagtactca accaagtcat tctgagaata gtgtatgcgg cgaccgagtt gctcttgccc    6180
```

```
ggcgtcaata cgggataata ccgcgccaca tagcagaact ttaaaagtgc tcatcattgg    6240
aaaacgttct tcggggcgaa aactctcaag gatcttaccg ctgttgagat ccagttcgat    6300
gtaacccact cgtgcaccca actgatcttc agcatctttt actttcacca gcgtttctgg    6360
gtgagcaaaa acaggaaggc aaaatgccgc aaaaaaggga ataagggcga cacggaaatg    6420
ttgaatactc atactcttcc tttttcaata ttattgaagc atttatcagg gttattgtct    6480
catgagcgga tacatatttg aatgtattta gaaaaataaa caataggggt tccgcgcac     6540 atttccccga aaagtgccac ctgggtcctt tcatcacgt gctataaaaa taattataat     6600
ttaaattttt taatataaat atataaatta aaaatagaaa gtaaaaaaag aaattaaaga    6660
aaaaatagtt tttgttttcc gaagatgtaa aagactctag ggggatcgcc aacaaatact    6720 acctttatc ttgctcttcc tgctctcagg tattaatgcc gaattgtttc atcttgtctg     6780
tgtagaagac cacacacgaa aatcctgtga ttttacattt tacttatcgt taatcgaatg    6840
tatatctatt taatctgctt ttcttgtcta ataaatatat atgtaaagta cgcttttttgt    6900 tgaaattttt taaacctttg tttattttttt tttcttcatt ccgtaactct tctaccttct    6960
ttatttactt tctaaaatcc aaatacaaaa cataaaaata aataaacaca gagtaaattc    7020
ccaaattatt ccatcattaa aagatacgag gcgcgtgtaa gttacaggca agcgatccgt    7080
cctaagaaac cattattatc atgacattaa cctataaaaa taggcgtatc acgaggccct    7140
ttcgtc                                                               7146

<210> SEQ ID NO 27
<211> LENGTH: 10231
<212> TYPE: DNA
<213> ORGANISM: Artificial Sequence
<220> FEATURE:
<223> OTHER INFORMATION: Synthetic polynucleotide

<400> SEQUENCE: 27
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt ccgcaatt tctttttcta      300 ttactcttgg cctcctctag tacactctat atttttttat gcctcggtaa tgattttcat    360 ttttttttt ccctagcgg atgactcttt ttttttctta gcgattggca ttatcacata      420
atgaattata cattatataa agtaatgtga tttcttcgaa gaatatacta aaaaatgagc     480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa   1020
ttaccctcca cgttgattgt ctgcgaggca agaatgatca tcaccgtagt gagagtgcgt    1080
```

-continued

```
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
tttccttttt tcttttttgct ttttcttttt ttttctcttg aactcgacgg atctatgcgg   1380
tgtgaaatac cgcacagatg cgtaaggaga aaataccgca tcaggaaatt gtaaacgtta    1440
atattttgtt aaaattcgcg ttaaattttt gttaaatcag ctcattttt aaccaatagg     1500 ccgaaatcgg caaaatccct tataaatcaa agaatagac cgagatagg ttgagtgttg      1560 ttccagtttg gaacaagagt ccactattaa agaacgtgga ctccaacgtc aaagggcgaa    1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaaggggga tgtgctgcaa    1980
ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaaa gaaaaatttg aaatataaat aacgttctta atactaacat    2220
aactataaaa aaataaatag ggacctagac ttcaggttgt ctaactcctt cctttttcggt   2280 tagagcggat gtgggggag ggcgtgaatg taagcgtgac ataactaatt acatgagcgg     2340
ccgcagatct ttaacccgca acagcaatac gtttcatatc tgtcatatag ccgcgcagtt    2400
tcttacctac ctgctcaatc gcatggctgc gaatcgcttc gttcacatca cgcagttgcc    2460
cgttatctac cgcgccttcc ggaatagctt tacccaggtc gcccggttgc agctctgcca    2520
taaacggttt cagcaacggc acacaagcgt aagagaacag atagttaccg tactcagcgg    2580
tatcagagat aaccacgttc atttcgtaca gacgcttacg ggcgatggtg ttggcaatca    2640
gcggcagctc gtgcagtgat tcataatatg cagactcttc aatgatgccg gaatcgacca    2700
tggtttcgaa cgccagttca acgcccgctt tcaccatcgc aatcatcagt acgcctttat    2760
cgaagtactc ctgctcgccg attttgcctt catactgcgg cgcggtttca aacgcggttt    2820
tgccggtctc ttcacgccag gtcagcagtt tcttatcatc gttggcccag tccgccatca    2880
taccggaaga gaattcgccg gagatgatgt cgtccatatg tttctggaac aggggtgcca    2940
tgatctcttt cagctgttca gaaagcgcat aagcacgcag tttcgccggg ttagagagac    3000
ggtccatcat cagggtgatg ccgccctgtt tcagtgcttc ggtgatggtt tcccaaccga    3060
actgaatcag ttttttctgcg tatgctggat cggtaccttc ttccaccagc ttgtcgaagc    3120
acagcagaga gccagcctgc aacataccgc acaggatggt ttgctcgccc atcaggtcag    3180
atttcacttc cgcaacgaag gacgattcca gcacacccgc acggtgacca ccggttgcag    3240
ccgcccaggc tttggcaatc gccatgcctt cgcctttcgg atcgttttcc gggtgaacgg    3300
caatcagcgt cggtacgccg aacccacgtt tgtactcttc acgcacttcg gtgcctgggc    3360
atttcggcgc aaccatcact acggtgatat ctttacggat ctgctcgccc acttcgacga    3420
```

```
tgttgaaacc gtgcgagtag cccagcgccg cgccgtctttt catcagtggc tgtacggtgc    3480
gcactacatc agagtgctgc ttgtccggcg tcaggttaat caccagatcc gcctgtggga    3540
tcagttcttc gtaagtaccc actttaaaac cattttcggt cgctttacgc caggacgcgc    3600
gcttctcggc aatcgcttct ttacgcagag cgtaggagat atcgagacca gaatcacgca    3660
tgttcaggcc ctggttcaga ccctgtgcgc cacagccgac gatgactact tttttaccct    3720
gaaggtagct cgcgccatcg gcgaattcat cgcggcccat ctcgagtcga aactaagttc    3780
tggtgtttta aaactaaaaa aaagactaac tataaaagta gaatttaaga agtttaagaa    3840
atagatttac agaattacaa tcaataccta ccgtctttat atacttatta gtcaagtagg    3900
ggataatttt cagggaactg gtttcaacct tttttttcag cttttttccaa atcagagaga    3960
gcagaaggta atagaaggtg taagaaaatg agatagatac atgcgtgggt caattgcctt    4020
gtgtcatcat ttactccagg caggttgcat cactccattg aggttgtgcc cgttttttgc    4080
ctgtttgtgc ccctgttctc tgtagttgcg ctaagagaat ggacctatga actgatggtt    4140
ggtgaagaaa acaatatttt ggtgctggga ttcttttttt ttctggatgc cagcttaaaa    4200
agcgggctcc attatattta gtggatgcca ggaataaact gttcacccag acacctacga    4260
tgttatatat tctgtgtaac ccgccccta ttttgggcat gtacgggtta cagcagaatt    4320
aaaaggctaa ttttttgact aaataaagtt aggaaaatca ctactattaa ttatttacgt    4380
attctttgaa atggcgagta ttgataatga taaactggat cctcatccac ccaacttcga    4440
tttgtctctt actgcccct tatcggctga agtagccaat gaagcataag ccctaagggc    4500
gaaacttact tgacgttctc tattttagg agtccaagcc ttatctcctc tggcatcttg    4560
tgcttctctt cttgcagcca attcagcgtc tgagacttgt aattggatac ctctatttgg    4620
gatatctatg gcgatcaaat ctccatcttc aatcaatcca atcgaccac cagaagctgc    4680
ctctggtgat acgtgaccga tacttaaacc cgaagtgcca ccagagaatc taccgtcagt    4740
gataagggca caagctttc ctagtcccat ggacttcaaa aatgaagttg ggtaaagcat    4800
ttcctgcata cctggtcctc cctttggtcc ctcatatctt atcactacca cgtctcctgc    4860
taccaccttt ccgccaagta tagcctcaac agcatcgtct tgactttcgt aaactttagc    4920
gggtccagta aatttcaaaa tactatcatc tacaccagca gttttcacaa tgcaaccatt    4980
ttcagcgaag tttccatata atactgctaa accaccatcc ttactataag catgctcaag    5040
cgatcttata catccatttg ctctatcatc gtccaaagtg tcccacctac agtcttgcga    5100
gaatgcttgg gtggttctga tccctgctgg acctgcctg aacatgtttt tcacggcatc    5160
atcttgagtt aacatgacat cgtattgctc taatgtctgt ggaagtgtta aacccaatac    5220
attcttcaca tccctgttta aaagaccggc tctgtccaac tcccctaaaa taccaataac    5280
ccctcctgca cgatgaacgt cttccatgtg atacttttga gttgatggtg caaccttaca    5340
taactgtgga accttacgtg aaagcttgtc gatatcagac atggtgaaat ctatctcagc    5400
ttcttgggct gcagctagaa gatgtaagac cgtgtttgta ctaccaccca ttgcaatatc    5460
caatgtcatg gcattttcga atgcagcctt tgaagctata ttcctcggta atgctgattc    5520
atcattttgt tcgtaatacc ttttcgttag ttccacaatt ctttttccgg catttaagaa    5580
caattgcttt ctgtctgcat gggtcgctaa taatgaacca tttcctggtt gagataaacc    5640
tagagcttca gtcaagcaat tcatagagtt agccgtgaac attccactgc aagaaccaca    5700
agttggacat gcacttcttt caacttggtc tgactgcgag tctgaaactt ttggatctgc    5760
accttgaatc attgcatcca caagatcaag tttgatgatc tgatcactta acttagtttt    5820
```

```
accagcctcc attgggccgc cagatacgaa gattactggg atgttcaatc tcaaggacgc    5880
catcaacata ccaggcgtta tcttatcaca attagagata caaaccattg catcggcaca    5940
atgagcatta accatatatt cgactgagtc tgcaattaat tctctcgatg gtaaagagta    6000
taacataccg ccatgcccca tagctatacc gtcgtccaca gcaatagtat taaactcttt    6060
tgcgacacca cctgcagctt caatttgttc ggcaacaagc ttacctagat cacgcaaatg    6120
gacatgaccc ggaacgaatt gtgtaaaaga gttgacgacg gcaatgattg gctttccgaa    6180
atctgcatca gtcatgccag tcatgtcgac aaacttagat tagattgcta tgctttcttt    6240
ctaatgagca agaagtaaaa aaagttgtaa tagaacaaga aaaatgaaac tgaaacttga    6300
gaaattgaag accgtttatt aacttaaata tcaatgggag gtcatcgaaa gagaaaaaaa    6360
tcaaaaaaaa aattttcaag aaaaagaaac gtgataaaaa ttttattgc cttttctcgac    6420 gaagaaaaag aaacgaggcg gtctcttttt tcttttccaa accttttagta cgggtaatta    6480 acgacaccct agaggaagaa agaggggaaa tttagtatgc tgtgcttggg tgttttgaag    6540
tggtacggcg atgcgcggag tccgagaaaa tctggaagag taaaaaagga gtagaaacat    6600
tttgaagcta tgagctccag cttttgttcc ctttagtgag ggttaattgc gcgcttggcg    6660
taatcatggt catagctgtt tcctgtgtga aattgttatc cgctcacaat tccacacaac    6720
ataggagccg gaagcataaa gtgtaaagcc tggggtgcct aatgagtgag gtaactcaca    6780
ttaattgcgt tgcgctcact gcccgctttc cagtcgggaa acctgtcgtg ccagctgcat    6840
taatgaatcg gccaacgcgc ggggagaggc ggtttgcgta ttgggcgctc ttccgcttcc    6900
tcgctcactg actcgctgcg ctcggtcgtt cggctgcggc gagcggtatc agctcactca    6960
aaggcggtaa tacggttatc cacagaatca ggggataacg caggaaagaa catgtgagca    7020
aaaggccagc aaaaggccag gaaccgtaaa aaggccgcgt tgctggcgtt tttccatagg    7080
ctccgccccc ctgacgagca tcacaaaaat cgacgctcaa gtcagaggtg gcgaaacccg    7140
acaggactat aaagatacca ggcgtttccc cctggaagct ccctcgtgcg ctctcctgtt    7200
ccgaccctgc cgcttaccgg atacctgtcc gcctttctcc cttcgggaag cgtggcgctt    7260
tctcatagct cacgctgtag gtatctcagt tcggtgtagg tcgttcgctc caagctgggc    7320
tgtgtgcacg aaccccccgt tcagcccgac cgctgcgcct tatccggtaa ctatcgtctt    7380
gagtccaacc cggtaagaca cgacttatcg ccactggcag cagccactgg taacaggatt    7440
agcagagcga ggtatgtagg cggtgctaca gagttcttga agtggtggcc taactacggc    7500
tacactagaa ggacagtatt tggtatctgc gctctgctga agccagttac cttcggaaaa    7560
agagttggta gctcttgatc cggcaaacaa accaccgctg gtagcggtgg tttttttgtt    7620
tgcaagcagc agattacgcg cagaaaaaaa ggatctcaag aagatccttt gatcttttct    7680
acggggtctg acgctcagtg gaacgaaaac tcacgttaag ggattttggt catgagatta    7740
tcaaaaagga tcttcaccta gatccttta aattaaaaat gaagttttaa atcaatctaa    7800
agtatatatg agtaaacttg gtctgacagt taccaatgct taatcagtga ggcacctatc    7860
tcagcgatct gtctatttcg ttcatccata gttgcctgac tccccgtcgt gtagataact    7920
acgatacggg agggcttacc atctggcccc agtgctgcaa tgataccgcg agacccacgc    7980
tcaccggctc cagatttatc agcaataaac cagccagccg gaagggccga gcgcagaagt    8040
ggtcctgcaa ctttatccgc ctccatccag tctattaatt gttgccggga agctagagta    8100
agtagttcgc cagttaatag tttgcgcaac gttgttgcca ttgctacagg catcgtggtg    8160
```

```
tcacgctcgt cgtttggtat ggcttcattc agctccggtt cccaacgatc aaggcgagtt    8220
acatgatccc ccatgttgtg caaaaaagcg gttagctcct tcggtcctcc gatcgttgtc    8280
agaagtaagt tggccgcagt gttatcactc atggttatgg cagcactgca taattctctt    8340
actgtcatgc catccgtaag atgcttttct gtgactggtg agtactcaac caagtcattc    8400
tgagaatagt gtatgcggcg accgagttgc tcttgcccgg cgtcaatacg ggataatacc    8460
gcgccacata gcagaacttt aaaagtgctc atcattggaa aacgttcttc ggggcgaaaa    8520
ctctcaagga tcttaccgct gttgagatcc agttcgatgt aacccactcg tgcacccaac    8580
tgatcttcag catcttttac tttcaccagc gtttctgggt gagcaaaaac aggaaggcaa    8640
aatgccgcaa aaaagggaat aagggcgaca cggaaatgtt gaatactcat actcttcctt    8700
tttcaatatt attgaagcat ttatcagggt tattgtctca tgagcggata catatttgaa    8760
tgtatttaga aaaataaaca ataggggtt ccgcgcacat ttccccgaaa agtgccacct    8820
gaacgaagca tctgtgcttc attttgtaga acaaaaatgc aacgcgagag cgctaatttt    8880
tcaaacaaag aatctgagct gcattttac agaacagaaa tgcaacgcga aagcgctatt    8940
ttaccaacga agaatctgtg cttcattttt gtaaaacaaa aatgcaacgc gagagcgcta    9000 attttttcaaa caagaatct gagctgcatt tttacagaac agaaatgcaa cgcgagagcg    9060 ctatttacc aacaaagaat ctatacttct tttttgttct acaaaaatgc atcccgagag    9120
cgctattttt ctaacaaagc atcttagatt acttttttc tcctttgtgc gctctataat    9180
gcagtctctt gataacttt tgcactgtag gtccgttaag gttagaagaa ggctactttg    9240
gtgtctattt tctcttccat aaaaaaagcc tgactccact tcccgcgttt actgattact    9300
agcgaagctg cgggtgcatt ttttcaagat aaaggcatcc ccgattatat tctataccga    9360
tgtggattgc gcatactttg tgaacagaaa gtgatagcgt tgatgattct tcattggtca    9420
gaaaattatg aacggtttct tctatttgt ctctatatac tacgtatagg aaatgtttac    9480 atttcgtat tgttttcgat tcactctatg aatagttctt actacaattt ttttgtctaa    9540
agagtaatac tagagataaa cataaaaaat gtagaggtcg agtttagatg caagttcaag    9600
gagcgaaagg tggatgggta ggttatatag ggatatagca cagagatata tagcaaagag    9660
atacttttga gcaatgtttg tggaagcggt attcgcaata ttttagtagc tcgttacagt    9720
ccggtgcgtt tttggttttt tgaaagtgcg tcttcagagc gcttttggtt ttcaaaagcg    9780
ctctgaagtt cctatacttt ctagagaata ggaacttcgg aataggaact tcaaagcgtt    9840
tccgaaaacg agcgcttccg aaaatgcaac gcgagctgcg cacatacagc tcactgttca    9900
cgtcgcacct atatctgcgt gttgcctgta tatatatata catgagaaga acggcatagt    9960
gcgtgtttat gcttaaatgc gtacttatat gcgtctattt atgtaggatg aaaggtagtc    10020
tagtacctcc tgtgatatta tcccattcca tgcggggtat cgtatgcttc cttcagcact    10080 acccttagc tgttctatat gctgccactc ctcaattgga ttagtctcat ccttcaatgc    10140
tatcatttcc tttgatattg gatcatctaa gaaaccatta ttatcatgac attaacctat    10200
aaaaataggc gtatcacgag gccctttcgt c                                  10231

<210> SEQ ID NO 28
<211> LENGTH: 9404
<212> TYPE: DNA
<213> ORGANISM: Artificial Sequence
<220> FEATURE:
<223> OTHER INFORMATION: Synthetic polynucleotide

<400> SEQUENCE: 28
```

-continued

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgcgtg   120
ttggcgggtg tcgggctgg cttaactatg cggcatcaga gcagattgta ctgagagtgc    180
accataaatt cccgttttaa gagcttggtg agcgctagga gtcactgcca ggtatcgttt   240
gaacacggca ttagtcaggg aagtcataac acagtccttt cccgcaattt tcttttttcta 300 ttactcttgg cctcctctag tacactctat atttttttat gcctcggtaa tgattttcat  360
tttttttttt cccctagcgg atgactcttt tttttcctta gcgattggca ttatcacata  420
atgaattata cattatataa agtaatgtga tttcttcgaa gaatatacta aaaaatgagc  480
aggcaagata aacgaaggca aagatgacag agcagaaagc cctagtaaag cgtattacaa  540
atgaaaccaa gattcagatt gcgatctctt taaagggtgg tcccctagcg atagagcact  600
cgatcttccc agaaaaagag gcagaagcag tagcagaaca ggccacacaa tcgcaagtga  660
ttaacgtcca cacaggtata gggtttctgg accatatgat acatgctctg gccaagcatt  720
ccggctggtc gctaatcgtt gagtgcattg gtgacttaca catagacgac catcacacca  780
ctgaagactg cgggattgct ctcggtcaag cttttaaaga ggccctaggg gccgtgcgtg  840
gagtaaaaag gtttggatca ggatttgcgc ctttggatga ggcactttcc agagcggtgg  900
tagatctttc gaacaggccg tacgcagttg tcgaacttgg tttgcaaagg gagaaagtag  960
gagatctctc ttgcgagatg atcccgcatt ttcttgaaag ctttgcagag gctagcagaa 1020
ttaccctcca cgttgattgt ctgcgaggca agaatgatca tcaccgtagt gagagtgcgt 1080
tcaaggctct tgcggttgcc ataagagaag ccacctcgcc caatggtacc aacgatgttc 1140
cctccaccaa aggtgttctt atgtagtgac accgattatt taaagctgca gcatacgata 1200
tatatacatg tgtatatatg tatacctatg aatgtcagta agtatgtata cgaacagtat 1260
gatactgaag atgacaaggt aatgcatcat tctatacgtg tcattctgaa cgaggcgcgc 1320
tttccttttt tcttttttgct ttttcttttt ttttctcttg aactcgacgg atctatgcgg 1380
tgtgaaatac cgcacagatg cgtaaggaga aataccgca tcaggaaatt gtaaacgtta 1440 atatttgtt aaaattcgcg ttaaattttt gttaaatcag ctcatttttt aaccaatagg  1500
ccgaaatcgg caaaatccct tataaatcaa agaatagac cgagataggg ttgagtgttg  1560
ttccagtttg gaacaagagt ccactattaa agaacgtgga ctccaacgtc aaagggcgaa 1620
aaaccgtcta tcagggcgat ggcccactac gtgaaccatc accctaatca agttttttgg 1680
ggtcgaggtg ccgtaaagca ctaaatcgga accctaaagg gagcccccga tttagagctt 1740
gacggggaaa gccggcgaac gtggcgagaa aggaagggaa gaaagcgaaa ggagcgggcg 1800
ctagggcgct ggcaagtgta gcggtcacgc tgcgcgtaac caccacaccc gccgcgctta 1860
atgcgccgct acagggcgcg tcgcgccatt cgccattcag gctgcgcaac tgttgggaag 1920
ggcgatcggt gcgggcctct tcgctattac gccagctggc gaaaggggga tgtgctgcaa 1980
ggcgattaag ttgggtaacg ccagggtttt cccagtcacg acgttgtaaa acgacggcca 2040
gtgagcgcgc gtaatacgac tcactatagg gcgaattggg taccggccgc aaattaaagc 2100
cttcgagcgt cccaaaacct tctcaagcaa ggttttcagt ataatgttac atgcgtacac 2160
gcgtctgtac agaaaaaaaa gaaaaatttg aaatataaat aacgttctta atactaacat 2220
aactataaaa aaataaatag ggacctagac ttcaggttgt ctaactcctt ccttttcggt 2280
tagagcggat gtgggggag ggcgtgaatg taagcgtgac ataactaatt acatgagcgg 2340
```

```
ccgcagatct ttaacccgca acagcaatac gtttcatatc tgtcatatag ccgcgcagtt    2400
tcttacctac ctgctcaatc gcatggctgc gaatcgcttc gttcacatca cgcagttgcc    2460
cgttatctac cgcgccttcc ggaatagctt acccaggtc gcccggttgc agctctgcca     2520
taaacggttt cagcaacggc acacaagcgt aagagaacag atagttaccg tactcagcgg    2580
tatcagagat aaccacgttc atttcgtaca gacgcttacg ggcgatggtg ttggcaatca    2640
gcggcagctc gtgcagtgat tcataatatg cagactcttc aatgatgccg gaatcgacca    2700
tggtttcgaa cgccagttca acgcccgctt tcaccatcgc aatcatcagt acgcctttat    2760
cgaagtactc ctgctcgccg attttgcctt catactgcgg cgcggtttca aacgcggttt    2820
tgccggtctc ttcacgccag gtcagcagtt tcttatcatc gttggcccag tccgccatca    2880
taccggaaga gaattcgccg gagatgatgt cgtccatatg tttctggaac agggtgcca    2940 tgatctcttt cagctgttca gaaagcgcat aagcacgcag tttcgccggg ttagagagac    3000
ggtccatcat cagggtgatg ccgccctgtt tcagtgcttc ggtgatggtt tcccaaccga    3060
actgaatcag tttttctgcg tatgctggat cggtaccttc ttccaccagc ttgtcgaagc    3120
acagcagaga gccagcctgc aacataccgc acaggatggt ttgctcgccc atcaggtcag    3180
atttcacttc cgcaacgaag gacgattcca gcacacccgc acggtgacca ccggttgcag    3240
ccgcccaggc tttggcaatc gccatgcctt cgcctttcgg atcgttttcc gggtgaacgg    3300
caatcagcgt cggtacgccg aacccacgtt tgtactcttc acgcacttcg gtgcctgggc    3360
atttcggcgc aaccatcact acggtgatat ctttacggat ctgctcgccc acttcgacga    3420
tgttgaaacc gtgcgagtag cccagcgccg cgccgtcttt catcagtggc gtacggtgc    3480 gcactacatc agagtgctgc ttgtccggcg tcaggttaat caccagatcc gcctgtggga    3540
tcagttcttc gtaagtaccc actttaaaac cattttcggt cgcttacgc caggacgcgc     3600 gcttctcggc aatcgcttct ttacgcagag cgtaggagat atcgagacca gaatcacgca    3660
tgttcaggcc ctggttcaga ccctgtgcgc cacagccgac gatgactact ttttaccct    3720 gaaggtagct cgcgccatcg gcgaattcat cgcggcccat ctcgagtcga aactaagttc    3780
tggtgtttta aaactaaaaa aaagactaac tataaaagta gaatttaaga agtttaagaa    3840
atagatttac agaattacaa tcaataccta ccgtctttat atacttatta gtcaagtagg    3900
ggaataattt cagggaactg gtttcaacct ttttttttcag cttttttccaa atcagagaga   3960 gcagaaggta atagaaggtg taagaaaatg agatagatac atgcgtgggt caattgcctt    4020
gtgtcatcat ttactccagg caggttgcat cactccattg aggttgtgcc cgttttttgc    4080
ctgtttgtgc ccctgttctc tgtagttgcg ctaagagaat ggacctatga actgatggtt    4140
ggtgaagaaa acaatatttt ggtgctggga ttcttttttt ttctggatgc cagcttaaaa    4200
agcgggctcc attatattta gtggatgcca ggaataaact gttcacccag acacctacga    4260
tgttatatat tctgtgtaac ccgcccccta ttttgggcat gtacgggtta cagcagaatt    4320
aaaaggctaa ttttttgact aaataaagtt aggaaaatca ctactattaa ttatttacgt    4380
attctttgaa atggcgagta ttgataatga taaactggat cctcatccac ccaacttcga    4440
tttgtctctt actgcccct tatcggctga agtagccaat gaagcataag ccctaagggc     4500
gaaacttact tgacgttctc tatttttagg agtccaagcc ttatctcctc tggcatcttg    4560
tgcttctctt cttgcagcca attcagcgtc tgagacttgt aattggatac ctctatttgg    4620
gatatctatg gcgatcaaat ctccatcttc aatcaatcca atcgaccac cagaagctgc     4680 ctctggtgat acgtgaccga tacttaaacc cgaagtgcca ccagagaatc taccgtcagt    4740
```

-continued

```
gataagggca caagcttttc ctagtcccat ggacttcaaa aatgaagttg ggtaaagcat    4800
ttcctgcata cctggtcctc cctttggtcc ctcatatctt atcactacca cgtctcctgc    4860 taccacctt ccgccaagta tagcctcaac agcatcgtct tgactttcgt aaactttagc    4920
gggtccagta aatttcaaaa tactatcatc tacaccagca gttttcacaa tgcaaccatt    4980
ttcagcgaag tttccatata atactgctaa accaccatcc ttactataag catgctcaag    5040
cgatcttata catccatttg ctctatcatc gtccaaagtg tcccacctac agtcttgcga    5100
gaatgcttgg gtggttctga tccctgctgg acctgccctg aacatgtttt tcacggcatc    5160
atcttgagtt aacatgacat cgtattgctc taatgtctgt ggaagtgtta aacccaatac    5220
attcttcaca tccctgttta aaagaccggc tctgtccaac tcccctaaaa taccaataac    5280
ccctcctgca cgatgaacgt cttccatgtg atacttttga gttgatggtg caaccttaca    5340
taactgtgga accttacgtg aaagcttgtc gatatcagac atggtgaaat ctatctcagc    5400
ttcttgggct gcagctagaa gatgtaagac cgtgtttgta ctaccaccca ttgcaatatc    5460
caatgtcatg gcattttcga atgcagcctt tgaagctata ttcctcggta atgctgattc    5520
atcattttgt tcgtaatacc ttttcgttag ttccacaatt cttttccgg catttaagaa    5580 caattgcttt ctgtctgcat gggtcgctaa taatgaacca tttcctggtt gagataaacc    5640
tagagcttca gtcaagcaat tcatagagtt agccgtgaac attccactgc aagaaccaca    5700
agttggacat gcacttcttt caacttggtc tgactgcgag tctgaaactt ttggatctgc    5760
accttgaatc attgcatcca caagatcaag tttgatgatc tgatcactta acttagttt    5820 accagcctcc attgggccgc cagatacgaa gattactggg atgttcaatc tcaaggacgc    5880
catcaacata ccaggcgtta tcttatcaca attagagata caaaccattg catcggcaca    5940
atgagcatta accatatatt cgactgagtc tgcaattaat tctctcgatg gtaaagagta    6000
taacataccg ccatgcccca tagctatacc gtcgtccaca gcaatagtat taaactcttt    6060
tgcgacacca cctgcagctt caatttgttc ggcaacaagc ttacctagat cacgcaaatg    6120
gacatgaccc ggaacgaatt gtgtaaaaga gttgacgacg gcaatgattg gctttccgaa    6180
atctgcatca gtcatgccag tcatgtcgac aaacttagat tagattgcta tgctttcttt    6240
ctaatgagca agaagtaaaa aaagttgtaa tagaacaaga aaaatgaaac tgaaacttga    6300
gaaattgaag accgtttatt aacttaaata tcaatgggag gtcatcgaaa gagaaaaaaa    6360
tcaaaaaaaa aattttcaag aaaaagaaac gtgataaaaa tttttattgc cttttcgac    6420 gaagaaaaag aaacgaggcg gtctcttttt tcttttccaa acctttagta cgggtaatta    6480
acgacaccct agaggaagaa agagggaaa tttagtatgc tgtgcttggg tgttttgaag    6540
tggtacggcg atgcgcggag tccgagaaaa tctggaagga taaaaaagga gtagaaacat    6600
tttgaagcta tgagctccag cttttgttcc ctttagtgag ggttaattgc gcgcttggcg    6660
taatcatggt catagctgtt tcctgtgtga aattgttatc cgctcacaat tccacacaac    6720
ataggagccg gaagcataaa gtgtaaagcc tggggtgcct aatgagtgag gtaactcaca    6780
ttaattgcgt tgcgctcact gcccgctttc cagtcgggaa acctgtcgtg ccagctgcat    6840
taatgaatcg gccaacgcgc ggggagaggc ggtttgcgta ttgggcgctc ttccgcttcc    6900
tcgctcactg actcgctgcg ctcggtcgtt cggctgcggc gagcggtatc agctcactca    6960
aaggcggtaa tacggttatc cacagaatca ggggataacg caggaaagaa catgtgagca    7020
aaaggccagc aaaaggccag gaaccgtaaa aaggccgcgt tgctggcgtt tttccatagg    7080
```

```
ctccgccccc ctgacgagca tcacaaaaat cgacgctcaa gtcagaggtg gcgaaacccg   7140
acaggactat aaagatacca ggcgtttccc cctggaagct ccctcgtgcg ctctcctgtt   7200
ccgaccctgc cgcttaccgg atacctgtcc gcctttctcc cttcgggaag cgtggcgctt   7260
tctcatagct cacgctgtag gtatctcagt tcggtgtagg tcgttcgctc caagctgggc   7320
tgtgtgcacg aaccccccgt tcagcccgac cgctgcgcct tatccggtaa ctatcgtctt   7380
gagtccaacc cggtaagaca cgacttatcg ccactggcag cagccactgg taacaggatt   7440
agcagagcga ggtatgtagg cggtgctaca gagttcttga agtggtggcc taactacggc   7500
tacactagaa ggacagtatt tggtatctgc gctctgctga agccagttac cttcggaaaa   7560
agagttggta gctcttgatc cggcaaacaa accaccgctg gtagcggtgg ttttttttgtt   7620
tgcaagcagc agattacgcg cagaaaaaaa ggatctcaag aagatccttt gatcttttct   7680
acggggtctg acgctcagtg gaacgaaaac tcacgttaag ggattttggt catgagatta   7740
tcaaaaagga tcttcaccta gatccttta aattaaaaat gaagttttaa atcaatctaa   7800
agtatatatg agtaaacttg gtctgacagt taccaatgct taatcagtga ggcacctatc   7860
tcagcgatct gtctatttcg ttcatccata gttgcctgac tccccgtcgt gtagataact   7920
acgatacggg agggcttacc atctggcccc agtgctgcaa tgataccgcg agacccacgc   7980
tcaccggctc cagatttatc agcaataaac cagccagccg aagggccga gcgcagaagt   8040
ggtcctgcaa ctttatccgc ctccatccag tctattaatt gttgccggga agctagagta   8100
agtagttcgc cagttaatag tttgcgcaac gttgttgcca ttgctacagg catcgtggtg   8160
tcacgctcgt cgtttggtat ggcttcattc agctccggtt cccaacgatc aaggcgagtt   8220
acatgatccc ccatgttgtg caaaaaagcg gttagctcct tcggtcctcc gatcgttgtc   8280
agaagtaagt tggccgcagt gttatcactc atggttatgg cagcactgca taattctctt   8340
actgtcatgc catccgtaag atgcttttct gtgactggtg agtactcaac caagtcattc   8400
tgagaatagt gtatgcggcg accgagttgc tcttgcccgg cgtcaatacg ggataatacc   8460
gcgccacata gcagaacttt aaaagtgctc atcattggaa aacgttcttc ggggcgaaaa   8520
ctctcaagga tcttaccgct gttgagatcc agttcgatgt aacccactcg tgcacccaac   8580
tgatcttcag catcttttac tttcaccagc gtttctgggt gagcaaaaac aggaaggcaa   8640
aatgccgcaa aaaagggaat aagggcgaca cggaaatgtt gaatactcat actcttcctt   8700
tttcaatatt attgaagcat ttatcagggt tattgtctca tgagcggata catatttgaa   8760
tgtatttaga aaaataaaca ataggggtt ccgcgcacat ttccccgaaa agtgccacct   8820
gggtcctttt catcacgtgc tataaaaata attataattt aaatttttta atataaatat   8880
ataaattaaa aatagaaagt aaaaaagaa attaagaaa aatagtttt tgttttccga   8940
agatgtaaaa gactctaggg ggatcgccaa caaatactac cttttatctt gctcttcctg   9000
ctctcaggta ttaatgccga attgtttcat cttgtctgtg tagaagacca cacacgaaaa   9060
tcctgtgatt ttacatttta cttatcgtta atcgaatgta tatctattta atctgctttt   9120
cttgtctaat aaatatatat gtaaagtacg ctttttgttg aaattttta aacctttgtt   9180
tattttttt tcttcattcc gtaactcttc taccttcttt atttactttc taaaatccaa   9240
atacaaaaca taaaaataaa taaacacaga gtaaattccc aaattattcc atcattaaaa   9300
gatacgaggc gcgtgtaagt tacaggcaag cgatccgtcc taagaaacca ttattatcat   9360
gacattaacc tataaaaata ggcgtatcac gaggcccttt cgtc                    9404
```

```
<210> SEQ ID NO 29
<211> LENGTH: 9404
<212> TYPE: DNA
<213> ORGANISM: Artificial Sequence
<220> FEATURE:
<223> OTHER INFORMATION: Synthetic polynucleotide

<400> SEQUENCE: 29
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcgggctgg cttaactatg cggcatcaga gcagattgta ctgagagtgc      180
accataaatt cccgttttaa gagcttggtg agcgctagga gtcactgcca ggtatcgttt     240
gaacacggca ttagtcaggg aagtcataac acagtccttt ccgcaatttc tcttttttcta   300 ttactcttgg cctcctctag tacactctat attttttat gcctcggtaa tgattttcat      360
tttttttttt cccctagcgg atgactcttt tttttcttaa gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa   1020
ttaccctcca cgttgattgt ctgcgaggca agaatgatca tcaccgtagt gagagtgcgt   1080
tcaaggctct tgcggttgcc ataagagaag ccacctcgcc caatggtacc aacgatgttc   1140
cctccaccaa aggtgttctt atgtagtgac accgattatt taaagctgca gcatacgata   1200
tatatacatg tgtatatatg tatacctatg aatgtcagta agtatgtata cgaacagtat   1260
gatactgaag atgacaaggt aatgcatcat tctatacgtg tcattctgaa cgaggcgcgc   1320
tttccttttt tctttttgct ttttcttttt ttttctcttg aactcgacgg atctatgcgg   1380
tgtgaaatac cgcacagatg cgtaaggaga aaataccgca tcaggaaatt gtaaacgtta   1440
atattttgtt aaaattcgcg ttaaattttt gttaaatcag ctcattttt aaccaatagg    1500 ccgaaatcgg caaaatccct tataaatcaa agaatagac cgagataggg ttgagtgttg    1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
```

```
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt cctttcggt    2280 tagagcggat gtgggggag ggcgtgaatg taagcgtgac ataactaatt acatgagcgg    2340
ccgcagatct ttaacccgca acagcaatac gtttcatatc tgtcatatag ccgcgcagtt   2400
tcttacctac ctgctcaatc gcatggctgc gaatcgcttc gttcacatca cgcagttgcc   2460
cgttatctac cgcgccttcc ggaatagctt tacccaggtc gcccggttgc agctctgcca   2520
taaacggttt cagcaacggc acacaagcgt aagagaacag atagttaccg tactcagcgg   2580
tatcagagat aaccacgttc atttcgtaca gacgcttacg ggcgatggtg ttggcaatca   2640
gcggcagctc gtgcagtgat tcataatatg cagactcttc aatgatgccg gaatcgacca   2700
tggtttcgaa cgccagttca acgcccgctt tcaccatcgc aatcatcagt acgcctttat   2760
cgaagtactc ctgctcgccg attttgcctt catactgcgg cgcggtttca aacgcggttt   2820
tgccggtctc ttcacgccag gtcagcagtt tcttatcatc gttggcccag tccgccatca   2880
taccggaaga gaattcgccg gagatgatgt cgtccatatg tttctggaac aggggtgcca   2940
tgatctcttt cagctgttca gaaagcgcat aagcacgcag tttcgccggg ttagagagac   3000
ggtccatcat cagggtgatg ccgccctgtt tcagtgcttc ggtgatggtt tcccaaccga   3060
actgaatcag tttttctgcg tatgctggat cggtaccttc ttccaccagc ttgtcgaagc   3120
acagcagaga gccagcctgc aacataccgc acaggatggt ttgctcgccc atcaggtcag   3180
atttcacttc cgcaacgaag gacgattcca gcacacccgc acggtgacca ccggttgcag   3240
ccgcccaggc tttggcaatc gccatgcctt cgcctttcgg atcgttttcc gggtgaacgg   3300
caatcagcgt cggtacgccg aacccacgtt tgtactcttc acgcacttcg gtgcctgggc   3360
atttcggcgc aaccatcact acggtgatat ctttacggat ctgctcgccc acttcgacga   3420
tgttgaaacc gtgcgagtag cccagcgccg cgccgtcttt catcagtggc tgtacggtgc   3480
gcactacatc agagtgctgc ttgtccggcg tcaggttaat caccagatcc gcctgtggga   3540
tcagttcttc gtaagtaccc actttaaaac cattttcggt cgcttacgc caggacgcgc    3600 gcttctcggc aatcgcttct ttacgcagag cgtaggagat atcgagacca gaatcacgca   3660
tgttcaggcc ctggttcaga ccctgtgcgc cacagccgac gatgactact ttttaccct    3720 gaaggtagct cgcgccatcg gcgaattcat cgcggcccat ctcgagtcga aactaagttc   3780
tggtgtttta aaactaaaaa aaagactaac tataaaagta gaatttaaga agtttaagaa   3840
atagatttac agaattacaa tcaataccta ccgtctttat atacttatta gtcaagtagg   3900
ggaataattt cagggaactg gtttcaacct ttttttcag ctttttccaa atcagagaga    3960
gcagaaggta atagaaggtg taagaaaatg agatagatac atgcgtgggt caattgcctt   4020
gtgtcatcat ttactccagg caggttgcat cactccattg aggttgtgcc cgttttttgc   4080
ctgtttgtgc ccctgttctc tgtagttgcg ctaagagaat ggacctatga actgatggtt   4140
ggtgaagaaa acaatatttt ggtgctggga ttcttttttt ttctggatgc cagcttaaaa   4200
agcgggctcc attatattta gtggatgcca ggaataaact gttcacccag acacctacga   4260
tgttatatat tctgtgtaac ccgcccccta tttttgggcat gtacgggtta cagcagaatt   4320
aaaaggctaa ttttttgact aaataaagtt aggaaaatca ctactattaa ttatttacgt   4380
attctttgaa atgcgcgagta ttgataatga taaactggat cctcatccac ccaacttcga   4440
tttgtctctt actgccccct tatcggctga agtagccaat gaagcataag ccctaagggc   4500
```

```
gaaacttact tgacgttctc tattttagg  agtccaagcc ttatctcctc tggcatcttg   4560
tgcttctctt cttgcagcca attcagcgtc tgagacttgt aattggatac ctctatttgg   4620
gatatctatg gcgatcaaat ctccatcttc aatcaatcca atcgaaccac cagaagctgc   4680
ctctggtgat acgtgaccga tacttaaacc cgaagtgcca ccagagaatc taccgtcagt   4740
gataagggca caagctttc  ctagtcccat ggacttcaaa aatgaagttg ggtaaagcat   4800
ttcctgcata cctggtcctc cctttggtcc ctcatatctt atcactacca cgtctcctgc   4860
taccacctt  ccgccaagta tagcctcaac agcatcgtct tgactttcgt aaactttagc   4920
gggtccagta aatttcaaaa tactatcatc tacaccagca gttttcacaa tgcaaccatt   4980
ttcagcgaag tttccatata atactgctaa accaccatcc ttactataag catgctcaag   5040
cgatcttata catccatttg ctctatcatc gtccaaagtg tcccacctac agtcttgcga   5100
gaatgcttgg gtggttctga tccctgctgg acctgccctg aacatgtttt tcacggcatc   5160
atcttgagtt aacatgacat cgtattgctc taatgtctgt ggaagtgtta aacccaatac   5220
attcttcaca tccctgttta aagaccggc  tctgtccaac tcccctaaaa taccaataac   5280
ccctcctgca cgatgaacgt cttccatgtg atactttga  gttgatggtg caaccttaca   5340
taactgtgga accttacgtg aaagcttgtc gatatcagac atggtgaaat ctatctcagc   5400
ttcttgggct gcagctagaa gatgtaagac cgtgtttgta ctaccaccca ttgcaatatc   5460
caatgtcatg gcatttcga  atgcagcctt tgaagctata ttcctcggta atgctgattc   5520
atcattttgt tcgtaatacc ttttcgttag ttccacaatt cttttccgg  catttaagaa   5580
caattgctt  ctgtctgcat gggtcgctaa taatgaacca tttcctggtt gagataaacc   5640
tagagcttca gtcaagcaat tcatagagtt agccgtgaac attccactgc aagaaccaca   5700
agttggacat gcacttcttt caacttggtc tgactgcgag tctgaaactt ttggatctgc   5760
acccttgaatc attgcatcca caagatcaag tttgatgatc tgatcactta acttagtttt   5820
accagcctcc attgggccgc cagatacgaa gattactggg atgttcaatc tcaaggacgc   5880
catcaacata ccaggcgtta tcttatcaca attagagata caaaccattg catcggcaca   5940
atgagcatta accatatatt cgactgagtc tgcaattaat tctctcgatg gtaaagagta   6000
taacataccg ccatgcccca tagctatacc gtcgtccaca gcaatagtat taaactcttt   6060
tgcgacacca cctgcagctt caatttgttc ggcaacaagc ttacctagat cacgcaaatg   6120
gacatgaccc ggaacgaatt gtgtaaaaga gttgacgacg gcaatgattg gctttccgaa   6180
atctgcatca gtcatgccag tcatgtcgac aaacttagat tagattgcta tgctttcttt   6240
ctaatgagca agaagtaaaa aaagttgtaa tagaacaaga aaatgaaac  tgaaacttga   6300
gaaattgaag accgtttatt aacttaaata tcaatgggag gtcatcgaaa gagaaaaaaa   6360
tcaaaaaaaa aattttcaag aaaagaaac  gtgataaaaa ttttattgc  cttttcgac   6420
gaagaaaaag aaacgaggcg gtctctttt  tcttttccaa acctttagta cgggtaatta   6480
acgacaccct agaggaagaa agagggaaa  tttagtatgc tgtgcttggg tgttttgaag   6540
tggtacggcg atgcgcggag tccgagaaaa tctggaagag taaaaaagga gtagaaacat   6600
tttgaagcta tgagctccag cttttgttcc ctttagtgag ggttaattgc gcgcttggcg   6660
taatcatggt catagctgtt tcctgtgtga aattgttatc cgctcacaat tccacacaac   6720
ataggagccg gaagcataaa gtgtaaagcc tggggtgcct aatgagtgag gtaactcaca   6780
ttaattgcgt tgcgctcact gcccgctttc cagtcgggaa acctgtcgtg ccagctgcat   6840
```

```
taatgaatcg gccaacgcgc ggggagaggc ggtttgcgta ttgggcgctc ttccgcttcc   6900
tcgctcactg actcgctgcg ctcggtcgtt cggctgcggc gagcggtatc agctcactca   6960
aaggcggtaa tacggttatc cacagaatca ggggataacg caggaaagaa catgtgagca   7020
aaaggccagc aaaaggccag gaaccgtaaa aaggccgcgt tgctggcgtt tttccatagg   7080
ctccgccccc ctgacgagca tcacaaaaat cgacgctcaa gtcagaggtg gcgaaacccg   7140
acaggactat aaagatacca ggcgtttccc cctggaagct ccctcgtgcg ctctcctgtt   7200
ccgaccctgc cgcttaccgg atacctgtcc gcctttctcc cttcgggaag cgtggcgctt   7260
tctcatagct cacgctgtag gtatctcagt tcggtgtagg tcgttcgctc caagctgggc   7320
tgtgtgcacg aaccccccgt tcagcccgac cgctgcgcct tatccggtaa ctatcgtctt   7380
gagtccaacc cggtaagaca cgacttatcg ccactggcag cagccactgg taacaggatt   7440
agcagagcga ggtatgtagg cggtgctaca gagttcttga agtggtggcc taactacggc   7500
tacactagaa ggacagtatt tggtatctgc gctctgctga agccagttac cttcggaaaa   7560
agagttggta gctcttgatc cggcaaacaa accaccgctg gtagcggtgg tttttttgtt   7620
tgcaagcagc agattacgcg cagaaaaaaa ggatctcaag aagatccttt gatcttttct   7680
acggggtctg acgctcagtg gaacgaaaac tcacgttaag ggattttggt catgagatta   7740
tcaaaaagga tcttcaccta gatccttttta aattaaaaat gaagttttaa atcaatctaa   7800
agtatatatg agtaaacttg gtctgacagt taccaatgct taatcagtga ggcacctatc   7860
tcagcgatct gtctatttcg ttcatccata gttgcctgac tccccgtcgt gtagataact   7920
acgatacggg agggcttacc atctggcccc agtgctgcaa tgataccgcg agacccacgc   7980
tcaccggctc cagatttatc agcaataaac cagccagccg aagggccga gcgcagaagt   8040 ggtcctgcaa cttatccgc ctccatccag tctattaatt gttgccggga agctagagta   8100
agtagttcgc cagttaatag tttgcgcaac gttgttgcca ttgctacagg catcgtggtg   8160
tcacgctcgt cgtttggtat ggcttcattc agctccggtt cccaacgatc aaggcgagtt   8220
acatgatccc ccatgttgtg caaaaaagcg gttagctcct tcggtcctcc gatcgttgtc   8280
agaagtaagt tggccgcagt gttatcactc atggttatgg cagcactgca taattctctt   8340
actgtcatgc catccgtaag atgcttttct gtgactggtg agtactcaac caagtcattc   8400
tgagaatagt gtatgcggcg accgagttgc tcttgcccgg cgtcaatacg ggataatacc   8460
gcgccacata gcagaacttt aaaagtgctc atcattggaa aacgttcttc ggggcgaaaa   8520
ctctcaagga tcttaccgct gttgagatcc agttcgatgt aacccactcg tgcacccaac   8580
tgatcttcag catcttttac tttcaccagc gtttctgggt gagcaaaaac aggaaggcaa   8640
aatgccgcaa aaaagggaat aagggcgaca cggaaatgtt gaatactcat actcttcctt   8700
tttcaatatt attgaagcat ttatcagggt tattgtctca tgagcggata catatttgaa   8760
tgtatttaga aaaataaaca aataggggtt ccgcgcacat ttccccgaaa agtgccacct   8820
gggtcctttt catcacgtgc tataaaaata attataattt aaattttta atataaatat   8880 ataaattaaa aatagaaagt aaaaaagaa attaagaaa aatagtttt tgttttccga   8940 agatgtaaaa gactctaggg ggatcgccaa caaatactac cttttatctt gctcttcctg   9000
ctctcaggta ttaatgccga attgtttcat cttgtctgtg tagaagacca cacacgaaaa   9060
tcctgtgatt ttacattttta cttatcgtta atcgaatgta tatctattta atctgctttt   9120
cttgtctaat aaatatatat gtaaagtacg ctttttgttg aaatttttta aaccttttgtt   9180 tattttttttt tcttcattcc gtaactcttc taccttcttt atttactttc taaaatccaa   9240
```

| | |
|---|---|
| atacaaaaca taaaaataaa taaacacaga gtaaattccc aaattattcc atcattaaaa | 9300 |
| gatacgaggc gcgtgtaagt tacaggcaag cgatccgtcc taagaaacca ttattatcat | 9360 |
| gacattaacc tataaaaata ggcgtatcac gaggcccttt cgtc | 9404 |

<210> SEQ ID NO 30
<211> LENGTH: 23
<212> TYPE: DNA
<213> ORGANISM: Artificial Sequence
<220> FEATURE:
<223> OTHER INFORMATION: Synthetic primer

<400> SEQUENCE: 30
agtcacatca agatcgttta tgg       23

<210> SEQ ID NO 31
<211> LENGTH: 23
<212> TYPE: DNA
<213> ORGANISM: Artificial Sequence
<220> FEATURE:
<223> OTHER INFORMATION: Synthetic primer

<400> SEQUENCE: 31
gcacggaata tgggactact tcg       23

<210> SEQ ID NO 32
<211> LENGTH: 23
<212> TYPE: DNA
<213> ORGANISM: Artificial Sequence
<220> FEATURE:
<223> OTHER INFORMATION: Synthetic primer

<400> SEQUENCE: 32
actccacttc aagtaagagt ttg       23

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
tattgtctca tgagcggata c       21

<210> SEQ ID NO 34
<211> LENGTH: 29
<212> TYPE: DNA
<213> ORGANISM: Artificial Sequence
<220> FEATURE:
<223> OTHER INFORMATION: Synthetic primer

<400> SEQUENCE: 34
acaacgagtg tcatggggag aggaagagg       29

<210> SEQ ID NO 35
<211> LENGTH: 27
<212> TYPE: DNA
<213> ORGANISM: Artificial Sequence
<220> FEATURE:
<223> OTHER INFORMATION: Synthetic primer

<400> SEQUENCE: 35
gatcttcggc tgggtcatgt gaggcgg       27

```
<210> SEQ ID NO 36
<211> LENGTH: 24
<212> TYPE: DNA
<213> ORGANISM: Artificial Sequence
<220> FEATURE:
<223> OTHER INFORMATION: Synthetic primer

<400> SEQUENCE: 36
acgctgaaca cgttggtgtc ttgc                                              24

<210> SEQ ID NO 37
<211> LENGTH: 23
<212> TYPE: DNA
<213> ORGANISM: Artificial Sequence
<220> FEATURE:
<223> OTHER INFORMATION: Synthetic primer

<400> SEQUENCE: 37
aacccttagc agcatcggca acc                                               23

<210> SEQ ID NO 38
<211> LENGTH: 21
<212> TYPE: DNA
<213> ORGANISM: Artificial Sequence
<220> FEATURE:
<223> OTHER INFORMATION: Synthetic primer

<400> SEQUENCE: 38
tattcatggg ccaatactac g                                                 21

<210> SEQ ID NO 39
<211> LENGTH: 31
<212> TYPE: DNA
<213> ORGANISM: Artificial Sequence
<220> FEATURE:
<223> OTHER INFORMATION: Synthetic primer

<400> SEQUENCE: 39
gtagaagacg tcacctggta gaccaaagat g                                      31

<210> SEQ ID NO 40
<211> LENGTH: 32
<212> TYPE: DNA
<213> ORGANISM: Artificial Sequence
<220> FEATURE:
<223> OTHER INFORMATION: Synthetic primer

<400> SEQUENCE: 40
catcgtgacg tcgctcaatt gactgctgct ac                                     32

<210> SEQ ID NO 41
<211> LENGTH: 32
<212> TYPE: DNA
<213> ORGANISM: Artificial Sequence
<220> FEATURE:
<223> OTHER INFORMATION: Synthetic primer

<400> SEQUENCE: 41
actaagcgac acgtgcggtt tctgtggtat ag                                     32

<210> SEQ ID NO 42
<211> LENGTH: 36
<212> TYPE: DNA
<213> ORGANISM: Artificial Sequence
<220> FEATURE:
<223> OTHER INFORMATION: Synthetic primer
```

<400> SEQUENCE: 42
gaaaccgcac gtgtcgctta gtttacattt ctttcc                                    36

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
tttgaagtgg tacggcgatg                                                      20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
aatcatatcg aacacgatgc                                                      20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
agctggtctg gtgattctac                                                      20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
tatcaccgta gtgatggttg                                                      20

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47
gtcagcagtt tcttatcatc g                                                    21

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
gcgaaactta cttgacgttc                                                      20

<210> SEQ ID NO 49

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
actttggacg atgatagagc                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
gcgttagatg gtacgaaatc                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
cttctaacac tagcgaccag                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
aaagatgatg agcaaacgac                                                    20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
cgagcaatac tgtaccaatg                                                    20

<210> SEQ ID NO 54
<211> LENGTH: 20
<212> TYPE: DNA
<213> ORGANISM: Artificial Sequence
<220> FEATURE:
<223> OTHER INFORMATION: Synthetic primer

<400> SEQUENCE: 54
tcacggatga tttccagggt                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
```

```
cacctgcgtt gttaccacaa                                              20
```

<210> SEQ ID NO 56
<211> LENGTH: 491
<212> TYPE: PRT
<213> ORGANISM: Escherichia coli

<400> SEQUENCE: 56

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365
```

```
Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
        450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 57
<211> LENGTH: 14056
<212> TYPE: DNA
<213> ORGANISM: Artificial Sequence
<220> FEATURE:
<223> OTHER INFORMATION: pGV2227

<400> SEQUENCE: 57
ttggatcata ctaagaaacc attattatca tgacattaac ctataaaaat aggcgtatca      60
cgaggccctt tcgtctcgcg cgtttcggtg atgacggtga aaacctctga cacatgcagc    120
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt tcaattcaa ttcatcattt ttttttatt       300 cttttttttg atttcggttt ctttgaaatt ttttttgattc ggtaatctcc gaacagaagg    360
aagaacgaag gaaggagcac agacttagat tggtatatat acgcatatgg caaattaaag    420
ccttcgagcg tcccaaaacc ttctcaagca aggttttcag tataatgtta catgcgtaca    480
cgcgtctgta cagaaaaaaa agaaaaattt gaaatataaa taacgttctt aatactaaca    540
taactataaa aaaataaata gggacctaga cttcaggttg tctaactcct tccttttcgg    600
ttagagcgga tgtgggggga gggcgtgaat gtaagcgtga cataactaat tacatgactc    660
gacctaggtt atttagtaaa atcaatgacc attcggcctt caattttttcc tgccttcatt   720 tcatcaataa tatcattgat ttcttccagt ttgcgtgtcg caacaattgg ttttaccta    780 ccttctgctc caaattgaaa agcttctgcc aagtcaagtc ttgttccgac aagtgaacct    840
gcaacctcca ctccgtcaaa acaactgtt ggaactgata aagtcatctc agtattggga     900
agtgccacag caaccatttt gcccataggt ttcaaagaag caaccgcttg ttcaaaagca    960
atccttgcaa cagcacaaac tattgcactt tgcaccccta agccgccagt tatttttta   1020 atttcatcaa ctggatttac atcaccagaa ttgataatca catcagctcc aattttttta   1080
gctaaattta atttatcttg attaatatca acagcaatta cttttgctcc aaaaacattt   1140
ttagcatatt gaattgctaa atttccaagt cctccagcac caaaaattac ttgccaatca   1200
ccaggtttta ctcctgatac tttgattgct ttgtaagttg ttactccagc acaagtaatt   1260
gagctagctt caattgggtc aagtccgtca ggaactttga cagcataatc ggcaacaaca   1320
```

```
attgcttctt cagccattcc gccatcaact gaatatcctg cattttaac ttctcgacaa    1380
aaagtttcat taccagatac acagtattca cagtgaccac atccttcaaa gaaccaagcc    1440
actgaaaccc gatcaccaac ttgaagcgag cttacatcag ctccaattc tttgacaatt    1500
ccaattcctt catgaccaag aacagtccct gctttgttgc cataatcacc tgctgcaacg    1560
tgcaaatcgg tatgacagac tccacaatac tccatgtcaa gcaaagcttc attaggtttg    1620
attgctcgaa gttccttttc aacaaggtcc gcataaccat ctggattgtg tcttactact    1680
gctgctttca ttggtaccta ttattgtatg ttatagtatt agttgcttgg tgttatgaaa    1740
gaaactaaga aagaaaaat aaataaaaa taaaagattg agacaaggga agaaaagata    1800
caaaataaga attaattaca attgcgtttg ctataaatac gttttaaca atcaactctg    1860
gtaggaagat aatgcttttt tttttatat atgcttggtg ccacttgtca catacaattc    1920
tacaaccttc gacaaaaatc caaatgatag taagatcaaa gccagaaagc aatggagaaa    1980
aaaaattaat gaaccacgat gaaccaaatg atcaatacaa ccaaagaaac taccctagtg    2040
aggtgtatgc tgacttggta tcacacttca tgaattttgc atatggcaaa gtccacgaaa    2100
gtgggcttca gaaaaaggc gtgcggtgtg tagatgtatc aattagtgga tgccagtttt    2160
ggaacgggat tccactttcc gcaagttggt gcacgtcgtt agtgacataa cgccgcgttc    2220
atctttggga agaagcagat gctgagcgag gaggtactat agagtaaaga accctttcta    2280
tacccgcagc cccatggtaa gtgacagtgc agtaataata tgaaccaatt tattttttcgt    2340
tacataaaaa tgcttataaa actttaacta ataattagag attaaatcgc ggccgcaaaa    2400
gatccttagg atttattctg ttcagcaaac agcttgccca tttctttcag taccttcggt    2460
gcgccttctt tcgccaggat cagttcgatc cagtacatac ggttcggatc ggcctgggcc    2520
tctttcatca cgctcacaaa ttcgttttcg gtacgcacaa ttttagacac aacacggtcc    2580
tcagttgcgc cgaaggactc cggcagttta gagtagttcc acatagggat atcgttgtaa    2640
gactggttcg gaccgtggat ctcacgctca acggtgtagc cgtcattgtt aataatgaag    2700
caaatcgggt tgatcttttc acgaattgcc agacccagtt cctgtacggt cagctgcagg    2760
gaaccgtcac cgatgaacag cagatgacga gattctttat cagcgatctg agagcccagc    2820
gctgccggga agtatagcc aatgctaccc cacagcggct gaccgataaa atggcttttg    2880
gatttcagaa agatagaaga cgcgccgaaa aagctcgtac cttgttccgc cacgatggtt    2940
tcattgctct gggtcaggtt ctccacggcc tgccacaggc gatcctggga cagcagtgcg    3000
ttagatggta cgaaatcttc ttgcttttg tcaatgtatt tgccttttata ctcgatttcg    3060
gacaggtcca gcagagagct gatcaggctt tcgaagtcga agttctggat acgctcgttg    3120
aagattttac cctcgtcgat gttcaggcta atcattttgt tttcgttcag atggtgagtg    3180
aatgcaccgg tagaagagtc ggtcagttta acgcccagca tcaggatgaa gtccgcagat    3240
tcaacaaatt ctttcaggtt cggttcgctc agagtaccgt tgtagatgcc caggaaagac    3300
ggcagagcct cgtcaacaga ggacttgccg aagttcaggg tggtaatcgg cagtttggtt    3360
ttgctgatga attgggtcac ggtcttctcc agaccaaaag aaatgatttc gtggccggtg    3420
atcacgattg gttctttgc gttttcaga gactcctgga ttttgttcag gatttcctgg    3480
tcgctagtgt tagaagtgga gttttctttc ttcagcggca ggctcggttt ttccgcttta    3540
gctgccgcaa catccacagg caggttgatg taaactggtt tgcgttcttt cagcagcgca    3600
gacagaacgc ggtcgatttc cacagtagcg ttctctgcag tcagcagcgt acgtgccgca    3660
gtcacaggtt catgcatttt catgaagtgt ttgaaatcgc cgtcagccag agtgtggtgg    3720
```

```
acgaatttac cttcgttctg aactttgctc gttgggctgc ctacgatctc caccaccggc   3780
aggttttcgg cgtaggagcc cgccagaccg ttgacggcgc tcagttcgcc aacaccgaaa   3840
gtggtcagaa atgccgcggc tttcttggta cgtgcataac catctgccat gtagcttgcg   3900
ttcagttcgt tagcgttacc cacccatttc atgtctttat gagagatgat ctgatccagg   3960
aactgcagat tgtaatcacc cggaacgccg aagatttctt cgatacccag ttcatgcaga   4020
cggtccagca gataatcacc aacagtatac atgtcgagct tgttttatat ttgttgtaaa   4080
aagtagataa ttacttcctt gatgatctgt aaaaagaga aaagaaagc atctaagaac    4140 ttgaaaaact acgaattaga aaagaccaaa tatgtatttc ttgcattgac caatttatgc   4200
aagtttatat atatgtaaat gtaagtttca cgaggttcta ctaaactaaa ccacccccctt  4260 ggttagaaga aaagagtgtg tgagaacagg ctgttgttgt cacacgattc ggacaattct   4320
gtttgaaaga gagagagtaa cagtacgatc gaacgaactt tgctctggag atcacagtgg   4380
gcatcatagc atgtggtact aaacccttc ccgccattcc agaaccttcg attgcttgtt    4440
acaaaacctg tgagccgtcg ctaggacctt gttgtgtgac gaaattggaa gctgcaatca   4500
ataggaagac aggaagtcga gcgtgtctgg gttttttcag ttttgttctt tttgcaaaca   4560
aatcacgagc gacggtaatt tctttctcga taagaggcca cgtgctttat gagggtaaca   4620
tcaattcaag aaggagggaa acacttcctt tttctggccc tgataatagt atgagggtga   4680
agccaaaata aaggattcgc gcccaaatcg gcatctttaa atgcaggtat gcgatagttc   4740
ctcactcttt ccttactcac gagtaattct tgcaaatgcc tattatgcag atgttataat   4800
atctgtgcgt cttgagttga gcctagaatt cttagaaaaa ctcatcgagc atcaaatgaa   4860
actgcaattt attcatatca ggattatcaa taccatattt ttgaaaaagc cgtttctgta   4920
atgaaggaga aaactcaccg aggcagttcc ataggatggc aagatcctgg tatcggtctg   4980
cgatcccgac tcgtccaaca tcaatacaac ctattaattt cccctcgtca aaaataaggt   5040
tatcaagtga gaaatcacca tgagtgacga ctgaatccgg tgagaatggc aaaagcttat   5100
gcatttcttt ccagacttgt tcaacaggcc agccattacg ctcgtcatca aaatcactcg   5160
cgtcaaccaa accgttattc attcgtgatt gcgcctgagc gaggcgaaat acgcgatcgc   5220
tgttaaaagg acaattacaa acaggaatcg aatgcaaccg cgcaggaac actgccagcg    5280 catcaacaat attttcacct gaatcaggat attcttctaa tacctggaat gctgttttgc   5340
cggggatcgc agtggtgagt aaccatgcat catcaggagt acggacaaaa tgcttgatgg   5400
tcggaagagg cataaattcc gtcagccagt ttagtctgac catctcatct gcaacatcat   5460
tggcaacgct acctttgcca tgtttcagaa acaactctgg cgcatcgggc ttcccataca   5520
atcgatagat tgtcgcacct gattgcccga cattatcgcg agcccattta tacccatata   5580
aatcagcatc catgttggaa tttaatcgcg gcctcgaaac gtgagtcttt tccttaccca   5640
tactagtttt tagtttatgt atgtgttttt tgtagttata gatttaagca agaaaagaat   5700
acaaacaaaa aattgaaaaa gattgattta gaattaaaaa gaaaaatatt tacgtaagaa   5760
gggaaaatag taaatgttgc aagttcacta aactcctaaa ttatgctgcc ctttatattc   5820
cctgttacag cagccgagcc aaaggtatat aggctccttt gcattagcat gcgtaacaaa   5880
ccacctgtca gtttcaaccg aggtggtatc cgagagaatt gtgtgattgc tttaattaat   5940
ttcggagaat ctcacatgcc actgaagatt aaaaactgga tgccagaaaa ggggtgtcca   6000
ggtgtaacat caatagagga agctgaaaag tcttagaacg ggtaatcttc caccaacctg   6060
```

```
atgggttcct agatataatc tcgaagggaa taagtagggt gataccgcag aagtgtctga    6120
atgtattaag gtcctcacag tttaaatccc gctcacacta acgtaggatt attataactc    6180
aaaaaaatgg cattattcta agtaagttaa atatccgtaa tctttaaaca gcggccgcgg    6240
atcttcatcc tgccactgca attcttttca tatcggtcat atatcctctc agcttttac     6300 ccacctgttc tatagcatgt gaacgaatag cttcatttac gtctctcagt tggccattgt    6360
caaccgctcc ttccggaata gccttcccca aatcaccagg ttgtaactcg gccatgaagg    6420
gctttaacaa cgggacacat gcgtagctaa ataagtaatt accatattct gcagtgtctg    6480
atatgacaac attcatctcg taaagtcttt tcttgcaat agtatttgct atcaaaggca     6540
attcatgcaa agactcatag tatgcagatt cttcaatgat accggagtca accatagttt    6600
cgaatgcaag ttctacccct gccttcacca tagctatcat caatactccc ttatcaaagt    6660
attcttgttc accaatttta ccttcgtatt gtggggctgt ctcgaatgcc gtcttgccgg    6720
tttcttctct ccacgtcaat aactttttat catcgtttgc ccaatctgcc atcattcctg    6780
aggaaaactc accggagata atatcgtcca tgtgcttttg gaataatggt gccatgatct    6840
cttttagttg ctcagataag gcgtaggctc ttagcttggc cggatttgaa agtctatcca    6900
tcatcaatgt tatgccacct tgtttaagtg cctcggtgat tgtctcccaa ccaaattgta    6960
tcaacttttc agcataggca ggatctgtac cctcttcgac caatttatca aagcatagta    7020
aagaccctgc ctgcaacatt ccgcacagaa tggtttgttc acccattaag tcactcttga    7080
cctcagctac gaaagaactc tctaacacac ccgctctatg acctccggtt gcggctgccc    7140
atgccttcgc aattgccata ccttcacctt tggggtcatt ttcaggatgt acggcgatca    7200
atgtaggtac accaaaaccc ctcttgtact cctctctgac ttccgtacct gggcactttg    7260
gtgcaaccat tacgactgtt atatcttttc tgatctgctc gcccacttca acgatattaa    7320
agccatgaga gtaacctaaa gctgccccat ccttcatcag cggttgaact gttcttacta    7380
cgtctgagtg aaccttatct ggtgttaggt taatcactaa atctgcctga gggatcagtt    7440
cttcgtaagt accaactttg aacccatttt ccgtcgcttt acgccaggag gccctctttt    7500
ctgcaattgc ctctttcctc aatgcatacg aaatatccag acctgaatct ctcatgttta    7560
aaccttggtt tagaccctga gcaccgcagc caacaattac tactttcttt ccttgcagat    7620
aagaagcacc atcagcaaac tcgtcccttc ccataaatct gcacttaccc agttgagcca    7680
attgttgtct caaatttaat gtgttaaaat agttggccat ctcgagtcga aactaagttc    7740
tggtgtttta aaactaaaaa aaagactaac tataaaagta gaatttaaga agtttaagaa    7800
atagatttac agaattacaa tcaataccta ccgtctttat atacttatta gtcaagtagg    7860
ggaataattt cagggaactg gtttcaacct ttttttcag ctttttccaa atcagagaga     7920
gcagaaggta atagaaggtg taagaaaatg agatagatac atgcgtgggt caattgcctt    7980
gtgtcatcat ttactccagg caggttgcat cactccattg aggttgtgcc cgttttttgc    8040
ctgtttgtgc ccctgttctc tgtagttgcg ctaagagaat ggacctatga actgatggtt    8100
ggtgaagaaa acaatatttt ggtgctggga ttctttttt ttctggatgc cagcttaaaa     8160
agcgggctcc attatattta gtggatgcca ggaataaact gttcacccag acacctacga    8220
tgttatatat tctgtgtaac ccgccccta ttttgggcat gtacgggtta cagcagaatt     8280
aaaaggctaa ttttttgact aaataaagtt aggaaaatca ctactattaa ttatttacgt    8340
attctttgaa atgcgagta ttgataatga taaactggat ccgcggccgc ttacagatca     8400
gtaacacacc cttccgatgc aggacggatt aatttagcga attttgccaa aactcccctg    8460
```

```
gtggctttcg gagttggctt ctgataatta gctcttctct ttgcgatttc ttcatcggaa    8520
actttcaggg atatagagtt gttgactgca tctatctcta ttatatcgtc atcttcaact    8580
aagccgatta gtccaccctc aacggcttca ggcacaatat ggccgacaac aaaaccgtga    8640
gtgccaccgg agaatctacc atccgtaatt aacgcgcaac ttttccctaa acccgcacca    8700
attaatgctg atgtaggctt cagcatttcg ggcataccag gtccgccgac gggacctata    8760
ttcctaatta ccgctacatc tccagcatgc aaacgaccag attctatgcc gtcgataaaa    8820
tgttgttcac catcaaagac tctggcagtg cctttgaaga actctccttc tttaccgcta    8880
atttttgcta cggaaccccc ttgagctaaa ttaccgtaca gaatctgcaa gtggccggtg    8940
gccttgatag gattctttag tggcctcatg atatcttgtg agtcgaaatc caagtctagg    9000
gcagtctcga cattctcggc taatgtttta cccgtcacag taaggcagtc accatgcaat    9060
tttccttcct ttagaaggta cttaagcact gctggcaagc ctccaatttt atgcaaatct    9120
tccatcatat atttacctga aggtttaaaa tcacctagta ctggagtaat gtcactaatt    9180
ctttggaagt catcctgagt tatttcgaca cctatcgcgt tagccattgc aataatatgc    9240
aagacagcat tagtactacc ccccaagacc atcacaatgg taatagcgtt ctcgaacgcc    9300
tccttagtca ttatatcact aggcttgatg tcttttttcca aaagattctt aatggctaat    9360
ccaatctcat cacattcttc ttgtttttct tgagatactg cagggttcga agaagaatac    9420
ggcaatgaca tacctagtgt ttcgatagcg gcagctaagg tattagctgt gtacatcccc    9480
ccacatgccc cttgaccagg aatagcatta caaataacac cgtgataatc ttcatcagag    9540
atattgccgg taattttctg gcctagagat tcaaaagccg atacgatgtt caatttctca    9600
cctttatatt caccgtgttc tattgttcct ccatacacca taatgcttgg cctattaagt    9660
cttgccatac caataataga acctggcata tttttgtcac aacctgggat ggctacaatt    9720
gcatcatagt attcagcgcc agcgttggtt tcaatagagt cagctataac ttctctggaa    9780
acaagggagt atctcattcc caactttcca tttgctatcc catcagaaac tcctatcgta    9840
tgaaattgta agccgatcag accatctgtc tgatttactg agcttttaat ctttgatcca    9900
agggttccta aatgcatgtt gcatggattt ccatcccagt ccatcgacac tatacccact    9960
tgagctttct tgaaatcttc gtcttttaaac ccgatgccgt aatacattgc ctgtgtggcg   10020
ggttgtgtgg gatcttgtgt caacgttttg ctgtacttat tcagttcaac agattcaact   10080
ttgccgttat acttaaactc catgtcgaca aacttagatt agattgctat gctttctttc   10140
taatgagcaa gaagtaaaaa aagttgtaat agaacaagaa aaatgaaact gaaacttgag   10200
aaattgaaga ccgtttatta acttaaatat caatgggagg tcatcgaaag agaaaaaaat   10260
caaaaaaaaa attttcaaga aaagaaacg tgataaaaat ttttattgcc tttttcgacg   10320
aagaaaaaga aacgaggcgg tctctttttt cttttccaaa cctttagtac gggtaattaa   10380
cgacacccta gaggaagaaa gagggggaaat ttagtatgct gtgcttgggt gttttgaagt   10440
ggtacggcga tgcgcggagt ccgagaaaat ctggaagagt aaaaaaggag tagaaacatt   10500
ttgaagctat gagctccagc ttttgttccc tttagtgagg gttaattgcg cgcttggcgt   10560
aatcatggtc atagctgttt cctgtgtgaa attgttatcc gctcacaatt ccacacaaca   10620
taggagccgg aagcataaag tgtaaagcct ggggtgccta atgagtgagg taactcacat   10680
taattgcgtt gcgctcactg cccgctttcc agtcgggaaa cctgtcgtgc cagctgcatt   10740
aatgaatcgg ccaacgcgcg gggagaggcg gtttgcgtat tgggcgctct tccgcttcct   10800
```

```
cgctcactga ctcgctgcgc tcggtcgttc ggctgcggcg agcggtatca gctcactcaa   10860
aggcggtaat acggttatcc acagaatcag gggataacgc aggaaagaac atgtgagcaa   10920
aaggccagca aaaggccagg aaccgtaaaa aggccgcgtt gctggcgttt ttccataggc   10980
tccgcccccc tgacgagcat cacaaaaatc gacgctcaag tcagaggtgg cgaaacccga   11040
caggactata aagataccag gcgtttcccc ctggaagctc cctcgtgcgc tctcctgttc   11100
cgaccctgcc gcttaccgga tacctgtccg cctttctccc ttcgggaagc gtggcgcttt   11160
ctcatagctc acgctgtagg tatctcagtt cggtgtaggt cgttcgctcc aagctgggct   11220
gtgtgcacga accccccgtt cagcccgacc gctgcgcctt atccggtaac tatcgtcttg   11280
agtccaaccc ggtaagacac gacttatcgc cactggcagc agccactggt aacaggatta   11340
gcagagcgag gtatgtaggc ggtgctacag agttcttgaa gtggtggcct aactacggct   11400
acactagaag gacagtattt ggtatctgcg ctctgctgaa gccagttacc ttcggaaaaa   11460
gagttggtag ctcttgatcc ggcaaacaaa ccaccgctgg tagcggtggt ttttttgttt   11520
gcaagcagca gattacgcgc agaaaaaaag gatctcaaga agatcctttg atcttttcta   11580
cggggtctga cgctcagtgg aacgaaaact cacgttaagg gattttggtc atgagattat   11640
caaaaaggat cttcacctag atccttttaa attaaaaatg aagttttaaa tcaatctaaa   11700
gtatatatga gtaaacttgg tctgacagtt accaatgctt aatcagtgag gcacctatct   11760
cagcgatctg tctatttcgt tcatccatag ttgcctgact ccccgtcgtg tagataacta   11820
cgatacggga gggcttacca tctggcccca gtgctgcaat gataccgcga cccacgct   11880
caccggctcc agatttatca gcaataaacc agccagccgg aagggccgag cgcagaagtg   11940
gtcctgcaac tttatccgcc tccatccagt ctattaattg ttgccgggaa gctagagtaa   12000
gtagttcgcc agttaatagt ttgcgcaacg ttgttgccat tgctacaggc atcgtggtgt   12060
cacgctcgtc gtttggtatg gcttcattca gctccggttc ccaacgatca aggcgagtta   12120
catgatcccc catgttgtgc aaaaaagcgg ttagctcctt cggtcctccg atcgttgtca   12180
gaagtaagtt ggccgcagtg ttatcactca tggttatggc agcactgcat aattctctta   12240
ctgtcatgcc atccgtaaga tgcttttctg tgactggtga gtactcaacc aagtcattct   12300
gagaatagtg tatgcggcga ccgagttgct cttgcccggc gtcaatacgg gataataccg   12360
cgccacatag cagaacttta aaagtgctca tcattggaaa acgttcttcg ggcgaaaac   12420
tctcaaggat cttaccgctg ttgagatcca gttcgatgta acccactcgt gcacccaact   12480
gatcttcagc atcttttact ttcaccagcg tttctgggtg agcaaaaaca ggaaggcaaa   12540
atgccgcaaa aaagggaata agggcgacac ggaaatgttg aatactcata ctcttccttt   12600
ttcaatatta ttgaagcatt tatcagggtt attgtctcat gagcggatac atatttgaat   12660
gtatttagaa aaataaacaa ataggggttc cgcgcacatt tccccgaaaa gtgccacctg   12720
aacgaagcat ctgtgcttca ttttgtagaa caaaaatgca acgcgagagc gctaattttt   12780
caaacaaaga atctgagctg cattttaca gaacagaaat gcaacgcgaa agcgctattt   12840
taccaacgaa gaatctgtgc ttcattttg taaacaaaa atgcaacgcg agagcgctaa   12900
ttttcaaac aaagaatctg agctgcattt ttacagaaca gaaatgcaac gcgagagcgc   12960
tattttacca acaaagaatc tatacttctt ttttgttcta caaaaatgca tcccgagagc   13020
gctatttttc taacaaagca tcttagatta cttttttct cctttgtgcg ctctataatg   13080
cagtctcttg ataacttttt gcactgtagg tccgttaagg ttagaagaag gctactttgg   13140
tgtctatttt ctcttccata aaaaaagcct gactccactt cccgcgttta ctgattacta   13200
```

```
gcgaagctgc gggtgcattt tttcaagata aaggcatccc cgattatatt ctataccgat   13260
gtggattgcg catactttgt gaacagaaag tgatagcgtt gatgattctt cattggtcag   13320
aaaattatga acggtttctt ctattttgtc tctatatact acgtatagga aatgtttaca   13380
ttttcgtatt gttttcgatt cactctatga atagttctta ctacaatttt tttgtctaaa   13440
gagtaatact agagataaac ataaaaaatg tagaggtcga gtttagatgc aagttcaagg   13500
agcgaaaggt ggatgggtag gttatatagg gatatagcac agagatatat agcaaagaga   13560
tacttttgag caatgtttgt ggaagcggta ttcgcaatat tttagtagct cgttacagtc   13620
cggtgcgttt ttggtttttt gaaagtgcgt cttcagagcg cttttggttt tcaaaagcgc   13680
tctgaagttc ctatactttc tagagaatag gaacttcgga ataggaactt caaagcgttt   13740
ccgaaaacga gcgcttccga aaatgcaacg cgagctgcgc acatacagct cactgttcac   13800
gtcgcaccta tatctgcgtg ttgcctgtat atatatatac atgagaagaa cggcatagtg   13860
cgtgtttatg cttaaaatgcg tacttatatg cgtctattta tgtaggatga aaggtagtct   13920
agtacctcct gtgatattat cccattccat gcggggtatc gtatgcttcc ttcagcacta   13980 cccctttagct gttctatatg ctgccactcc tcaattggat tagtctcatc cttcaatgct   14040
atcatttcct ttgata                                                  14056
```

<210> SEQ ID NO 58
<211> LENGTH: 1716
<212> TYPE: DNA
<213> ORGANISM: Bacillus subtilis

<400> SEQUENCE: 58

```
atgttgacta aagctacaaa agagcagaaa tcattggtga aaaataggggg tgcagaactt     60 gttgtggact gtttggtaga acagggcgta acacatgttt ttggtatccc aggtgcaaaa    120
atcgacgccg tgtttgatgc attacaagac aagggtccag aaattattgt tgctagacat    180
gagcaaaatg ccgcatttat ggcgcaagct gtaggtaggc ttacaggtaa acctggtgtt    240
gtcctagtta cgtctggccc aggagcctcc aatttagcaa ctggtctatt gacagctaat    300
actgagggag atcctgtagt tgcgttagcc ggtaatgtaa ttagagctga taggcttaag    360
agaactcacc agtctctaga caacgctgct ttattccaac cgatcaccaa gtactcagta    420
gaggtacaag acgtaaagaa tatacctgaa gctgtgacaa acgcatttcg tatagcttct    480
gctggtcagg ctggtgccgc gtttgtttct tttcctcaag acgttgtcaa tgaagtgacc    540
aatactaaaa acgttagagc ggttgcagcc cctaaactag gtccagccgc agacgacgca    600
attagcgctg caattgctaa aattcagacg gcgaaactac cagtagtcct tgtcggtatg    660
aagggcggaa gaccagaagc aataaaaagct gttcgtaagt tattgaagaa agtccaatta    720
cctttcgttg agacttacca agcagcaggt actttatcta gagatttaga ggatcagtat    780
tttggaagga taggtctatt tagaaaccaa ccaggagatt tactattaga acaagctgat    840
gttgtactta ctatcggtta tgatcctata gagtatgacc caaagttttg gaacataaat    900
ggggatagaa caattataca tctagacgag ataatcgccg acatcgatca cgcttatcaa    960
ccagatttag aactaatcgg agatatcccg tcaacaatca atcatattga acatgatgct   1020
gtaaaggttg agttcgctga acgtgagcag aaaatcttat ctgatctaaa gcaatatatg   1080
catgagggtg aacaagttcc agcagactgg aaatctgacc gtgcacatcc tttggaaatc   1140
gttaaggaac taagaaatgc ggtcgatgat catgtgactg ttacatgtga tatcggttca   1200
```

```
catgcaattt ggatgtcacg ttattttagg agctacgaac cattaacttt aatgatatct   1260
aacgggatgc aaactctggg ggttgcactt ccttgggcta ttggcgctag tttagttaag   1320
cccggtgaga aggtggtatc ggtatcaggt gatggtggct ttctgttttc ggctatggaa   1380
ttagaaactg cagtccgttt aaaagctccc attgtgcata ttgtctggaa tgattctact   1440
tacgacatgg ttgcttttca acagttgaag aaatacaata gaacttcggc tgtagacttt   1500
ggtaacatcg atattgtgaa atatgctgag tcttttggcg caacaggcct gagggtggaa   1560
agtccagatc agttagctga tgtgttgaga caagggatga atgccgaggg accggtaatc   1620
atagatgtgc cagttgacta ctcagacaat attaatttgg cttctgataa acttcctaaa   1680
gagtttggcg agctaatgaa gaccaaagcc ttataa                             1716

<210> SEQ ID NO 59
<211> LENGTH: 1647
<212> TYPE: DNA
<213> ORGANISM: Lactococcus lactis

<400> SEQUENCE: 59
atgtatactg ttggtgatta tctgctggac cgtctgcatg aactgggtat cgaagaaatc     60
ttcggcgttc cgggtgatta caatctgcag ttcctggatc agatcatctc tcataaagac    120
atgaaatggg tgggtaacgc taacgaactg aacgcaagct acatggcaga tggttatgca    180
cgtaccaaga aagccgcggc atttctgacc actttcggtg ttggcgaact gagcgccgtc    240
aacggtctgg cgggctccta cgccgaaaac ctgccggtgg tggagatcgt aggcagccca    300
acgagcaaag ttcagaacga aggtaaattc gtccaccaca ctctggctga cggcgatttc    360
aaacacttca tgaaaatgca tgaacctgtg actgcggcac gtacgctgct gactgcagag    420
aacgctactg tggaaatcga ccgcgttctg tctgcgctgc tgaaagaacg caaaccagtt    480
tacatcaacc tgcctgtgga tgttgcggca gctaaagcgg aaaaaccgag cctgccgctg    540
aagaaagaaa actccacttc taacactagc gaccaggaaa tcctgaacaa aatccaggag    600
tctctgaaaa acgcaaagaa accaatcgtg atcaccggcc acgaaatcat ttcttttggt    660
ctggagaaga ccgtgaccca attcatcagc aaaaccaaac tgccgattac cacctgaac    720 ttcggcaagt cctctgttga cgaggctctg ccgtctttcc tgggcatcta caacggtact    780
ctgagcgaac cgaaccctgaa agaatttgtt gaatctgcgg acttcatcct gatgctgggc    840
gttaaactga ccgactcttc taccggtgca ttcactcacc atctgaacga aaacaaaatg    900
attagcctga acatcgacga gggtaaaaat cttcaacgagc gtatccagaa cttcgacttc    960
gaaagcctga tcagctctct gctggacctg tccgaaatcg agtataaagg caaatacatt   1020
gacaaaaagc aagaagattt cgtaccatct aacgcactgc tgtcccagga tcgcctgtgg   1080
caggccgtgg agaacctgac ccagagcaat gaaaccatcg tggcggaaca aggtacgagc   1140
tttttcggcg cgtcttctat cttttctgaaa tccaaaagcc attttatcgg tcagccgctg   1200
tggggtagca ttggctatac tttcccggca gcgctgggct ctcagatcgc tgataaagaa   1260
tctcgtcatc tgctgttcat cggtgacggt tccctgcagc tgaccgtaca ggaactgggt   1320
ctggcaattc gtgaaaagat caacccgatt tgcttcatta ttaacaatga cggctacacc   1380
gttgagcgtg agatccacgg tccgaaccag tcttacaacg atatccctat gtggaactac   1440
tctaaactgc cggagtcctt cggcgcaact gaggaccgtg ttgtgtctaa aattgtgcgt   1500
accgaaaacg aatttgtgag cgtgatgaaa gaggcccagg ccgatccgaa ccgtatgtac   1560
tggatcgaac tgatcctggc gaaagaaggc gcaccgaagg tactgaagaa aatgggcaag   1620
```

```
ctgtttgctg aacagaataa atcctaa                                      1647
```

<210> SEQ ID NO 60
<211> LENGTH: 771
<212> TYPE: DNA
<213> ORGANISM: Drosophila melanogaster

<400> SEQUENCE: 60

```
atgtcgttta ctttgaccaa caagaacgtg attttcgttg ccggtctggg aggcattggt   60
ctggacacca gcaaggagct gctcaagcgc gatctgaaga acctggtgat cctcgaccgc  120
attgagaacc cggctgccat tgccgagctg aaggcaatca atccaaaggt gaccgtcacc  180
ttctacccct atgatgtgac cgtgcccatt gccgagacca ccagctgct gaagaccatc   240
ttcgcccagc tgaagaccgt cgatgtcctg atcaacggag ctggtatcct ggacgatcac  300
cagatcgagc gcaccattgc cgtcaactac actggcctgg tcaacaccac gacggccatt  360
ctggacttct gggacaagcg caagggcggt cccgtggta tcatctgcaa cattggatcc   420
gtcactggat tcaatgccat ctaccaggtg cccgtctact ccggcaccaa ggccgccgtg  480
gtcaacttca ccagctccct ggcgaaactg gcccccatta ccggcgtgac ggcttacact  540
gtgaaccccg gcatcacccg caccaccctg gtgcacacgt tcaactcctg gttggatgtt  600
gagcctcagg ttgccgagaa gctcctggct catcccaccc agccctcgtt ggcctgcgcc  660
gagaacttcg tcaaggctat cgagctgaac cagaacggag ccatctggaa actggacttg  720
ggcaccctgg aggccatcca gtggaccaag cactgggact ccggcatcta a           771
```

<210> SEQ ID NO 61
<211> LENGTH: 1476
<212> TYPE: DNA
<213> ORGANISM: Artificial Sequence
<220> FEATURE:
<223> OTHER INFORMATION: Ec_ilvC_coSc_Q110V

<400> SEQUENCE: 61

```
atggccaact attttaacac attaaatttg agacaacaat ggctcaact gggtaagtgc    60
agatttatgg aagggacga gtttgctgat ggtgcttctt atctgcaagg aaagaaagta   120
gtaattgttg gctgcggtgc tcagggtcta aaccaaggtt taaacatgag agattcaggt  180
ctggatattt cgtatgcatt gaggaaagag gcaattgcag aaaagagggc ctcctggcgt  240
aaagcgacgg aaaatggggtt caaagttggt acttacgaag aactgatccc tcaggcagat  300
ttagtgatta acctaacacc agataaggtt cactcagacg tagtaagaac agttcaaccg  360
ctgatgaagg atggggcagc tttaggttac tctcatggct ttaatatcgt gaagtgggc   420
gagcagatca gaaaagatat aacagtcgta atggttgcac aaagtgccc aggtacggaa   480
gtcagagagg agtacaagag gggttttggt gtacctacat tgatcgccgt acatcctgaa  540
aatgaccca aggtgaagg tatggcaatt gcgaaggcat gggcagccgc aaccggaggt   600
catagagcgg gtgtgttaga gagttctttc gtagctgagg tcaagagtga cttaatgggt  660
gaacaaacca ttctgtgcgg aatgttgcag gcagggtctt tactatgctt tgataaattg  720
gtcgaagagg gtacagatcc tgcctatgct gaaaagttga acaattggg tgggagaca   780
atcaccgagg cacttaaaca aggtggcata acattgatga tggatagact ttcaaatccg  840
gccaagctaa gagcctacgc cttatctgag caactaaaag agatcatggc accattattc  900
caaaagcaca tggacgatat tatctccggt gagttttcct caggaatgat ggcagattgg  960
```

```
gcaaacgatg ataaaaagtt attgacgtgg agagaagaaa ccggcaagac ggcattcgag    1020
acagccccac aatacgaagg taaaattggt gaacaagaat actttgataa gggagtattg    1080
atgatagcta tggtgaaggc aggggtagaa cttgcattcg aaactatggt tgactccggt    1140
atcattgaag aatctgcata ctatgagtct ttgcatgaat tgcctttgat agcaaatact    1200
attgcaagaa aaagacttta cgagatgaat gttgtcatat cagacactgc agaatatggt    1260
aattacttat ttagctacgc atgtgtcccg ttgttaaagc ccttcatggc cgagttacaa    1320
cctggtgatt tggggaaggc tattccggaa ggagcggttg acaatggcca actgagagac    1380
gtaaatgaag ctattcgttc acatgctata aacaggtgg gtaaaaagct gagaggatat    1440
atgaccgata tgaaaagaat tgcagtggca ggatga                             1476
```

<210> SEQ ID NO 62
<211> LENGTH: 1698
<212> TYPE: DNA
<213> ORGANISM: Artificial Sequence
<220> FEATURE:
<223> OTHER INFORMATION: Sc_ILV3 N20 deletion

<400> SEQUENCE: 62

```
atgaagaagc tcaacaagta ctcgtatatc atcactgaac ctaagggcca aggtgcgtcc      60
caggccatgc tttatgccac cggtttcaag aaggaagatt tcaagaagcc tcaagtcggg    120
gttggttcct gttggtggtc cggtaaccca tgtaacatgc atctattgga cttgaataac    180
agatgttctc aatccattga aaaagcgggt ttgaaagcta tgcagttcaa caccatcggt    240
gtttcagacg gtatctctat gggtactaaa ggtatgagat actcgttaca aagtagagaa    300
atcattgcag actccttga aaccatcatg atggcacaac actacgatgc taacatcgcc    360
atcccatcat gtgacaaaaa catgcccggt gtcatgatgg ccatgggtag acataacaga    420
ccttccatca tggtatatgg tggtactatc ttgcccggtc atccaacatg tggttcttcg    480
aagatctcta aaaacatcga tatcgtctct gcgttccaat cctacggtga atatatttcc    540
aagcaattca ctgaagaaga agagaagat gttgtggaac atgcatgccc aggtcctggt    600
tcttgtggtg gtatgtatac tgccaacaca atggcttctg ccgctgaagt gctaggttg    660 accattccaa actcctcttc cttcccagcc gtttccaagg agaagttagc tgagtgtgac    720
aacattggtg aatacatcaa gaagacaatg gaattgggta ttttacctcg tgatatcctc    780
acaaaagagg cttttgaaaa cgccattact tatgtcgttg caaccggtgg gtccactaat    840
gctgttttgc atttggtggc tgttgctcac tctgcgggtg tcaagttgtc accagatgat    900
ttccaaagaa tcagtgatac tacaccattg atcggtgact caaaccttc tggtaaatac    960 gtcatggccg atttgattaa cgttggtggt acccaatctg tgattaagta tctatatgaa    1020
aacaacatgt tgcacggtaa cacaatgact gttaccggtg acactttggc agaacgtgca    1080
aagaaagcac caagcctacc tgaaggacaa gagattatta gccactctc ccacccaatc    1140 aaggccaacg tcacttgca aattctgtac ggttcattgg caccaggtgg agctgtgggt    1200
aaaattaccg gtaaggaagg tacttacttc aagggtagag cacgtgtgtt cgaagaggaa    1260
ggtgccttta ttgaagcctt ggaaagaggt gaaatcaaga agggtgaaaa accgttgtt    1320 gttatcagat atgaaggtcc aagaggtgca ccaggtatgc ctgaaatgct aaagccttcc    1380
tctgctctga tgggttacgg tttgggtaaa gatgttgcat tgttgactga tggtagattc    1440 tctggtggt ctcacgggt cttaatcggc acattgttc ccgaagccgc tgaaggtggt    1500
cctatcgggt tggtcagaga cggcgatgag attatcattg atgctgataa taacaagatt    1560
```

```
gacctattag tctctgataa ggaaatggct caacgtaaac aaagttgggt tgcacctcca    1620
cctcgttaca caagaggtac tctatccaag tatgctaagt tggtttccaa cgcttccaac    1680
ggttgtgttt tagatgct                                                  1698
```

<210> SEQ ID NO 63
<211> LENGTH: 14056
<212> TYPE: DNA
<213> ORGANISM: Artificial Sequence
<220> FEATURE:
<223> OTHER INFORMATION: pGV2247

<400> SEQUENCE: 63

```
ttggatcata ctaagaaacc attattatca tgacattaac ctataaaaat aggcgtatca      60
cgaggcccct tcgtctcgcg cgtttcggtg atgacggtga aaacctctga cacatgcagc     120
tcccggagac ggtcacagct tgtctgtaag cggatgccgg gagcagacaa gcccgtcagg     180
gcgcgtcagc gggtgttggc gggtgtcggg gctggcttaa ctatgcggca tcagagcaga     240
ttgtactgag agtgcaccat accacagctt tcaattcaa ttcatcattt ttttttatt      300 cttttttttg atttcggttt ctttgaaatt ttttgattc ggtaatctcc gaacagaagg     360
aagaacgaag gaaggagcac agacttagat tggtatatat acgcatatgg caaattaaag     420
ccttcgagcg tcccaaaacc ttctcaagca aggttttcag tataatgtta catgcgtaca     480
cgcgtctgta cagaaaaaaa agaaaaattt gaaatataaa taacgttctt aatactaaca     540
taactataaa aaaataaata gggacctaga cttcaggttg tctaactcct tcctttttcgg    600 ttagagcgga tgtggggggga gggcgtgaat gtaagcgtga cataactaat tacatgactc    660
gacctaggtt atttagtaaa atcaatgacc attcggcctt caattttttcc tgccttcatt    720 tcatcaataa tatcattgat ttcttccagt ttgcgtgtcg caacaattgg ttttacctta    780
ccttctgctc caaattgaaa agcttctgcc aagtcaagtc ttgttccgac aagtgaacct    840
gcaacctcca ctccgtcaaa acaactgtt ggaactgata aagtcatctc agtattggga    900
agtgccacag caaccatttt gcccataggt ttcaaagaag caaccgcttg ttcaaaagca    960
atccttgcaa cagcacaaac tattgcactt tgcaccccta agccgccagt tatttttttta   1020 atttcatcaa ctggatttac atcaccagaa ttgataatca catcagctcc aatttttttta   1080 gctaaattta atttatcttg attaatatca acagcaatta cttttgctcc aaaaacattt    1140
ttagcatatt gaattgctaa atttccaagt cctccagcac caaaaattac ttgccaatca    1200
ccaggtttta ctcctgatac tttgattgct ttgtaagttg ttactccagc acaagtaatt    1260
gagctagctt caattgggtc aagtccgtca ggaactttga cagcataatc ggcaacaaca    1320
attgcttctt cagccattcc gccatcaact gaatatcctg cattttaac ttctcgacaa    1380 aaagtttcat taccagatac acagtattca cagtgaccac atccttcaaa gaaccaagcc    1440
actgaaaccc gatcaccaac ttgaagcgag cttacatcag ctccaatttc tttgacaatt    1500
ccaattcctt catgaccaag aacagtccct gctttgttgc cataatcacc tgctgcaacg    1560
tgcaaatcgg tatgacagac tccacaatac tccatgtcaa gcaaagcttc attaggtttg    1620
attgctcgaa gttccttttc aacaaggtcc gcataaccat ctggattgtg tcttactact    1680
gctgctttca ttggtaccta ttattgtatg ttatagtatt agttgcttgg tgttatgaaa    1740
gaaactaaga aaagaaaaat aaaataaaaa taaagattg agacaaggga agaaaagata     1800
caaaataaga attaattaca attgcgtttg ctataaatac gttttaaca atcaactctg    1860
```

```
gtaggaagat aatgcttttt tttttatat atgcttggtg ccacttgtca catacaattc    1920
tacaaccttc gacaaaaatc caaatgatag taagatcaaa gccagaaagc aatggagaaa    1980
aaaaattaat gaaccacgat gaaccaaatg atcaatacaa ccaagaaac  taccctagtg    2040 aggtgtatgc tgacttggta tcacacttca tgaattttgc atatggcaaa gtccacgaaa    2100
gtgggcttca gaaaaaggc  gtgcggtgtg tagatgtatc aattagtgga tgccagtttt    2160
ggaacgggat tccactttcc gcaagttggt gcacgtcgtt agtgacataa cgccgcgttc    2220
atctttggga agaagcagat gctgagcgag gaggtactat agagtaaaga accctttcta    2280
tacccgcagc cccatggtaa gtgacagtgc agtaataata tgaaccaatt tattttcgt     2340 tacataaaaa tgcttataaa actttaacta ataattagag attaaatcgc ggccgcaaaa    2400
gatccttagg atttattctg ttcagcaaac agcttgccca ttttcttcag taccttcggt    2460
gcgccttctt tcgccaggat cagttcgatc cagtacatac ggttcggatc ggcctgggcc    2520
tctttcatca cgctcacaaa ttcgttttcg gtacgcacaa ttttagacac aacacggtcc    2580
tcagttgcgc cgaaggactc cggcagttta gagtagttcc acatagggat atcgttgtaa    2640
gactggttcg gaccgtggat ctcacgctca acggtgtagc cgtcattgtt aataatgaag    2700
caaatcgggt tgatcttttc acgaattgcc agacccagtt cctgtacggt cagctgcagg    2760
gaaccgtcac cgatgaacag cagatgacga gattctttat cagcgatctg agagcccagc    2820
gctgccggga agtatagcc  aatgctaccc cacagcggct gaccgataaa atggcttttg    2880
gatttcagaa agatagaaga cgcgccgaaa aagctcgtac cttgttccgc cacgatggtt    2940
tcattgctct gggtcaggtt ctccacggcc tgccacaggc gatcctggga cagcagtgcg    3000
ttagatggta cgaaatcttc ttgcttttg  tcaatgtatt tgcctttata ctcgatttcg    3060
gacaggtcca gcagagagct gatcaggctt tcgaagtcga agttctggat acgctcgttg    3120
aagattttac cctcgtcgat gttcaggcta atcattttgt tttcgttcag atggtgagtg    3180
aatgcaccgg tagaagagtc ggtcagttta acgcccagca tcaggatgaa gtccgcagat    3240
tcaacaaatt ctttcaggtt cggttcgctc agagtaccgt tgtagatgcc caggaaagac    3300
ggcagagcct cgtcaacaga ggacttgccg aagttcaggg tggtaatcgg cagtttggtt    3360
ttgctgatga attgggtcac ggtcttctcc agaccaaaag aaatgatttc gtggccggtg    3420
atcacgattg gttctttgc  gttttcaga  gactcctgga ttttgttcag gatttcctgg    3480
tcgctagtgt tagaagtgga gttttctttc ttcagcggca ggctcggttt ttccgcttta    3540
gctgccgcaa catccacagg caggttgatg taaactggtt tgcgttcttt cagcagcgca    3600
gacagaacgc ggtcgatttc cacagtagcg ttctctgcag tcagcagcgt acgtgccgca    3660
gtcacaggtt catgcatttt catgaagtgt ttgaaatcgc cgtcagccag agtgtggtgg    3720
acgaatttac cttcgttctg aactttgctc gttgggctgc ctacgatctc caccaccggc    3780
aggttttcgg cgtaggagcc cgccagaccg ttgacggcgc tcagttcgcc aacaccgaaa    3840
gtggtcagaa atgccgcggc tttcttggta cgtgcataac catctgccat gtagcttgcg    3900
ttcagttcgt tagcgttacc cacccatttc atgtctttat gagagatgat ctgatccagg    3960
aactgcagat tgtaatcacc cggaacgccg aagatttctt cgatacccag ttcatgcaga    4020
cggtccagca gataatcacc aacagtatac atgtcgagct tgttttatat ttgttgtaaa    4080
aagtagataa ttacttcctt gatgatctgt aaaaagaga  aaagaaagc  atctaagaac    4140 ttgaaaaact acgaattaga aaagaccaaa tatgtatttc ttgcattgac caatttatgc    4200
aagtttatat atatgtaaat gtaagtttca cgaggttcta ctaaactaaa ccaccccctt    4260
```

```
ggttagaaga aaagagtgtg tgagaacagg ctgttgttgt cacacgattc ggacaattct    4320
gtttgaaaga gagagagtaa cagtacgatc gaacgaactt tgctctggag atcacagtgg    4380
gcatcatagc atgtggtact aaacccttc ccgccattcc agaaccttcg attgcttgtt    4440
acaaaacctg tgagccgtcg ctaggacctt gttgtgtgac gaaattggaa gctgcaatca    4500
ataggaagac aggaagtcga gcgtgtctgg gttttttcag ttttgttctt tttgcaaaca    4560
aatcacgagc gacggtaatt tctttctcga taagaggcca cgtgctttat gagggtaaca    4620
tcaattcaag aaggagggaa acacttcctt tttctggccc tgataatagt atgagggtga    4680
agccaaaata aaggattcgc gcccaaatcg gcatctttaa atgcaggtat gcgatagttc    4740
ctcactcttt ccttactcac gagtaattct tgcaaatgcc tattatgcag atgttataat    4800
atctgtgcgt cttgagttga gcctagaatt cttagaaaaa ctcatcgagc atcaaatgaa    4860
actgcaattt attcatatca ggattatcaa taccatattt ttgaaaaagc cgtttctgta    4920
atgaaggaga aaactcaccg aggcagttcc ataggatggc aagatcctgg tatcggtctg    4980
cgatcccgac tcgtccaaca tcaatacaac ctattaattt cccctcgtca aaataaggt    5040 tatcaagtga gaaatcacca tgagtgacga ctgaatccgg tgagaatggc aaaagcttat    5100
gcatttcttt ccagacttgt tcaacaggcc agccattacg ctcgtcatca aaatcactcg    5160
cgtcaaccaa accgttattc attcgtgatt gcgcctgagc gaggcgaaat acgcgatcgc    5220
tgttaaaagg acaattacaa acaggaatcg aatgcaaccg gcgcaggaac actgccagcg    5280
catcaacaat attttcacct gaatcaggat attcttctaa tacctggaat gctgttttgc    5340
cggggatcgc agtggtgagt aaccatgcat catcaggagt acgacaaaa tgcttgatgg    5400 tcggaagagg cataaattcc gtcagccagt ttagtctgac catctcatct gcaacatcat    5460
tggcaacgct accttgcca tgtttcagaa acaactctgg cgcatcgggc ttcccataca    5520
atcgatagat tgtcgcacct gattgcccga cattatcgcg agcccattta tacccatata    5580
aatcagcatc catgttggaa tttaatcgcg gcctcgaaac gtgagtcttt tccttaccca    5640
tactagtttt tagtttatgt atgtgttttt tgtagttata gatttaagca agaaaagaat    5700
acaaacaaaa aattgaaaaa gattgattta gaattaaaaa gaaaaatatt tacgtaagaa    5760
gggaaaatag taaatgttgc aagttcacta aactcctaaa ttatgctgcc ctttatattc    5820
cctgttacag cagccgagcc aaaggtatat aggctccttt gcattagcat gcgtaacaaa    5880
ccacctgtca gtttcaaccg aggtggtatc cgagagaatt gtgtgattgc tttaattaat    5940
ttcggagaat ctcacatgcc actgaagatt aaaaactgga tgccagaaaa ggggtgtcca    6000
ggtgtaacat caatagagga agctgaaaag tcttagaacg ggtaatcttc caccaacctg    6060
atgggttcct agatataatc tcgaagggaa taagtagggt gataccgcag aagtgtctga    6120
atgtattaag gtcctcacag tttaaatccc gctcacacta acgtaggatt attataactc    6180
aaaaaaatgg cattattcta agtaagttaa atatccgtaa tctttaaaca gcggccgcgg    6240
atcttcatcc tgccactgca attctttca tatcggtcat atatcctctc agcttttac    6300 ccacctgttc tatagcatgt gaacgaatag cttcatttac gtctctcagt tggccattgt    6360
caaccgctcc ttccggaata gccttcccca aatcaccagg ttgtaactcg gccatgaagg    6420
gctctaacaa cggacacac gcgtagctaa ataagtaatt accatattct gcagtgtctg    6480
atatgacaac attcatctcg taaagtcttt ttccttgcaat agtatttgct atcaaaggca    6540
attcatgcaa agactcatag tatgcagatt cttcaatgat accggagtca accatagttt    6600
```

```
cgaatgcaag ttctacccct gccttcacca tagctatcat caatactccc ttatcaaagt    6660
attcttgttc accaatttta ccttcgtatt gtggggctgt ctcgaatgcc gtcttgccgg    6720
tttcttctct ccacgtcaat aactttttat catcgtttgc ccaatctgcc atcattcctg    6780
aggaaaactc accggagata atatcgtcca tgtgcttttg gaataatggt gccatgatct    6840
cttttagttg ctcagataag gcgtaggctc ttagcttggc cggatttgaa agtctatcca    6900
tcatcaatgt tatgccacct tgtttaagtg cctcggtgat tgtctcccaa ccaaattgta    6960 tcaactttc agcataggca ggatctgtac cctcttcgac caatttatca aagcatagta    7020
aagaccctgc ctgcaacatt ccgcacagaa tggtttgttc acccattaag tcactcttga    7080
cctcagctac gaaagaactc tctaacacac ccgctctatg acctccggtt gcggctgccc    7140
atgccttcgc tattgccata ccttcacgtt tggggtcatt ttcaggatgt acggcgatca    7200
atgtaggtac accaaaaccc ctcttgtact cctctctgac ttccgtacct gggcactttg    7260
gcgcaaccat tacgactgtt ataccttttc tgatctgctc gcccacttca acgatattaa    7320
agccatgaga gtaacctaaa gctgccccat ccttcatcag cggttgaact gttcttacta    7380
cgtctgagtg aaccttatct ggtgttaggt taatcactaa atctgcctga gggatcagtt    7440
cttcgtaagt accaactttg aacccatttt ccgtcgcttt acgccaatcg gcatcctttt    7500
ctgcaataga ctcttttcctc aatgcatacg aaatatccag acctgaatct ctcatgttta    7560
aaccttggtt tagaccctga gcaccgcagc caacaattac tactttcttt ccttgcagat    7620
aagaagcacc atcagcaaac tcgtcccttc ccataaatct gcacttaccc agttgagcca    7680
attgttgtct caaatttaat gtgttaaaat agttggccat gtcgagtcga aactaagttc    7740
tggtgtttta aaactaaaaa aaagactaac tataaaagta gaatttaaga agtttaagaa    7800
atagatttac agaattacaa tcaataccta ccgtctttat atacttatta gtcaagtagg    7860
ggaataattt cagggaactg gtttcaacct ttttttcag cttttttccaa atcagagaga    7920 gcagaaggta atagaaggtg taagaaaatg agatagatac atgcgtgggt caattgcctt    7980
gtgtcatcat ttactccagg caggttgcat cactccattg aggttgtgcc cgttttttgc    8040
ctgtttgtgc ccctgttctc tgtagttgcg ctaagagaat ggacctatga actgatggtt    8100
ggtgaagaaa acaatatttt ggtgctggga ttcttttttt ttctggatgc cagcttaaaa    8160
agcgggctcc attatattta gtggatgcca ggaataaact gttcacccag acacctacga    8220
tgttatatat tctgtgtaac ccgcccccta ttttgggcat gtacgggtta cagcagaatt    8280
aaaaggctaa ttttttgact aaataaagtt aggaaaatca ctactattaa ttatttacgt    8340
attctttgaa atggcgagta ttgataatga taaactggat ccgcggccgc ttacagatca    8400
gtaacacacc cttccgatgc aggacggggt aatttagcga attttgccaa aactcccctg    8460
gtggctttcg gagttggctt ctgataatta gctcttctct ttgcgatttc ttcatcggaa    8520
actttcaggg atatagagtt gttgactgca tctatctcta ttatatcgtc atcttcaact    8580
aagccgatta gtccaccctc aacggcttca ggcacaatat ggccgacaac aaaaccgtga    8640
gtgccaccgg agaatctacc atccgtaatt aacgcgcaac ttttccctaa acccgcacca    8700
attaatgctg atgtaggctt cagcatttcg ggcataccag gtccgccgac gggacctata    8760
ttcctaatta ccgctacatc tccagcatgc aaacgaccag attctatgcc gtcgataaaa    8820
tgttgttcac catcaaagac tctggcagtg cctttgaaga actctccttc tttaccgcta    8880 attttttgcta cggaaccccc ttgagctaaa ttaccgtaca gaatctgcaa gtggccggtg    8940
gccttgatag gattctttag tggcctcatg atatcttgtg agtcgaaatc caagtctagg    9000
```

```
gcagtctcga cattctcggc taatgttttta cccgtcacag taaggcagtc accatgcaat    9060
tttccttcct ttagaaggta cttaagcact gctggcaagc ctccaatttt atgcaaatct    9120
tccatcatat atttacctga aggtttaaaa tcacctagta ctggagtaat gtcactaatt    9180
ctttggaagt catcctgagt tatttcgaca cctatcgcgt tagccattgc aataatatgc    9240
aagacagcat tagtactacc ccccaagacc atcacaatgg taatagcgtt ctcgaacgcc    9300
tccttagtca ttatatcact aggcttgatg tcttttttcca aaagattctt aatggctaat    9360
ccaatctcat cacattcttc ttgttttttct tgagatactg cagggttcga agaagaatac    9420
ggcaatgaca tacctagtgt ttcgatagcg gcagctaagg tattagctgt gtacatcccc    9480
ccacatgccc cttgaccagg aatagcatta caaataacac cgtgataatc ttcatcagag    9540
atattgccgg taattttctg gcctagagat tcaaaagccg atacgatgtt caatttctca    9600
cctttatatt caccgtgttc tattgttcct ccatacacca taatgcttgg cctattaagt    9660
cttgccatac caataataga acctggcata ttttttgtcac aacctgggat ggctacaatt    9720
gcatcatagt attcagcgcc agcgttggtt tcaatagagt cagctataac ttctctggaa    9780
acaagggagt atctcattcc caactttcca tttgctatcc catcagaaac tcctatcgta    9840
tgaaattgta agccgatcag accatctgtc tgatttactg agcttttaat ctttgatcca    9900
agggttccta aatgcatgtt gcatggattt ccatcccagt ccatcgacac tatacccact    9960
tgagctttct tgaaatcttc gtctttaaac ccgatgccgt aatacattgc ctgtgtggcg   10020
ggttgtgtgg gatcttgtgt caacgttttg ctgtacttat tcagttcaac agattcaact   10080
ttgccgttat acttaaactc catgtcgaca aacttagatt agattgctat gctttctttc   10140
taatgagcaa gaagtaaaaa aagttgtaat agaacaagaa aaatgaaact gaaacttgag   10200
aaattgaaga ccgtttatta acttaaatat caatgggagg tcatcgaaag agaaaaaaat   10260
caaaaaaaaa attttcaaga aaagaaacg tgataaaaat ttttattgcc tttttcgacg   10320
aagaaaaaga aacgaggcgg tctcttttttt cttttccaaa cctttagtac gggtaattaa   10380
cgacacccta gaggaagaaa gaggggaaat ttagtatgct gtgcttgggt gttttgaagt   10440
ggtacggcga tgcgcggagt ccgagaaaat ctggaagagt aaaaaaggag tagaaacatt   10500
ttgaagctat gagctccagc ttttgttccc tttagtgagg gttaattgcg cgcttggcgt   10560
aatcatggtc atagctgttt cctgtgtgaa attgttatcc gctcacaatt ccacacaaca   10620
taggagccgg aagcataaag tgtaaagcct ggggtgccta atgagtgagg taactcacat   10680
taattgcgtt gcgctcactg cccgcttttcc agtcgggaaa cctgtcgtgc cagctgcatt   10740
aatgaatcgg ccaacgcgcg gggagaggcg gttttgcgtat gggcgctct ccgcttcct   10800
cgctcactga ctcgctgcgc tcggtcgttc ggctgcggcg agcggtatca gctcactcaa   10860
aggcggtaat acggttatcc acagaatcag gggataacgc aggaaagaac atgtgagcaa   10920
aaggccagca aaaggccagg aaccgtaaaa aggccgcgtt gctggcgttt ttccataggc   10980
tccgccccc tgacgagcat cacaaaaatc gacgctcaag tcagaggtgg cgaaacccga   11040
caggactata aagataccag gcgtttcccc ctggaagctc cctcgtgcgc tctcctgttc   11100
cgaccctgcc gcttaccgga tacctgtccg cctttctccc ttcgggaagc gtggcgcttt   11160
ctcatagctc acgctgtagg tatctcagtt cggtgtaggt cgttcgctcc aagctgggct   11220
gtgtgcacga accccccgtt cagcccgacc gctgcgcctt atccggtaac tatcgtcttg   11280
agtccaaccc ggtaagacac gacttatcgc cactggcagc agccactggt aacaggatta   11340
```

```
gcagagcgag gtatgtaggc ggtgctacag agttcttgaa gtggtggcct aactacggct    11400
acactagaag gacagtattt ggtatctgcg ctctgctgaa gccagttacc ttcggaaaaa    11460
gagttggtag ctcttgatcc ggcaaacaaa ccaccgctgg tagcggtggt ttttttgttt    11520
gcaagcagca gattacgcgc agaaaaaaag gatctcaaga agatcctttg atcttttcta    11580
cggggtctga cgctcagtgg aacgaaaact cacgttaagg gattttggtc atgagattat    11640
caaaaaggat cttcacctag atccttttaa attaaaaatg aagttttaaa tcaatctaaa    11700
gtatatatga gtaaacttgg tctgacagtt accaatgctt aatcagtgag gcacctatct    11760
cagcgatctg tctatttcgt tcatccatag ttgcctgact ccccgtcgtg tagataacta    11820
cgatacggga gggcttacca tctggcccca gtgctgcaat gataccgcga acccacgct     11880 caccggctcc agatttatca gcaataaacc agccagccgg aagggccgag cgcagaagtg    11940
gtcctgcaac tttatccgcc tccatccagt ctattaattg ttgccgggaa gctagagtaa    12000
gtagttcgcc agttaatagt ttgcgcaacg ttgttgccat tgctacaggc atcgtggtgt    12060
cacgctcgtc gtttggtatg gcttcattca gctccggttc ccaacgatca aggcgagtta    12120
catgatcccc catgttgtgc aaaaaagcgg ttagctcctt cggtcctccg atcgttgtca    12180
gaagtaagtt ggccgcagtg ttatcactca tggttatggc agcactgcat aattctctta    12240
ctgtcatgcc atccgtaaga tgcttttctg tgactggtga gtactcaacc aagtcattct    12300
gagaatagtg tatgcggcga ccgagttgct cttgcccggc gtcaatacgg gataataccg    12360
cgccacatag cagaacttta aaagtgctca tcattggaaa acgttcttcg gggcgaaaac    12420
tctcaaggat cttaccgctg ttgagatcca gttcgatgta acccactcgt gcacccaact    12480
gatcttcagc atcttttact ttcaccagcg tttctgggtg agcaaaaaca ggaaggcaaa    12540
atgccgcaaa aaagggaata agggcgacac ggaaatgttg aatactcata ctcttccttt    12600
ttcaatatta ttgaagcatt tatcagggtt attgtctcat gagcggatac atatttgaat    12660
gtatttagaa aaataaacaa ataggggttc cgcgcacatt tccccgaaaa gtgccacctg    12720
aacgaagcat ctgtgcttca ttttgtagaa caaaaatgca acgcgagagc gctaattttt    12780
caaacaaaga atctgagctg cattttaca gaacagaaat gcaacgcgaa agcgctattt     12840
taccaacgaa gaatctgtgc ttcattttg taaaacaaaa atgcaacgcg agagcgctaa     12900
tttttcaaac aaagaatctg agctgcattt ttacagaaca gaaatgcaac gcgagagcgc    12960
tattttacca acaaagaatc tatacttctt ttttgttcta caaaaatgca tcccgagagc    13020 gctattttc taacaaagca tcttagatta ctttttttct cctttgtgcg ctctataatg    13080
cagtctcttg ataactttt gcactgtagg tccgttaagg ttagaagaag gctactttgg    13140
tgtctatttt ctcttccata aaaaaagcct gactccactt cccgcgttta ctgattacta    13200
gcgaagctgc gggtgcattt tttcaagata aaggcatccc cgattatatt ctataccgat    13260
gtggattgcg catactttgt gaacagaaag tgatagcgtt gatgattctt cattggtcag    13320
aaaattatga acggtttctt ctattttgtc tctatatact acgtatagga atgtttaca     13380 ttttcgtatt gttttcgatt cactctatga atagttctta ctacaatttt tttgtctaaa    13440
gagtaatact agagataaac ataaaaaatg tagaggtcga gtttagatgc aagttcaagg    13500
agcgaaaggt ggatgggtag gttatatagg gatatagcac agagatatat agcaaagaga    13560 tactttgag caatgtttgt ggaagcggta ttcgcaatat tttagtagct cgttacagtc      13620
cggtgcgttt tggttttttt gaagtgcgt cttcagagcg cttttggttt tcaaaagcgc      13680
tctgaagttc ctatactttc tagagaatag gaacttcgga ataggaactt caaagcgttt    13740
```

-continued

```
ccgaaaacga gcgcttccga aaatgcaacg cgagctgcgc acatacagct cactgttcac    13800
gtcgcaccta tatctgcgtg ttgcctgtat atatatac atgagaagaa cggcatagtg    13860
cgtgtttatg cttaaatgcg tacttatatg cgtctattta tgtaggatga aaggtagtct    13920
agtacctcct gtgatattat cccattccat gcggggtatc gtatgcttcc ttcagcacta    13980 cccttagct gttctatatg ctgccactcc tcaattggat tagtctcatc cttcaatgct    14040
atcatttcct tgata                                                     14056
```

<210> SEQ ID NO 64
<211> LENGTH: 1476
<212> TYPE: DNA
<213> ORGANISM: Artificial Sequence
<220> FEATURE:
<223> OTHER INFORMATION: Ec_ilvC_coSc_P2D1-A1

<400> SEQUENCE: 64

```
atggccaact attttaacac attaaatttg agacaacaat ggctcaact gggtaagtgc       60 agatttatgg gaagggacga gtttgctgat ggtgcttctt atctgcaagg aaagaaagta      120
gtaattgttg gctgcggtgc tcagggtcta accaaggtt taaacatgag agattccaggt     180 ctggatattt cgtatgcatt gaggaaagag tctattgcag aaaaggatgc cgattggcgt      240
aaagcgacgg aaaatgggtt caaagttggt acttacgaag aactgatccc tcaggcagat     300
ttagtgatta acctaacacc agataaggtt cactcagacg tagtaagaac agttcaaccg    360
ctgatgaagg atggggcagc tttaggttac tctcatggct ttaatatcgt tgaagtgggc   420
gagcagatca gaaaaggtat aacagtcgta atggttgcgc caaagtgccc aggtacggaa    480
gtcagagagg agtacaagag gggttttggt gtacctacat tgatcgccgt acatcctgaa    540
aatgacccca acgtgaagg tatggcaata gcgaaggcat gggcagccgc aaccggaggt    600
catagagcgg gtgtgttaga gagttctttc gtagctgagg tcaagagtga cttaatgggt    660
gaacaaacca ttctgtgcgg aatgttgcag gcagggtctt tactatgctt tgataaattg    720
gtcgaagagg gtacagatcc tgcctatgct gaaaagttga tacaatttgg ttgggagaca    780
atcaccgagg cacttaaaca aggtggcata acattgatga tggatagact ttcaaatccg    840
gccaagctaa gagcctacgc cttatctgag caactaaaag agatcatggc accattattc    900
caaaagcaca tggacgatat tatctccggt gagttttcct caggaatgat ggcagattgg    960
gcaaacgatg ataaaaagtt attgacgtgg agagaagaaa ccggcaagac ggcattcgag    1020
acagccccac aatacgaagg taaaattggt gaacaagaat actttgataa gggagtattg    1080
atgatagcta tggtgaaggc aggggtagaa cttgcattcg aaactatggt tgactccggt    1140
atcattgaag aatctgcata ctatgagtct ttgcatgaat tgcctttgat agcaaatact    1200
attgcaagaa aaagacttta cgagatgaat gttgtcatat cagacactgc agaatatggt    1260
aattacttat ttagctacgc gtgtgtcccg ttgttagagc ccttcatggc cgagttacaa    1320
cctggtgatt tggggaaggc tattccggaa ggagcggttg acaatggcca actgagagac    1380
gtaaatgaag ctattcgttc acatgctata gaacaggtgg gtaaaaagct gagaggatat    1440
atgaccgata tgaaaagaat tgcagtggca ggatga                              1476
```

<210> SEQ ID NO 65
<211> LENGTH: 1713
<212> TYPE: DNA
<213> ORGANISM: Artificial Sequence
<220> FEATURE:

<223> OTHER INFORMATION: Ll_ilvD_coSc

<400> SEQUENCE: 65

```
atggagttta agtataacgg caaagttgaa tctgttgaac tgaataagta cagcaaaacg      60
ttgacacaag atcccacaca acccgccaca caggcaatgt attacggcat cgggtttaaa     120
gacgaagatt tcaagaaagc tcaagtgggt atagtgtcga tggactggga tggaaatcca     180
tgcaacatgc atttaggaac ccttggatca aagattaaaa gctcagtaaa tcagacagat     240
ggtctgatcg gcttacaatt tcatacgata ggagtttctg atgggatagc aaatggaaag     300
ttgggaatga gatactccct tgtttccaga gaagttatag ctgactctat tgaaaccaac     360
gctggcgctg aatactatga tgcaattgta gccatcccag ttgtgacaa aaatatgcca      420
ggttctatta ttggtatggc aagacttaat aggccaagca ttatggtgta tggaggaaca     480
atagaacacg gtgaatataa aggtgagaaa ttgaacatcg tatcggcttt tgaatctcta     540
ggccagaaaa ttaccggcaa tatctctgat gaagattatc acggtgttat ttgtaatgct     600
attcctggtc aaggggcatg tgggggatg tacacagcta ataccttagc tgccgctatc      660
gaaacactag gtatgtcatt gccgtattct tcttcgaacc ctgcagtatc tcaagaaaaa     720
caagaagaat gtgatgagat tggattagcc attaagaatc ttttggaaaa agacatcaag     780
cctagtgata taatgactaa ggaggcgttc gagaacgcta ttaccattgt gatggtcttg     840
gggggtagta ctaatgctgt cttgcatatt attgcaatgg ctaacgcgat aggtgtcgaa     900
ataactcagg atgacttcca agaattagt gacattactc cagtactagg tgatttaaa      960
ccttcaggta aatatatgat ggaagatttg cataaaattg gaggcttgcc agcagtgctt    1020
aagtaccttc taaggaagg aaaattgcat ggtgactgcc ttactgtgac gggtaaaaca     1080
ttagccgaga atgtcgagac tgccctagac ttggatttcg actcacaaga tatcatgagg    1140
ccactaaaga atcctatcaa ggccaccggc cacttgcaga ttctgtacgg taatttagct    1200
caaggggggtt ccgtagcaaa aattagcggt aaagaaggag agttcttcaa aggcactgcc    1260
agagtctttg atggtgaaca acatttttatc gacggcatag aatctggtcg tttgcatgct    1320
ggagatgtag cggtaattag gaatataggt cccgtcggcg gacctggtat gcccgaaatg    1380
ctgaagccta catcagcatt aattggtgcg ggtttaggga aaagttgcgc gttaattacg    1440
gatggtagat tctccggtgg cactcacggt tttgttgtcg gccatattgt gcctgaagcc    1500
gttgagggtg gactaatcgg cttagttgaa gatgacgata atagagagt agatgcagtc     1560
aacaactcta tatccctgaa agtttccgat gaagaaatcg caaagagaag agctaattat    1620
cagaagccaa ctccgaaagc caccagggga gttttggcaa aattcgctaa attaacccgt    1680
cctgcatcgg aagggtgtgt tactgatctg taa                                 1713
```

<210> SEQ ID NO 66
<211> LENGTH: 1023
<212> TYPE: DNA
<213> ORGANISM: Lactococcus lactis

<400> SEQUENCE: 66

```
ttatttagta aaatcaatga ccattcggcc ttcaattttt cctgccttca tttcatcaat      60
aatatcattg atttcttcca gtttgcgtgt cgcaacaatt ggttttacct taccttctgc     120
tccaaattga aaagcttctg ccaagtcaag tcttgttccg acaagtgaac ctgcaacctc     180
cactccgtca aaaacaactg ttggaactga taaagtcatc tcagtattgg aagtgccac      240
agcaaccatt ttgcccatag gtttcaaaga agcaaccgct tgttcaaaag caatccttgc     300
```

```
aacagcacaa actattgcac tttgcaccc  taagccgcca gttatttttt taatttcatc      360
aactggattt acatcaccag aattgataat cacatcagct ccaattttt  tagctaaatt      420 taatttatct tgattaatat caacagcaat tactttgct  ccaaaaacat ttttagcata      480
ttgaattgct aaatttccaa gtcctccagc accaaaaatt acttgccaat caccaggttt      540
tactcctgat actttgattg ctttgtaagt tgttactcca gcacaagtaa ttgagctagc      600
ttcaattggg tcaagtccgt caggaacttt gacagcataa tcggcaacaa caattgcttc      660
ttcagccatt ccgccatcaa ctgaatatcc tgcatttta  acttctcgac aaaaagtttc      720
attaccagat acacagtatt cacagtgacc acatccttca agaaccaag  ccactgaaac      780 ccgatcacca acttgaagcg agcttacatc agctccaatt tctttgacaa ttccaattcc      840
ttcatgacca agaacagtcc ctgctttgtt gccataatca cctgctgcaa cgtgcaaatc      900
ggtatgacag actccacaat actccatgtc aagcaaagct tcattaggtt tgattgctcg      960
aagttccttt tcaacaaggt ccgcataacc atctggattg tgtcttacta ctgctgcttt     1020
cat                                                                   1023

<210> SEQ ID NO 67
<211> LENGTH: 13805
<212> TYPE: DNA
<213> ORGANISM: Artificial Sequence
<220> FEATURE:
<223> OTHER INFORMATION: pGV2082

<400> SEQUENCE: 67
ttggatcata ctaagaaacc attattatca tgacattaac ctataaaaat aggcgtatca       60
cgaggccctt tcgtctcgcg cgtttcggtg atgacggtga aacctctga  cacatgcagc      120 tcccggagac ggtcacagct tgtctgtaag cggatgccgg gagcagacaa gcccgtcagg      180
gcgcgtcagc gggtgttggc gggtgtcggg gctggcttaa ctatgcggca tcagagcaga      240
ttgtactgag agtgcaccat accacagctt ttcaattcaa ttcatcattt tttttttatt      300
cttttttttg atttcggttt ctttgaaatt ttttgattc  ggtaatctcc gaacagaagg      360
aagaacgaag gaaggagcac agacttagat tggtatatat acgcatatgg caaattaaag      420
ccttcgagcg tcccaaaacc ttctcaagca aggttttcag tataatgtta catgcgtaca      480
cgcgtctgta cagaaaaaaa agaaaaattt gaaatataaa taacgttctt aatactaaca      540
taactataaa aaaataaata gggacctaga cttcaggttg tctaactcct tccttttcgg      600
ttagagcgga tgtggggggga gggcgtgaat gtaagcgtga cataactaat tacatgactc      660
gagcggccgc ttagatgccg gagtcccagt gcttggtcca ctggatggcc tccagggtgc      720
ccaagtccag tttccagatg gctccgttct ggttcagctc gatagccttg acgaagttct      780
cggcgcaggc caacgagggc tgggtgggat gagccaggag cttctcggca acctgaggct      840
caacatccaa ccaggagttg aacgtgtgca ccagggtggt gcgggtgatg ccggggttca      900
cagtgtaagc cgtcacgccg gtaatggggg ccagtttcgc cagggagctg gtgaagttga      960
ccacggcggc cttggtgccg gagtagacgg gcacctggta gatggcattg aatccagtga     1020
cggatccaat gttgcagatg ataccaccgg gaccgcccct gcgcttgtcc cagaagtcca     1080
gaatggccgt cgtggtgttg accaggccag tgtagttgac ggcaatggtg cgctcgatct     1140
ggtgatcgtc caggatacca gctccgttga tcaggacatc gacggtcttc agctgggcga     1200
agatggtctt cagcagcttg gtggtctcgg caatgggcac ggtcacatca tagggggtaga     1260
```

```
aggtgacggt cacctttgga ttgattgcct tcagctcggc aatggcagcc gggttctcaa    1320
tgcggtcgag gatcaccagg ttcttcagat cgcgcttgag cagctccttg ctggtgtcca    1380
gaccaatgcc tcccagaccg gcaacgaaaa tcacgttctt gttggtcaaa gtaaacgaca    1440
tggtacctat tattgtatgt tatagtatta gttgcttggt gttatgaaag aaactaagaa    1500
aagaaaaata aataaaaat aaaagattga dacaagggaa gaaagatac aaaataagaa    1560
```

```
agcgttaccc acccatttca tgtctttatg agagatgatc tgatccagga actgcagatt    3720
gtaatcaccc ggaacgccga agatttcttc gatacccagt tcatgcagac ggtccagcag    3780
ataatcacca acagtataca tgtcgagctt gttttatatt tgttgtaaaa agtagataat    3840
tacttccttg atgatctgta aaaagagaaa aagaaagca tctaagaact tgaaaaacta    3900
cgaattagaa aagaccaaat atgtatttct tgcattgacc aatttatgca agtttatata    3960
tatgtaaatg taagtttcac gaggttctac taaactaaac cacccccttg gttagaagaa    4020
aagagtgtgt gagaacaggc tgttgttgtc acacgattcg gacaattctg tttgaaagag    4080
agagagtaac agtacgatcg aacgaacttt gctctggaga tcacagtggg catcatagca    4140
tgtggtacta aaccctttcc cgccattcca gaaccttcga ttgcttgtta caaaacctgt    4200
gagccgtcgc taggaccttg ttgtgtgacg aaattggaag ctgcaatcaa taggaagaca    4260
ggaagtcgag cgtgtctggg ttttttcagt tttgttcttt ttgcaaacaa atcacgagcg    4320
acggtaattt cttctcgat aagaggccac gtgcttatg agggtaacat caattcaaga    4380
aggagggaaa cacttccttt ttctggccct gataatagta tgagggtgaa gccaaaataa    4440
aggattcgcg cccaaatcgg catctttaaa tgcaggtatg cgatagttcc tcactctttc    4500
cttactcacg agtaattctt gcaaatgcct attatgcaga tgttataata tctgtgcgtc    4560
ttgagttgag cctagaattc ttagaaaaac tcatcgagca tcaaatgaaa ctgcaattta    4620
ttcatatcag gattatcaat accatatttt tgaaaagcc gtttctgtaa tgaaggagaa    4680
aactcaccga gcagttcca taggatggca agatcctggt atcggtctgc gatcccgact    4740
cgtccaacat caatacaacc tattaatttc ccctcgtcaa aaataaggtt atcaagtgag    4800
aaatcaccat gagtgacgac tgaatccggt gagaatggca aaagcttatg catttctttc    4860
cagacttgtt caacaggcca gccattacgc tcgtcatcaa aatcactcgc gtcaaccaaa    4920
ccgttattca ttcgtgattg cgcctgagcg aggcgaaata cgcgatcgct gttaaaagga    4980
caattacaaa caggaatcga atgcaaccgg cgcaggaaca ctgccagcgc atcaacaata    5040
ttttcacctg aatcaggata ttcttctaat acctggaatg ctgttttgcc ggggatcgca    5100
gtggtgagta accatgcatc atcaggagta cggacaaaat gcttgatggt cggaagaggc    5160
ataaattccg tcagccagtt tagtctgacc atctcatctg caacatcatt ggcaacgcta    5220
cctttgccat gtttcagaaa caactctggc gcatcgggct tcccatacaa tcgatagatt    5280
gtcgcacctg attgcccgac attatcgcga gcccatttat acccatataa atcagcatcc    5340
atgttggaat ttaatcgcgg cctcgaaacg tgagtctttt ccttacccat actagttttt    5400
agtttatgta tgtgttttt gtagttatag atttaagcaa gaaaagaata caaacaaaaa    5460
attgaaaaag attgatttag aattaaaaag aaaatatttt acgtaagaag ggaaaatagt    5520
aaatgttgca agttcactaa actcctaaat tatgctgccc tttatattcc ctgttacagc    5580
agccgagcca aagtatata ggctccttg cattagcatg cgtaacaaac cacctgtcag    5640
tttcaaccga ggtggtatcc gagagaattg tgtgattgct ttaattaatt tcggagaatc    5700
tcacatgcca ctgaagatta aaactggat gccagaaaag gggtgtccag gtgtaacatc    5760
aatagaggaa gctgaaaagt cttagaacgg gtaatcttcc accaacctga tgggttccta    5820
gatataatct cgaagggaat aagtagggtg ataccgcaga agtgtctgaa tgtattaagg    5880
tcctcacagt ttaaatcccg ctcacactaa cgtaggatta ttataactca aaaaaatggc    5940
attattctaa gtaagttaaa tatccgtaat ctttaaacag cggccgcgga tcttcatcct    6000
```

```
gccactgcaa ttcttttcat atcggtcata tatcctctca gcttttacc cacctgttct    6060 atagcatgtg aacgaatagc ttcatttacg tctctcagtt ggccattgtc aaccgctcct    6120
tccggaatag ccttccccaa atcaccaggt tgtaactcgg ccatgaaggg ctttaacaac    6180
gggacacatg cgtagctaaa taagtaatta ccatattctg cagtgtctga tatgacaaca    6240
ttcatctcgt aaagtctttt tcttgcaata gtatttgcta tcaaaggcaa ttcatgcaaa    6300
gactcatagt atgcagattc ttcaatgata ccggagtcaa ccatagtttc gaatgcaagt    6360 tctaccctg ccttcaccat agctatcatc aatactccct tatcaaagta ttcttgttca    6420
ccaattttac cttcgtattg tggggctgtc tcgaatgccg tcttgccggt ttcttctctc    6480
cacgtcaata acttttatc atcgtttgcc caatctgcca tcattcctga ggaaaactca    6540
ccggagataa tatcgtccat gtgcttttgg aataatggtg ccatgatctc ttttagttgc    6600
tcagataagg cgtaggctct tagcttggcc ggatttgaaa gtctatccat catcaatgtt    6660
atgccacctt gtttaagtgc ctcggtgatt gtctcccaac caaattgtat caacttttca    6720
gcataggcag gatctgtacc ctcttcgacc aatttatcaa agcatagtaa agaccctgcc    6780
tgcaacattc cgcacagaat ggtttgttca cccattaagt cactcttgac ctcagctacg    6840
aaagaactct ctaacacacc cgctctatga cctccggttg cggctgccca tgccttcgca    6900
attgccatac cttcaccttt ggggtcattt tcaggatgta cggcgatcaa tgtaggtaca    6960
ccaaaacccc tctctgtactc ctctctgact tccgtacctg ggcactttgg tgcaaccatt    7020
acgactgtta tatcttttct gatctgctcg cccacttcaa cgatattaaa gccatgagag    7080
taacctaaag ctgccccatc cttcatcagc ggttgaactg ttcttactac gtctgagtga    7140
accttatctg gtgttaggtt aatcactaaa tctgcctgag ggatcagttc ttcgtaagta    7200
ccaactttga acccatttc cgtcgcttta cgccaggagg ccctcttttc tgcaattgcc    7260
tctttcctca atgcatacga aatatccaga cctgaatctc tcatgtttaa accttggttt    7320
agaccctgag caccgcagcc aacaattact actttctttc cttgcagata agaagcacca    7380
tcagcaaact cgtcccttcc cataaatctg cacttaccca gttgagccaa ttgttgtctc    7440
aaatttaatg tgttaaaata gttggccatc tcgagtcgaa actaagttct ggtgttttaa    7500
aactaaaaaa aagactaact ataaaagtag aatttaagaa gtttaagaaa tagatttaca    7560
gaattacaat caatacctac cgtctttata tacttattag tcaagtaggg gaataatttc    7620
agggaactgg tttcaacctt ttttttcagc tttttccaaa tcagagagag cagaaggtaa    7680
tagaaggtgt aagaaaatga gatagataca tgcgtgggtc aattgccttg tgtcatcatt    7740
tactccaggc aggttgcatc actccattga ggttgtgccc gtttttgcc tgtttgtgcc    7800 cctgttctct gtagttgcgc taagagaatg gacctatgaa ctgatggttg gtgaagaaaa    7860
caatattttg gtgctgggat tcttttttt tctggatgcc agcttaaaaa gcgggctcca    7920
ttatatttag tggatgccag gaataaactg ttcacccaga cacctacgat gttatatatt    7980
ctgtgtaacc cgcccctat tttgggcatg tacgggttac agcagaatta aaaggctaat    8040
tttttgacta aataaagtta ggaaaatcac tactattaat tatttacgta ttctttgaaa    8100
tggcgagtat tgataatgat aaactggatc cgcggccgct tacagatcag taacacaccc    8160
ttccgatgca ggacgggtta atttagcgaa ttttgccaaa actcccctgg tggctttcgg    8220
agttggcttc tgataattag ctcttctctt tgcgatttct tcatcggaaa ctttcaggga    8280
tatagagttg ttgactgcat ctatctctat tatatcgtca tcttcaacta gccgattag    8340 tccacccctca acggcttcag gcacaatatg gccgacaaca aaaccgtgag tgccaccgga    8400
```

```
gaatctacca tccgtaatta acgcgcaact tttccctaaa cccgcaccaa ttaatgctga   8460
tgtaggcttc agcatttcgg gcataccagg tccgccgacg ggacctatat tcctaattac   8520
cgctacatct ccagcatgca aacgaccaga ttctatgccg tcgataaaat gttgttcacc   8580
atcaaagact ctggcagtgc ctttgaagaa ctctccttct ttaccgctaa ttttttgctac  8640
ggaaccccct tgagctaaat taccgtacag aatctgcaag tggccggtgg ccttgatagg   8700
attctttagt ggcctcatga tatcttgtga gtcgaaatcc aagtctaggg cagtctcgac   8760
attctcggct aatgttttac ccgtcacagt aaggcagtca ccatgcaatt ttccttcctt   8820
tagaaggtac ttaagcactg ctggcaagcc tccaattta tgcaaatctt ccatcatata    8880
tttacctgaa ggtttaaaat cacctagtac tggagtaatg tcactaattc tttggaagtc   8940
atcctgagtt atttcgacac ctatcgcgtt agccattgca ataatatgca agacagcatt   9000
agtactaccc cccaagacca tcacaatggt aatagcgttc tcgaacgcct ccttagtcat   9060
tatatcacta ggcttgatgt cttttccaa aagattctta atggctaatc caatctcatc    9120
acattcttct tgttttctt gagatactgc agggttcgaa gaagaatacg gcaatgacat    9180
acctagtgtt tcgatagcgg cagctaaggt attagctgtg tacatccccc cacatgcccc   9240
ttgaccagga atagcattac aaataacacc gtgataatct tcatcagaga tattgccggt   9300
aattttctgg cctagagatt caaaagccga tacgatgttc aatttctcac ctttatattc   9360
accgtgttct attgttcctc catacaccat aatgcttggc ctattaagtc ttgccatacc   9420
aataatagaa cctggcatat ttttgtcaca acctgggatg gctacaattg catcatagta   9480
ttcagcgcca gcgttggttt caatagagtc agctataact tctctggaaa caagggagta   9540
tctcattccc aactttccat ttgctatccc atcagaaact cctatcgtat gaaattgtaa   9600
gccgatcaga ccatctgtct gatttactga gcttttaatc tttgatccaa gggttcctaa   9660
atgcatgttg catggatttc catcccagtc catcgacact atacccactt gagctttctt   9720
gaaatcttcg tctttaaacc cgatgccgta atacattgcc tgtgtggcgg gttgtgtggg   9780
atcttgtgtc aacgttttgc tgtacttatt cagttcaaca gattcaactt gccgttata    9840
cttaaactcc atgtcgacaa acttagatta gattgctatg ctttctttct aatgagcaag   9900
aagtaaaaaa agttgtaata gaacaagaaa aatgaaactg aaacttgaga aattgaagac   9960
cgtttattaa cttaaatatc aatgggaggt catcgaaaga gaaaaaatc aaaaaaaaaa    10020
ttttcaagaa aaagaaacgt gataaaaatt tttattgcct ttttcgacga agaaaaagaa   10080
acgaggcggt ctctttttc ttttccaaac ctttagtacg ggtaattaac gacacctag    10140
aggaagaaag aggggaaatt tagtatgctg tgcttgggtg ttttgaagtg gtacggcgat   10200
gcgcggagtc cgagaaaatc tggaagagta aaaaggagt agaaacattt tgaagctatg    10260
agctccagct tttgttccct ttagtgaggg ttaattgcgc gcttggcgta atcatggtca   10320
tagctgtttc ctgtgtgaaa ttgttatccg ctcacaattc cacacaacat aggagccgga   10380
agcataaagt gtaaagcctg gggtgcctaa tgagtgaggt aactcacatt aattgcgttg   10440
cgctcactgc ccgctttcca gtcgggaaac ctgtcgtgcc agctgcatta atgaatcggc   10500
caacgcgcgg ggagaggcgg tttgcgtatt gggcgctctt ccgcttcctc gctcactgac   10560
tcgctgcgct cggtcgttcg gctgcggcga gcggtatcag ctcactcaaa ggcggtaata   10620
cggttatcca cagaatcagg ggataacgca ggaaagaaca tgtgagcaaa aggccagcaa   10680
aaggccagga accgtaaaaa ggccgcgttg ctggcgtttt tccataggct ccgcccccct   10740
```

-continued

| | | | | | |
|---|---|---|---|---|---|
| gacgagcatc | acaaaaatcg | acgctcaagt | cagaggtggc | gaaacccgac | aggactataa | 10800 |
| agataccagg | cgtttccccc | tggaagctcc | ctcgtgcgct | ctcctgttcc | gaccctgccg | 10860 |
| cttaccggat | acctgtccgc | ctttctccct | tcgggaagcg | tggcgctttc | tcatagctca | 10920 |
| cgctgtaggt | atctcagttc | ggtgtaggtc | gttcgctcca | agctgggctg | tgtgcacgaa | 10980 |
| ccccccgttc | agcccgaccg | ctgcgcctta | tccggtaact | atcgtcttga | gtccaacccg | 11040 |
| gtaagacacg | acttatcgcc | actggcagca | gccactggta | acaggattag | cagagcgagg | 11100 |
| tatgtaggcg | gtgctacaga | gttcttgaag | tggtggccta | actacggcta | cactagaagg | 11160 |
| acagtatttg | gtatctgcgc | tctgctgaag | ccagttacct | tcggaaaaag | agttggtagc | 11220 |
| tcttgatccg | gcaaacaaac | caccgctggt | agcggtggtt | tttttgtttg | caagcagcag | 11280 |
| attacgcgca | gaaaaaaagg | atctcaagaa | gatcctttga | tcttttctac | ggggtctgac | 11340 |
| gctcagtgga | acgaaaactc | acgttaaggg | attttggtca | tgagattatc | aaaaaggatc | 11400 |
| ttcacctaga | tccttttaaa | ttaaaaatga | agttttaaat | caatctaaag | tatatatgag | 11460 |
| taaacttggt | ctgacagtta | ccaatgctta | atcagtgagg | cacctatctc | agcgatctgt | 11520 |
| ctatttcgtt | catccatagt | tgcctgactc | cccgtcgtgt | agataactac | gatacgggag | 11580 |
| ggcttaccat | ctggccccag | tgctgcaatg | ataccgcgag | acccacgctc | accggctcca | 11640 |
| gatttatcag | caataaacca | gccagccgga | agggccgagc | gcagaagtgg | tcctgcaact | 11700 |
| ttatccgcct | ccatccagtc | tattaattgt | tgccgggaag | ctagagtaag | tagttcgcca | 11760 |
| gttaatagtt | tgcgcaacgt | tgttgccatt | gctacaggca | tcgtggtgtc | acgctcgtcg | 11820 |
| tttggtatgg | cttcattcag | ctccggttcc | caacgatcaa | ggcgagttac | atgatccccc | 11880 |
| atgttgtgca | aaaaagcggt | tagctccttc | ggtcctccga | tcgttgtcag | aagtaagttg | 11940 |
| gccgcagtgt | tatcactcat | ggttatggca | gcactgcata | attctcttac | tgtcatgcca | 12000 |
| tccgtaagat | gcttttctgt | gactggtgag | tactcaacca | agtcattctg | agaatagtgt | 12060 |
| atgcggcgac | cgagttgctc | ttgcccggcg | tcaatacggg | ataataccgc | gccacatagc | 12120 |
| agaactttaa | aagtgctcat | cattggaaaa | cgttcttcgg | ggcgaaaact | ctcaaggatc | 12180 |
| ttaccgctgt | tgagatccag | ttcgatgtaa | cccactcgtg | cacccaactg | atcttcagca | 12240 |
| tcttttactt | tcaccagcgt | ttctgggtga | gcaaaaacag | gaaggcaaaa | tgccgcaaaa | 12300 |
| aagggaataa | gggcgacacg | gaaatgttga | atactcatac | tcttcctttt | tcaatattat | 12360 |
| tgaagcattt | atcagggtta | ttgtctcatg | agcggataca | tatttgaatg | tatttagaaa | 12420 |
| aataaacaaa | taggggttcc | gcgcacattt | ccccgaaaag | tgccacctga | acgaagcatc | 12480 |
| tgtgcttcat | tttgtagaac | aaaaatgcaa | cgcgagagcg | ctaattttc | aaacaaagaa | 12540 |
| tctgagctgc | atttttacag | aacagaaatg | caacgcgaaa | gcgctatttt | accaacgaag | 12600 |
| aatctgtgct | tcatttttgt | aaaacaaaaa | tgcaacgcga | gagcgctaat | ttttcaaaca | 12660 |
| aagaatctga | gctgcatttt | tacagaacag | aaatgcaacg | cgagagcgct | attttaccaa | 12720 |
| caaagaatct | atacttcttt | tttgttctac | aaaaatgcat | cccgagagcg | ctatttttct | 12780 |
| aacaaagcat | cttagattac | tttttttctc | ctttgtgcgc | tctataatgc | agtctcttga | 12840 |
| taacttttg | cactgtaggt | ccgttaaggt | tagaagaagg | ctactttggt | gtctattttc | 12900 |
| tcttccataa | aaaaagcctg | actccacttc | ccgcgtttac | tgattactag | cgaagctgcg | 12960 |
| ggtgcatttt | ttcaagataa | aggcatcccc | gattatattc | tataccgatg | tggattgcgc | 13020 |
| atactttgtg | aacagaaagt | gatagcgttg | atgattcttc | attggtcaga | aaattatgaa | 13080 |
| cggtttcttc | tattttgtct | ctatatacta | cgtataggaa | atgtttacat | ttcgtattg | 13140 |

| | | | | | |
|---|---|---|---|---|---|
| ttttcgattc | actctatgaa | tagttcttac | tacaattttt | ttgtctaaag | agtaatacta | 13200 |
| gagataaaca | taaaaaatgt | agaggtcgag | tttagatgca | agttcaagga | gcgaaaggtg | 13260 |
| gatgggtagg | ttatataggg | atatagcaca | gagatatata | gcaaagagat | acttttgagc | 13320 |
| aatgtttgtg | gaagcggtat | tcgcaatatt | ttagtagctc | gttacagtcc | ggtgcgtttt | 13380 |
| tggttttttg | aaagtgcgtc | ttcagagcgc | ttttggtttt | caaaagcgct | ctgaagttcc | 13440 |
| tatactttct | agagaatagg | aacttcggaa | taggaacttc | aaagcgtttc | cgaaaacgag | 13500 |
| cgcttccgaa | aatgcaacgc | gagctgcgca | catacagctc | actgttcacg | tcgcacctat | 13560 |
| atctgcgtgt | tgcctgtata | tatatataca | tgagaagaac | ggcatagtgc | gtgtttatgc | 13620 |
| ttaaatgcgt | acttatatgc | gtctatttat | gtaggatgaa | aggtagtcta | gtacctcctg | 13680 |
| tgatattatc | ccattccatg | cggggtatcg | tatgcttcct | tcagcactac | cctttagctg | 13740 |
| ttctatatgc | tgccactcct | caattggatt | agtctcatcc | ttcaatgcta | tcatttcctt | 13800 |
| tgata | | | | | 13805 |

<210> SEQ ID NO 68
<211> LENGTH: 11561
<212> TYPE: DNA
<213> ORGANISM: Artificial Sequence
<220> FEATURE:
<223> OTHER INFORMATION: pGV2563

<400> SEQUENCE: 68

| | | | | | |
|---|---|---|---|---|---|
| ttggatcata | ctaagaaacc | attattatca | tgacattaac | ctataaaaat | aggcgtatca | 60 |
| cgaggcccctt | tcgtctcgcg | cgtttcggtg | atgacggtga | aaacctctga | cacatgcagc | 120 |
| tcccggagac | ggtcacagct | tgtctgtaag | cggatgccgg | gagcagacaa | gcccgtcagg | 180 |
| gcgcgtcagc | gggtgttggc | gggtgtcggg | gctggcttaa | ctatgcggca | tcagagcaga | 240 |
| ttgtactgag | agtgcaccat | accacagctt | tcaattcaa | ttcatcattt | ttttttatt | 300 |
| cttttttttg | atttcggttt | ctttgaaatt | ttttgattc | ggtaatctcc | gaacagaagg | 360 |
| aagaacgaag | gaaggagcac | agacttagat | tggtatatat | acgcatatgg | caaattaaag | 420 |
| ccttcgagcg | tcccaaaacc | ttctcaagca | aggttttcag | tataatgtta | catgcgtaca | 480 |
| cgcgtctgta | cagaaaaaaa | agaaaaattt | gaaatataaa | taacgttctt | aatactaaca | 540 |
| taactataaa | aaaataaata | gggacctaga | cttcaggttg | tctaactcct | tccttttcgg | 600 |
| ttagagcgga | tgtgggggga | gggcgtgaat | gtaagcgtga | cataactaat | tacatgactc | 660 |
| gacctaggtt | agtggtggtg | gtggtggtgc | ttcgtgaagt | ctataaccat | tctaccttca | 720 |
| atcttccccg | ccttcatctc | atcaatgatg | tcattgattt | cctccaactt | tctggtagcg | 780 |
| acaataggct | taaccttccc | ttctgcaccg | aattggaaag | cttcggccaa | atcgagtctt | 840 |
| gttccaacaa | gactacctgc | tacttcaact | ccatcaaaca | cgactgttgg | cacagataat | 900 |
| gtcatttctg | tgtttggcac | agcaacggct | accattttgc | ccataggctt | tagtgaggct | 960 |
| acagcctgct | cgaatgcaat | tctcgcaacg | gcacatacaa | tcgcggattg | aacacctaaa | 1020 |
| ccgccagtga | tctttttgat | ttcgtctaca | gggttaacgt | caccagagtt | aattgtgaca | 1080 |
| tcagcaccta | tctttttggc | aagattgagc | ttatcttgat | tgatatctac | agcgatcacc | 1140 |
| ttcgcaccaa | atacgttttt | ggcgtactgg | atagctaagt | tgcccaggcc | accagctccg | 1200 |
| aagataactt | gccagtctcc | tggcttaacg | ccagacacct | tgatagcttt | gtaagtggtg | 1260 |
| acgcctgcac | aagttataga | tgatgcttct | attggatcta | ggccatctgg | gactttaacg | 1320 |

-continued

```
gcataatctg caaccacgat cgcttcctct gccattccac catcaacgct ataaccagcg    1380
tttttgactt ctcggcaaaa tgtctcgtta cctgacacac agtattcgca atgtccacac    1440
ccttcgaaaa accaagcaac actcactcta tcacctactt ggagagaact aacatcggca    1500
ccaatctctt tcacaatacc tataccttca tgtcctaaaa ctgtccctgc cttgttgccg    1560
aaatctccgg cagcaacatg taggtcagtg tgacagacac cgcagtattc catatccaac    1620
aatgcctcat ttggcttaat ggccctcaac tcttttttcta caagatcagc gtacccatca    1680
ggattgtgac ggacaactgc agccttcatg gtacctatta ttgtatgtta tagtattagt    1740
tgcttggtgt tatgaaagaa actaagaaaa gaaaaataaa ataaaaataa aagattgaga    1800
caagggaaga aaagatacaa aataagaatt aattacaatt gcgtttgcta taaatacgtt    1860
tttaacaatc aactctggta ggaagataat gctttttttt tttatatatg cttggtgcca    1920
cttgtcacat acaattctac aaccttcgac aaaaatccaa atgatagtaa gatcaaagcc    1980
agaaagcaat ggagaaaaaa aattaatgaa ccacgatgaa ccaaatgatc aatacaacca    2040
aagaaactac cctagtgagg tgtatgctga cttggtatca cacttcatga attttgcata    2100
tggcaaagtc cacgaaagtg ggcttcagaa aaaaggcgtg cggtgtgtag atgtatcaat    2160
tagtggatgc cagttttgga acgggattcc actttccgca agttggtgca cgtcgttagt    2220
gacataacgc cgcgttcatc tttgggaaga agcagatgct gagcgaggag gtactataga    2280
gtaaagaacc ctttctatac ccgcagcccc atgaattctt agaaaaactc atcgagcatc    2340
aaatgaaact gcaatttatt catatcagga ttatcaatac catattttg aaaaagccgt    2400 ttctgtaatg aaggagaaaa ctcaccgagg cagttccata ggatggcaag atcctggtat    2460
cggtctgcga tcccgactcg tccaacatca atacaaccta ttaatttccc ctcgtcaaaa    2520
ataaggttat caagtgagaa atcaccatga gtgacgactg aatccggtga aatggcaaa    2580 agcttatgca tttctttcca gacttgttca acaggccagc cattacgctc gtcatcaaaa    2640
tcactcgcgt caaccaaacc gttattcatt cgtgattgcg cctgagcgag gcgaaatacg    2700
cgatcgctgt taaaaggaca attacaaaca ggaatcgaat gcaaccggcg caggaacact    2760
gccagcgcat caacaatatt ttcacctgaa tcaggatatt cttctaatac ctggaatgct    2820
gttttgccgg ggatcgcagt ggtgagtaac catgcatcat caggagtacg gacaaaatgc    2880
ttgatggtcg gaagaggcat aaattccgtc agccagttta gtctgaccat ctcatctgca    2940
acatcattgg caacgctacc tttgccatgt ttcagaaaca actctggcgc atcgggcttc    3000
ccatacaatc gatagattgt cgcacctgat tgcccgacat atcgcgagc ccatttatac    3060 ccatataaat cagcatccat gttggaattt aatcgcggcc tcgaacgtg agtcttttcc    3120 ttacccatac tagttttttag tttatgtatg tgttttttgt agttatagat ttaagcaaga    3180
aaagaataca aacaaaaaat tgaaaaagat tgatttagaa ttaaaagaa aaatatttac    3240 gtaagaaggg aaaatagtaa atgttgcaag ttcactaaac tcctaaatta tgctgccctt    3300
tatattccct gttacagcag ccgagccaaa ggtatatagg ctcctttgca ttagcatgcg    3360
taacaaacca cctgtcagtt tcaaccgagg tggtatccga gagaattgtg tgattgcttt    3420
aattaatttc ggagaatctc acatgccact gaagattaaa aactggatgc cagaaaaggg    3480
gtgtccaggt gtaacatcaa tagaggaagc tgaaaagtct tagaacgggt aatcttccac    3540
caacctgatg ggttcctaga tataatctcg aagggaataa gtagggtgat accgcagaag    3600
tgtctgaatg tattaaggtc ctcacagttt aaatcccgct cacactaacg taggattatt    3660
ataactcaaa aaaatggcat tattctaagt aagttaaata tccgtaatct ttaaacagcg    3720
```

```
gccgcagatc cttagtggtg gtggtggtgg tgtcctgcca ctgcaattct tttcatatcg    3780
gtcatatatc ctctcagctt tttacccacc tgttctatag catgcgaacg aatagcttca    3840
tttacgtctc tcagttggcc attgtcaacc gctccttccg gaatagcctt ccccaaatca    3900
ccaggttgta actcggccat gaagggctct aacaacggga cacacgcgta gctaaataag    3960
taattaccat attctgcagt gtctgatatg acaacattca tctcgtaaag tcttttctt    4020
gcaatagtat ttgctatcaa aggcaattca tgcaaagact catagtatgc agattcttca    4080
atgataccgg agtcaaccat agtttcgaat gcaagttcta cccctgcctt caccatagct    4140
atcatcaata ctcccttatc aaagtattct tgttcaccaa ttttaccttc gtattgtggg    4200
gctgtctcga atgccgtctt gccggtttct tctctccacg tcaataactt tttatcatcg    4260
tttgcccaat ctgccatcat tcctgaggaa aactcaccgg agataatatc gtccatgtgc    4320
ttttggaata atggtgccat gatctctttt agttgctcag ataaggcgta ggctcttagc    4380
ttggccggat ttgaaagtct atccatcatc aatgttatgc caccttgttt aagtgcctcg    4440
gtgattgtct cccaaccaaa ttgtatcaac ttttcagcat aggcaggatc tgtaccctct    4500
tcgaccaatt tatcaaagca tagtaaagac cctgcctgca acattccgca cagaatggtt    4560
tgttcaccca ttaagtcact cttgacctca gctacgaaag aactctctaa cacacccgct    4620
ctatgacctc cggttgcggc tgcccatgcc ttcgctattg ccataccttc acgtttgggg    4680
tcattttcag gatgtacggc gatcaatgta ggtacaccaa aacccctctt gtactcctct    4740
ctgacttccg tacctgggca cttttggcgca accattacga ctgttatacc ttttctgatc    4800
tgctcgccca cttcaacgat attaaagcca tgagagtaac ctaaagctgc cccatccttc    4860
atcagcggtt gaactgttct tactacgtct gagtgaacct tatctggtgt taggttaatc    4920
actaaatctg cctgagggat cagttcttcg taagtaccaa ctttgaaccc attttccgtc    4980
gctttacgcc aatcggcatc cttttctgca atagactctt tcctcaatgc atacgaaata    5040
tccagacctg aatctctcat gtttaaacct tggtttagac cctgagcacc gcagccaaca    5100
attactactt tctttccttg cagataagaa gcaccatcag caaactcgtc ccttcccata    5160
aatctgcact tacccagttg agccaattgt tgtctcaaat ttaatgtgtt aaaatagttg    5220
gccatgtcga gtcgaaacta agttctggtg ttttaaaact aaaaaaaaga ctaactataa    5280
aagtagaatt taagaagttt aagaaataga tttacagaat tacaatcaat acctaccgtc    5340
tttatatact tattagtcaa gtaggggaat aatttcaggg aactggtttc aacctttttt    5400
ttcagctttt tccaaatcag agagagcaga aggtaataga aggtgtaaga aaatgagata    5460
gatacatgcg tgggtcaatt gccttgtgtc atcatttact ccaggcaggt tgcatcactc    5520
cattgaggtt gtgcccgttt tttgcctgtt tgtgccctg ttctctgtag ttgcgctaag    5580
agaatggacc tatgaactga tggttggtga agaaaacaat attttggtgc tgggattctt    5640
ttttttctg gatgccagct taaaagcgg gctccattat atttagtgga tgccaggaat    5700
aaactgttca cccagacacc tacgatgtta tatattctgt gtaacccgcc ccctatttg    5760
ggcatgtacg ggttacagca gaattaaaag gctaattttt tgactaaata aagttaggaa    5820
aatcactact attaattatt tacgtattct ttgaaatggc gagtattgat aatgataaac    5880
tggatccgcg gccgcttaca gatcagtaac acacccttcc gatgcaggac gggttaattt    5940
agcgaatttt gccaaaactc ccctggtggc tttcggagtt ggcttctgat aattagctct    6000
tctctttgcg atttcttcat cggaaacttt cagggatata gagttgttga ctgcatctat    6060
```

-continued

```
ctctattata tcgtcatctt caactaagcc gattagtcca ccctcaacgg cttcaggcac    6120
aatatggccg acaacaaaac cgtgagtgcc accggagaat ctaccatccg taattaacgc    6180
gcaacttttc cctaaacccg caccaattaa tgctgatgta ggcttcagca tttcgggcat    6240
accaggtccg ccgacgggac ctatattcct aattaccgct acatctccag catgcaaacg    6300
accagattct atgccgtcga taaaatgttg ttcaccatca aagactctgg cagtgccttt    6360
gaagaactct ccttctttac cgctaatttt tgctacggaa cccccttgag ctaaattacc    6420
gtacagaatc tgcaagtggc cggtggcctt gataggattc tttagtggcc tcatgatatc    6480
ttgtgagtcg aaatccaagt ctagggcagt ctcgacattc tcggctaatg ttttacccgt    6540
cacagtaagg cagtcaccat gcaatttttcc ttcctttaga aggtacttaa gcactgctgg    6600
caagcctcca attttatgca aatcttccat catatattta cctgaaggtt taaaatcacc    6660
tagtactgga gtaatgtcac taattctttg gaagtcatcc tgagttattt cgacacctat    6720
cgcgttagcc attgcaataa tatgcaagac agcattagta ctacccccca agaccatcac    6780
aatggtaata gcgttctcga acgcctcctt agtcattata tcactaggct tgatgtcttt    6840
ttccaaaaga ttcttaatgg ctaatccaat ctcatcacat tcttcttgtt tttcttgaga    6900
tactgcaggg ttcgaagaag aatacggcaa tgacatacct agtgtttcga tagcggcagc    6960
taaggtatta gctgtgtaca tccccccaca tgccccttga ccaggaatag cattacaaat    7020
aacaccgtga taatcttcat cagagatatt gccggtaatt ttctggccta gagattcaaa    7080
agccgatacg atgttcaatt tctcaccttt atattcaccg tgttctattg ttcctccata    7140
caccataatg cttggcctat taagtcttgc cataccaata atagaacctg gcatattttt    7200
gtcacaacct gggatggcta caattgcatc atagtattca gcgccagcgt tggtttcaat    7260
agagtcagct ataacttctc tggaaacaag ggagtatctc attcccaact ttccatttgc    7320
tatcccatca gaaactccta tcgtatgaaa ttgtaagccg atcagaccat ctgtctgatt    7380
tactgagctt ttaatctttg atccaagggt tcctaaatgc atgttgcatg gatttccatc    7440
ccagtccatc gacactatac ccacttgagc tttcttgaaa tcttcgtctt taaacccgat    7500
gccgtaatac attgcctgtg tggcgggttg tgtgggatct tgtgtcaacg ttttgctgta    7560
cttattcagt tcaacagatt caactttgcc gttatactta aactccatgt cgacaaactt    7620
agattagatt gctatgcttt cttttctaatg agcaagaagt aaaaaaagtt gtaatagaac    7680
aagaaaaatg aaactgaaac ttgagaaatt gaagaccgtt tattaactta aatatcaatg    7740
ggaggtcatc gaaagagaaa aaaatcaaaa aaaaatttt caagaaaaag aaacgtgata    7800
aaaatttta ttgccttttt cgacgaagaa aaagaaacga ggcggtctct ttttcttt    7860
ccaaaccttt agtacgggta attaacgaca ccctagagga agaaagaggg gaaatttagt    7920
atgctgtgct tgggtgtttt gaagtggtac ggcgatgcgc ggagtccgag aaaatctgga    7980
agagtaaaaa aggagtagaa acattttgaa gctatgagct ccagcttttg ttccctttag    8040
tgagggttaa ttgcgcgctt ggcgtaatca tggtcatagc tgtttcctgt gtgaaattgt    8100
tatccgctca caattccaca acatagga gccggaagca taaagtgtaa agcctggggt    8160
gcctaatgag tgaggtaact cacattaatt gcgttgcgct cactgcccgc tttccagtcg    8220
ggaaacctgt cgtgccagct gcattaatga atcggccaac gcgcggggag aggcggtttg    8280
cgtattgggc gctcttccgc ttcctcgctc actgactcgc tgcgctcggt cgttcggctg    8340
cggcgagcgg tatcagctca ctcaaaggcg gtaatacggt tatccacaga atcagggat    8400
aacgcaggaa agaacatgtg agcaaaaggc cagcaaaagg ccaggaaccg taaaaaggcc    8460
```

```
gcgttgctgg cgtttttcca taggctccgc cccctgacg agcatcacaa aaatcgacgc    8520
tcaagtcaga ggtggcgaaa cccgacagga ctataaagat accaggcgtt tccccctgga    8580
agctccctcg tgcgctctcc tgttccgacc ctgccgctta ccggatacct gtccgccttt    8640
ctcccttcgg gaagcgtggc gctttctcat agctcacgct gtaggtatct cagttcggtg    8700
taggtcgttc gctccaagct gggctgtgtg cacgaacccc ccgttcagcc cgaccgctgc    8760
gccttatccg gtaactatcg tcttgagtcc aacccggtaa gacacgactt atcgccactg    8820
gcagcagcca ctggtaacag gattagcaga gcgaggtatg taggcggtgc tacagagttc    8880
ttgaagtggt ggcctaacta cggctacact agaaggacag tatttggtat ctgcgctctg    8940
ctgaagccag ttaccttcgg aaaaagagtt ggtagctctt gatccggcaa acaaaccacc    9000
gctggtagcg gtggtttttt tgtttgcaag cagcagatta cgcgcagaaa aaaggatct    9060 caagaagatc ctttgatctt ttctacgggg tctgacgctc agtggaacga aaactcacgt    9120
taagggattt tggtcatgag attatcaaaa aggatcttca cctagatcct tttaaattaa    9180
aaatgaagtt ttaaatcaat ctaaagtata tatgagtaaa cttggtctga cagttaccaa    9240
tgcttaatca gtgaggcacc tatctcagcg atctgtctat ttcgttcatc catagttgcc    9300
tgactccccg tcgtgtagat aactacgata cgggagggct taccatctgg ccccagtgct    9360
gcaatgatac cgcgagaccc acgctcaccg gctccagatt tatcagcaat aaaccagcca    9420
gccggaaggg ccgagcgcag aagtggtcct gcaactttat ccgcctccat ccagtctatt    9480
aattgttgcc gggaagctag agtaagtagt tcgccagtta atagtttgcg caacgttgtt    9540
gccattgcta caggcatcgt ggtgtcacgc tcgtcgtttg gtatggcttc attcagctcc    9600
ggttcccaac gatcaaggcg agttacatga tcccccatgt tgtgcaaaaa agcggttagc    9660
tccttcggtc ctccgatcgt tgtcagaagt aagttggccg cagtgttatc actcatggtt    9720
atggcagcac tgcataattc tcttactgtc atgccatccg taagatgctt ttctgtgact    9780
ggtgagtact caaccaagtc attctgagaa tagtgtatgc ggcgaccgag ttgctcttgc    9840
ccggcgtcaa tacgggataa taccgcgcca catagcagaa ctttaaaagt gctcatcatt    9900
ggaaaacgtt cttcggggcg aaaactctca aggatcttac cgctgttgag atccagttcg    9960
atgtaaccca ctcgtgcacc caactgatct tcagcatctt ttactttcac cagcgtttct   10020
gggtgagcaa aaacaggaag gcaaaatgcc gcaaaaaagg gaataagggc gacacggaaa   10080
tgttgaatac tcatactctt cctttttcaa tattattgaa gcatttatca gggttattgt   10140
ctcatgagcg gatacatatt tgaatgtatt tagaaaaata aacaaatagg ggttccgcgc   10200
acatttcccc gaaaagtgcc acctgaacga agcatctgtg cttcattttg tagaacaaaa   10260
atgcaacgcg agagcgctaa ttttcaaac aaagaatctg agctgcattt ttacagaaca   10320
gaaatgcaac gcgaaagcgc tattttacca acgaagaatc tgtgcttcat ttttgtaaaa   10380
caaaaatgca acgcgagagc gctaattttt caaacaaaga atctgagctg catttttaca   10440
gaacagaaat gcaacgcgag agcgctattt taccaacaaa gaatctatac ttcttttttg   10500
ttctacaaaa atgcatcccg agagcgctat tttctaaca agcatcttga gattactttt   10560
tttctccttt gtgcgctcta atgcagtc tcttgataac ttttttgcact gtaggtccgt    10620 taaggttaga agaaggctac tttggtgtct attttctctt ccataaaaaa agcctgactc   10680
cacttcccgc gttactgat tactagcgaa gctgcgggtg cattttttca agataaaggc    10740
atccccgatt atattctata ccgatgtgga ttgcgcatac tttgtgaaca gaaagtgata   10800
```

```
gcgttgatga ttcttcattg gtcagaaaat tatgaacggt ttcttctatt ttgtctctat    10860
atactacgta taggaaatgt ttacattttc gtattgtttt cgattcactc tatgaatagt    10920
tcttactaca attttttgt ctaaagagta atactagaga taaacataaa aaatgtagag      10980
gtcgagttta gatgcaagtt caaggagcga aaggtggatg ggtaggttat atagggatat    11040
agcacagaga tatatagcaa agagatactt ttgagcaatg tttgtggaag cggtattcgc    11100
aatattttag tagctcgtta cagtccggtg cgttttggt tttttgaaag tgcgtcttca      11160
gagcgctttt ggttttcaaa agcgctctga agttcctata ctttctagag aataggaact    11220
tcggaatagg aacttcaaag cgtttccgaa acgagcgct tccgaaaatg caacgcgagc      11280
tgcgcacata cagctcactg ttcacgtcgc acctatatct gcgtgttgcc tgtatatata    11340
tatacatgag aagaacggca tagtgcgtgt ttatgcttaa atgcgtactt atatgcgtct    11400
atttatgtag gatgaaaggt agtctagtac ctcctgtgat attatcccat tccatgcggg    11460
gtatcgtatg cttccttcag cactacccctt tagctgttct atatgctgcc actcctcaat    11520
tggattagtc tcatccttca atgctatcat ttcctttgat a                         11561

<210> SEQ ID NO 69
<211> LENGTH: 9043
<212> TYPE: DNA
<213> ORGANISM: Artificial Sequence
<220> FEATURE:
<223> OTHER INFORMATION: pGV2164

<400> SEQUENCE: 69
ctgcttaatt aaccgttgat gacagcaatt cgggagggcg aaaaataaaa actggagcaa      60
ggaattacca tcaccgtcac catcaccatc atatcgcctt agcctctagc catagccatc     120
atgcaagcgt gtatcttcta agattcagtc atcatcatta ccgagtttgt tttccttcac     180
atgatgaaga aggtttgagt atgctcgaaa caataagacg acgatggctc tgccattgtt     240
atattacgct tttgcggcga ggtgccgatg ggttgctgag gggaagagtg tttagcttac     300
ggacctattg ccattgttat tccgattaat ctattgttca gcagctcttc tctaccctgt     360
cattctagta ttttttttt ttttttttg gttttacttt ttttttcttct tgccttttt       420 tcttgttact ttttttctag ttttttttcc ttccactaag cttttttcctt gatttatcct    480 tgggttcttc tttctactcc tttagatttt tttttatat attaatttt aagtttatgt       540 attttggtag attcaattct ctttcccttt ccttttcctt cgctcccctt ccttatcaga     600
gctcgccgat cccattaccg acatttgggc gctatacgtg catatgttca tgtatgtatc    660
tgtatttaaa acacttttgt attattttc ctcatatatg tgtataggtt tatacggatg     720
atttaattat tacttcacca ccctttattt caggctgata tcttagcctt gttactagtt    780
agaaaaagac attttgctg tcagtcactg tcaagagatt cttttgctgg catttcttct     840
agaagcaaaa agagcgatgc gtcttttccg ctgaaccgtt ccagcaaaaa agactaccaa     900
cgcaatatgg attgtcagaa tcatataaaa gagaagcaaa taactccttg tcttgtatca    960
attgcattat aatatcttct tgttagtgca atatcatata gaagtcatcg aaatagatat    1020
taagaaaaac aaactgtaca atcaatcaat caatcatcac ataaagtcga catgttgaca    1080
aaagcaacaa aagaacaaaa atcccttgtg aaaagcagag gggcggagct tgttgttgat    1140
tgcttagcgg agcaaggtgt cacacatgta tttggcattc caggtgcaaa aattgatgcg    1200
gtatttgacg ctttacaaga taagggcct gaaattatcg ttgcccggca tgaacaaaat    1260
gcagcattta tggcgcaagc agtcggccgt ttaactggaa aaccgggagt cgtgttagtc    1320
```

```
acatcaggac caggtgcttc gaacttggca acaggactgc tgacagcaaa cactgaaggt   1380
gaccctgtcg ttgcgcttgc tgggaacgtg atccgtgcag atcgtttaaa acggacacat   1440
caatctttgg ataatgcggc gctattccag ccgattacaa aatacagtgt agaagttcaa   1500
gatgtaaaaa atataccgga agctgttaca aatgcgttta ggatagcgtc agcagggcag   1560
gctggggccg cttttgtgag ttttccgcaa gatgttgtga atgaagtcac aaatacaaaa   1620
aacgtacgtg ctgtcgcagc gccaaaactt ggtcccgcag cagatgacgc aatcagtatg   1680
gccattgcaa aaattcaaac agcaaaactt cctgtcgttt tagtcggcat gaagggcgga   1740
agaccggaag cgattaaagc ggttcgcaag ctattgaaaa aagtgcagct tccattcgtt   1800
gaaacatatc aagctgccgg tactcttacg agagatttag aggatcagta ttttggccgg   1860
atcggtttat tccgcaacca gcctggcgat ctgctgcttg agcaggctga tgttgttctg   1920
acaatcggct atgacccaat tgaatatgat ccgaaattct ggaatgtcaa tggagaccgg   1980
acgatcatcc atttagacga gattctggct gacattgatc atgcttacca gccggatctt   2040
gaactgatcg gtgatattcc atctacgatc aatcatatcg aacacgatgc tgtgaaagta   2100
gactttgcgg aacgtgagca gaagatcctt tctgatttaa aacaatatat gcatgagggt   2160
gagcaggtgc ctgcagattg gaaatcagac agagtgcatc ctcttgaaat cgttaaagaa   2220
ttgcgaaacg cagtcgatga tcatgttaca gtgacttgcg atatcggttc acacgcgatt   2280
tggatgtcac gttatttccg cagctacgag ccgttaacat taatgattag taacggtatg   2340
caaacactcg gcgttgcgct tccttgggca atcggcgctt cattggtgaa accgggagaa   2400
aaagtagtat cagtctccgg tgatggcggt ttcttattct cagctatgga attagagaca   2460
gcagttcgtt taaaagcacc aattgtacac attgtatgga acgacagcac atatgacatg   2520
gttgcattcc agcaattgaa aaaatataat cgtacatctg cggtcgattt cggaaatatc   2580
gatatcgtga aatacgcgga aagcttcgga gcaactggct tacgcgtaga atcaccagac   2640
cagctggcag atgttctgcg tcaaggcatg aacgctgagg ggcctgtcat cattgatgtc   2700
ccggttgact acagtgataa cgttaattta gcaagtgaca agcttccgaa agaattcggg   2760
gaactcatga aaacgaaagc tctctaggga tcctcatgta attagttatg tcacgcttac   2820
attcacgccc tccccccaca tccgctctaa ccgaaaagga aggagttaga caacctgaag   2880
tctaggtccc tatttatttt tttatagtta tgttagtatt aagaacgtta tttatatttc   2940
aaattttttct ttttttttctg tacagacgcg tgtacgcatg taacattata ctgaaaacct   3000
tgcttgagaa ggttttggga cgctcgaagg ctttaatttg ccctaggctc aactcaagac   3060
gcacagatat tataacatct gcataatagg catttgcaag aattactcgt gagtaaggaa   3120
agagtgagga actatcgcat acctgcattt aaagatgccg atttgggcgc gaatccttta   3180
ttttggcttc accctcatac tattatcagg ccagaaaaa ggaagtgttt ccctccttct   3240
tgaattgatg ttaccctcat aaagcacgtg gcctcttatc gagaaagaaa ttaccgtcgc   3300
tcgtgatttg tttgcaaaaa gaacaaaact gaaaaaaccc agacacgctc gacttcctgt   3360
cttcctattg attgcagctt ccaatttcgt cacacaacaa ggtcctagcg acggctcaca   3420
ggttttgtaa caagcaatcg aaggttctgg aatggcggga aagggtttag taccacatgc   3480
tatgatgccc actgtgatct ccagagcaaa gttcgttcga tcgtactgtt actctctctc   3540
tttcaaacag aattgtccga atcgtgtgac aacaacagcc tgttctcaca cactcttttc   3600
ttctaaccaa gggggtggtt tagtttagta gaaccctcgtg aaacttacat ttacatatat   3660
```

```
ataaacttgc ataaattggt caatgcaaga aatacatatt tggtcttttc taattcgtag    3720
tttttcaagt tcttagatgc tttcttttc tcttttttac agatcatcaa ggaagtaatt    3780
atctactttt tacaacaaat ataaaacaag ctcgacatgt atactgttgg tgattatctg    3840
ctggaccgtc tgcatgaact gggtatcgaa gaaatcttcg gcgttccggg tgattacaat    3900
ctgcagttcc tggatcagat catctctcat aaagacatga aatgggtggg taacgctaac    3960
gaactgaacg caagctacat ggcagatggt tatgcacgta ccaagaaagc cgcggcattt    4020
ctgaccactt tcggtgttgg cgaactgagc gccgtcaacg gtctggcggg ctcctacgcc    4080
gaaaacctgc cggtggtgga gatcgtaggc agcccaacga gcaaagttca gaacgaaggt    4140
aaattcgtcc accacactct ggctgacggc gatttcaaac acttcatgaa aatgcatgaa    4200
cctgtgactg cggcacgtac gctgctgact gcagagaacg ctactgtgga aatcgaccgc    4260
gttctgtctg cgctgctgaa agaacgcaaa ccagtttaca tcaacctgcc tgtggatgtt    4320
gcggcagcta aagcggaaaa accgagcctg ccgctgaaga agaaaactc cacttctaac    4380 actagcgacc aggaaatcct gaacaaaatc caggagtctc tgaaaaacgc aaagaaacca    4440
atcgtgatca ccggccacga aatcatttct tttggtctgg agaagaccgt gacccaattc    4500
atcagcaaaa ccaaactgcc gattaccacc ctgaacttcg gcaagtcctc tgttgacgag    4560
gctctgccgt ctttcctggg catctacaac ggtactctga gcgaaccgaa cctgaaagaa    4620
tttgttgaat ctgcggactt catcctgatg ctgggcgtta aactgaccga ctcttctacc    4680
ggtgcattca ctcaccatct gaacgaaaac aaaatgatta gcctgaacat cgacgagggt    4740
aaaatcttca cgagcgtat ccagaacttc gacttcgaaa gcctgatcag ctctctgctg    4800
gacctgtccg aaatcgagta taaggcaaa tacattgaca aaaagcaaga agatttcgta    4860
ccatctaacg cactgctgtc ccaggatcgc ctgtggcagg ccgtggagaa cctgacccag    4920
agcaatgaaa ccatcgtggc ggaacaaggt acgagctttt tcggcgcgtc ttctatctt    4980 ctgaaatcca aaagccattt tatcggtcag ccgctgtggg gtagcattgg ctatacttc    5040 ccggcagcgc tgggctctca gatcgctgat aaagaatctc gtcatctgct gttcatcggt    5100
gacggttccc tgcagctgac cgtacaggaa ctgggtctgg caattcgtga aaagatcaac    5160
ccgatttgct tcattattaa caatgacggc tacaccgttg agcgtgagat ccacggtccg    5220
aaccagtctt acaacgatat ccctatgtgg aactactcta aactgccgga gtccttcggc    5280
gcaactgagg accgtgttgt gtctaaaatt gtgcgtaccg aaaacgaatt tgtgagcgtg    5340
atgaaagagg cccaggccga tccgaaccgt atgtactgga tcgaactgat cctggcgaaa    5400
gaaggcgcac cgaaggtact gaagaaaatg ggcaagctgt ttgctgaaca gaataaatcc    5460
taaggatctt ttgcggccta gtattgaatt cttatacagg aaacttaata gaacaaatca    5520
catatttaat ctaatagcca cctgcattgg cacggtgcaa cactacttca acttcatctt    5580
acaaaaagat cacgtgatct gttgtattga actgaaaatt ttttgtttgc ttctctctct    5640
ctctttcatt atgtgagatt taaaaccag aaactacatc atcgaaaaag agttttaaac    5700
cattacaacc attgcgataa gccctctcaa actataacaa tactgacagt actaaataat    5760
tgcctacttg gcttcacata cgttgcatac gtcgatatag ataataatga taatgacagc    5820
aggattatcg taatacgtaa tagttgaaaa tctcaaaaat gtgtgggtca ttacgtaaat    5880
aatgatagga atgggattct tctatttttc cttttccat tctagcagcc gtcgggaaaa    5940
cgtggcatcc tctctttcgg gctcaattgg agtcacgctg ccgtgagcat cctctctttc    6000
catatctaac aactgagcac gtaaccaatg gaaaagcatg agcttagcgt tgctccaaaa    6060
```

```
aagtattgga tggttaatac catttgtctg ttctcttctg actttgactc ctcaaaaaaa    6120
aaaaatctac aatcaacaga tcgcttcaat tacgccctca caaaaacttt tttccttctt    6180
cttcgcccac gttaaatttt atccctcatg ttgtctaacg gatttctgca cttgatttat    6240
tataaaaaga caaagacata atacttctct atcaatttca gttattgttc ttccttgcgt    6300
tattcttctg ttcttctttt tcttttgtca tatataacca taaccaagta atacatattc    6360
aaaatgtcca caaaatcata taccagtaga gctgagactc atgcaagtcc ggttgcatcg    6420
aaacttttac gtttaatgga tgaaagaag accaatttgt gtgcttctct tgacgttcgt     6480
tcgactgatg agctattgaa acttgttgaa acgttgggtc catacatttg ccttttgaaa    6540
acacacgttg atatcttgga tgatttcagt tatgagggta ctgtcgttcc attgaaagca    6600
ttggcagaga aatacaagtt cttgatattt gaggacagaa aattcgccga tatcggtaac    6660
acagtcaaat tacaatatac atcgggcgtt taccgtatcg cagaatggtc tgatatcacc    6720
aacgcccacg gggttactgg tgctggtatt gttgctggct tgaaacaagg tgcgcaagag    6780
gtcaccaaag aaccaagggg attattgatg cttgctgaat tgtcttccaa gggttctcta    6840
gcacacggtg aatatactaa gggtaccgaa gcttggcgta atcatggtca tagctgtttc    6900
ctgtgtgaaa ttgttatccg ctcacaattc cacacaacat acgagccgga agcataaagt    6960
gtaaagcctg gggtgcctaa tgagtgagct aactcacatt aattgcgttg cgctcactgc    7020
ccgctttcca gtcgggaaac ctgtcgtgcc agctgcatta atgaatcggc caacgcgcgg    7080
ggagaggcgg tttgcgtatt gggcgctctt ccgcttcctc gctcactgac tcgctgcgct    7140
cggtcgttcg gctgcggcga gcggtatcag ctcactcaaa ggcggtaata cggttatcca    7200
cagaatcagg ggataacgca ggaaagaaca tgtgagcaaa aggccagcaa aaggccagga    7260
accgtaaaaa ggccgcgttg ctggcgtttt tccataggct ccgcccccct gacgagcatc    7320
acaaaaatcg acgctcaagt cagaggtggc gaaacccgac aggactataa agataccagg    7380
cgtttccccc tggaagctcc ctcgtgcgct ctcctgttcc gaccctgccg cttaccggat    7440
acctgtccgc ctttctccct tcgggaagcg tggcgctttc tcatagctca cgctgtaggt    7500
atctcagttc ggtgtaggtc gttcgctcca agctgggctg tgtgcacgaa ccccccgttc    7560
agcccgaccg ctgcgcctta tccggtaact atcgtcttga gtccaacccg gtaagacacg    7620
acttatcgcc actggcagca gccactggta acaggattag cagagcgagg tatgtaggcg    7680
gtgctacaga gttcttgaag tggtggccta actacggcta cactagaagg acagtatttg    7740
gtatctgcgc tctgctgaag ccagttacct tcggaaaaag agttggtagc tcttgatccg    7800
gcaaacaaac caccgctggt agcggtggtt tttttgtttg caagcagcag attacgcgca    7860
gaaaaaaagg atctcaagaa gatcctttga tcttttctac ggggtctgac gctcagtgga    7920
acgaaaactc acgttaaggg attttggtca tgagattatc aaaaaggatc ttcacctaga    7980
tccttttaaa ttaaaaatga agttttaaat caatctaaag tatatatgag taaacttggt    8040
ctgacagtta ccaatgctta atcagtgagg cacctatctc agcgatctgt ctatttcgtt    8100
catccatagt tgcctgactc cccgtcgtgt agataactac gatacgggag ggcttaccat    8160
ctggccccag tgctgcaatg ataccgcgag acccacgctc accggctcca gatttatcag    8220
caataaacca gccagccgga agggccgagc gcagaagtgg tcctgcaact ttatccgcct    8280
ccatccagtc tattaattgt tgccgggaag ctagagtaag tagttcgcca gttaatagtt    8340
tgcgcaacgt tgttgccatt gctacaggca tcgtggtgtc acgctcgtcg tttggtatgg    8400
```

| | |
|---|---|
| cttcattcag ctccggttcc caacgatcaa ggcgagttac atgatccccc atgttgtgca | 8460 |
| aaaaagcggt tagctccttc ggtcctccga tcgttgtcag aagtaagttg gccgcagtgt | 8520 |
| tatcactcat ggttatggca gcactgcata attctcttac tgtcatgcca tccgtaagat | 8580 |
| gcttttctgt gactggtgag tactcaacca agtcattctg agaatagtgt atgcggcgac | 8640 |
| cgagttgctc ttgcccggcg tcaatacggg ataataccgc gccacatagc agaactttaa | 8700 |
| aagtgctcat cattggaaaa cgttcttcgg ggcgaaaact ctcaaggatc ttaccgctgt | 8760 |
| tgagatccag ttcgatgtaa cccactcgtg cacccaactg atcttcagca tcttttactt | 8820 |
| tcaccagcgt ttctgggtga gcaaaaacag gaaggcaaaa tgccgcaaaa aagggaataa | 8880 |
| gggcgacacg gaaatgttga atactcatac tcttcctttt tcaatattat tgaagcattt | 8940 |
| atcagggtta ttgtctcatg agcggataca tatttgaatg tatttagaaa aataaacaaa | 9000 |
| tagggggttcc gcgcacattt ccccgaaaag tgccacctga cgt | 9043 |

<210> SEQ ID NO 70
<211> LENGTH: 7721
<212> TYPE: DNA
<213> ORGANISM: Artificial Sequence
<220> FEATURE:
<223> OTHER INFORMATION: pGV1954

<400> SEQUENCE: 70

| | |
|---|---|
| ccagttaact gtgggaatac tcaggtatcg taagatgcaa gagttcgaat ctcttagcaa | 60 |
| ccattatttt tttcctcaac ataacgagaa cacacagggg cgctatcgca cagaatcaaa | 120 |
| ttcgatgact ggaaattttt tgttaatttc agaggtcgcc tgacgcatat acctttttca | 180 |
| actgaaaaat tgggagaaaa aggaaaggtg agagcgccgg aaccggcttt tcatatagaa | 240 |
| tagagaagcg ttcatgacta atgcttgcat cacaatact tgaagttgac aatattattt | 300 |
| aaggacctat tgttttttcc aataggtggt tagcaatcgt cttactttct aacttttctt | 360 |
| accttttaca tttcagcaat atatatatat atatttcaag gatataccat tctaatgtct | 420 |
| gcccctaaga agatcgtcgt tttgccaggt gaccacgttg gtcaagaaat cacagccgaa | 480 |
| gccattaagg ttcttaaagc tatttctgat gttcgttcca atgtcaagtt cgatttcgaa | 540 |
| aatcatttaa ttggtggtgc tgctatcgat gctacaggtg ttccacttcc agatgaggcg | 600 |
| ctggaagcct ccaagaaggc tgatgccgtt ttgttaggtg ctgtgggtgg tcctaaatgg | 660 |
| ggtaccggta gtgttagacc tgaacaaggt ttactaaaaa tccgtaaaga acttcaattg | 720 |
| tacgccaact taagaccatg taactttgca tccgactctc ttttagactt atctccaatc | 780 |
| aagccacaat tgctaaagg tactgacttc gttgttgtca gagaattagt gggaggtatt | 840 |
| tactttggta agagaaagga agacgatggt gatggtgtcg cttgggatag tgaacaatac | 900 |
| accgttccag aagtgcaaag aatcacaaga atggccgctt tcatggccct acaacatgag | 960 |
| ccaccattgc ctatttggtc cttggataaa gctaatgttt tggcctcttc aagattatgg | 1020 |
| agaaaaactg tggaggaaac catcaagaac gaattcccta cattgaaggt tcaacatcaa | 1080 |
| ttgattgatt ctgccgccat gatcctagtt aagaacccaa cccacctaaa tggtattata | 1140 |
| atcaccagca acatgtttgg tgatatcatc tccgatgaag cctccgttat cccaggttcc | 1200 |
| ttgggtttgt tgccatctgc gtccttggcc tctttgccag acaagaacac cgcatttggt | 1260 |
| ttgtacgaac catgccacgg ttctgctcca gatttgccaa agaataaggt caaccctatc | 1320 |
| gccactatct tgtctgctgc aatgatgttg aaattgtcat tgaacttgcc tgaagaaggt | 1380 |
| aaggccattg aagatgcagt taaaaaggtt ttggatgcag gtatcagaac tggtgattta | 1440 |

```
ggtggttcca acagtaccac cgaagtcggt gatgctgtcg ccgaagaagt taagaaaatc    1500
cttgcttaaa aagattctct tttttttatga tatttgtaca taaactttat aaatgaaatt   1560
cataatagaa acgacacgaa attacaaaat ggaatatgtt cataggggtag acgaaactat   1620 atacgcaatc tacatacatt tatcaagaag gagaaaaagg aggatgtaaa ggaatacagg    1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860
aaaacactca atgacctgac catttgatgg agttgccggc ttgatcgaga atggcagctc    1920
ttatatacaa gttctttttag caagcgccgc tgcattattc aagtctcatc atatgaaatt   1980
tctttcgaga gattgtcata atcaaaaaat tgcataatgc atttcttgca acacattttc    2040
tgatataatc ttaccttaat gcaggtttac gtattagttt ttctaaaaga aacgcgacct    2100
ttggatatgg aggcttttcc cataaacgca tgtagtatgc atttacgatg agaatcaatt    2160
tttttccaag gggcgcaaaa cgcataaacg cataaagtat gcatcagaag gattctcacc    2220
tggttgcaac catacaggtg ttagcgacag taatagaaaa aaaattaaaa taatggtgtt    2280
attgttattt gctttatttc cttggccttt gttgaaggaa ttcgtatacg tattacaaat    2340
aactagtatc gaggaacttg aaagagctga aattttttgca ttcttcttcg gtgattatgc   2400
ctaagccaat gaggtcgccc caaaagaccg caatcttgtc acgaccataa gccatataat    2460
cgcgaacaaa aacccgtttt taggaaggac agaggtccat atcaatataa ttaagaaggc    2520
atgttggcct ctgtttctta atatattcta aataagatgt aaggccttgt aattcagttt    2580
gttcacaaaa ttaaaaactg tttaatgttt tttgttttgt tgtagtattc gagcattaag    2640
gataaaaaaa gcttgtgaat aaaaatcttt cgctaaaaat caatataaga aaatggtaag    2700
cagctgaaag ataataaggt atggttaaag atcacaccac cctcttcaat tagctaagat    2760
catagctaaa ggtacaaaac cgaatacgaa agtaaataaa ttaatcagca taaaattaaa    2820
taataaacca cctaaaatat tagaagctaa tctttaacct ggaagacagg acagaaaagt    2880
aattacaaga acatatgtga aaaaaaatag ttgatatttt aaaccaaatc agaaatttat    2940
tatactaaaa ctatatctat gccaattatt tacctaaaca tctataacct tcaaaagtaa    3000
aaaaatacac aaacgttgaa tcatgagttt tatgttaatt agcggccgca gatcttcatc    3060
ctgccactgc aattctttc atatcggtca tatatcctct cagcttttta cccacctgtt    3120
ctatagcatg tgaacgaata gcttcattta cgtctctcag ttggccattg tcaaccgctc    3180
cttccggaat agccttcccc aaatcaccag gttgtaactc ggccatgaag ggctttaaca    3240
acgggacaca tgcgtagcta aataagtaat taccatattc tgcagtgtct gatatgacaa    3300
cattcatctc gtaaagtctt tttcttgcaa tagtatttgc tatcaaaggc aattcatgca    3360
aagactcata gtatgcagat tcttcaatga taccggagtc aaccatagtt tcgaatgcaa    3420
gttctacccc tgccttcacc atagctatca tcaatactcc cttatcaaag tattcttgtt    3480
caccaatttt accttcgtat tgtggggctg tctcgaatgc cgtcttgccg gtttcttctc    3540
tccacgtcaa taacttttta tcatcgtttg cccaatctgc catcattcct gaggaaaact    3600
caccggagat aatatcgtcc atgtgctttt ggaataatgg tgccatgatc tctttttagtt   3660 gctcagataa ggcgtaggct cttagcttgg ccggatttga aagtctatcc atcatcaatg    3720
ttatgccacc ttgtttaagt gcctcggtga ttgtctccca accaaattgt atcaactttt    3780
```

```
cagcataggc aggatctgta ccctcttcga ccaatttatc aaagcatagt aaagaccctg    3840
cctgcaacat tccgcacaga atggtttgtt cacccattaa gtcactcttg acctcagcta    3900
cgaaagaact ctctaacaca cccgctctat gacctccggt tgcggctgcc catgccttcg    3960
caattgccat accttcacct ttggggtcat tttcaggatg tacggcgatc aatgtaggta    4020
caccaaaacc cctcttgtac tcctctctga cttccgtacc tgggcacttt ggtgcaacca    4080
ttacgactgt tatatctttt ctgatctgct cgcccacttc aacgatatta aagccatgag    4140
agtaacctaa agctgcccca tccttcatca gcggttgaac tgttcttact acgtctgagt    4200
gttgcttatc tggtgttagg ttaatcacta aatctgcctg agggatcagt tcttcgtaag    4260
taccaacttt gaacccattt tccgtcgctt tacgccagga ggccctcttt tctgcaattg    4320
cctctttcct caatgcatac gaaatatcca gacctgaatc tctcatgttt aaaccttggt    4380
ttagaccctg agcaccgcag ccaacaatta ctactttctt tccttgcaga taagaagcac    4440
catcagcaaa ctcgtccctt cccataaatc tgcacttacc cagttgagcc aattgttgtc    4500
tcaaatttaa tgtgttaaaa tagttggcca tctcgactat tgatatagtg tttaagcgaa    4560
tgacagaaga ttaatttctt ggtatgttag gaaagaataa aggagaataa gaataattag    4620
aacaatgtag gatggaaaga aagattatca agcatgccga ctttatatac ttgaacggag    4680
gcaaaggatg caaatttttc tcacatttct ttctgccgtt atgttggaag taagactccc    4740
attatcgcaa tactgcaaca cgaatatgca aaatttgctg agttatcgca gatagttgtt    4800
gcaaagatag cggcgtaggt ggccgcgaaa tggggaattc caaaacaaac ggttttttta    4860
ctcctgagaa atacttgtac gggataatcc agggcctacc acccacgctt cgaggattgg    4920 ctttttatttt ttttttttttg gtggcgtttt atttctttcc cgctttctgg gacttgtgcg    4980 gagtttgag aggggcgcgc ggcaaaggat tcccaaaacg gaaatcagac gccaatagcc    5040
agcactcaaa gcagttctgg acccattccg attttcccat ttggttcttg cgcgtgctga    5100
ttccgacacg cgcgtctata aatagcatga agtatccgca caccgcagcg ttagtgaggt    5160
gagggtggca gcaagctaat tcccgcatct ggaatctgaa ctgccccttt tggactaacc    5220
gtgtggttca tgggtgggcg aagtgcgcaa cctcgaaggt tttcttttgc gtgtcggatt    5280
ttacatccgg cggtagcgca tgatgccatg gctggctcca gatacatcct cagggcacca    5340
gcatctataa ttagattggc gcaacatggc tggctgcact gctgtcttca cttcttcctt    5400
tttccggcaa tgaatgatgt atgttttgtg gcaaaagggt ccgcattgta cctgtttaca    5460
gttgagatta tcgttttggg tagcccttca ttacggcata acgtattgag ctccagcttt    5520
tgttcccttt agtgagggtt aattgcgcgc ttggcgtaat catggtcata gctgtttcct    5580
gtgtgaaatt gttatccgct cacaattcca cacaacatag gagccggaag cataaagtgt    5640
aaagcctggg gtgcctaatg agtgaggtaa ctcacattaa ttgcgttgcg ctcactgccc    5700
gctttccagt cgggaaacct gtcgtgccag ctgcattaat gaatcggcca acgcgcgggg    5760
agaggcggtt tgcgtattgg gcgctcttcc gcttcctcgc tcactgactc gctgcgctcg    5820
gtcgttcggc tgcggcgagc ggtatcagct cactcaaagg cggtaatacg ttatccaca    5880 gaatcagggg ataacgcagg aaagaacatg tgagcaaaag gccagcaaaa ggccaggaac    5940
cgtaaaaagg ccgcgttgct ggcgtttttc cataggctcc gccccctga cgagcatcac    6000 aaaaatcgac gctcaagtca gaggtggcga aacccgacag gactataaag ataccaggcg    6060
tttccccctg gaagctccct cgtgcgctct cctgttccga ccctgccgct taccggatac    6120
ctgtccgcct ttctcccttc gggaagcgtg gcgctttctc atagctcacg ctgtaggtat    6180
```

```
ctcagttcgg tgtaggtcgt tcgctccaag ctgggctgtg tgcacgaacc ccccgttcag    6240
cccgaccgct gcgccttatc cggtaactat cgtcttgagt ccaacccggt aagacacgac    6300
ttatcgccac tggcagcagc cactggtaac aggattagca gagcgaggta tgtaggcggt    6360
gctacagagt tcttgaagtg gtggcctaac tacggctaca ctagaaggac agtatttggt    6420
atctgcgctc tgctgaagcc agttaccttc ggaaaaagag ttggtagctc ttgatccggc    6480
aaacaaacca ccgctggtag cggtggtttt tttgtttgca agcagcagat tacgcgcaga    6540
aaaaaaggat ctcaagaaga tcctttgatc ttttctacgg ggtctgacgc tcagtggaac    6600
gaaaactcac gttaagggat tttggtcatg agattatcaa aaaggatctt cacctagatc    6660
cttttaaatt aaaaatgaag ttttaaatca atctaaagta tatatgagta aacttggtct    6720
gacagttacc aatgcttaat cagtgaggca cctatctcag cgatctgtct atttcgttca    6780
tccatagttg cctgactccc cgtcgtgtag ataactacga tacgggaggg cttaccatct    6840
ggccccagtg ctgcaatgat accgcgagac ccacgctcac cggctccaga tttatcagca    6900
ataaaccagc cagccggaag ggccgagcgc agaagtggtc ctgcaacttt atccgcctcc    6960
atccagtcta ttaattgttg ccgggaagct agagtaagta gttcgccagt taatagtttg    7020
cgcaacgttg ttgccattgc tacaggcatc gtggtgtcac gctcgtcgtt tggtatggct    7080
tcattcagct ccggttccca acgatcaagg cgagttacat gatcccccat gttgtgcaaa    7140
aaagcggtta gctccttcgg tcctccgatc gttgtcagaa gtaagttggc cgcagtgtta    7200
tcactcatgg ttatggcagc actgcataat tctcttactg tcatgccatc cgtaagatgc    7260
ttttctgtga ctggtgagta ctcaaccaag tcattctgag aatagtgtat gcggcgaccg    7320
agttgctctt gcccggcgtc aatacgggat aataccgcgc cacatagcag aactttaaaa    7380
gtgctcatca ttggaaaacg ttcttcgggg cgaaaactct caaggatctt accgctgttg    7440
agatccagtt cgatgtaacc cactcgtgca cccaactgat cttcagcatc ttttactttc    7500
accagcgttt ctgggtgagc aaaaacagga aggcaaaatg ccgcaaaaaa gggaataagg    7560
gcgacacgga aatgttgaat actcatactc ttcctttttc aatattattg aagcatttat    7620
cagggttatt gtctcatgag cggatacata tttgaatgta tttagaaaaa taaacaaata    7680
ggggttccgc gcacatttcc ccgaaaagtg ccacctgacg t                        7721
```

<210> SEQ ID NO 71
<211> LENGTH: 7685
<212> TYPE: DNA
<213> ORGANISM: Artificial Sequence
<220> FEATURE:
<223> OTHER INFORMATION: pGV7024

<400> SEQUENCE: 71

```
ttggatcata ctaagaaacc attattatca tgacattaac ctataaaaat aggcgtatca     60
cgaggccctt tcgtctcgcg cgtttcggtg atgacggtga aaacctctga cacatgcagc    120
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt tcaattcaa ttcatcattt tttttttatt     300 ctttttttg atttcggttt ctttgaaatt ttttgattc ggtaatctcc gaacagaagg     360
aagaacgaag gaaggagcac agacttagat tggtatatat acgcatatgg caaattaaag    420
ccttcgagcg tcccaaaacc ttctcaagca aggttttcag tataatgtta catgcgtaca    480
```

```
cgcgtctgta cagaaaaaaa agaaaaattt gaaatataaa taacgttctt aatactaaca   540
taactataaa aaaataaata gggacctaga cttcaggttg tctaactcct tccttttcgg   600
ttagagcgga tgtgggggga gggcgtgaat gtaagcgtga cataagaatt cttattcctt   660
tgccctcgga cgagtgctgg ggcgtcggtt ccactatcg gcgagtactt ctacacagcc    720
atcggtccag acggccgcgc ttctgcgggc gatttgtgta cgcccgacag tcccggctcc   780
ggatcggacg attgcgtcgc atcgaccctg cgcccaagct gcatcatcga aattgccgtc   840
aaccaagctc tgatagagtt ggtcaagacc aatgcggagc atatacgccc ggaggcgcgg   900
cgatcctgca agctccggat gcctccgctc gaagtagcgc gtctgctgct ccatacaagc   960
caaccacggc ctccagaaga ggatgttggc gacctcgtat tgggaatccc cgaacatcgc  1020
ctcgctccag tcaatgaccg ctgttatgcg gccattgtcc gtcaggacat tgttggagcc  1080
gaaatccgca tgcacgaggt gccggacttc ggggcagtcc tcggcccaaa gcatcagctc  1140
atcgagagcc tgcgcgacgg acgcactgac ggtgtcgtcc atcacagttt gccagtgata  1200
cacatgggga tcagcaatcg cgcatatgaa atcacgccat gtagtgtatt gaccgattcc  1260
ttgcggtccg aatgggccga acccgctcgt ctggctaaga tcggccgcag cgatcgcatc  1320
catgccctcc gcgaccggct ggagaacagc gggcagttcg gtttcaggca ggtcttgcaa  1380
cgtgacaccc tgtgcacggc gggagatgca ataggtcagg ctctcgctga actcccaat   1440 gtcaagcact tccggaatcg ggagcgcggc cgatgcaaag tgccgataaa cataacgatc  1500
tttgtagaaa ccatcggcgc agctatttac ccgcaggaca tatccacgcc tcctacatc   1560 gaagctgaaa gcacgagatt cttcgccctc cgagagctgc atcaggtcgg agacgctgtc  1620
gaacttttcg atcagaaact tctcgacaga cgtcgcggtg agttcaggct ttttacccat  1680
actagttttt agtttatgta tgtgtttttt gtagttatag atttaagcaa gaaaagaata  1740
caaacaaaaa attgaaaaag attgatttag aattaaaaag aaaaatattt acgtaagaag  1800
ggaaaatagt aaatgttgca agttcactaa actcctaaat tatgctgccc tttatattcc  1860
ctgttacagc agccgagcca aaggtatata ggctcctttg cattagcatg cgtaacaaac  1920
cacctgtcag tttcaaccga ggtggtatcc gagagaattg tgtgattgct ttaattaatt  1980
tcggagaatc tcacatgcca ctgaagatta aaaactggat gccagaaaag gggtgtccag  2040
gtgtaacatc aatagaggaa gctgaaaagt cttagaacgg gtaatcttcc accaacctga  2100
tgggttccta gatataatct cgaagggaat aagtagggtg ataccgcaga agtgtctgaa  2160
tgtattaagg tcctcacagt ttaaatcccg ctcacactaa cgtaggatta ttataactca  2220 aaaaatggc attattctaa gtaagttaaa tatccgtaat ctttaaacag cggccgcaga   2280
tctctcgagt cgaaactaag ttctggtgtt taaaactaa aaaaaagact aactataaaa   2340
gtagaattta agaagtttaa gaaatagatt tacagaatta caatcaatac ctaccgtctt  2400
tatatactta ttagtcaagt aggggaataa tttcagggaa ctggtttcaa ccttttttt   2460 cagcttttc caaatcagag agagcagaag gtaatagaag gtgtaagaaa atgagataga   2520
tacatgcgtg ggtcaattgc cttgtgtcat catttactcc aggcaggttg catcactcca  2580
ttgaggttgt gcccgttttt tgcctgtttg tgccctgtt ctctgtagtt gcgctaagag   2640
aatggaccta tgaactgatg gttggtgaag aaaacaatat tttggtgctg ggattctttt  2700
tttttctgga tgccagctta aaagcgggc tccattatat ttagtggatg ccaggaataa   2760
actgttcacc cagacaccta cgatgttata tattctgtgt aacccgcccc ctattttggg  2820
catgtacggg ttacagcaga attaaaaggc taatttttg actaaataaa gttaggaaaa    2880
```

-continued

```
tcactactat taattattta cgtattcttt gaaatggcga gtattgataa tgataaactg    2940
gatccgtcga caaacttaga ttagattgct atgctttctt tctaatgagc aagaagtaaa    3000
aaaagttgta atagaacaag aaaaatgaaa ctgaaacttg agaaattgaa gaccgtttat    3060
taacttaaat atcaatggga ggtcatcgaa agagaaaaaa atcaaaaaaa aattttcaa     3120 gaaaaagaaa cgtgataaaa attttattg cctttttcga cgaagaaaaa gaaacgaggc     3180
ggtctctttt ttcttttcca aacctttagt acgggtaatt aacgacaccc tagaggaaga    3240 aagagggaa atttagtatg ctgtgcttgg gtgttttgaa gtggtacggc gatgcgcgga     3300
gtccgagaaa atctggaaga gtaaaaaagg agtagaaaca ttttgaagct atgagctcag    3360
atctgttaac cttgttttat atttgttgta aaaagtagat aattacttcc ttgatgatct    3420
gtaaaaaaga gaaaagaaa gcatctaaga acttgaaaaa ctacgaatta gaaaagacca    3480
aatatgtatt tcttgcattg accaatttat gcaagtttat atatatgtaa atgtaagttt    3540
cacgaggttc tactaaacta aaccacccc ttggttagaa gaaaagagtg tgtgagaaca    3600
ggctgttgtt gtcacacgat tcggacaatt ctgtttgaaa gagagagagt aacagtacga    3660
tcgaacgaac tttgctctgg agatcacagt gggcatcata gcatgtggta ctaaacccctt   3720 tcccgccatt ccagaacctt cgattgcttg ttacaaaacc tgtgagccgt cgctaggacc    3780
ttgttgtgtg acgaaattgg aagctgcaat aataggaag acaggaagtc gagcgtgtct    3840 gggtttttttc agttttgttc tttttgcaaa caaatcacga gcgacggtaa tttctttctc    3900
gataagaggc cacgtgcttt atgagggtaa catcaattca agaaggaggg aaacacttcc    3960
tttttctggc cctgataata gtatgagggt gaagccaaaa taaggattc gcgcccaaat    4020 cggcatcttt aaatgcaggt atgcgatagt tcctcactct ttccttactc acgagtaatt    4080
cttgcaaatg cctattatgc agatgttata atatctgtgc gtcttgagtt gagcctaggg    4140
agctccagct tttgttccct ttagtgaggg ttaattgcgc gcttggcgta atcatggtca    4200
tagctgtttc ctgtgtgaaa ttgttatccg ctcacaattc cacacaacat aggagccgga    4260
agcataaagt gtaaagcctg gggtgcctaa tgagtgaggt aactcacatt aattgcgttg    4320
cgctcactgc ccgctttcca gtcgggaaac ctgtcgtgcc agctgcatta atgaatcggc    4380
caacgcgcgg ggagaggcgg tttgcgtatt gggcgctctt ccgcttcctc gctcactgac    4440
tcgctgcgct cggtcgttcg gctgcggcga gcggtatcag ctcactcaaa ggcggtaata    4500
cggttatcca cagaatcagg ggataacgca ggaaagaaca tgtgagcaaa aggccagcaa    4560
aaggccagga accgtaaaaa ggccgcgttg ctggcgtttt tccataggct ccgcccccct    4620
gacgagcatc acaaaaatcg acgctcaagt cagaggtggc gaaacccgac aggactataa    4680
agataccagg cgtttccccc tggaagctcc ctcgtgcgct ctcctgttcc gaccctgccg    4740
cttaccggat acctgtccgc ctttctccct tcgggaagcg tggcgctttc tcatagctca    4800
cgctgtaggt atctcagttc ggtgtaggtc gttcgctcca agctgggctg tgtgcacgaa    4860
ccccccgttc agcccgaccg ctgcgcctta tccggtaact atcgtcttga gtccaacccg    4920
gtaagacacg acttatcgcc actggcagca gccactggta acaggattag cagagcgagg    4980
tatgtaggcg gtgctacaga gttcttgaag tggtggccta actacggcta cactagaagg    5040
acagtatttg gtatctgcgc tctgctgaag ccagttacct tcggaaaaag agttggtagc    5100
tcttgatccg gcaaacaaac caccgctggt agcggtggtt ttttgtttg caagcagcag    5160 attacgcgca gaaaaaaagg atctcaagaa gatcctttga tcttttctac ggggtctgac    5220
```

```
gctcagtgga acgaaaactc acgttaaggg attttggtca tgagattatc aaaaaggatc    5280
ttcacctaga tccttttaaa ttaaaaatga agtttttaaat caatctaaag tatatatgag    5340
taaacttggt ctgacagtta ccaatgctta atcagtgagg cacctatctc agcgatctgt    5400
ctatttcgtt catccatagt tgcctgactc cccgtcgtgt agataactac gatacgggag    5460
ggcttaccat ctggccccag tgctgcaatg ataccgcgag acccacgctc accggctcca    5520
gatttatcag caataaacca gccagccgga agggccgagc gcagaagtgg tcctgcaact    5580
ttatccgcct ccatccagtc tattaattgt tgccgggaag ctagagtaag tagttcgcca    5640
gttaatagtt tgcgcaacgt tgttgccatt gctacaggca tcgtggtgtc acgctcgtcg    5700
tttggtatgg cttcattcag ctccggttcc caacgatcaa ggcgagttac atgatccccc    5760
atgttgtgca aaaagcggt tagctccttc ggtcctccga tcgttgtcag aagtaagttg    5820
gccgcagtgt tatcactcat ggttatggca gcactgcata attctcttac tgtcatgcca    5880
tccgtaagat gcttttctgt gactggtgag tactcaacca agtcattctg agaatagtgt    5940
atgcggcgac cgagttgctc ttgcccggcg tcaatacggg ataataccgc gccacatagc    6000
agaactttaa aagtgctcat cattggaaaa cgttcttcgg ggcgaaaact ctcaaggatc    6060
ttaccgctgt tgagatccag ttcgatgtaa cccactcgtg cacccaactg atcttcagca    6120
tcttttactt tcaccagcgt ttctgggtga gcaaaaacag gaaggcaaaa tgccgcaaaa    6180
aagggaataa gggcgacacg gaaatgttga atactcatac tcttcctttt tcaatattat    6240
tgaagcattt atcagggtta ttgtctcatg agcggataca tatttgaatg tatttagaaa    6300
aataaacaaa taggggttcc gcgcacattt ccccgaaaag tgccacctga acgaagcatc    6360
tgtgcttcat tttgtagaac aaaaatgcaa cgcgagagcg ctaatttttc aaacaaagaa    6420
tctgagctgc attttacag aacagaaatg caacgcgaaa gcgctatttt accaacgaag    6480
aatctgtgct tcatttttgt aaaacaaaaa tgcaacgcga gagcgctaat ttttcaaaca    6540
aagaatctga gctgcatttt tacagaacag aaatgcaacg cgagagcgct attttaccaa    6600
caaagaatct atacttcttt tttgttctac aaaaatgcat cccgagagcg ctatttttct    6660
aacaaagcat cttagattac tttttttctc ctttgtgcgc tctataatgc agtctcttga    6720
taactttttg cactgtaggt ccgttaaggt tagaagaagg ctactttggt gtctattttc    6780
tcttccataa aaaagcctg actccacttc ccgcgtttac tgattactag cgaagctgcg    6840
ggtgcatttt ttcaagataa aggcatcccc gattatattc tataccgatg tggattgcgc    6900
atactttgtg aacagaaagt gatagcgttg atgattcttc attggtcaga aaattatgaa    6960
cggtttcttc tattttgtct ctatatacta cgtataggaa atgtttacat tttcgtattg    7020
ttttcgattc actctatgaa tagttcttac tacaattttt ttgtctaaag agtaatacta    7080
gagataaaca taaaaaatgt agaggtcgag tttagatgca agttcaagga gcgaaaggtg    7140
gatgggtagg ttataataggg atatagcaca gagatatata gcaaagagat acttttgagc    7200
aatgtttgtg gaagcggtat tcgcaatatt ttagtagctc gttacagtcc ggtgcgtttt    7260
tggttttttg aaagtgcgtc ttcagagcgc ttttggtttt caaaagcgct ctgaagttcc    7320
tatactttct agagaatagg aacttcggaa taggaacttc aaagcgtttc cgaaaacgag    7380
cgcttccgaa aatgcaacgc gagctgcgca catacagctc actgttcacg tcgcacctat    7440
atctgcgtgt tgcctgtata tatatataca tgagaagaac ggcatagtgc gtgtttatgc    7500
ttaaatgcgt acttatatgc gtctatttat gtaggatgaa aggtagtcta gtacctcctg    7560
tgatattatc ccattccatg cggggtatcg tatgcttcct tcagcactac cctttagctg    7620
```

```
ttctatatgc tgccactcct caattggatt agtctcatcc ttcaatgcta tcatttcctt    7680
tgata                                                                7685

<210> SEQ ID NO 72
<211> LENGTH: 4105
<212> TYPE: DNA
<213> ORGANISM: Artificial Sequence
<220> FEATURE:
<223> OTHER INFORMATION: pGV2359

<400> SEQUENCE: 72
ctgcttaatt aagatcaggt cagtacaaac gcaacacgaa agaacaaaaa aagaagaaaa      60
cagaaggcca agacagggtc aatgagactg ttgtcctcct actgtcccta tgtctctggc     120
cgatcacgcg ccattgtccc tcagaaacaa atcaaacacc cacaccccgg gcacccaaag     180
tccccaccca caccaccaat acgtaaacgg ggcgcccct gcaggccctc ctgcgcgcgg      240
cctcccgcct tgcttctctc cccttccttt tcttttttcca gttttcccta ttttgtccct    300
ttttccgcac aacaagtatc agaatggggtt catcaaatct atccaaccta attcgcacgt    360
agactggctt ggtattggca gtttcgtagt tatatatata ctaccatgag tgaaactgtt     420
acgttacctt aaattctttc tccctttaat tttcttttat cttactctcc tacataagac    480
atcaagaaac aattgtatat tgtacacccc cccctccac aaacacaaat attgataata      540 taaggagaa ttcttataca ggaaacttaa tagaacaaat cacatattta atctaatagc      600
cacctgcatt ggcacggtgc aacactactt caacttcatc ttacaaaaag atcacgtgat    660
ctgttgtatt gaactgaaaa ttttttgttt gcttctctct ctctctttca ttatgtgaga    720
tttaaaaacc agaaactaca tcatcgaaaa agagttttaa accattacaa ccattgcgat    780
aagccctctc aaactataac aatactgaca gtactaaata attgcctact ggcttcaca     840 tacgttgcat acgtcgatat agataataat gataatgaca gcaggattat cgtaatacgt    900
aatagttgaa aatctcaaaa atgtgtgggt cattacgtaa ataatgatag gaatgggatt    960
cttctatttt tcctttttcc attctagcag ccgtcgggaa aacgtggcat cctctctttc    1020
gggctcaatt ggagtcacgc tgccgtgagc atcctctctt tccatatcta acaactgagc   1080
acgtaaccaa tggaaaagca tgagcttagc gttgctccaa aaagtattg atggttaat     1140 accatttgtc tgttctcttc tgactttgac tcctcaaaaa aaaaaatct acaatcaaca    1200 gatcgcttca attacgccct cacaaaaact ttttccttc ttcttcgccc acgttaaatt    1260
ttatccctca tgttgtctaa cggatttctg cacttgattt attataaaaa gacaaagaca    1320
taatacttct ctatcaattt cagttattgt tcttccttgc gttattcttc tgttcttctt    1380
tttcttttgt catatataac cataaccaag taatacatat tcaaaatgtc cacaaaatca    1440
tataccagta gagctgagac tcatgcaagt ccggttgcat cgaaactttt acgtttaatg    1500
gatgaaaaga agaccaattt gtgtgcttct cttgacgttc gttcgactga tgagctattg    1560
aaacttgttg aaacgttggg tccatacatt tgccttttga aaacacacgt tgatatcttg    1620
gatgatttca gttatgaggg tactgtcgtt ccattgaaag cattggcaga gaaatacaag    1680
ttcttgatat ttgaggacag aaaattcgcc gatatcggta acacagtcaa attacaatat    1740
acatcgggcg tttaccgtat cgcagaatgg tctgatatca ccaacgccca cggggttact    1800
ggtgctggta ttgttgctgg cttgaaacaa ggtgcgcaag aggtcaccaa agaaccaagg    1860
ggattattga tgcttgctga attgtcttcc aagggttctc tagcacacgg tgaatatact    1920
```

```
aagggtaccg aagcttggcg taatcatggt catagctgtt tcctgtgtga aattgttatc   1980
cgctcacaat tccacacaac atacgagccg aagcataaa  gtgtaaagcc tggggtgcct   2040
aatgagtgag ctaactcaca ttaattgcgt tgcgctcact gcccgctttc cagtcgggaa   2100
acctgtcgtg ccagctgcat taatgaatcg gccaacgcgc ggggagaggc ggtttgcgta   2160
ttgggcgctc ttccgcttcc tcgctcactg actcgctgcg ctcggtcgtt cggctgcggc   2220
gagcggtatc agctcactca aaggcggtaa tacggttatc cacagaatca ggggataacg   2280
caggaaagaa catgtgagca aaaggccagc aaaaggccag gaaccgtaaa aaggccgcgt   2340
tgctggcgtt tttccatagg ctccgccccc ctgacgagca tcacaaaaat cgacgctcaa   2400
gtcagaggtg gcgaaacccg acaggactat aaagatacca ggcgtttccc cctggaagct   2460
ccctcgtgcg ctctcctgtt ccgaccctgc cgcttaccgg atacctgtcc gcctttctcc   2520
cttcgggaag cgtggcgctt tctcatagct cacgctgtag gtatctcagt tcggtgtagg   2580
tcgttcgctc caagctgggc tgtgtgcacg aaccccccgt tcagcccgac cgctgcgcct   2640
tatccggtaa ctatcgtctt gagtccaacc cggtaagaca cgacttatcg ccactggcag   2700
cagccactgg taacaggatt agcagagcga ggtatgtagg cggtgctaca gagttcttga   2760
agtggtggcc taactacggc tacactagaa ggacagtatt tggtatctgc gctctgctga   2820
agccagttac cttcggaaaa agagttggta gctcttgatc cggcaaacaa accaccgctg   2880
gtagcggtgg tttttttgtt tgcaagcagc agattacgcg cagaaaaaaa ggatctcaag   2940
aagatccttt gatcttttct acggggtctg acgctcagtg gaacgaaaac tcacgttaag   3000
ggattttggt catgagatta tcaaaaagga tcttcaccta gatcctttta aattaaaaat   3060
gaagttttaa atcaatctaa agtatatatg agtaaacttg gtctgacagt taccaatgct   3120
taatcagtga ggcacctatc tcagcgatct gtctatttcg ttcatccata gttgcctgac   3180
tccccgtcgt gtagataact acgatacggg agggcttacc atctggcccc agtgctgcaa   3240
tgataccgcg agacccacgc tcaccggctc cagatttatc agcaataaac cagccagccg   3300
gaagggccga gcgcagaagt ggtcctgcaa ctttatccgc ctccatccag tctattaatt   3360
gttgccggga agctagagta agtagttcgc cagttaatag tttgcgcaac gttgttgcca   3420
ttgctacagg catcgtggtg tcacgctcgt cgtttggtat ggcttcattc agctccggtt   3480
cccaacgatc aaggcgagtt acatgatccc ccatgttgtg caaaaaagcg gttagctcct   3540
tcggtcctcc gatcgttgtc agaagtaagt tggccgcagt gttatcactc atggttatgg   3600
cagcactgca taattctctt actgtcatgc catccgtaag atgcttttct gtgactggtg   3660
agtactcaac caagtcattc tgagaatagt gtatgcggcg accgagttgc tcttgcccgg   3720
cgtcaatacg ggataatacc gcgccacata gcagaacttt aaaagtgctc atcattggaa   3780
aacgttcttc ggggcgaaaa ctctcaagga tcttaccgct gttgagatcc agttcgatgt   3840
aacccactcg tgcacccaac tgatcttcag catcttttac tttcaccagc gtttctgggt   3900
gagcaaaaac aggaaggcaa aatgccgcaa aaaagggaat aagggcgaca cggaaatgtt   3960
gaatactcat actcttcctt tttcaatatt attgaagcat ttatcagggt tattgtctca   4020
tgagcggata catatttgaa tgtatttaga aaaataaaca ataggggtt  ccgcgcacat   4080
ttccccgaaa agtgccacct gacgt                                         4105
```

<210> SEQ ID NO 73
<211> LENGTH: 8009
<212> TYPE: DNA
<213> ORGANISM: Artificial Sequence
<220> FEATURE:
<223> OTHER INFORMATION: pGV2157

<400> SEQUENCE: 73

| | | | | | |
|---|---|---|---|---|---|
| ttggatcata | ctaagaaacc | attattatca | tgacattaac | ctataaaaat | aggcgtatca | 60 |
| cgaggcccctt | tcgtctcgcg | cgtttcggtg | atgacggtga | aaacctctga | cacatgcagc | 120 |
| tcccggagac | ggtcacagct | tgtctgtaag | cggatgccgg | gagcagacaa | gcccgtcagg | 180 |
| gcgcgtcagc | gggtgttggc | gggtgtcggg | gctggcttaa | ctatgcggca | tcagagcaga | 240 |
| ttgtactgag | agtgcaccat | accacagctt | tcaattcaa | ttcatcattt | ttttttatt | 300 |
| cttttttttg | atttcggttt | ctttgaaatt | tttttgattc | ggtaatctcc | gaacagaagg | 360 |
| aagaacgaag | gaaggagcac | agacttagat | tggtatatat | acgcatatgt | agtgttgaag | 420 |
| aaacatgaaa | ttgcccagta | ttcttaaccc | aactgcacag | aacaaaaacc | tgcaggaaac | 480 |
| gaagataaat | catgtcgaaa | gctacatata | aggaacgtgc | tgctactcat | cctagtcctg | 540 |
| ttgctgccaa | gctatttaat | atcatgcacg | aaaagcaaac | aaacttgtgt | gcttcattgg | 600 |
| atgttcgtac | caccaaggaa | ttactggagt | tagttgaagc | attaggtccc | aaaatttgtt | 660 |
| tactaaaaac | acatgtggat | atcttgactg | atttttccat | ggagggcaca | gttaagccgc | 720 |
| taaaggcatt | atccgccaag | tacaattttt | tactcttcga | agacagaaaa | tttgctgaca | 780 |
| ttggtaatac | agtcaaattg | cagtactctg | cgggtgtata | cagaatagca | gaatgggcag | 840 |
| acattacgaa | tgcacacggt | gtggtgggcc | caggtattgt | tagcggtttg | aagcaggcgg | 900 |
| cagaagaagt | aacaaaggaa | cctagaggcc | ttttgatgtt | agcagaattg | tcatgcaagg | 960 |
| gctccctatc | tactggagaa | tatactaagg | gtactgttga | cattgcgaag | agcgacaaag | 1020 |
| attttgttat | cggctttatt | gctcaaagag | acatgggtgg | aagagatgaa | ggttacgatt | 1080 |
| ggttgattat | gacacccggt | gtgggtttag | atgacaaggg | agacgcattg | ggtcaacagt | 1140 |
| atagaaccgt | ggatgatgtg | gtctctacag | gatctgacat | tattattgtt | ggaagaggac | 1200 |
| tatttgcaaa | gggaagggat | gctaaggtag | agggtgaacg | ttacagaaaa | gcaggctggg | 1260 |
| aagcatattt | gagaagatgc | ggccagcaaa | actaaaaaac | tgtattataa | gtaaatgcat | 1320 |
| gtatactaaa | ctcacaaatt | agagcttcaa | tttaattata | tcagttatta | ccctatgcgg | 1380 |
| tgtgaaatac | cgcacagatg | cgtaaggaga | aaataccgca | tcaggaaatt | gtaaacgtta | 1440 |
| atattttgtt | aaaattcgcg | ttaaattttt | gttaaatcag | ctcatttttt | aaccaatagg | 1500 |
| ccgaaatcgg | caaaatccct | tataaatcaa | aagaatagac | cgagatagggg | ttgagtgttg | 1560 |
| ttccagtttg | gaacaagagt | ccactattaa | agaacgtgga | ctccaacgtc | aaagggcgaa | 1620 |
| aaaccgtcta | tcagggcgat | ggcccactac | gtgaaccatc | accctaatca | agttttttgg | 1680 |
| ggtcgaggtg | ccgtaaagca | ctaaatcgga | accctaaagg | gagcccccga | tttagagctt | 1740 |
| gacggggaaa | gccggcgaac | gtggcgagaa | aggaagggaa | gaaagcgaaa | ggagcgggcg | 1800 |
| ctagggcgct | ggcaagtgta | gcggtcacgc | tgcgcgtaac | caccacaccc | gccgcgctta | 1860 |
| atgcgccgct | acagggcgcg | tcgcgccatt | cgccattcag | gctgcgcaac | tgttgggaag | 1920 |
| ggcgatcggt | gcgggcctct | tcgctattac | gccagctggc | gaaagggggga | tgtgctgcaa | 1980 |
| ggcgattaag | ttgggtaacg | ccagggtttt | cccagtcacg | acgttgtaaa | acgacggcca | 2040 |
| gtgagcgcgc | gtaatacgac | tcactatagg | gcgaattggg | taccggccgc | aaattaaagc | 2100 |
| cttcgagcgt | cccaaaacct | tctcaagcaa | ggttttcagt | ataatgttac | atgcgtacac | 2160 |
| gcgtctgtac | agaaaaaaaa | gaaaaatttg | aaatataaat | aacgttctta | atactaacat | 2220 |

| | | |
|---|---|---|
| aactataaaa aaataaatag ggacctagac ttcaggttgt ctaactcctt ccttttcggt | 2280 |
| tagagcggat gtgggggagg ggcgtgaatg taagcgtgac ataactaatt acatgactcg | 2340 |
| agcggccgcg gatcctcaag catctaaaac acaaccgttg gaagcgttgg aaaccaactt | 2400 |
| agcatacttg gatagagtac ctcttgtgta acgaggtgga ggtgcaaccc aactttgttt | 2460 |
| acgttgagcc atttccttat cagagactaa taggtcaatc ttgttattat cagcatcaat | 2520 |
| gataatctca tcgccgtctc tgaccaaccc gataggacca ccttcagcgg cttcgggaac | 2580 |
| aatgtggccg attaagaacc cgtgagaacc accagagaat ctaccatcag tcaacaatgc | 2640 |
| aacatcttta cccaaaccgt aacccatcag agcagaggaa ggctttagca tttcaggcat | 2700 |
| acctggtgca cctcttggac cttcatatct gataacaaca acggttttt cacccttctt | 2760 |
| gatttcacct ctttccaagg cttcaataaa ggcaccttcc tcttcgaaca cacgtgctct | 2820 |
| acccttgaag taagtacctt ccttaccggt aattttaccc acagctccac ctggtgccaa | 2880 |
| tgaaccgtac agaatttgca agtgaccgtt ggccttgatt gggtgggaga gtggcttaat | 2940 |
| aatctcttgt ccttcaggta ggcttggtgc tttctttgca cgttctgcca aagtgtcacc | 3000 |
| ggtaacagtc attgtgttac cgtgcaacat gttgttttca tatagatact taatcacaga | 3060 |
| ttgggtacca ccaacgttaa tcaaatcggc catgacgtat ttaccagaag gtttgaagtc | 3120 |
| accgatcaat ggtgtagtat cactgattct ttggaaatca tctggtgaca acttgacacc | 3180 |
| cgcagagtga gcaacagcca ccaaatgcaa aacagcatta gtggaccac cggttgcaac | 3240 |
| gacataagta atggcgtttt caaaagcctc ttttgtgagg atatcacgag gtaaaatacc | 3300 |
| caattccatt gtcttcttga tgtattcacc aatgttgtca cactcagcta acttctcctt | 3360 |
| ggaaacggct gggaaggaag aggagtttgg aatggtcaaa cctagcactt cagcggcaga | 3420 |
| agccattgtg ttggcagtat acataccacc acaagaacca ggacctgggc atgcatgttc | 3480 |
| cacaacatct tctctttctt cttcagtgaa ttgcttggaa atatattcac cgtaggattg | 3540 |
| gaacgcagag acgatatcga tgttttaga gatcttcgaa gaaccacatg ttggatgacc | 3600 |
| gggcaagata gtaccaccat ataccatgat ggaaggtctg ttatgtctac ccatggccat | 3660 |
| catgacaccg ggcatgtttt tgtcacatga tgggatggcg atgttagcat cgtagtgttg | 3720 |
| tgccatcatg atggtttcaa aggagtctgc aatgatttct ctactttgta acgagtatct | 3780 |
| cataccttta gtacccatag agataccgtc tgaaacaccg atggtgttga actgcatagc | 3840 |
| tttcaaaccc gcttttcaa tggattgaga acatctgtta ttcaagtcca atagatgcat | 3900 |
| gttacatggg ttaccggacc accaacagga accaaccccg acttgaggct tcttgaaatc | 3960 |
| ttccttcttg aaaccggtgg cataaagcat ggcctgggac gcaccttggc ccttaggttc | 4020 |
| agtgatgata tacgagtact tgttgagctt cttcatgtcg acaaacttag attagattgc | 4080 |
| tatgctttct ttctaatgag caagaagtaa aaaagttgt aatagaacaa gaaaatgaa | 4140 |
| actgaaactt gagaaattga agaccgttta ttaacttaaa tatcaatggg aggtcatcga | 4200 |
| aagagaaaaa aatcaaaaaa aaaattttca agaaaaagaa acgtgataaa aattttatt | 4260 |
| gccttttttcg acgaagaaaa agaaacgagg cggtctcttt tttcttttcc aaacctttag | 4320 |
| tacgggtaat taacgacacc ctagaggaag aaagagggga aatttagtat gctgtgcttg | 4380 |
| ggtgttttga agtggtacgg cgatgcgcgg agtccgagaa aatctggaag agtaaaaaag | 4440 |
| gagtagaaac atttttgaagc tatgagctcc agctttttgtt ccctttagtg agggttaatt | 4500 |
| gcgcgcttgg cgtaatcatg gtcatagctg tttcctgtgt gaaattgtta tccgctcaca | 4560 |
| attccacaca acataggagc cggaagcata aagtgtaaag cctggggtgc ctaatgagtg | 4620 |

```
aggtaactca cattaattgc gttgcgctca ctgcccgctt tccagtcggg aaacctgtcg    4680
tgccagctgc attaatgaat cggccaacgc gcggggagag gcggtttgcg tattgggcgc    4740
tcttccgctt cctcgctcac tgactcgctg cgctcggtcg ttcggctgcg gcgagcggta    4800
tcagctcact caaaggcggt aatacggtta tccacagaat caggggataa cgcaggaaag    4860
aacatgtgag caaaaggcca gcaaaaggcc aggaaccgta aaaaggccgc gttgctggcg    4920
tttttccata ggctccgccc ccctgacgag catcacaaaa atcgacgctc aagtcagagg    4980
tggcgaaacc cgacaggact ataaagatac caggcgtttc ccctggaag ctccctcgtg    5040
cgctctcctg ttccgaccct gccgcttacc ggatacctgt ccgcctttct cccttcggga    5100
agcgtggcgc tttctcatag ctcacgctgt aggtatctca gttcggtgta ggtcgttcgc    5160
tccaagctgg gctgtgtgca cgaacccccc gttcagcccg accgctgcgc cttatccggt    5220
aactatcgtc ttgagtccaa cccggtaaga cacgacttat cgccactggc agcagccact    5280
ggtaacagga ttagcagagc gaggtatgta ggcggtgcta cagagttctt gaagtggtgg    5340
cctaactacg gctacactag aaggacagta tttggtatct gcgctctgct gaagccagtt    5400
accttcggaa aaagagttgg tagctcttga tccggcaaac aaaccaccgc tggtagcggt    5460
ggtttttttg tttgcaagca gcagattacg cgcagaaaaa aaggatctca agaagatcct    5520
ttgatctttt ctacggggtc tgacgctcag tggaacgaaa actcacgtta agggattttg    5580
gtcatgagat tatcaaaaag gatcttcacc tagatccttt taaattaaaa atgaagtttt    5640
aaatcaatct aaagtatata tgagtaaact tggtctgaca gttaccaatg cttaatcagt    5700
gaggcaccta tctcagcgat ctgtctattt cgttcatcca tagttgcctg actccccgtc    5760
gtgtagataa ctacgatacg ggagggctta ccatctggcc ccagtgctgc aatgataccg    5820
cgagacccac gctcaccggc tccagattta tcagcaataa accagccagc cggaagggcc    5880
gagcgcagaa gtggtcctgc aactttatcc gcctccatcc agtctattaa ttgttgccgg    5940
gaagctagag taagtagttc gccagttaat agtttgcgca acgttgttgc cattgctaca    6000
ggcatcgtgg tgtcacgctc gtcgtttggt atggcttcat tcagctccgg ttcccaacga    6060
tcaaggcgag ttacatgatc ccccatgttg tgcaaaaaag cggttagctc cttcggtcct    6120
ccgatcgttg tcagaagtaa gttggccgca gtgttatcac tcatggttat ggcagcactg    6180
cataattctc ttactgtcat gccatccgta agatgctttt ctgtgactgg tgagtactca    6240
accaagtcat tctgagaata gtgtatgcgg cgaccgagtt gctcttgccc ggcgtcaata    6300
cgggataata ccgcgccaca tagcagaact ttaaaagtgc tcatcattgg aaaacgttct    6360
tcggggcgaa aactctcaag gatcttaccg ctgttgagat ccagttcgat gtaacccact    6420
cgtgcaccca actgatcttc agcatctttt actttcacca gcgtttctgg gtgagcaaaa    6480
acaggaaggc aaaatgccgc aaaaaaggga ataagggcga cacggaaatg ttgaatactc    6540
atactcttcc tttttcaata ttattgaagc atttatcagg gttattgtct catgagcgga    6600
tacatatttg aatgtatttta gaaaaataaa caaatagggg ttccgcgcac atttccccga    6660
aaagtgccac ctgaacgaag catctgtgct tcattttgta gaacaaaaat gcaacgcgag    6720
agcgctaatt tttcaaacaa agaatctgag ctgcattttt acagaacaga aatgcaacgc    6780
gaaagcgcta ttttaccaac gaagaatctg tgcttcattt ttgtaaaaca aaaatgcaac    6840
gcgagagcgc taatttttca aacaaagaat ctgagctgca ttttacaga acagaaatgc    6900
aacgcgagag cgctatttta ccaacaaaga atctatactt ctttttttgtt ctacaaaaat    6960
```

| gcatcccgag agcgctattt ttctaacaaa gcatcttaga ttactttttt tctcctttgt | 7020 |
| gcgctctata atgcagtctc ttgataactt tttgcactgt aggtccgtta aggttagaag | 7080 |
| aaggctactt tggtgtctat tttctcttcc ataaaaaaag cctgactcca cttcccgcgt | 7140 |
| ttactgatta ctagcgaagc tgcgggtgca ttttttcaag ataaaggcat ccccgattat | 7200 |
| attctatacc gatgtggatt gcgcatactt tgtgaacaga aagtgatagc gttgatgatt | 7260 |
| cttcattggt cagaaaatta tgaacggttt cttctatttt gtctctatat actacgtata | 7320 |
| ggaaatgttt acattttcgt attgttttcg attcactcta tgaatagttc ttactacaat | 7380 |
| tttttttgtct aaagagtaat actagagata aacataaaaa atgtagaggt cgagtttaga | 7440 |
| tgcaagttca aggagcgaaa ggtggatggg taggttatat agggatatag cacagagata | 7500 |
| tatagcaaag agatactttt gagcaatgtt tgtggaagcg gtattcgcaa tattttagta | 7560 |
| gctcgttaca gtccggtgcg ttttttggttt tttgaaagtg cgtcttcaga gcgcttttgg | 7620 |
| ttttcaaaag cgctctgaag ttcctatact ttctagagaa taggaacttc ggaataggaa | 7680 |
| cttcaaagcg tttccgaaaa cgagcgcttc cgaaaatgca acgcgagctg cgcacataca | 7740 |
| gctcactgtt cacgtcgcac ctatatctgc gtgttgcctg tatatatata tacatgagaa | 7800 |
| gaacggcata gtgcgtgttt atgcttaaat gcgtacttat atgcgtctat ttatgtagga | 7860 |
| tgaaaggtag tctagtacct cctgtgatat tatcccattc catgcggggt atcgtatgct | 7920 |
| tccttcagca ctacccttta gctgttctat atgctgccac tcctcaattg gattagtctc | 7980 |
| atccttcaat gctatcattt cctttgata | 8009 |

<210> SEQ ID NO 74
<211> LENGTH: 8990
<212> TYPE: DNA
<213> ORGANISM: Artificial Sequence
<220> FEATURE:
<223> OTHER INFORMATION: pGV2163

<400> SEQUENCE: 74

| ctgcttaatt aagatcaggt cagtacaaac gcaacacgaa agaacaaaaa aagaagaaaa | 60 |
| cagaaggcca agacagggtc aatgagactg ttgtcctcct actgtcccta tgtctctggc | 120 |
| cgatcacgcg ccattgtccc tcagaaacaa atcaaacacc cacaccccgg gcacccaaag | 180 |
| tccccaccca caccaccaat acgtaaacgg ggcgcccccct gcaggccctc ctgcgcgcgg | 240 |
| cctcccgcct tgcttctctc cccttccttt tcttttttcca gttttcccta ttttgtccct | 300 |
| ttttccgcac aacaagtatc agaatggggtt catcaaatct atccaaccta attcgcacgt | 360 |
| agactggctt ggtattggca gtttcgtagt tatatatata ctaccatgag tgaaactgtt | 420 |
| acgttacctt aaattctttc tccctttaat tttcttttat cttactctcc tacataagac | 480 |
| atcaagaaac aattgtatat tgtacacccc cccctccac aaacacaaat attgataata | 540 |
| taaaggagct cgccgatccc attaccgaca tttgggcgct atacgtgcat atgttcatgt | 600 |
| atgtatctgt atttaaaaca cttttgtatt attttttcctc atatatgtgt ataggtttat | 660 |
| acggatgatt taattattac ttcaccaccc tttatttcag gctgatatct tagccttgtt | 720 |
| actagttaga aaaagacatt tttgctgtca gtcactgtca agagattctt ttgctggcat | 780 |
| ttcttctaga agcaaaaaga gcgatgcgtc ttttccgctg aaccgttcca gcaaaaaaga | 840 |
| ctaccaacgc aatatggatt gtcagaatca tataaaagag aagcaaataa ctccttgtct | 900 |
| tgtatcaatt gcattataat atcttcttgt tagtgcaata tcatatagaa gtcatcgaaa | 960 |
| tagatattaa gaaaaacaaa ctgtacaatc aatcaatcaa tcatcacata aagtcgacat | 1020 |

```
gttgacaaaa gcaacaaaag aacaaaaatc ccttgtgaaa agcagagggg cggagcttgt   1080
tgttgattgc ttagcggagc aaggtgtcac acatgtattt ggcattccag gtgcaaaaat   1140
tgatgcggta tttgacgctt tacaagataa agggcctgaa attatcgttg cccggcatga   1200
acaaaatgca gcatttatgg cgcaagcagt cggccgttta actggaaaac cgggagtcgt   1260
gttagtcaca tcaggaccag gtgcttcgaa cttggcaaca ggactgctga cagcaaacac   1320
tgaaggtgac cctgtcgttg cgcttgctgg aacgtgatc cgtgcagatc gtttaaaacg   1380
gacacatcaa tctttggata atgcggcgct attccagccg attacaaaat acagtgtaga   1440
agttcaagat gtaaaaaata taccggaagc tgttacaaat gcgttaggta tagcgtcagc   1500
agggcaggct ggggccgctt ttgtgagttt ccgcaagat gttgtgaatg aagtcacaaa   1560
tacaaaaaac gtacgtgctg tcgcagcgcc aaaacttggt cccgcagcag atgacgcaat   1620
cagtatggcc attgcaaaaa ttcaaacagc aaaacttcct gtcgttttag tcggcatgaa   1680
gggcggaaga ccggaagcga ttaaagcggt tcgcaagcta ttgaaaaaag tgcagcttcc   1740
attcgttgaa acatatcaag ctgccggtac tcttacgaga gatttagagg atcagtattt   1800
tggccggatc ggtttattcc gcaaccagcc tggcgatctg ctgcttgagc aggctgatgt   1860
tgttctgaca atcggctatg acccaattga atatgatccg aaattctgga atgtcaatgg   1920
agaccggacg atcatccatt tagacgagat tctggctgac attgatcatg cttaccagcc   1980
ggatcttgaa ctgatcggtg atattccatc tacgatcaat catatcgaac acgatgctgt   2040
gaaagtagac tttgcggaac gtgagcagaa gatcctttct gatttaaaac aatatatgca   2100
tgagggtgag caggtgcctg cagattggaa atcagacaga gtgcatcctc ttgaaatcgt   2160
taaagaattg cgaaacgcag tcgatgatca tgttacagtg acttgcgata tcggttcaca   2220
cgcgatttgg atgtcacgtt atttccgcag ctacgagccg ttaacattaa tgattagtaa   2280
cggtatgcaa acactcggcg ttgcgcttcc ttgggcaatc ggcgcttcat tggtgaaacc   2340
gggagaaaaa gtagtatcag tctccggtga tggcggtttc ttattctcag ctatggaatt   2400
agagacagca gttcgtttaa aagcaccaat tgtacacatt gtatggaacg acagcacata   2460
tgacatggtt gcattccagc aattgaaaaa atataatcgt acatctgcgg tcgatttcgg   2520
aaatatcgat atcgtgaaat acgcggaaag cttcggagca actggcttac gcgtagaatc   2580
accagaccag ctggcagatg ttctgcgtca aggcatgaac gctgagggc ctgtcatcat   2640 tgatgtcccg gttgactaca gtgataacgt taatttagca agtgacaagc ttccgaaaga   2700
attcggggaa ctcatgaaaa cgaaagctct ctagggatcc tcatgtaatt agttatgtca   2760
cgcttacatt cacgccctcc ccccacatcc gctctaaccg aaaggaagg agttagacaa   2820 cctgaagtct aggtccctat ttatttttt atagttatgt tagtattaag aacgttattt   2880
atatttcaaa tttttctttt ttttctgtac agacgcgtgt acgcatgtaa cattatactg   2940
aaaaccttgc ttgagaaggt tttgggacgc tcgaaggctt taatttgccc taggctcaac   3000
tcaagacgca cagatattat aacatctgca taataggcat ttgcaagaat tactcgtgag   3060
taaggaaaga gtgaggaact atcgcatacc tgcatttaaa gatgccgatt tgggcgcgaa   3120
tcctttattt tggcttcacc ctcatactat tatcagggcc agaaaaagga agtgtttccc   3180
tccttcttga attgatgtta ccctcataaa gcacgtggcc tcttatcgag aaagaaatta   3240
ccgtcgctcg tgatttgttt gcaaaaagaa caaaactgaa aaacccaga cacgctcgac   3300 ttcctgtctt cctattgatt gcagcttcca atttcgtcac acaacaaggt cctagcgacg   3360
```

```
gctcacaggt tttgtaacaa gcaatcgaag gttctggaat ggcgggaaag ggtttagtac    3420
cacatgctat gatgcccact gtgatctcca gagcaaagtt cgttcgatcg tactgttact    3480
ctctctcttt caaacagaat tgtccgaatc gtgtgacaac aacagcctgt tctcacacac    3540
tcttttcttc taaccaaggg ggtggtttag tttagtagaa cctcgtgaaa cttacattta    3600
catatatata aacttgcata aattggtcaa tgcaagaaat acatatttgg tcttttctaa    3660
ttcgtagttt ttcaagttct tagatgcttt cttttttctct tttttacaga tcatcaagga    3720
agtaattatc tacttttttac aacaaatata aaacaagctc gacatgtata ctgttggtga    3780
ttatctgctg gaccgtctgc atgaactggg tatcgaagaa atcttcggcg ttccgggtga    3840
ttacaatctg cagttcctgg atcagatcat ctctcataaa gacatgaaat gggtgggtaa    3900
cgctaacgaa ctgaacgcaa gctacatggc agatggttat gcacgtacca agaaagccgc    3960
ggcatttctg accactttcg gtgttggcga actgagcgcc gtcaacggtc tggcgggctc    4020
ctacgccgaa aacctgccgg tggtggagat cgtaggcagc ccaacgagca aagttcagaa    4080
cgaaggtaaa ttcgtccacc acactctggc tgacggcgat ttcaaacact tcatgaaaat    4140
gcatgaacct gtgactgcgg cacgtacgct gctgactgca gagaacgcta ctgtggaaat    4200
cgaccgcgtt ctgtctgcgc tgctgaaaga acgcaaacca gtttacatca acctgcctgt    4260
ggatgttgcg gcagctaaag cggaaaaacc gagcctgccg ctgaagaaag aaaactccac    4320
ttctaacact agcgaccagg aaatcctgaa caaaatccag gagtctctga aaacgcaaa     4380 gaaaccaatc gtgatcaccg gccacgaaat catttctttt ggtctggaga agaccgtgac    4440
ccaattcatc agcaaaacca aactgccgat taccaccctg aacttcggca agtcctctgt    4500
tgacgaggct ctgccgtctt tcctgggcat ctacaacggt actctgagcg aaccgaacct    4560
gaaagaattt gttgaatctg cggacttcat cctgatgctg ggcgttaaac tgaccgactc    4620
ttctaccggt gcattcactc accatctgaa cgaaaacaaa atgattagcc tgaacatcga    4680
cgagggtaaa atcttcaacg agcgtatcca gaacttcgac ttcgaaagcc tgatcagctc    4740
tctgctggac ctgtccgaaa tcgagtataa aggcaaatac attgacaaaa agcaagaaga    4800
tttcgtacca tctaacgcac tgctgtccca ggatcgcctg tggcaggccg tggagaacct    4860
gacccagagc aatgaaacca tcgtggcgga acaaggtacg agcttttttcg gcgcgtcttc    4920 tatctttctg aaatccaaaa gccattttat cggtcagccg ctgtggggta gcattggcta    4980
tactttcccg gcagcgctgg gctctcagat cgctgataaa gaatctcgtc atctgctgtt    5040
catcggtgac ggttccctgc agctgaccgt acaggaactg ggtctggcaa ttcgtgaaaa    5100
gatcaacccg atttgcttca ttattaacaa tgacggctac accgttgagc gtgagatcca    5160
cggtccgaac cagtccttaca acgatatccc tatgtggaac tactctaaac tgccggagtc    5220
cttcggcgca actgaggacc gtgttgtgtc taaaattgtg cgtaccgaaa acgaatttgt    5280
gagcgtgatg aaagaggccc aggccgatcc gaaccgtatg tactggatcg aactgatcct    5340
ggcgaaagaa ggcgcaccga aggtactgaa gaaaatgggc aagctgtttg ctgaacagaa    5400
taaatcctaa ggatctttttg cggcctagta ttgaattctt atacaggaaa cttaatagaa    5460
caaatcacat atttaatcta atagccacct gcattggcac ggtgcaacac tacttcaact    5520
tcatcttaca aaaagatcac gtgatctgtt gtattgaact gaaaattttt tgtttgcttc    5580
tctctctctc tttcattatg tgagatttaa aaaccagaaa ctacatcatc gaaaagagt    5640 tttaaaccat tacaaccatt gcgataagcc ctctcaaact ataacaatac tgacagtact    5700
aaataattgc ctacttggct tcacatacgt tgcatacgtc gatatagata ataatgataa    5760
```

```
tgacagcagg attatcgtaa tacgtaatag ttgaaaatct caaaaatgtg tgggtcatta    5820
cgtaaataat gataggaatg ggattcttct attttttcctt tttccattct agcagccgtc   5880
gggaaaacgt ggcatcctct ctttcgggct caattggagt cacgctgccg tgagcatcct    5940
ctctttccat atctaacaac tgagcacgta accaatggaa aagcatgagc ttagcgttgc    6000
tccaaaaaag tattggatgg ttaataccat ttgtctgttc tcttctgact ttgactcctc    6060
aaaaaaaaaa aatctacaat caacagatcg cttcaattac gccctcacaa aaactttttt    6120
ccttcttctt cgcccacgtt aaattttatc cctcatgttg tctaacggat ttctgcactt    6180
gatttattat aaaaagacaa agacataata cttctctatc aatttcagtt attgttcttc    6240
cttgcgttat tcttctgttc ttcttttttct tttgtcatat ataaccataa ccaagtaata   6300
catattcaaa atgtccacaa aatcatatac cagtagagct gagactcatg caagtccggt    6360
tgcatcgaaa cttttacgtt taatggatga aaagaagacc aatttgtgtg cttctcttga    6420
cgttcgttcg actgatgagc tattgaaact tgttgaaacg ttgggtccat acatttgcct    6480
tttgaaaaca cacgttgata tcttggatga tttcagttat gagggtactg tcgttccatt    6540
gaaagcattg gcagagaaat acaagttctt gatatttgag gacagaaaat tcgccgatat    6600
cggtaacaca gtcaaattac aatatacatc gggcgtttac cgtatcgcag aatggtctga    6660
tatcaccaac gcccacgggg ttactggtgc tggtattgtt gctggcttga aacaaggtgc    6720
gcaagaggtc accaaagaac caaggggatt attgatgctt gctgaattgt cttccaaggg    6780
ttctctagca cacggtgaat atactaaggg taccgaagct tggcgtaatc atggtcatag    6840
ctgtttcctg tgtgaaattg ttatccgctc acaattccac acaacatacg agccggaagc    6900
ataaagtgta aagcctgggg tgcctaatga gtgagctaac tcacattaat tgcgttgcgc    6960
tcactgcccg ctttccagtc gggaaacctg tcgtgccagc tgcattaatg aatcggccaa    7020
cgcgcgggga gaggcggttt gcgtattggg cgctcttccg cttcctcgct cactgactcg    7080
ctgcgctcgg tcgttcggct gcggcgagcg gtatcagctc actcaaaggc ggtaatacgg    7140
ttatccacag aatcagggga taacgcagga aagaacatgt gagcaaaagg ccagcaaaag    7200
gccaggaacc gtaaaaaggc cgcgttgctg gcgtttttcc ataggctccg ccccccctgac   7260 gagcatcaca aaaatcgacg ctcaagtcag aggtggcgaa acccgacagg actataaaga    7320
taccaggcgt ttccccctgg aagctccctc gtgcgctctc ctgttccgac cctgccgctt    7380
accggatacc tgtccgcctt tctcccttcg ggaagcgtgg cgctttctca tagctcacgc    7440
tgtaggtatc tcagttcggt gtaggtcgtt cgctccaagc tgggctgtgt gcacgaaccc    7500
cccgttcagc ccgaccgctg cgccttatcc ggtaactatc gtcttgagtc aacccggta    7560 agacacgact tatcgccact ggcagcagcc actggtaaca ggattagcag agcgaggtat    7620
gtaggcggtg ctacagagtt cttgaagtgg tggcctaact acggctacac tagaaggaca    7680
gtatttggta tctgcgctct gctgaagcca gttaccttcg gaaaaagagt tggtagctct    7740
tgatccggca aacaaaccac cgctggtagc ggtggttttt ttgtttgcaa gcagcagatt    7800
acgcgcagaa aaaaggatc tcaagaagat cctttgatct tttctacggg gtctgacgct    7860
cagtggaacg aaaactcacg ttaagggatt ttggtcatga gattatcaaa aaggatcttc    7920
acctagatcc ttttaaatta aaaatgaagt tttaaatcaa tctaaagtat atatgagtaa    7980
acttggtctg acagttacca atgcttaatc agtgaggcac ctatctcagc gatctgtcta    8040
tttcgttcat ccatagttgc ctgactcccc gtcgtgtaga taactacgat acgggagggc    8100
```

```
ttaccatctg gccccagtgc tgcaatgata ccgcgagacc cacgctcacc ggctccagat    8160
ttatcagcaa taaaccagcc agccggaagg gccgagcgca gaagtggtcc tgcaacttta    8220
tccgcctcca tccagtctat taattgttgc cgggaagcta gagtaagtag ttcgccagtt    8280
aatagtttgc gcaacgttgt tgccattgct acaggcatcg tggtgtcacg ctcgtcgttt    8340
ggtatggctt cattcagctc cggttcccaa cgatcaaggc gagttacatg atccccatg     8400 ttgtgcaaaa aagcggttag ctccttcggt cctccgatcg ttgtcagaag taagttggcc    8460
gcagtgttat cactcatggt tatggcagca ctgcataatt ctcttactgt catgccatcc    8520
gtaagatgct tttctgtgac tggtgagtac tcaaccaagt cattctgaga atagtgtatg    8580
cggcgaccga gttgctcttg cccggcgtca atacgggata ataccgcgcc acatagcaga    8640
actttaaaag tgctcatcat tggaaaacgt tcttcggggc gaaaactctc aaggatctta    8700
ccgctgttga gatccagttc gatgtaaccc actcgtgcac ccaactgatc ttcagcatct    8760
tttactttca ccagcgtttc tgggtgagca aaaacaggaa ggcaaaatgc cgcaaaaaag    8820
ggaataaggg cgacacggaa atgttgaata ctcatactct ccttttttca atattattga    8880
agcatttatc agggttattg tctcatgagc ggatacatat ttgaatgtat ttagaaaaat    8940
aaacaaatag gggttccgcg cacatttccc cgaaaagtgc cacctgacgt               8990
```

<210> SEQ ID NO 75
<211> LENGTH: 8990
<212> TYPE: DNA
<213> ORGANISM: Artificial Sequence
<220> FEATURE:
<223> OTHER INFORMATION: pGV2360

<400> SEQUENCE: 75

```
ctgcttaatt aagatcaggt cagtacaaac gcaacacgaa agaacaaaaa aagaagaaaa      60
cagaaggcca agacagggtc aatgagactg ttgtcctcct actgtcccta tgtctctggc     120
cgatcacgcg ccattgtccc tcagaaacaa atcaaacacc cacaccccgg gcacccaaag    180
tccccaccca caccaccaat acgtaaacgg ggcgcccctc gcaggccctc ctgcgcgcgg    240
cctcccgcct tgcttctctc cccttccttt tcttttttcca gttttccctaa ttttgtccct   300 ttttccgcac aacaagtatc agaatggggtt catcaaatct atccaaccta attcgcacgt    360
agactggctt ggtattggca gtttcgtagt tatatatata ctaccatgag tgaaactgtt    420
acgttacctt aaattctttc tcccttttaat tttcttttat cttactctcc tacataagac     480
atcaagaaac aattgtatat tgtacacccc cccctccac aaacacaaat attgataata    540
taaaggagct cgccgatccc attaccgaca tttgggcgct atacgtgcat atgttcatgt   600
atgtatctgt atttaaaaca cttttgtatt atttttcctc atatatgtgt ataggtttat   660
acggatgatt taattattac ttccaccacc tttatttcag gctgatatct tagccttgtt    720
actagttaga aaaagacatt tttgctgtca gtcactgtca agagattctt ttgctggcat    780
ttcttctaga agcaaaaaga gcgatgcgtc ttttccgctg aaccgttcca gcaaaaaaga    840
ctaccaacgc aatatggatt gtcagaatca tataaaagag aagcaaataa ctccttgtct    900
tgtatcaatt gcattataat atcttcttgt tagtgcaata tcatatagaa gtcatcgaaa    960
tagatattaa gaaaaacaaa ctgtacaatc aatcaatcaa tcatcacata aagtcgacat    1020
gttgacaaaa gcaacaaaag aacaaaaatc ccttgtgaaa agcagagggg cggagcttgt    1080
tgttgattgc ttagcggagc aaggtgtcac acatgtatt ggcattccag gtgcaaaaat     1140
tgatgcggta tttgacgctt tacaagataa agggcctgaa attatcgttg cccggcatga    1200
```

-continued

```
acaaaatgca gcatttatgg cgcaagcagt cggccgttta actggaaaac cgggagtcgt    1260
gttagtcaca tcaggaccag gtgcttcgaa cttggcaaca ggactgctga cagcaaacac    1320
tgaaggtgac cctgtcgttg cgcttgctgg gaacgtgatc cgtgcagatc gtttaaaacg    1380
gacacatcaa tctttggata atgcggcgct attccagccg attacaaaat acagtgtaga    1440
agttcaagat gtaaaaaata taccggaagc tgttacaaat gcgtttagga tagcgtcagc    1500
agggcaggct ggggccgctt ttgtgagttt tccgcaagat gttgtgaatg aagtcacaaa    1560
tacaaaaaac gtacgtgctg tcgcagcgcc aaaacttggt cccgcagcag atgacgcaat    1620
cagtatggcc attgcaaaaa ttcaaacagc aaaacttcct gtcgttttag tcggcatgaa    1680
gggcggaaga ccggaagcga ttaaagcggt tcgcaagcta ttgaaaaaag tgcagcttcc    1740
attcgttgaa acatatcaag ctgccggtac tcttacgaga gatttagagg atcagtattt    1800
tggccggatc ggtttattcc gcaaccagcc tggcgatctg ctgcttgagc aggctgatgt    1860
tgttctgaca atcggctatg acccaattga atatgatccg aaattctgga atgtcaatgg    1920
agaccggacg atcatccatt tagacgagat tctggctgac attgatcatg cttaccagcc    1980
ggatcttgaa ctgatcggtg atattccatc tacgatcaat catatcgaac acgatgctgt    2040
gaaagtagac tttgcggaac gtgagcagaa gatcctttct gatttaaaac aatatatgca    2100
tgagggtgag caggtgcctg cagattggaa atcagacaga gtgcatcctc ttgaaatcgt    2160
taaagaattg cgaaacgcag tcgatgatca tgttacagtg acttgcgata tcggttcaca    2220
cgcgatttgg atgtcacgtt atttccgcag ctacgagccg ttaacattaa tgattagtaa    2280
cggtatgcaa acactcggcg ttgcgcttcc ttgggcaatc ggcgcttcat tggtgaaacc    2340
gggagaaaaa gtagtatcag tctccggtga tggcggtttc ttattctcag ctatggaatt    2400
agagacagca gttcgtttaa aagcaccaat tgtacacatt gtatggaacg acagcacata    2460
tgacatggtt gcattccagc aattgaaaaa atataatcgt acatctgcgg tcgatttcgg    2520
aaatatcgat atcgtgaaat acgcggaaag cttcggagca actggcttac gcgtagaatc    2580
accagaccag ctggcagatg ttctgcgtca aggcatgaac gctgagggggc ctgtcatcat    2640 tgatgtcccg gttgactaca gtgataacgt taatttagca agtgacaagc ttccgaaaga    2700
attcggggaa ctcatgaaaa cgaaagctct ctagggatcc tcatgtaatt agttatgtca    2760
cgcttacatt cacgccctcc ccccacatcc gctctaaccg aaaaggaagg agttagacaa    2820
cctgaagtct aggtccctat ttattttttt atagttatgt tagtattaag aacgttattt    2880
atatttcaaa ttttttcttt tttctgtac agacgcgtgt acgcatgtaa cattatactg    2940
aaaaccttgc ttgagaaggt tttgggacgc tcgaaggctt taatttgccc taggctcaac    3000
tcaagacgca cagatattat aacatctgca taataggcat ttgcaagaat tactcgtgag    3060
taaggaaaga gtgaggaact atcgcatacc tgcatttaaa gatgccgatt gggcgcgaa    3120 tcctttattt tggcttcacc ctcatactat tatcagggcc agaaaaagga agtgtttccc    3180
tccttcttga attgatgtta ccctcataaa gcacgtggcc tcttatcgag aaagaaatta    3240
ccgtcgctcg tgatttgttt gcaaaaagaa caaaactgaa aaacccaga cacgctcgac    3300 ttcctgtctt cctattgatt gcagcttcca atttcgtcac acaacaaggt cctagcgacg    3360
gctcacaggt tttgtaacaa gcaatcgaag gttctggaat ggcgggaaag ggtttagtac    3420
cacatgctat gatgcccact gtgatctcca gagcaaagtt cgttcgatcg tactgttact    3480
ctctctcttt caaacagaat tgtccgaatc gtgtgacaac aacagcctgt tctcacacac    3540
```

```
tcttttcttc taaccaaggg ggtggtttag tttagtagaa cctcgtgaaa cttacattta   3600
catatatata aacttgcata aattggtcaa tgcaagaaat acatatttgg tcttttctaa   3660
ttcgtagttt ttcaagttct tagatgcttt cttttctct ttttacaga tcatcaagga    3720 agtaattatc tacttttac aacaaatata aaacaagctc gacatgtata ctgttggtga   3780
ttatctgctg gaccgtctgc atgaactggg tatcgaagaa atcttcggcg ttccgggtga   3840
ttacaatctg cagttcctgg atcagatcat ctctcataaa gacatgaaat gggtgggtaa   3900
cgctaacgaa ctgaacgcaa gctacatggc agatggttat gcacgtacca agaaagccgc   3960
ggcatttctg accactttcg gtgttggcga actgagcgcc gtcaacggtc tggcgggctc   4020
ctacgccgaa aacctgccgg tggtggagat cgtaggcagc ccaacgagca agttcagaa    4080 cgaaggtaaa ttcgtccacc acactctggc tgacggcgat ttcaaacact tcatgaaaat   4140
gcatgaacct gtgactgcgg cacgtacgct gctgactgca gagaacgcta ctgtggaaat   4200
cgaccgcgtt ctgtctgcgc tgctgaaaga acgcaaacca gtttacatca acctgcctgt   4260
ggatgttgcg gcagctaaag cggaaaaacc gagcctgccg ctgaagaaag aaaactccac   4320
ttctaacact agcgaccagg aaatcctgaa caaaatccag gagtctctga aaaacgcaaa   4380
gaaaccaatc gtgatcaccg gccacgaaat catttctttt ggtctggaga agaccgtgac   4440
ccaattcatc agcaaaacca aactgccgat taccaccctg aacttcggca agtcctctgt   4500
tgacgaggct ctgccgtctt tcctgggcat ctacaacggt actctgagcg aaccgaacct   4560
gaaagaattt gttgaatctg cggacttcat cctgatgctg ggcgttaaac tgaccgactc   4620
ttctaccggt gcattcactc accatctgaa cgaaaacaaa atgattagcc tgaacatcga   4680
cgagggtaaa atcttcaacg agcgtatcca gaacttcgac ttcgaaagcc tgatcagctc   4740
tctgctggac ctgtccgaaa tcgagtataa aggcaaatac attgacaaaa agcaagaaga   4800
tttcgtacca tctaacgcac tgctgtccca ggatcgcctg tggcaggccg tggagaacct   4860
gacccagagc aatgaaacca tcgtggcgga acaaggtacg agcttttttcg gcgcgtcttc   4920 tatctttctg aaatccaaaa gccatttat cggtcagccg ctgtggggta gcattggcta   4980
tactttcccg gcagcgctgg gctctcagat cgctgataaa gaatctcgtc atctgctgtt   5040
catcggtgac ggttccctgc agctgaccgt acaggaactg ggtctggcaa ttcgtgaaaa   5100
gatcaacccg atttgcttca ttattaacaa tgacggctac accgttgagc gtgagatcca   5160
cggtccgaac cagtcttaca cgatatccc tatgtggaac tactctaaac tgccggagtc   5220
cttcggcgca actgaggacc gtgttgtgtc taaaattgtg cgtaccgaaa acgaatttgt   5280
gagcgtgatg aaagaggccc aggccgatcc gaaccgtatg tactggatcg aactgatcct   5340
ggcgaaagaa ggcgcaccga aggtactgaa gaaaatgggc aagctgtttg ctgaacagaa   5400
taaatcctaa ggatcttttg cggcctagta ttgaattctt atacaggaaa cttaatagaa   5460
caaatcacat atttaatcta atagccacct gcattggcac ggtgcaacac tacttcaact   5520
tcatcttaca aaagatcac gtgatctgtt gtattgaact gaaaattttt tgtttgcttc    5580
tctctctctc tttcattatg tgagatttaa aaaccagaaa ctacatcatc gaaaagagt    5640 tttaaaccat tacaaccatt gcgataagcc ctctcaaact ataacaatac tgacagtact   5700
aaataattgc ctacttggct tcacatacgt tgcatacgtc gatatagata ataatgataa   5760
tgacagcagg attatcgtaa tacgtaatag ttgaaaatct caaaaatgtg tgggtcatta   5820
cgtaaataat dataggaatg ggattcttct atttttcctt tttccattct agcagccgtc   5880
gggaaaacgt ggcatcctct ctttcgggct caattggagt cacgctgccg tgagcatcct   5940
```

-continued

```
ctctttccat atctaacaac tgagcacgta accaatggaa aagcatgagc ttagcgttgc    6000
tccaaaaaag tattggatgg ttaataccat ttgtctgttc tcttctgact ttgactcctc    6060
aaaaaaaaaa aatctacaat caacagatcg cttcaattac gccctcacaa aaactttttt    6120
ccttcttctt cgcccacgtt aaattttatc cctcatgttg tctaacggat ttctgcactt    6180
gatttattat aaaaagacaa agacataata cttctctatc aatttcagtt attgttcttc    6240
cttgcgttat tcttctgttc ttcttttct tttgtcatat ataaccataa ccaagtaata    6300
catattcaaa atgtccacaa aatcatatac cagtagagct gagactcatg caagtccggt    6360
tgcatcgaaa cttttacgtt taatggatga aagaagacc aatttgtgtg cttctcttga    6420
cgttcgttcg actgatgagc tattgaaact tgttgaaacg ttgggtccat acatttgcct    6480
tttgaaaaca cacgttgata tcttggatga tttcagttat gagggtactg tcgttccatt    6540
gaaagcattg gcagagaaat acaagttctt gatatttgag gacagaaaat tcgccgatat    6600
cggtaacaca gtcaaattac aatatacatc gggcgtttac cgtatcgcag aatggtctga    6660
tatcaccaac gcccacgggg ttactggtgc tggtattgtt gctggcttga aacaaggtgc    6720
gcaagaggtc accaaagaac caaggggatt attgatgctt gctgaattgt cttccaaggg    6780
ttctctagca cacggtgaat atactaaggg taccgaagct tggcgtaatc atggtcatag    6840
ctgtttcctg tgtgaaattg ttatccgctc acaattccac acaacatacg agccggaagc    6900
ataaagtgta aagcctgggg tgcctaatga gtgagctaac tcacattaat tgcgttgcgc    6960
tcactgcccg ctttccagtc gggaaacctg tcgtgccagc tgcattaatg aatcggccaa    7020
cgcgcgggga gaggcggttt gcgtattggg cgctcttccg cttcctcgct cactgactcg    7080
ctgcgctcgg tcgttcggct gcggcgagcg gtatcagctc actcaaaggc ggtaatacgg    7140
ttatccacag aatcagggga taacgcagga aagaacatgt gagcaaaagg ccagcaaaag    7200
gccaggaacc gtaaaaaggc cgcgttgctg gcgtttttcc ataggctccg ccccctgac    7260 gagcatcaca aaaatcgacg ctcaagtcag aggtggcgaa acccgacagg actataaaga    7320
taccaggcgt ttccccctgg aagctccctc gtgcgctctc ctgttccgac cctgccgctt    7380
accggatacc tgtccgcctt tctcccttcg ggaagcgtgg cgctttctca tagctcacgc    7440
tgtaggtatc tcagttcggt gtaggtcgtt cgctccaagc tgggctgtgt gcacgaaccc    7500
cccgttcagc ccgaccgctg cgccttatcc ggtaactatc gtcttgagtc caacccggta    7560
agacacgact tatcgccact ggcagcagcc actggtaaca ggattagcag agcgaggtat    7620
gtaggcggtg ctacagagtt cttgaagtgg tggcctaact acggctacac tagaaggaca    7680
gtatttggta tctgcgctct gctgaagcca gttaccttcg gaaaagagt tggtagctct    7740 tgatccggca aacaaccac cgctggtagc ggtggttttt ttgtttgcaa gcagcagatt    7800
acgcgcagaa aaaaaggatc tcaagaagat cctttgatct tttctacggg gtctgacgct    7860
cagtggaacg aaaactcacg ttaagggatt ttggtcatga gattatcaaa aaggatcttc    7920
acctagatcc tttttaaatta aaaatgaagt tttaaatcaa tctaaagtat atatgagtaa    7980
acttggtctg acagttacca atgcttaatc agtgaggcac ctatctcagc gatctgtcta    8040
tttcgttcat ccatagttgc ctgactcccc gtcgtgtaga taactacgat acgggagggc    8100
ttaccatctg gccccagtgc tgcaatgata ccgcgagacc cacgctcacc ggctccagat    8160
ttatcagcaa taaccagcc agccggaagg gccgagcgca gaagtggtcc tgcaacttta    8220
tccgcctcca tccagtctat taattgttgc cgggaagcta gagtaagtag ttcgccagtt    8280
```

```
aatagtttgc gcaacgttgt tgccattgct acaggcatcg tggtgtcacg ctcgtcgttt      8340
ggtatggctt cattcagctc cggttcccaa cgatcaaggc gagttacatg atcccccatg      8400
ttgtgcaaaa aagcggttag ctccttcggt cctccgatcg ttgtcagaag taagttggcc      8460
gcagtgttat cactcatggt tatggcagca ctgcataatt ctcttactgt catgccatcc      8520
gtaagatgct tttctgtgac tggtgagtac tcaaccaagt cattctgaga atagtgtatg      8580
cggcgaccga gttgctcttg cccggcgtca atacgggata ataccgcgcc acatagcaga      8640
actttaaaag tgctcatcat tggaaaacgt tcttcgggge gaaaactctc aaggatctta      8700
ccgctgttga gatccagttc gatgtaaccc actcgtgcac ccaactgatc ttcagcatct      8760
tttactttca ccagcgtttc tgggtgagca aaaacaggaa ggcaaaatgc cgcaaaaaag      8820
ggaataaggg cgacacggaa atgttgaata ctcatactct tccttttca atattattga      8880 agcatttatc agggttattg tctcatgagc ggatacatat ttgaatgtat ttagaaaaat      8940
aaacaaatag gggttccgcg cacatttccc cgaaaagtgc cacctgacgt                 8990

<210> SEQ ID NO 76
<211> LENGTH: 8990
<212> TYPE: DNA
<213> ORGANISM: Artificial Sequence
<220> FEATURE:
<223> OTHER INFORMATION: pGV2381

<400> SEQUENCE: 76
ctgcttaatt aagatcaggt cagtacaaac gcaacacgaa agaacaaaaa aagaagaaaa        60
cagaaggcca agacagggtc aatgagactg ttgtcctcct actgtcccta tgtctctggc       120
cgatcacgcg ccattgtccc tcagaaacaa atcaaacacc cacacccgg gcacccaaag        180 tccccaccca caccaccaat acgtaaacgg ggcgccccct gcaggccctc ctgcgcgcgg       240
cctcccgcct tgcttctctc cccttccttt tcttttttca gttttcccta ttttgtccct      300
ttttccgcac aacaagtatc agaatggggtt catcaaatct atccaaccta attcgcacgt     360
agactggctt ggtattggca gtttcgtagt tatatatata ctaccatgag tgaaactgtt      420
acgttacctt aaaattcttc tccctttaat ttttctttat cttactctcc tacataagac      480
atcaagaaac aattgtatat tgtacacccc ccccctccac aaacacaaat attgataata      540
taaaggagct cgccgatccc attaccgaca tttgggcgct atacgtgcat atgttcatgt      600
atgtatctgt atttaaaaca cttttgtatt attttttcctc atatatgtgt ataggtttat    660
acggatgatt taattattac ttcaccaccc tttatttcag gctgatatct tagccttgtt    720
actagttaga aaaagacatt tttgctgtca gtcactgtca agagattctt ttgctggcat      780
ttcttctaga agcaaaaaga gcgatgcgtc ttttccgctg aaccgttcca gcaaaaaga      840 ctaccaacgc aatatggatt gtcagaatca tataaaagag aagcaaataa ctccttgtct     900
tgtatcaatt gcattataat atcttcttgt tagtgcaata tcatatagaa gtcatcgaaa     960
tagatattaa gaaaaacaaa ctgtacaatc aatcaatcaa tcatcacata agtcgacat      1020 gttgacaaaa gcaacaaaag aacaaaaatc ccttgtgaaa agcagagggg cggagcttgt    1080
tgttgattgc ttagcggagc aaggtgtcac acatgtattt ggcattccag gtgcaaaaat    1140
tgatgcggta tttgacgctt tacaagataa agggcctgaa attatcgttg cccggcatga    1200
acaaaatgca gcatttatgg cgcaagcagt cggccgttta actggaaaac cgggagtcgt    1260
gttagtcaca tcaggaccag gtgcttcgaa cttggcaaca ggactgctga cagcaaacac    1320
tgaaggtgac cctgtcgttg cgcttgctgg gaacgtgatc cgtgcagatc gtttaaaacg    1380
```

```
gacacatcaa tctttggata atgcggcgct attccagccg attacaaaat acagtgtaga   1440
agttcaagat gtaaaaaata taccggaagc tgttacaaat gcgtttagga tagcgtcagc   1500
agggcaggct ggggccgctt ttgtgagttt tccgcaagat gttgtgaatg aagtcacaaa   1560
tacaaaaaac gtacgtgctg tcgcagcgcc aaaacttggt cccgcagcag atgacgcaat   1620
cagtatggcc attgcaaaaa ttcaaacagc aaaacttcct gtcgttttag tcggcatgaa   1680
gggcggaaga ccgaagcga ttaaagcggt tcgcaagcta ttgaaaaaag tgcagcttcc   1740
attcgttgaa acatatcaag ctgccggtac tcttacgaga gatttagagg atcagtattt   1800
tggccggatc ggtttattcc gcaaccagcc tggcgatctg ctgcttgagc aggctgatgt   1860
tgttctgaca atcggctatg acccaattga atatgatccg aaattctgga atgtcaatgg   1920
agaccggacg atcatccatt tagacgagat tctggctgac attgatcatg cttaccagcc   1980
ggatcttgaa ctgatcggtg atattccatc tacgatcaat catatcgaac acgatgctgt   2040
gaaagtagac tttgcggaac gtgagcagaa gatcctttct gatttaaaac aatatatgca   2100
tgagggtgag caggtgcctg cagattggaa atcagacaga gtgcatcctc ttgaaatcgt   2160
taaagaattg cgaaacgcag tcgatgatca tgttacagtg acttgcgata tcggttcaca   2220
cgcgatttgg atgtcacgtt atttccgcag ctacgagccg ttaacattaa tgattagtaa   2280
cggtatgcaa acactcggcg ttgcgcttcc ttgggcaatc ggcgcttcat tggtgaaacc   2340
gggagaaaaa gtagtatcag tctccggtga tggcggtttc ttattctcag ctatggaatt   2400
agagacagca gttcgtttaa aagcaccaat tgtacacatt gtatggaacg acagcacata   2460
tgacatggtt gcattccagc aattgaaaaa atataatcgt acatctgcgg tcgatttcgg   2520
aaatatcgat atcgtgaaat acgcggaaag cttcggagca actggcttac gcgtagaatc   2580
accagaccag ctggcagatg ttctgcgtca aggcatgaac gctgaggggc ctgtcatcat   2640
tgatgtcccg gttgactaca gtgataacgt taatttagca agtgacaagc ttccgaaaga   2700
attcggggaa ctcatgaaaa cgaaagctct ctagggatcc tcatgtaatt agttatgtca   2760
cgcttacatt cacgcccctcc ccccacatcc gctctaaccg aaaaggaagg agttagacaa   2820
cctgaagtct aggtccctat ttatttttt atagttatgt tagtattaag aacgttattt   2880
atatttcaaa tttttctttt ttttctgtac agacgcgtgt acgcatgtaa cattatactg   2940
aaaaccttgc ttgagaaggt tttgggacgc tcgaaggctt taatttgccc taggctcaac   3000
tcaagacgca cagatattat aacatctgca taataggcat ttgcaagaat tactcgtgag   3060
taaggaagga gtgaggaact atcgcatacc tgcatttaaa gatgccgatt tgggcgcgaa   3120
tcctttattt tggcttcacc ctcatactat tatcagggcc agaaaaagga agtgtttccc   3180
tccttcttga attgatgtta ccctcataaa gcacgtggcc tcttatcgag aaagaaatta   3240
ccgtcgctcg tgatttgttt gcaaaaagaa caaaactgaa aaacccaga cacgctcgac    3300 ttcctgtctt cctattgatt gcagcttcca atttcgtcac acaacaaggt cctagcgacg   3360
gctcacaggt tttgtaacaa gcaatcgaag gttctggaat ggcgggaaag ggtttagtac   3420
cacatgctat gatgcccact gtgatctcca gagcaaagtt cgttcgatcg tactgttact   3480
ctctctcttt caaacagaat tgtccgaatc gtgtgacaac aacagcctgt tctcacacac   3540
tcttttcttc taaccaaggg ggtggtttag tttagtagaa cctcgtgaaa cttacattta   3600
catatatata aacttgcata aattggtcaa tgcaagaaat acatatttgg tcttttctaa   3660
ttcgtagttt ttcaagttct tagatgcttt cttttctct ttttacaga tcatcaagga   3720
```

-continued

```
agtaattatc tacttttac aacaaatata aaacaagctc gacatgtata ctgttggtga   3780
ttatctgctg gaccgtctgc atgaactggg tatcgaagaa atcttcggcg ttccgggtga   3840
ttacaatctg cagttcctgg atcagatcat ctctcataaa gacatgaaat gggtgggtaa   3900
cgctaacgaa ctgaacgcaa gctacatggc agatggttat gcacgtacca agaaagccgc   3960
ggcatttctg accactttcg gtgttggcga actgagcgcc gtcaacggtc tggcgggctc   4020
ctacgccgaa aacctgccgg tggtggagat cgtaggcagc ccaacgagca agttcagaa    4080
cgaaggtaaa ttcgtccacc acactctggc tgacggcgat ttcaaacact tcatgaaaat   4140
gcatgaacct gtgactgcgg cacgtacgct gctgactgca gagaacgcta ctgtggaaat   4200
cgaccgcgtt ctgtctgcgc tgctgaaaga acgcaaacca gtttacatca acctgcctgt   4260
ggatgttgcg gcagctaaag cggaaaaacc gagcctgccg ctgaagaaag aaaactccac   4320
ttctaacact agcgaccagg aaatcctgaa caaaatccag gagtctctga aaacgcaaa    4380
gaaaccaatc gtgatcaccg ccacgaaat catttctttt ggtctggaga agaccgtgac    4440
ccaattcatc agcaaaacca aactgccgat taccaccctg aacttcggca agtcctctgt   4500
tgacgaggct ctgccgtctt tcctgggcat ctacaacggt actctgagcg aaccgaacct   4560
gaaagaattt gttgaatctg cggacttcat cctgatgctg ggcgttaaac tgaccgactc   4620
ttctaccggt gcattcactc accatctgaa cgaaaacaaa atgattagcc tgaacatcga   4680
cgagggtaaa atcttcaacg agcgtatcca gaacttcgac ttcgaaagcc tgatcagctc   4740
tctgctggac ctgtccgaaa tcgagtataa aggcaaatac attgacaaaa agcaagaaga   4800
tttcgtacca tctaacgcac tgctgtccca ggatcgcctg tggcaggccg tggagaacct   4860
gacccagagc aatgaaacca tcgtggcgga acaaggtacg agcttttcg gcgcgtcttc   4920
tatctttctg aaatccaaaa gccatttat cggtcagccg ctgtgggta gcattggcta    4980
tactttcccg gcagcgctgg gctctcagat cgctgataaa gaatctcgtc atctgctgtt   5040
catcggtgac ggttccctgc agctgaccgt acaggaactg ggtctggcaa ttcgtgaaaa   5100
gatcaacccg atttgcttca ttattaacaa tgacggctac accgttgagc gtgagatcca   5160
cggtccgaac cagtcttaca acgatatccc tatgtggaac tactctaaac tgccggagtc   5220
cttcggcgca actgaggacc gtgttgtgtc taaaattgtg cgtaccgaaa acgaatttgt   5280
gagcgtgatg aaagaggccc aggccgatcc gaaccgtatg tactggatcg aactgatcct   5340
ggcgaaagaa ggcgcaccga aggtactgaa gaaaatgggc aagctgtttg ctgaacagaa   5400
taaatcctaa ggatcttttg cggcctagta ttgaattctt atacaggaaa cttaatagaa   5460
caaatcacat atttaatcta atagccacct gcattggcac ggtgcaacac tacttcaact   5520
tcatcttaca aaaagatcac gtgatctgtt gtattgaact gaaaattttt tgtttgcttc   5580
tctctctctc tttcattatg tgagatttaa aaaccagaaa ctacatcatc gaaaagagt    5640
tttaaaccat tacaaccatt gcgataagcc ctctcaaact ataacaatac tgacagtact   5700
aaataattgc ctacttggct tcacatacgt tgcatacgtc gatatagata ataatgataa   5760
tgacagcagg attatcgtaa tacgtaatag ttgaaaatct caaaaatgtg tgggtcatta   5820
cgtaaataat gataggaatg ggattcttct atttttcctt tttccattct agcagccgtc   5880
gggaaaacgt ggcatcctct ctttcgggct caattggagt cacgctgccg tgagcatcct   5940
ctctttccat atctaacaac tgagcacgta accaatggaa aagcatgagc ttagcgttgc   6000
tccaaaaaag tattggatgg ttaataccat ttgtctgttc tcttctgact ttgactcctc   6060
aaaaaaaaaa aatctacaat caacagatcg cttcaattac gccctcacaa aactttttt    6120
```

```
ccttcttctt cgcccacgtt aaattttatc cctcatgttg tctaacggat ttctgcactt    6180 gattattat aaaaagacaa agacataata cttctctatc aatttcagtt attgttcttc    6240
cttgcgttat tcttctgttc ttcttttttct tttgtcatat ataaccataa ccaagtaata  6300
catattcaaa atgtccacaa aatcatatac cagtagagct gagactcatg caagtccggt   6360
tgcatcgaaa cttttacgtt taatggatga aaagaagacc aatttgtgtg cttctcttga   6420
cgttcgttcg actgatgagc tattgaaact tgttgaaacg ttgggtccat acatttgcct   6480
tttgaaaaca cacgttgata tcttggatga tttcagttat gagggtactg tcgttccatt   6540
gaaagcattg gcagagaaat acaagttctt gatatttgag gacagaaaat tcgccgatat   6600
cggtaacaca gtcaaattac aatatacatc gggcgtttac cgtatcgcag aatggtctga   6660
tatcaccaac gcccacgggg ttactggtgc tggtattgtt gctggcttga aacaaggtgc   6720
gcaagaggtc accaaagaac caaggggatt attgatgctt gctgaattgt cttccaaggg   6780
ttctctagca cacggtgaat atactaaggg taccgaagct tggcgtaatc atggtcatag   6840
ctgtttcctg tgtgaaattg ttatccgctc acaattccac acaacatacg agccggaagc   6900
ataaagtgta aagcctgggg tgcctaatga gtgagctaac tcacattaat tgcgttgcgc   6960
tcactgcccg ctttccagtc gggaaacctg tcgtgccagc tgcattaatg aatcggccaa   7020
cgcgcgggga gaggcggttt gcgtattggg cgctcttccg cttcctcgct cactgactcg   7080
ctgcgctcgg tcgttcggct gcggcgagcg gtatcagctc actcaaaggc ggtaatacgg   7140
ttatccacag aatcagggga taacgcagga aagaacatgt gagcaaaagg ccagcaaaag   7200
gccaggaacc gtaaaaaggc cgcgttgctg gcgtttttcc ataggctccg cccccctgac   7260
gagcatcaca aaaatcgacg ctcaagtcag aggtggcgaa acccgacagg actataaaga   7320
taccaggcgt ttccccctgg aagctccctc gtgcgctctc ctgttccgac cctgccgctt   7380
accggatacc tgtccgcctt tctcccttcg ggaagcgtgg cgctttctca tagctcacgc   7440
tgtaggtatc tcagttcggt gtaggtcgtt cgctccaagc tgggctgtgt gcacgaaccc   7500
cccgttcagc ccgaccgctg cgccttatcc ggtaactatc gtcttgagtc caacccggta   7560
agacacgact tatcgccact ggcagcagcc actggtaaca ggattagcag agcgaggtat   7620
gtaggcggtg ctacagagtt cttgaagtgg tggcctaact acggctacac tagaaggaca   7680
gtatttggta tctgcgctct gctgaagcca gttaccttcg gaaaaagagt tggtagctct   7740
tgatccggca aacaaaccac cgctggtagc ggtggttttt tgtttgcaa gcagcagatt    7800 acgcgcagaa aaaaaggatc tcaagaagat cctttgatct tttctacggg gtctgacgct   7860
cagtggaacg aaaactcacg ttaagggatt ttggtcatga gattatcaaa aaggatcttc   7920
acctagatcc ttttaaatta aaatgaagt tttaaatcaa tctaaagtat atatgagtaa    7980
acttggtctg acagttacca atgcttaatc agtgaggcac ctatctcagc gatctgtcta   8040
tttcgttcat ccatagttgc ctgactcccc gtcgtgtaga taactacgat acgggagggc   8100
ttaccatctg gccccagtgc tgcaatgata ccgcgagacc cacgctcacc ggctccagat   8160
ttatcagcaa taaaccagcc agccggaagg gccgagcgca gaagtggtcc tgcaacttta   8220
tccgcctcca tccagtctat taattgttgc cgggaagcta gagtaagtag ttcgccagtt   8280
aatagtttgc gcaacgttgt tgccattgct acaggcatcg tggtgtcacg ctcgtcgttt   8340
ggtatggctt cattcagctc cggttcccaa cgatcaaggc gagttacatg atcccccatg   8400
ttgtgcaaaa aagcggttag ctccttcggt cctccgatcg ttgtcagaag taagttggcc   8460
```

-continued

```
gcagtgttat cactcatggt tatggcagca ctgcataatt ctcttactgt catgccatcc     8520
gtaagatgct tttctgtgac tggtgagtac tcaaccaagt cattctgaga atagtgtatg     8580
cggcgaccga gttgctcttg cccggcgtca atacgggata ataccgcgcc acatagcaga     8640
actttaaaag tgctcatcat tggaaaacgt tcttcggggc gaaaactctc aaggatctta     8700
ccgctgttga gatccagttc gatgtaaccc actcgtgcac ccaactgatc ttcagcatct     8760
tttactttca ccagcgtttc tgggtgagca aaaacaggaa ggcaaaatgc cgcaaaaaag     8820
ggaataaggg cgacacggaa atgttgaata ctcatactct cctttttca atattattga      8880 agcatttatc agggttattg tctcatgagc ggatacatat ttgaatgtat ttagaaaaat     8940
aaacaaatag gggttccgcg cacatttccc cgaaaagtgc cacctgacgt                8990
```

<210> SEQ ID NO 77
<211> LENGTH: 561
<212> TYPE: PRT
<213> ORGANISM: Trichoderma atraviride

<400> SEQUENCE: 77

```
Met Thr Lys Asp Thr Val Asp Ile Leu Ile Asp Ser Leu Lys Ala Ala
1               5                   10                  15

Gly Val Lys Tyr Val Phe Gly Val Pro Gly Ala Lys Ile Asp Ser Val
            20                  25                  30

Phe Asn Ala Leu Ile Asp His Pro Asp Ile Lys Leu Val Val Cys Arg
        35                  40                  45

His Glu Gln Asn Ala Ala Phe Ile Ala Ala Met Gly Lys Val Thr
    50                  55                  60

Gly Arg Pro Gly Val Cys Ile Ala Thr Ser Gly Pro Gly Thr Ser Asn
65                  70                  75                  80

Leu Val Thr Gly Leu Val Thr Ala Thr Asp Glu Gly Ala Pro Val Val
                85                  90                  95

Ala Ile Val Gly Ser Val Lys Arg Ser Gln Ser Leu Gln Arg Thr His
            100                 105                 110

Gln Ser Leu Arg Gly Ala Asp Leu Leu Ala Pro Val Thr Lys Lys Val
        115                 120                 125

Val Ser Ala Val Val Glu Asp Gln Val Ala Glu Ile Met Leu Asp Ala
    130                 135                 140

Phe Arg Val Ala Ala Ala Ser Pro Pro Gly Ala Thr Ala Val Ser Leu
145                 150                 155                 160

Pro Ile Asp Leu Met Thr Pro Ala Lys Ser Thr Ser Thr Val Thr Ala
                165                 170                 175

Phe Pro Ala Glu Cys Phe Ile Pro Pro Lys Tyr Gly Lys Ser Pro Glu
            180                 185                 190

Thr Thr Leu Gln Ala Ala Ala Asp Leu Ile Ser Ala Ala Lys Ala Pro
        195                 200                 205

Val Leu Phe Leu Gly Met Arg Val Ser Glu Ser Asp Asp Thr Ile Ser
    210                 215                 220

Ala Val His Gly Phe Leu Arg Lys His Pro Val Pro Val Val Glu Thr
225                 230                 235                 240

Phe Gln Ala Ala Gly Ala Ile Ser Lys Glu Leu Val His Leu Phe Tyr
                245                 250                 255

Gly Arg Ile Gly Leu Phe Ser Asn Gln Pro Gly Asp Gln Leu Leu Gln
            260                 265                 270

His Ala Asp Leu Val Ile Ala Ile Gly Leu Asp Gln Ala Glu Tyr Asp
        275                 280                 285
```

-continued

Ala Asn Met Trp Asn Ala Arg Gly Thr Thr Ile Leu His Val Asp Ile
    290                 295                 300

Gln Pro Ala Asp Phe Val Ala His Tyr Lys Pro Lys Ile Glu Leu Val
305                 310                 315                 320

Gly Ser Leu Ala Asp Asn Met Thr Asp Leu Thr Ser Arg Leu Asp Thr
            325                 330                 335

Val Ala Arg Leu Gln Leu Thr Lys Pro Gly Glu Ala Ile Arg Thr Asn
        340                 345                 350

Met Trp Glu Trp Gln Asn Ser Pro Glu Ala Ser Gly Arg Ser Thr Gly
    355                 360                 365

Pro Val His Pro Leu His Phe Ile Arg Leu Phe Gln Ser Ile Ile Asp
370                 375                 380

Pro Ser Thr Thr Val Ile Ser Asp Val Gly Ser Val Tyr Ile Trp Leu
385                 390                 395                 400

Cys Arg Tyr Phe Tyr Ser Tyr Ala Arg Arg Thr Phe Leu Met Ser Asn
            405                 410                 415

Val Gln Gln Thr Leu Gly Val Ala Met Pro Trp Ala Ile Gly Val Ser
        420                 425                 430

Leu Ser Gln Thr Pro Pro Ser Ser Lys Lys Val Val Ser Ile Ser Gly
    435                 440                 445

Asp Gly Gly Phe Met Phe Ser Ser Gln Glu Leu Val Thr Ala Val Gln
450                 455                 460

Gln Gly Cys Asn Ile Thr His Phe Ile Trp Asn Asp Gly Lys Tyr Asn
465                 470                 475                 480

Met Val Glu Phe Gln Glu Val Asn Lys Tyr Gly Arg Ser Ser Gly Val
            485                 490                 495

Asp Leu Gly Gly Val Asp Phe Val Lys Leu Ala Asp Ser Met Gly Ala
        500                 505                 510

Lys Gly Leu Arg Val Ser Ser Ala Gly Asp Leu Glu Ala Val Met Lys
    515                 520                 525

Glu Ala Leu Ala Tyr Asp Gly Val Cys Leu Val Asp Ile Glu Ile Asp
530                 535                 540

Tyr Ser Gln Asn His Asn Leu Met Met Asp Leu Val Thr Ser Asp Val
545                 550                 555                 560

Ser

<210> SEQ ID NO 78
<211> LENGTH: 568
<212> TYPE: PRT
<213> ORGANISM: Talaromyces stipitatus

<400> SEQUENCE: 78

Met Ser Asn Arg Asn Pro Ser His Val Ile Val Glu Ser Leu Ser Asn
1               5                   10                  15

Ala Gly Val Lys Ile Val Phe Gly Ile Pro Gly Ala Lys Val Asp Gly
            20                  25                  30

Ile Phe Asp Ala Leu Ser Asp His Pro Thr Ile Lys Leu Ile Val Cys
        35                  40                  45

Arg His Glu Gln Asn Ala Ala Phe Met Ala Ala Val Gly Arg Leu
    50                  55                  60

Thr Gly Ala Pro Gly Val Cys Leu Val Thr Ser Gly Pro Gly Thr Ser
65                  70                  75                  80

Asn Leu Val Thr Gly Leu Ala Thr Ala Thr Thr Glu Gly Asp Pro Val
            85                  90                  95

```
Leu Ala Ile Ala Gly Thr Val Ser Arg Leu Gln Ala Ala Arg His Thr
                100                 105                 110

His Gln Ser Leu Asp Val Asn Lys Val Leu Glu Gly Val Cys Lys Ser
            115                 120                 125

Val Ile Gln Val Gly Val Glu Asp Gln Val Ser Glu Val Ile Ala Asn
        130                 135                 140

Ala Phe Arg His Ala Arg Gln Phe Pro Gln Gly Ala Thr Ala Val Ala
145                 150                 155                 160

Leu Pro Met Asp Ile Ile Lys Ser Thr Ser Val Gly Val Pro Pro Phe
                165                 170                 175

Pro Ser Leu Ser Phe Glu Ala Pro Gly Tyr Gly Ser Ser Asn Thr Lys
            180                 185                 190

Leu Cys Lys Val Ala Val Asp Lys Leu Ile Ala Ala Lys Tyr Pro Val
        195                 200                 205

Ile Leu Leu Gly Met Arg Ser Ser Asp Pro Glu Ile Val Ala Ser Val
        210                 215                 220

Arg Arg Met Ile Lys Asp His Thr Leu Pro Val Val Glu Thr Phe Gln
225                 230                 235                 240

Ala Ala Gly Ala Ile Ser Glu Asp Leu Leu His Arg Tyr Tyr Gly Arg
                245                 250                 255

Val Gly Leu Phe Arg Asn Gln Pro Gly Asp Lys Val Leu Ala Arg Ala
            260                 265                 270

Asp Leu Ile Ile Ala Val Gly Tyr Asp Pro Tyr Glu Tyr Asp Ala Glu
        275                 280                 285

Thr Trp Asn Val Asn Asn Pro Ala Thr Ile His Asn Ile Ile His Ile
        290                 295                 300

Asp Tyr Thr His Ser Arg Val Ser Gln His Tyr Met Pro His Val Glu
305                 310                 315                 320

Leu Leu Gly Asn Pro Ala Asp Ile Val Asp Glu Leu Thr Ala Ser Leu
                325                 330                 335

Gln Ala Leu Lys Pro Asn Phe Trp Ser Gly Ala Glu Asp Thr Leu Glu
            340                 345                 350

Asn Ile Arg Gln Glu Ile Ala Arg Cys Glu Ala Thr Ala Thr His Thr
        355                 360                 365

Glu Ser Leu Gln Asp Gly Ala Val Gln Pro Thr His Phe Val Tyr Gln
        370                 375                 380

Leu Arg His Leu Leu Pro Lys Glu Thr Ile Val Ala Val Asp Val Gly
385                 390                 395                 400

Thr Val Tyr Ile Tyr Met Met Arg Tyr Phe Gln Thr Tyr Ser Pro Arg
                405                 410                 415

His Leu Leu Cys Ser Asn Gly Gln Gln Thr Leu Gly Val Gly Leu Pro
            420                 425                 430

Trp Ala Ile Ala Ala Ser Leu Ile Gln Glu Pro Pro Cys Ser Arg Lys
        435                 440                 445

Val Val Ser Ile Ser Gly Asp Gly Gly Phe Met Phe Ser Ser Gln Glu
        450                 455                 460

Leu Ala Thr Ala Val Leu Gln Lys Cys Asn Ile Thr His Phe Ile Trp
465                 470                 475                 480

Asn Asp Ser Gly Tyr Asn Met Val Glu Phe Gln Glu Glu Ala Lys Tyr
                485                 490                 495

Gly Arg Ser Ser Gly Ile Lys Leu Gly Gly Ile Asp Phe Val Lys Phe
            500                 505                 510
```

-continued

```
Ala Glu Ala Phe Asp Gly Ala Arg Gly Phe Arg Ile Asn Ser Thr Lys
        515                 520                 525

Glu Val Lys Glu Val Ile Lys Glu Ala Leu Ala Phe Glu Gly Val Ala
        530                 535                 540

Ile Val Asp Val Arg Ile Asp Tyr Ser Arg Ser His Glu Leu Met Lys
545                 550                 555                 560

Asp Ile Ile Pro Lys Asp Tyr Gln
                565
```

YEAST ORGANISM PRODUCING ISOBUTANOL AT A HIGH YIELD

CROSS-REFERENCE TO RELATED APPLICATIONS

This application is a continuation of U.S. application Ser. No. 13/907,394, now abandoned, filed May 31, 2013, which is a continuation of U.S. application Ser. No. 12/820,505, filed Jun. 22, 2010, which issued as U.S. Pat. No. 8,455,239, which claims the benefit and priority of U.S. Provisional Application Ser. No. 61/219,173, filed Jun. 22, 2009, and is a continuation-in-part of U.S. application Ser. No. 12/696, 645, now abandoned, filed Jan. 29, 2010, which is a divisional of U.S. application Ser. No. 12/343,375, filed Dec. 23, 2008, which issued as U.S. Pat. No. 8,017,375, which claims the benefit of U.S. Provisional Application Ser. No. 61/016, 483, filed Dec. 23, 2007, all of which are herein incorporated by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_027_10US_SeqList.txt, date recorded: Sep. 8, 2014, file size 436 kilobytes).

TECHNICAL FIELD

Metabolically engineered microorganisms and methods of producing such organisms are provided. Also provided are methods of producing metabolites that are biofuels by contacting a suitable substrate with metabolically engineered microorganisms and enzymatic preparations there from.

BACKGROUND

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s coupled to the decrease in US oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivations for developing biofuels are of economical, political, and environmental nature.

One is the threat of 'peak oil', the point at which the consumption rate of crude oil exceeds the supply rate, thus leading to significantly increased fuel cost results in an increased demand for alternative fuels. In addition, instability in the Middle East and other oil-rich regions has increased the demand for domestically produced biofuels. Also, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

Ethanol is the most abundant fermentatively produced fuel today but has several drawbacks when compared to gasoline. Butanol, in comparison, has several advantages over ethanol as a fuel: it can be made from the same feedstocks as ethanol but, unlike ethanol, it is compatible with gasoline at any ratio and can also be used as a pure fuel in existing combustion engines without modifications. Unlike ethanol, butanol does not absorb water and can thus be stored and distributed in the existing petrochemical infrastructure. Due to its higher energy content which is close to that of gasoline, the fuel economy (miles per gallon) is better than that of ethanol. Also, butanol-gasoline blends have lower vapor pressure than ethanol-gasoline blends, which is important in reducing evaporative hydrocarbon emissions.

Isobutanol has the same advantages as butanol with the additional advantage of having a higher octane number due to its branched carbon chain. Isobutanol is also useful as a commodity chemical and is also a precursor to isobutylene and isobutylene-derived fuels and chemicals. Isobutanol has been produced recombinantly in yeast microorganisms expressing a heterologous metabolic pathway (See, e.g., WO/2007/050671 to Donaldson et al., and WO/2008/098227 to Liao et al.). However, these yeast microorganisms fall short of commercial relevance due to their low performance characteristics, including low productivity, low titer, low yield, and the requirement for oxygen during the fermentation process. One of the primary reasons for the sub-optimal performance observed in existing isobutanol-producing microorganisms is the undesirable conversion of pathway intermediates to unwanted by-products.

Thus, there is an existing need to identify and reduce and/or eliminate the metabolic processes catalyzing the conversion of isobutanol pathway intermediates to unwanted by-products. The present inventors have addressed this need by providing recombinant microorganisms with reduced pyruvate decarboxylase (PDC) activity and reduced glycerol-3-phosphate dehydrogenase (GPD) activity.

SUMMARY OF THE INVENTION

The present inventors have observed that by combining the expression of a cytosolically localized acetolactate synthase enzyme with reduced pyruvate decarboxylase (PDC) activity and/or reduced glycerol-3-phosphate dehydrogenase (GPD) activity, an unexpectedly high flux from pyruvate to acetolactate can be achieved. Thus, the invention provides yeast cells that are engineered to exhibit an efficient conversion of pyruvate to acetolactate in the cytoplasm due to suppression of competing metabolic pathways. Therefore, as would be understood in the art, the present invention has utility for the production of any acetolactate-derived product, including, but not limited to, isobutanol, 2-butanol, 1-butanol, 2-butanone, 2,3-butanediol, valine, leucine, and 3-methyl-1-butanol.

Accordingly, in a first aspect, the invention provides a recombinant microorganism, such as a yeast cell, comprising a cytosolically-localized polypeptide having acetolactate synthase activity wherein the yeast cell is substantially free of an enzyme having pyruvate decarboxylase (PDC) activity and/or glycerol-3-phosphate dehydrogenase (GPD) activity, and wherein the cell converts pyruvate to acetolactate.

Thus, in various embodiments described herein, the present invention provides recombinant microorganisms engineered to include reduced pyruvate decarboxylase (PDC) activity as compared to a parental microorganism. In one embodiment, PDC activity is eliminated. PDC catalyzes the decarboxylation of pyruvate to acetaldehyde, which is reduced to ethanol by alcohol dehydrogenases via the oxidation of NADH to NAD+. In one embodiment, the recombinant microorganism includes a mutation in at least one PDC gene resulting in a reduction of PDC activity of a polypeptide encoded by said gene. In another embodiment, the recombinant microorganism includes a partial deletion of a PDC gene resulting in a reduction of PDC activity of a polypeptide encoded by said gene. In another embodiment, the recombinant microorganism comprises a complete deletion of a PDC gene resulting in a reduction of PDC activity of a polypeptide encoded by said gene. In yet another embodiment, the recombinant microorganism includes a modification of the regulatory region associated with at least one PDC gene resulting in a reduction of PDC activity of a polypeptide encoded by said gene. In yet another embodiment, the recombinant microorganism comprises a modification of the transcriptional regulator resulting in a reduction of PDC gene transcription. In yet another embodiment, the recombinant microorganism comprises mutations in all PDC genes resulting in a reduction of PDC activity of the polypeptides encoded by said genes. In another embodiment, the recombinant microorganism includes partial deletions of all PDC genes resulting in a reduction of PDC activity of the polypeptides encoded by said genes. In yet another embodiment, the recombinant microorganism comprises a deletion of all PDC genes resulting in the elimination of PDC activity of the polypeptides encoded by said genes.

In additional embodiments, the present invention provides recombinant microorganisms engineered to exhibit reduced glycerol-3-phosphate dehydrogenase (GPD) activity as compared to a parental microorganism. In one embodiment, GPD activity is eliminated. GPD catalyzes the reduction of dihydroxyacetone phosphate (DHAP) to glycerol-3-phosphate (G3P) via the oxidation of NADH to NAD$^+$. Glycerol is produced from G3P by Glycerol-3-phosphatase (GPP). In one embodiment, the recombinant microorganism includes a mutation in at least one GPD gene resulting in a reduction of GPD activity of a polypeptide encoded by said gene. In another embodiment, the recombinant microorganism includes a partial deletion of a GPD gene resulting in a reduction of GPD activity of a polypeptide encoded by the gene. In another embodiment, the recombinant microorganism comprises a complete deletion of a GPD gene resulting in a reduction of GPD activity of a polypeptide encoded by the gene. In yet another embodiment, the recombinant microorganism includes a modification of the regulatory region associated with at least one GPD gene resulting in a reduction of GPD activity of a polypeptide encoded by said gene. In yet another embodiment, the recombinant microorganism comprises a modification of the transcriptional regulator resulting in a reduction of GPD gene transcription. In another embodiment, the recombinant microorganism includes partial deletions of all GPD genes resulting in a reduction of GPD activity of the polypeptides encoded by said genes. In yet another embodiment, the recombinant microorganism comprises mutations in all GPD genes resulting in a reduction of GPD activity of the polypeptides encoded by said genes. In yet another embodiment, the recombinant microorganism comprises a deletion of all GPD genes resulting in the elimination of GPDs activity of the polypeptides encoded by said genes.

In an exemplary embodiment, the present invention provides a recombinant microorganism engineered to exhibit reduced pyruvate decarboxylase (PDC) activity and reduced glycerol-3-phosphate dehydrogenase (GPD) activity as compared to a parental microorganism.

In additional embodiments, the present invention provides recombinant microorganisms engineered to exhibit reduced pyruvate dehydrogenase (PDH) activity as compared to a parental microorganism. In one embodiment, the recombinant microorganism is engineered to have reduced pyruvate decarboxylase (PDC) activity and reduced pyruvate dehydrogenase (PDH) activity. In another embodiment, the recombinant microorganism is engineered to have reduced glycerol-3-phosphate dehydrogenase (GPD) activity and reduced pyruvate dehydrogenase (PDH) activity. In yet another embodiment, the recombinant microorganism is engineered to have reduced pyruvate decarboxylase (PDC) activity, reduced glycerol-3-phosphate dehydrogenase (GPD) activity, and reduced pyruvate dehydrogenase (PDH) activity.

In various embodiments described herein, the present invention provides recombinant microorganisms, including, but not limited to those, that comprise an isobutanol producing metabolic pathway. In some embodiments, the recombinant microorganisms can be engineered to express an isobutanol producing metabolic pathway comprising at least one exogenous gene that catalyzes a step in the conversion of pyruvate to isobutanol. In one embodiment, the recombinant microorganism may be engineered to express an isobutanol producing metabolic pathway comprising at least two exogenous genes. In another embodiment, the recombinant microorganism may be engineered to express an isobutanol producing metabolic pathway comprising at least three exogenous genes. In another embodiment, the recombinant microorganism may be engineered to express an isobutanol producing metabolic pathway comprising at least four exogenous genes. In another embodiment, the recombinant microorganism may be engineered to express an isobutanol producing metabolic pathway comprising five exogenous genes.

In various embodiments described herein, isobutanol producing metabolic pathway comprises at least one exogenous gene that catalyzes a step in the conversion of pyruvate to isobutanol. In one embodiment, the exogenous gene encodes a polypeptide selected from the group consisting of acetolactate synthase (ALS), ketol-acid reductoisomerase (KARI), dihydroxyacid dehydratase (DHAD), 2-keto-acid decarboxylase (KIVD), and alcohol dehydrogenase (ADH). In another embodiment, the exogenous gene encodes an acetolactate synthase (ALS). In an exemplary embodiment, the acetolactate synthase is a cytosolically-localized acetolactate synthase. In one specific embodiment, the cytosolically-localized acetolactate synthase is encoded by the *Lactococcus lactis* gene alsS. In another specific embodiment, the cytosolically-localized acetolactate synthase is encoded by the *Bacillus subtilis* gene alsS.

In additional embodiments, the recombinant microorganism comprises an isobutanol producing metabolic pathway comprising genes encoding an NADH-dependent KARI and an NADH-dependent ADH. In one embodiment, the KARI and/or the ADH show at least a 10-fold higher catalytic efficiency using NADH as the cofactor as compared to the wild-type *E. coli* KARI ilvC and a native *E. coli* ADH yqhD, respectively. In another embodiment, the KARI and/or the ADH have been modified or mutated to be NADH-dependent. In yet another embodiment, the KARI and/or the ADH has been identified in nature with increased activity using NADH as a cofactor as compared to the wild-type *E. coli* KARI ilvC and a native *E. coli* ADH yqhD, respectively.

In some embodiments, the invention provides a recombinant microorganism comprising an isobutanol producing metabolic pathway, wherein said recombinant microorganism comprises a reduction in pyruvate decarboxylase (PDC) activity as compared to a parental microorganism. In additional embodiments, the recombinant microorganism comprises a reduction in glycerol-3-phosphate dehydrogenase (GPD) activity as compared to a parental microorganism. In yet other embodiments, the recombinant microorganism comprises a reduction in pyruvate decarboxylase (PDC) activity and glycerol-3-phosphate dehydrogenase (GPD) activity as compared to a parental microorganism. In still yet other embodiments, the recombinant microorganism comprises a reduction in pyruvate decarboxylase (PDC) activity, a reduction in glycerol-3-phosphate dehydrogenase (GPD) activity, and a reduction in pyruvate dehydrogenase (PDH) activity as compared to a parental microorganism.

In various embodiments described herein, the present invention provides recombinant microorganisms that comprise a pathway for the fermentation of isobutanol from a pentose sugar. In one embodiment, the pentose sugar is xylose. In one embodiment, the recombinant microorganism is engineered to express a functional xylose isomerase (XI). In another embodiment, the recombinant microorganism further comprises a deletion or disruption of a native gene encoding for an enzyme that catalyzes the conversion of xylose to xylitol. In one embodiment, the native gene is xylose reductase (XR). In another embodiment, the native gene is xylitol dehydrogenase (XDH). In yet another embodiment, both native genes are deleted or disrupted. In yet another embodiment, the recombinant microorganism further engineered to express, xylulose kinase which catalyzes the conversion of xylulose to xylulose-5-phosphate.

In some embodiments, the microorganisms of the present invention are engineered to grow on glucose independently of C2-compounds at a growth rate substantially equivalent to the growth rate of a parental microorganism without altered PDC activity.

In various embodiments described herein, the recombinant microorganisms may be microorganisms of the *Saccharomyces* clade, *Saccharomyces sensu stricto* microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces sensu stricto* microorganisms. In one embodiment, the *Saccharomyces sensu stricto* is selected from the group consisting of *S. cerevisiae, S. kudriavzevii, S. mikatae, S. bayanus, S. uvarum, S. carocanis* and hybrids thereof.

In some embodiments, the recombinant microorganisms may be Crabtree-negative recombinant yeast microorganisms. In one embodiment, the Crabtree-negative yeast microorganism is classified into a genera selected from the group consisting of *Kluyveromyces, Pichia, Hansenula,* or *Candida*. In additional embodiments, the Crabtree-negative yeast microorganism is selected from *Kluyveromyces lactis, Kluyveromyces marxianus, Pichia anomala, Pichia stipitis, P. kudriavzevii, Hansenula anomala, Candida utilis* and *Kluyveromyces waltii*.

In some embodiments, the recombinant microorganisms may be Crabtree-positive recombinant yeast microorganisms. In one embodiment, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces*. In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. bailli, Z. rouxii, Debaryomyces hansenii, Pichia pastorius, Schizosaccharomyces pombe,* and *Saccharomyces uvarum*.

In some embodiments, the recombinant microorganisms may be post-WGD (whole genome duplication) yeast recombinant microorganisms. In one embodiment, the post-WGD yeast recombinant microorganism is classified into a genera selected from the group consisting of *Saccharomyces* or *Candida*. In additional embodiments, the post-WGD yeast is selected from the group consisting of *Saccharomyces cerevisiae, Saccharomyces uvarum, Saccharomyces bayanus, Saccharomyces paradoxus, Saccharomyces castelli,* and *Candida glabrata*.

In some embodiments, the recombinant microorganisms may be pre-WGD (whole genome duplication) yeast recombinant microorganisms. In one embodiment, the pre-WGD yeast recombinant microorganism is classified into a genera selected from the group consisting of *Saccharomyces, Kluyveromyces, Candida, Pichia, Debaryomyces, Hansenula, Pachysolen, Yarrowia* and *Schizosaccharomyces*. In additional embodiments, the pre-WGD yeast is selected from the group consisting of *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Debaryomyces hansenii, Hansenula anomala, Pachysolen tannophilis, Yarrowia lipolytica,* and *Schizosaccharomyces pombe*.

In some embodiments, the recombinant microorganisms may be microorganisms that are non-fermenting yeast microorganisms, including, but not limited to those, classified into a genera selected from the group consisting of *Tricosporon, Rhodotorula,* or *Myxozyma*.

In another aspect, the present invention provides methods of producing isobutanol using a recombinant microorganism of the invention. In one embodiment, the method includes cultivating the recombinant microorganism in a culture medium containing a feedstock providing the carbon source until a recoverable quantity of the isobutanol is produced and optionally, recovering the isobutanol. In one embodiment, the microorganism is selected to produce isobutanol from a carbon source at a yield of at least about 5 percent theoretical. In another embodiment, the microorganism is selected to produce isobutanol at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, or at least about 95 percent theoretical.

In one embodiment, the microorganism is selected to produce isobutanol from a carbon source at a specific productivity of at least about 0.7 mg/L/hr per OD. In another embodiment, the microorganism is selected to produce isobutanol from a carbon source at a specific productivity of at least about 1 mg/L/hr per OD, at least about 10 mg/L/hr per OD, at least about 50 mg/L/hr per OD, at least about 100 mg/L/hr per OD, at least about 250 mg/L/hr per OD, or at least about 500 mg/L/hr per OD.

BRIEF DESCRIPTION OF DRAWINGS

Illustrative embodiments of the invention are illustrated in the drawings, in which.

DETAILED DESCRIPTION

Figure 1:
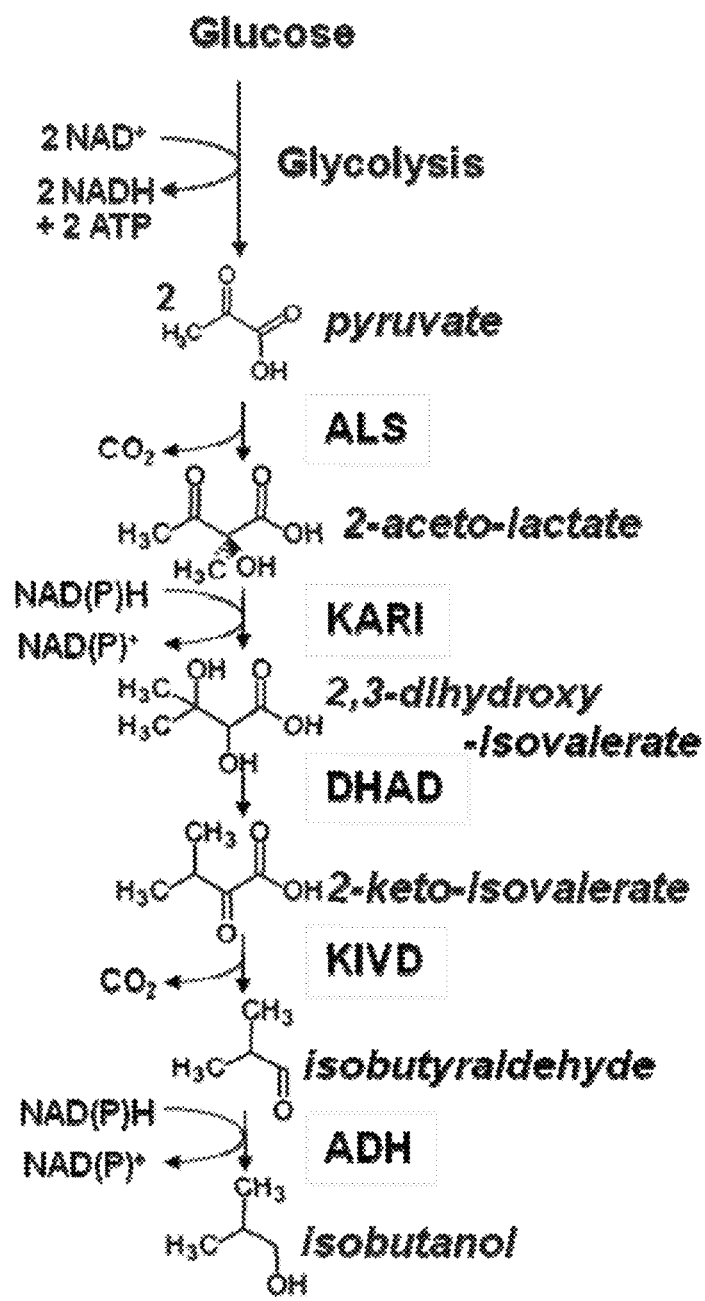
FIG. 1 illustrates an exemplary embodiment of an isobutanol pathway.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007)

The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The term "recombinant microorganism," "modified microorganism," and "recombinant host cell" are used interchangeably herein and refer to microorganisms that have been genetically modified to express or over-express endogenous polynucleotides, or to express heterologous polynucleotides, such as those included in a vector, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that are recognize and bind reacting the protein. See Sambrook et al., 1989, supra. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or over-express a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism The term "engineer" refers to any manipulation of a microorganism that result in a detectable change in the microorganism, wherein the manipulation includes but is not limited to inserting a polynucleotide and/or polypeptide heterologous to the microorganism and mutating a polynucleotide and/or polypeptide native to the microorganism. The term "metabolically engineered" or "metabolic engineering" involves rational pathway design and assembly of biosynthetic genes, genes associated with operons, and control elements of such polynucleotides, for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

The terms "metabolically engineered microorganism" and "modified microorganism" are used interchangeably herein and refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial selection pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "heterologous" as used herein with reference to molecules and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate.

The term "fermentation" or "fermentation process" is defined as a process in which a microorganism is cultivated in a culture medium containing raw materials, such as feedstock and nutrients, wherein the microorganism converts raw materials, such as a feedstock, into products. The term "cell dry weight" or "CDW" refers to the weight of the microorganism after the water contained in the microorganism has been removed using methods known to one skilled in the art. CDW is reported in grams.

The term "biofuel" refers to a fuel in which all carbon contained within the fuel is derived from biomass and is biochemically converted, at least in part, in to a fuel by a microorganism. A biofuel is further defined as a non-ethanol compound which contains less than 0.5 oxygen atoms per carbon atom. A biofuel is a fuel in its own right, but may be blended with petroleum-derived fuels to generate a fuel. A biofuel may be used as a replacement for petrochemically-derived gasoline, diesel fuel, or jet fuel.

The term "volumetric productivity" or "production rate" is defined as the amount of product formed per volume of medium per unit of time. Volumetric productivity is reported in gram per liter per hour (g/L/h).

The term "specific productivity" or "specific production rate" is defined as the amount of product formed per volume of medium per unit of time per amount of cells. Volumetric productivity is reported in gram or milligram per liter per hour per OD (g/Lh/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 gig would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. Methods for the production of isobutanol under anaerobic conditions are described in commonly owned and co-pending applications U.S. Ser. No. 12/610,784 and PCT/US09/62952 (published as WO/2010/051527), the disclosures of which are herein incorporated by reference in their entireties for all purposes.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to acetaldehyde, yielding ethanol. Fermentative pathways are usually active under anaerobic conditions but may also occur under aerobic conditions, under conditions where NADH is not fully oxidized via the respiratory chain. For example, above certain glucose concentrations, Crabtree-positive yeasts produce large amounts of ethanol under aerobic conditions.

The term "byproduct" or "by-product" means an undesired product related to the production of a biofuel or biofuel precursor. Byproducts are generally disposed as waste, adding cost to a production process.

The term "substantially free" when used in reference to the presence or absence of enzymatic activities (PDC, GPD, PDH, etc.) in carbon pathways that compete with the desired metabolic pathway (e.g. an isobutanol-producing metabolic pathway) means the level of the enzyme is substantially less than that of the same enzyme in the wild-type host, wherein less than about 50% of the wild-type level is preferred and less than about 30% is more preferred. The activity may be less than about 20%, less than about 10%, less than about 5%, or less than about 1% of wild-type activity.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. 3 edition. p. 28-29. Cambridge University Press, Cambridge, UK.) or by monitoring the production of fermentation productions such as ethanol and $CO_2$.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers.

The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

As used herein and as would be understood by one of ordinary skill in the art, "reduced activity and/or expression" of an endogenous protein such an enzyme can mean either a reduced specific catalytic activity of the protein (e.g. reduced activity) and/or decreased concentrations of the protein in the cell (e.g. reduced expression), while "deleted activity and/or expression" of an endogenous protein such an enzyme can mean either no or negligible specific catalytic activity of the enzyme (e.g. deleted activity) and/or no or negligible concentrations of the enzyme in the cell (e.g. deleted expression).

The term "reduced pyruvate decarboxylase activity" means either a decreased concentration of the pyruvate decarboxylase enzyme in the cell or reduced or no specific catalytic activity of the pyruvate decarboxylase enzyme.

The term "reduced glycerol-3-phosphate dehydrogenase activity" means either a decreased concentration of the glycerol-3-phosphate dehydrogenase enzyme in the cell or reduced or no specific catalytic activity of the glycerol-3-phosphate dehydrogenase enzyme.

The term "reduced pyruvate dehydrogenase activity" means either a decreased concentration of the pyruvate dehydrogenase enzyme in the cell or reduced or no specific catalytic activity of the pyruvate dehydrogenase enzyme.

The term "reduced xylose reductase activity" means either a decreased concentration of the xylose reductase enzyme in the cell or reduced or no specific catalytic activity of the xylose reductase enzyme.

The term "reduced xylitol dehydrogenase activity" means either a decreased concentration of xylitol dehydrogenase enzyme in the cell or reduced or no specific catalytic activity of the xylitol dehydrogenase enzyme.

The Microorganism in General

Native producers of 1-butanol, such as *Clostridium acetobutylicum*, are known, but these organisms also generate byproducts such as acetone, ethanol, and butyrate during fermentations. Furthermore, these microorganisms are relatively difficult to manipulate, with significantly fewer tools available than in more commonly used production hosts such as *E. coli* and yeast (e.g. *S. cerevisiae*).

Yeast cells produce pyruvate from sugars, which is then utilized in a number of pathways of cellular metabolism. Yeast cells can be engineered to produce a number of desirable products with the initial biosynthetic pathway step being conversion of endogenous pyruvate to acetolactate. The present inventors have observed that by combining the expression of a cytosolically localized acetolactate synthase enzyme with reduced pyruvate decarboxylase (PDC) activity and/or reduced glycerol-3-phosphate dehydrogenase (GPD) activity, an unexpectedly high flux from pyruvate to acetolactate can be achieved. Thus, the invention provides yeast cells that are engineered to exhibit an efficient conversion of pyruvate to acetolactate in the cytoplasm due to suppression of competing metabolic pathways. Therefore, as would be understood in the art, the present invention has utility for the production of any acetolactate-derived product, including, but not limited to, isobutanol, 2-butanol, 1-butanol, 2-butanone, 2,3-butanediol, valine, leucine, and 3-methyl-1-butanol.

Engineered biosynthetic pathways for synthesis of isobutanol are described in commonly owned and co-pending applications U.S. Ser. No. 12/343,375 (published as US 2009/0226991), U.S. Ser. No. 12/696,645, U.S. Ser. No. 12/610,784, PCT/US09/62952 (published as WO/2010/051527), and PCT/US09/69390, all of which are herein incorporated by reference in their entireties for all purposes. Additional pathways have been described for the synthesis of 1-butanol (See, e.g., commonly owned U.S. Provisional Application Nos. 60/940,877 and 60/945,576, as well as WO/2010/017230 and WO/2010/031772), 2-butanol (See, e.g., WO/2007/130518, WO/2007/130521, and WO/2009/134276), 2-butanone (See, e.g., WO/2007/130518, WO/2007/130521, and WO/2009/134276), 2,3-butanediol (See, e.g., WO/2007/130518, WO/2007/130521, and WO/2009/134276), valine (See, e.g., WO/2001/021772, and McCourt et al., 2006, *Amino Acids* 31: 173-210), leucine (See, e.g., WO/2001/021772, and McCourt et al., 2006, *Amino Acids* 31: 173-210), pantothenic acid (See, e.g., WO/2001/021772), and 3-methyl-1-butanol (See, e.g., WO/2008/098227, Atsumi et al., 2008, *Nature* 451: 86-89, and Connor et al., 2008, *Appl. Environ. Microbiol.* 74: 5769-5775). Each of these pathways shares the common intermediate acetolactate. Therefore, the product yield from these biosynthetic pathways will in part depend upon the amount of acetolactate that is available to downstream enzymes of said biosynthetic pathways.

In various embodiments described herein, the present invention provides recombinant microorganisms that comprise an isobutanol producing metabolic pathway. Recombinant microorganisms provided herein can express a plurality of heterologous and/or native target enzymes involved in pathways for the production isobutanol from a suitable carbon source.

Accordingly, metabolically "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material into and/or the modification of the expression of native genes in a parental microorganism results in a new or modified ability to produce isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

In addition to the introduction of a genetic material into a host or parental microorganism, an engineered or modified microorganism can also include alteration, disruption, deletion or knocking-out of a gene or polynucleotide to alter the cellular physiology and biochemistry of the microorganism. Through the alteration, disruption, deletion or knocking-out of a gene or polynucleotide the microorganism acquires new or improved properties (e.g., the ability to produce a new metabolite or greater quantities of an intracellular metabolite, improve the flux of a metabolite down a desired pathway, and/or reduce the production of byproducts).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, and isobutanol. The metabolite isobutanol can be produced by a recombinant microorganism metabolically engineered to express or over-express a metabolic pathway that converts pyruvate to isobutanol. An exemplary metabolic pathway that converts pyruvate to isobutanol may be comprised of an acetohydroxy acid synthase (ALS), a ketolacid reductoisomerase (KARI), a dihyroxy-acid dehydratase (DHAD), a 2-keto-acid decarboxylase (KIVD), and an alcohol dehydrogenase (ADH). Exemplary metabolic pathways that convert pyruvate to isobutanol are disclosed in WO/2007/050671, WO/2008/098227, and Atsumi et al., Nature, 2008 Jan. 3; 451(7174):86-9.

Accordingly, provided herein are recombinant microorganisms that produce isobutanol and in some aspects may include the elevated expression of target enzymes such as ALS, KARI, DHAD, KIVD, and ADH.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson W. R. Using the FASTA program to search protein and DNA sequence databases, Methods in Molecular Biology, 1994, 25:365-89, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutant protein thereof. See, e.g., GCG Version 6.1.

A typical algorithm used comparing a molecule sequence to a database containing a large number of sequences from different organisms is the computer program BLAST (Altschul, S. F., et al. (1990) "Basic local alignment search tool." J. Mol. Biol. 215:403-410; Gish, W. and States, D. J. (1993) "Identification of protein coding regions by database similarity search." Nature Genet. 3:266-272; Madden, T. L., et al. (1996) "Applications of network BLAST server" Meth. Enzymol. 266:131-141; Altschul, S. F., et al. (1997) "Gapped BLAST and PSI-BLAST: a new generation of protein database search programs." Nucleic Acids Res. 25:3389-3402; Zhang, J. and Madden, T. L. (1997) "PowerBLAST: A new network BLAST application for interactive or automated sequence analysis and annotation." Genome Res. 7:649-656), especially blastp or tblastn (Altschul, S. F., et al. (1997) "Gapped BLAST and PSI-BLAST: a new generation of protein database search programs." Nucleic Acids Res. 25:3389-3402). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, W. R. (1990) "Rapid and Sensitive Sequence Comparison with FASTP and FASTA" Meth. Enzymol. 183:63-98). For example, a percent sequence identity between amino acid sequences can be determined using FASTA with its default parameters (a word size of 2 and the PAM250 scoring matrix), as provided in GCG Version 6.1, hereby incorporated herein by reference.

The disclosure provides metabolically engineered microorganisms comprising a biochemical pathway for the production of isobutanol from a suitable substrate at a high yield. A metabolically engineered microorganism of the disclosure comprises one or more recombinant polynucleotides within the genome of the organism or external to the genome within the organism. The microorganism can comprise a reduction, disruption or knockout of a gene found in the wild-type organism and/or introduction of a heterologous polynucleotide and/or expression or overexpression of an endogenous polynucleotide.

In one aspect, the disclosure provides a recombinant microorganism comprising elevated expression of at least one target enzyme as compared to a parental microorganism or encodes an enzyme not found in the parental organism. In another or further aspect, the microorganism comprises a reduction, disruption or knockout of at least one gene encoding an enzyme that competes with a metabolite necessary for the production of isobutanol. The recombinant microorganism produces at least one metabolite involved in a biosynthetic pathway for the production of isobutanol. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of isobutanol. The target enzyme is encoded by, and expressed from, a polynucleotide derived from a suitable biological source. In some embodiments, the polynucleotide comprises a gene derived from a prokaryotic or eukaryotic source and recombinantly engineered into the microorganism of the disclosure. In other embodiments, the polynucleotide comprises a gene that is native to the host organism.

It is understood that a range of microorganisms can be modified to include a recombinant metabolic pathway suitable for the production of isobutanol. In various embodiments, microorganisms may be selected from yeast microorganisms. Yeast microorganisms for the production of isobutanol may be selected based on certain characteristics:

One characteristic may include the property that the microorganism is selected to convert various carbon sources into isobutanol. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose. The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feed stock for fermentations using a biocatalyst.

Accordingly, in one embodiment, the recombinant microorganism herein disclosed can convert a variety of carbon sources to products, including but not limited to glucose, galactose, mannose, xylose, arabinose, lactose, sucrose, and mixtures thereof.

The recombinant microorganism may thus further include a pathway for the fermentation of isobutanol from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via a xylulokinase (XK) enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugar. Accordingly, a yeast species that can efficiently ferment xylose and other pentose sugars into a desired fermentation product is therefore very desirable.

Thus, in one embodiment, the recombinant is engineered to express a functional exogenous xylose isomerase. Exogenous xylose isomerases functional in yeast are known in the art. See, e.g., Rajgarhia et al, US20060234364, which is herein incorporated by reference in its entirety. In another embodiment, the exogenous xylose isomerase gene is operatively linked to promoter and terminator sequences that are functional in the yeast cell.

In another embodiment, the recombinant microorganism has a deletion or disruption of a native gene that encodes for an enzyme (e.g. XR and/or XDH) that catalyzes the conversion of xylose to xylitol. Thus, in one embodiment, the recombinant microorganism is engineered to exhibit reduced xylose reductase (XR) activity. In another embodiment, the recombinant microorganism is engineered to exhibit reduced xylitol dehydrogenase (XDH) activity. In yet another embodiment, the recombinant microorganism also contains a functional, exogenous xylulokinase (XK) gene operatively linked to promoter and terminator sequences that are functional in the yeast cell. In one embodiment, the xylulokinase (XK) gene is overexpressed.

In one embodiment, the microorganism has reduced or no pyruvate decarboxylase (PDC) activity. PDC catalyzes the decarboxylation of pyruvate to acetaldehyde, which is then reduced to ethanol by ADH via an oxidation of NADH to NAD+. Ethanol production is the main pathway to oxidize the NADH from glycolysis. Deletion of this pathway increases the pyruvate and the reducing equivalents (NADH) available for the isobutanol pathway. Accordingly, deletion of PDC genes further increases the yield of isobutanol.

In another embodiment, the microorganism has reduced or no glycerol-3-phosphate dehydrogenase (GPD) activity. GPD catalyzes the reduction of dihydroxyacetone phosphate (DHAP) to glycerol-3-phosphate (G3P) via the oxidation of NADH to NAD+. Glycerol is then produced from G3P by Glycerol-3-phosphatase (GPP). Glycerol production is a secondary pathway to oxidize excess NADH from glycolysis. Reduction or elimination of this pathway increases the pyruvate and reducing equivalents (NADH) available for the isobutanol pathway. Thus, deletion of GPD genes further increases the yield of isobutanol.

In yet another embodiment, the microorganism has reduced or no PDC activity and reduced or no GPD activity.

Another characteristic may include the property that the wild-type or parental microorganism is non-fermenting. In other words, it cannot metabolize a carbon source anaerobically while the yeast is able to metabolize a carbon source in the presence of oxygen. Non-fermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). Thus, in one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the isobutanol pathway. Fermentative pathways contribute to low yield and low productivity of isobutanol. Accordingly, deletion of PDC may increase yield and productivity of isobutanol.

A third characteristic may include the property that the biocatalyst is selected to convert various carbon sources into isobutanol.

Figure 2:
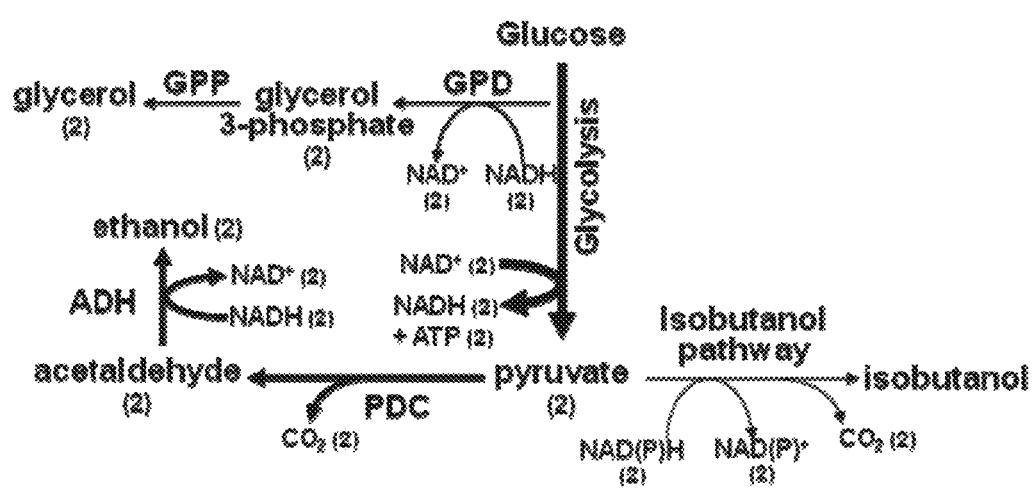
FIG. 2 illustrates production of pyruvate via glycolysis, together with an isobutanol pathway which converts pyruvate to isobutanol and a PDC pathway which converts pyruvate to acetaldehyde and carbon dioxide.

In one embodiment, the yeast microorganisms may be selected from the "*Saccharomyces* Yeast *Clade*", defined as an *ascomycetous* yeast taxonomic class by Kurtzman and Robnett in 1998 ("Identification and phylogeny of *ascomycetous* yeast from analysis of nuclear large subunit (26S) ribosomal DNA partial sequences." Antonie van Leeuwenhoek 73: 331-371, See FIG. 2 of Leeuwenhoek reference). They were able to determine the relatedness of approximately 500 yeast species by comparing the nucleotide sequence of the D1/D2 domain at the 5' end of the gene encoding the large ribosomal subunit 26S. In pair-wise comparisons of the D1/D2 nucleotide sequences of *S. cerevisiae* and the two most distant yeast from *S. cerevisiae*, *K. lactis* and *K. marxianus*, share greater than 80% identity.

The term "*Saccharomyces sensu stricto*" taxonomy group is a cluster of yeast species that are highly related to *S. cerevisiae* (Rainieri, S. et at 2003. *Saccharomyces Sensu Stricto*: Systematics, Genetic Diversity and Evolution. J. Biosci Bioengin 96(1)1-9. *Saccharomyces sensu stricto* yeast species include but are not limited to *S. cerevisiae*, *S. cerevisiae*, *S. kudriavzevii*, *S. mikatae*, *S. bayanus*, *S. uvarum*, *S. carocanis* and hybrids derived from these species (Masneuf et al. 1998. New Hybrids between *Saccharomyces Sensu Stricto* Yeast Species Found Among Wine and Cider Production Strains. *Yeast* 7(1)61-72).

An ancient whole genome duplication (WGD) event occurred during the evolution of the hemiascomycete yeast and was discovered using comparative genomic tools (Kellis et al 2004 "Proof and evolutionary analysis of ancient genome duplication in the yeast *S. cerevisiae*." *Nature*

428:617-624. Dujon et al 2004 "Genome evolution in yeasts." *Nature* 430:35-44. Langkjaer et al 2003 "Yeast genome duplication was followed by asynchronous differentiation of duplicated genes." *Nature* 428:848-852. Wolfe and Shields 1997 "Molecular evidence for an ancient duplication of the entire yeast genome." *Nature* 387:708-713.) Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae, S. uvarum, S. bayanus, S. paradoxus, S. castelli*, and *C. glabrata*.

In another embodiment, the yeast microorganism may be selected from a pre-whole genome duplication (pre-WGD) yeast genus including but not limited to *Saccharomyces, Kluyveromyces, Candida, Pichia, Issatchenkia, Debaryomyces, Hansenula, Yarrowia* and, *Schizosaccharomyces*. Representative pre-WGD yeast species include: *S. kluyveri, K. thermotolerans, K. marxianus, K. waltii, K. lactis, C. tropicalis, P. pastoris, P. anomala, P. stipitis, I. orientalis, I. occidentalis, I. scutulata, D. hansenii, H. anomala, Y. lipolytica*, and *S. pombe*.

A yeast microorganism may be either Crabtree-negative or Crabtree-positive. A yeast cell having a Crabtree-negative phenotype is any yeast cell that does not exhibit the Crabtree effect. The term "Crabtree-negative" refers to both naturally occurring and genetically modified organisms. Briefly, the Crabtree effect is defined as the inhibition of oxygen consumption by a microorganism when cultured under aerobic conditions due to the presence of a high concentration of glucose (e.g., 50 g-glucose $L^{-1}$). In other words, a yeast cell having a Crabtree-positive phenotype continues to ferment irrespective of oxygen availability due to the presence of glucose, while a yeast cell having a Crabtree-negative phenotype does not exhibit glucose mediated inhibition of oxygen consumption.

Accordingly, in one embodiment the yeast microorganism may be selected from yeast with a Crabtree-negative phenotype including but not limited to the following genera: *Kluyveromyces, Pichia, Issatchenkia, Hansenula*, and *Candida*. Crabtree-negative species include but are not limited to: *K. lactis, K. marxianus, P. anomala, P. stipitis, I. orientalis, I. occidentalis, I. scutulata, H. anomala*, and *C. utilis*.

In another embodiment, the yeast microorganism may be selected from a yeast with a Crabtree-positive phenotype, including but not limited to *Saccharomyces, Kluyveromyces, Zygosaccharomyces, Debaryomyces, Pichia* and *Schizosaccharomyces*. Crabtree-positive yeast species include but are not limited to: *S. cerevisiae, S. uvarum, S. bayanus, S. paradoxus, S. castelli, S. kluyveri, K. thermotolerans, C. glabrata, Z. bailli, Z. rouxii, D. hansenii, P. pastorius*, and *S. pombe*.

In some embodiments, the recombinant microorganisms may be microorganisms that are non-fermenting yeast microorganisms, including, but not limited to those, classified into a genera selected from the group consisting of *Tricosporon, Rhodotorula*, or *Myxozyma*.

In one embodiment, a yeast microorganism is engineered to convert a carbon source, such as glucose, to pyruvate by glycolysis and the pyruvate is converted to isobutanol via an engineered isobutanol pathway (See, e.g., WO/2007/050671, WO/2008/098227, and Atsumi et al., *Nature*, 2008 Jan. 3; 451(7174):86-9). Alternative pathways for the production of isobutanol have been described in WO/2007/050671 and in Dickinson et al., *Journal of Biological Chemistry* 273:25751-15756 (1998).

Accordingly, in one embodiment, the engineered isobutanol pathway to convert pyruvate to isobutanol can be comprised of the following reactions:
1. 2 pyruvate→acetolactate+$CO_2$
2. acetolactate+NAD(P)H→2,3-dihydroxyisovalerate+NAD(P)$^+$
3. 2,3-dihydroxyisovalerate→alpha-ketoisovalerate
4. alpha-ketoisovalerate→isobutyraldehyde+$CO_2$
5. isobutyraldehyde+NAD(P)H→isobutanol+NAD(P)$^+$ These reactions are carried out by the enzymes 1) Acetolactate Synthase (ALS), 2) Keto-acid Reducto-Isomerase (KARI), 3) Dihydroxy-acid dehydratase (DHAD), 4) Keto-isovalerate decarboxylase (KIVD), and 5) an Alcohol dehydrogenase (ADH).

In another embodiment, the yeast microorganism is engineered to overexpress these enzymes. For example, these enzymes can be encoded by native genes. Alternatively, these enzymes can be encoded by heterologous genes. For example, ALS can be encoded by the alsS gene of *B. subtilis*, alsS of *L. lactis*, or the ilvK gene of *K. pneumonia*. For example, KARI can be encoded by the ilvC genes of *E. coli, C. glutamicum, M. maripaludis*, or *Piromyces* sp E2. For example, DHAD can be encoded by the ilvD genes of *E. coli, C. glutamicum*, or *L. lactis*. KIVD can be encoded by the kivD gene of *L. lactis*. ADH can be encoded by ADH2, ADH6, or ADH7 of *S. cerevisiae*.

In one embodiment, pathway steps 2 and 5 may be carried out by KARI and ADH enzymes that utilize NADH (rather than NADPH) as a co-factor. Such enzymes are described in commonly owned and co-pending applications U.S. Ser. No. 12/610,784 and PCT/US09/62952 (published as WO/2010/051527), which are herein incorporated by reference in their entireties for all purposes. The present inventors have found that utilization of NADH-dependent KARI and ADH enzymes to catalyze pathway steps 2 and 5, respectively, surprisingly enables production of isobutanol under anaerobic conditions. Thus, in one embodiment, the recombinant microorganisms of the present invention may use an NADH-dependent KARI to catalyze the conversion of acetolactate (+NADH) to produce 2,3-dihydroxyisovalerate. In another embodiment, the recombinant microorganisms of the present invention may use an NADH-dependent ADH to catalyze the conversion of isobutyraldehyde (+NADH) to produce isobutanol. In yet another embodiment, the recombinant microorganisms of the present invention may use both an NADH-dependent KARI to catalyze the conversion of acetolactate (+NADH) to produce 2,3-dihydroxyisovalerate, and an NADH-dependent ADH to catalyze the conversion of isobutyraldehyde (+NADH) to produce isobutanol.

The yeast microorganism of the invention may be engineered to have increased ability to convert pyruvate to isobutanol. In one embodiment, the yeast microorganism may be engineered to have increased ability to convert pyruvate to isobutyraldehyde. In another embodiment, the yeast microorganism may be engineered to have increased ability to convert pyruvate to keto-isovalerate. In another embodiment, the yeast microorganism may be engineered to have increased ability to convert pyruvate to 2,3-dihydroxyisovalerate. In another embodiment, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y. stipitis*, *Torulaspora* spp, including *T. pretoriensis*, *Schizosaccharomyces* spp., including *S. pombe*, *Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Methods in General

Identification of PDC in a Yeast Microorganism

Any method can be used to identify genes that encode for enzymes with pyruvate decarboxylase (PDC) activity. PDC catalyzes the decarboxylation of pyruvate to form acetaldehyde. Generally, homologous or similar PDC genes and/or homologous or similar PDC enzymes can be identified by functional, structural, and/or genetic analysis. In most cases, homologous or similar PDC genes and/or homologous or similar PDC enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a PDC gene by PCR using primers based on a published sequence of a gene/enzyme or by degenerate PCR using degenerate primers designed to amplify a conserved region among PDC genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, PDC activity can be determined phenotypically. For example, ethanol production under fermentative conditions can be assessed. A lack of ethanol production may be indicative of a yeast microorganism with no PDC activity. Examples of yeast pyruvate decarboxylase genes that may be targeted for disruption may be found in U.S. Pat. No. 7,326,550. Target genes for disruption include, but are not limited to, PDC1 (GenBank Accession No. CAA97573.1), PDC5 (GenBank Accession No. CAA97705.1), and PDC6 (GenBank Accession No. CAA97089.1) from *S. cerevisiae*, as well as genes encoding pyruvate decarboxylases from *K. lactis* (GenBank Accession No. CAA59953.1), *K. marxianus*(AAA35267.1), *P. stipitis* (GenBank Accession No. AAC03164.3), *C. glabrata* (AAN77243.1), *S. pombe* (GenBank Accession No. NP_592796.2), and *Y. lipolytica* (CAG80835.1). Other target genes, such as those encoding pyruvate decarboxylase proteins having at least about 50-55%, 55%-60%, 60-65%, 65%-70%, 75-80%, 80-85%, 85%-90%, 90%-95%, or at least about 98% sequence identity to the *S. cerevisiae* pyruvate decarboxylases may be identified in the literature and in bioinformatics databases well known to the skilled person.

Identification of GPD in a Yeast Microorganism

Any method can be used to identify genes that encode for enzymes with glycerol-3-phosphate dehydrogenase (GPD) activity. GPD catalyzes the reduction of dihydroxyacetone phosphate (DHAP) to glycerol-3-phosphate (G3P) with the corresponding oxidation of NADH to NAD+. Generally, homologous or similar GPD genes and/or homologous or similar GPD enzymes can be identified by functional, structural, and/or genetic analysis. In most cases, homologous or similar GPD genes and/or homologous or similar GPD enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a GPD gene by PCR using primers based on a published sequence of a gene/enzyme or by degenerate PCR using degenerate primers designed to amplify a conserved region among GPD genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, GPD activity can be determined phenotypically. For example, glycerol production under fermentative conditions can be assessed. A lack of glycerol production may be indicative of a yeast microorganism with no GPD activity. Examples of yeast glycerol-3-phosphate dehydrogenase genes that may be targeted for disruption may be found in US 2009/0053782. Other target genes, such as those encoding glycerol-3-phosphate dehydrogenase proteins having at least about 50-55%, 55%-60%, 60-65%, 65%-70%, 75-80%, 80-85%, 85%-90%, 90%-95%, or at least about 98% sequence identity to the S. cerevisiae glycerol-3-phosphate dehydrogenases may be identified in the literature and in bioinformatics databases well known to the skilled person.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., *Nucleic Acids Res.* 27:69-74 (1992); Ito et al., *J. Bacteriol.* 153:163-168 (1983); and Becker and Guarente, *Methods in Enzymology* 194:182-187 (1991).

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., *Proc Natl Acad Sci USA* 78:6354-6358 (1981))

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the yeast microorganism may occur via random integration (Kooistra, R., Hooykaas, P. J. J., Steensma, H. Y. 2004. *Yeast* 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke, J. et al, 1984, *Mol. Gen. Genet*, 197, 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced pyruvate decarboxylase activity. The term "reduced" as used herein with respect to a particular enzymatic activity refers to a lower level of enzymatic activity than that measured in a comparable yeast cell of the same species. The term reduced also refers to the elimination of enzymatic activity than that measured in a comparable yeast cell of the same species. Thus, yeast cells lacking pyruvate decarboxylase activity are considered to have reduced pyruvate decarboxylase activity since most, if not all, comparable yeast strains have at least some pyruvate decarboxylase activity. Such reduced enzymatic activities can be the result of lower enzyme concentration, lower specific activity of an enzyme, or a combination thereof. Many different methods can be used to make yeast having reduced enzymatic activity. For example, a yeast cell can be engineered to have a disrupted enzyme-encoding locus using common mutagenesis or knock-out technology. See, e.g., Methods in Yeast Genetics (1997 edition), Adams, Gottschling, Kaiser, and Stems, Cold Spring Harbor Press (1998). In addition, certain point-mutation(s) can be introduced which results in an enzyme with reduced activity.

Alternatively, antisense technology can be used to reduce enzymatic activity. For example, yeast can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Yeast having a reduced enzymatic activity can be identified using many methods. For example, yeast having reduced pyruvate decarboxylase activity can be easily identified using common methods, which may include, for example, measuring ethanol formation via gas chromatography.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any yeast within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, *Appl. Microbiol. Biotechnol.* 38:17-22 (1992).

Increase of Enzymatic Activity

Yeast microorganisms of the invention may be further engineered to have increased activity of enzymes. The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the Km for the substrate, or by directed evolution. See, e.g., Methods in Molecular Biology (vol. 231), ed. Arnold and Georgiou, Humana Press (2003).

Carbon Source

The biocatalyst herein disclosed can convert various carbon sources into isobutanol. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "traditional carbohydrates" refers to sugars and starches generated from specialized plants, such as sugar cane, corn, and wheat. Frequently, these specialized plants concentrate sugars and starches in portions of the plant, such as grains, that are harvested and processed to extract the sugars and starches. Traditional carbohydrates are used as food and also to a lesser extent as carbon sources for fermentation processes to generate biofuels, such as and chemicals The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feed stock for fermentations using a biocatalyst.

The term "starch" as used herein refers to a polymer of glucose readily hydrolyzed by digestive enzymes. Starch is usually concentrated in specialized portions of plants, such as potatoes, corn kernels, rice grains, wheat grains, and sugar cane stems.

The term "lignin" as used herein refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

The term "cellulose" as used herein refers is a long-chain polymer polysaccharide carbohydrate of beta-glucose of formula $(C_6H_{10}O_5)_n$, usually found in plant cell walls in combination with lignin and any hemicellulose.

The term "hemicellulose" refers to a class of plant cell-wall polysaccharides that can be any of several heteropolymers. These include xylane, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

Microorganism Characterized by Producing Isobutanol at High Yield

For a biocatalyst to produce isobutanol most economically, it is desired to produce a high yield. Preferably, the only product produced is isobutanol. Extra products lead to a reduction in product yield and an increase in capital and operating costs, particularly if the extra products have little or no value. Extra products also require additional capital and operating costs to separate these products from isobutanol.

The microorganism may convert one or more carbon sources derived from biomass into isobutanol with a yield of greater than 5% of theoretical. In one embodiment, the yield is greater than 10%. In one embodiment, the yield is greater than 50% of theoretical. In one embodiment, the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment, the yield is greater than 90% of theoretical. In yet another embodiment, the yield is greater than 95% of theoretical. In still another embodiment, the yield is greater than 97.5% of theoretical.

More specifically, the microorganism converts glucose, which can be derived from biomass into isobutanol with a yield of greater than 5% of theoretical. In one embodiment, the yield is greater than 10% of theoretical. In one embodiment, the yield is greater than 50% of theoretical. In one embodiment the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment the yield is greater than 90% of theoretical. In yet another embodiment, the yield is greater than 95% of theoretical. In still another embodiment, the yield is greater than 97.5% of theoretical Microorganism Expressing a Cytosolically Localized Acetolactate Synthase (ALS)

In yeasts such as *S. cerevisiae*, the native acetolactate synthase, encoded in *S. cerevisiae* by the ILV2 gene, is naturally expressed in the yeast mitochondria. Unlike the endogenous acetolactate synthase of yeast, expression of heterologous, acetolactate synthases such as the *B. subtilis* alsS and the *L. lactis* alsS in yeast occurs in the yeast cytosol (i.e. cytosolically-localized). Thus, cytosolic expression of acetolactate synthase is achieved by transforming a yeast with a gene encoding an acetolactate synthase protein (EC 2.2.1.6).

ALS homologs that could be cytosolically expressed and localized in yeast are predicted to lack a mitochondrial targeting sequence as analyzed using mitoprot (Claros et al., 1996, *Eur. J. Biochem* 241: 779-86). Such cytosolically localized ALS proteins can be used as the first step in the isobutanol pathway. ALS homologs include, but are not limited to, the following: the *Serratia marcescens* ALS (GenBank Accession No. ADH43113.1) (probability of mitochondrial localization 0.07), the *Enterococcus faecalis* ALS (GenBank Accession No. NP_814940) (probability of mitochondrial localization 0.21), the *Leuconostoc mesenteroides* (GenBank Accession No. YP_818010.1) (probability of mitochondrial localization 0.21), the *Staphylococcus aureus* ALS (GenBank Accession No. YP_417545) (probability of mitochondrial localization 0.13), the *Burkholderia cenocepacia* ALS (GenBank Accession No. YP_624435) (probability of mitochondrial localization 0.15), *Trichoderma atroviride* ALS (SEQ ID NO: 77) probability of mitochondrial localization 0.19), *Talaromyces stipitatus* ALS (SEQ ID NO: 78) (probability of mitochondrial localization 0.19), and *Magnaporthe grisea* ALS (GenBank Accession No. EDJ99221) (probability of mitochondrial localization 0.02).

In alternative embodiments described herein, an ALS enzyme that is predicted to be mitochondrially localized may be mutated or modified to remove or modify an N-terminal mitochondrial targeting sequence (MTS) to remove or eliminate its ability to target the ALS enzyme to the mitochondria. Removal of the MTS can increase cytosolic localization of the ALS and/or increase the cytosolic activity of the ALS as compared to the parental ALS.

Methods for gene expression in yeasts are known in the art (See, e.g., *Methods in Enzymology*, 2004, Vol 194, *Guide to Yeast Genetics and Molecular and Cell Biology*). As is understood in the art, the expression of heterologous, prokaryotic genes in yeast typically requires a promoter, operably linked to a coding region of interest, and a transcriptional terminator. A number of yeast promoters can be used in constructing expression cassettes for genes encoding an acetolactate synthase, including, but not limited to constitutive promoters FBA, GPD1, ADH1, and GPM, and the inducible promoters GAL1, GAL10, and CUP1. Suitable transcriptional terminators include, but are not limited to FBA, GPD, GPM, ERG10, GAL1, CYC1, and ADH1.

Figure 3:
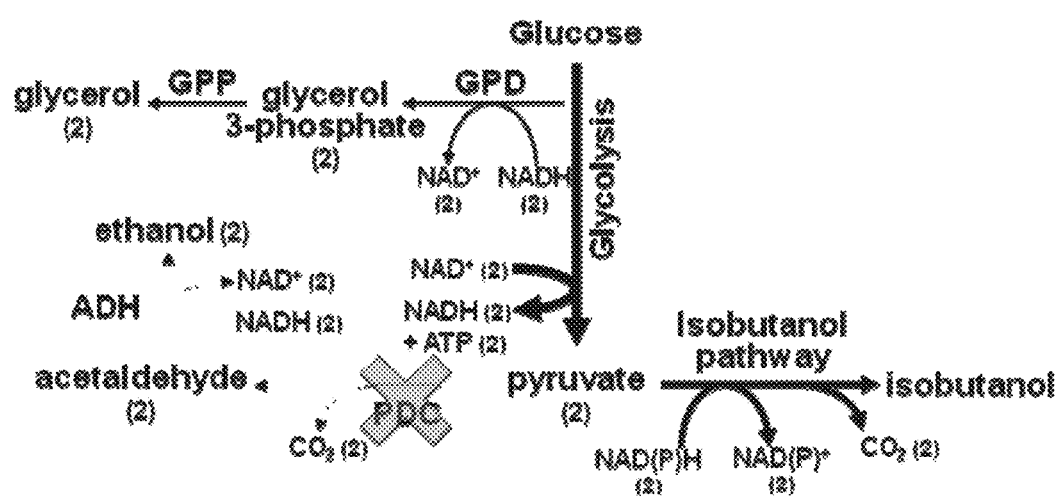
FIG. 3 illustrates an isobutanol pathway receiving additional pyruvate to form isobutanol at higher yield due to the deletion or reduction of the PDC pathway.

Microorganism Characterized by Production of Isobutanol from Pyruvate Via an Overexpressed Isobutanol Pathway and a Pdc-Minus Phenotype In yeast, the conversion of pyruvate to acetaldehyde is a major drain on the pyruvate pool (FIG. 2), and, hence, a major source of competition with the isobutanol pathway. This reaction is catalyzed by the pyruvate decarboxylase (PDC) enzyme. Reduction of this enzymatic activity in the yeast microorganism results in an increased availability of pyruvate and reducing equivalents to the isobutanol pathway and may improve isobutanol production and yield in a yeast microorganism that expresses a pyruvate-dependent isobutanol pathway (FIG. 3).

Reduction of PDC activity can be accomplished by 1) mutation or deletion of a positive transcriptional regulator for the structural genes encoding for PDC or 2) mutation or deletion of all PDC genes in a given organism. The term "transcriptional regulator" can specify a protein or nucleic acid that works in trans to increase or to decrease the transcription of a different locus in the genome. For example, in *S. cerevisiae*, the PDC2 gene, which encodes for a positive transcriptional regulator of PDC1,5,6 genes can be deleted; a *S. cerevisiae* in which the PDC2 gene is deleted is reported to have only ~10% of wildtype PDC activity (Hohmann, *Mol Gen Genet*, 241:657-666 (1993)). Alternatively, for example, all structural genes for PDC (e.g. in *S. cerevisiae*, PDC1, PDC5, and PDC6, or in *K. lactis*, PDC1) are deleted.

Crabtree-positive yeast strains such as *S. cerevisiae* strain that contains disruptions in all three of the PDC alleles no longer produce ethanol by fermentation. However, a downstream product of the reaction catalyzed by PDC, acetyl-CoA, is needed for anabolic production of necessary molecules. Therefore, the Pdc-mutant is unable to grow solely on glucose, and requires a two-carbon carbon source, either ethanol or acetate, to synthesize acetyl-CoA. (Flikweert M T, de Swaaf M, van Dijken J P, Pronk J T. FEMS Microbiol Lett. 1999 May 1; 174(1):73-9. PMID:10234824 and van Maris A J, Geertman J M, Vermeulen A, Groothuizen M K, Winkler A A, Piper M D, van Dijken J P, Pronk J T. Appl Environ Microbiol. 2004 January; 70(1):159-66. PMID: 14711638).

Thus, in an embodiment, such a Crabtree-positive yeast strain may be evolved to generate variants of the PDC mutant yeast that do not have the requirement for a two-carbon molecule and has a growth rate similar to wild type on glucose. Any method, including chemostat evolution or serial dilution may be utilized to generate variants of strains with deletion of three PDC alleles that can grow on glucose as the sole carbon source at a rate similar to wild type (van Maris et al., Directed Evolution of Pyruvate Decarboxylase-Negative *Saccharomyces cerevisiae*, Yielding a C2-Independent, Glucose-Tolerant, and Pyruvate-Hyperproducing Yeast, Applied and Environmental Microbiology, 2004, 70(1), 159-166).

Microorganism Characterized by Production of Isobutanol from Pyruvate Via an Overexpressed Isobutanol Pathway and a PDC-Minus GPD-Minus Phenotype Another pathway for NADH oxidation is through the production of glycerol. Dihydroxyacetone-phosphate, an intermediate of glycolysis is reduced to glycerol 3-phosphate by glycerol 3-phosphate dehydrogenase (GPD). Glycerol 3-phosphatase (GPP) converts glycerol 3-phosphate to glycerol. This pathway consumes carbon from glucose as well as reducing equivalents (NADH) resulting in less pyruvate and reducing equivalents available for the isobutanol pathway. These pathways contribute to low yield and low productivity of isobutanol. Accordingly, deletions of PDC and GPD would increase yield and productivity of isobutanol. As exemplified in Examples 9 and 13, the yield may increase to 70% by the additional deletion of GPD. In an embodiment, a yeast microorganism may include a recombinant microorganism having an engineered pathway to convert a carbon source, such as glucose, to isobutanol.

Figure 4:
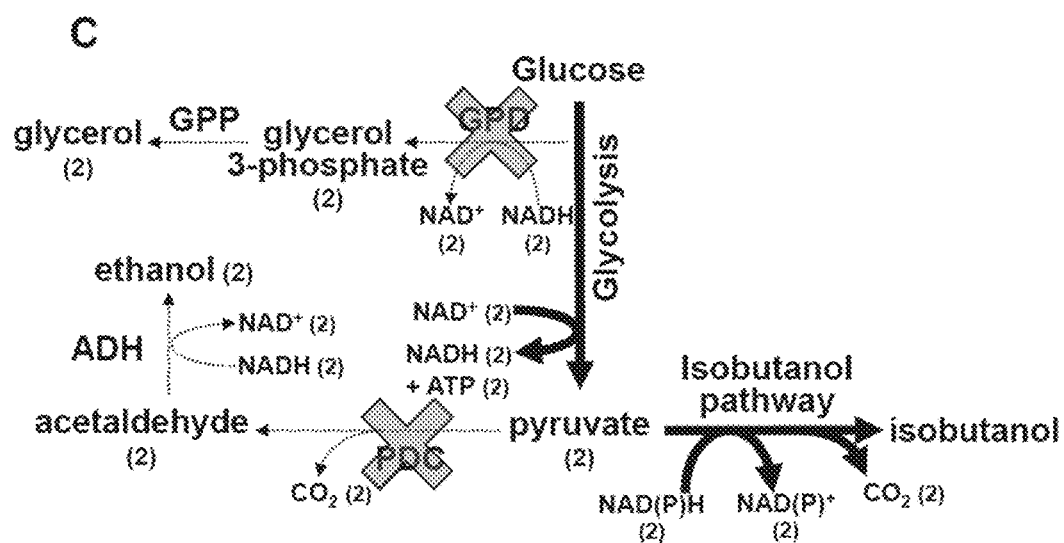
FIG. 4 illustrates an isobutanol pathway receiving additional pyruvate to form isobutanol at higher yield due to deletion or reduction of the PDC pathway and the deletion or reduction of the GPD pathway.

Looking at FIG. 4, an additional deletion of GPD results in a reduction in the production of glycerol 3-phosphate and glycerol. This results in an increase in the amount of carbon from glucose being converted to pyruvate and also a decrease in the consumption of reducing equivalents. Both of these factors combined results in a further increase in yield of isobutanol.

Yield of isobutanol can be increased also by reduction of the glycerol 3-phosphate dehydrogenase (GPD, EC1.1.1.8) activity, which is involved in the production of glycerol (FIG. 2). This enzyme catalyzes the reduction of the glycolysis intermediate, dihydroxyacetone-phosphate, to glycerol 3-phosphate. In this reaction, an NADH is oxidized to NAD+. Therefore, glycerol production would be a drain on the reducing equivalent (NADH) as well as on the carbon from glucose. This pathway can be eliminated by deleting the glycerol-3-phosphate dehydrogenases (e.g. GPD1 and GPD2 in *S. cerevisiae*, GPD1 in *K. lactis*) in the yeast.

Additionally, activities of other gene products may function as drains on metabolic intermediates. For example, reductions of the following activities may increase yield of isobutanol. Pyruvate dehydrogenase (PDH) activity, supplied by a multi-gene product complex, represents another route of pyruvate dissimilation. Reduction of PDH activity may increase pyruvate availability. Branched-chain amino acid transaminase (EC 2.6.1.42) interconverts valine⇌keto-isovalerate in the cytosol, and may therefore reduce or limit available keto-isovalerate to isobutanol pathway. 3-methyl-2-oxobutanoate hydroxymethyltransferase (EC 2.1.2.11) directs the isobutanol pathway intermediate, keto-isovalerate, to the coenzyme A synthesis pathway. Alphaisopropylmalate isomerase (EC 4.1.3.12) directs the isobutanol pathway intermediate, keto-isovalerate, to the synthesis of leucine. Therefore, all of these enzymatic activities represent possible additional targets for disruption, deletion, or both.

Microorganism Characterized by Production of Isobutanol from Pyruvate Via an Overexpressed Balanced Isobutanol Pathway and a PDC-Minus GPD-Minus Phenotype To further increase yield from the pathway the imbalance in the use of reducing equivalents need to be corrected. Glycolysis generates 2 moles NADHs and 2 moles of pyruvate per mole of glucose, while the isobutanol pathway consumes either 2 NADPHs or 1 NADH and 1 NADPH for every 2 moles of pyruvate utilized. KARI enzymes typically use NADPH. There exists both an NADH and NADPH dependent alcohol dehydrogenase that can be used for the isobutanol pathway. For example, *S. cerevisiae* Adh2p is an NADH-dependent enzyme that is able to reduce isobutyraldehyde to isobutanol. Alternatively, this conversion can be performed by *S. cerevisiae* Adh6p or Adh7p, which are NADPH-dependent alcohol dehydrogenases. The additional NADPH can be obtained from the pentose phosphate pathway, but this results in a reduced yield as only 5 moles of pyruvate is generated from 3 moles of glucose, while glycolysis generates 6 moles of pyruvate from 3 moles of glucose.

This imbalance can be balanced in several ways. In one embodiment, glycolysis can be engineered to generate NADPH instead of NADH. This is accomplished by replacing the endogenous NAD+-dependent glyceraldehydes 3-phosphate dehydrogenase (GAPDH, EC 1.2.1.12) with an NADP+-dependent GAPDH (EC 1.2.1.13). Such NADP+-dependent GAPDHs have been identified in bacteria (i.e. gapB in *B. subtilis*), yeast (GDPI in *K. lactis*) and plants. (Fillinger et al., *J Biol Chem*. 275:14031-14037, Verho et al., *Biochemistry*, 41:13833-13838) This may result in glycolysis producing 2 moles of NADPH which balances the 2 moles of NADPH that are consumed by the isobutanol pathway utilizing an NADPH-dependent alcohol dehydrogenase. See, for example, Richard, et al, U.S. Patent Application Publication Number US 2005/0106734 A1. In addition to balancing the pathway, this method may result in the reduction of available NADH and hence a reduction in the ability of the glycerol 3-phosphate dehydrogenase to generate glycerol.

In a second embodiment, an NADP$^+$-dependent GAPDH is co-expressed with the endogenous NAD+-dependent GAPDH. This may allow the production of both NADPH and NADH from glycolysis and balance the consumption of 1 mole of NADPH and 1 mole of NADH by an isobutanol pathway utilizing an NADH-dependent alcohol dehydrogenase.

In yet another embodiment, the NADPH-dependent KARI enzyme in the pathway is engineered to use NADH. This has been shown with the *E. coli* KARI (ilvC) (Rane M J and Calvo K C, *Arch Biochem Biophys.*, 338(1):83-89). Alternatively, a KARI from *Methanococcus* species can be used. These KARI enzymes have been reported to be able to utilize NADH with roughly 60% the activity with NADPH (Xing et al., *Journal of Bacteriology* 1990). The use of these NADH-utilizing ilvC in combination with an NADH-dependent alcohol dehydrogenase also balances the NADH/NADPH imbalance.

Furthermore any of the genes encoding the foregoing enzymes (or any others mentioned herein (or any of the regulatory elements that control or modulate expression thereof) may be subject to directed evolution using methods known to those of skill in the art. Such action allows those of skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y. stipitis*, *Torulaspora pretoriensis*, *Schizosaccharomyces* spp., incl. *Schizosaccharomyces pombe*, *Cryptococcus* spp., *Aspergillus* spp., *Neurospora* spp. or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Microorganism Characterized by Balanced Isobutanol Pathway

In the various embodiments described herein, the engineered metabolic pathway may be balanced with respect to NADH and NADPH as compared to a native or unmodified metabolic isobutanol pathway from a corresponding parental microorganism, wherein the native or unmodified metabolic pathway is not balanced with respect to NADH and NADPH.

The ideal production microorganism produces a desirable product at close to theoretical yield. For example the ideal isobutanol producing organism produces isobutanol according to the following equation: 1 glucose→isobutanol+2 $CO_2$+$H_2O$.

Accordingly, 66% of the glucose carbon results in isobutanol, while 33% is lost as $CO_2$. In exemplary metabolic pathways for the conversion of pyruvate to isobutanol described by Atsumi et al. (WO/2008/098227, and Atsumi et al., *Nature*, 2008 Jan. 3; 451(7174):86-9), two of the five enzymes used to convert pyruvate into isobutanol according to the metabolic pathway outlined in FIG. 1 require the reduced cofactor nicotinamide adenine dinucleotide phosphate (NADPH). NADPH is produced only sparingly by the cell—the reduced cofactor nicotinamide adenine dinucleotide (NADH) is the preferred equivalent. Respiration is required to produce NADPH in the large quantities required to support high-level production of isobutanol.

Even if competing pathways can be eliminated or reduced in activity by metabolic engineering, yield is limited to about 83% of theoretical. Carbon loss to carbon dioxide ($CO_2$) remains the main limitation on yield in the aforementioned metabolic pathway for the production of isobutanol. Reducing the oxygen uptake rate (OUR) of the cells should decrease the loss of carbon to $CO_2$ because it decreases the metabolic flux through the $CO_2$-generating tricarboxylic acid (TCA) cycle and/or pentose phosphate pathway (PPP). However, a modified microorganism utilizing the aforementioned metabolic pathway for the production of isobutanol exhibits drastically decreased specific productivity under conditions where the OUR is decreased and isobutanol production under anaerobic conditions may not be possible.

The decreased yield and the loss of productivity upon $O_2$ limitation indicate that the strain uses one or more metabolic pathways to generate the NADPH needed to support isobutanol production. In a modified cell utilizing the aforementioned metabolic pathway the production of isobutanol from glucose results in an imbalance between the cofactors reduced during glycolysis and the cofactors oxidized during the conversion of pyruvate to isobutanol. While glycolysis produces two moles of NADH, the isobutanol pathway consumes two moles of NADPH. This leads to a deficit of two moles of NADPH and overproduction of two moles of NADH per isobutanol molecule produced, a state described henceforth as cofactor imbalance.

The terms "cofactor balance" or "balanced with respect to cofactor usage" refer to a recombinant microorganism comprising a metabolic pathway converting a carbon source to a fermentation product and a modification that leads to the regeneration of all redox cofactors within the recombinant microorganism producing said fermentation product from a carbon source and wherein the re-oxidation or re-reduction of said redox cofactors does not require the pentose phosphate pathway, the TCA cycle or the generation of additional fermentation products.

Stated another way, the terms "cofactor balance" or "balanced with respect to cofactor usage" can refer to an advantageous modification that leads to the regeneration of all redox cofactors within the recombinant microorganism producing a fermentation product from a carbon source and wherein said re-oxidation or re-reduction of all redox cofactors does not require the production of byproducts or co-products.

Stated another way, the terms "cofactor balance" or "balanced with respect to cofactor usage" can refer to an advantageous modification that leads to the regeneration of all redox cofactors within the recombinant microorganism producing a fermentation product from a carbon source under anaerobic conditions and wherein the production of additional fermentation products is not required for re-oxidation or re-reduction of redox cofactors.

Stated another way, the terms "cofactor balance" or "balanced with respect to cofactor usage" can refer to an advantageous modification that leads to the regeneration of all redox cofactors within the recombinant microorganism producing a fermentation product from a carbon source and wherein said modification increases production of said fermentation product under anaerobic conditions compared to the parental or wild type microorganism and wherein additional fermentation products are not required for the regeneration of said redox cofactors.

The cell has several options for resolving a cofactor imbalance. One is to change the relative fluxes going from glucose through glycolysis and through the pentose phosphate pathway (PPP). For each glucose molecule metabolized through the PPP, two moles of NADPH are generated in addition to the two moles of NADH that are generated through glycolysis (a total of 4 reducing equivalents). Therefore, use of the PPP results in the generation of excess reducing equivalents since only two moles are consumed during the production of isobutanol. Under anaerobic conditions, and without an alternate electron acceptor, the cell has no way to reoxidize or regenerate these extra cofactors to $NADP^+$ and metabolism thus stops. The excess reducing equivalents must instead be utilized for energy production through aerobic respiration which is only possible under aerobic conditions or for the production of byproducts. Another result of the flux through the PPP is that one additional molecule of $CO_2$ is lost per molecule of glucose consumed, which limits the yield of isobutanol that can be achieved under aerobic conditions.

Another way the cell can generate NADPH is via the TCA cycle. Flux through the TCA cycle results in carbon loss through $CO_2$ and in production of NADH in addition to the NADPH required for the isobutanol pathway. The NADH would have to be utilized for energy production through respiration under aerobic conditions (and without an alternate electron acceptor) or for the production of byproducts. In addition, the TCA cycle likely is not functional under anaerobic conditions and is therefore unsuitable for the production of stoichiometric amounts of NADPH in an anaerobic isobutanol process.

An economically competitive isobutanol process requires a high yield from a carbon source. Lower yield means that more feedstock is required to produce the same amount of isobutanol. Feedstock cost is the major component of the overall operating cost, regardless of the nature of the feedstock and its current market price. From an economical perspective, this is important because the cost of isobutanol is dependent on the cost of the biomass-derived sugars. An increase in feedstock cost results in an increase in isobutanol cost. Thus, it is desirable to utilize NADH-dependent enzymes for the conversion of pyruvate to isobutanol.

An enzyme is "NADH-dependent" if it catalyzes the reduction of a substrate coupled to the oxidation of NADH with a catalytic efficiency that is greater than the reduction of the same substrate coupled to the oxidation of NADPH at equal substrate and cofactor concentrations.

Thus, in one embodiment of the invention, a microorganism is provided in which cofactor usage is balanced during the production of a fermentation product.

In a specific aspect, a microorganism is provided in which cofactor usage is balanced during the production of isobutanol, in this case, production of isobutanol from pyruvate utilizes the same cofactor that is produced during glycolysis.

In another embodiment, a microorganism is provided in which cofactor usage is balanced during the production of a fermentation product and the microorganism produces the fermentation product at a higher yield compared to a modified microorganism in which the cofactor usage in not balanced.

In a specific aspect, a microorganism is provided in which cofactor usage is balanced during the production of isobutanol and the microorganism produces isobutanol at a higher yield compared to a modified microorganism in which the cofactor usage in not balanced.

In yet another embodiment, a modified microorganism in which cofactor usage is balanced during the production of a fermentation product may allow the microorganism to produce said fermentation product under anaerobic conditions at higher rates, and yields as compared to a modified microorganism in which the cofactor usage in not balanced during production of a fermentation product.

In a specific aspect, a modified microorganism in which cofactor usage is balanced during the production of isobutanol may allow the microorganism to produce isobutanol under anaerobic conditions at higher rates, and yields as compared to a modified microorganism in which the cofactor usage is not balanced during production of isobutanol.

One compound to be produced by the recombinant microorganism according to the present invention is isobutanol. However, the present invention is not limited to isobutanol. The invention may be applicable to any metabolic pathway that is imbalanced with respect to cofactor usage. One skilled in the art is able to identify pathways that are imbalanced with respect to cofactor usage and apply this invention to provide recombinant microorganisms in which the same pathway is balanced with respect to cofactor usage. One skilled in the art will recognize that the identified pathways may be of longer or shorter length, contain more or fewer genes or proteins, and require more or fewer cofactors than the exemplary isobutanol pathway. Further, one skilled in the art will recognize that in certain embodiments, such as a recombinant microbial host that produces an excess of NADPH, certain embodiments of the present invention may be adapted to convert NADPH to NADH.

Microorganisms Characterized by Providing Cofactor Balance Via Engineered Enzymes Conversion of one mole of glucose to two moles of pyruvate via glycolysis leads to the production of two moles of NADH. A metabolic pathway that converts pyruvate to a target product that consumes either two moles of NADPH or one mole of NADH and one mole of NADPH leads to cofactor imbalance. One example of such a metabolic pathway is the isobutanol metabolic pathway described by Atsumi et al. (Atsumi et al., 2008, *Nature* 451: 86-9), which converts two moles of pyruvate to one mole of isobutanol. In this five enzyme pathway, two enzymes are dependent upon NADPH: (1) KARI and (2) ADH, encoded by the *E. coli* ilvC and *E. coli* yqhD, respectively.

To resolve this cofactor imbalance, the present invention provides a recombinant microorganism in which the NADPH-dependent enzymes KARI and ADH are replaced with enzymes that preferentially depend on NADH (i.e. KARI and ADH enzymes that are NADH-dependent).

To further resolve this cofactor imbalance, the present invention in another embodiment provides recombinant microorganisms wherein the NADH-dependent KARI and ADH enzymes are overexpressed.

In one aspect, such enzymes may be identified in nature. In an alternative aspect, such enzymes may be generated by protein engineering techniques including but not limited to directed evolution or site-directed mutagenesis.

In one embodiment, the two NADPH-dependent enzymes within an isobutanol biosynthetic pathway that converts pyruvate to isobutanol may be replaced with ones that utilize NADH. These two enzymes may be KARI and an alcohol dehydrogenase (ADH).

In another embodiment, two NADH-dependent enzymes that catalyze the same reaction as the NADH-dependent enzymes are overexpressed. These two enzymes may be KARI and an alcohol dehydrogenase.

In one aspect, NADH-dependent KARI and ADH enzymes are identified in nature. In another aspect, the NADPH-dependent KARI and ADH enzymes may be engineered using protein engineering techniques including but not limited to directed evolution and site-directed mutagenesis.

There exist two basic options for engineering NADH-dependent isobutyraldehyde dehydrogenases or ketol-acid reductoisomerases: (1) increase the NADH-dependent activity of an NADPH-dependent enzyme that is active towards the substrate of interest and/or (2) increase the activity of an NADH-dependent enzyme that is not sufficiently active towards the substrate of interest.

There exist two basic options for engineering NADH-dependent isobutyraldehyde dehydrogenases or ketol-acid reductoisomerases: (1) increase the NADH-dependent activity of an NADPH-dependent enzyme that is active towards the substrate of interest and/or (2) increase the activity of an NADH-dependent enzyme that is not sufficiently active towards the substrate of interest.

NADH-Dependent KARI Enzymes

As shown in FIG. 1, the ketol-acid reductoisomerase (KARI) enzyme of the isobutanol biosynthetic pathway as disclosed by Atsumi et al. (Atsumi et al., 2008, Nature 45: 86-9), requires the cofactor nicotinamide dinucleotide phosphate (NADPH) to convert acetolactate to 2,3-dihydroxyisovalerate. However, under anaerobic conditions, NADPH is produced only sparingly by the cell—nicotinamide adenine dinucleotide (NADH) is the preferred equivalent. Therefore, oxygen is required to produce NADPH in the large quantities to support high-level production of isobutanol. Thus, the production of isobutanol is feasible only under aerobic conditions and the maximum yield that can be achieved with this pathway is limited. Accordingly, KARI enzymes that preferentially utilize NADH rather than NADPH are desirable.

Other biosynthetic pathways utilize KARI enzymes for the conversion of acetolactate to 2,3-dihydroxyisovalerate. For example, KARI enzymes convert acetolactate to 2,3-dihydroxyisovalerate as part of the biosynthetic pathway for the production of 3-methyl-1-butanol (Atsumi et al., 2008, Nature 45: 86-9).

Yet other biosynthetic pathways utilize KARI to convert 2-aceto-2-hydroxy-butyrate to 2,3-dihydroxy-3-methylvalerate. This reaction is part of the biosynthetic pathway for the production of 2-methyl-1-butanol. (Atsumi et al., 2008, Nature 45: 86-9).

As used herein, the term "KARI" or "KARI enzyme" or "ketol-acid reductoisomerase" are used interchangeably herein to refer to an enzyme that catalyzes the conversion of acetolactate to 2,3-dihydroxyisovalerate and/or the conversion of 2-aceto-2-hydroxy-butyrate to 2,3-dihydroxy-3-methylvalerate. Moreover, these terms can be used interchangeably herein with the terms "acetohydroxy acid isomeroreductase" and "acetohydroxy acid reductoisomerase."

Enzymes for use in the compositions and methods of the invention include any enzyme having the ability to convert acetolactate to 2,3-dihydroxyisovalerate and/or the ability to convert 2-aceto-2-hydroxy-butyrate to 2,3-dihydroxy-3-methylvalerate. Such enzymes include, but are not limited to, the *E. coli* ilvC gene product and the *S. cerevisiae* ILV5 gene product, and the KARI enzyme from *Piromyces* sp, *Buchnera aphidicola, Spinacia oleracea, Oryza sativa, Chlamydomonas reinhardtii, Neurospora crassa, Schizosaccharomyces pombe, Laccaria bicolor, Ignicoccus hospitalis, Picrophilus torridus, Acidiphilium cryptum, Cyanobacteria/Synechococcus* sp., *Zymomonas mobilis, Bacteroides thetaiotaomicron, Methanococcus maripaludis, Vibrio fischen, Shewanella* sp, *Gramella forsetti, Psychromonas ingrhamaii*, and *Cytophaga hutchinsonii*.

KARI sequences are available from a vast array of microorganisms, including, but not limited to, *Escherichia coli* (GenBank Nos: NP_418222 and NC_000913, *Saccharomyces cerevisiae* (GenBank Nos: NP_013459 and NC_001144, *Methanococcus maripaludis* (GenBank Nos: CAF30210 and BX957220, and *Bacillus subtilis* (GenBank Nos: CAB14789 and Z99118) and the KARI enzymes from *Piromyces* sp (GenBank No: CAA76356), *Buchnera aphidicola* (GenBank No: AAF13807), *Spinacia oleracea* (GenBank Nos: Q01292 and CAA40356), *Oryza sativa* (GenBank No: NP_001056384) *Chlamydomonas reinhardtii* (GenBank No: XP_001702649), *Neurospora crassa* (GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrhamaii* (GenBank No: YP_942294), and *Cytophaga hutchinsonii* (GenBank No: YP_677763).

As will be understood by one of ordinary skill in the art, modified KARI enzymes may be obtained by recombinant or genetic engineering techniques that are routine and well-known in the art. Mutant KARI enzymes can, for example, be obtained by mutating the gene or genes encoding the KARI enzyme of interest by site-directed or random mutagenesis. Such mutations may include point mutations, deletion mutations and insertional mutations. For example, one or more point mutations (e.g., substitution of one or more amino acids with one or more different amino acids) may be used to construct mutant KARI enzymes of the invention.

Ketol-acid reductoisomerase (KARI) catalyzes the reduction of acetolactate to 2,3-dihydroxyisovalerate. The two-step reaction involves an alkyl migration and a ketone reduction that occurs at a single active site on the enzyme without dissociation of any reaction intermediates. The enzyme is NADPH-dependent. The cofactor specificity may be expanded or switched so that it will utilize both cofactors and preferentially NADH during the production of isobutanol. A study published in 1997 (Rane, M. J. and K. C. Calvo, Archives of Biochemistry and Biophysics, 1997. 338: p. 83-89) describes a supposed cofactor-switched KARI quadruplet variant of the *E. coli* ilvC gene product with mutations R68D, K69L, K75V and R76D). However, in-house studies indicate that although the ratio NADH/NADPH was 2.5, the specific activity of this variant on NADH was actually worse than wildtype, rendering this enzyme not suited for the purpose of this disclosure.

Modified or Mutated KARI Enzymes

In accordance with the invention, any number of mutations can be made to the KARI enzymes, and in a preferred aspect, multiple mutations can be made to result in an increased ability to utilize NADH for the conversion of acetolactate to 2,3-dihydroxyisovalerate. Such mutations include point mutations, frame shift mutations, deletions, and insertions, with one or more (e.g., one, two, three, or four, etc.) point mutations preferred.

Mutations may be introduced into the KARI enzymes of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the mutant KARI enzymes which allows for all possible classes of base pair changes at any determined site along the encoding DNA molecule. In general, this technique involves annealing an oligonucleotide complementary (except for one or more mismatches) to a single stranded nucleotide sequence coding for the KARI enzyme of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

The invention further includes homologous KARI enzymes which are 5%, 10%, 20%, 30%, 40%, 50%, 60%, 70%, 75%, 80%, 85%, 90%, 95%, 96%, 97%, 98%, or 99% identical at the amino acid level to a wild-type KARI enzyme (e.g., encoded by the Ec_ilvC gene or *S. cerevisiae* ilv5 gene) and exhibit an increased ability to utilize NADH for the conversion of acetolactate to 2,3-dihydroxyisovalerate. Also included within the invention are KARI enzymes which are 50%, 60%, 70%, 75%, 80%, 85%, 90%, 95%, 96%, 97%, 98%, or 99% identical at the amino acid level to a KARI enzyme comprising the amino acid sequence set out in SEQ ID NO: 56 and exhibit an increased ability to utilize NADH for the conversion of acetolactate to 2,3-dihydroxyisovalerate. The invention also includes nucleic acid molecules which encode the above described KARI enzymes.

The invention also includes fragments of KARI enzymes which comprise at least 50, 100, 150, 200, 250, 300, 350, 400, 450, 500, 550, or 600 amino acid residues and retain one or more activities associated with KARI enzymes. Such fragments may be obtained by deletion mutation, by recombinant techniques that are routine and well-known in the art, or by enzymatic digestion of the KARI enzyme(s) of interest using any of a number of well-known proteolytic enzymes. The invention further includes nucleic acid molecules which encode the above described mutant KARI enzymes and KARI enzyme fragments.

By a protein or protein fragment having an amino acid sequence at least, for example, 50% "identical" to a reference amino acid sequence it is intended that the amino acid sequence of the protein is identical to the reference sequence except that the protein sequence may include up to 50 amino acid alterations per each 100 amino acids of the amino acid sequence of the reference protein. In other words, to obtain a protein having an amino acid sequence at least 50% identical to a reference amino acid sequence, up to 50% of the amino acid residues in the reference sequence may be deleted or substituted with another amino acid, or a number of amino acids up to 50% of the total amino acid residues in the reference sequence may be inserted into the reference sequence. These alterations of the reference sequence may occur at the amino (N—) and/or carboxy (C—) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 50% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673 4680 (1994)).

In one aspect, amino acid substitutions are made at one or more of the above identified positions (i.e., amino acid positions equivalent or corresponding to A71, R76, S78, or Q110 of *E. coli* llvC). Thus, the amino acids at these positions may be substituted with any other amino acid including Ala, Asn, Arg, Asp, Cys, Gln, Glu, Gly, His, Ile, Leu, Lys, Met, Phe, Pro, Ser, Thr, Trp, Tyr, and Val. A specific example of a KARI enzyme which exhibits an increased ability to utilize NADH includes an *E. coli* llvC KARI enzyme in which (1) the alanine at position 71 has been replaced with a serine, (2) the arginine at position 76 has been replaced with an aspartic acid, (3) the serine at position 78 has been replaced with an aspartic acid, and/or (4) the glutamine at position 110 has been replaced with valine (as described in commonly owned and co-pending applications U.S. Ser. No. 12/610,784 and PCT/US09/62952 (published as WO/2010/051527).

Polypeptides having the ability to convert acetolactate to 2,3-dihydroxyisovalerate and/or 2-aceto-2-hydroxy-butyrate to 2,3-dihydroxy-3-methylvalerate for use in the invention may be isolated from their natural prokaryotic or eukaryotic sources according to standard procedures for isolating and purifying natural proteins that are well-known to one of ordinary skill in the art (see, e.g., Houts, G. E., et al., *J. Virol.* 29:517 (1979)). In addition, polypeptides having the ability to convert acetolactate to 2,3-dihydroxyisovalerate and/or 2-aceto-2-hydroxy-butyrate to 2,3-dihydroxy-3-methylvalerate may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372 3376 (1988)).

In accordance with the invention, one or more mutations may be made in any KARI enzyme of interest in order to increase the ability of the enzyme to utilize NADH, or confer other properties described herein upon the enzyme, in accordance with the invention. Such mutations include point mutations, frame shift mutations, deletions and insertions. Preferably, one or more point mutations, resulting in one or more amino acid substitutions, are used to produce KARI enzymes having an enhanced or increased ability to utilize NADH, particularly to facilitate the conversion of acetolactate to 2,3-dihydroxyisovalerate and/or the conversion of 2-aceto-2-hydroxy-butyrate to 2,3-dihydroxy-3-methylvalerate. In a preferred aspect of the invention, one or more mutations at positions equivalent or corresponding to position A71 (e.g., A71S), R76 (e.g., R76D), S78 (e.g. S78D), and/or Q110 (e.g. Q110V) and/or D146 (e.g. D146G), and/or G185 (e.g. G185R) and/or K433 (e.g. K433E) of the *E. coli* llvC KARI enzyme may be made to produce the desired result in other KARI enzymes of interest.

The corresponding positions of the KARI enzymes identified herein (e.g. *E. coli* llvC may be readily identified for other KARI enzymes by one of skill in the art. Thus, given the defined region and the assays described in the present application, one with skill in the art can make one or a number of modifications which would result in an increased ability to utilize NADH, particularly for the conversion of acetolactate to 2,3-dihydroxyisovalerate, in any KARI enzyme of interest.

In a preferred embodiment, the modified or mutated KARI enzymes have from 1 to 4 amino acid substitutions in amino acid regions involved in cofactor specificity as compared to the wild-type KARI enzyme proteins. In other embodiments, the modified or mutated KARI enzymes have additional amino acid substitutions at other positions as compared to the respective wild-type KARI enzymes. Thus, modified or mutated KARI enzymes may have at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different residues in other positions as compared to the respective wild-type KARI enzymes. As will be appreciated by those of skill in the art, the number of additional positions that may have amino acid substitutions will depend on the wild-type KARI enzyme used to generate the variants. Thus, in some instances, up to 50 different positions may have amino acid substitutions.

The nucleotide sequences for several KARI enzymes are known. For instance, the sequences of KARI enzymes are available from a vast array of microorganisms, including, but not limited to, *Escherichia coli* (GenBank No: NP_418222), *Saccharomyces cerevisiae* (GenBank Nos: NP_013459, *Methanococcus maripaludis* (GenBank No: YP_001097443), *Bacillus subtilis* (GenBank Nos: CAB14789), and the KARI enzymes from *Piromyces* sp (GenBank No: CAA76356), *Buchnera aphidicola* (GenBank No: AAF13807), *Spinacia oleracea* (GenBank Nos: Q01292 and CAA40356), *Oryza sativa* (GenBank No: NP_001056384) *Chlamydomonas reinhardtii* (GenBank No: XP_001702649), *Neurospora crassa*(GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrahamii* (GenBank No: YP_942294), and *Cytophaga hutchinsonii* (GenBank No: YP_677763)

Improved NADH-Dependent Activity

In one aspect, the NADH-dependent activity of the modified or mutated KARI enzyme is increased.

In a preferred embodiment, the catalytic efficiency of the modified or mutated KARI enzyme is improved for the cofactor NADH. Preferably, the catalytic efficiency of the modified or mutated KARI enzyme is improved by at least about 5% as compared to the wild-type or parental KARI for NADH. More preferably the catalytic efficiency of the modified or mutated KARI enzyme is improved by at least about 15% as compared to the wild-type or parental KARI for NADH. More preferably, the catalytic efficiency of the modified or mutated KARI enzyme is improved by at least about 25% as compared to the wild-type or parental KARI for NADH. More preferably, the catalytic efficiency of the modified or mutated KARI enzyme is improved by at least about 50% as compared to the wild-type or parental KARI for NADH. More preferably, the catalytic efficiency of the modified or mutated KARI enzyme is improved by at least about 75% as compared to the wild-type or parental KARI for NADH. More preferably, the catalytic efficiency of the modified or mutated KARI enzyme is improved by at least about 100% as compared to the wild-type or parental KARI for NADH. More preferably, the catalytic efficiency of the modified or mutated KARI enzyme is improved by at least about 300% as compared to the wild-type or parental KARI for NADH. More preferably, the catalytic efficiency of the modified or mutated KARI enzyme is improved by at least about 500% as compared to the wild-type or parental KARI for NADH. More preferably, the catalytic efficiency of the modified or mutated KARI enzyme is improved by at least about 1000% as compared to the wild-type or parental KARI for NADH. More preferably, the catalytic efficiency of the modified or mutated KARI enzyme is improved by at least about 5000% as compared to the wild-type or parental KARI for NADH.

In a preferred embodiment, the catalytic efficiency of the modified or mutated KARI enzyme with NADH is increased with respect to the catalytic efficiency of the wild-type or parental enzyme with NADPH. Preferably, the catalytic efficiency of the modified or mutated KARI enzyme is at least about 10% of the catalytic efficiency of the wild-type or parental KARI enzyme for NADPH. More preferably, the catalytic efficiency of the modified or mutated KARI enzyme is at least about 25% of the catalytic efficiency of the wild-type or parental KARI enzyme for NADPH. More preferably, the catalytic efficiency of the modified or mutated KARI enzyme is at least about 50% of the catalytic efficiency of the wild-type or parental KARI enzyme for NADPH. More preferably, the catalytic efficiency of the modified or mutated KARI enzyme is at least about 75%, 85%, 95% of the catalytic efficiency of the wild-type or parental KARI enzyme for NADPH.

In a preferred embodiment, the $K_M$ of the KARI enzyme for NADH is decreased relative to the wild-type or parental enzyme. A change in $K_M$ is evidenced by at least a 5% or greater increase or decrease in $K_M$ compared to the wild-type KARI enzyme. In certain embodiments, modified or mutated KARI enzymes of the present invention may show greater than 10 times decreased $K_M$ for NADH compared to the wild-type or parental KARI enzyme. In certain embodiments, modified or mutated KARI enzymes of the present invention may show greater than 30 times decreased $K_M$ for NADH compared to the wild-type or parental KARI enzyme.

In a preferred embodiment, the $k_{cat}$ of the KARI enzyme with NADH is increased relative to the wild-type or parental enzyme. A change in $k_{cat}$ is evidenced by at least a 5% or greater increase or decrease in $K_M$ compared to the wild-type KARI enzyme. In certain embodiments, modified or mutated KARI enzymes of the present invention may show greater than 50% increased $k_{cat}$ for NADH compared to the wild-type or parental KARI enzyme. In certain embodiments, modified or mutated KARI enzymes of the present invention may show greater than 100% increased $k_{cat}$ for NADH compared to the wild-type or parental KARI enzyme. In certain embodiments, modified or mutated KARI enzymes of the present invention may show greater than 200% increased $k_{cat}$ for NADH compared to the wild-type or parental KARI enzyme.

Cofactor Switch

In preferred embodiments, the cofactor specificity of the modified or mutated KARI enzyme is altered such that there is a cofactor switch from NADPH to NADH. In other words, these modified or mutated KARI enzymes will have an increase in NADH-dependent activity and a substantially simultaneous decrease in NADPH dependent activity. Thus, the methods of the present invention can be used to change the cofactor preference from NADPH to NADH.

"Cofactor specificity" is a measure of the specificity of an enzyme for one cofactor over another. Thus, the methods of the present invention may be used to alter the cofactor preference of the target enzyme, such that the preference for the less favored cofactor is increased by 20%, 50%, 100%, 300%, 500%, 1000%, up to 2000%. For example, a number of reductase enzymes have been described that favor NADPH over NADH (see WO/2002/022526; WO/2002/029019; Mittl et al., 1994, *Protein Sci.*, 3: 1504-14; Banta et al., (2002) *Protein Eng.*, 15: 131-140; all of which are hereby incorporated by reference in their entirety). As the availability of NADPH is often limiting, both in vivo and in vitro, the overall activity of the target protein is often limited. For target proteins that prefer NADPH as a cofactor, it would be desirable to alter the cofactor specificity of the target protein (e.g. a KARI enzyme) to a cofactor that is more readily available, such as NADH.

In a preferred embodiment, the cofactor specificity of the KARI enzyme is switched. By "switched" herein is meant, that the cofactor preference (in terms of catalytic efficiency ($k_{cat}/K_M$) of the KARI enzyme is changed to another cofactor Preferably, in one embodiment, by switching cofactor specificity, activity in terms of catalytic efficiency ($k_{cat}/K_M$) with the cofactor preferred by the wild-type KARI enzyme is reduced, while the activity with the less preferred cofactor is increased. This can be achieved, for example by increasing the $k_{cat}$ for less preferred cofactor over the preferred cofactor or by decreasing $K_M$ for the less preferred cofactor over the preferred cofactor or both.

In a preferred embodiment, the KARI enzyme is modified or a mutated to become NADH-dependent. The term "NADH-dependent" refers to the property of an enzyme to preferentially use NADH as the redox cofactor. An NADH-dependent enzyme has a higher catalytic efficiency ($k_{cat}/K_M$) with the cofactor NADH than with the cofactor NADPH as determined by in vitro enzyme activity assays. Accordingly, the term "NADPH-dependent" refers to the property of an enzyme to preferentially use NADPH as the redox cofactor. An NADPH dependent enzyme has a higher catalytic efficiency ($k_{cat}/K_M$) with the cofactor NADPH than with the cofactor NADH as determined by in vitro enzyme activity assays.

In a preferred embodiment, the catalytic efficiency of the KARI enzyme for NADH is enhanced relative to the catalytic efficiency with NADPH. The term "catalytic efficiency" describes the ratio of the rate constant $k_{cat}$ over the Michaelis-Menten constant $K_M$. In one embodiment, the invention is directed to a modified or mutated KARI enzyme that exhibits at least about a 1:10 ratio of catalytic efficiency ($k_{cat}/K_M$) with NADH over catalytic efficiency with NADPH. In another embodiment, the modified or mutated KARI enzyme exhibits at least about a 1:1 ratio of catalytic efficiency ($k_{cat}/K_M$) with NADH over catalytic efficiency with NADPH. In yet another embodiment, the modified or mutated KARI enzyme exhibits at least about a 10:1 ratio of catalytic efficiency ($k_{cat}/K_M$) with NADH over catalytic efficiency with NADPH. In yet another embodiment, the modified or mutated KARI enzyme exhibits at least about a 100:1 ratio of catalytic efficiency ($k_{cat}/K_M$) with NADH over catalytic efficiency with NADPH. In an exemplary embodiment, the modified or mutated KARI enzyme exhibits at least about a 100:1 ratio of catalytic efficiency ($k_{cat}/K_M$) with NADH over catalytic efficiency with NADPH.

In a preferred embodiment, the $K_M$ of the KARI enzyme for NADH is decreased relative to the $K_M$ of the KARI enzyme for NADPH. In one embodiment, the invention is directed to a modified or mutated KARI enzyme that exhibits at least about a 10:1 ratio of $K_M$ for NADH over $K_M$ for NADPH. In one embodiment, the invention is directed to a modified or mutated KARI enzyme that exhibits at least about a 1:1 ratio of $K_M$ for NADH over $K_M$ for NADPH. In a preferred embodiment, the invention is directed to a modified or mutated KARI enzyme that exhibits at least about a 1:10 ratio of $K_M$ for NADH over $K_M$ for NADPH. In yet another embodiment, the invention is directed to a modified or mutated KARI enzyme that exhibits at least about a 1:20, 1:100, 1:1000 ratio of $K_M$ for NADH over $K_M$ for NADPH.

In another preferred embodiment, the $k_{cat}$ of the KARI enzyme with NADH is increased relative to $k_{cat}$ with NADPH. In certain embodiments, modified or mutated KARI enzymes of the present invention may show greater than 0.8:1 ratio of $k_{cat}$ with NADH over $k_{cat}$ with NADPH. In certain embodiments, modified or mutated KARI enzymes of the present invention may show greater than 1:1 ratio of $k_{cat}$ with NADH over $k_{cat}$ with NADPH. In a preferred embodiment, modified or mutated KARI enzymes of the present invention may show greater than 10:1 ratio of $k_{cat}$ with NADH over $k_{cat}$ with NADPH. In certain embodiments, modified or mutated KARI enzymes of the present invention may show greater than 100:1 ratio of $k_{cat}$ with NADH over $k_{cat}$ with NADPH.

Identification of Corresponding Amino Acid Substitutions in Homologous Enzymes

An amino acid sequence alignment of 22 KARIs (including E. coli llvC, spinach KARI and rice KARI) was described in commonly owned and co-pending applications U.S. Ser. No. 12/610,784 and PCT/US09/62952 (published as WO/2010/051527). Various KARIs aligned with the E. coli KARI sequence at amino acid positions 71, 76, 78, and 110 and this allows to conclude that the beneficial mutations found for E. coli KARI confer the same effects in these KARI enzymes.

A structure alignment of E. coli KARI (PDB ID NO. 1YRL) with rice KARI (PDB ID NO. 3FR8) as a representative of the shorter loop group has been performed and the sites of useful mutations in the E. coli context corresponded reasonably well with specific residues in the context of the shorter loop: Ser165, Lys166, and Ser167. Ser165 of (corresponding to A71 in E. coli) therefore may be substituted with aspartate. A charge reversal at position K166 (corresponding to position R76D) may yield the same result. Ser167 may correspond to Ser78 and a mutation to aspartate corresponds to a beneficial mutation at Q110, and thus can be transferable in the aligned KARIs.

NADH-Dependent ADH Enzymes

Several alcohol dehydrogenases may be suitable candidates for conversion into an NADH-dependent isobutyraldehyde dehydrogenase. Among the exemplary enzymes for conversion are S. cerevisiae ADH1, Zymomonas mobilis ADHII, E. coli YqhD, herein referred to as Ec_YqhD, and S. cerevisiae ADH7.

As described in WO/2008/098227, the S. cerevisiae ADH2 gene is expected to be functionally expressed from pSA55 and required for catalyzing the final step of the isobutanol biosynthetic pathway, namely the conversion of isobutyraldehyde to isobutanol. Thus, no isobutanol should be produced with the plasmid combination lacking ADH2 as adhE is deleted in JCL260. However, the results of a fermentation using a strain without overexpression of any gene encoding an enzyme with ADH activity for the conversion of isobutyraldehyde to isobutanol showed that overexpression of an ADH enzyme is not required for isobutanol production in E. coli. In fact, isobutanol production for the system lacking ADH2 was higher than for the system with ADH2 expression. Volumetric productivity and titer showed 42% increase, specific productivity showed 18% increase and yield 12% increase. This suggests strongly that a native E. coli dehydrogenase is responsible for the conversion of isobutyraldehyde to isobutanol.

Surprisingly, this last step of the isobutanol biosynthetic pathway was found to be carried out by a native E. coli dehydrogenase. Approximately ~80% of the isobutyraldehyde reduction activity is due to Ec_YqhD under certain culture conditions. Available literature on Ec_YqhD suggests that while it does prefer long-chain alcohols, it also utilizes NADPH (versus NADH) (Perez et al., 2008, J. Biol. Chem. 283: 7346-53).

Switching the cofactor specificity of an NADPH-dependent alcohol dehydrogenase may be complicated by the fact that cofactor binding induces a conformational change, resulting in an anhydrous binding pocket that facilitates hydride transfer from the reduced cofactor to the aldehyde (Leskovac et al., 2002, Ferns Yeast Research, 2: 481-94; Reid et al., 1994, Critical Reviews in Microbiology, 20: p. 13-56). Mutations that are beneficial for binding NADH may have deleterious effects with respect to this conformational change.

Alternatively, isobutyraldehyde reduction activity of an NADH-dependent enzyme with little native activity towards this substrate may be increased. This approach has the advantages that (1) several specialized enzymes exist in nature that are highly active under fermentative conditions, (2) the binding sites of several of these enzymes are known, (3) mutational studies indicate that substrate specificity can easily be altered to achieve high activity on a new substrate.

Several alcohol dehydrogenase enzymes may be suitable candidates for conversion into an NADH-dependent isobutyraldehyde dehydrogenase: S. cerevisiae ADH1 and Zymomonas mobilis ADHII are NADH-dependent enzymes responsible for the conversion of acetaldehyde to ethanol under anaerobic conditions. These enzymes are highly active. The substrate specificity for these enzymes has been analyzed (Leskovac et al., 2002, Ferns Yeast Research, 2: 481-94; Rellos et al., 1997, Protein Expression and Purification, 9: 89-90), the amino acid residues comprising the substrate binding pocket are known (Leskovac et al., 2002, Ferns Yeast Research, 2: 481-94; Rellos et al., 1997, Protein Expression and Purification, 9: 89-90), and attempts to alter the substrate specificity by mutation have revealed that the substrate specificity can be altered (Rellos et al., 1997, Protein Expression and Purification, 9: 89-90; Green et al., 1993, J. Biol. Chem., 268: 7792-98). Ec_YqhD and S. cerevisiae ADH7 are NADPH-dependent enzymes whose physiological functions are not as well understood. Ec_YqhD has been implicated in the protection of the cell from peroxide-derived aldehydes (Perez et al., 2008, J. Biol. Chem. 283: 7346-53). The substrate specificity of both enzymes is understood, and amino acids lining the substrate binding pocket are known (Perez et al., 2008, J. Biol. Chem. 283: 7346-53). Based on the known amino acid residues implicated in substrate binding (S. cerevisiae ADH1, Z. mobilis ADHII) or the cofactor binding site (Ec_yqhD), sites with the highest likelihood of affecting desired enzyme features such as substrate specificity or cofactor specificity may be mutated to generate the desired function.

One approach to increase activity of enzymes with NADH as the cofactor is saturation mutagenesis with NNK libraries at each of the residues that interact with the cofactor. These libraries can be screened for activity in the presence of NADPH and NADH in order to identify which single mutations contribute to increased activity on NADH and altered specificity for NADH over NADPH. Combinations of mutations at aforementioned residues can be investigated by any method known in the art. For example, a combinatorial library of mutants may be designed based on the results of the saturation mutagenesis studies. For example, a combinatorial library of mutants may be designed including only those mutations that do not lead to decrease in NADH-dependent activity.

Another approach to increase the NADH-dependent activity of the enzyme is to perform saturation mutagenesis of a first amino acid that interacts with the cofactor, then isolate the mutant with the highest activity using NADH as the cofactor, then perform saturation mutagenesis of a second amino acid that interacts with the cofactor, and so on. Similarly, a limited number of amino acids that interact with the cofactor may be targeted for randomization simultaneously and then be screened for improved activity with NADH as the cofactor. The selected, best mutant can then be subjected to the same procedure again and this approach may be repeated iteratively until the desired result is achieved.

Another approach is to use random oligonucleotide mutagenesis to generate diversity by incorporating random mutations, encoded on a synthetic oligonucleotide, into the cofactor binding region of the enzyme. The number of mutations in individual enzymes within the population may be controlled by varying the length of the target sequence and the degree of randomization during synthesis of the oligonucleotides. The advantages of this more defined approach are that all possible amino acid mutations and also coupled mutations can be found.

If the best variants from the experiments described above are not sufficiently active with NADH as the cofactor, directed evolution via error-prone PCR may be used to obtain further improvements. Error-prone PCR mutagenesis of the first domain containing the cofactor binding pocket may be performed followed by screening for ADH activity with NADH and/or increased specificity for NADH over NADPH as the cofactor.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase. Preferred enzymes of this disclosure include enzymes listed in Table 1 of co-pending and commonly owned U.S. Ser. No. 12/610,784 and PCT/US09/62952 (published as WO/2010/051527). These enzymes exhibit NADH-dependent isobutyraldehyde reduction activity, measured as Unit per minute per mg of crude cell lysate (U $min^{-1}$ $mg^{-1}$) that is approximately six-fold to seven-fold greater than the corresponding NADPH-dependent isobutyraldehyde reduction activity.

In addition to exhibiting increased activity with NADH as the cofactor as compared to the NADPH, alcohol dehydrogenases of the present invention may further be more active as compared to the native E. coli alcohol dehydrogenase Ec_YqhD. In particular, alcohol dehydrogenases of the present invention may exhibit increased activity and/or decreased $K_M$ values with NADH as the cofactor as compared to Ec_YqhD with NADPH as the cofactor. Exemplary enzymes that exhibit greater NADH-dependent alcohol dehydrogenase activity than the NADPH-dependent alcohol dehydrogenase activity are listed include the Drosophila melanogaster ADH, the L. lactis adhA, K. pneumoniae dhaT, and E. coli fucO (see Table 1 of U.S. Ser. No. 12/610,784).

Alcohol dehydrogenases of the present disclosure may also be utilized in metabolically-modified microorganisms that include recombinant biochemical pathways useful for producing additional alcohols such as 2-methyl-1-butanol, 3-methyl-1-butanol, 2-phenylethanol, 1-propanol, or 1-butanol via conversion of a suitable substrate by a modified microorganism.

Microorganisms producing such compounds have been described (WO/2008/098227). For example, these alcohols can be 1-propanol, 1-butanol, 2-methyl-1-butanol, 3-methyl-1-butanol or 2-phenylethanol and are generally produced from a metabolite comprising a 2-keto acid. In some aspects, the 2-keto acid includes 2-ketobutyrate, 2-ketovalerate, 2-keto-3-methylvalerate, 2-keto-4-methyl-pentanoate, or phenylpyruvate. The 2-ketoacid is converted to the respective aldehyde by a 2-ketoacid decarboxylase. For example, 2-ketobutyrate is converted to 1-propanal, 2-ketovalerate is converted to 1-butanal, 2-keto-3-methylvalerate is converted to 2-methyl-1-butanol, 2-keto-4-methyl-pentanoate is converted to 3-methyl-1-butanal, and phenylpyruvate is converted to phenylethanal by a 2-ketoacid decarboxylase. Thus, the recombinant microorganism includes elevated expression or activity of a 2-keto-acid decarboxylase, as compared to a parental microorganism. The 2-keto-acid decarboxylase may be encoded by kivD from *Lactococcus lactis*, or homologs thereof. The 2-keto-acid decarboxylase can be encoded by a polynucleotide derived from a gene selected from kivD from *L. lactis*, or homologs thereof.

In earlier publications (See, e.g., WO/2008/098227), only NADPH-dependent alcohol dehydrogenases are described that convert the aforementioned aldehyde to an alcohol. In particular, *S. cerevisiae* Adh2p is described that converts the aldehyde to the respective aldehyde.

Thus, in one embodiment of this disclosure, a microorganism is provided in which the cofactor dependent final step for the conversion of the aldehyde to the respective alcohol is catalyzed by an NADH-dependent alcohol dehydrogenase. In particular, NADH-dependent alcohol dehydrogenases are disclosed that catalyze the reduction aldehydes to alcohols, for example, of 1-propanal to 1propanol, 1-butanal to 1-butanol, 2-methyl-1-butanal to 2-methyl-1-butanol, 3-methyl-1-butanal to 3-methyl-1-butanol, or phenylethanal to phenylethanol.

In a specific aspect, such an alcohol dehydrogenase may be encoded by the *Drosophila melanogaster* alcohol dehydrogenase Dm_Adh or homologs thereof. In another specific aspect, such an alcohol dehydrogenase may be encoded by the *Lactococcus lactis* alcohol dehydrogenase (Ll_AdhA) or homologs thereof.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase.

In another embodiment, a method of producing an alcohol is provided. The method includes providing a recombinant microorganism provided herein; culturing the microorganism of in the presence of a suitable substrate or metabolic intermediate and under conditions suitable for the conversion of the substrate to an alcohol; and detecting the production of the alcohol. In various aspects, the alcohol is selected from 1-propanol, 1-butanol, 2-methyl 1-butanol, 3-methyl 1-butanol, and 2-phenylethanol. In another aspect, the substrate or metabolic intermediate includes a 2-keto acid-derived aldehyde, such as 1-propanal, 1-butanal, 2-methyl-1-butanal, 3-methyl-1-butanal, or phenylethanal.

Recombinant Host Cells Comprising a NADH-Dependent KARI and/or ADH Enzymes

In an additional aspect, the present invention is directed to recombinant host cells (i.e. metabolically "engineered" or "modified" microorganisms) comprising NADH-dependent KARI and/or ADH enzymes of the invention. Recombinant microorganisms provided herein can express a plurality of additional heterologous and/or native target enzymes involved in pathways for the production of beneficial metabolites such as isobutanol from a suitable carbon source.

Accordingly, metabolically "engineered" or "modified" microorganisms are produced via the introduction of genetic material (i.e. a NADH-dependent KARI and/or ADH enzymes) into a host or parental microorganism of choice, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material and/or the modification of the expression of native genes into a parental microorganism results in a new or modified ability to produce beneficial metabolites such as isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., 1-propanol, 1-butanol, isobutanol, 2-methyl-1-butanol, 3-methyl-1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, 1-propanol, 1-butanol, isobutanol, 2-methyl-1-butanol, and 3-methyl-1-butanol.

The metabolite 1-propanol can be produced by a recombinant microorganism engineered to express or over-express a metabolic pathway that converts pyruvate to 1-propanol. An exemplary metabolic pathway that converts pyruvate to 1-propanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite isobutanol can be produced by a recombinant microorganism engineered to express or over-express a metabolic pathway that converts pyruvate to isobutanol. An exemplary metabolic pathway that converts pyruvate to isobutanol may be comprised of a acetohydroxy acid synthase (ALS) enzyme encoded by, for example, alsS from *B. subtilis*, a ketolacid reductoisomerase (KARI) of the present invention, a dihydroxy-acid dehydratase (DHAD), encoded by, for example ilvD from *E. coli* or *L. lactis*, a 2-keto-acid decarboxylase (KIVD) encoded by, for example kivd from *L. lactis*, and an alcohol dehydrogenase (ADH) of the present invention.

The metabolite 3-methyl-1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 2-methyl-1-butanol can be produced by a recombinant microorganism engineered to express or over-express a metabolic pathway that converts pyruvate to 2-methyl-1-butanol. An exemplary metabolic pathway that converts pyruvate to 2-methyl-1-butanol has been described in WO/2008/098227 and by Atsumi et al. (Atsumi et al., 2008, *Nature* 451: 86-9), the disclosures of which are herein incorporated by reference in their entireties. In an exemplary embodiment, metabolic pathway comprises a KARI and/or an ADH enzyme of the present invention.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art. In addition, homologs of enzymes useful for generating metabolites are encompassed by the microorganisms and methods provided herein.

Microorganism Characterized by Increased Capacity to Produce Intermediates of the Isobutanol Pathway As a consequence of increased yield of isobutanol, it follows that this yeast microorganism exhibits a higher capacity to produce the intermediates of the isobutanol pathway including, but not limited to, acetolactate, 2,3-dihydroxyisovalerate, keto-isovalerate, and isobutyraldehyde.

Method of Using Microorganism for High-Yield Isobutanol Fermentation

In a method to produce isobutanol from a carbon source at high yield, the yeast microorganism is cultured in an appropriate culture medium containing a carbon source.

Another exemplary embodiment provides a method for producing isobutanol comprising a recombinant yeast microorganism of the invention in a suitable culture medium containing a carbon source that can be converted to isobutanol by the yeast microorganism of the invention.

In certain embodiments, the method further includes isolating isobutanol from the culture medium. For example, isobutanol may be isolated from the culture medium by any method known to those skilled in the art, such as distillation, pervaporation, or liquid-liquid extraction.

EXAMPLES

General Methods

Sample Preparation:

Samples (2 mL) from the fermentation broth were stored at −20° C. for later substrate and product analysis. Prior to analysis, samples were thawed and then centrifuged at 14,000×g for 10 min. The supernatant was filtered through a 0.2 μm filter. Analysis of substrates and products was performed using authentic standards (>99%, obtained from Sigma-Aldrich), and a 5-point calibration curve (with 1-pentanol as an internal standard for analysis by gas chromatography).

Determination of Optical Density and Cell Dry Weight:

The optical density of the yeast cultures was determined at 600 nm using a DU 800 spectrophotometer (Beckman-Coulter, Fullerton, Calif., USA). Samples were diluted as necessary to yield an optical density of between 0.1 and 0.8. The cell dry weight was determined by centrifuging 50 mL of culture prior to decanting the supernatant. The cell pellet was washed once with 50 mL of milliQ $H_2O$, centrifuged and the pellet was washed again with 25 mL of milliQ $H_2O$. The cell pellet was then dried at 80° C. for at least 72 hours. The cell dry weight was calculated by subtracting the weight of the centrifuge tube from the weight of the centrifuge tube containing the dried cell pellet.

Gas Chromatography:

Analysis of ethanol and isobutanol was performed on a HP 5890 gas chromatograph fitted with a DB-FFAP column (Agilent Technologies; 30 m length, 0.32 mm ID, 0.25 ρM film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min.

High Performance Liquid Chromatography:

Analysis of glucose and organic acids was performed on a HP-1100 High Performance Liquid Chromatography system equipped with an Aminex HPX-87H Ion Exclusion column (Bio-Rad, 300×7.8 mm) or equivalent and an $H^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was Isocratic with 0.008N sulfuric acid in water as mobile phase. Flow was set at 0.6 mL/min. Injection size was 20 μL and the run time was 30 minutes.

Anaerobic Batch Fermentations:

Anaerobic batch cultivations were performed at 30° C. in stoppered 100 mL serum bottles. A total of 20 mL of synthetic medium with an initial glucose concentration of 20 g-glucose $L^{-1}$ was used (Kaiser et al., Methods in Yeast Genetics, a Cold Spring Harbor Laboratory Manual (1994)). 2 mL samples are taken at 24 and 48 hours. The fermentation is ended after 48 hours or when all glucose is consumed. Samples are processed and analyzed by Gas Chromatography and/or High Performance Liquid Chromatography as described above.

Yeast Transformations—*K. lactis*:

Transformations were performed by electroporation according to Kooistra et al., *Yeast* 21:781-792 (2004).

Lithium Acetate transformations of *S. cerevisiae* strains were transformed by the Lithium Acetate method (Gietz et al., *Nucleic Acids Res.* 27:69-74 (1992). Cells were collected from overnight cultures grown in 50 mL of defined (SC) ethanol media at an $OD_{600}$ of approximately 0.8 to 1.0 by centrifugation at 2700 rcf for 2 minutes at room temperature. The cell pellet was resuspended in 50 mL sterile water, collected by centrifugation (2700 rcf; 2 min; room temp.), and resuspended in 25 mL sterile water. The cells were collected by centrifugation (2700 rcf; 2 min; room temp.) and resuspended in 1 mL 100 mM lithium acetate. The cell suspension was transferred to a sterile 1.5 mL tube and collected by centrifugation at full speed for 10 seconds. The cells were resuspended in 100 mM lithium acetate with a volume four times the volume of the cell pellet (e.g. 400 μL for 100 μL cell pellet). To the prepared DNA Mix (72 μl 50% PEG, 10 μl 1M Lithium Acetate, 3 μl boiled salmon sperm DNA, and 5 μl of each plasmid), 15 μl of the cell suspension was added and mixed by vortexing with five short pulses. The cell/DNA suspensions were incubated at 30° C. for 30 minutes and at 42° C. for 22 minutes. The cells were collected by centrifugation for 10 seconds at full speed and resuspended in 100 μl SOS (1M Sorbitol, 0.34% (w/v) Yeast Extract, 0.68% (w/v) Peptone, 6.5 mM CaCl). The cell suspensions were top spread over appropriate selective agar plates.

Yeast Colony PCR:

Yeast cells were taken from agar medium and transferred to 30 μl 0.2% SDS and heated for 4 mins at 90° C. The cells were spun down and 1 μl of the supernatant was used for PCR using standard Taq (NEB).

Molecular Biology:

Standard molecular biology methods for cloning and plasmid construction were generally used, unless otherwise noted (Sambrook & Russell).

Media:

YP: contains 1% (w/v) yeast extract, 2% (w/v) peptone. YPD is YP containing 2% (w/v) glucose, YPE is YP containing 2% (w/v) Ethanol.

SC+Complete: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.076 g/L tryptophan, 0.380 g/L leucine, and 0.076 g/L uracil.

SC-HWUL: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base SC-WLU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.076 g/L histidine.

SC-HWU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.380 g/L leucine.

SC-Ethanol-HWU: 2% (w/v) ethanol, 14 g/L Sigma™ Synthetic Dropout Media supplement (includes amino acids and nutrients excluding histidine, tryptophan, uracil, and leucine), 6.7 g/L Difco™ Yeast Nitrogen Base, and 0.380 g/L leucine.

Solid versions of the above described media contain 2% (w/v) agar.

Strains, Plasmids and Primer Sequences

TABLE 1 details the genotype of strains diclosed herein:

| GEVO No. | Genotype and/or Reference |
|---|---|
| GEVO1187 | S. cerevisiae CEN.PK MAT a ho his3- leu2 trp1 ura3 PDC1 PDC5 PDC6 |
| GEVO1188 | S. cerevisiae CEN.PK MAT alpha ho his3- leu2 trp1 ura3 PDC1 PDC5 PDC6 |
| GEVO1287[1] | K. lactis MATα uraA1 trp1 leur2 lysA1 ade1 lac4-8 [pKD1] (ATCC #87365) |
| GEVO1537[2] | S. cerevisiae HO/HO pdc1::Tn5ble/pdc1::Tn5ble pdc5::Tn5ble/pdc5::Tn5ble pdc6::APT1/pdc6::APT1 HIS3/HIS, LEU2/LEU2, URA3/URA3, TRP1/TRP1 |
| Gevo1538 | S. cerevisiae MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO |
| GEVO1581 | S. cerevisiae MAT a/alpha, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO |
| Gevo1715 | S. cerevisiae MAT a, leu2, ura3, pdc1::ble, pdc5::ble, pdc6::apt1(kanR), ho |
| GEVO1584 | S. cerevisiae MAT a, his3, trp1, ura3, leu2, pdc1::ble, pdc5::ble, pdc6::apt1(kanR), ho- |
| GEVO1742 | K. lactis MATα uraA1 trp1 leur2 lysA1 ade1 lac4-8 [pKD1] Klpdc1Δ::pGV1537 (G418$^R$)] |
| GEVO1794 | K. lactis MATalpha uraA1 trp1 leu2 lysA1 ade1 lac4-8 [pKD1] pdc1::kan {Ll-kivd; Sc-Adh7:KmURA3 integrated} |
| GEVO1818 | K. lactis MATalpha uraA1 trp1 leu2 lysA1 ade1 lac4-8 [pKD1] pdc1::kan {Ec-ilvC-deltaN; Ec-ilvD-deltaN(codon opt for K. lactis):Sc-LEU2 integrated} {Ll-kivd; Sc-Adh7:KmURA3 integrated} |
| GEVO1829 | K. lactis MATalpha uraA1 trp1 leu2 lysA1 ade1 lac4-8 [pKD1] pdc1::kan {Ec-ilvC-deltaN; Ec-ilvD-deltaN(codon opt for K. lactis):Sc-LEU2 integrated} {Ll-kivd; Sc-Adh7:KmURA3 integrated} {ScCUP1-1 promoter:Bs alsS, TRP1 random integrated} |
| Gevo1863 | S. cerevisiae MAT a, his3, trp1, ura3, leu2, pdc1::ble, pdc5::ble, pdc6::apt1(kanR), ho-, chemostat-evolved to be C2-independent. |

[1]same as ATCC200826
[2]The strains Gevo1537 and Gevo1538 were originally designated GG570 (derived from strain T2-3D)and was obtained from Paul van Heusden from the University of Leiden, the Netherlands. For complete references for both strains, see: Flikweert, M. T. et al., (1996) Yeast 12: 247-257.

TABLE 2 outlines the plasmids disclosed herein:

| GEVO No. | FIG. | Genotype or Reference |
|---|---|---|
| pGV1056 | 23 | bla(amp$^r$) S.c. TDH3 promoter - polylinker - CYC1 terminator CEN6/ARSH4 HIS3 pUC ori |
| pGV1062 | 24 | bla(amp$^r$) S.c. TDH3 promoter - polylinker - CYC1 terminator CEN6/ARSH4 URA3 pUC ori |

TABLE 2-continued outlines the plasmids disclosed herein:

| GEVO No. | FIG. | Genotype or Reference |
|---|---|---|
| pGV1102 | 25 | bla(amp<sup>r</sup>) S.c. TEF1 promoter - HA tag - polylinker - CYC1 terminator 2 micron URA3 pUC ori |
| pGV1103 | 26 | bla(amp<sup>r</sup>) S.c. TDH3 promoter - myc tag - polylinker - CYC1 terminator 2 micron HIS3 pUC ori |
| pGV1104 | 27 | bla(amp<sup>r</sup>) S.c. TDH3 promoter - myc tag - polylinker - CYC1 terminator 2 micron TRP1 pUC ori |
| pGV1106 | 28 | bla(amp<sup>r</sup>) S.c. TDH3 promoter - myc tag - polylinker - CYC1 terminator 2 micron URA3 pUC ori |
| pGV1254 | 16 | bla(amp<sup>r</sup>) S.c. TEF1 promoter - HA-L.l. KIVD - S.c. TDH3 promoter - myc-S.c. ADH2 - CYC1 terminator 2 micron URA3 pUC ori |
| pGV1295 | 17 | bla(amp<sup>r</sup>) S.c. TDH3 promoter - myc-ilvC - CYC1 terminator 2 micron TRP1 pUC ori |
| pGV1390 | 18 | bla(amp<sup>r</sup>) S.c. CUP1-1 promoter - L.l. alsS - CYC1 terminator 2 micron HIS3 pUC ori |
| pGV1438 | 19 | bla(amp<sup>r</sup>) S.c. TDH3 promoter - myc-ilvD- CYC1 terminator 2 micron LEU2 pUC ori |
| pGV1503 | 8 | bla(amp<sup>r</sup>) S.c. TEF1 promoter - KanR pUC ori |
| pGV1537 | 9 | bla(amp<sup>r</sup>) S.c. TEF1 promoter - KanR pUC ori K. lactis PDC1 5' region - PmlI - K. lactis PDC1 3' region |
| pGV1429 | 10 | bla(amp<sup>r</sup>) S.c. TDH3 promoter - myc tag - polylinker - CYC1 terminator 1.6 micron TRP1 pUC ori |
| pGV1430 | 11 | bla(amp<sup>r</sup>) S.c. TDH3 promoter - myc tag - polylinker - CYC1 terminator 1.6 micron LEU2 pUC ori |
| pGV1431 | 12 | bla(amp<sup>r</sup>) S.c. TDH3 promoter - myc tag - polylinker - CYC1 terminator 1.6 micron K.m. URA3 pUC ori |
| pGV1472 | 13 | bla(amp<sup>r</sup>) S.c. TEF1 promoter - AU1(x2)-L.l. alsS- CYC1 terminator 1.6 micron LEU2 pUC ori |
| pGV1473 | 14 | bla(amp<sup>r</sup>) S.c. TEF1 promoter - AU1(x2)-E.c. ilvD - S.c. TDH3 promoter - myc-E.c. ilvC - CYC1 terminator 1.6 micron TRP1 pUC ori |
| pGV1475 | 15 | bla(amp<sup>r</sup>) S.c. TEF1 promoter - HA-L.l. KIVD - S.c. TDH3 promoter - myc-S.c. ADH7 - CYC1 terminator 1.6 micron K.m. URA3 pUC ori |
| pGV1590 | 20 | bla(amp<sup>r</sup>) S.c. TEF1 promoter - L.l. KIVD - S.c. TDH3 promoter - S.c. ADH7 - CYC1 terminator 1.6 micron K.m. URA3 pUC ori |
| pGV1726 | 21 | bla(amp<sup>r</sup>) S.c. CUP1-1 promoter - B.s. alsS - CYC1 terminator TRP1 pUC ori |
| pGV1727 | 22 | bla(amp<sup>r</sup>) S.c. TEF1 promoter - E.c. ilvD deltaN- S.c. TDH3 promoter -E.c. ilvC deltaN- CYC1 terminator LEU2 pUC ori |
| pGV1649 | 29 | bla(amp<sup>r</sup>) S.c. CUP1-1 promoter - B.s. alsS - CYC1 terminator 2 micron TRP1 pUC ori |
| pGV1664 | 30 | bla(amp<sup>r</sup>) S.c. TEF1 promoter - L.l. KIVD - S.c. TDH3 promoter - S.c. ADH7 - CYC1 terminator 2 micron URA3 pUC ori |
| pGV1672 | 31 | bla(amp<sup>r</sup>) S.c. CUP1-1 promoter - polylinker - CYC1 terminator CEN6/ARSH4 TRP1 pUC ori |
| pGV1673 | 32 | bla(amp<sup>r</sup>) S.c. CUP1-1 promoter - B.s. alsS - CYC1 terminator CEN6/ARSH4 TRP1 pUC ori |
| pGV1677 | 33 | bla(amp<sup>r</sup>) S.c. TEF1 promoter - E.c. ilvD deltaN- S.c. TDH3 promoter -E.c. ilvC deltaN- CYC1 terminator 2 micron HIS3 pUC ori |
| pGV1679 | 34 | bla(amp<sup>r</sup>) S.c. TEF1 promoter - E.c. ilvD deltaN- S.c. TDH3 promoter -E.c. ilvC deltaN- CYC1 terminator CEN6/ARSH4 HIS3 pUC ori |
| pGV1683 | 35 | bla(amp<sup>r</sup>) S.c. TEF1 promoter - L.l. KIVD - S.c. TDH3 promoter - S.c. ADH7 - CYC1 terminator CEN6/ARSH4 URA3 pUC ori |

TABLE 3 outlines the primers sequences disclosed herein:

| No. | Name | SEQ ID NO: | Sequence |
|---|---|---|---|
| 489 | MAT common | 30 | AGTCACATCAAGATCGTTTATGG |
| 490 | MAT alpha | 31 | GCACGGAATATGGGACTACTTCG |
| 491 | MAT a | 32 | ACTCCACTTCAAGTAAGAGTTTG |
| 838 | pGV1423-seq1 (838) | 33 | TATTGTCTCATGAGCGGATAC |
| 965 | KlPDC1 −616 FOR | 34 | ACAACGAGTGTCATGGGGAGAGGAAGAGG |

TABLE 3-continued outlines the primers sequences disclosed herein:

| No. | Name | SEQ ID NO: | Sequence |
|---|---|---|---|
| 966 | KlPDC1 +2528 REV | 35 | GATCTTCGGCTGGGTCATGTGAGGCGG |
| 995 | KlPDC1 internal | 36 | ACGCTGAACACGTTGGTGTCTTGC |
| 996 | KlPDC1 internal | 37 | AACCCTTAGCAGCATCGGCAACC |
| 1010 | KI-PDC1-prom-seq-c | 38 | TATTCATGGGCCAATACTACG |
| 1006 | KI-FDC1-prom-3c | 39 | GTAGAAGACGTCACCTGGTAGACCAAAGATG |
| 1009 | KI-PDC1-term-5c | 40 | CATCGTGACGTCGCTCAATTGACTGCTGCTAC |
| 1016 | KI-PDC1-prom-5-v2 (1016) | 41 | ACTAAGCGACACGTGCGGTTTCTGTGGTATAG |
| 1017 | KI-PDC1-term-3c-v2 (1017) | 42 | GAAACCGCACGTGTCGCTTAGTTTACATTTCTTTCC |
| 1019 | TEF1 prom-5c (1019) | 43 | TTTGAAGTGGTACGGCGATG |
| 1321 | Bs-alsS-Q-A5 (1321) | 44 | AATCATATCGAACACGATGC |
| 1324 | Bs-alsS-Q-B3 (1324) | 45 | AGCTGGTCTGGTGATTCTAC |
| 1325 | Ec-ilvC-dN-Q-A5 (1325) | 46 | TATCACCGTAGTGATGGTTG |
| 1328 | Ec-livC-dN-Q-B3 (1328) | 47 | GTCAGCAGTTTCTTATCATCG |
| 1330 | Ec-ilvD-dN-co-KI-Q-A3 (1330) | 48 | GCGAAACTTACTTGACGTTC |
| 1331 | Ec-ilvD-ON-co-KI-Q-B5 (1331) | 49 | ACTTTGGACGATGATAGAGC |
| 1334 | Ll-kivd-co-Ec-Q-A3 (1334) | 50 | GCGTTAGATGGTACGAAATC |
| 1335 | Ll-kivd-co-Ec-Q-B5 (1335) | 51 | CTTCTAACACTAGCGACCAG |
| 1338 | Sc-ADH7-Q-A3 (1338) | 52 | AAAGATGATGAGCAAACGAC |
| 1339 | Sc-ADH7-Q-B5 (1339) | 53 | CGAGCAATACTGTACCAATG |
| 1375 | HO + 1300 F | 54 | TCACGGATGATTTCCAGGGT |
| 1376 | HO + 1761 R | 55 | CACCTGCGTTGTTACCACAA |

Example 1: Construction and Confirmation of PDC Deletion in *K. lactis*

The purpose of this Example is to describe how a PDC-deletion variant of a member of the *Saccharomyces clade*, Crabtree-negative yeast, pre-WGD yeast *K. lactis* was constructed and confirmed.

Figure 8:
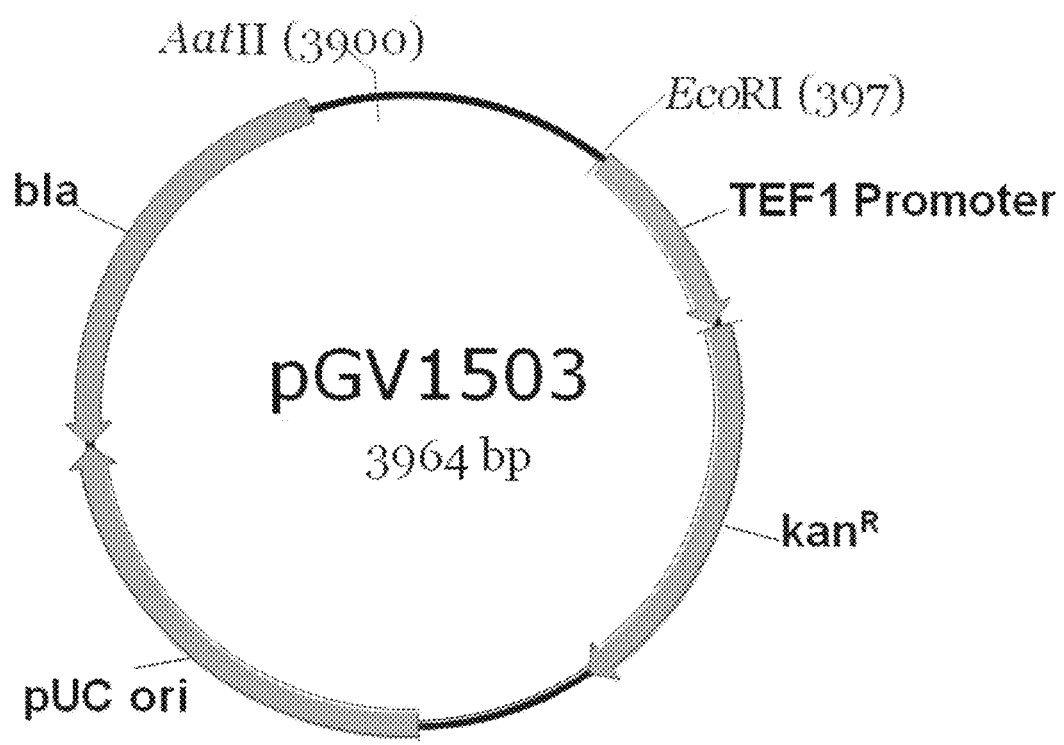
FIG. 8 illustrates a schematic map of plasmid pGV1503.
Figure 9:
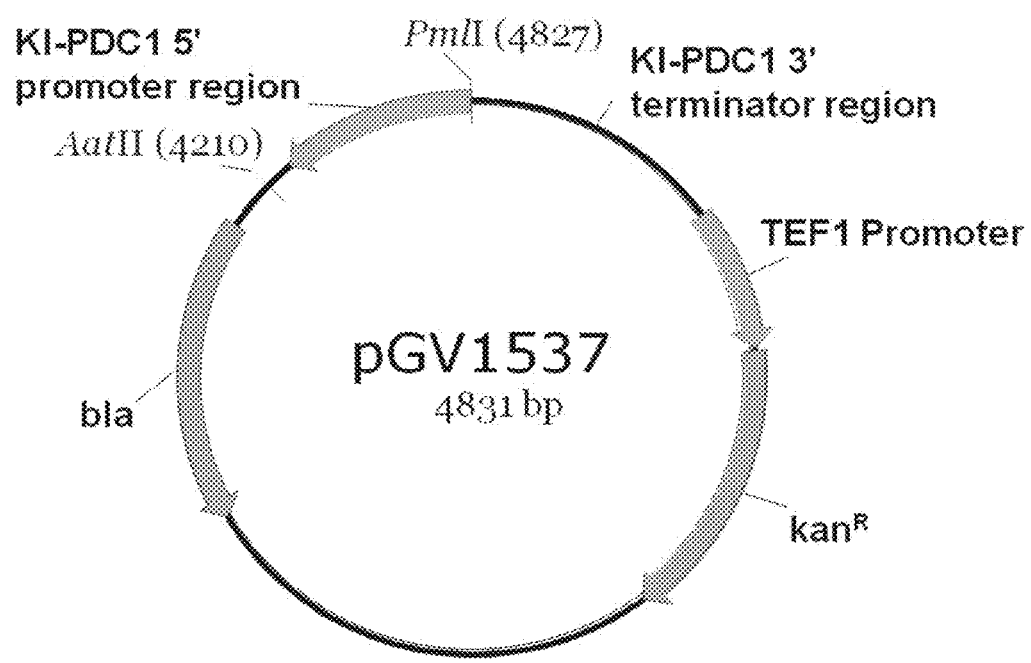
FIG. 9 illustrates a schematic map of plasmid pGV1537.

Construction of Plasmid pGV1537:

Plasmid pGV1537 (SEQ ID NO: 1) was constructed by the following series of steps. All PCR reactions carried out to generate pGV1537 used KOD polymerase (Novagen, Inc., Gibbstown, N.J.) and standard reaction conditions according to the manufacturer. A first round of two PCR reactions was carried out, wherein one PCR reaction contained primers 1006 and 1016 and used approximately 100 ng of genomic DNA from *K. lactis* strain GEVO1287 as a template. The other first-round PCR reaction contained primers 1017 and 1009 and approximately 100 ng of genomic DNA from *K. lactis* strain GEVO1287 as a template. The two resulting PCR products (approximately 530 bp and 630 bp in size, respectively) were gel purified using a Zymo Research Gel DNA Extraction kit (Zymo Research, Orange, Calif.) according to manufacturer's instructions and eluted into 10 µL of water. Two (2) microliters of each eluted PCR product were then used as a template for a final round of KOD polymerase-catalyzed PCR, which also included primers 1006 plus 1009. The resulting product was purified (Zymo Research DNA Clean & Concentrate kit, Zymo Research, Orange, Calif.), digested to completion with the enzymes MfeI and AatII, and the resulting product gel purified and eluted as described above. This DNA was ligated into the vector pGV1503 (FIG. 8), which had been digested with EcoRI plus AatII, treated with calf alkaline phosphatase, and gel purified as described above. Colonies arising from transformation of the ligated DNA were screened by restriction digest analysis and confirmed by DNA sequencing reactions using primers 838, 1010, and 1019. Correct recombinant DNA resulting from the ligation and subsequent analysis was named pGV1537 (FIG. 9).

Construction of a *K. lactis* Klpdc1Δ Strain:

Strain GEVO1287 was transformed with PmlI-digested, linearized plasmid pGV1537. Transformation was carried out by electroporation with approximately 300 ng of linearized pGV1537, essentially as described by Kooistra et al. (Kooistra, R., Hooykaas, P. J. J., and Steensman, H. Y. (2004) "Efficient gene targeting in *Kluyveromyces lactis*". Yeast 21:781-792). Transformed cells were selected by plating onto YPD plates containing 0.2 mg/mL geneticin (G418). Colonies arising from the transformation were further selected by patching colonies onto YPD plates and then replica plating onto YPD containing 5 µM (final concentration) of the respiratory inhibitor Antimycin A, as Pdc-variants of *K. lactis* are unable to grow on glucose in the presence of Antimycin A (Bianchi, M., et al., (1996). "The petite negative yeast *Kluyveromyces lactis* has a single gene expressing pyruvate decarboxylase activity". Molecular Microbiology 19(1):27-36) and can therefore be identified by this method. Of the 83 G418-resistant colonies patched onto YPD+Antimycin A, six colonies (~7%) were unable to grow and were therefore identified as candidate Klpdc1:: pGV1537 disruption strains.

Confirmation of a *K. lactis* Klpdc1ΔStrain by Colony PCR:

Candidate Klpdc1::pGV1537 disruption strains were confirmed by colony PCR analysis. To do so, genomic DNA from candidate lines was obtained by the following method. A small amount (equivalent to a matchhead) of yeast cells were resuspended in 50 μL of 0.2% SDS and heated to 95° C. for 6 minutes. The suspension was pelleted by centrifugation (30 sec, 16,000×g) and 1 μL of the supernatant was used as template in 50 μL PCR reactions. In addition to standard components, the reactions contained Triton X-100 at a final concentration of 1.5% and DMSO at a final concentration of 5%. The various primer sets used, and the expected amplicon sizes expected, are indicated in Table EX1-1. By these analyses, a correct Klpdc1Δ::pGV1537 strain was identified and was named GEVO1742.

TABLE EX1-1

Primer pairs and expected amplicon sizes predicted for colony PCR screening of candidate Klpdc1Δ::pGV1537 cells.

| Primer Pair | Expected product size for Klpdc1Δ:pGV1537 | Expected product size for KlPDC1+ |
| --- | --- | --- |
| 965 & 838 | 796 bp | (none) |
| 1019 & 966 | 947 bp | (none) |
| 995 & 996 | (none) | 765 bp |

Confirmation of GEVO1742 Klpdc1Δ::DGV1537 by Fermentation:

Strains of *K. lactis* lacking KlPdc1p (Klpdc1Δ) have been shown to produce significantly lower levels of ethanol when grown on glucose (Bianchi, M., et al., (1996). "The petite negative yeast *Kluyveromyces lactis* has a single gene expressing pyruvate decarboxylase activity". Molecular Microbiology 19(1):27-36). To confirm this phenotype, fermentations with strains GEVO1287 and GEVO1742 were carried out. Briefly, a saturated overnight (3 mL) culture of each strain grown in YPD was inoculated into 25 mL of YPD at a starting $OD_{600}$ of 0.1 and grown aerobically in a loosely-capped flask in a shaker for 24 hours at 30° C., 250 rpm. Following growth, 2 mL of culture were collected, the cells pelleted by centrifugation (5 minutes, 14,000×g) and the supernatant subjected to analysis by gas chromatography and liquid chromatography. A summary of the data from these analyses is summarized in Table EX1-2. The strongly diminished production of ethanol and the increased accumulation of pyruvate in the fermentation medium are characteristic of *K. lactis* strains in which PDC1 has been deleted. Thus, these observations confirm the molecular genetics conclusions that strain GEVO1742 is in fact Klpdc1Δ.

TABLE EX1-2

Ethanol and pyruvate produced and glucose consumed in aerobic fermentations of GEVO1287 and GEVO1742.

| STRAIN | Ethanol produced (g/L) | Pyruvate produced (g/L) | Glucose consumed (g/L) |
| --- | --- | --- | --- |
| GEVO1287 | 8.129 | (not detected) | 17.56 |
| GEVO1742 | 0.386 | 1.99 | 5.25 |

Example 2: Construction and Confirmation of PDC Deletion in *S. cerevisiae*

The purpose of this Example is to describe how a PDC deletion variant of a member of the *Saccharomyces sensu stricto* yeast group, the *Saccharomyces* yeast *clade*, a Crabtree-positive yeast, and a post-WGD yeast, *S. cerevisiae* was constructed and confirmed.

Strains GEVO1537 and GEVO1538 were incubated in 1% potassium acetate for 3-4 days which induces sporulation. The resulting haploid spores were recovered by random spore analysis. Briefly, a culture of sporulating cells was examined microscopically to ensure that a sufficient fraction of cells had sporulated (>10%). Five (5) mL of a culture of sporulated cells were collected by centrifugation (5 minutes at 3000×g) and washed once in 1 mL of water. The cells were resuspended in 5 mL water to which was added 0.5 mL of a 1 mg/mL solution (freshly made) of Zymolyase-T (in water) as well as 10 μL of β-mercaptoethanol. The cell suspension was incubated overnight at 30° C. in a shaker at 50 rpm. Five mL of 1.5% Triton X-100 were added and the mixture was incubated on ice for 15 minutes. The solution was sonicated three times for 30 seconds per cycle at 50% power, with 2 minutes rest on ice in between sonication cycles. The suspension was centrifuged (1200×g, 5 minutes) and washed twice with 5 mL of water. The final cell pellet was resuspended in 1 mL water and cells were plated to YP+2% EtOH.

Following this procedure, the separate individual spores, were plated onto solid medium to obtain colonies, all of genotype HO pdc1::Tn5ble pdc5::Tn5ble pdc6:APT1 HIS3 LEU2 TRP1 URA3 and of unknown mating type. Some fraction of the cells were (homozygous) diploid due to the HO+ gene status and resultant mating type switching and re-mating to form diploids.

The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT a locus (primers #490 and #491). Colonies that generated a single PCR product with one of the two possible primer sets primer set and no product when tested with the other were putative haploid Pdc-minus strains. To confirm the mating type, such strains were crossed to Gevol1187 and Gevol188 (CEN.PK). Resulting diploid progeny were selected on medium containing glucose (to select for the presence of PDC+ genes introduced by CEN.PK background) and also lacking at least one of the following nutrients: histidine, leucine, tryptophan, or uracil (to select for the appropriate prototrophy as provided by the wild-type allele of the corresponding gene from the Gevol537 or GEVO1538 background.

Diploid cells were sporulated and germinated on agar plates containing YP+2% ethanol (to permit growth of Pdc-minus isolates). To identify Pdc-minus candidates, viable colonies were streaked on to YPD agar plates and colonies that were inviable on glucose were isolated. Inability to grow on glucose confirms that these candidates are pdc1::ble and pdc5::ble. The pdc6::apt1 was confirmed their ability to grow on YP+Ethanol plates containing the antibiotic G418. The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT a locus (primers #490 and #491). The presence of a product from both sets of PCR reactions indicated that both mating type alleles were present in the population, as a consequence of mating type allele switching by an active HO-encoded enzyme. The presence of a PCR product for one set of MAT locus-specific primers but not the other indicated that the strain lacks this activity and was therefore ho-. Based upon these analyses, six candidates colonies were identified as ho-strains and one candidate #4 was HO.

These Pdc-minus strains were streaked to SC+Ethanol plates lacking one of: leucine, histidine, tryptophan, or uracil, to determine presence of auxotrophic mutations within these strains. One Pdc-minus strain, GEVO1581, was auxotrophic for histidine, uracil, and tryptophan, and thus carried three of the makers (his3, ura3, and trp1). Another Pdc-minus strain, GEVO1715, was auxotrophic for uracil and leucine and thus carried the two markers, ura3 and leu2.

GEVO1581 and GEVO1715 were screened by RFLP analysis to verify the presence of the ho allele. A 447 bp portion of the HO locus was amplified by PCR that contained the codon that is altered in the ho allele (H475L) using primers 1375 and 1376. This mutation introduces an AluI restriction site, and consequently, digestion with AluI (New England BioLabs, Ipswich, Mass.) yielded either a 447 bp fragment (HO) or a 122 bp fragment plus a 325 bp fragment (ho). Based upon RFLP analysis, GEVO1581 was HO and GEVO1715 was ho.

To obtain a Pdc-minus strain with all four auxotrophic markers, GEVO1715 was crossed to GEVO1188 and diploids generated as described above. The resulting diploid was sporulated and Pdc-minus candidates were isolated by plating onto YP+Ethanol containing both Phleomycin and G418. These candidates were then streaked onto YPD agar plates and tested for their inviability on glucose. Those that did not grow on glucose were isolated as this phenotype, in addition to their resistance to Phleomycin and G418 confirms that these candidates are pdc1::ble, pdc5::ble and pdc6::apt1. These isolates were streaked to SC+Ethanol plates lacking one of: leucine, histidine, tryptophan, or uracil, to determine presence of auxotrophic mutations within these strains. One of these Pdc-minus strains, GEVO1584, was auxotrophic for histidine, uracil, tryptophan and leucine and thus carried all four markers, his3, ura3, trp1, and leu2. GEVO1584 was also confirmed to be MATa and ho by colony PCR and RFLP analysis, respectively, as described above.

TABLE EX2-1

Summary table of *S. cerevisiae* Pdc-minus strains obtained

| GEVO No. | GENOTYPE | STRAIN SOURCE |
|---|---|---|
| 1537 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1538 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1581 | MAT a/α, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO | candidate #4 GEVO1537 × GEVO1187 |
| 1584 | MAT a, his3, trp1, ura3, leu2, pdc1::ble, pdc5::ble, pdc6::apt1(kanR), ho | candidate #201 GEVO1715 × GEVO1188 |
| 1715 | MAT a, leu2, ura3, pdc1::ble, pdc5::ble, pdc6::apt1(kanR), ho | candidate #104 GEVO1187 × GEVO1537 |

Example 3: Other Pdc-Minus *S. cerevisiae* Strains

*S. cerevisiae* engineered to be deficient in PDC activity have been previously described: (Flikweert, M. T., van der Zanden, L., Janssen, W. M. T. M, Steensma, H. Y., van Dijken J. P., Pronk J. T. (1996) Yeast 12(3):247-57). Such strains may be obtained from these sources.

Example 4: Chemostat Evolution of *S. cerevisiae* PDC Triple-Mutant

This example demonstrates that a PDC deletion variant of a member *Saccharomyces sensu stricto* yeast group, the *Saccharomyces clade* yeast, Crabtree-positive, post-WGD yeast, *S. cerevisiae*, can be evolved so that it does not have the requirement for a two-carbon molecule and has a growth rate similar to the parental strain on glucose.

A DasGip fermentor vessel was sterilized and filled with 200 ml of YNB (Yeast Nitrogen Base; containing per liter of distilled water: 6.7 g YNB without amino acids from Difco, the following were added per liter of medium: 0.076 g histidine, 0.076 g tryptophan, 0.380 g leucine, and/or 0.076 g uracil; medium was adjusted pH to 5 by adding a few drops of HCL or KOH) and contained 2% w/v ethanol. The vessel was installed and all probes were calibrated according to DasGip instructions. The vessel was also attached to an off-gas analyzer of the DasGip system, as well as to a mass spectrometer. Online measurements of oxygen, carbon dioxide, isobutanol, and ethanol were taken throughout the experiment. The two probes that were inside the vessel measured pH and dissolved oxygen levels at all times. A medium inlet and an outlet were also set up on the vessel. The outlet tube was placed at a height just above the 200 ml level, and the pump rate was set to maximum. This arrangement helped maintain the volume in the vessel at 200 ml. Air was sparged into the fermentor at 12 standard liters per hour (slph) at all times. The temperature of the vessel was held constant at 31.8° C. and the agitation rate was kept at 300 rpm. The off-gas was analyzed for $CO_2$, $O_2$, ethanol and isobutanol concentrations. The amount of carbon dioxide ($X_{CO2}$) and oxygen ($X_{O2}$) levels in the off-gas were used to assess the metabolic state of the cells. An increase $X_{CO2}$ levels and decrease in $X_{O2}$ levels indicated an increase in growth rate and glucose consumption rate. The ethanol levels were monitored to ensure that there was no contamination, either from other yeast cells or from potential revertants of the mutant strain since the S. cerevisiae PDC triple-mutant (GEVO1584) does not produce ethanol. The minimum pH in the vessel was set to 5, and a base control was set up to pump in potassium hydroxide into the vessel when the pH dropped below 5.

GEVO1584 was inoculated into 10 ml of YNB medium with 2% w/v ethanol as the carbon source. The culture was incubated at 30° C. overnight with shaking. The overnight culture was used to inoculate the DasGip vessel. Initially, the vessel was run in batch mode, to build up a high cell density. When about 3 g CDW/L of cell biomass was reached, the vessel was switched to chemostat mode and the dilution of the culture began. The medium pumped into the vessel was YNB with 7.125 g/L glucose and 0.375 g/L of acetate (5% carbon equivalent). The initial dilution rate was set to 0.1 $h^{-1}$, but as the cell density started dropping, the dilution rate was decreased to 0.025 $h^{-1}$ to avoid washout. GEVO1584 was mating type a. A PCR check for the mating type of the chemostat population several days into the experiment indicated that the strain still present was mating type a.

Figure 5:
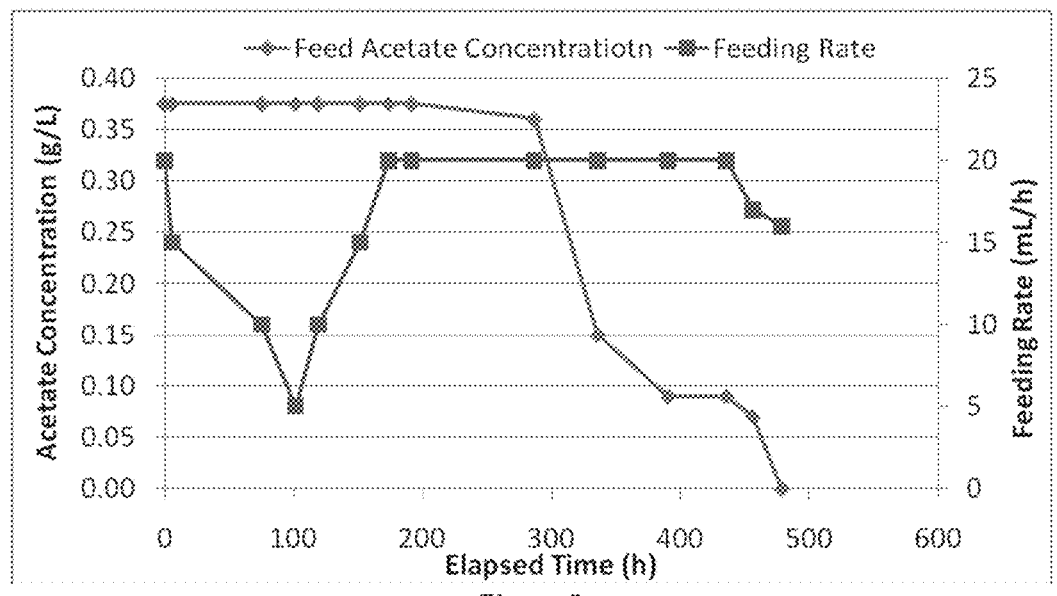
FIG. 5 illustrates the carbon source composition and feeding rate over time during chemostat evolution of the *S. cerevisiae* Pdc-minus strain GEVO1584. This graph shows how the acetate was decreased over a period of 480 hours from 0.375 g/L to 0 g/L. It also shows the total feeding rate. Higher feeding rate meant that growth rate was higher. Since the chemostat contained 200 ml of culture, dilution rate can be calculated by dividing the feeding rate by 200 ml.

The culture in the chemostat was stabilized and the dilution rate increased to 0.1 $h^{-1}$. After steady state was reached at the 0.1 $h^{-1}$ dilution rate, the concentration of acetate was slowly decreased. This was achieved by using a two pump system, effectively producing a gradient pumping scheme. Initially pump A was pumping YNB with 7.125 g/L glucose, and 0.6 g/L of acetate at a rate of 12.5 mL/h and pump C was pumping YNB with only 7.125 g/L glucose at a rate of 7.5 mL/h. The combined acetate going into the vessel was 0.375 g/L. Then, over a period of 3 weeks, the rate of pump A was slowly decreased and the rate of pump C was increased by the same amount so that the combined rate of feeding was always 20 mL/h. When the rate of pump A dropped below 3 mL/h the culture started to slowly wash out. To avoid complete washout the dilution rate was decreased to 0.075 $h^{-1}$ from 0.1 $h^{-1}$ (FIG. 5). At this dilution rate, the rate of pump A was finally reduced to 0, and the evolved strain was able to grow on glucose only. Over the period of about five weeks, a sample was occasionally removed, either from the vessel directly or from the effluent line. Samples were analyzed for glucose, acetate, and pyruvate using HPLC, and were plated on YNB with glucose, YNB with ethanol, and YNB (w/o uracil) plus glucose or ethanol as negative control. Strains isolated from the chemostat did not grow on the YNB plates without uracil. $OD_{600}$ was taken regularly to make sure the chemostat did not wash out. Freezer stocks of samples of the culture were made regularly for future characterization of the strains.

Figure 6:
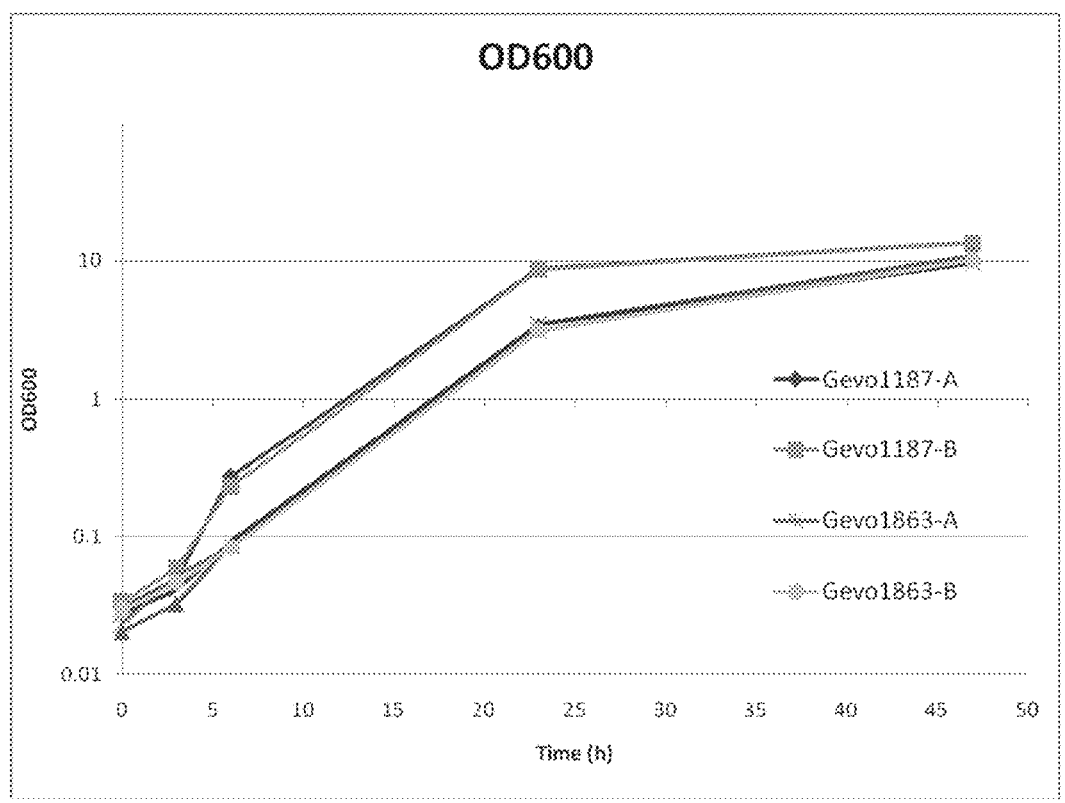
FIG. 6 illustrates growth of evolved Pdc-minus mutant strain GEVO1863 in YPD compared to the parental strain, GEVO1187.
Figure 7:
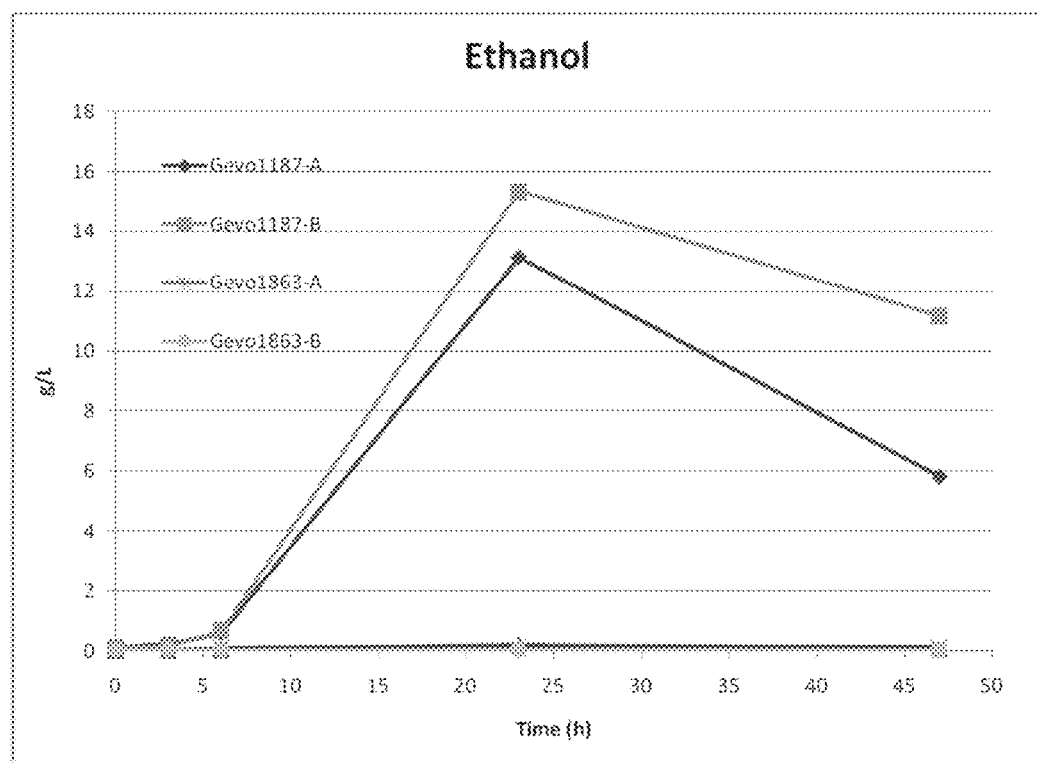
FIG. 7 illustrates that the evolved PCD mutant, GEVO1863, does not produce ethanol in YPD medium, unlike the parental strain GEVO1187.

To characterize growth of the evolved strains YNB, YPD (yeast extract, peptone, dextrose), and YPE (yeast extract, peptone, ethanol) were used with various concentrations of glucose or ethanol. The growth characterization was performed in either snap-cap test tubes or 48-well plates (7.5 ml). The snap-cap test tubes were not closed completely so that air would vent in/out of the tubes, and the 48-well plates were covered with an air permeable membrane to allow for oxygen transfer. To check for contaminations, YPD or YPE agar plates were used with the antibiotics G418 and Phleomycin. The PDC triple mutant strain (GEVO1584) has both G418 and Phleomycin resistance markers, so the progeny of that strain were able to grow on the antibiotics. Single colonies isolated from each chemostat sample were studied for growth rates. A single colony isolated from the 35-day chemostat population was selected because of high growth rates on glucose as a sole carbon source, was resistant to both G418 and Phleomycin, and grew without the need for ethanol or acetate. The single colony was further evolved through 24 successive serial transfers in test tubes on YPD at 30° C., 250 rpm shaking. The resulting strain, GEVO1863, grew similarly to the wild-type yeast parent on glucose (FIG. 6), did not produce ethanol (FIG. 7), and did not require ethanol or acetate for growth.

Example 5: Isobutanol Production in Pdc-Plus K. lactis

This example demonstrates isobutanol production in a member of the Saccharomyces clade, Crabtree-negative, pre-WGD yeast, K. lactis.

Figure 10:
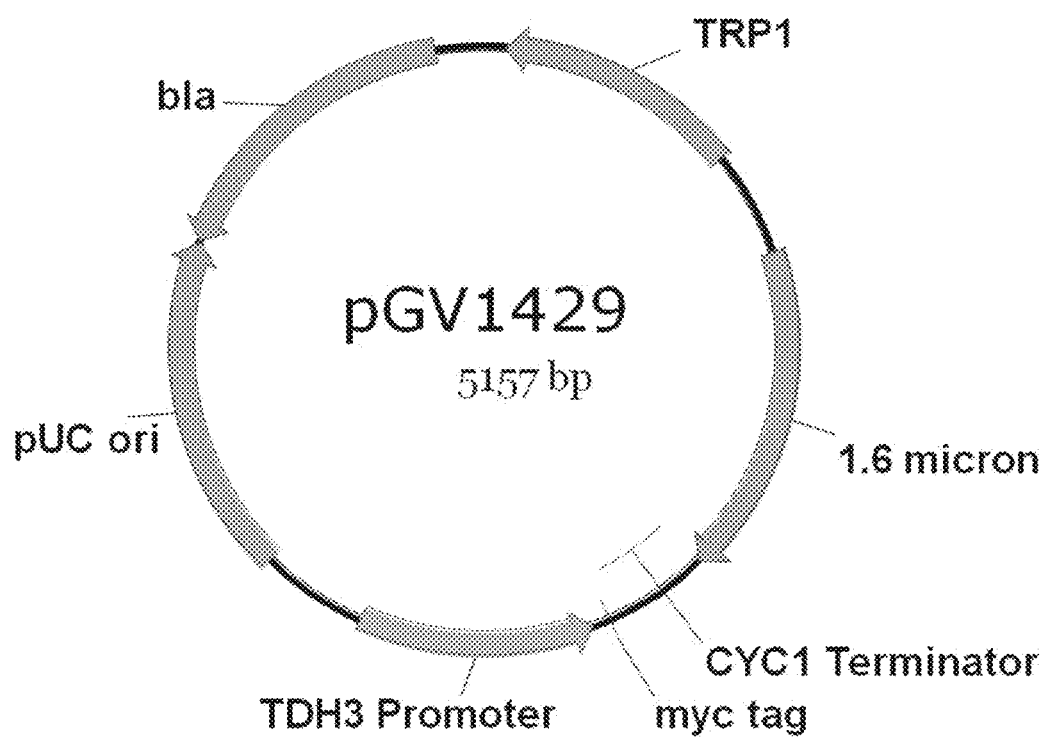
FIG. 10 illustrates a schematic map of plasmid pGV1429.
Figure 11:
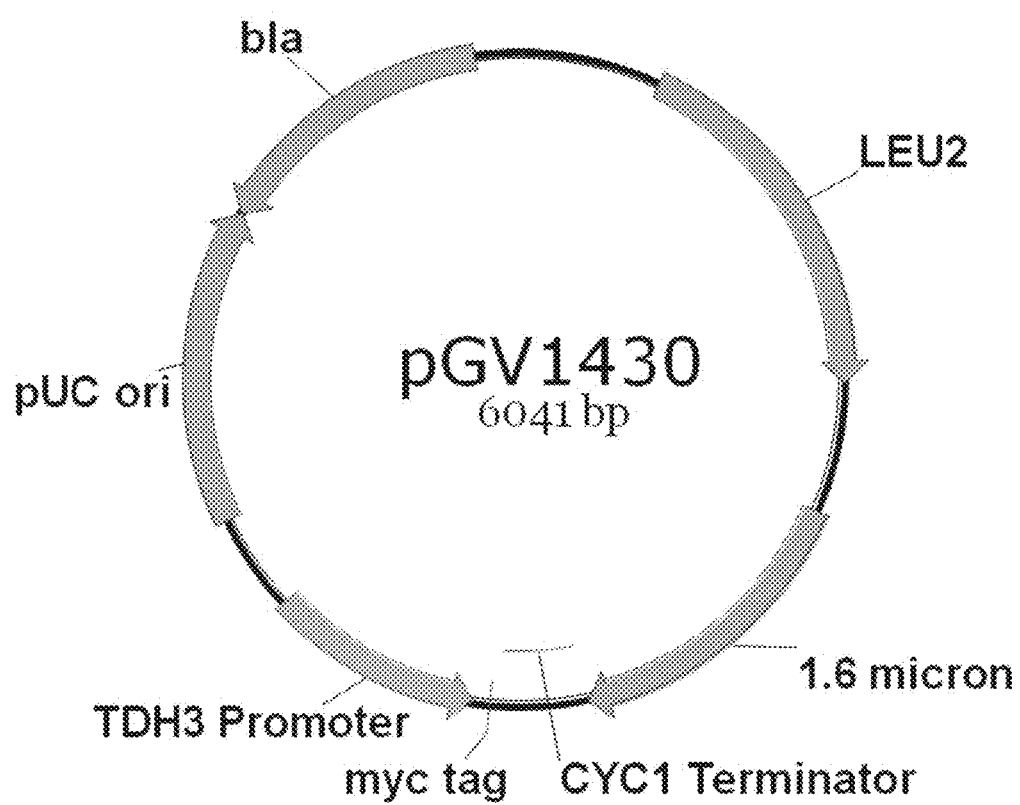
FIG. 11 illustrates a schematic map of plasmid pGV1430.
Figure 12:
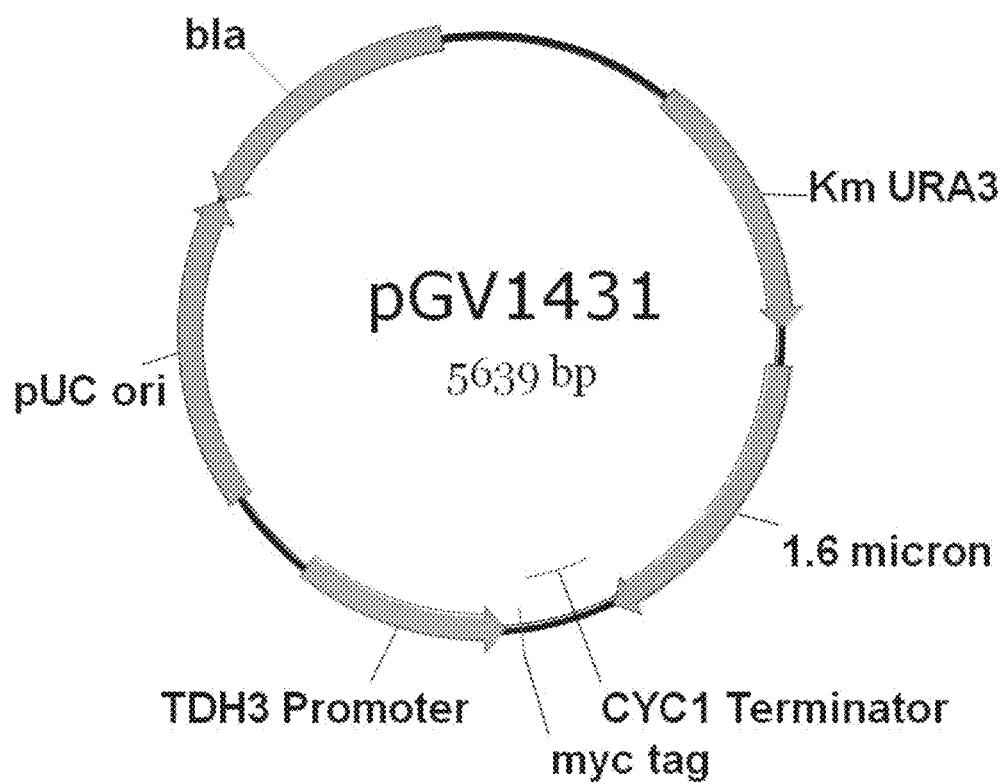
FIG. 12 illustrates a schematic map of plasmid pGV1431.
Figure 13:
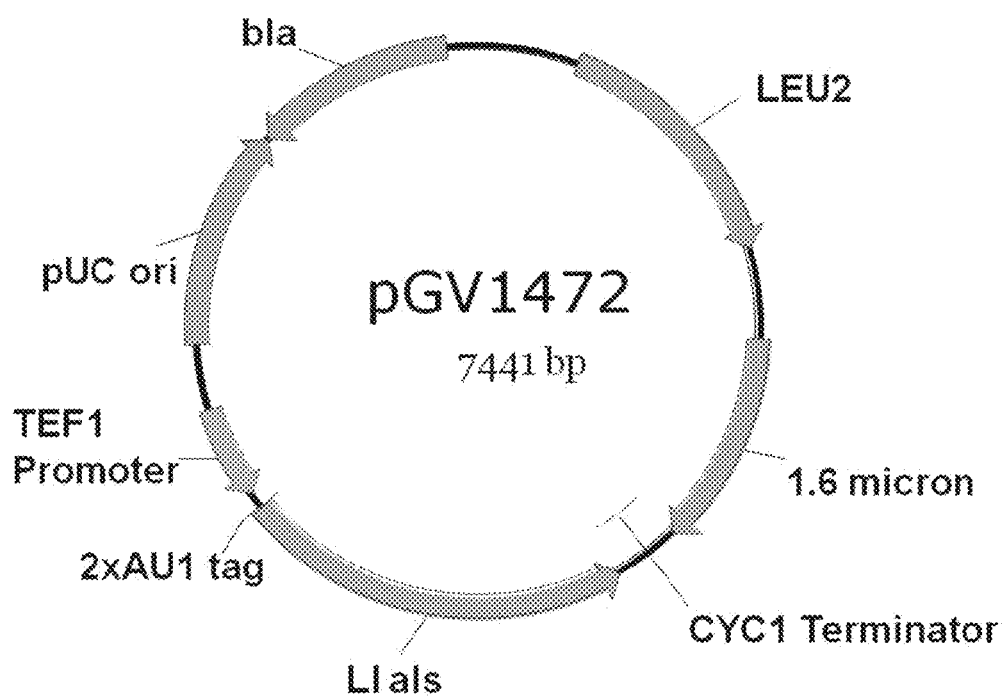
FIG. 13 illustrates a schematic map of plasmid pGV1472.
Figure 14:
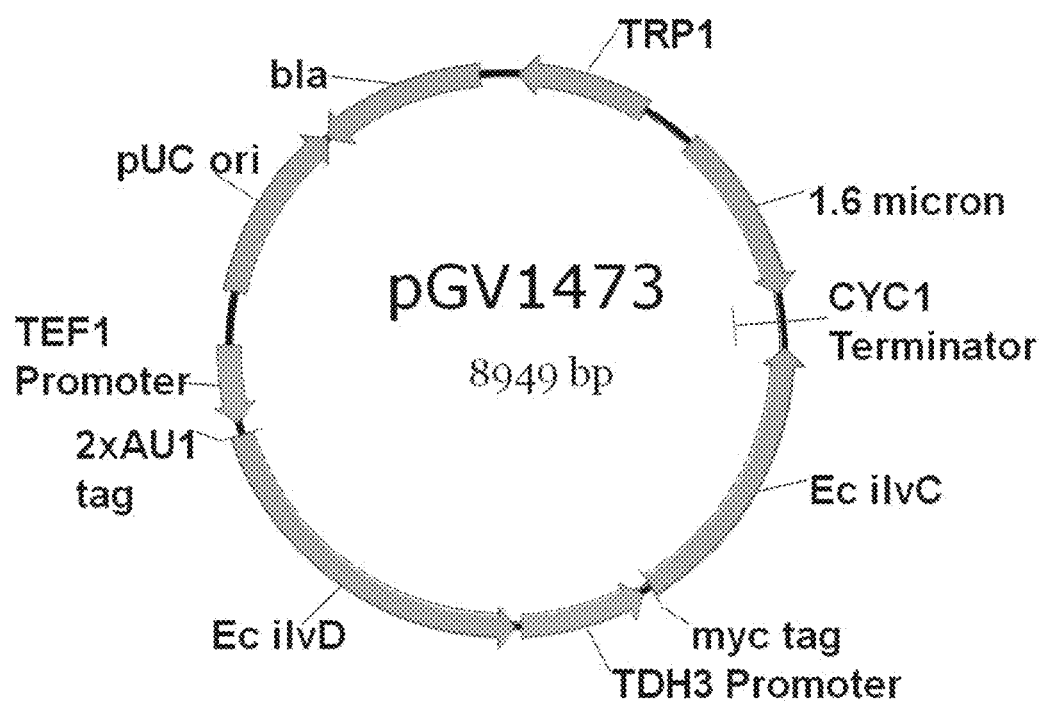
FIG. 14 illustrates a schematic map of plasmid pGV1473.
Figure 15:
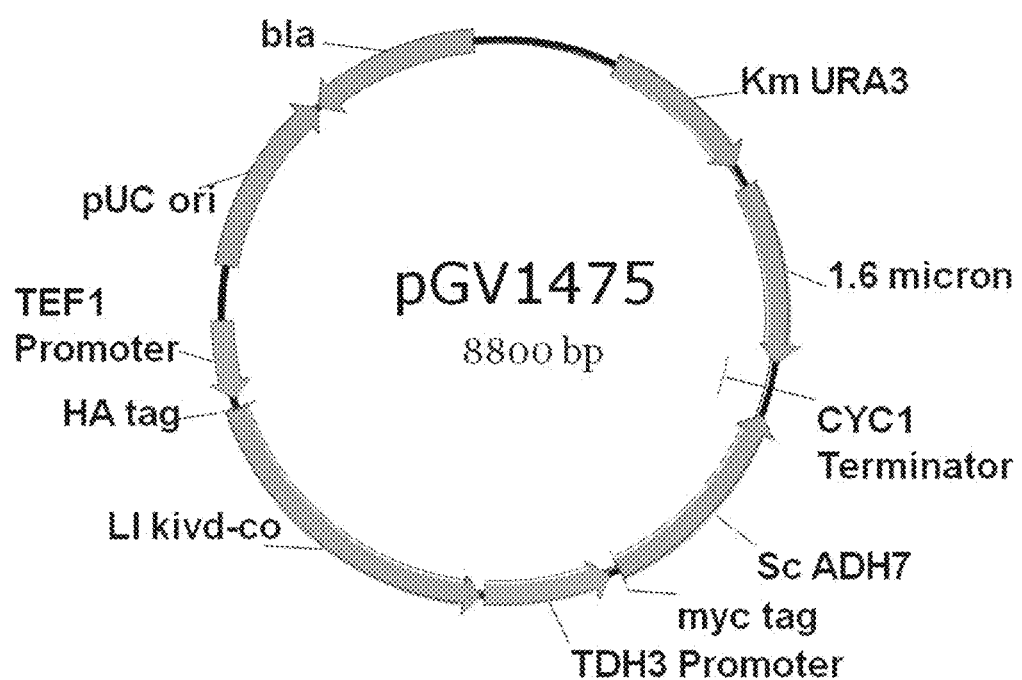
FIG. 15 illustrates a schematic map of plasmid pGV1475.

The isobutanol production pathway was cloned in a K. lactis vector-based expression system: a SacI-MluI fragment containing the TEF1 promoter. Lactococcus lactis alsS and part of the CYC1 terminator sequence was cloned into the same sites of the K. lactis expression plasmid, pGV1430 (FIG. 11), to generate pGV1472 (FIG. 13, SEQ ID NO: 2). A SacI-MluI fragment containing the TEF1 promoter, E. coli ilvD, TDH3 promoter, E. coli ilvC, and part of the CYC1 terminator was cloned into the same sites of the K. lactis expression plasmid, pGV1429 (FIG. 10), to generate pGV1473 (FIG. 14, SEQ ID NO: 3). A BssHII-NotI fragment containing the TEF1 promoter, L. lactis kivD, TDH3 promoter and S. cerevisiae ADH7. ScAdh7 was cloned into the K. lactis expression plasmid, pGV1431 (FIG. 12), to obtain pGV1475 (FIG. 15, SEQ ID NO: 4).

The K. lactis strain GEVO1287 was transformed with the above plasmids, pGV1472, pGV1473, and pGV1475 (Table EX5-1) to express the isobutanol pathway. As a control, K. lactis GEVO1287 was also transformed with empty vectors pGV1430, pGV1429, and pGV1431 (Table EX5-1).

TABLE EX 5-1

K. lactis clones expressing an isobutanol pathway

| clone | Host | Plasmid 1 | Plasmid 2 | Plasmid 3 | ALS | KARI | DHAD | KIVD | ADH |
|---|---|---|---|---|---|---|---|---|---|
| iB165 | GEVO1287 | PGV1430 | pGV1429 | pGV1431 | — | — | — | — | — |
| iB173 | GEVO1287 | pGV1472 | pGV1473 | pGV1475 | Ptef1-Ll. alsS | Ec. ilvC | Ec. ilvD | Ll. Kivd | Sc. Adh7 |

Transformed cells were grown overnight and transferred to 100 mL fermentation bottles using 20 mL SC-WLU medium. Two mL samples were taken at 24 and 48 hours for GC analysis. At each time point, 2 mL of a 20% glucose was added after removing samples for GC analysis. At 48 hours the fermentation was ended. GC samples were processed as described. Results are shown in Table EX5-2 Up to 0.25 g/L isobutanol was produced in *K. lactis* transformed with an isobutanol pathway whereas the control strain without the pathway only produced 0.022 g/L in 48 hours.

TABLE EX5-2

*K. lactis* fermentation results

| clone | Isobutanol titer (mg/L) | Isobutanol yield (% theoretical) | Ethanol (g/L) |
|---|---|---|---|
| iB165 | 0.022 | 0.13 | 11.4 |
| iB173 | 0.25 | 1.5 | 12.6 |

To determine if isobutanol titers can be increased by using a rich complex media, fermentations were performed as described above with iB165 (vector only control) and iB173 using YPD instead of SC-WLU medium. In addition, fermentations were also carried out in 250 mL screw-cap flasks (microaerobic conditions) and in 125 mL metal-cap flasks (aerobic conditions). Samples were taken at 24, 48, and 72 and the isobutanol levels obtained are shown in Table EX5-3.

TABLE EX5-3

*K. lactis* fermentation results using YPD

| clone | Condition | Isobutanol titer (mg/L) | Isobutanol yield (% theoretical) | Ethanol (g/L) |
|---|---|---|---|---|
| iB165 | Anaerobic | 66 | 0.4 | 27.4 |
| iB165 | Microaerobic | 117 | 0.7 | 24.5 |
| iB165 | Aerobic | 104 | 0.6 | 11.7 |
| iB173 | Anaerobic | 297 | 1.8 | 25.8 |
| iB173 | Microaerobic | 436 | 2.6 | 23.4 |
| iB173 | Aerobic | 452 | 2.7 | 13.4 |

Example 6: Isobutanol Production in Pdc Plus *S. cerevisiae*

This example demonstrates isobutanol production in a member of *Saccharomyces sensu stricto* group, *Saccharomyces* clade, Crabtree-positive, post-WGD yeast, *S. cerevisiae*.

Figure 16:
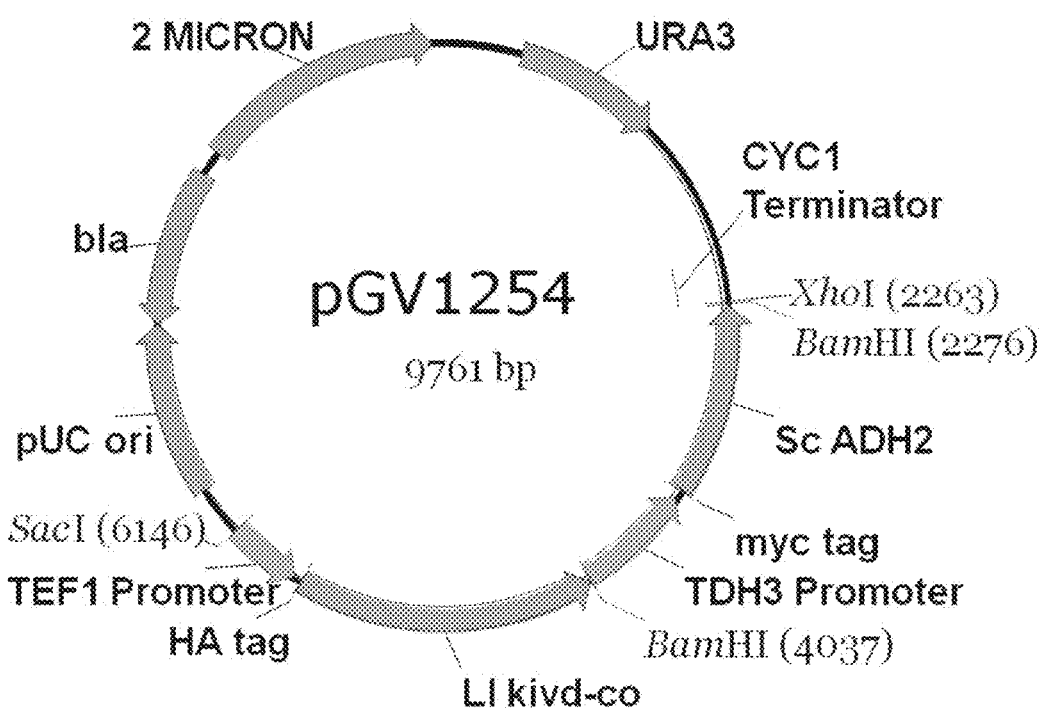
FIG. 16 illustrates a schematic map of plasmid pGV1254.
Figure 17:
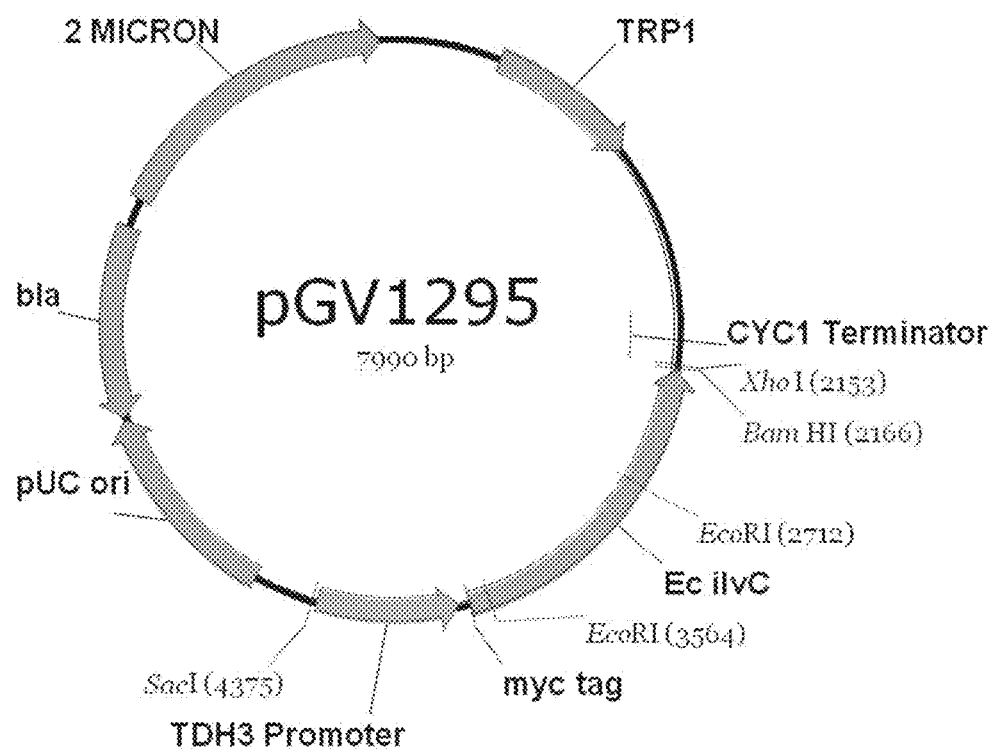
FIG. 17 illustrates a schematic map of plasmid pGV1295.
Figure 18:
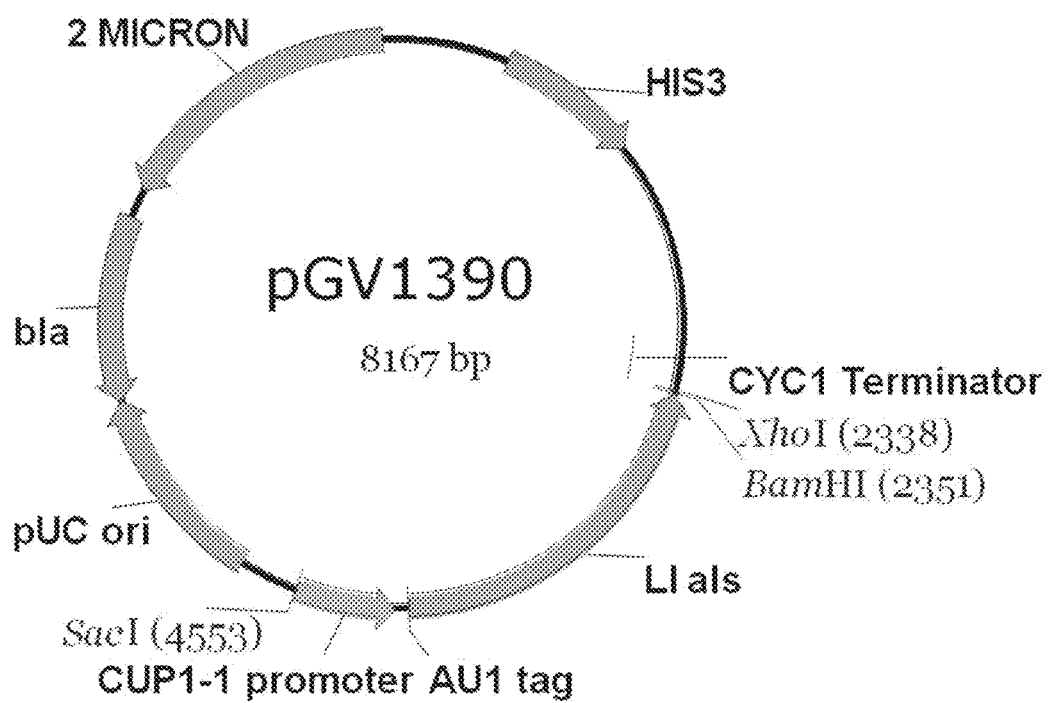
FIG. 18 illustrates a schematic map of plasmid pGV1390.
Figure 19:
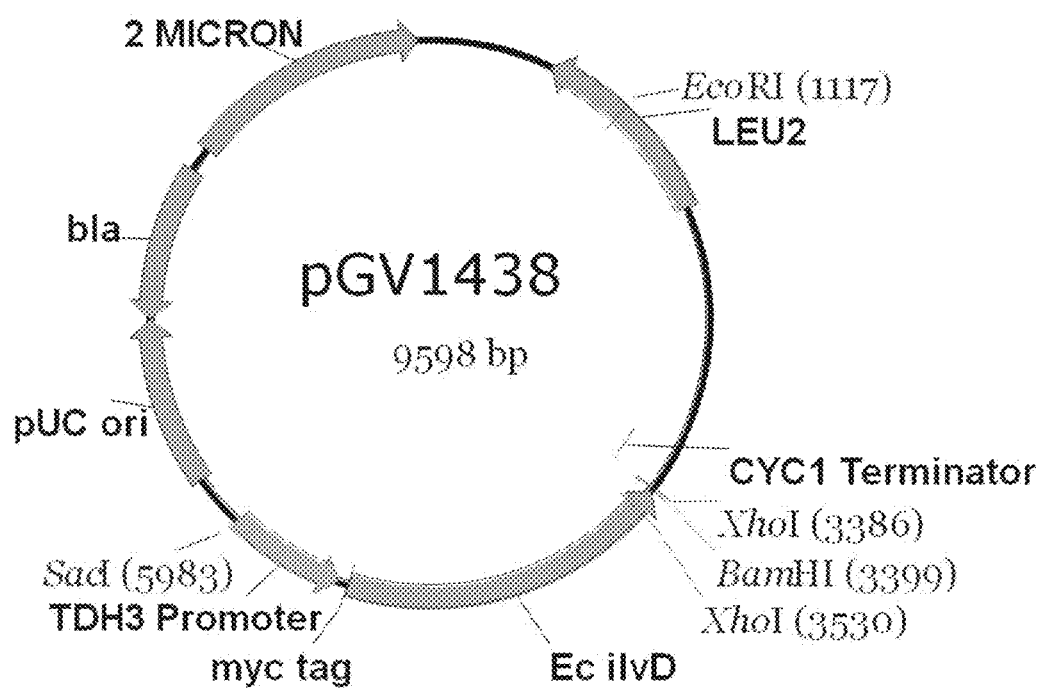
FIG. 19 illustrates a schematic map of plasmid pGV1438.

Various plasmids carrying the isobutanol production pathway were constructed for expression of this metabolic pathway in a Pdc-plus variant of *S. cerevisiae*, GEVO1187. Plasmids pGV1254 (FIG. 16; SEQ ID NO: 10), pGV1295 (FIG. 17; SEQ ID NO: 11) pGV1390 (FIG. 18; SEQ ID NO: 12), and pGV1438 (FIG. 19; SEQ ID NO: 13) were high copy *S. cerevisiae* plasmids that together expressed the five genes of the isobutanol pathway (TABLE EX6-1). pGV1390 was generated by cloning a SalI-BamHI fragment containing the *L. lactis* alsS (SEQ ID NO: 5) into the high copy *S. cerevisiae* expression plasmid, pGV1387, where the *L. lactis* alsS would be expressed under the CUP1 promoter. pGV1295 was generated by cloning a SalI-BamHI fragment containing the *E. coli* ilvC (SEQ ID NO: 6) into the high copy *S. cerevisiae* expression plasmid, pGV1266, where the *E. coli* ilvC would be expressed using the TDH3 promoter. pGV1438 was generated by cloning a SalI-BamHI fragment containing the *E. coli* ilvD (SEQ ID NO: 7) into the high copy *S. cerevisiae* expression plasmid, pGV1267, where the *E. coli* ilvD would be expressed using the TDH3 promoter. pGV1254 was made by cloning an EcoRI (filled in by Klenow polymerase treatment)—XhoI fragment containing the TDH3 promoter and *S. cerevisiae* ADH2 from pGV1241 into the BamHI (filled in by Klenow) and XhoI sites of pGV1186. pGV1186 was made by cloning a SalI-BamHI fragment containing the *L. lactis* kivD (SEQ ID NO: 8) into a high copy *S. cerevisiae* expression plasmid, pGV1102, where the *L. lactis* kivD would be expressed using the TEF1 promoter. pGV1241 was made by cloning a SalI-BamHI fragment containing the *S. cerevisiae* ADH2 (SEQ ID NO: 9) into a high copy *S. cerevisiae* expression plasmid, pGV1106, where the *S. cerevisiae* ADH2 would be expressed using the TDH3 promoter.

Figure 23:
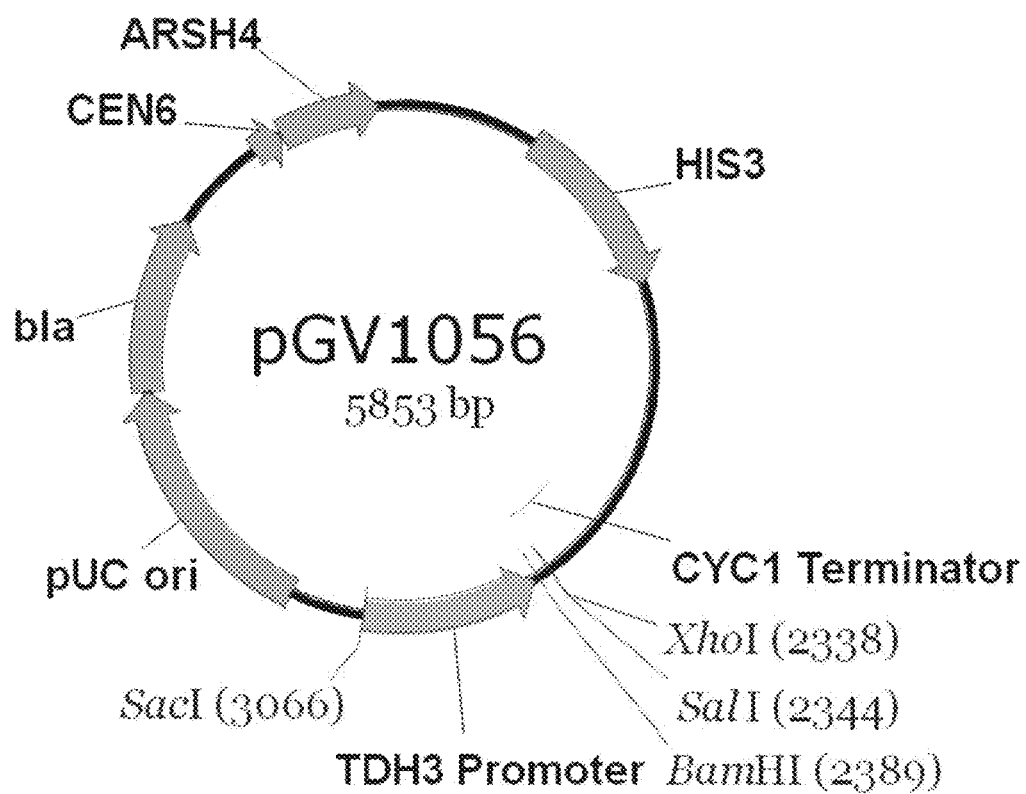
FIG. 23 illustrates a schematic map of plasmid pGV1056.

GEVO1187 was transformed with plasmids as shown in Table EX6-1. As a defective isobutanol pathway control, cells were transformed with pGV1056 (FIG. 23, empty vector control) instead of pGV1390. The transformants were plated onto appropriate selection plates. Single colonies from the transformation were isolated and tested for isobutanol production by fermentation.

TABLE EX6-1

| pGV# | Promoter | Gene | Plasmid type | Plasmid marker |
|---|---|---|---|---|
| pGV1254 | Sc TEF1 | *L. lactis* kivD | High copy | Sc URA3 |
| pGV1295 | Sc TDH3 | *E. coli* ilvC | High copy | Sc TRP1 |
| pGV1390 | Sc CUP1 | *L. lactis* alsS | High copy | Sc HIS3 |
| pGV1438 | Sc TDH3 | *E. coli* ilvD | High copy | Sc LEU1 |

The cells were grown overnight and anaerobic batch fermentations were carried out as described in General Methods. SC-HWUL was used as the media. 2 mL samples were taken at 24, 48 and 72 hours for GC At each time point, the cultures were fed 2 mL of a 40% glucose solution. The fermentation was ended after 72 hours. Samples were processed and analyzed as described. The results are shown in Table EX6-2. As shown, isobutanol was produced in GEVO1187 transformed with the isobutanol-pathway containing plasmids.

TABLE EX6-2

Isobutanol production in *S. cerevisiae*, GEVO1187, after 72 hours

| | | Isobutanol | | Ethanol | |
|---|---|---|---|---|---|
| Strain | Plasmids | Titer [g L$^{-1}$] | Yield [%] | Titer [gL$^{-1}$] | Yield [%] |
| GEVO1187 | pGV1254, pGV1438, pGV1390, pGV1438 | 0.13 | 0.31 | 31 | 60 |
| GEVO1187 | pGV1056, pGV1295, pGV1438, pGV1254 | 0.04 | 0.10 | 42 | 82 |

This example demonstrates isobutanol production in a Pdc-minus member of the *Saccharomyces* clade, Crabtree-negative, pre-WGD yeast, *K. lactis*.

Figure 20:
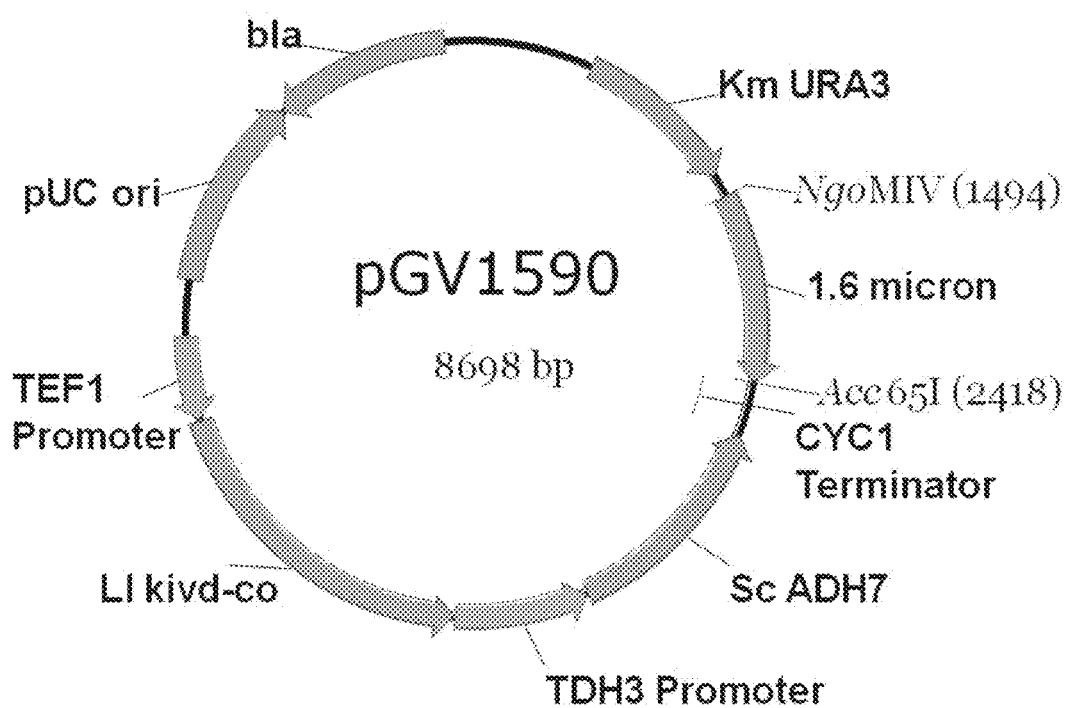
FIG. 20 illustrates a schematic map of plasmid pGV1590.
Figure 21:
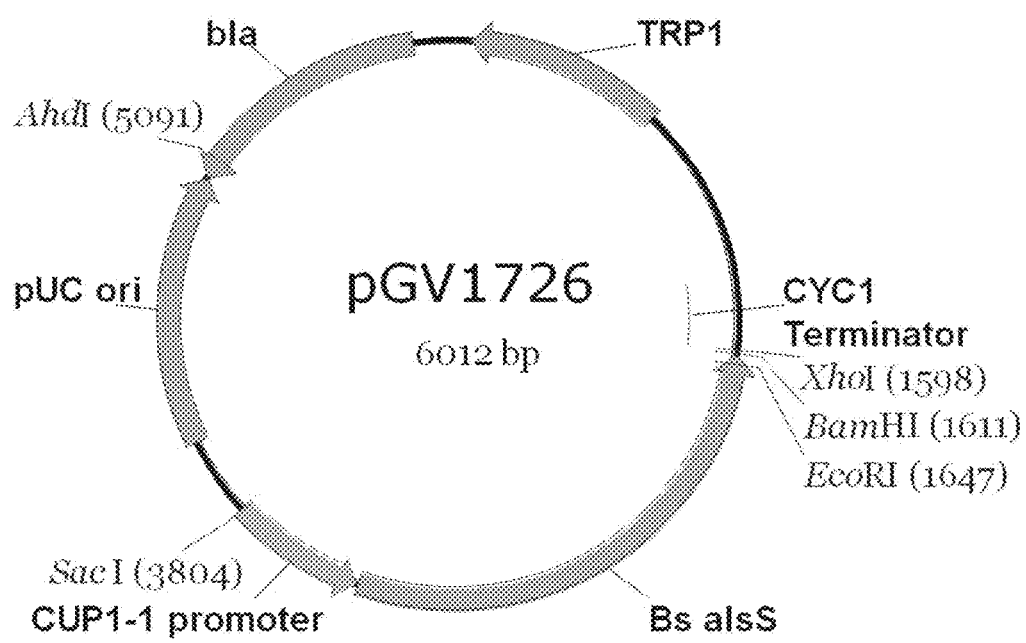
FIG. 21 illustrates a schematic map of plasmid pGV1726.
Figure 22:
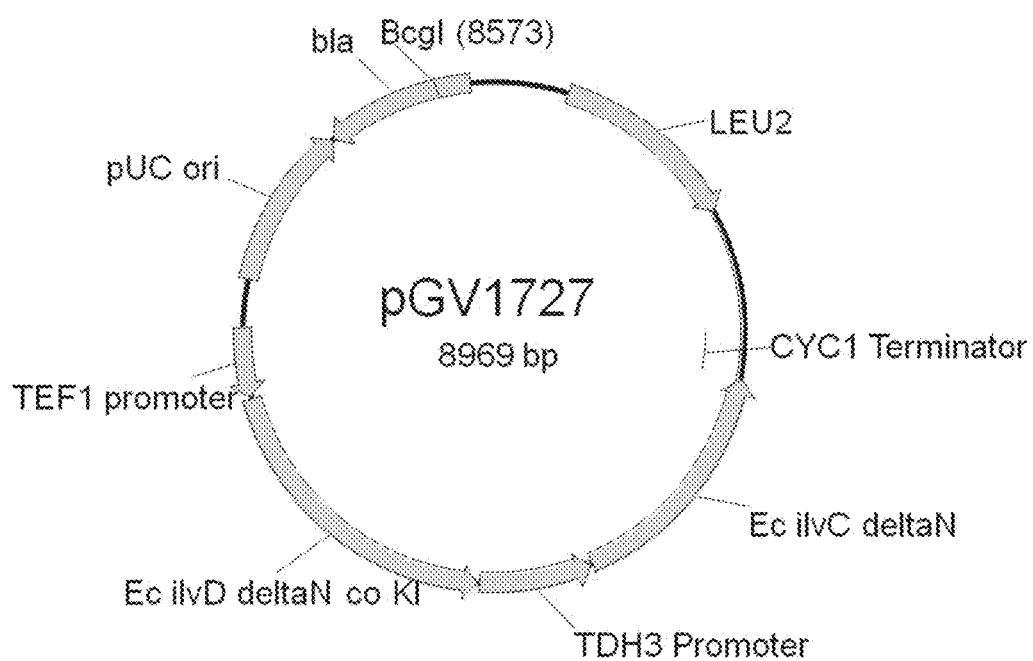
FIG. 22 illustrates a schematic map of plasmid pGV1727.

Description of Plasmids pGV1590, pGV1726, pGV1727:
pGV1590 (FIG. 20, SEQ ID NO: 14) is a *K. lactis* expression plasmid used to express *L. lactis* kivD (under TEF1 promoter) and *S. cerevisiae* ADH7 (under TDH3 promoter). This plasmid also carries the *K. marxianus* URA3 gene and the 1.6 micron replication origin that allow for DNA replication in *K. lactis*. pGV1726 (FIG. 21, SEQ ID NO: 15) is a yeast integration plasmid carrying the TRP1 marker and expressing *B. subtilis* alsS using the CUP1 promoter. pGV1727 (FIG. 22, SEQ ID NO: 16) is a yeast integration plasmid carrying the LEU2 marker and expressing *E. coli* ilvD under the TEF1 promoter and *E. coli* ilvC under the TDH3 promoter. Neither pGV1726 or pGV1727 carry a yeast replication origin.

Construction of GEVO1829, a *K. lactis* Strain with Pathway Integrated:

The isobutanol pathway was introduced into the Pdc-minus *K. lactis* strain GEVO1742 by random integrations of the pathway genes. GEVO1742 was transformed with the Acc651-NgoMIV fragment of pGV1590 containing the *L. lactis* kivd and *S. cerevisiae* ADH7 but without the yeast replication origin, to generate GEVO1794. The presence of both *L. lactis* kivd and *S. cerevisiae* ADH7 was confirmed by colony PCR using primer sets 1334+1335 and 1338+1339, respectively. GEVO1794 was transformed with pGV1727, a yeast integration plasmid carrying *E. coli* ilvD (under the TEF1 promoter) and *E. coli* ilvC (under TDH3 promoter), that had been linearized by digesting with BcgI. The resulting strain, GEVO1818, was confirmed by colony PCR for the presence of *E. coli* ilvD and *E. coli* ilvC using primer sets 1330+1331 and 1325+1328, respectively. GEVO1818 was then transformed with pGV1726, a yeast integration plasmid carrying *B. subtilis* alsS (under the CUP1 promoter), that had been linearized by digesting with AhdI to generate GEVO1829. The presence of *B. subtilis* alsS was confirmed by colony PCR using primers 1321+1324.

Aerobic fermentations were carried out to test isobutanol production by the Pdc-minus strain carrying the isobutanol pathway, GEVO1829. The Pdc-minus strain without the isobutanol pathway, GEVO1742, was used as a control. These strains were cultured in YPD overnight at 30° C., 250 rpm, then diluted into 20 mL fresh YPD in a 125 mL flask and grown at 30° C., 250 rpm. 2 mL samples were taken at 24 and 48 hours, cells pelleted for 5 minutes at 14,000×g and the supernatant was analyzed for isobutanol by GC. In addition glucose concentrations were analyzed by LC. The results are shown in Table EX7-1. At 48 hours, the OD of the GEVO1742 strain had reached over 8.5 while the OD of the GEVO1829 was less than 5. GEVO1829 consumed around 15.7 g/L glucose while GEVO1742 consumed roughly 7.7 g/L glucose. GEVO1829 produced 0.17 g/L isobutanol while GEVO1742 did not produce any isobutanol above media background.

TABLE EX7-1

*K. lactis* fermentation results

| Clone | Isobutanol titer (mg/L) | Isobutanol yield (% theoretical) | Ethanol (mg/L) |
| --- | --- | --- | --- |
| GEVO1742 | 0 | 0 | 17 |
| GEVO1829 | 170 | 2.6 | 53 |

Example 8A: Isobutanol Production in Pdc-Minus *S. cerevisiae* GEVO1581

This example demonstrates isobutanol production in a Pdc-minus member of the *Saccharomyces sensu stricto* group, *Saccharomyces* clade yeast, Crabtree-positive yeast, post-WGD yeast, *S. cerevisiae*.

Figure 26:
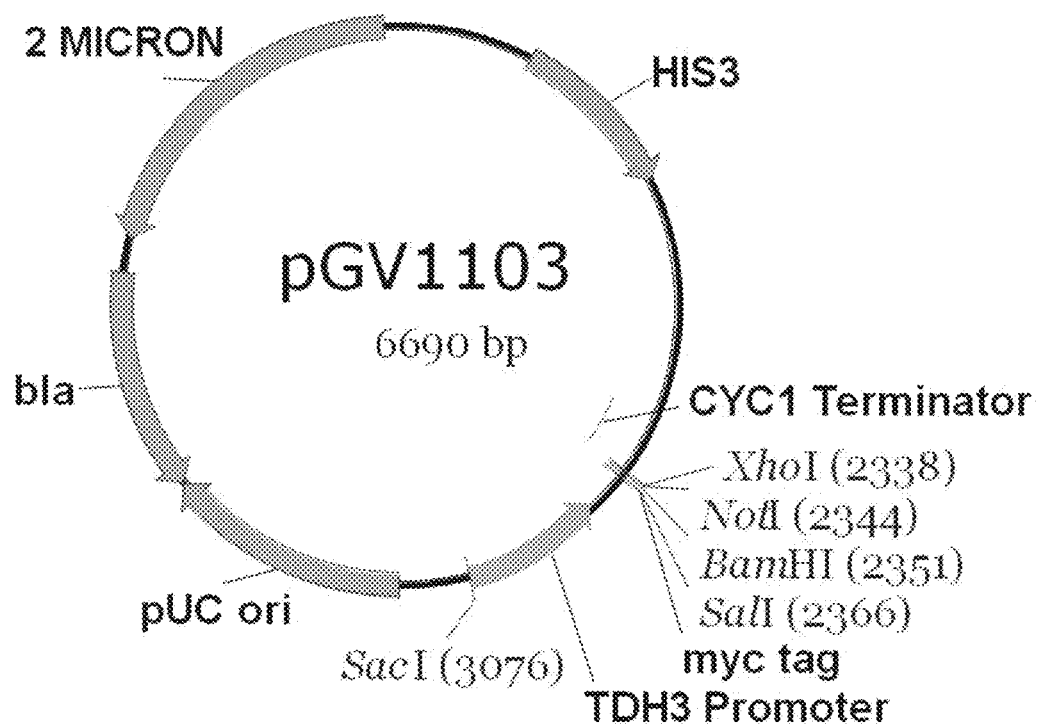
FIG. 26 illustrates a schematic map of plasmid pGV1103.
Figure 27:
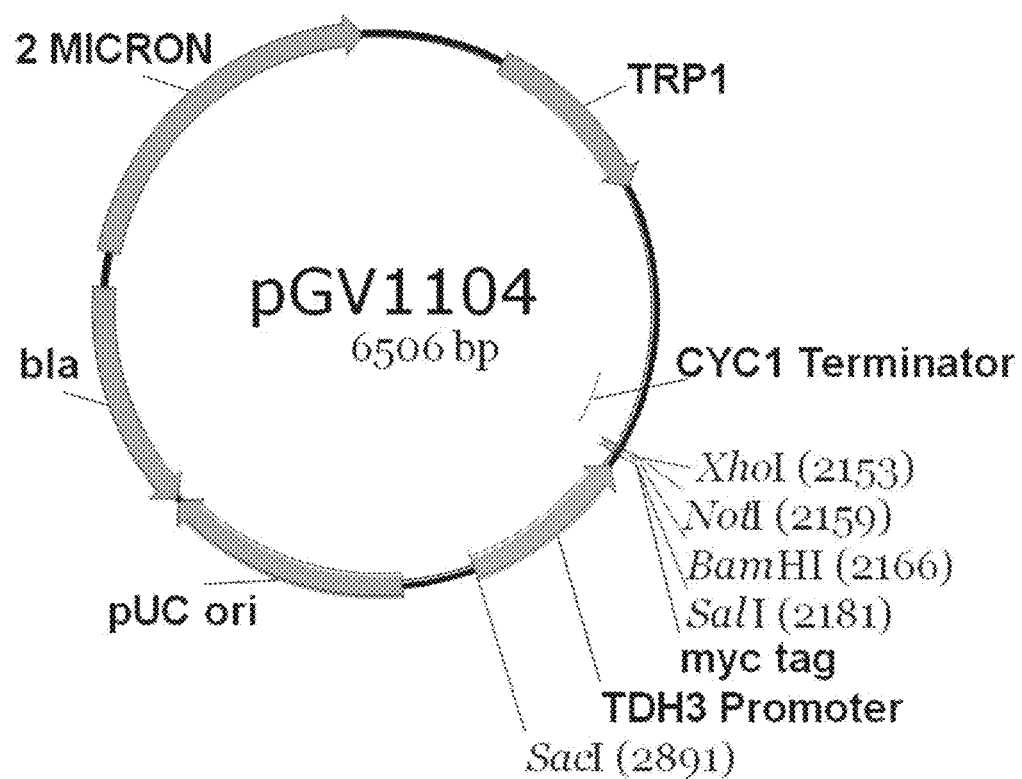
FIG. 27 illustrates a schematic map of plasmid pGV1104.
Figure 28:
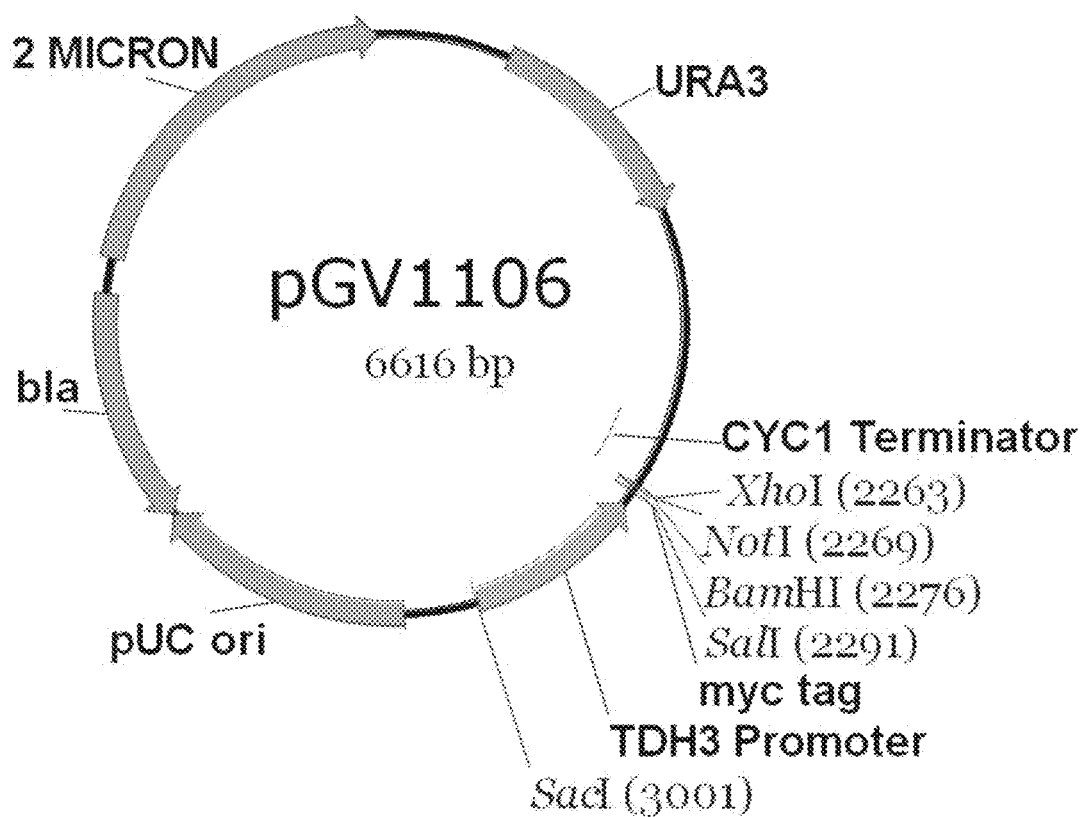
FIG. 28 illustrates a schematic map of plasmid pGV1106.
Figure 29:
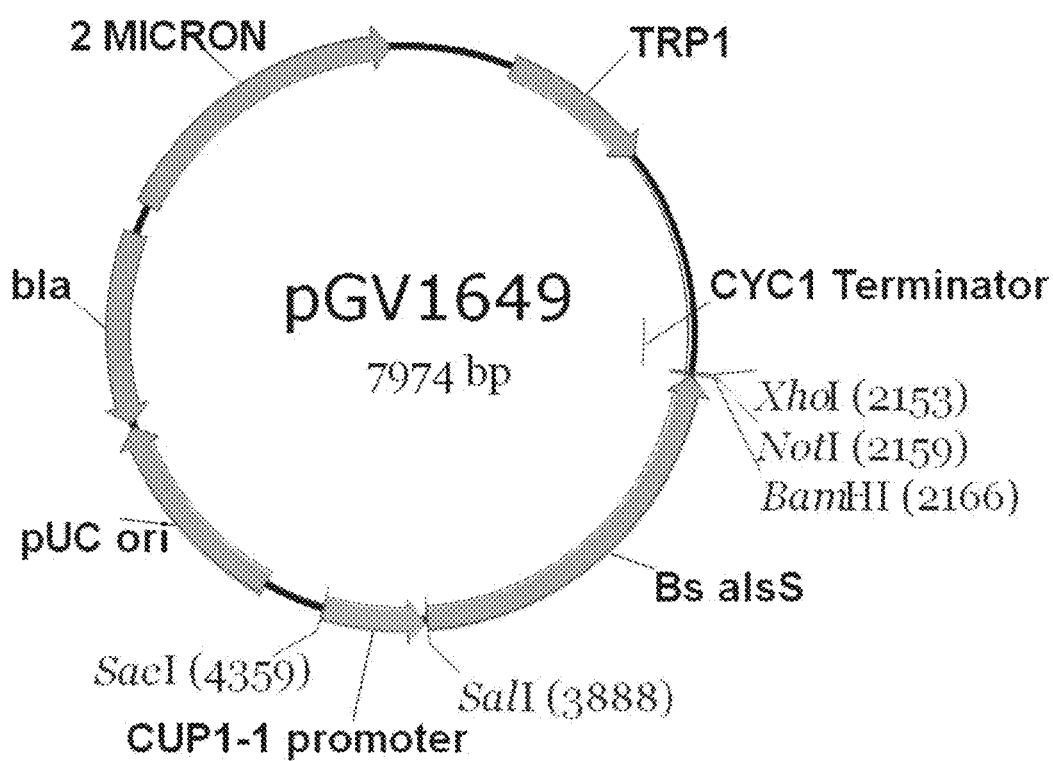
FIG. 29 illustrates a schematic map of plasmid pGV1649.
Figure 30:
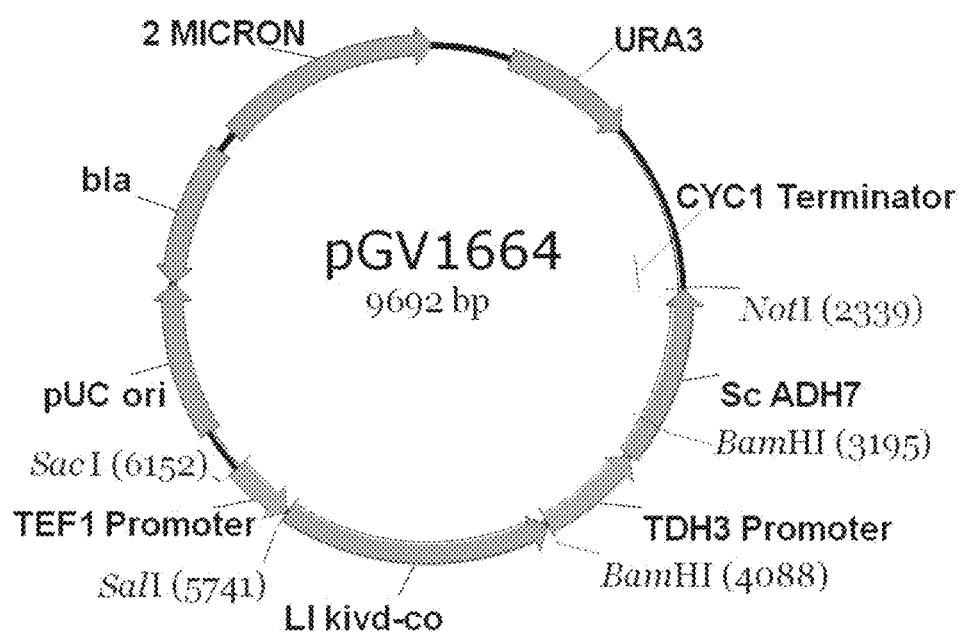
FIG. 30 illustrates a schematic map of plasmid pGV1664.
Figure 32:
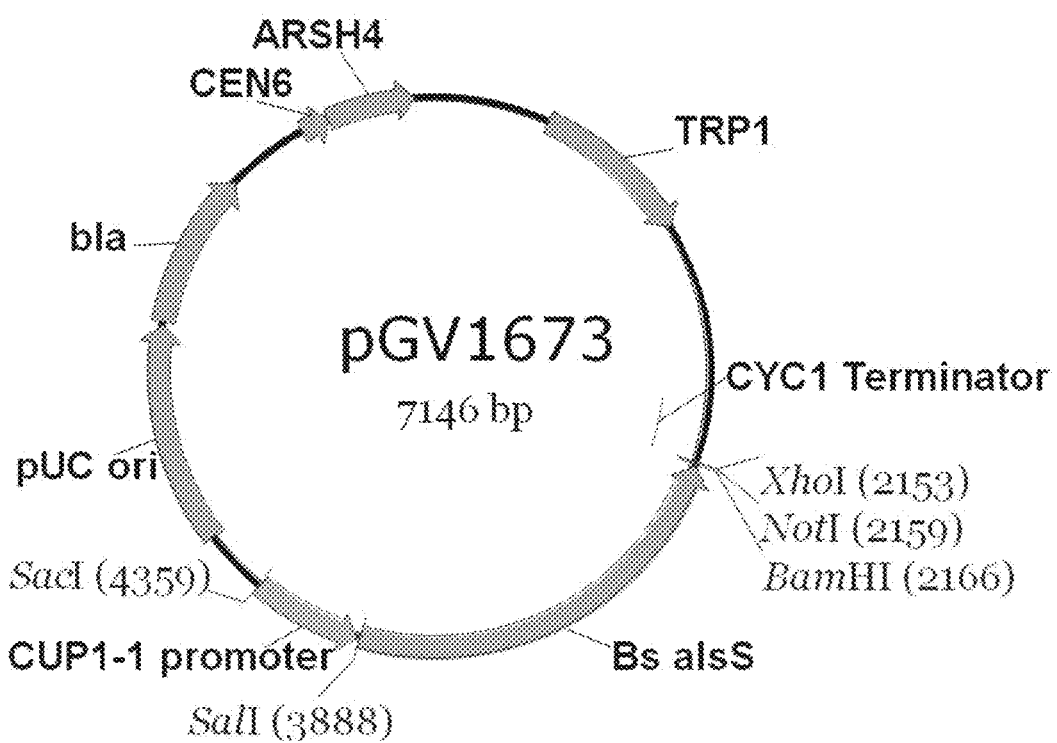
FIG. 32 illustrates a schematic map of plasmid pGV1673.
Figure 33:
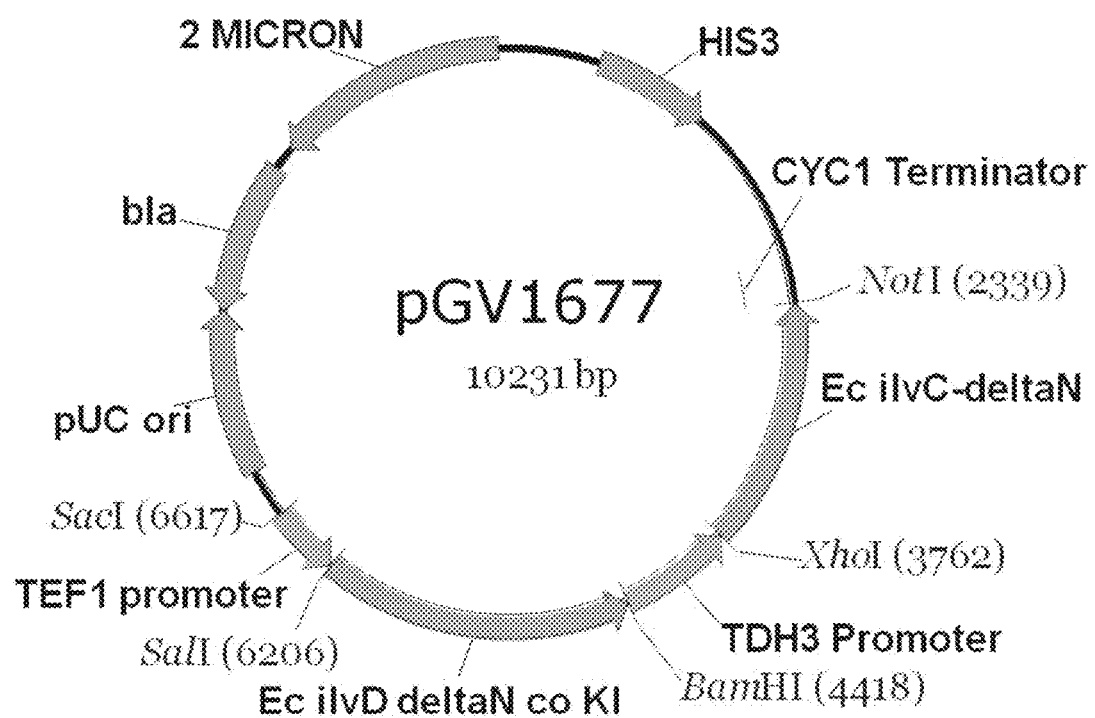
FIG. 33 illustrates a schematic map of plasmid pGV1677.

Strain GEVO1581 with the three genes encoding PDC activity deleted (pdc1Δ, pdc5Δ, and pdc6Δ) was used to produce isobutanol. Isobutanol pathway enzymes were encoded by genes cloned into three plasmids. pGV1103 (FIG. 26, SEQ ID NO: 20), pGV1104 (FIG. 27, SEQ ID NO: 21) and pGV1106 (FIG. 28, SEQ ID NO: 22) were empty high copy expression vectors that carry as marker genes, URA3, HIS3 and TRP1, respectively. The *B. subtilis* alsS gene, express using the CUP1 promoter, was encoded on either a low copy CEN plasmid, pGV1673 (FIG. 32, SEQ ID NO: 26) or a high copy plasmid, pGV1649 (FIG. 29, SEQ ID NO: 23). Both of these plasmids used TRP1 as a marker gene. *E. coli* ilvD (expressed using the TEF1 promoter) and *E. coli* ilvC (expressed using the TDH3 promoter) were expressed off of the high copy plasmid pGV1677 (FIG. 33, SEQ ID NO: 27). This plasmid utilized HIS3 as a marker gene. *L. lactis* kivD (expressed using the TEF1 promoter) and *S. cerevisiae* ADH7 (expressed using the TDH3 promoter) were expressed off of the high copy plasmid pGV1664 (FIG. 30, SEQ ID NO: 24). This plasmid utilized URA3 as a marker gene. Combination of these plasmids (Table EX8-1) to reconstitute the isobutanol pathway were introduced into GEVO1581 by lithium acetate transformation (described in General Methods).

TABLE EX8-1

Plasmids transformed into GEVO1581

| Fermentation # | Strain | Plasmids | Notes |
| --- | --- | --- | --- |
| iB250 | GEVO1581 | pGV1103, pGV1104, pGV1106 | Vector Control |
| iB251 | GEVO1581 | pGV1677, pGV1649, pGV1664 | iBuOH Pathway, alsS on 2 micron plasmid |
| iB252 | GEVO1581 | pGV1677, pGV1673, pGV1664 | iBuOH Pathway, alsS on CEN plasmid |

Fermentation experiments were carried out with GEVO1581 transformed with plasmids according to Table EX8-1 to determine the amount of isobutanol produced (titer) and the percentage of isobutanol to consumed glucose (yield).

Fermentations with Transformants of GEVO1581:

Using cells grown in 3 mL defined (SC-Ethanol) medium, 20 mL cultures were inoculated with transformants of GEVO1581 (3 independent colonies per transformation set) to an $OD_{600}$ of approximately 0.1. The cultures were incubated at 30° C. at 250 RPM in 125 mL metal cap flasks until they reached an $OD_{600}$ of approximately 1. Glucose was added to a final concentration of 5% and a 2 mL aliquot was removed from each sample (T=0 sample). The $OD_{600}$ of each sample was measured, the cells in each sample were pelleted by centrifugation (14,000×g, 5 min), and the supernatant from each sample was stored at −20° C. The remaining cultures were incubated at 30° C. at 125 RPM for another 48 hours. Samples (2 mL) were removed after 24 and 48 hours and prepared as just described. The samples were thawed, and prepared as described in General Methods. Three individual transformants were used for each set of plasmids during the fermentations. The amount of glucose consumed and the amount of pyruvate, glycerol, ethanol, and isobutanol produced after 48 hours are listed in Table EX8A-2.

TABLE EX8A-2

| | Glucose consumed (g/L) | Isobutanol (mg/L) | Yield (% theoretical) |
|---|---|---|---|
| iB250 | 3.6 ± .7 | 4.7 ± 0.00 | 0.31 ± 0.04 |
| iB251 | 2.8 ± 1.6 | 122 ± 41 | 11.0 ± 5.0 |
| iB252 | 1.2 ± .5 | 62 ± 11 | 12.8 ± 2.8 |

48 hour time point data are shown as an average of three replicates

Again using cells grown in 3 mL defined (SC-Ethanol) medium, 20 mL cultures were inoculated with transformants of GEVO1581 to an $OD_{600}$ of approximately 0.1. The cultures were incubated at 30° C. at 250 RPM in 125 mL metal cap flasks until they reached an $OD_{600}$ of approximately 1. Biomass was pelleted and resuspended in 20 ml media with 2% glucose as the sole carbon source and a 2 mL aliquot was removed from each sample (T=0 sample). The $OD_{600}$ of each sample was measured and each sample was stored at −20° C. The remaining cultures were incubated at 30° C. at 125 RPM for another 48 hours. Samples (2 mL) were removed after 24 and 48 hours and stored at −20° C. The samples were thawed, and prepared as described in General Methods. The amounts of ethanol and isobutanol produced after 48 hours are listed in Table EX8A-3.

TABLE EX8A-3

48 hour time point data for fermentation in glucose, shown as an average of three replicates

| | Isobutanol (mg/L) | Isobutanol yield (% theoretical) | Ethanol (mg/L) | Ethanol yield (% theoretical) |
|---|---|---|---|---|
| iB250 | 0 | 0 | 0 | 0 |
| iB251 | 210 | 3.5 | 110 | 1.8 |

Example 8B: Isobutanol Production in Pdc-Minus S. cerevisiae GEVO1584

This example demonstrates isobutanol production in a Pdc-minus member of the *Saccharomyces sensu stricto* group, *Saccharomyces clade*, Crabtree-positive yeast, WGD yeast, *S. cerevisiae*.

GEVO1581 is a diploid strain, thus, a second backcross of a Pdc-minus yeast into the CEN.PK background was performed, yielding a Pdc-minus haploid strain GEVO1584 with the required auxotrophic markers for plasmid propagation.

Figure 24:
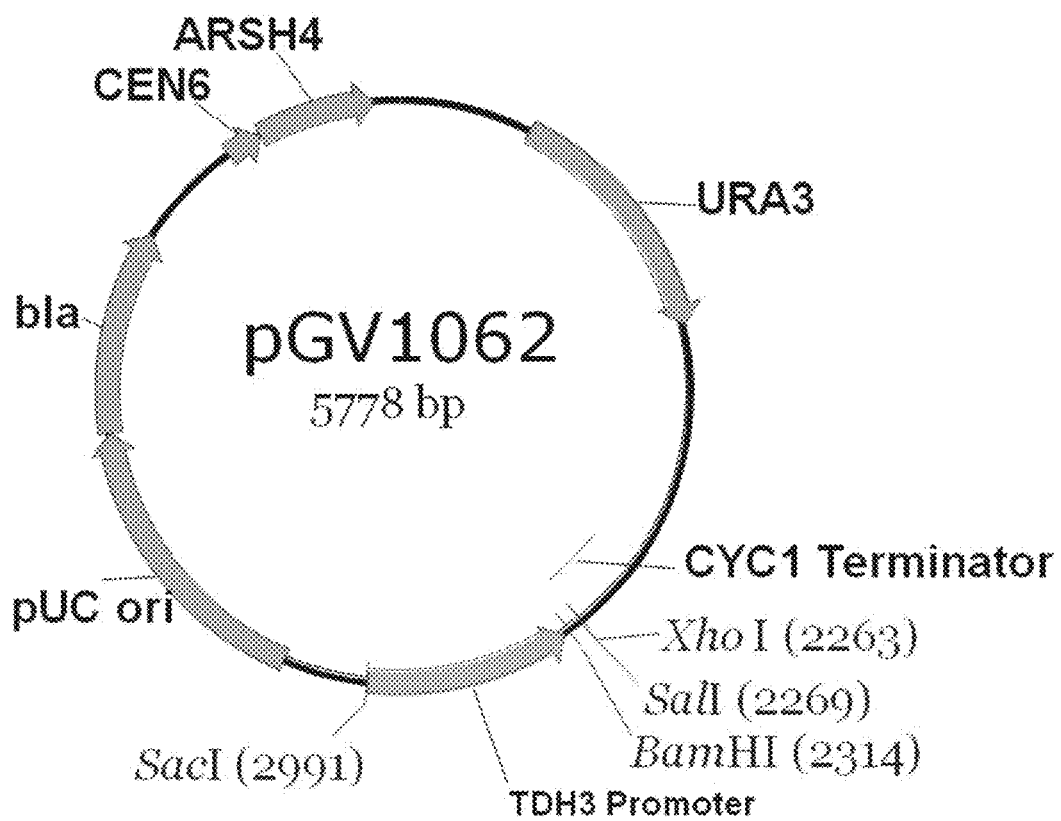
FIG. 24 illustrates a schematic map of plasmid pGV1062.
Figure 25:
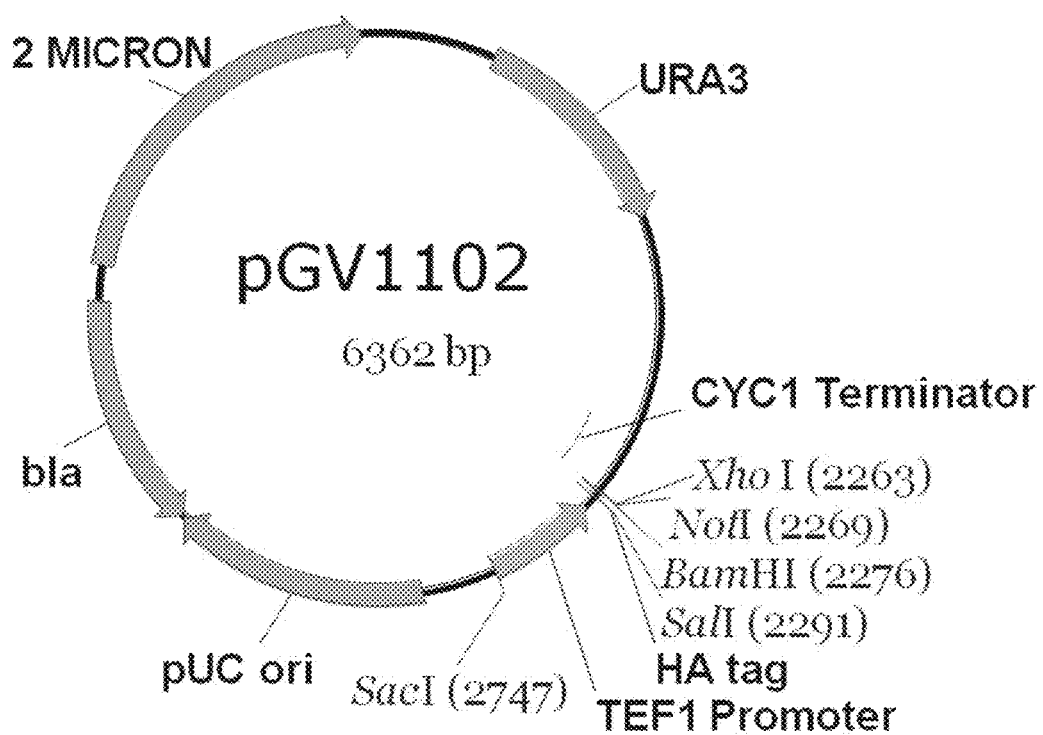
FIG. 25 illustrates a schematic map of plasmid pGV1102.
Figure 31:
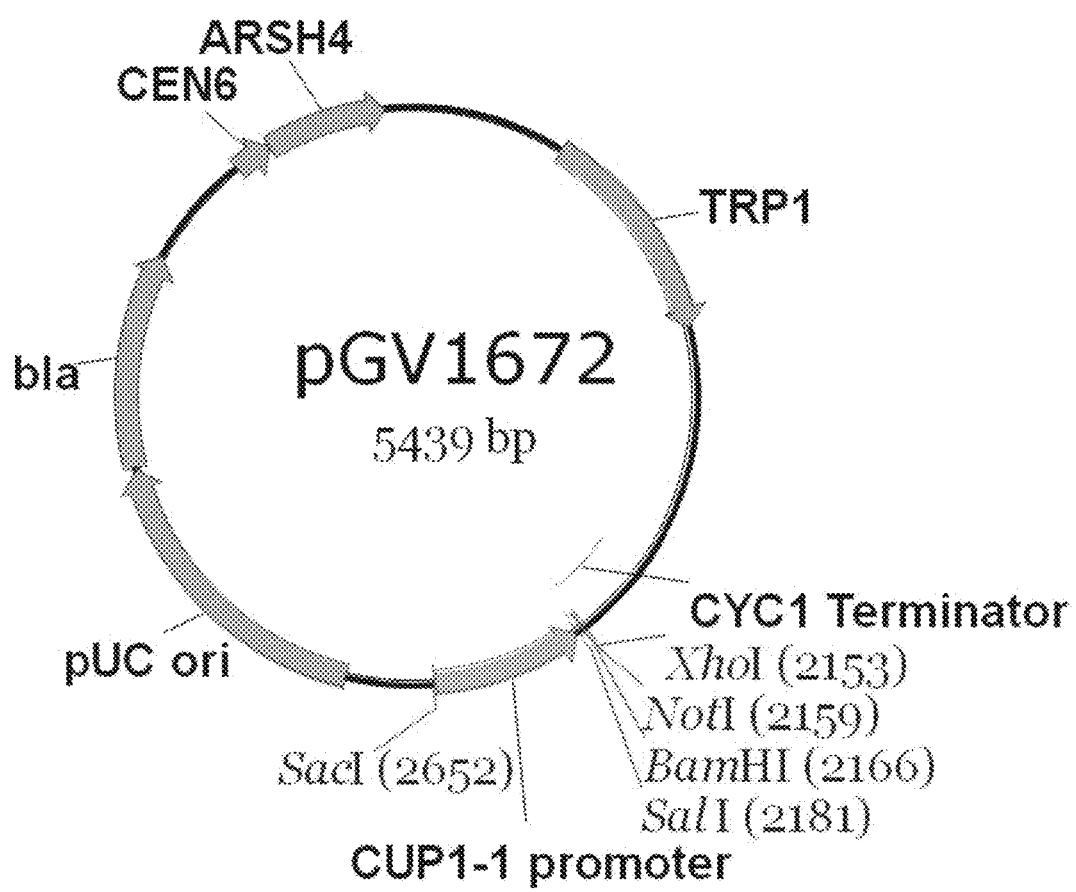
FIG. 31 illustrates a schematic map of plasmid pGV1672.
Figure 34:
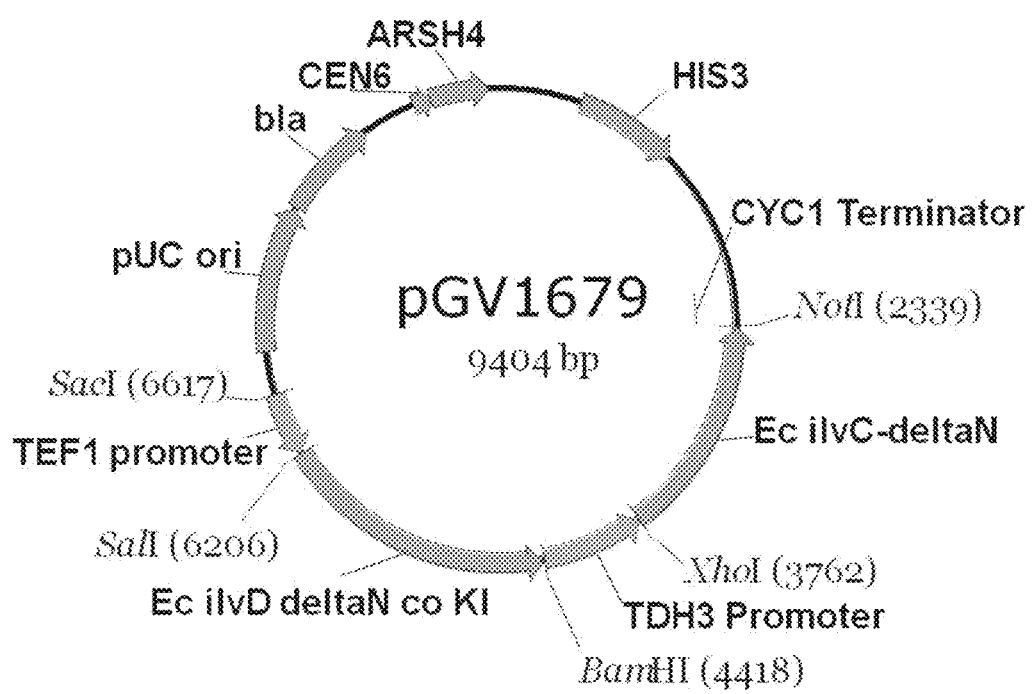
FIG. 34 illustrates a schematic map of plasmid pGV1679.
Figure 35:
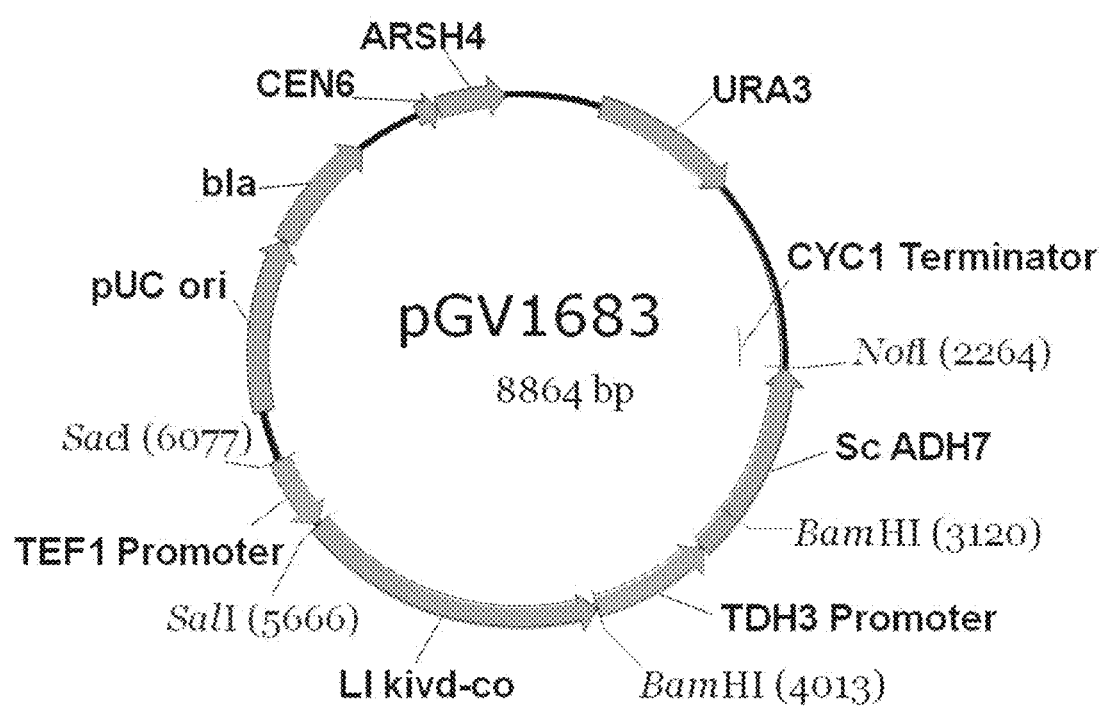
FIG. 35 illustrates a schematic map of plasmid pGV1683.

Transformations of GEVO1584:

The following combinations of plasmids were transformed into GEVO1584 (Table EX8B-1) using lithium acetate transformation (described in General Methods) followed by selection on appropriate minimal media. pGV1672 (FIG. 31, SEQ ID NO: 25), pGV1056 (FIG. 23, SEQ ID NO: 17), and pGV1062 (FIG. 24, SEQ ID NO: 18) were empty low copy CEN expression vectors that carry as marker genes, TRP1, HIS3, and URA3. pGV1103 (FIG. 26, SEQ ID NO: 20), pGV1104 (FIG. 27, SEQ ID NO: 21) and pGV1102 (FIG. 25, SEQ ID NO: 19) were empty high copy expression vectors that carry as marker genes, URA3, HIS3 and TRP1, respectively. The isobutanol pathway was expressed off of low copy CEN plasmids pGV1673 (FIG. 32, SEQ ID NO: 26), pGV1679 (FIG. 34, SEQ ID NO: 28) and pGV1683 (FIG. 35, SEQ ID NO: 29). pGV1673 carried the *B. subtilis* alsS under the CUP1 promoter and utilized the TRP1 marker gene. pGV1679 carried the *E. coli* ilvD and *E. coli* ilvC genes expressed using the TEF1 and TDH3 promoters, respectively, and utilized the HIS3 marker gene. pGV1683 carried the *L. lactis* kivd and the *S. cerevisiae* ADH7 genes expressed using the TEF1 and TDH3 promoters, respectively, and utilized the URA3 marker gene. The isobutanol pathway was also expressed off of high copy plasmids pGV1649 (FIG. 29, SEQ ID NO: 23), pGV1677 (FIG. 33, SEQ ID NO: 27) and pGV1664 (FIG. 30, SEQ ID NO: 24). pGV1649 carried the *B. subtilis* alsS under the CUP1 promoter and utilized the TRP1 marker gene. pGV1677 carried the *E. coli* ilvD and *E. coli* ilvC genes expressed using the TEF1 and TDH3 promoters, respectively, and utilized the HIS3 marker gene. pGV1664 carried the *L. lactis* kivd and the *S. cerevisiae* ADH7 genes expressed using the TEF1 and TDH3 promoters, respectively, and utilized the URA3 marker gene.

TABLE EX8B-1

| Fermentation # | Strain | Plasmids | Notes |
|---|---|---|---|
| iB300 | GEVO1584 | pGV1672, pGV1056, pGV1062 | Vector Control (CEN plasmids) |
| iB301 | GEVO1584 | pGV1673, pGV1679, pGV1683 | Isobutanol pathway (CEN plasmids) |
| iB302 | GEVO1584 | pGV1103, pGV1104, pGV1102 | Vector Control (2μ plasmids) |
| iB303 | GEVO1584 | pGV1677, pGV1649, pGV1664 | Isobutanol pathway (2μ plasmids) |

Fermentations with Transformants of GEVO1584:

Using cells grown in 3 mL defined (SC) media containing ethanol (SC+Ethanol-HWU), 200 mL cultures were inoculated with transformants of GEVO1584 and incubated in SC+Ethanol-HWU at 30° C. at 250 RPM in 500 mL shake flasks for 72 hours. The $OD_{600}$ values measured after 72 hours ranged from 1.4 to 3.5. The cultures were diluted 1:10 into fresh 250 mL SC+Ethanol-HWU media and incubated at 30° C. at 250 RPM in 500 mL shake for 24 hours. The cells were collected by centrifugation at 3000 RPM for 3 minutes and resuspended in 20 mL SC+Glucose-HWU media in 125 mL metal cap flasks. 250 μL of 100% ethanol was added to each culture to bring the concentration of ethanol to 1%. A 2 mL aliquot was removed, the $OD_{600}$ was measured using 100 μL, and the remaining aliquot was centrifuged to pellet cells (14,000×g, 5 min) and the supernatants were stored at −20° C. The cultures were incubated at 125 rpm at 30° C. A 2 mL aliquot was removed from each culture after 24 and 48 hours of incubation, and the $OD_{600}$ was measured as before (see Table 3, t=24 and t=48) and the sample centrifuged and stored as described above. The samples were thawed, and the samples were prepared and analyzed via GC and HPLC as described in General Methods. Results are shown in Table EX8B-2.

TABLE EX8B-2

48 hour time point data are shown as an average of three replicates

| Fermentation # | | Isobutanol Titer (g/L) | Glucose Consumed (g/L) | Ethanol Consumed (g/L) | Yield (% theor.)] |
|---|---|---|---|---|---|
| iB300 | Vector Control (CEN plasmids) | 0.012 ± 0.003 | 9.75 ± 4.17 | 2.47 ± 0.30 | 0.30% |
| iB301 | Isobutanol pathway (CEN plasmids) | 0.392 ± 0.087 | 9.31 ± 5.03 | 0.95 ± 0.64 | 10.27% |
| iB302 | Vector Control (2µ plasmids) | 0.013 ± 0.006 | 8.61 ± 4.51 | 0.64 + 0.17 | 0.37% |
| iB303 | Isobutanol pathway (2µ plasmids) | 0.248 ± 0.032 | 9.51 ± 1.25 | 0.77 ± 0.59 | 6.36% |

All Pdc-minus yeast (GEVO1584) consumed approximately 10 g/L of glucose and less than 2 g/L of ethanol after 48 hours. All strains accumulated ~1.5 g/L pyruvate, except for those carrying the isobutanol pathway on 2p plasmids (<0.5 g/L). The accumulation of pyruvate and failure of the yeast to produce ethanol from glucose is confirmation that all lacked PDC activity. After 48 hours, the Pdc-minus yeast with the isobutanol pathway encoded on 2p plasmids generated 0.248±0.032 g/L isobutanol at a theoretical yield of 6.36% of the consumed glucose (Table EX8B-2). The CEN plasmid isobutanol pathway strain generated 0.392±0.087 g/L isobutanol at a yield of 10.27% (Table EX8B-2). Isobutanol titers were well above the equivalent vector control strains.

Example 9: High-Yield Isobutanol Fermentation Using Crabtree-Negative PDC-Minus and GPD-Minus K. lactis In yeast, excess NADH is oxidized to NAD+ through the generation of glycerol. The key enzyme involved in this reaction is the glycerol 3-phosphate dehydrogenase. Deletion of the gene encoding this protein, Kl-Gpd1p, would eliminate loss of NADH as well as carbons from glucose. This would lead to an increased yield of isobutanol.

Figure 36:
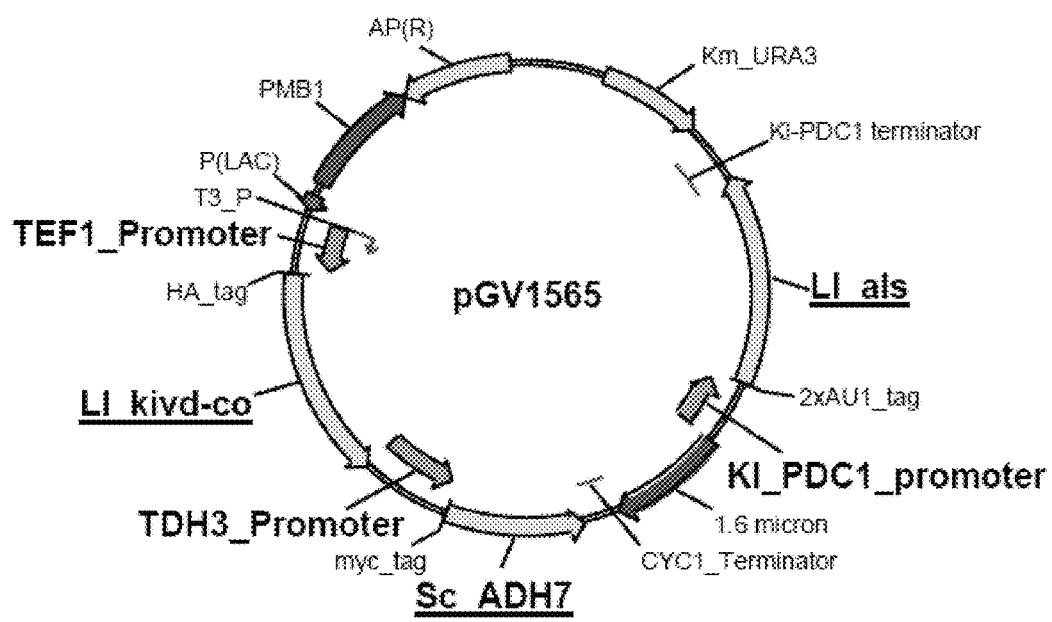
FIG. 36 illustrates a schematic map of plasmid pGV1565.
Figure 37:
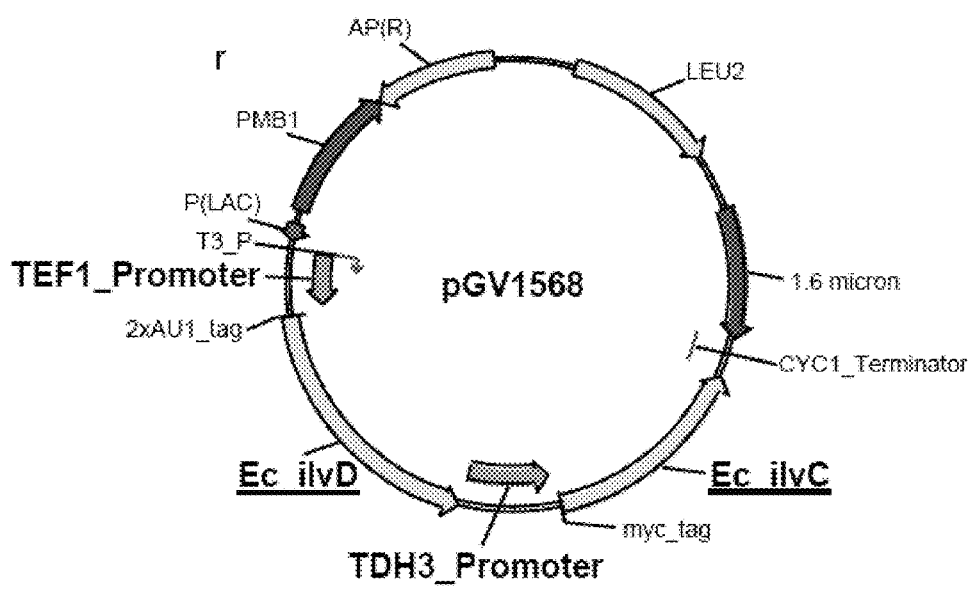
FIG. 37 illustrates a schematic map of plasmid pGV1568.
Figure 38:
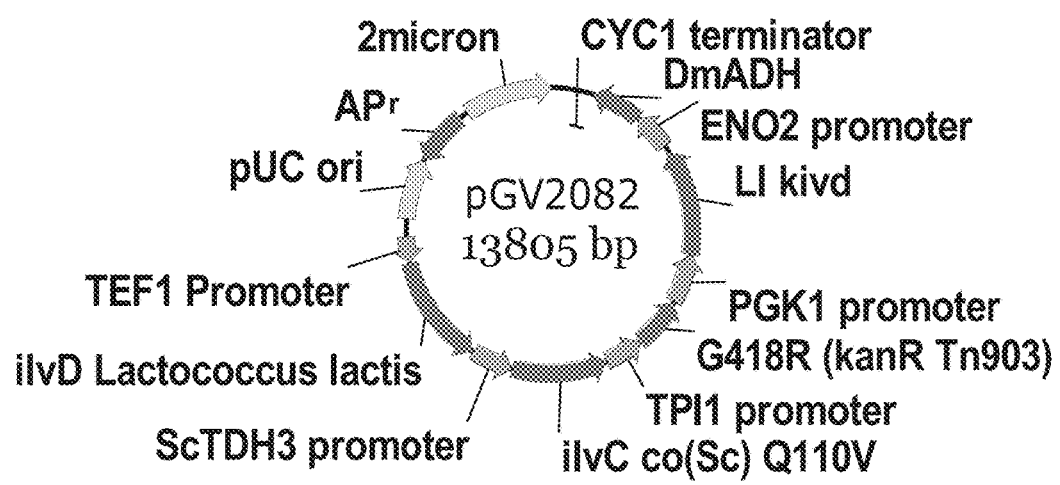
FIG. 38 illustrates a schematic map of plasmid pGV2082.
Figure 39:
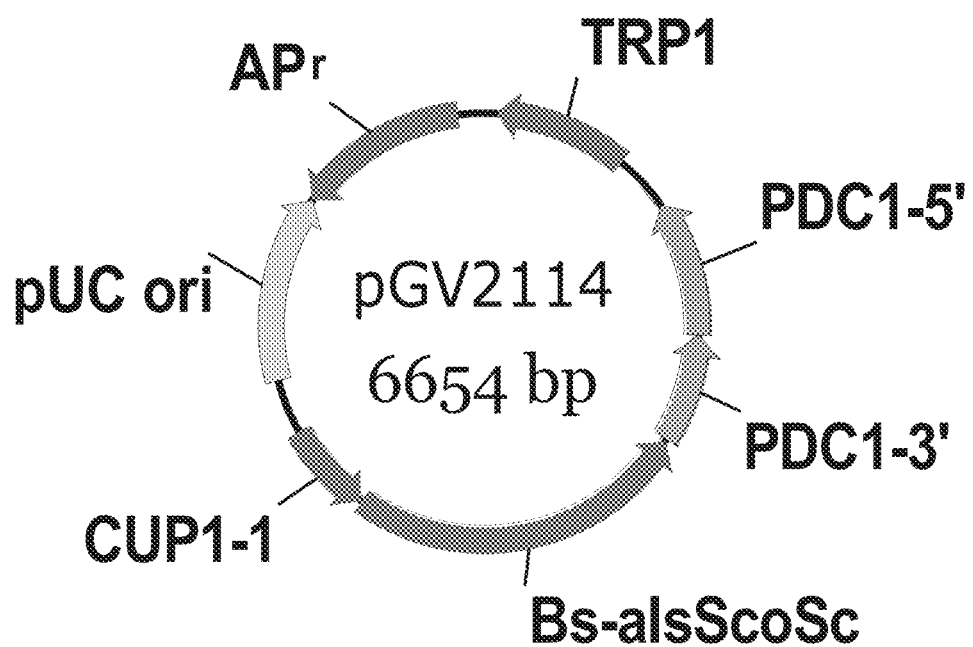
FIG. 39 illustrates a schematic map of plasmid pGV2114.
Figure 40:
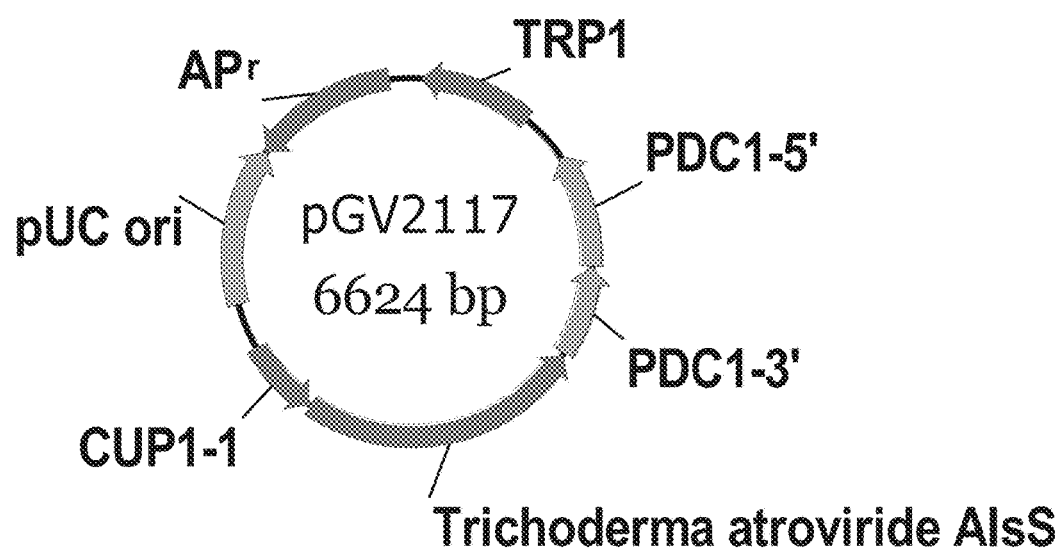
FIG. 40 illustrates a schematic map of plasmid pGV2117.
Figure 41:
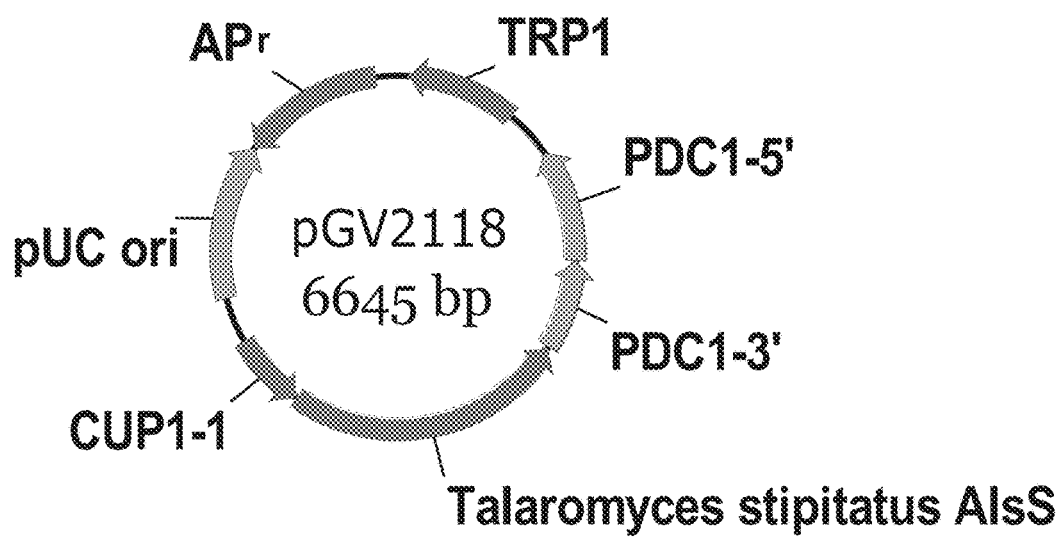
FIG. 41 illustrates a schematic map of plasmid pGV2118.

The PDC-minus K. lactis strain, GEVO1488, is engineered to delete GPD1 gene of K. lactis. This PDC-minus GPD-minus strain is transformed with pGV1565 and pGV1568 (FIG. 36 and FIG. 37). These transformants are then subjected to anaerobic batch fermentation and samples analyzed as described. As shown in Table EX9-1, the additional deletion of GPD1 is expected to result in a significant increase in isobutanol yield.

Example 10: High-Yield Isobutanol Fermentation Using Crabtree-Negative PDC-Minus and GPD-Minus K. lactis with Balanced Isobutanol Pathway Yield is further increased by the use of a pathway in which there is a balanced usage of NADH and NADPH. This balance is accomplished by the use of an engineered ilvC which is able to utilize NADH and the NADH-dependent alcohol dehydrogenase, Adh2. These constructs are used to express the isobutanol pathway in a PDC-minus and GPD-minus K. lactis. This strain is subjected to anaerobic batch fermentation as described above and samples are analyzed for isobutanol. As shown in Table EX9-1, the yield of isobutanol using this pathway in a PDC-minus K. lactis is expected to result in a significant increase in yield.

Example 11: High-Yield Isobutanol Fermentation Using Crabtree-Negative PDC-Minus and GPD-Minus K. lactis with Balanced Isobutanol Pathway An alternative route to balancing the NADH and NADPH usage is to overexpress an $NADP^+$-dependent glyceraldehyde 3-phosphate dehydrogenase (GAPDH) in addition to the endogenous $NAD^+$-dependent GAPDH, such that both NADH and NADPH are generated from glycolysis. The isobutanol pathway can utilize an NADPH-dependent KARI enzyme and the NADH-dependent Adh2p. In this case, PDC-minus and GPD-minus K. lactis is transformed with a construct expressing a NADP+-dependent GAPDH and an isobutanol pathway using Adh2. This strain is subjected to anaerobic batch fermentation as described above and samples analyzed for isobutanol. As shown in Table EX9-1, introduction of this $NADP^+$-dependent GAPDH is expected to result in a significant increase in productivity of isobutanol.

Example 12: High-Yield Isobutanol Fermentation Using Crabtree-Negative PDC-Minus and GPD-Minus K. lactis with Balanced Isobutanol Pathway Yet another alternative route to balancing the NADH and NADPH usage is to replace the endogenous $NAD^+$-dependent GAPDH with an $NADP^+$-dependent GAPDH in a PDC-minus and GPD-minus K. lactis. This strain is transformed with the isobutanol pathway and subjected to anaerobic batch fermentation as described above and samples analyzed for isobutanol. As shown in Table EX9-1, introduction of this $NADP^+$-dependent GAPDH is expected to result in a significant increase in productivity of isobutanol.

TABLE EX9-1

Isobutanol productivity in *K. lactis* strains after 48 hours.
(Listed numbers for the pdc-minus strains are expected numbers).

| | | Isobutanol | | Ethanol | |
|---|---|---|---|---|---|
| Genotype | Plasmid | Titer [g L$^{-1}$] | Yield [%] | Titer [g L$^{-1}$] | Yield [%] |
| PDC+ GPD+ | pathway genes | 0.25 | 1.5 | 12.6 | 62 |
| pdc– GPD+ | pathway genes | 8.2 | 50 | 0.01 | 0.05 |
| pdc– gpd– | pathway genes | 11.5 | 70 | 0.01 | 0.05 |
| pdc– gpd– | balanced pathway (NADH utilizing pathway) | 13.2 | 80 | 0.01 | 0.05 |
| pdc– gpd– | balanced pathway (NADH and NADPH production from glycolysis) | 13.2 | 80 | 0.01 | 0.05 |
| pdc– gpd– | balanced pathway (NADPH production from glycolysis) | 13.2 | 80 | 0.01 | 0.05 |

Example 13: High-Yield Isobutanol Fermentation Using Crabtree-Positive PDC-Minus and GPD-Minus *S. cerevisiae*

The PDC-minus *S. cerevisiae* strain is engineered to delete both GPD1 and GPD2. This PDC-minus GPD-minus strain is transformed with plasmids expressing the isobutanol pathway in *S. cerevisiae*. These transformants are then subjected to anaerobic batch fermentation and samples analyzed as described. As is seen in Table EX13-1, the additional deletions of GPD1 and GPD2 is expected to result in a significant increase in isobutanol yield.

Example 14: High-Yield Isobutanol Fermentation Using Crabtree-Positive PDC-Minus and GPD-Minus *S. cerevisiae* with Balanced Isobutanol Pathway Yield is further increased by the use of a pathway in which there is balanced usage of NADH and NADPH usage. This balance is accomplished by the use of an engineered KARI which is able to utilize NADH and the NADH-dependent alcohol dehydrogenase, Adh2p. These constructs are used to express the isobutanol pathway in a PDC-minus and GPD-minus *S. cerevisiae*. This strain is subjected to anaerobic batch fermentation as described above and samples are analyzed for isobutanol. As shown in Table EX13-1, the yield of isobutanol using this pathway in a PDC-minus *S. cerevisiae* is expected to result in a significant increase in yield.

Example 15: High-Yield Isobutanol Fermentation Using Crabtree-Positive PDC-Minus GPD-Minus *S. cerevisiae* with Balanced Isobutanol Pathway An alternative route to balancing the NADH and NADPH usage is to overexpress an NADP$^+$-dependent glyceraldehydes 3-phosphate dehydrogenase (GAPDH) in addition to the endogenous NAD$^+$-dependent GAPDH, such that both NADH and NADPH are generated from glycolysis. The isobutanol pathway can utilize an NADPH-dependent KARI enzyme and the NADH-dependent Adh2. In this case, PDC-minus and GPD-minus *S. cerevisiae* is transformed with a construct expressing a NADP$^+$-dependent GAPDH and an isobutanol pathway using Adh2. This strain is subjected to anaerobic batch fermentation as described above and samples analyzed for isobutanol. As shown in Table EX13-1, introduction of this NADP$^+$-dependent GAPDH is expected to result in a significant increase in productivity of isobutanol.

Example 16: High-Yield Isobutanol Fermentation Using Crabtree-Positive PDC-Minus *S. cerevisiae* with Balanced Isobutanol Pathway Yet another alternative route to balancing the NADH and NADPH usage is to replace the endogenous NAD$^+$-dependent GAPDH with an NADP$^+$-dependent GAPDH in a PDC-minus and GPD-minus *S. cerevisiae*. This strain is transformed with the isobutanol pathway and subjected to anaerobic batch fermentation as described above and samples analyzed for isobutanol. As shown in Table EX13-1, introduction of this NADP$^+$-dependent GAPDH is expected to result in a significant increase in productivity of isobutanol.

TABLE EX13-1

Isobutanol productivity in *S. cerevisiae* strains after 48 hours.
(Listed numbers for the pdc-minus strains are expected numbers).

| | | Isobutanol | | Ethanol | |
|---|---|---|---|---|---|
| Genotype | Plasmid | Titer [g L$^{-1}$] | Yield [%] | Titer [g L$^{-1}$] | Yield [%] |
| WT | pathway genes | 0.13 | 0.31 | 31 | 60 |
| pdc– | pathway genes | 8.2 | 50 | 0.01 | 0.05 |
| pdc– gpd– | pathway genes | 9.9 | 70 | 0.01 | 0.05 |
| pdc– gpd– | balanced pathway (NADH utilizing pathway) | 13.2 | 80 | 0.01 | 0.05 |
| pdc– gpd– | balanced pathway (NADH and NADPH production from glycolysis) | 13.2 | 80 | 0.01 | 0.05 |
| pdc– gpd– | balanced pathway (NADPH production from glycolysis) | 13.2 | 80 | 0.01 | 0.05 |

Example 17: High-Yield Isobutanol Fermentation Using Crabtree-Negative PDC-Minus GPD-Minus Evolved *K. lactis* with Balanced Isobutanol Pathway In an embodiment, the yield for isobutanol may be increased by further engineering yeast microorganism to reduce production of minor byproducts. Isobutanol may be produced at a yield of about 90% theoretical.

Example 18: High-Yield Isobutanol Fermentation Using Crabtree-Positive PDC-Minus GPD-Minus Evolved *S. cerevisiae* with Balanced Isobutanol Pathway In another embodiment, the yield for isobutanol may be increased by further engineering a yeast microorganism to reduce production of minor byproducts. Isobutanol may be produced at a yield of about 90% theoretical.

General Methods for Examples 19-24

Sample Preparation:

Samples were prepared from various timepoints for analysis by liquid chromatography and gas chromatography. 2 mL of media was removed and centrifuged at 14,000×g for 10 min. The supernatant was removed and stored at 4° C. until analysis.

Determination of Optical Density:

The optical density of the yeast cultures was determined at 600 nm using a DU 800 spectrophotometer (Beckman-Coulter, Fullerton, Calif., USA). Samples were diluted as necessary to yield an optical density of between 0.1 and 0.8.

Gas Chromatography:

Analysis of ethanol and isobutanol was performed on a HP 5890 gas chromatograph fitted with a ZB-FFAP column (Phenomenex; 30 m length, 0.32 mm ID, 0.25 µM film thickness) or equivalent connected to a flame ionization detector (FID). The temperature program was as follows: 200° C. for the injector with Agilent cyclo-splitter insert, 300° C. for the detector, 100° C. oven for 1 minute, 70° C./minute gradient to 235° C., and then hold until a final run time of 5.54 min. Injection volume was 0.5 µl, with a split ratio of 50:1; Helium flow rate was approximately 2.3 ml/min using a constant pressure of 0.88 bar.

High Performance Liquid Chromatography:

Analysis of glucose and organic acids was performed on a HP-1100 High Performance Liquid Chromatography system equipped with two Rezex RFQ-"Fast Fruit" columns in series (Phenomenex, 100×7.8 mm, 8 µm particles), or equivalent, and an H cation guard column (Bio-Rad) or equivalent. Pyruvate and HMF were detected using an HP-1100 UV detector (210 nm, 8 nm 360 nm reference) while all other organic acids and glucose were detected using an HP-1100 refractive index detector. The column and RI temperatures were 60° C. This method was Isocratic with 0.018N sulfuric acid in water as mobile phase. Flow was set at 1.1 mL/min. Injection size was 20 µL and the run time was 15 minutes Lithium Acetate transformations of S. cerevisiae strains were transformed by the Lithium Acetate method (Gietz et al., Nucleic Acids Res. 27:69-74 (1992). Cells were collected from overnight cultures grown in 50 mL of defined (SC) ethanol media at an $OD_{600}$ of approximately 0.8 to 1.0 by centrifugation at 2700 rcf for 2 minutes at room temperature. The cell pellet was resuspended in 50 mL sterile water, collected by centrifugation (2700 rcf; 2 min; room temp.), and resuspended in 25 mL sterile water. The cells were collected by centrifugation (2700 rcf; 2 min; room temp.) and resuspended in 1 mL 100 mM lithium acetate. The cell suspension was transferred to a sterile 1.5 mL tube and collected by centrifugation at full speed for 10 seconds. The cells were resuspended in 100 mM lithium acetate with a volume four times the volume of the cell pellet (e.g. 400 µL for 100 µL cell pellet). To the prepared DNA Mix (72 µl 50% PEG, 10 µl 1M Lithium Acetate, 3 µl boiled salmon sperm DNA, and 5 µl of each plasmid), 15 µl of the cell suspension was added and mixed by vortexing with five short pulses. The cell/DNA suspensions were incubated at 30° C. for 30 minutes and at 42° C. for 22 minutes. The cells were collected by centrifugation for 10 seconds at full speed and resuspended in 100 µl SOS (1M Sorbitol, 0.34% (w/v) Yeast Extract, 0.68% (w/v) Peptone, 6.5 mM CaCl). The cell suspensions were top spread over appropriate selective agar plates.

Yeast Colony PCR:

Yeast cells were taken from agar medium and transferred to 30 µl 0.2% SDS and heated for 4 mins at 90° C. The cells were spun down and 1 µl of the supernatant was used for PCR using standard Taq (NEB).

Molecular Biology:

Standard molecular biology methods for cloning and plasmid construction were generally used, unless otherwise noted (Sambrook & Russell).

Media:

YP: contains 1% (w/v) yeast extract, 2% (w/v) peptone.

YPD is YP containing 2% (w/v) glucose, YPE is YP containing 2% (w/v) Ethanol.

YPD80 medium (Difco) is YP containing 80 g/L glucose, 0.2 g/L G418 antibiotic, 20 pM $CuSO_4$, and 1% ethanol.

SC+Complete: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.076 g/L tryptophan, 0.380 g/L leucine, and 0.076 g/L uracil.

Solid versions of the above described media contain 2% (w/v) agar.

Strains, Plasmids and Primer Sequences for Examples 19-24

TABLE EX 19-1

Genotype of strains for Examples 19-24.

| GEVO No. | Genotype and/or Reference |
|---|---|
| GEVO2712 | S. cerevisiae CEN.PK2; MATa ura3 leu2 his3 trp1 pdc1::{$P_{CUP1}$-Bs_alsS2, TRP1} pdc5::{$P_{TEF1}$:Sc_ILV3ΔN $P_{TDH3}$:Ec_ilvC_coSc$^{Q110V}$, LEU2} pdc6::{$P_{TEF1}$: Ll_kivd2_coEc $P_{TDH3}$:Dm_ADH, URA3}, evolved for C2 supplement-independence, glucose tolerance and faster growth |
| GEVO2843 | S. cerevisiae, MATa ura3 leu2 his3 trp1 pdc1Δ::$P_{CUP1}$:[Bs_alsS1_coSc:$T_{CYC1}$: $P_{PGK1}$: Ll_kivD2: $P_{ENO2}$: Sp_HIS5] pdc5Δ::[LEU2-bla-$P_{TEF1}$: ILV3ΔN: $P_{TDH3}$: Ec_ilvC_coSc$^{Q110V}$] pdc6Δ::[URA3: bla; $P_{TEF1}$: Ll_kivD2: $P_{TDH3}$: Dm_ADH] {evolved for C2 supplement-independence, glucose tolerance and faster growth} |
| GEVO2962 | S. cerevisiae CEN.PK2; MATa ura3 leu2 his3 trp1 pdc1::PCUP1-Bs_alsS_coSc-TCYC1-PPGK1-Ll_kivd-PENO2-Sp_HIS5 pdc5::LEU2-bla-PTEF1-ILV3ΔN-PTDH3-ilvC_coSc_Q110V pdc6::URA3-bla-PTEF1-Ll_kivd-PTDH3-DmADH {evolved for C2 supplement-independence, glucose tolerance and faster growth} pGV2227 |
| GEVO2994 | S. cerevisiae CEN.PK2; MATa ura3 leu2 his3 trp1 pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |

TABLE EX 19-1-continued

Genotype of strains for Examples 19-24.

| GEVO No. | Genotype and/or Reference |
|---|---|
| GEVO3059 | S. cerevisiae CEN.PK2; MATa ura3 leu2 his3 trp1 gpd1::$T_{Kl\_URA3\_short}$-$P_{FBA1}$-Kl_URA3-$T_{Kl\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3061 | S. cerevisiae CEN.PK2; MATa ura3 leu2 his3 trp1 gpd2::$T_{Kl\_URA3\_short}$-$P_{FBA1}$-Kl_URA3-$T_{Kl\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_ Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3124 | S. cerevisiae CEN.PK2; MATa ura3 leu2 his3 trp1 gpd1::$T_{Kl\_URA3\_short}$-$P_{FBA1}$-Kl_URA3-$T_{Kl\_URA3}$ gpd2::$P_{CCW12}$-Hph pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3128 | S. cerevisiae CEN.PK2; MATa ura3 leu2 his3 trp1 gpd1::$P_{CCW12}$-Hph gpd2::$T_{Kl\_URA3\_short}$-$P_{FBA1}$-Kl_URA3-$T_{Kl\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3158 | S. cerevisiae CEN.PK2; MATa ura3 leu2 his3 trp1 gpd1::$T_{Kl\_URA3\_short}$-$P_{FBA1}$-Kl_URA3-$T_{Kl\_URA3}$ gpd2::$P_{CCW12}$-Hph pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2227] {evolved for C2 supplement-independence, glucose tolerance and faster growth} |
| GEVO3159 | S. cerevisiae CEN.PK2; MATa ura3 leu2 his3 trp1 gpd1::$T_{Kl\_URA3\_short}$-$P_{FBA1}$-Kl_URA3-$T_{Kl\_URA3}$ gpd2::$P_{CCW12}$-Hph pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2082] {evolved for C2 supplement-independence, glucose tolerance and faster growth} |
| GEVO3160 | S. cerevisiae CEN.PK2; MATa ura3 leu2 his3 trp1 gpd1::$P_{CCW12}$-Hph gpd2::$T_{Kl\_URA3\_short}$-$P_{FBA1}$-Kl_URA3-$T_{Kl\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2247] {evolved for C2 supplement-independence, glucose tolerance and faster growth} |
| GEVO3532 | S. cerevisiae CEN.PK2; MATa ura3 leu2 his3 trp1 gpd1::$T_{Kl\_URA3}$ gpd2::$T_{Kl\_URA3}$ pdc1::$P_{CUP1}$-Bs_alsS1_coSc-$T_{CYC1}$-$P_{PGK1}$-Ll_kivd2_coEc-$P_{ENO2}$-Sp_HIS5 pdc5::$T_{Kl\_URA3\_short}$-$P_{FBA1}$-Kl_URA3-$T_{Kl\_URA3}$ pdc6::$P_{TEF1}$-Ll_ilvD_$P_{TDH3}$-Ec_ilvC_coSc$^{P2D1-A1}$-$P_{ENO2}$-Ll_adhA-$P_{FBA1}$-Sc_TRP1 {evolved for C2 supplement-independence, glucose tolerance and faster growth} (first described here) |

TABLE EX 19-2

Plasmids disclosed for Examples 19-24.

| GEVO No. | Genotype or Reference |
|---|---|
| pGV2082 | $P_{TEF1}$-Ll_ilvD_coSc-$P_{TDH3}$-Ec_ilvC_coSc_ Q110V-$P_{TPI1}$-G418R-$P_{PGK1}$-Ll_kivD2_coEc-$P_{ENO2}$-Dm_ADH, 2μ ori, bla, pUC-ori. |
| pGV2227 | $P_{TEF1}$-Ll_ilvD_coSc-$P_{TDH3}$-Ec_ilvC_coSc$^{Q110V}$-$P_{TPI1}$-G418R-$P_{PGK1}$-Ll_kivd2_coEc-PDC1-3'region-$P_{ENO2}$-Ll_adhA 2μ bla, pUC-ori |
| pGV2247 | $P_{TEF1}$-Ll_ilvD_coSc-$P_{TDH3}$-Ec_ilvC_coSc_P2D1-A1-$P_{TPI1}$-G418R-$P_{PGK1}$-Ll_kivD2_coEc-$P_{ENO2}$-Ll_adhA, 2μ ori, bla, pUC-ori. |
| pGV2563 | $P_{TEF1}$-Ll_ilvD_coSc, $P_{TDH3}$-Ec_ilvC_coSc$^{P2D1-A1-his8}$, $P_{ENO2}$-Ll_adhA_coSc$^{RE1-his8}$, 2μ-ori, pUC ori, bla, G418r |

Example 19: Isobutanol Production in Pdc-Yeast

This example demonstrates isobutanol production at greater than 30% yield in a Pdc-minus member of the Saccharomyces sensu stricto group, Saccharomyces clade yeast, Crabtree-positive yeast, post-WGD yeast S. cerevisiae.

GEVO2962 is a modified yeast biocatalyst that contains genes within the chromosome of the biocatalyst which encode a pathway of enzymes that convert pyruvate into isobutanol. GEVO2962 is GEVO2843 transformed with pGV2227 (SEQ ID NO: 57), which is a high copy yeast expression plasmid used to overexpress Ec_ilvC_Q110V (Escherichia coli ilvC containing a Q to V mutation at position 110), Ll_ilvD (Lactococcus lactis ilvD), Ll_kivD2 (Lactococcus lactis kivD), and LlU_AdhA (Lactococcus lactis adhA). The strain GEVO2843 is PDC-deficient and able to grow in high glucose media without addition of C2-compounds. GEVO2843 has integrated into the PDC1 locus the Bs_alsS1_coSc (Bacillus subtilis alsS; SEQ ID NO: 58) and LI_kivD2_coEc (*Lactococcus lactis* kivD, SEQ ID NO: 59) genes under the CUP1 and PGK1 promoters, respectively. This strain also has the LI_kivD2_coEc (*Lactococcus lactis* kivD, SEQ ID NO: 59) and Dm_ADH (*Drosophila melanogaster* ADH, SEQ ID NO: 60) under the TEF1 and TDH3 promoters, respectively, integrated into the PDC6 locus. Lastly, this strain has the Ec_ilvC_coSc_Q110V (SEQ ID NO: 61) and Sc_ILV3ΔN20 (SEQ ID NO: 62) under the TDH3 and TEF1 promoters, respectively, integrated at the PDC5 locus.

When the biocatalyst GEVO2962 was contacted with glucose in a medium suitable for growth of the biocatalyst, at about 30° C., the biocatalyst produced isobutanol from the glucose. A 24-hour starter culture was started in a 50 mL conical tube with GEVO2962 cells from a frozen glycerol stock. The tube contained a 5 mL volume of YPD80 medium (Difco) at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 1 L of YPD80 medium in a 2.8 L baffled Fembach flask. The seed flask culture was grown for approximately 24 hrs in a 30° C. shaker at 250 rpm.

A portion of the flask seed culture was transferred to a 2 L DasGip seed fermenter containing about 750 mL of YPD80 medium to achieve a 1 $OD_{600}$ initial cell concentration. The fermenter vessel was attached to a computer control system to monitor and control pH at 5.0 through addition of base, temperature at 30° C., oxygen transfer rate (OTR), and agitation. The vessel was agitated, with a fixed agitation of 1000 rpm and 2 sL/h air flow overlay. Cells were grown until the $OD_{600}$ was about 10. Some of the seed fermenter culture was then transferred to a 2 L DasGip fermenter vessel containing about 1100 mL of YPD80. The vessel was attached to a computer control system to monitor and control pH at 6.0 through addition of base, temperature at about 30° C., dissolved oxygen, and agitation. Initially, during the cell growth phase, the vessel was agitated with a variable agitation of 400-600 rpm using a 10 sL/h air sparge until the $OD_{600}$ was about 8. Cell growth continued for approximately 16 hrs, after which time, the agitation was fixed at 600 rpm with 5 sL/h airflow. The dissolved oxygen was approximately zero throughout this experiment with an OTR of about 4-8 mM/h. Continuous measurement of the fermentor vessel off-gas by mass spectrometer analysis was performed for oxygen, isobutanol, ethanol, and carbon dioxide throughout the experiment. Samples were aseptically removed from the fermenter vessel throughout the experiment and used to measure $OD_{600}$, glucose concentration, and isobutanol concentration in the broth.

At about 48 h intervals throughout the 470 h experiment, the fermenter whole broth was removed from the fermenter, cells were separated from the broth using centrifugation at about 20° C. and 4000×g in 500 mL centrifuge bottles. The cell pellets were resuspended in fresh YPD medium that contained 80 g/L glucose, 0.2 g/L G418 antibiotic, 20 μM $CuSO_4$, and 1% ethanol and returned to the fermenter. At six points throughout the fermentation, about 1 L of a flask culture of GEVO2962 at about 7 $OD_{600}$ was concentrated to 50-100 mL by centrifugation and then added to the fermenter vessel aseptically.

The fermenter vessel was attached by tubing to a smaller 400 mL fermenter vessel that served as a flash tank and operated in a recirculation loop with the fermenter. Whole fermentation broth was recirculated between the flash tank and fermenter at a rate of about 10-30 mL per min. The volume in the flash tank was approximately 100 mL and the hydraulic retention time in the flash tank was about 3-10 minutes. Heat and vacuum were applied to the flash tank. The vacuum level applied to the flash tank was initially set at about 60 mBar and the flash tank was set at approximately 36° C. Generally, the vacuum ranged from 50-65 mBar and the flash tank temperature ranged from 35° C. to 37° C. throughout the experiment. Vapor from the heated flash tank was condensed into a collection vessel as distillate. Whole fermentation broth was continuously returned from the flash tank back to the fermentation vessel. When the concentration of isobutanol in the broth dropped below 1.5 g/L, the flash recycle system was turned off. The flash recycle was turned back on when the broth concentration of isobutanol reached above 2.5 g/L.

The distillate recovered in the experiment was strongly enriched for isobutanol. Isobutanol formed an azeotrope with water and lead to a two phase distillate: an isobutanol rich top phase and an isobutanol lean bottom phase. Distillate samples were analyzed by GC for isobutanol concentration.

Isobutanol production reached a maximum at around 470 hrs with a total effective titer of about 111 g/L. The isobutanol production rate was about 0.24 g/L/h on average over the course of the experiment. The percent theoretical yield of isobutanol was approximately 36% at the end of the experiment.

Example 20: Isobutanol Production in Pdc-Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*.

The modified yeast biocatalyst, GEVO3158, encodes a heterologous pathway of enzymes that convert pyruvate into isobutanol. Genes for the pathway are located on the chromosome and on a single plasmid. GEVO3158 is GEVO3124 transformed with pGV2247 (SEQ ID NO: 63), which is a high copy yeast expression plasmid used to overexpress Ec_ilvC_Q110V (*Escherichia coli* ilvC containing a Q to V mutation at position 110), LI_ilvD (*Lactococcus lactis* ilvD), LI_kivD (*Lactococcus lactis* kivD), and LI_adhA (*Lactococcus lactis* adhA). The strain GEVO3124 is both GPD-deficient, PDC-deficient and able to grow in high glucose media without addition of C2-compounds. GEVO3124 has integrated into the PDC1 locus the Bs_alsS1_coSc (*Bacillus subtilis* alsS; SEQ ID NO: 58) and LI_kivD2_coEc (*Lactococcus lactis* kivD, SEQ ID NO: 59) genes under the CUP1 and PGK1 promoters, respectively. This strain also has the Ec_ilvC_coSc_P2D1-A (*Escherichia coli* ilvC variant; SEQ ID NO: 64), LI_ilvD_coSc, and LI_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3124 was generated by deletion of GPD2 using Hph as marker in strain GEVO3059. Deletion of GPD2 was carried out by transforming a hygromycin resistance marker, Hph, flanked by the GPD2 5' and 3' targeting sequences. This gpd2::Hph disruption cassette was generated by multiple rounds of SOE PCR. First, the GPD2 5' targeting sequence was amplified from pGV2164 (SEQ ID NO: 69), the CCW12 promoter was amplified from pGV1954 (SEQ ID NO: 70), the Hph ORF was amplified from pGV2074 (SEQ ID NO: 71), and the GPD2 3' targeting sequence was also amplified. Second, the GPD2 5' targeting sequence and the CCW12 promoter were stitched together by SOE-PCR, and the Hph ORF and GPD2 3' targeting sequence were stitched together by SOE-PCR. Lastly, these two SOE-PCR products were stitched together in another round of SOE-PCR. The resulting product was then transformed into GEVO3059 recovered overnight in YPD+1% EtOH+G418 or YPD+1% EtOH+G418+1 g/L glycerol, and selected on YPD+G418+Hygro+1 g/L glycerol or YPD+G418+Hygro+ 10 g/L glycerol plates. Twelve colonies were re-streaked for singles and colony PCRs were performed in single colony isolates to test for correct 5' and 3' junctions and the loss of GPD2.

GEVO3059 was generated by deletion of GPD1 using K_URA3 as marker in strain GEVO2994. Deletion of GPD1 was carried out by a bipartite integration scheme using the KI_URA3 marker. The 5' bipartite fragment contained the GPD1_5' targeting sequence-$T_{KI\_URA3\_short}$-$P_{FBA1}$-KI_URA3_3' truncated and was generated by PCR with pGV2359 (SEQ ID NO: 72) as template. The 3' bipartite fragment contained KI_URA3_5' truncated-$T_{KI\_URA3}$-GPD1_3' targeting sequence and was generated by PCR with pGV2157 (SEQ ID NO: 73) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), LI_ilvD_coSc, (*Lactococcus lactis* ilvD, SEQ ID NO: 65) and LI_adhA (*Lactococcus lactis* adhA, SEQ ID NO: 66) under the TDH3, TEF1 and ENO2 promoters, respectively, into the PDC6 locus of GEVO2843. This integration replaced the LI_kivD2_coEc (*Lactococcus lactis* kivD, SEQ ID NO: 59) and the Dm_ADH (*Drosophila melanogaster* ADH, SEQ ID NO: 60) that were present at the PDC6 locus in GEVO2843. GEVO2843 was generated by integrating the Bs_alsS1_coSc (*Bacillus subtilis* alsS; SEQ ID NO: 58) and LI_kivD2_coEc (*Lactococcus lactis* kivD, SEQ ID NO: 59) into the PDC1 locus of GEVO2712.

When the biocatalyst GEVO3158 was contacted with glucose in a medium suitable for growth of the biocatalyst, at about 30° C., the biocatalyst produced isobutanol from the glucose. A 24-hour starter culture was started in a 50 mL conical tube with GEVO3158 cells from a frozen glycerol stock. The tube contained a 5 mL volume of YPD80 at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.7 mM/h by reducing agitation to a fixed 250-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 7 days with a titer of about 10 g/L. Yield of the fermentation, calculated when the titer of isobutanol was between 3.7 g/L and 10 g/L, was approximately 74% maximum theoretical. Yield of the fermentation, calculated when the titer of isobutanol was between 0 g/L and 10 g/L, was approximately 52% maximum theoretical. Yield of the fermentation, calculated when the titer of isobutanol was between 0.5 g/L and 10 g/L, was approximately 61% maximum theoretical.

Example 21: Isobutanol Production in Pdc-Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*.

The modified yeast biocatalyst, GEVO3159, encodes a heterologous pathway of enzymes that convert pyruvate into isobutanol. Genes for the pathway are located on the chromosome and on a single plasmid. GEVO3159 is GEVO3124 transformed with pGV2082 (SEQ ID NO: 67), which is a high copy yeast expression plasmid used to overexpress Ec_ilvC_Q110V (*Escherichia coli* ilvC containing a Q to V mutation at position 110), LI_ilvD (*Lactococcus lactis* ilvD), LI_kivD2 (*Lactococcus lactis* kivD), and Dm_ADH (*Drosophila melanogaster* ADH).

The strain GEVO3124 is both GPD-deficient, PDC-deficient and able to grow in high glucose media without addition of C2-compounds. GEVO3124 has integrated into the PDC1 locus the Bs_alsS1_coSc (*Bacillus subtilis* alsS; SEQ ID NO: 58) and LI_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), LI_ilvD_coSc (*Lactococcus lactis* ilvD, SEQ ID NO: 65), and LI_adhA (*Lactococcus lactis* adhA, SEQ ID NO: 66) under the TDH3, TEF1 and ENO2 promoters, repectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3124 was generated by deletion of GPD2 using Hph as marker in strain GEVO3059. Deletion of GPD2 was carried out by transforming a hygromycin resistance marker, Hph, flanked by the GPD2 5' and 3' targeting sequences. This gpd2::Hph disruption cassette was generated by multiple rounds of SOE-PCR. First, the GPD2 5' targeting sequence was amplified from pGV2164 (SEQ ID NO: 69), the CCW12 promoter was amplified from pGV1954 (SEQ ID NO: 70), the HPH ORF was amplified from pGV2074

(SEQ ID NO: 71), and the GPD2 3' targeting sequence was also amplified. Second, the GPD2 5' targeting sequence and the CCW12 promoter were stitched together by SOE-PCR, and the Hph ORF and GPD2 3' targeting sequence were also stitched together by SOE-PCR. Lastly, these two SOE-PCR products were stitched together in another round of SOE-PCR. The resulting product was then transformed into GEVO3059 recovered overnight in YPD+1% EtOH+G418 or YPD+1% EtOH+G418+1 g/L glycerol, and selected on YPD+G418+Hygro+1 g/L glycerol or YPD+G418+Hygro+ 10 g/L glycerol plates. Twelve colonies were re-streaked for singles and colony PCRs were performed in single colony isolates to test for correct 5' and 3' junctions and the loss of GPD2.

GEVO3059 was generated by deletion of GPD1 using KI_URA3 as marker in strain GEVO2994. Deletion of GPD1 was carried out by a bipartite integration scheme using the KI_URA3 marker. The 5' bipartite fragment contained the GPD1_5' targeting sequence-$T_{KI\_URA3\_short}$-$P_{FBA1}$-KI_URA3_3' truncated and was generated by PCR with pGV2359 (SEQ ID NO: 72) as template. The 3' bipartite fragment contained KI_URA3_5' truncated-$T_{KI\_URA3}$-GPD1_3' targeting sequence and was generated by PCR with pGV2175 (SEQ ID NO: 73) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), LI_ilvD_coSc (*Lactococcus lactis* ilvD, SEQ ID NO: 65), and LI_adhA (*Lactococcus lactis* adhA, SEQ ID NO: 66) under the TDH3, TEF1 and ENO2 promoters, repectively, into the PDC6 locus of GEVO2843. GEVO2843 was generated by integrating the Bs_alsS1_coSc (*Bacillus subtilis* alsS; SEQ ID NO: 58 and LI_kivD2_coEc (*Lactococcus lactis* kivD, SEQ ID NO: 59) into the PDC1 locus of GEVO2712.

When the biocatalyst GEVO3159 was contacted with glucose in a medium suitable for growth of the biocatalyst, at about 30° C., the biocatalyst produced isobutanol from the glucose. A 24-hour starter culture was started in a 50 mL conical tube with GEVO3159 cells from a frozen glycerol stock. The tube contained a 5 mL volume of YPD80 at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.7 mM/h by reducing agitation to a fixed 250-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 5 days with a titer of about 8.5 g/L. Yield of the fermentation, calculated when the titer of isobutanol was between 3.2 g/L and 8.5 g/L, was approximately 75% maximum theoretical. Yield of the fermentation, calculated when the titer of isobutanol was between 0 g/L and 8.5 g/L, was approximately 48% maximum theoretical. Yield of the fermentation, calculated when the titer of isobutanol was between 1 g/L and 8.5 g/L, was approximately 58% maximum theoretical.

Example 22: Isobutanol Production in Pdc-Gpd-, Co-Factor Balanced Yeast

This example demonstrates isobutanol production at greater than 70% yield in a Pdc-minus, Gpd-minus member of the *Saccharomyces sensu stricto* group, *Saccharomyces clade* yeast, Crabtree-positive yeast, post-WGD yeast, *S. cerevisiae*, expressing an NADH-dependent isobutanol biosynthetic pathway.

The recombinant yeast microorganism, GEVO3160, encodes a heterologous biosynthetic pathway that converts pyruvate into isobutanol. Genes for the pathway are located on the chromosome and on a single plasmid. GEVO3160 is GEVO3128 transformed with pGV2247(SEQ ID NO: 63), which is a high copy yeast expression plasmid used to overexpress Ec_ilvC_P2D1-A1 (*Escherichia coli* ilvC variant), LI_ilvD (*Lactococcus lactis* ilvD), LL_kivD (*Lactococcus lactis* kivD), and LI_adhA (*Lactococcus lactis* adhA). The strain GEVO3128 is both GPD-deficient, PDC-deficient and able to grow in high glucose media without addition of C2-compounds. GEVO3128 has integrated into the PDC1 locus the Bs_alsS1_coSc (*Bacillus subtilis* alsS; SEQ ID NO: 58) and LI_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), LI_ilvD_coSc (*Lactococcus lactis* ilvD, SEQ ID NO: 65), and LI_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3128 was generated by deletion of GPD1 using Hph as marker in strain GEVO3061. To obtain a gpd1 gpd2 double deletion, deletion of GPD1 was pursued in the gpd2::KI_URA3 deletion strains GEVO3061 Deletion of GPD1 was carried out by transforming a hygromycin resistance marker, Hph, flanked by the GPD1 5' and 3' targeting sequences. This gpd1::Hph disruption cassette was generated by multiple rounds of SOE PCR. First, the GPD1 5' targeting sequence was amplified from pGV2163 (SEQ ID NO: 74), the CCW12 promoter was amplified from pGV1954 (SEQ ID NO: 70), the Hph ORF was amplified from pGV2074 (SEQ ID NO: 71), and the GPD1 3' targeting sequence was amplified by PCR. Second, the GPD1 5' targeting sequence and the CCW12 promoter were stitched together by SOE-PCR, and the Hph ORF and GPD1 3' targeting sequence were also stitched together by SOE-PCR. Lastly, these two SOE-PCR products were stitched together in another round of SOE-PCR. The resulting product was then transformed into GEVO3061, recovered overnight in YPD+1% EtOH+G418 or YPD+1% EtOH+G418+1 g/L glycerol, and selected on YPD+G418+Hygro+1 g/L glycerol or YPD+G418+Hygro+10 g/L glycerol plates GEVO3061 was generated by deletion of GPD2 using KI_URA3 as marker in strain GEVO2994. Deletion of GPD2 was carried out by a bipartite integration scheme using the KI_URA3 marker. The 5' bipartite fragment contained the GPD2_5' targeting sequence-$T_{KI\_URA3\_short}$-$P_{FBA1}$-KI_URA3_3' truncated and was generated by PCR with pGV2360 (SEQ ID NO: 75) as template. The 3' bipartite fragment contained KI_URA3_5' truncated-$T_{KI\_URA3}$-GPD2_3' targeting sequence and was generated by PCR with pGV2381 (SEQ ID NO: 76) as a template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, repectively, into the PDC6 locus of GEVO2843. GEVO2843 was generated by integrating the Bs_alsS1_coSc (*Bacillus subtilis* alsS; SEQ ID NO: 58) and Ll_kivD2_coEc (*Lactococcus lactis* kivD, SEQ ID NO: 59) into the PDC1 locus of GEVO2712.

When the biocatalyst GEVO3160 was contacted with glucose in a medium suitable for growth of the biocatalyst, at about 30° C., the biocatalyst produced isobutanol from the glucose. A 24-hour starter culture was started in a 50 mL conical tube with GEVO3160 cells from a frozen glycerol stock. The tube contained a 5 mL volume of YPD80 medium at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell density. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.4 mM/h by reducing agitation to a fixed 200 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 7 days with a titer of about 10.5 g/L.

Yield of the fermentation, calculated when the titer of isobutanol was between 5.7 g/L and 10.2 g/L, was approximately 74% of theoretical (max yield calculation). Yield of the fermentation, calculated when the titer of isobutanol was between 0 g/L and 10.5 g/L, was approximately 48% of theoretical (yield calculation including growth of biomass). Yield of the fermentation, calculated when the titer of isobutanol was between 0.6 g/L and 10.5 g/L, was approximately 57% of theoretical (yield calculation for production phase only).

Example 23: Isobutanol Production in Pdc-Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*, expressing an NADH-dependent isobutanol biosynthetic pathway.

The recombinant yeast microorganism, GEVO3160, encodes a heterologous biosynthetic pathway that converts pyruvate into isobutanol. Genes for the pathway are located on the chromosome and on a single plasmid. GEVO3160 is GEVO3128 transformed with pGV2247 (SEQ ID NO: 63), which is a high copy yeast expression plasmid used to overexpress Ec_ilvC_P2D1-A1 (*Escherichia coli* ilvC variant), Ll_ilvD (*Lactococcus lactis* ilvD), Ll_kivD (*Lactococcus lactis* kivD), and Ll_adhA (*Lactococcus lactis* adhA). The strain GEVO3128 is both GPD-deficient, PDC-deficient and able to grow in high glucose media without addition of C2-compounds. GEVO3128 has integrated into the PDC1 locus the Bs_alsS1_coSc (*Bacillus subtilis* alsS; SEQ ID NO: 58) and Ll_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3128 was generated by deletion of GPD1 using Hph as marker in strain GEVO3061. To obtain a gpd1 gpd2 double deletion, deletion of GPD1 was pursued in the gpd2::KI_URA3 deletion strains GEVO3061 Deletion of GPD1 was carried out by transforming a hygromycin resistance marker, Hph, flanked by the GPD1 5' and 3' targeting sequences. This gpd1::Hph disruption cassette was generated by multiple rounds of SOE PCR. First, the GPD1 5' targeting sequence was amplified from pGV2163 (SEQ ID NO: 74), the CCW12 promoter was amplified from pGV1954 (SEQ ID NO: 70), the Hph ORF was amplified from pGV2074 (SEQ ID NO: 71), and the GPD1 3' targeting sequence was amplified by PCR. Second, the GPD1 5' targeting sequence and the CCW12 promoter were stitched together by SOE-PCR, and the Hph ORF and GPD1 3' targeting sequence were also stitched together by SOE-PCR. Lastly, these two SOE-PCR products were stitched together in another round of SOE-PCR. The resulting product was then transformed into GEVO3061, recovered overnight in YPD+1% EtOH+G418 or YPD+1% EtOH+G418+1 g/L glycerol, and selected on YPD+G418+Hygro+1 g/L glycerol or YPD+G418+Hygro+10 g/L glycerol plates GEVO3061 was generated by deletion of GPD2 using KI_URA3 as marker in strain GEVO2994. Deletion of GPD2 was carried out by a bipartite integration scheme using the KI_URA3 marker. The 5' bipartite fragment contained the GPD2_5' targeting sequence-$T_{KI\_URA3}$-$P_{FBA1}$-KI_URA3_3' truncated and was generated by PCR with pGV2360 (SEQ ID NO: 75) as template. The 3' bipartite fragment contained KI_URA3_5' truncated-$T_{KI\_URA3}$-GPD2_3' targeting sequence and was generated by PCR with pGV2381 (SEQ ID NO: 76) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, repectively, into the PDC6 locus of GEVO2843. GEVO2843 was generated by integrating the Bs_alsS1_coSc (*Bacillus subtilis* alsS; SEQ ID NO: 58) and Ll_kivD2_coEc (*Lactococcus lactis* kivD, SEQ ID NO: 59) into the PDC1 locus of GEVO2712.

When the biocatalyst GEVO3160 was contacted with glucose in a medium suitable for growth of the biocatalyst, at about 30° C., the biocatalyst produced isobutanol from the glucose. A 24-hour starter culture was started in a 50 mL conical tube with GEVO3160 cells from a frozen glycerol stock. The tube contained a 5 mL volume of YPD80 medium at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.3-0.8 mM/h by reducing agitation to a fixed 180-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 7 days with a titer of about 14 g/L. Yield of the fermentation, calculated when the titer of isobutanol was between 7.2 g/L and 12.6 g/L, was approximately 71% maximum theoretical. Yield of the fermentation, calculated when the titer of isobutanol was between 0 g/L and 14 g/L, was approximately 52% maximum theoretical. Yield of the fermentation, calculated when the titer of isobutanol was between 0.5 g/L and 14 g/L, was approximately 60% maximum theoretical.

Example 24: Isobutanol Production in Pdc-Gpd-Yeast

This example demonstrates isobutanol production at greater than 70% yield in a Pdc-minus, Gpd-minus member of the *Saccharomyces sensu stricto* group, *Saccharomyces clade* yeast, Crabtree-positive yeast, post-WGD yeast, *S. cerevisiae*, expressing an NADH-dependent isobutanol biosynthetic pathway.

GEVO3647 contains $P_{ADH1}$-Bs_alsS1_coSc (*Bacillus subtilis* alsS; SEQ ID NO: 58) with two copies of the *Lactococcus lactis* kivD gene (SEQ ID NO: 59) integrated at the PDC1 locus. The strain is a transformation product of the parent strain GEVO3532 with plasmid pGV2563 (SEQ ID NO: 68).

Medium used for the fermentation was YP+80 g/L glucose+1% v/v Ethanol+0.2 g/L G418. The medium was filter sterilized using a 1 L bottle top Corning PES 0.22 μm filter (431174). Medium was pH adjusted 6.0 in the fermenter vessels using 6N KOH. Table EX 15-1 outlines medium components per liter of Di-$H_2O$.

Inoculum cultures were started from patch plates and placing them in 500 mL baffled flasks containing 80 ml YP+20 g/L glucose+1% v/v ethanol+0.2 g/L G418 medium. The cultures were incubated for 32.5 h at 30° C. in an orbital shaker at 250 rpm. Cell density after incubation was as at $OD_{600}$ of 2.5. Batch fermentations were conducted using a 2 L top drive motor DasGip vessel with a working volume of 1.2 L per vessel. The operating conditions are summarized in Table EX15-1 below.

TABLE EX15-1

| Process control parameters. | | |
|---|---|---|
| Initial volume | mL | 1200 |
| Temperature | ° C. | 30 |
| pH | | 6.0 |
| Growth Phase (0-32 hours): | | |
| Oxygen transfer rate (OTR) | mM/h | 10.0 |
| Air flow (overlay) | slph | 5.0 |
| Agitation | rpm | 900 |
| Dissolved oxygen (DO) | % | Not controlled |
| Production phase (32-84.3 hours): | | |
| Oxygen transfer rate (OTR) | mM/h | 0.5 |
| Air flow (overlay) | slph | 5.0 |
| Agitation | rpm | 300 |
| Dissolved oxygen (DO) | % | Not controlled |

Fermenter vessels were sterilized, along with the appropriate dissolved oxygen probes and pH probes, for 60 minutes at 121° C. pH probes were calibrated prior to sterilization however, dissolved oxygen probes were calibrated post sterilization in order to achieve complete polarization prior to calibration. Table EX15-1 outlines the process control parameters used during the fermentation. Note that pH was controlled using 6N KOH and 2N $H_2SO_4$.

The fermentation was run for 84.3 h. Vessels were sampled every 6-10 h or 3 times daily. Sterile 5 mL syringes were used to collect 3 mL of fermenter broth via a sterile sample port. The sample was placed in a 2 mL microfuge tube and a portion was used to measure cell density ($OD_{600}$) on a Genesys 10 spectrophotometer (Thermo Scientific). The remaining sample was filtered through a 0.22 μm Corning filter. The supernatant from each vessel was refrigerated in a 96-well deep well plate, and stored at 4° C. prior to gas and liquid chromatography analysis.

Analysis of volatile organic compounds, including ethanol and isobutanol was performed on a HP 5890/6890/7890 gas chromatograph fitted with an HP 7673 Autosampler, a DB-FFAP column (J&W; 30 m length, 0.32 mm ID, 0.25-μM film thickness) or equivalent connected to a flame ionization detector (FID). The temperature program was as follows: 200° C. for the injector, 300° C. for the detector, 100° C. oven for 1 minute, 70° C./minute gradient to 230° C., and then hold for 2.5 min. Analysis was performed using authentic standards (>99%, obtained from Sigma-Aldrich, and a 5-point calibration curve with 1-pentanol as the internal standard).

Analysis of organic acid metabolites was performed on an HP-1200 High Performance Liquid Chromatography system equipped with two Restek RFQ 150×4.6 mm columns in series. Organic acid metabolites were detected using an HP-1100 UV detector (210 nm) and refractive index. The column temperature was 60° C. This method was isocratic with 0.0180 N $H_2SO_4$ in Milli-Q water as mobile phase. Flow was set to 1.1 mL/min. Injection volume was 20 μL and run time was 16 min. Analysis was performed using authentic standards (>99%, obtained from Sigma-Aldrich, with the exception of DHIV (2,3-dihydroxy-3-methyl-butanoate, CAS 1756-18-9), which was custom synthesized at Caltech (Cioffi, E. et al. Anal Biochem 104 pp. 485 (1980)), and a 5-point calibration curve.

Additionally, on-line continuous measurement of the fermenter vessel off-gas by GC-MS analysis was performed for oxygen, isobutanol, ethanol, carbon dioxide, and nitrogen throughout the experiment.

At the end of the fermentation, the isobutanol titer had reached 6.4 g/L. Yield of the fermentation, calculated over the entire production phase, i.e. from 32 to 84.3 hours, was approximately 71% of theoretical.

Example 25: Cytosolic ALS Homologs that Support Isobutanol Production

This example demonstrates isobutanol production using expression of cytosolically localized ALS genes in the presence of the rest of the isobutanol pathway. The ALS genes were integrated into the PDC1 locus of *S. cerevisiae* strain GEVO1187 and isobutanol production was achieved by expression from plasmid of the other genes in the isobutanol pathway. Isobutanol production in strains carrying the ALS genes from *T. atroviride* (Ta_ALS) and *T. stipitatus* (Ts_ALS) was compared to isobutanol production in strains carrying the ALS gene from *B. subtilis* (either Bs_alsS2 or Bs_alsS1_coSc). Strains, and plasmids are listed in Tables EX16-1 and EX16-2, respectively.

TABLE EX16-1

Genotype of strains disclosed herein

| GEVO No. | Genotype |
|---|---|
| Gevo 1187 | *S. cerevisiae*, CEN.PK; MATa ura3 leu2 his3 trp1 |
| Gevo 2280 | *S. cerevisiae* MATa ura3 leu2 his3 trp1 ADE2 pdc1::$P_{CUP1-1}$-Bs_AlsS2, TRP1 Note that this is TRP1+. Transformed with plasmid pGV1730. Original isolate A2 |
| Gevo 2618 | *S. cerevisiae*, MATa ura3 leu2 his3 trp1 pdc1::$P_{CUP1-1}$-Bs_AlsS1_coSc, TRP1. Transformed with plasmid pGV2114. |
| Gevo 2621 | *S. cerevisiae*, MATa ura3 leu2 his3 trp1 pdc1::$P_{CUP1-1}$-Ta_Als, TRP1. Transformed with plasmid pGV2117. |
| Gevo 2622 | *S. cerevisiae*, MATa ura3 leu2 his3 trp1 pdc1::$P_{CUP1-1}$-Ts_Als, TRP1. Transformed with plasmid pGV2118. |

TABLE EX16-2

Plasmids disclosed herein

| Plasmid name | Relevant Genes/Usage | Genotype |
|---|---|---|
| pGV1730 | Integration plasmid that will integrate $P_{CUP1-1}$:Bs_alsS2 into PDC1 using digestion with NruI for targeting. This was the parent vector for cloning the ALS homologs. | $P_{CUP1-1}$:Bs_alsS2, pUC ORI, $Amp^R$, TRP1, PDC1 3'-fragment-NruI-PDC1 5'-fragment. |
| pGV1773 | Vector with *Bacillus subtilis* AlsS codon optimized for *S. cerevisiae*. | $P_{PDC1}$:Bs_AlsS1_coSc, $P_{TDH3}$:Ll_kivD, $P_{ADH1}$:Sc_ADH7_coSc, URA3 5'-end, pUC ORI, $kan^R$. |
| pGV1802 | DNA2.0 plasmid carrying the *Trichoderma atroviride* ALS. | Ta_ALS_coSc in DNA 2.0 vector |
| pGV1803 | DNA2.0 plasmid carrying the *Talaromyces stipitatus* ALS. | Ts_ALS_coSc in DNA 2.0 vector |
| pGV2082 | High copy 2μ plasmid with 4 isobutanol pathway genes without an ALS gene. | Ec_ilvC_coSc$^{Q110V}$, Ll_ilvD_coSc, Ll_kivD2_coEc, and Dm_ADH, 2μ ori, bla, G418R. |
| pGV2114 | Integration plasmid that will integrate into PDC1 using digestion with NruI for targeting. It carries the *Bacillus subtilis* AlsS gene codon optimized for *S. cerevisiae*. | $P_{CUP1-1}$:Bs_alsS1_coSc, pUC ORI, $Amp^R$, TRP1, PDC1 3'-fragment-NruI-PDC1 5'-fragment. |

TABLE EX16-2-continued

Plasmids disclosed herein

| Plasmid name | Relevant Genes/Usage | Genotype |
| --- | --- | --- |
| pGV2117 | Integration plasmid that will integrate into PDC1 using digestion with NruI for targeting. It carries the *Trichoderma atroviride* ALS gene codon optimized for *S. cerevisiae*. | $P_{CUP1-1}$:Ta_ALS_coSc, pUC ORI, $Amp^R$, TRP1, PDC1 3'-fragment-NruI-PDC1 5'-fragment. |
| pGV2118 | Integration plasmid that will integrate into PDC1 using digestion with NruI for targeting. It carries the *Talaromyces stipitatus* ALS gene codon optimized for *S. cerevisiae*. | $P_{CUP1-1}$:Ts_ALS_coSc, pUC ORI, $Amp^R$, TRP1, PDC1 3'-fragment-NruI-PDC1 5'-fragment. |

Materials and Methods for Example 25

Standard molecular biology methods for cloning and plasmid construction were generally used, unless otherwise noted (Sambrook, J., Russel, D. W. *Molecular Cloning, A Laboratory Manual*. 3$^{rd}$ ed. 2001, Cold Spring Harbor, New York: Cold Spring Harbor Laboratory Press).

Cloning techniques included digestion with restriction enzymes, gel purification of DNA fragments (using the Zymoclean Gel DNA Recovery Kit, Cat#D4002, Zymo Research Corp, Orange, Calif.), ligations of two DNA fragments (using the Roche rapid ligation kit, Cat#11 635 379 001, Roche Diagnostics, Mannheim, Germany), Klenow treatment of fragments to give blunt ends (using the NEB DNA Polymerase I, Large (Klenow), cat#M0210S, Ipswich, Mass.), and bacterial transformations into chemically competent *E. coli* cells made at GEVO (TOP10). Plasmid DNA was purified from *E. coli* cells using the Qiagen QIAprep Spin Miniprep Kit (Cat#27106, Qiagen, Valencia, Calif.).

PCR was performed on an Eppendorf Mastercycler (Cat#71086, Novagen, Madison Wis.). The following PCR program was followed for all primer sets unless otherwise noted: 94° C. for 2 min then 40 cycles of (94° C. 30 sec, 54° C. 30 sec, 72° C. 1 min) then 72° C. for 10 min. Yeast colony PCR used the FailSafe™ PCR System EPICENTRE® Biotechnologies, Madison, Wis.; Catalog #FS99250). A PCR cocktail containing 15 µl of Master Mix E buffer, 10.5 µl water, 2 µl of each primer at 10 µM concentration, 0.5 µl polymerase enzyme mix from the kit was added to a 0.2 mL PCR tube for each sample (30 µl each). For each candidate a small amount of cells was added to the reaction tube using a sterile P10 pipette tip. Presence of the positive PCR product was assessed using agarose gel electrophoresis. The following primer pairs were used. Primers 1432 and 1433 for the 5'-ends of all integrations (800 bp band), primers 1435 and 2233 for the 3'-ends of pGV2114 integrations (1.1 Kb band), primers 1435 and 2234 for the 3'-end of the pGV2115 integrations (1.1 Kb band), primers 1435 and 2236 for the 3'-ends of the pGV2117 integrations (1.1 Kb band), primers 1435 and 2237 for the 3'-ends of the pGV2118 integrations (1.1 Kb band).

Transformation of integration plasmids was performed according to the lithium acetate protocol described above. Integration plasmids were digested with NruI, checked by gel electrophoresis for complete digestion and used directly from digestion. Integrative transformants were selected by plating the transformed cells on SCD-Trp agar medium. Once the transformants were single colony purified they were maintained on SCD-Trp plates. Once transformants were screened by PCR as described above for proper integration, each strain was transformed with the plasmid pGV2082. Transformants were plated to YPD plates containing 0.2 g/L G418.

SCD-Trp: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.380 g/L leucine, and 0.076 g/L uracil.

Fermentations

Strains with integrated ALS genes expressed from the CUP1 promoter were transformed with pGV2082 (which carries the other 4 isobutanol pathway genes Ec_ilvC_coScQ110V (SEQ ID NO: 61), Ll_ilvD (SEQ ID NO: 65), Ll_kivd2_coEc (SEQ ID NO: 59), and Dm_ADH (SEQ ID NO: 60)). Strains were patched onto YPD plates containing 0.2 mg/mL G418. The following morning cells were removed from the plate with a sterile toothpick and resuspended in 4 mL of YPD with 0.2 mg/mL G418. The $OD_{600}$ was determined for each culture. Cells were added to 50 mL YP with 5% dextrose and 0.2 mg/mL G418 such that a final $OD_{600}$ of 0.1 was obtained. 1 mL of media was removed and the $OD_{600}$ for this undiluted sample determined, leftover media was stored at 4° C. to act as media blank for the analytics submission, and to act as the t=0 sample for the fermentation. At t=24 h, 2 mL of media was removed and 25 µL used at a 1:40 dilution to determine $OD_{600}$. The remaining culture was centrifuged in a microcentrifuge at maximum speed for 10 min and a 1:10 dilution read on the YSI. 50% glucose containing 0.2 mg/mL G418 was added to a final concentration of 100 g/L glucose. 1 mL of supernatant was analyzed by gas chromatography as described above. At t=48 h, 2 mL of media was removed and 25 µL used at a 1:40 dilution to determine $OD_{600}$. The remaining culture was centrifuged in a microcentrifuge at maximum speed for 10 min and a 1:10 dilution read on the YSI. 50% glucose plus water (with 0.2 mg/mL G418) were added to give a final concentration of glucose of 100 g/L. 1 mL of supernatant was analyzed by gas chromatography. At t=72 h, 2 mL of media was removed and 25 µL used at a 1:40 dilution to determine $OD_{600}$. The remaining culture was centrifuged in a microcentrifuge at maximum speed for 10 min and a 1:10 dilution read on the YSI. 1 mL of supernatant was analyzed by gas chromatography and high performance liquid chromatography.

Yeast Strain Construction

GEVO2280 was constructed by transforming GEVO1187 with the integration plasmid pGV1730. The plasmid pGV1730 was first linearized with NruI, which cuts such that the linear plasmid will integrate into the PDC1 locus, and the DNA was transformed using the standard yeast transformation protocol. Transformants were selected by plating to SCGal-Trp plates. Individual integrants were verified using colony PCR with primers 1432 and 1433 to detect proper integration at the 5'-end (803 bp fragment) and primers 1220 and 1435 to detect proper integration at the 3'-end (772 bp).

GEVO2618 was constructed by transforming GEVO1187 with the integration plasmid pGV2114. The plasmid was first linearized with NruI, which cuts such that the linear plasmid will integrate into the PDC1 locus, and the DNA was transformed using the standard yeast transformation protocol described above. Correct integration was verified with colony PCR using primers 1432 and 1433 to check the 5'-end of the integration (800 bp band) and primers 1435 and 2233 for the 3'-end of pGV2114 integration (1,100 bp band).

GEVO2621 was constructed by transforming GEVO1187 with the integration plasmid pGV2117. The plasmid was first linearized with NruI, which cuts such that the linear plasmid will integrate into the PDC1 locus, and the DNA was transformed using the standard yeast transformation protocol described above. integration was verified with colony PCR using primers 1432 and 1433 to check the 5'-end of the integration (800 bp band) and primers 1435 and 2236 for the 3'-end of pGV2117 integration (1,100 bp band).

GEVO2622 was constructed by transforming GEVO1187 with the integration plasmids pGV2118. The plasmid was first linearized with NruI, which cuts such that the linear plasmid will integrate into the PDC1 locus, and the DNA was transformed using the standard yeast transformation protocol described above. Twelve transformants were single colony purified. Correct integration was verified with colony PCR using primers 1432 and 1433 to check the 5'-end of the integration (800 bp band) and primers 1435 and 2237 for the 3'-end of pGV2118 integration (1,100 bp band).

Each ALS-containing strain was transformed with the 4 component pathway plasmid, pGV2082 (SEQ ID NO: 67), as described above. Control strains GEVO2280 (Bs_alsS2) and GEVO1187 (no ALS) were also transformed with pGV2082. Transformants were single colony purified and maintained on YPD plates with 0.2 mg/mL G418.

Plasmid Construction

Construction of Plasmid pGV2082.

The plasmid pGV2044 carries the genes Ec_ilvC_coSc$^{Q110V}$, Bs_AlsS2, Ll_ilvD_coSc and Dm_ADH. The plasmid pGV2082 was created from pGV2044 by replacing the Bs_AlsS2 with Ll_kivD2_coEc as follows: the Ll_kivD2_coEc gene and associated PGK1 promoter were removed from pGV2047 by digestion with AvrII and NcoI. The 2530 bp fragment was purified by gel electrophoresis and the fragment was prepared using the Zymoclean kit described above. Plasmid pGV2044 was digested with EcoRI and SbfI to remove the Bs_AlsS2 gene and associated CUP1 promoter and the 11275 bp vector fragment was gel purified. The vector and insert were treated with Klenow fragment to produce blunt ends. The pGV2044 vector fragment and the $P_{PGK1}$:Ll_kivD2_coEc insert were ligated using standard methods in an approximately 5:1 insert:vector molar ratio and transformed into TOP10 chemically competent E. coli cells. Plasmid DNA was isolated and correct clones were confirmed using restriction enzyme analysis consisting of digestion of potential clones with the following enzymes: EcoRV to give correct fragments of 6.3 and 7.5 kb, EcoRV plus NruI to give correct fragments of 2.9, 3.4, and 7.5 kb), EcoRI plus NcoI to give correct fragments of 2.5 and 11.2 Kb.

pGV1730 was digested with BamHI and SalI and the vector fragment of 4.9 kb was gel purified by agarose gel electrophoresis. pGV1773 was digested with BamHI and SalI and the 1.7 Kb fragment containing the Bs_AlsS_coSc was gel purified by agarose gel electrophoresis. The pGV1730 vector fragment was ligated to the pGV1773 insert fragment using the Roche rapid ligation kit in a ratio of 5:1 insert to vector ratio and transformed into TOP10 chemically competent E. coli cells. Plasmid DNA was isolated and correct clones were confirmed using restriction enzyme analysis consisting of digestion of potential clones with ScaI plus PstI to give correct fragments of 2.7, 1.7, 1.4 and 0.9 Kb, AflII to give correct fragments of 1.5 and 5.1 kb, NaeI plus StuI to give correct fragments of 1.4, 5.2 kb.

Construction of pGV2117:

pGV1730 was digested with BamHI and SalI and the vector fragment of 4.9 kb was gel purified by agarose gel electrophoresis. pGV1802 was digested with BamHI and SalI and the 1.8 kb fragment containing the Ta_ALS was gel purified by agarose gel electrophoresis. The pGV1730 vector fragment was ligated to the pGV1802 insert fragment using the Roche rapid ligation kit in a ration of 5:1 insert to vector ratio and transformed into TOP-10 chemically competent E. coli cells. Plasmid DNA was isolated and correct clones were confirmed using restriction enzyme analysis consisting of digestion of potential clones with BamHI plus StuI to give correct fragments of 1.4 and 5.2 kb, SalI plus PstI to give correct fragments of 0.7 and 5.9 kb, and AhdI to give correct fragments of 1.9 and 4.7 kb.

Construction of pGV2118:

pGV1730 was digested with BamHI and SalI and the vector fragment of 4.9 kb was gel purified by agarose gel electrophoresis. pGV1803 was digested with BamHI and SalI and the 1.8 kb fragment containing the Ts_ALS gel purified by agarose gel electrophoresis. The pGV1730 vector fragment was ligated to the pGV1803 insert fragment using the Roche rapid ligation kit in a ration of 5:1 insert to vector ratio and transformed into TOP-10 chemically competent E. coli cells. Plasmid DNA was isolated and correct clones were confirmed using restriction enzyme analysis consisting of digestion of potential clones with NaeI to give correct bands of 2.9 and 3.7 kb, EcoRV to give correct bands of 0.7 and 5.9 kb, and HpaI plus SacI to give correct bands of 1.9 and 4.7 kb.

Results

Fermentations of GEVO1187, GEVO2280, GEVO2618, GEVO2621, GEVO2622 and transformed with pGV2082 were carried out as described above (except G418 was not added to the glucose at 24 h). In this experiment strains containing the ALS genes Ta_ALS_coSc and Ts_ALS_coSc produced more isobutanol than the strain containing the Bs_Als2. The Bs_Als1_coSc produced the most isobutanol. Table EX16-3 shows the final OD, glucose consumption, and isobutanol titer for each of the strains. The integration of the cytosolic genes Ta_ALS_coSc and Ts_ALS_coSc led to production of isobutanol that was in each case 6-fold above that of a strain without an integrated ALS gene, demonstrating that these strains are producing isobutanol using a cytosolic pathway.

TABLE EX16-3

Results of fermentation with cytosolic ALS homologs, at 72 h

| Strain | $OD_{600}$ | Glucose consumed g/L | Isobutanol produced g/L |
|---|---|---|---|
| GEVO1187 | 10.9 ± 0.3 | 233 ± 36 | 0.3 ± 0.0 |
| GEVO2280 | 9.9 ± 0.3 | 274 ± 26 | 1.3 ± 0.11 |
| GEVO2618 | 9.4 ± 0.2 | 138 ± 9 | 2.6 ± .09 |
| GEVO2621 | 9.9 ± 0.3 | 161 ± 52 | 1.9 ± .18 |
| GEVO2622 | 10.8 ± 0.6 | 182 ± 47 | 1.8 ± .15 |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A recombinant yeast microorganism for producing isobutanol, the recombinant yeast microorganism comprising an isobutanol producing metabolic pathway, wherein said isobutanol producing metabolic pathway comprises the following substrate to product conversions:
   (i) pyruvate to acetolactate;
   (ii) acetolactate to 2,3-dihydroxyisovalerate;
   (iii) 2,3-dihydroxyisovalerate to α-ketoisovalerate;
   (iv) α-ketoisovalerate to isobutyraldehyde; and
   (v) isobutyraldehyde to isobutanol;
wherein the recombinant yeast microorganism expresses
   (a) a heterologous acetolactate synthase (ALS) to catalyze the conversion of pyruvate to acetolactate;
   (b) a heterologous ketol-acid reductoisomerase to catalyze the conversion of acetolactate to 2,3-dihydroxyisovalerate;
   (c) a heterologous dihydroxyacid dehydratase to catalyze the conversion of 2,3-dihydroxyisovalerate to α-ketoisovalerate;
   (d) an heterologous α-ketoisovalerate decarboxylase to catalyze the conversion of α-ketoisovalerate to isobutyraldehyde; and
   (e) an heterologous alcohol dehydrogenase to catalyze the conversion of isobutyraldehyde to isobutanol;
wherein the recombinant yeast microorganism has been engineered to:
   (A) disrupt, mutate, or delete one or more endogenous pyruvate decarboxylase (PDC) genes, wherein said recombinant yeast microorganism has reduced endogenous PDC activity as compared to the corresponding yeast microorganism that has not been engineered to have reduced endogenous PDC activity; and
   (B) disrupt, mutate, or delete one or more endogenous glycerol-3-phosphate dehydrogenase (GPD) genes, wherein said recombinant yeast microorganism has reduced endogenous GPD activity as compared to the corresponding yeast microorganism that has not been engineered to have reduced endogenous GPD activity;
and wherein the recombinant yeast microorganism produces isobutanol at a yield which is at least 70% of the theoretical yield of isobutanol from glucose.

2. The recombinant yeast microorganism of claim 1, wherein all endogenous PDC genes and all endogenous GPD genes are disrupted, mutated, or deleted.

3. The recombinant yeast microorganism of claim 1, wherein said one or more endogenous PDC genes are selected from the group consisting of PDC1, PDC2, PDC5, and PDC6.

4. The recombinant yeast microorganism of claim 1, wherein said one or more endogenous GPD genes are selected from the group consisting of GPD1 and GPD2.

5. The recombinant yeast microorganism of claim 1, wherein said acetolactate synthase (ALS) is a cytosolically-localized acetolactate synthase (ALS).

6. The recombinant yeast microorganism of claim 5, wherein said cytosolically-localized acetolactate synthase (ALS) is encoded by the *Lactococcus lactis* alsS gene.

7. The recombinant yeast microorganism of claim 5, wherein said cytosolically-localized acetolactate synthase (ALS) is encoded by the *Bacillus subtilis* alsS gene.

8. The recombinant yeast microorganism of claim 1, wherein said recombinant yeast microorganism has been engineered to disrupt or delete an endogenous pyruvate dehydrogenase (PDH) gene.

9. The recombinant yeast microorganism of claim 1, wherein said heterologous α-ketoisovalerate decarboxylase is obtained from *Lactococcus lactis*.

10. The recombinant yeast microorganism of claim 1, wherein said recombinant yeast microorganism is a yeast of a genus selected from the group consisting of *Saccharomyces, Kluyveromyces, Candida, Pichia, Hansenula*, and *Schizosaccharomyces*.

11. The recombinant yeast microorganism of claim 1, wherein said ketol-acid reductoisomerase is an NADH-dependent ketol-acid reductoisomerase.

12. The recombinant yeast microorganism of claim 1, wherein said recombinant yeast microorganism has an increased capacity to produce acetolactate as compared to the corresponding yeast microorganism that has not been engineered to have reduced endogenous PDC activity and reduced endogenous GPD activity.

13. The recombinant yeast microorganism of claim 1, wherein said alcohol dehydrogenase is an NADH-dependent alcohol dehydrogenase.

14. A method of producing isobutanol, comprising:
   (a) providing a recombinant yeast microorganism according to claim 1;
   (b) cultivating the microorganism in a culture medium containing a feedstock providing the carbon source, until the isobutanol is produced; and
   (c) recovering the isobutanol.

* * * * *